(12) United States Patent
Fischmann et al.

(10) Patent No.: US 8,440,443 B1
(45) Date of Patent: May 14, 2013

(54) MEK1 POLYPEPTIDES

(75) Inventors: Thierry O. Fischmann, Scotch Plains, NJ (US); Hung V. Le, Rockaway, NJ (US); Vincent S. Madison, Mountain Lakes, NJ (US); Anthony F. Mannarino, North Plainfield, NJ (US); Todd W. Mayhood, Randolph, NJ (US); Paul Reichert, Montville, NJ (US); Catherine Smith, Union, NJ (US); Tin-Yau Chan, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 467 days.

(21) Appl. No.: 11/749,550

(22) Filed: May 16, 2007

Related U.S. Application Data

(60) Provisional application No. 60/800,876, filed on May 16, 2006.

(51) Int. Cl.
*C12N 9/12* (2006.01)

(52) U.S. Cl.
USPC .......................................... 435/194

(58) Field of Classification Search .................. None
See application file for complete search history.

(56) References Cited

U.S. PATENT DOCUMENTS

| | | |
|---|---|---|
| 5,441,734 A | 8/1995 | Reichert et al. |
| 6,027,565 A | 2/2000 | Bugg et al. |
| 6,303,287 B1 | 10/2001 | Kim et al. |
| 2003/0224500 A1 | 12/2003 | Ohren et al. |
| 2008/0201123 A1* | 8/2008 | Cosgrove ........................ 703/11 |

FOREIGN PATENT DOCUMENTS

| | | |
|---|---|---|
| EP | 1321518 A1 | 6/2003 |
| WO | WO03/054180 | 7/2003 |

OTHER PUBLICATIONS

Zheng et al., J. Biol. Chem. 268:11435-11439, 1993.*
Amersham Protein Purification Handbook, Oct. 2001, p. 59.*
Delaney et al., Mol. Cell. Biol. 22:7593-7602, 2002.*
Resing et al., Biochemistry 34:2610-2620, 1995.*
GenBank Accession No. NP_002746, Jul. 1999, 5 pages.*
Nagabhushan, Tattanahalli L., et al., Type I interferon structures: Possible scaffolds for the interferon-alpha receptor complex, Cancer Journal Chem., 80:1166-1173 (2002).
Ohren, Jeffrey F., et al., Structures of Human MAP kinase kinase 1 (MEK1) and MEK2 describe novel noncompetitive kinase inhibition, Nature Structural & Molecular Biology, 11(12):1192-1197 (2004).

* cited by examiner

*Primary Examiner* — David J Steadman

(57) ABSTRACT

The present invention provides, inter alia, crystals of the MEK1 polypeptide which are particularly useful for structure based drug design as well as methods of use thereof.

4 Claims, 3 Drawing Sheets

SEQUENCE LISTING

```
<160> NUMBER OF SEQ ID NOS: 14

<210> SEQ ID NO 1
<211> LENGTH: 383
<212> TYPE: PRT
<213> ORGANISM: Artificial Sequence
<220> FEATURE:
<223> OTHER INFORMATION: MEK1/N35/NKF

<400> SEQUENCE: 1

Met Gly Tyr Tyr His His His His His His Asp Tyr Asp Ile Pro Thr
1               5                   10                  15

Thr Glu Asn Leu Tyr Phe Gln Gly Lys Leu Glu Glu Leu Glu Leu
            20                  25                  30

Asp Glu Gln Gln Arg Lys Arg Leu Glu Ala Phe Leu Thr Gln Lys Gln
        35                  40                  45

Lys Val Gly Glu Leu Lys Asp Asp Phe Glu Lys Ile Ser Glu Leu
    50                  55                  60

Gly Ala Gly Asn Gly Gly Val Val Phe Lys Val Ser His Lys Pro Ser
65                  70                  75                  80

Gly Leu Val Met Ala Arg Lys Leu Ile His Leu Glu Ile Lys Pro Ala
                85                  90                  95

Ile Arg Asn Gln Ile Ile Arg Glu Leu Gln Val Leu His Glu Cys Asn
            100                 105                 110

Ser Pro Tyr Ile Val Gly Phe Tyr Gly Ala Phe Tyr Ser Asp Gly Glu
        115                 120                 125

Ile Ser Ile Cys Met Glu His Met Asp Gly Gly Ser Leu Asp Gln Val
    130                 135                 140

Leu Lys Lys Ala Gly Arg Ile Pro Glu Gln Ile Leu Gly Lys Val Ser
145                 150                 155                 160

Ile Ala Val Ile Lys Gly Leu Thr Tyr Leu Arg Glu Lys His Lys Ile
                165                 170                 175

Met His Arg Asp Val Lys Pro Ser Asn Ile Leu Val Asn Ser Arg Gly
            180                 185                 190

Glu Ile Lys Leu Cys Asp Phe Gly Val Ser Gly Gln Leu Ile Asp Ser
        195                 200                 205

Met Ala Asn Ser Phe Val Gly Thr Arg Ser Tyr Met Ser Pro Glu Arg
    210                 215                 220

Leu Gln Gly Thr His Tyr Ser Val Gln Ser Asp Ile Trp Ser Met Gly
225                 230                 235                 240

Leu Ser Leu Val Glu Met Ala Val Gly Arg Tyr Pro Ile Pro Pro
                245                 250                 255

Asp Ala Lys Glu Leu Glu Leu Met Phe Gly Cys Gln Val Glu Gly Asp
            260                 265                 270

Ala Ala Glu Thr Pro Pro Arg Pro Arg Thr Pro Gly Arg Pro Leu Asn
        275                 280                 285

Lys Phe Gly Met Asp Ser Arg Pro Pro Met Ala Ile Phe Glu Leu Leu
    290                 295                 300

Asp Tyr Ile Val Asn Glu Pro Pro Lys Leu Pro Ser Gly Val Phe
305                 310                 315                 320

Ser Leu Glu Phe Gln Asp Phe Val Asn Lys Cys Leu Ile Lys Asn Pro
                325                 330                 335
```

```
Ala Glu Arg Ala Asp Leu Lys Gln Leu Met Val His Ala Phe Ile Lys
                340                 345                 350

Arg Ser Asp Ala Glu Glu Val Asp Phe Ala Gly Trp Leu Cys Ser Thr
            355                 360                 365

Ile Gly Leu Asn Gln Pro Ser Thr Pro Thr His Ala Ala Gly Val
    370                 375                 380

<210> SEQ ID NO 2
<211> LENGTH: 373
<212> TYPE: PRT
<213> ORGANISM: Artificial Sequence
<220> FEATURE:
<223> OTHER INFORMATION: MEK1/N35/NKF/Cdel383

<400> SEQUENCE: 2

Met Gly Tyr Tyr His His His His His Asp Tyr Asp Ile Pro Thr
1               5                   10                  15

Thr Glu Asn Leu Tyr Phe Gln Gly Lys Lys Leu Glu Glu Leu Glu Leu
                20                  25                  30

Asp Glu Gln Gln Arg Lys Arg Leu Glu Ala Phe Leu Thr Gln Lys Gln
            35                  40                  45

Lys Val Gly Glu Leu Lys Asp Asp Phe Glu Lys Ile Ser Glu Leu
    50                  55                  60

Gly Ala Gly Asn Gly Gly Val Val Phe Lys Val Ser His Lys Pro Ser
65                  70                  75                  80

Gly Leu Val Met Ala Arg Lys Leu Ile His Leu Glu Ile Lys Pro Ala
                85                  90                  95

Ile Arg Asn Gln Ile Ile Arg Glu Leu Gln Val Leu His Glu Cys Asn
            100                 105                 110

Ser Pro Tyr Ile Val Gly Phe Tyr Gly Ala Phe Tyr Ser Asp Gly Glu
        115                 120                 125

Ile Ser Ile Cys Met Glu His Met Asp Gly Gly Ser Leu Asp Gln Val
    130                 135                 140

Leu Lys Lys Ala Gly Arg Ile Pro Glu Gln Ile Leu Gly Lys Val Ser
145                 150                 155                 160

Ile Ala Val Ile Lys Gly Leu Thr Tyr Leu Arg Glu Lys His Lys Ile
                165                 170                 175

Met His Arg Asp Val Lys Pro Ser Asn Ile Leu Val Asn Ser Arg Gly
            180                 185                 190

Glu Ile Lys Leu Cys Asp Phe Gly Val Ser Gly Gln Leu Ile Asp Ser
        195                 200                 205

Met Ala Asn Ser Phe Val Gly Thr Arg Ser Tyr Met Ser Pro Glu Arg
    210                 215                 220

Leu Gln Gly Thr His Tyr Ser Val Gln Ser Asp Ile Trp Ser Met Gly
225                 230                 235                 240

Leu Ser Leu Val Glu Met Ala Val Gly Arg Tyr Pro Ile Pro Pro Pro
                245                 250                 255

Asp Ala Lys Glu Leu Glu Leu Met Phe Gly Cys Gln Val Glu Gly Asp
            260                 265                 270

Ala Ala Glu Thr Pro Pro Arg Pro Arg Thr Pro Gly Arg Pro Leu Asn
        275                 280                 285

Lys Phe Gly Met Asp Ser Arg Pro Pro Met Ala Ile Phe Glu Leu Leu
    290                 295                 300

Asp Tyr Ile Val Asn Glu Pro Pro Pro Lys Leu Pro Ser Gly Val Phe
305                 310                 315                 320

Ser Leu Glu Phe Gln Asp Phe Val Asn Lys Cys Leu Ile Lys Asn Pro
```

```
                     325                 330                 335
Ala Glu Arg Ala Asp Leu Lys Gln Leu Met Val His Ala Phe Ile Lys
            340                 345                 350

Arg Ser Asp Ala Glu Glu Val Asp Phe Ala Gly Trp Leu Cys Ser Thr
            355                 360                 365

Ile Gly Leu Asn Gln
        370

<210> SEQ ID NO 3
<211> LENGTH: 64
<212> TYPE: DNA
<213> ORGANISM: Artificial Sequence
<220> FEATURE:
<223> OTHER INFORMATION: fTOPOI primer

<400> SEQUENCE: 3
atcccaacga ccgaaaacct gtattttcag ggcatgccca agaagaagcc gacgcccatc      60
cagc                                                                   64

<210> SEQ ID NO 4
<211> LENGTH: 76
<212> TYPE: DNA
<213> ORGANISM: Artificial Sequence
<220> FEATURE:
<223> OTHER INFORMATION: fTOPOII primer

<400> SEQUENCE: 4
caccatgtcg tactaccatc accatcacca tcacgattac gatatcccaa cgaccgaaaa      60
cctgtatttt cagggc                                                      76

<210> SEQ ID NO 5
<211> LENGTH: 32
<212> TYPE: DNA
<213> ORGANISM: Artificial Sequence
<220> FEATURE:
<223> OTHER INFORMATION: rTOPO primer

<400> SEQUENCE: 5
ttagacgcca gcagcatggg ttggtgtgct gg                                    32

<210> SEQ ID NO 6
<211> LENGTH: 38
<212> TYPE: DNA
<213> ORGANISM: Artificial Sequence
<220> FEATURE:
<223> OTHER INFORMATION: fN35 primer

<400> SEQUENCE: 6
gctctagctc ctccagcttc ttgccctgaa aatacagg                              38

<210> SEQ ID NO 7
<211> LENGTH: 38
<212> TYPE: DNA
<213> ORGANISM: Artificial Sequence
<220> FEATURE:
<223> OTHER INFORMATION: rN35 primer

<400> SEQUENCE: 7
cctgtatttt cagggcaaga agctggagga gctagagc                              38

<210> SEQ ID NO 8
<211> LENGTH: 41
<212> TYPE: DNA
<213> ORGANISM: Artificial Sequence
```

```
<220> FEATURE:
<223> OTHER INFORMATION: fNKF primer

<400> SEQUENCE: 8
ggaggcccct taacaaattt ggaatggaca gccgacctcc c                    41

<210> SEQ ID NO 9
<211> LENGTH: 41
<212> TYPE: DNA
<213> ORGANISM: Artificial Sequence
<220> FEATURE:
<223> OTHER INFORMATION: rNKF primer

<400> SEQUENCE: 9
gggaggtcgg ctgtccattc caaatttgtt aagggcctc c                     41

<210> SEQ ID NO 10
<211> LENGTH: 62
<212> TYPE: DNA
<213> ORGANISM: Artificial Sequence
<220> FEATURE:
<223> OTHER INFORMATION: fCdel383 primer

<400> SEQUENCE: 10
gcaggttggc tctgctccac catcggcctt aaccagtaaa agggtgggcg cgccgaccca    60
gc                                                                  62

<210> SEQ ID NO 11
<211> LENGTH: 62
<212> TYPE: DNA
<213> ORGANISM: Artificial Sequence
<220> FEATURE:
<223> OTHER INFORMATION: rCdel383 primer

<400> SEQUENCE: 11
gctgggtcgg cgcgcccacc cttttactgg ttaaggccga tggtggagca gagccaacct    60
gc                                                                  62

<210> SEQ ID NO 12
<211> LENGTH: 393
<212> TYPE: PRT
<213> ORGANISM: Homo sapiens

<400> SEQUENCE: 12

Met Pro Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
                20                  25                  30

Leu Gln Lys Lys Leu Glu Glu Leu Glu Leu Asp Glu Gln Gln Arg Lys
            35                  40                  45

Arg Leu Glu Ala Phe Leu Thr Gln Lys Gln Lys Val Gly Glu Leu Lys
        50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
        115                 120                 125

Phe Tyr Gly Ala Phe Tyr Ser Asp Gly Glu Ile Ser Ile Cys Met Glu
```

```
                130                 135                 140
His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
                180                 185                 190

Pro Ser Asn Ile Leu Val Asn Ser Arg Gly Glu Ile Lys Leu Cys Asp
                195                 200                 205

Phe Gly Val Ser Gly Gln Leu Ile Asp Ser Met Ala Asn Ser Phe Val
210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Val Gly Arg Tyr Pro Ile Pro Pro Asp Ala Lys Glu Leu Glu
                260                 265                 270

Leu Met Phe Gly Cys Gln Val Glu Gly Asp Ala Ala Glu Thr Pro Pro
                275                 280                 285

Arg Pro Arg Thr Pro Gly Arg Pro Leu Ser Ser Tyr Gly Met Asp Ser
290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
                340                 345                 350

Lys Gln Leu Met Val His Ala Phe Ile Lys Arg Ser Asp Ala Glu Glu
                355                 360                 365

Val Asp Phe Ala Gly Trp Leu Cys Ser Thr Ile Gly Leu Asn Gln Pro
370                 375                 380

Ser Thr Pro Thr His Ala Ala Gly Val
385                 390

<210> SEQ ID NO 13
<211> LENGTH: 8
<212> TYPE: PRT
<213> ORGANISM: Artificial Sequence
<220> FEATURE:
<223> OTHER INFORMATION: Strep tag

<400> SEQUENCE: 13

Trp Ser His Pro Gln Phe Glu Lys
1               5

<210> SEQ ID NO 14
<211> LENGTH: 6
<212> TYPE: PRT
<213> ORGANISM: Artificial Sequence
<220> FEATURE:
<223> OTHER INFORMATION: His tag

<400> SEQUENCE: 14

His His His His His His
1               5
```

MEK1 POLYPEPTIDES

This application claims the benefit of U.S. provisional patent application No. 60/800,876; filed May 16, 2006; which is herein incorporated by reference in its entirety.

FIELD OF THE INVENTION

The present invention relates, inter alga, to crystals comprising MEK1 polypeptide and methods of use thereof.

BACKGROUND OF THE INVENTION

The protein kinases that constitute mitogen activated protein kinase (MAPK) pathways are of interest for their central role in mediating cellular responses to stimuli such as growth factors and cytokines. The MAPK kinase, MEK1, is activated by a phosphorylation signaling cascade in response to hormones and growth factors. Known oncogenes such as Ras and Raf are upstream activators of MEK1 and MEK1 is aberrantly activated in multiple common tumor types. Inhibition of MEK1 reverses cellular transformation. Hence, there is considerable interest in the role MEK1 signaling plays in oncogenic transformation and in targeting MEK1 for cancer therapies using, for example, small molecules. Structure assisted drug design is a tool used to optimize the success of identifying such therapeutic compounds. However, use of this powerful methodology requires three-dimensional structural information (e.g., as obtained via X-ray diffraction of the target protein). The crystal structures of unphosphorylated MEK1 have been reported, by Chen et al., in a ternary complex with ATP and 5-bromo-N-(2,3-dihydroxyl-propoxy)-3,4-difluoro-2(2-fluoro-4-iodo-phenylamino)-benzamide or {5-[3,4-difluoro-2-(2-fluoro-4-iodo-phenylamino)-phenyl]-1,3,4-oxadiazol-2-yl}-(2-morpholin-4-yl-ethyl)-amine ("Chen crystal"; see EP1321518A1; WO 2003/54180 or U.S. 2003/0224500). This crystals suffers from several drawbacks. For example, the ATP and the benzamide compound in the MEK1 crystal disclosed by Chen at al.

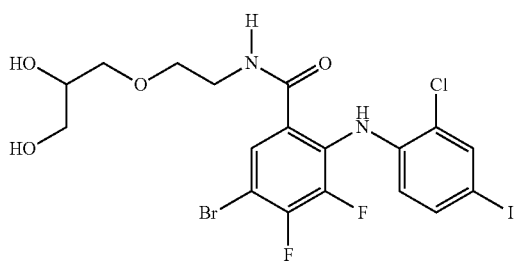 [SMILES: O=C(NCCOCC(O)CO)c1cc(Br)c(F)c(F)c1Nc1ccc(I)cc1Cl]

(Cpd.3)) is extremely difficult to displace, e.g., by soaking, with another compound. The Chen crystal is likely not soakabie because cpd.3 is an allosteric compound that makes a complex network of interactions with both the MEK1 protein and any nucleotide bound to MEK1. The inhibitor in the Chen crystal binds to MEK1, along with a nucleotide, with particularly high affinity making its replacement with any other compound, by soaking, impractical. This shortcoming limits the utility of this Chen crystal in identifying new therapeutically useful MEK1 inhibitors. Moreover, the crystal disclosed by Chen of al. comprises a large N-terminal deletion. The deleted region comprises an α-helical region important to the negative regulation of MEK1. The crystal structures revealed in the crystals of the present invention indicate that the region deleted in the Chen crystal is an integral part of MEK1. The deleted negative-regulatory domain makes the biological accuracy and relevance of any structural data obtained from the crystal less certain.

There remains a need in the art for crystals of MEK1 into which various inhibitors can be soaked for the purpose of evaluating the inhibitor as well as obtaining structural data for the purpose of performing structure-based drug design.

SUMMARY OF THE INVENTION

The present invention addresses the need for high quality crystals for studying complexes between MEK1 and any other inhibitor of MEK1. The crystals of the present invention comprise MEK1 complexed with compound 2 or ATPγS. The MEK1 complex crystals of the present invention, unlike the crystals presently in the art (e.g., Chen crystals), are very amenable to soaking wherein new complexes between MEK1 and a different MEK1 inhibitor (ATP competitive, non-competitive or uncompetitive) can be formed, studied and evaluated.

The inhibitors and, thus, the crystalline complexes of the present invention are also superior (e.g., to the Chen crystals) due to the fact that they bind to the MEK1 hinge region (discussed below). Since the hinge region is the region to which ATP binds, the inhibitors of the present invention (e.g., compound 2) are ATP competitive. The hinge region is characterized by its relatively high resistance to mutation and is distinct from the MEK1 binding pocket to which the inhibitors in the Chen crystal bind. Since the hinge region exhibits a low mutation frequency, the MEK1 enzyme is less likely to develop resistance to inhibitors that bind the hinge region. This characteristic, in turn, makes inhibitors identifiable using the compositions and methods of the present invention very effective anti-cancer treatments because tumors being treated with the inhibitors are unlikely to develop resistance. Additional hinge region binding inhibitors can be identified (in addition to compound 2) by computer assisted modeling techniques of the present invention or by soaking a candidate inhibitor into a crystal of the present invention and, subsequently, determining the crystalline complex structure.

Furthermore, the crystals of the present invention comprise the N-terminal negative regulatory domain discussed above, thus making structural data obtained from the present crystals more biologically relevant (see e.g., Mansour et al. Science 265:966-970 (1994)). As mentioned above, structural data from the crystals of the present invention reveal that this region is an integral part of the MEK1 structure. The region exhibits extended surface interactions with the rest of the protein.

The present invention provides an isolated polypeptide comprising amino acids 35-383 or 35-393 of human MEK1 optionally comprising mutations at S298, S299 and Y300 e.g., S298N, S299K and Y300F. In an embodiment of the invention, the polypeptide comprises amino acids 25-373 of SEQ ID NO: 2, amino acids 25-383 of SEQ ID NO: 1 or the amino acid sequence of SEQ ID NO: 1 or 2. In an embodiment of the invention, the polypeptide is complexed with

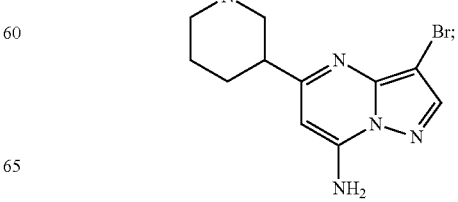

-continued

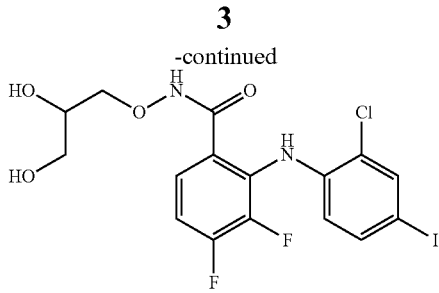

or ATPγS or any combination thereof. In an embodiment of the invention, the polypeptide comprises a binding pocket whose three-dimensional orientation is characterized by the structural coordinates of amino acids 70-84; 93-98; 117-120; 128-129; 140-152; 193-197 and 205-208 according to Table 2, 3 or 4 wherein one or more of said binding pocket amino acids can be conservatively substituted and/or a hinge region whose three-dimensional orientation is characterized by the structural coordinates of amino acids E144, H145 and M146 according to Table 1 or amino acids E143, H144 and M145 according to Table 2, 3 or 4 wherein one or more of said hinge region amino acids can be conservatively substituted. in an embodiment of the invention, the polypeptide comprises amino acids whose three dimensional orientation is characterized by the structural coordinates of Table 1, 2, 3 or 4. In an embodiment of the invention, the polypeptide is crystalline. The present invention also comprises any polypeptide herein in a crystallizable composition. For example, in an embodiment of the invention, the crystallizable composition comprises a MEK1 polypeptide (e.g., 19.2 mg/ml concentration) of the invention, a precipitant (e.g., PEG4000 e.g., at a concentration of about 18%), a buffer (e.g., TRIS e.g., at a concentration of about 90 mM) and about 1% to about 15%, (e.g., 3%) dimethylsulfoxide (DMSO) and optionally $Ca^{2+}$ (e.g., $CaCl_2$ e.g., at a concentration of about 0.18M). In an embodiment of the invention, the crystallizable composition is at a temperature of about 4° C. In an embodiment of the invention, the polypeptide is fused to a heterologous protein. The present invention also comprise an isolated polynucleotide encoding any polypeptide set forth herein along with an isolated vector thereof or an isolated host cell comprising said vector.

The present invention also comprises a crystalline composition comprising a MEK1 binding pocket characterized by the structural coordinates of amino acid 70-84; 93-98; 117-120; 128-129; 140-152; 193-197 and 205-208 according to Table 2, 3 or 4 wherein one or more of said binding pocket amino acids can be conservatively substituted and/or a hinge region whose three-dimensional orientation is characterized by the structural coordinates of amino acids E144, H145 and M146 according to Table 1 or amino acids E143, H144 and M145 according to Table 2, 3 or 4 wherein one or more of said hinge region amino acids can be conservatively substituted. In an embodiment of the invention, the polypeptide is complexed with ATPγS and/or

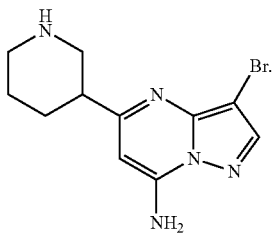 [SMILES: Nc1cc(C2CCCNC2)nc2c(Br)cnn12]

The present invention also provides a crystalline composition of comprising a complex wherein the complex three dimensional structure is characterized by structural coordinates comprising a root mean square deviation of common residue backbone atoms or alpha carbon atoms of less than about 1.5 Å when superimposed on backbone atoms or alpha carbon atoms described by structural coordinates of any of Tables 1, 2, 3 or 4. In an embodiment of the invention, the polypeptide comprises the amino acid sequence of SEQ ID NO: 2 complexed with ATPγS or a compound represented by structural formula 2

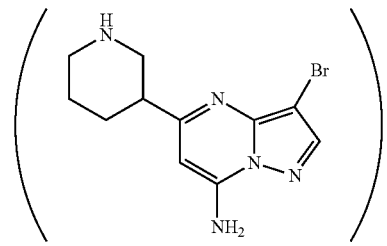

which is characterized by structural coordinates set forth in Table 3 or 4. In an embodiment of the invention, the crystal comprises comprising unit cell dimensions of a=about 76.8 Å, b=about 76.8 Å, c=about 222.4 Å, a=13=about 90°; γ=about 120°; unit cell dimensions of a=about 77.2 Å, b=about 77.2 Å, c=about 222.2 Å, α=β=about 90° γ=about 120°; belongs to space group P $6_1$ 2 2; diffracts X-rays to a resolution of about 2.55 Å or a lower number; or diffracts X-rays to a resolution of about 2.45 Å or a lower number. In an embodiment of the invention, the crystalline composition comprises a polypeptide complex defined by the structural coordinates set forth in any of Tables 1-4. In an embodiment of the invention, the crystalline composition comprises an isolated polypeptide comprising amino acids 35-383 of MEK1 (e.g., 25-373 of SEQ ID NO: 2) complexed with ATPγS or

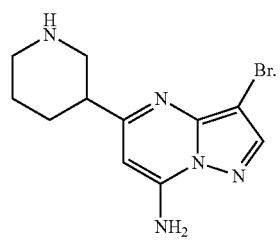 [SMILES: Nc1cc(C2CCCNC2)nc2c(Br)cnn12]

The present invention also provides a compound, an enantiomer, stereoisomer, rotamer or tautomer thereof, or a pharmaceutically acceptable salt or solvate thereof, said compound having the structure shown in Formula 2:

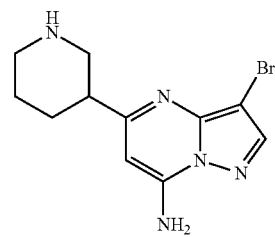 [SMILES: Nc1cc(C2CCCNC2)nc2c(Br)cnn12]

or a pharmaceutical composition thereof comprising a pharmaceutically acceptable carrier.

The present invention also provides a hanging-drop/sitting drop vapor diffusion method for making a crystal comprising a MEK1 polypeptide of the invention complexed with ATPγS or with compound 2 or both comprising incubating an aqueous solution comprising said polypeptide, DMSO (e.g., about 1.5% DMSO) and a precipitant (PEG4000 e.g., about 9% PEG4000) in close proximity to a precipitant solution comprising the precipitant (e.g., about 18% PEG4000) and DMSO (e.g., about 1% to about 15%, for example, about 3% DMSO) in a sealed chamber. In an embodiment of the invention, the solution comprising the polypeptide comprises a lower concentration of precipitant and the precipitant solution comprises the approximate final concentration of precipitant which the solution comprising the polypeptide will reach during incubation. In an embodiment of the invention, the polypeptide is at a concentration of about 9.6 mg/ml. In an embodiment of the invention, the precipitant solution comprises about 90 mM TRIS, pH 8.5, about 18% PEG 4000, about 0.18 M calcium chloride and about 3% DMSO. In an embodiment of the invention, the incubation occurs for about 5 to about 7 days (e.g., at 4° C.).

The present invention also provides a method for making a crystal comprising amino acids 35-373 of human MEK1 polypeptide (e.g., amino acids 25-373 of SEQ ID NO: 2) complexed with a compound represented by structural formula 2:

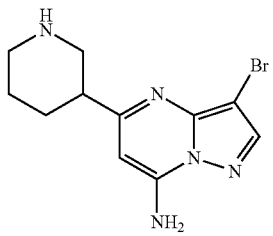 [SMILES: Nc1cc(C2CCCNC2)nc2c(Br)cnn12]

comprising soaking a crystal comprising said polypeptide complexed with ATPγS, with said compound. In an embodiment of the invention, about 0.1 μl of a 100 mM solution of said compound is combined with a drop of a solution comprising said crystal comprising said polypeptide complexed with ATPγS.

The present invention also provides a method for evaluating the potential of a candidate MEK1 inhibitor to associate with MEK1 comprising soaking the crystalline composition which comprises an isolated polypeptide comprising amino acids 35-373 of MEK1 complexed with ATP'S or with

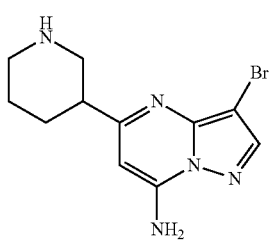

with the candidate MEK1 inhibitor to form a complex between said polypeptide and said candidate and determining the three-dimensional structure of said complex.

The present invention also provides a method for making a crystalline complex between an ATP competitive inhibitor and a polypeptide comprising amino acids 35-383 of MEK1 comprising soaking a crystalline composition comprising a MEK1/N35/NKF/Cdel383-cpd2 complex wherein the complex three dimensional structure is characterized by structural coordinates comprising a root mean square deviation of common residue backbone atoms or alpha carbon atoms of less than about 1.5 Å when superimposed on backbone atoms or alpha carbon atoms described by structural coordinates of Table 3 or 4 with the ATP competitive inhibitor.

The present invention also provides a method for evaluating the potential of a candidate MEK1 inhibitor to associate with: a) a polypeptide or complex thereof wherein said polypeptide comprises a binding pocket defined by structural coordinates of MEK1/N35/NKF/Cdel383 amino acids 70-84; 93-98; 117-120; 128-129; 140-152; 193-197 and 205-208 according to Table 2, 3 or 4 wherein one or more of said binding pocket amino acids can be conservatively substituted and/or a hinge region whose three-dimensional orientation is characterized by the structural coordinates of amino acids E144, H145 and M146 according to Table 1 or amino acids E143, H144 and M145 according to Table 2, 3 or 4 wherein one or more of said hinge region amino acids can be conservatively substituted; or b) a homologue of said polypeptide of complex thereof, wherein said homologue comprises a binding pocket or hinge region comprising a three dimensional structure characterized by structural coordinates comprising a root mean square deviation of common residue backbone atoms or alpha carbon atoms of less than about 1.5 Å when superimposed on backbone atoms or alpha carbon atoms of said binding pocket or hinge region described by structural coordinates of Table 1, 2, 3 or 4 comprising the steps of: (i) employing computational means to perform a fitting operation between the candidate and the binding pocket or hinge region of the molecule or molecular complex; and (ii) analyzing the results of said fitting operation to quantify the association between the candidate and the binding pocket or hinge region; optionally, further comprising making a crystalline composition comprising said complex and determining the three-dimensional structure of said complex; optionally, further comprising modifying said candidate inhibitor and repeating said method. In an embodiment of the invention, any atom of said candidate located within 3.5 Å of any of said hinge region amino acids in said fitting operation is considered to interact with the hinge region (e.g., by hydrophobic contact or by polar interaction). In an embodiment of the invention, said crystalline composition is made by soaking a crystalline composition comprising said polypeptide complexed with ATPγS or with a compound represented by structural formula 2

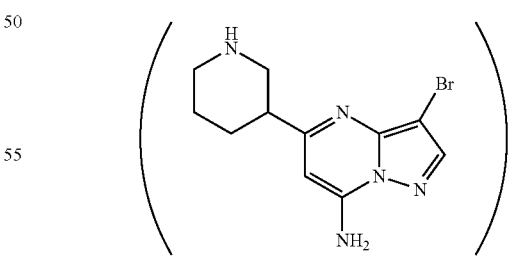

with said candidate inhibitor. In an embodiment of the invention, said structural coordinates according to Table 3 or 4 describe a complex in a crystalline composition comprising unit cell dimensions of a=about 77.2 Å, b=about 77.2 Å, c=about 222.2 Å, α=β=about 90° γ=about 120°; said structural coordinates according to Table 3 or 4 describe a complex in a crystalline composition comprising unit cell dimensions of a=about 76.8 Å, b=about 76.8 Å, c=about 222.4 Å, α=β=about 90°; γ=about 120°; said structural coordinates according to Table 3 or 4 describe a complex in a crystalline composition which belongs to space group P 6₁ 2 2; said structural coordinates according to Table 3 or 4 describe a complex in a crystalline composition which diffracts X-rays to a resolution of about 2.55 Å or a lower number; or said structural coordinates according to Table 3 or 4 describe a complex in a crystalline composition which diffracts X-rays to a resolution of about 2.45 Å or a lower number.

The present invention also provides a method for treating or preventing cancer, in a patient, comprising administering a therapeutically effective amount of a compound represented by structural formula 2 in association with a pharmaceutically acceptable composition thereof to said patient.

The present invention provides a method of utilizing molecular replacement to obtain structural information about a molecule or a molecular complex of unknown structure comprising: crystallizing said molecule or molecular complex; generating an X-ray diffraction pattern from said crystallized molecule or molecular complex; and applying at least a portion of the structural coordinates set forth in Table 1, 2, 3 or 4, or a related set of structural coordinates having a root mean square deviation of not more than about 1.5 Å away from the amino acid backbone atoms or only alpha carbon atoms of said coordinates as set forth in Table 1, 2, 3 or 4, to the X-ray diffraction pattern to generate a three-dimensional electron density map of at least a portion of the molecule or molecular complex whose structure is unknown.

The present invention further provides a method for making a crystal comprising a polypeptide comprising amino acids 35-383 of human MEK1 polypeptide (e.g., amino acids 24-373 of SEQ ID NO: 2) complexed with a candidate inhibitor of MEK1 comprising soaking a crystal comprising amino acids 35-383 of human MEK1 polypeptide complexed with a compound represented by structural formula 2:

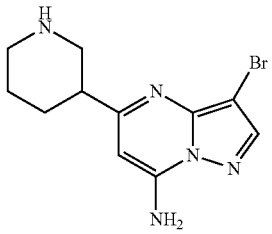

or complexed with ATPγS with said candidate; optionally further comprising determining the three-dimensional structural coordinates of the atoms in said crystal e.g., by X-ray diffraction analysis.

DETAILED DESCRIPTION OF THE INVENTION

Figure 1:
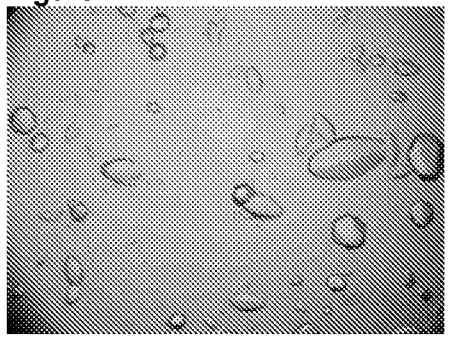
FIG. 1. Photomicrograph of MEK1 N35 NKF ternary complex crystals.

"Compound 1" or "cpd.1" is represented by the following structural formula:

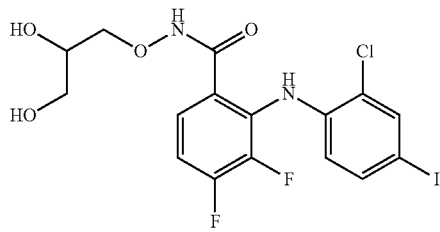 [SMILES: O=C(NOCC(O)CO)c1ccc(F)c(F)c1Nc1ccc(I)cc1Cl]

"Compound 2" or "pd.2" is represented by the following structural formula:

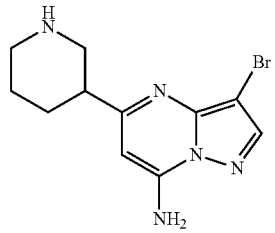 [SMILES: Nc1cc(C2CCCNC2)nc2c(Br)cnn12]

ATPγS is represented by the following structural formula:

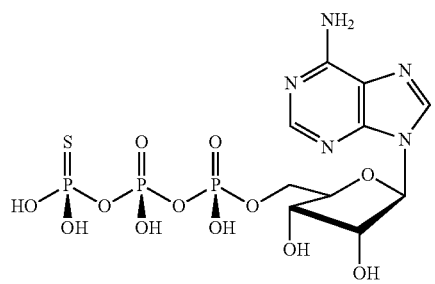

(Adenosine-5'-(3-thiotriphosphate); Adenosine 5'-O-(3-thiotriphosphate)).

Human MEK1 is a well known polypeptide and polynucleotide. There are several examples of MEK1 known in the art. See for example, the following accession numbers: Q02750 (UniProtKB/Swiss-Prot); NP_002746.1 (RefSeq peptide); L05624 (EMBL); IPI00219604.2 (IPI); AAA36318.1 (protein_id); NM_002755.2 (RefSeq DNA); and ENSG00000169032 (Ensembl Gene ID). An example of a MEK1 polypeptide amino acid sequence is as follows:

(SEQ ID NO: 12)
```
  1  mpkkkptpiq lnpapdgsav ngtssaetnl ealqkkleel eldeqqrkrl eafltqkqkv
 61  gelkdddfek iselgagngg vvfkvshkps glvmarklih leikpairnq iirelqvlhe
121  cnspyivgfy gafysdgeis icmehmdggs ldqvlkkagr ipeqilgkvs iavikgltyl
```

```
181  rekhkimhrd vkpsnilvns rgeiklcdfg vsgqlidsma nsfvgtrsym sperlqgthy 241  svqsdiwsmg lslvemavgr ypipppdake lelmfgcqve gdaaetpprp rtpgrplssy

301  gmdsrppmai felldyivne pppklpsgvf slefqdfvnk cliknpaera dlkqlmvhaf 361  ikrsdaeevd fagwlcstig lnqpstptha agv
```

The MEK1 hinge region amino acids are underscored.

In an embodiment of the invention, MEK1/N35/NKF comprises the following amino acid sequence:

```
                                                            (SEQ ID NO: 1)
  1  MGYYHHHHHH DYDIPTTENL YFQGKKLEEL ELDEQQRKRL EAFLTQKQKV GELKDDDFEK   60

61  ISELGAGNGG VVFKVSHKPS GLVMARKLIH LEIKPAIRNQ IIRELQVLHE CNSPYIVGFY  120

121  GAFYSDGEIS ICMEHMDGGS LDQVLKKAGR IPEQILGKVS IAVIKGLTYL REKHKIMHRD  180

181  VKPSNILVNS RGEIKLCDFG VSGQLIDSMA NSFVGTRSYM SPERLQGTHY SVQSDIWSMG  240

241  LSLVEMAVGR YPIPPPDAKE LELMFGCQVE GDAAETPPRP RTPGRPLNKF GMDSRPPMAI  300

301  FELLDYIVNE PPPKLPSGVF SLEFQDFVNK CLIKNPAERA DLKQLMVHAF IKRSDAEEVD  360

361  FAGWLCSTIG LNQPSTPTHA AGV
```

The MEK1/N35/NKF polypeptide comprises a His6 tag in the first 10 residues (HHHHHH) (SEQ ID NO: 14). The underlined sequence indicates the portion of the sequence that is MEK1 sequence (residues 35-393 of MEK1; residues 25-383 of SEQ ID NO: 1). The portion of the MEK1/N35/NKF polypeptide that was crystallized in the examples set forth below comprises amino acids 24-383 of SEQ ID NO: 1. The MEK1/N35/NKF polypeptide comprises a mutation changing SSY (MEK1 residues 298-300) to NKF; the NKF residues are in bold font.

in an embodiment of the invention MEK1/N35/NKF/Cdel383 comprises the following amino acid sequence:

```
                                                            (SEQ ID NO: 2)
  1  MGYYHHHHHH DYDIPTTENL YFQGKKLEEL ELDEQQRKRL EAFLTQKQKV GELKDDDFEK   60

61  ISELGAGNGG VVFKVSHKPS GLVMARKLIH LEIKPAIRNQ IIRELQVLHE CNSPYIVGFY  120

121  GAFYSDGEIS ICMEHMDGGS LDQVLKKAGR IPEQILGKVS IAVIKGLTYL REKHKIMHRD  180

181  VKPSNILVNS RGEIKLCDFG VSGQLIDSMA NSFVGTRSYM SPERLQGTHY SVQSDIWSMG  240

241  LSLVEMAVGR YPIPPPDAKE LELMFGCQVE GDAAETPPRP RTPGRPLNKF GMDSRPPMAI  300

301  FELLDYIVNE PPPKLPSGVF SLEFQDFVNK CLIKNPAERA DLKQLMVHAF IKRSDAEEVD  360

361  FAGWLCSTIG LNQ
```

The MEK1/N35/NKF/Cdel383 polypeptide comprises a His6 tag in the first 10 residues (HHHHHH) (SEQ ID NO: 14). The underlined sequence indicates the portion of the sequence that is MEK1 sequence (residues 35-383 of MEK1; residues 25-373 of SEQ ID NO: 2). The portion of the MEK1/N35/NKF/Cdel383 polypeptide that was crystallized in the examples set forth below comprises amino acids 24-373 of SEQ ID NO: 2. The MEK1/N35/NKF/Cdel383 polypeptide comprises a mutation changing SSY (MEK1 residues 298-300) to NKF; the NKF residues are in bold font.

An isolated polypeptide comprising, consisting of or consisting essentially of the amino acid sequence of SEQ ID NO: 1 and 2 or any mature fragment thereof (e.g., missing residues 1-24) or any fusion thereof form part of the present invention along with any composition or crystal thereof (e.g., a crystallizable compositon).

In accordance with the present invention, there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring. Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1996) (herein "Ausubel et al., 1996").

The terms "express" and "expression" mean allowing or causing the information in a gene or DNA sequence to become manifest, e.g., producing a protein by activating the cellular functions involved in transcription and, optionally, translation of a corresponding gene or DNA sequence. A DNA sequence can be expressed using in vitro translation systems (e.g., rabbit reticulocyte lysate-based systems) or in or by a cell to form an "expression product" such as a mRNA or a protein. The expression product, e.g. the resulting protein, may also be referred to as "expressed".

An insect cell used in this invention includes any cell derived from an organism of the class Insecta. In an embodiment of the invention, the insect is *Spodoptera fruigiperda* (Sf9 or Sf21) or *Trichoplusia ni* (High 5). Examples of insect expression systems that can be used with the present invention, for example to produce MEK1 polypeptides, include Bac-To-Bac (Invitrogen Corporation, Carlsbad, Calif.) or Gateway (Invitrogen Corporation, Carlsbad, Calif.).

It may also be desirable to add a heterologous protein (i.e., other than a MEK1 polypeptide of the invention) at the amino- or carboxy-terminus of a MEK1 polypeptide of the invention, e.g., to prepare a fusion protein. In one embodiment, the addition is a polyhistidine or a histidine tag comprising 12 or 18 histidines. In an embodiment of the invention, a myc tag is added to a MEK1 polypeptide of the invention. The myc tag may be used for detection or immunopurification of the MEK1. For example, the myc tag and the polyhistidine tag may both be located at the carboxy-terminus or amino-terminus in a doubly-tagged MEK1. Other heterologous proteins include, for example, GST, maltose binding protein (MBP), FLAG tag, biotin, green fluorescent protein (GFP), Strep tag (WSHPQFEK) (SEQ ID NO: 13), protein A, protein G or NusA. Detectable tags that may be fused to a MEK1 polypeptide of the invention include $^{32}$P, $^{35}$S, $^{3}$H, $^{99m}$Tc, $^{123}$I, $^{111}$In, $^{68}$Ga, $^{18}$F, $^{125}$I, $^{131}$I, $^{113m}$In, $^{76}$Br, $^{67}$Ga, $^{99m}$Tc, $^{123}$I, $^{111}$In and $^{68}$Ga. Methods for constructing and using such fusions are very conventional and well known in the art.

The terms "isolated polynucleotide" or "isolated polypeptide" include a polynucleotide (e.g., RNA or DNA molecule, or a mixed polymer) or a polypeptide, respectively, which are partially or fully separated from other components that are normally found in cells or in recombinant DNA expression systems. These components include, but are not limited to, cell membranes, cell walls, ribosomes, polymerases, serum components and extraneous genomic sequences.

An isolated polynucleotide or polypeptide will, in an embodiment of the invention, be an essentially homogeneous composition of molecules.

The term "host cell" includes any cell of any organism that is selected, modified, transfected, transformed, grown, or used or manipulated in any way, for the production of a substance by the cell, for example the expression or replication, by the cell, of a gene, a DNA or RNA sequence or a protein. In an embodiment of the invention, a host cell is a bacterial cell, such as *E. coli* or a Chinese hamster ovary (CHO) cell.

The term "vector" includes a vehicle (e.g., a plasmid) by which a DNA or RNA sequence can be introduced into a host cell, so as to transform the host and, optionally, promote expression and/or replication of the introduced sequence.

Vectors that can be used in this invention include plasmids, viruses, bacteriophage, integratable DNA fragments, and other vehicles that may facilitate introduction of the nucleic acids into the genome of the host. Plasmids are the most commonly used form of vector but all other forms of vectors which serve a similar function and which are, or become, known in the art are suitable for use herein. See, e.g., Pouwels, at al., Cloning Vectors: A Laboratory Manual, 1985 and Supplements, Elsevier, N.Y., and Rodriguez at al. (eds.), Vectors: A Survey of Molecular Cloning Vectors and Their Uses, 1988, Buttersworth, Boston, Mass.

Prokaryotic host-vector systems include a wide variety of vectors for many different species. A representative vector for amplifying DNA is pBR322 or many of its derivatives (e.g., pUC18 or 19). Vectors that can be used to express a MEK1 polypeptide of the invention include, but are not limited to, those containing the lac promoter (pUC-series); trp promoter (pBR322-trp); Ipp promoter (the pIN-series); lambda-pP or pR promoters (pOTS); or hybrid promoters such as ptac (pDR540). See Brosius at al., "Expression Vectors Employing Lambda-, trp-, lac-, and Ipp-derived Promoters", in Rodriguez and Denhardt (eds.) Vectors: A Survey of Molecular Cloning Vectors and Their Uses, 1988, Buttersworth, Boston, pp. 205-236. Many polypeptides can be expressed, at high levels, in an *E. coli*/T7 expression system as disclosed in U.S. Pat. Nos. 4,952,496, 5,693,489 and 5,869,320 and in Davanloo, P., at al., (1984) Proc. Natl. Acad. Sci. USA 81: 2035-2039; Studier, F. W., et al., (1986) J. Mol. Biol. 189: 113-130; Rosenberg, A. H., et at., (1987) Gene 56: 125-135; and Dunn, J. J., et al., (1988) Gene 68: 259.

Crystals

The present invention comprises mutant MEK1 polypeptide crystals which are complexed with ATPγS, AMP-PNP, AMP-PCP and/or a compound represented by structural formula 1 or 2. The present invention includes crystals comprising MEK1/N35/NKF complexed with ATPγS and compound 1 (MEK1/N35/NKF-ATPγS, cpd1); MEK1/N35/NKF/Cdel383 complexed with ATPγS alone (MEK1/N35/NKF/Cdel383-ATP-(S) or with ATPγS and compound 1 (MEK11N35/NKF/Cdel383-ATPγS, cpd1) as well as MEK1/N35/NKF/Cdel383 complexed with compound 2 (MEK1/N35/NKF/Cdel383-cpd2).

The present invention further comprises any crystal comprising a human MEK1 binding pocket characterized by the three dimensional configuration of amino acids 70-84; 93-98; 117-120; 128-129; 140-152; 193-197 and 205-208 in any of tables 2-4 and/or a hinge region comprising amino acids E144, H145 and M146 according to Table 1 or amino acids E143, H144 and M145 according to Table 2, 3 or 4 or a complex thereof wherein the binding pocket or hinge region is complexed with ATPγS, compound 1 or compound 2 or a combination thereof. Moreover, for the purpose of this invention, any crystalline molecule comprising a binding pocket or hinge region, optionally, complexed with ATPγS, compound 1 or compound 2 or a combination thereof, characterized by structural coordinates having a root mean square deviation (RMSD) (discussed below) of conserved residue backbone atoms (N, Cα, C, O) or of alpha carbon atoms (Cα) only of said human MEK1 binding pocket or hinge region residues of less than about 1.5 Å when superimposed—using backbone atoms or alpha carbon atoms—on the relevant binding pocket or hinge region structure coordinates of any of Tables 1-4 are considered identical and are within the scope of the present invention. In an embodiment of the invention, the crystal comprises a polypeptide comprising the amino acid sequence of SEQ ID NO: 1 or 2. In an embodiment, the root mean square deviation is about 1.0 Å or about 0.75 Å or about 0.5 Å or about 0.25 Å or about 0.10 Å.

Several crystallization methods are known in the art (Giegé, et al., (1994) Acta Crystallogr. D50: 339-350; McPherson, (1990) Eur. J. Biochem. 189: 1-23). Such methods include microbatch, hanging drop, seeding and dialysis. In an embodiment of the invention, hanging-drop vapor diffusion (McPherson, (1976) J. Biol. Chem. 251: 6300-6303) or microbatch methods (Chayen (1997) Structure 5: 1269-1274) are used. In each of these methods, it is important to promote continued crystal growth after nucleation by maintaining a supersaturated solution.

In an embodiment of the invention, in a sitting drop vapor diffusion technique, a drop composed of a mixture of MEK1 protein of the invention and precipitation reagent (e.g., PEG4000) is seated in a drop chamber in vapor equilibration with a liquid reservoir of reagent. Typically the drop contains a lower precipitation reagent concentration than the reservoir. To achieve equilibrium, water vapor leaves the drop and eventually ends up in the reservoir. As water leaves the drop, the sample undergoes an increase in relative supersaturation. Both the sample and reagent increase in concentration as water leaves the drop for the reservoir. Equilibration is reached when the reagent concentration in the drop is approximately the same as that in the reservoir. In an embodiment of the invention, the hanging drop vapor diffusion technique is essentially identical to the sitting drop vapor diffusion method, except that the protein/reagent drop is located on the underside of a surface above the reservoir. Typically the protein drops are deposited on a plate that is inverted and used as a cover over the plate containing the reservoir wells. As with sitting drop, water vapor leaves the drop and eventually ends up in the reservoir until the reagent concentration in the drop is approximately the same as that in the reservoir. In an embodiment of the invention, in the microbatch method a small drop of sample combined with the precipitation reagent of choice (e.g., PEG4000) is pipetted under a layer of paraffin oil. In a batch, or microbatch experiment, all of the reagents involved in the crystallization are present at a specific concentration and no significant concentration change of protein or reagents can occur in the drop. A modification of the microbatch under oil technique is where silicon oil is used in a mixture of 1:1 with the paraffin oil, allowing diffusion of water from the drop through the oil, hence a microbatch experiment that does allow for concentration of the sample and the reagents in the drop. In the dialysis method, polypeptide is retained in a sealed dialysis membrane which is placed into a solution containing precipitant. Equilibration across the membrane increases the precipitant concentration thereby causing the polypeptide to reach supersaturation levels. In an embodiment of the invention, it is desirable to use MEK1 preparation having a concentration of at least about 10 mg/mL, for example, 15, 20, 25 or 30 mg/mL. It may also be desirable to include a protein stabilizing agent.

Crystallization itself can be used as a purification method. In some instances, a polypeptide or protein crystallizes from a heterogeneous mixture into crystals. Isolation of such crystals by filtration and/or centrifugation, followed by redissolving the polypeptide affords a purified solution suitable for use in growing high-quality crystals which are preferred for diffraction analysis.

Once a crystal of the present invention is grown or otherwise made, X-ray diffraction data can be collected. One method for determining structure with X-ray diffraction data includes use of synchrotron radiation, under standard cryogenic condition; however, alternative methods may also be used. For example, crystals can be characterized by using X-rays produced by a conventional source, such as a sealed tube or a rotating anode. Methods of characterization include, but are not limited to, precession photography, oscillation photography and diffractometer data collection.

The crystallizable compositions provided by this invention are amenable to X-ray crystallography for providing the three-dimensional structure of MEK1 or a mutant or complex thereof. The present invention includes crystals which effectively diffract X-rays for the determination of the atomic coordinates of MEK1 or a mutant or complex thereof to a resolution of greater than about 5.0 Angstroms (e.g., about 4.5 Å, about 4.0 Å, about 3 Å, about 2.5 Å, about 2 Å, about 1.95 Å, about 1 Å), preferably greater than about 4.0 Angstroms (e.g., about 3 Å, about 2.5 Å, about 2 Å, about 1.95 Å, about 1 Å), more preferably greater than about 2.8 Angstroms (e.g., about 2.5 Å, about 2 Å, about 1.95 Å, about 1 Å) and most preferably greater than about 2.0 Angstroms (e.g., about 1.95 Å, about 1.5 Å, about 1.0 Å). in an embodiment of the invention, the resolution of a crystal of the present invention is 3.4 Å, 2.2 Å, 2.45 Å or 2.55 Å.

The present invention includes MEK1/N35/NKF-ATPγS, cpd1; MEK1/N35/NKF/Cdel383-ATPγS; MEK1/N35/NKF/Cdel383-ATPγS, cpd1 and MEK1/N35/NKF/Cdel383-cpd2 crystals whose three-dimensional structure is described by the structure coordinates set forth in Tables 1-4. The scope of the present invention also includes crystals that possess structural coordinates which are similar to those set forth in Tables 1-4. Structural similarity between crystals is discussed in detail below.

The term "structure coordinates" refers to Cartesian coordinates derived from mathematical equations related to the patterns obtained on diffraction of a beam of X-rays by the atoms (scattering centers) of a molecule. The diffraction data are used to calculate electron density maps and to establish the positions of the individual atoms of the molecule.

The present invention includes crystals exhibiting structural coordinates which are similar to those set forth in Tables 1-4 but for crystallographic permutations of the structure coordinates, fractionalization of the structure coordinates, additions, subtractions, rotations or translations to sets of the structure coordinates or any combinations of the above. Alternatively, modifications in the crystal structure due to mutations, additions, substitutions, and/or deletions of amino acids, or other changes in any of the components that make up the crystal may also account for variations in structure coordinates. If such variations are within an acceptable standard error as compared to the coordinates of Tables 1-4, the resulting three-dimensional shape is considered to be the same and, accordingly, the modified crystal is considered to be within the scope of the present invention.

Various computational analyses may be used to determine whether a crystal is sufficiently similar to the crystals whose structural coordinates are set forth in Tables 1-4 as to be considered the same. Such analyses may be carried out in current software applications, such as the Molecular Similarity application of QUANTA (Molecular Simulations Inc., San Diego, Calif.) version 4.1, and as described in the accompanying User's Guide.

The Molecular Similarity application permits comparisons between different structures, different conformations of the same structure, and different parts of the same structure. In general, the procedure used in Molecular Similarity to compare structures is divided into four steps: 1) input the structures to be compared; 2) define the atom equivalences in these structures; 3) perform a fitting operation; and 4) analyze the results. Each structure is identified by a name. One structure is identified as the target (i.e., the fixed structure); all remaining structures are working structures (i.e., moving structures). Since atom equivalency within QUANTA is defined by user input, for the purpose of this invention we will define equivalent atoms as alpha carbon atoms (Cα) or all protein backbone atoms (N, Cα, C and O) for all conserved residues between the two structures being compared. When a rigid fitting method is used, the working structure is translated and rotated to obtain an optimum fit with the target structure. The fitting operation uses a least squares fitting algorithm that computes the optimum translation and rotation to be applied to the moving structure, such that the root mean square difference of the fit over the specified pairs of equivalent atom is an absolute minimum. This number, given in Angströms, is reported by QUANTA.

The term "root mean square deviation" (RMSD) is a commonly known term in the art which, in general, means the square root of the arithmetic mean of the squares of the deviations from the mean distance of corresponding atoms. It is a way to express the deviation or variation from a trend or object.

The term "least squares" relates to a method based on the principle that the best estimate of a value is that in which the sum of the squares of the deviations of observed values is a minimum.

For the purpose of this invention, any crystalline molecule characterized by a set of structure coordinates that has a RMSD of conserved residue backbone atoms (N, Cα, C, O) or of alpha carbon atoms (Cα) only of less than about 1.5 Å when superimposed—using backbone atoms or alpha carbon atoms—on the relevant structure coordinates of any of Tables 1-4 are considered identical and are within the scope of the present invention. In an embodiment of the invention, the crystal comprises a polypeptide comprising the amino acid sequence of SEQ ID NO: 1 or 2. In an embodiment, the root mean square deviation is about 1.0 Å or about 0/5 Å or about 0.5 Å or about 0.25 Å or about 0.10 Å.

Computers

In accordance with the present invention, the structure coordinates of MEK1/N35/NKF-ATPγS, cpd1; MEK1/N35/NKF/Cdel383-ATPγS; MEK1/N35/NKF/Cdel383-ATPγS, cpd1 or MEK1/N35/NKF/Cdel383-cpd2 may be stored in a machine-readable storage medium. Such data may be used for a variety of purposes, such as X-ray crystallographic analysis of a protein crystal. Accordingly, one aspect of this invention provides a machine-readable data storage medium comprising a data storage material encoded with the structure coordinates set forth in Tables 1, 2, 3 or 4. The machine-readable data storage medium may also include any set of structure coordinates of a molecule that has a root mean square deviation of alpha carbon atoms (Cα) or of conserved residue backbone atoms (N, Cα, C, O) of less than about 1.5 Å, preferably, less than about 1.0 Å, more preferably less than about 0.5 Å and even more preferably less than about 0.1 Å when superimposed—using backbone atoms or only alpha carbon atoms (Cα)—on the relevant structure coordinates of Table 1-4 (discussed above).

A computer system, useful in reading the machine readable data storage medium, includes a computer comprising a central processing unit ("CPU") and a memory storage device and is also within the scope of the present invention. In general, the computer system may be any computer with an operating system such as MS-DOS, PC-DOS, Windows, OS/2, Unix, Unix variant or MacOS. Examples of such computer systems are the Silicon Graphics Octane workstation or Compaq AlphaServer DS20. Other hardware systems and software packages will be known to those skilled in the art. Input hardware coupled to the computer system by input line, may be implemented in a variety of ways. Machine-readable data of this invention may be input via the use of a modem or modems connected by a telephone line or a dedicated data line. Alternatively or additionally, the input hardware may comprise CD-ROM drives or disk drives. A keyboard may also be used as an input device.

Output hardware, coupled to the computer system by output lines, may similarly be implemented by conventional devices. By way of example, output hardware may include a display terminal (e.g., a cathode ray tube (CRT)) for displaying a graphical representation of the three dimensional structure of MEK1 or a mutant or complex thereof or a portion thereof using a program such as INSIGHT (Molecular Simulations Inc., San Diego, Calif.) or QUANTA as described herein. In an embodiment of the invention, output hardware also includes a printer, so that hard copy output may be produced, or a disk drive, to store system output for later use.

In an embodiment of the invention, the computer possesses a display which is displaying a three dimensional representation of MEK1 or a mutant or complex thereof or a fragment or homologue thereof.

In operation, the central processing unit (CPU) coordinates the use of the various input and output devices, coordinates data accesses from mass storage and accesses to and from working memory, and determines the sequence of data processing steps. A number of programs may be used to process the machine-readable data of this invention. Specific references to components of the computer system are included as appropriate throughout the following description of the data storage medium. A magnetic data storage medium can be encoded with a machine-readable data by a computer system as described above. Storage medium may be, for example, a conventional floppy diskette or hard disk, having a suitable substrate, which may be conventional, and a suitable coating, which may be conventional, on one or both sides, containing magnetic domains whose polarity or orientation can be altered magnetically. The magnetic domains of the coating of medium may be polarized or oriented so as to encode, in a manner which may be conventional, machine readable data, such as that described herein, for execution by a system as described herein. Storage medium may also have an opening for receiving the spindle of a disk drive or other data storage device. Alternatively, an optically-readable data storage medium can be encoded with such machine-readable data, or a set of instructions. Medium can be a conventional compact disk read only memory (CD-ROM) or a rewritable medium such as a magneto-optical disk which is optically readable and magneto-optically writable.

In general, in the case of CD-ROM, as is well known, disk coating is reflective and is impressed with a plurality of pits to encode the machine-readable data. The arrangement of the pits is read by reflecting laser light off the surface of the coating. A protective coating, which, in an embodiment of the invention, is substantially transparent, is provided on top of the coating.

In general, in the case of a magneto-optical disk, as is well known, disk coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

Drug Design

The present invention permits the use of structure-based drug design techniques to design, select, and synthesize chemical entities, including inhibitory compounds that are capable of binding to a MEK1 or a mutant or complex thereof. De novo and iterative drug design methods can be used to develop drugs from the structure of the MEK1 crystals of this invention.

One useful drug design technique enabled by this invention is structure-based drug design. Structure-based drug design is a method for optimizing binding interactions between a protein and a compound by determining and evaluating the three-dimensional structures of successive sets of protein/compound complexes.

Those skilled in the art will appreciate that association of natural ligands or substrates with the binding pockets or hinge regions of their corresponding enzymes is the basis of many biological mechanisms of action. The term "binding pocket", as used herein, includes any region of a molecule or molecular complex, that, as a result of its shape, favorably associates with another chemical entity or compound. In an embodiment of the invention, the binding pocket of MEK1 comprises amino acids 70-84; 93-98; 117-120; 128-129; 140-152; 193-197 and 205-208 as defined by the structural coordinates of any of Tables 2-4. The term "hinge region", as used herein, includes the polypeptide strand that connects the two domains of the MEK1 kinase. In an embodiment of the invention, the hinge region comprises amino acids E144, H145 and M146 according to Table 1 or amino acids E143, H144 and M145 according to Table 2, 3 or 4. One of more of said binding pocket or hinge region residues can be conservatively substituted. For example, polar/hydrophilic amino acids which may be interchangeable/conservative include asparagine, glutamine, serine, cysteine, threonine, lysine, arginine, histidine, aspartic acid and glutamic acid; nonpolar/hydrophobic amino acids which may be interchangeable/conservative include glycine, alanine, valine, leucine, isoleucine, proline, tyrosine, phenylalanine, tryptophan and methionine; acidic amino acids which may be interchangeable/conservative include aspartic acid and glutamic acid and basic amino acids which may be interchangeable/conservative include histidine, lysine and arginine. Similarly, drugs may exert their biological effects through association with the binding pockets or hinge regions of enzymes. Such association may occur with all or any part of the binding pockets or hinge regions. An understanding of such associations will help lead to the design of drugs having more favorable associations with the target enzyme, and thus, improved biological effects. Therefore, this information is valuable in designing potential enzyme inhibitors, such as inhibitors of MEK1.

In iterative structure-based drug design, crystals of a series of protein/compound complexes are obtained and then the three-dimensional structure of each complex is solved. Such an approach provides insight into the association between the proteins and compounds of each complex. This is accomplished by selecting compounds with inhibitory activity, obtaining crystals of the protein complexed with each inhibitor, solving the three-dimensional structure of each complex, and comparing the protein/inhibitor interactions in each complex. By observing how changes in the compound affected the protein/compound interactions, the binding potency may be optimized. In some cases, iterative structure-based drug design is carried out by forming successive protein-compound complexes and then crystallizing each new complex. Alternatively, a pre-formed protein crystal is soaked in the presence of an inhibitor, thereby forming a protein/compound complex and obviating the need to crystallize each individual protein/compound complex. Advantageously, MEK1 crystals provided by this invention may be soaked in the presence of a compound or compounds, such as MEK1 inhibitors, substrates or other ligands to provide novel MEK1/compound crystal complexes. As used herein, the term "soaked" includes a process in which the crystal is transferred to a solution containing the compound of interest Accordingly, the present invention includes a method for making a crystal comprising amino acids 35-373 of human MEK1 polypeptide (e.g., 24-373 of SEQ ID NO: 2) complexed with a compound represented by structural formula 2:

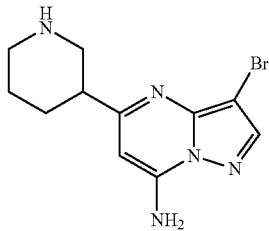

by soaking a crystal comprising the MEK1 polypeptide complexed with ATPγS, with compound 2. In a more specific embodiment of the invention, the crystal is soaked by a process wherein about 0.1p. 1 of a 100 mM solution of said compound is combined with a drop of a solution comprising said crystal comprising said polypeptide complexed with ATPγS.

The present invention includes a soaking-based process by which any MEK1 crystal of the invention can be used to generate a crystalline composition between a MEK1 polypeptide of the invention and another ATP competitive inhibitor. Accordingly, the present invention includes a method for making a crystalline complex between an ATP competitive inhibitor and a polypeptide comprising amino acids 35-373 of MEK1 (e.g., MEK1/N35/NKF/Cdel383) comprising soaking a crystalline MEK1 composition (e.g., MEK1/N35/NKF/Cdel383-cpd2 or MEK1/N351NKF/Cdel383-ATPγS) with the ATP competitive inhibitor.

A method for identifying a MEK1 inhibitor or for evaluating the potential of a candidate MEK1 inhibitor to associate with MEK1 is within the scope of the present invention. The method comprises soaking a crystalline composition such as MEK1/N35/NKF/Cdel383-cpd2 or MEK1/N35/NKF/Cdel383-ATPγS with the candidate MEK1 inhibitor to form a complex between said polypeptide and said candidate and determining the three-dimensional structure of said complex. The candidate is considered a MEK1 inhibitor if it is shown to bind to the binding pocket or hinge region of MEK1. A candidate inhibitor that is shown to bind to MEK1 can then be confirmed to inhibit MEK1 kinase activity by subjecting it to any of the many kinase assays known in the art, e.g., as set forth below in the Examples section (see also the scintillation proximity assays (SPA) of McDonald et al., Anal. Biochem. 268:318 (1999), the in vitro assay of MacDonald et al. Molec. Cell, Biol. 13(11): 6615-6620 (1993) or coupled assays similar to those described by Jin et al., Biochemistry 35:1423-1431 (1996)).

The structure coordinates set forth in Tables 1-4 can also be used for determining at least a portion of the three-dimensional structure of molecules or molecular complexes which contain at least some structurally similar features to a MEK1 crystal of the invention. In particular, structural information about another crystallized molecule or molecular complex may be obtained by well-known techniques, including molecular replacement.

By using molecular replacement, all or part of the structure coordinates of the MEK1 polypeptide provided by this invention (and set forth in any of Tables 1-4) can be used to determine the previously unknown structure of a crystallized molecule or molecular complex more quickly and efficiently than attempting to determine such information ab initio.

Molecular replacement provides an accurate estimation of the phases for an unknown structure. Phases are a factor in equations used to solve crystal structures that cannot be measured experimentally. Obtaining accurate values for the phases, by methods other than molecular replacement, is a time-consuming process. However, when the crystal structure of a protein containing a homologous portion has been solved, the phases from the known structure may provide a satisfactory estimate of the phases for the unknown structure.

Phase information from the structure coordinates of the present invention may be used to elucidate the structure of other crystals. For example, the structure of MEK1 in complex with other atoms or molecules may be elucidated. Such complexes include, for example, those containing atoms soaked into or co-crystallized within the crystal lattice. Other structures which can be elucidated using the phase information of the present invention include for example other kinases or homologues or mutants thereof having sufficient three-dimensional structure similarity to a MEK1 complex of the invention as to be solved using molecular replacement. Also, these protein molecules in a complex with a small molecule substrate(s), inhibitor(s), transition state analog(s), product(s) or analog(s) of any of these may also be solved using the phase information of the present invention. Other complexes whose structure can be elucidated from the phase information of the present invention include a MEK1 complexed with an inhibitor. Complexes containing a combination of the above molecules may also be solved using the phase information of the present invention.

The difference Fourier method simply calculates an electron density map using phases calculated from the structure coordinates and observed diffraction amplitudes from a crystal of an unknown structure. This method is often used to solve structures of protein/ligand complexes where the ligand is small and does not affect the crystal form significantly.

An aspect of this invention provides a method of utilizing molecular replacement to obtain structural information about a crystallized molecule or molecular complex, whose structure is unknown, comprising the steps of generating an X-ray diffraction pattern from said crystallized molecule or molecular complex and applying crystallographic phases derived from at least a portion of the structure coordinates set forth in any of Tables 1-4 to the X-ray diffraction pattern to generate a three-dimensional electron density map of the molecule or molecular complex whose structure is unknown.

The scope of the present invention includes a method involving generating a preliminary model of a new molecule or molecular complex whose structure coordinates are unknown, by orienting and positioning the relevant portion of a MEK1 crystal according to any of Tables 1-4 within the unit cell of the crystal of the unknown molecule or molecular complex so as best to account for observed X-ray diffraction pattern amplitudes relating to the unknown crystal to generate an election density map of the structure whose coordinates are unknown. This, in turn, can be subjected to any well-known model building and structure refinement techniques to provide a final, accurate structure of the unknown crystallized molecule or molecular complex (Lattman, "Use of the Rotation and Translation Functions", in *Meth. Enzymol.*, 115: 55-77 (1985); Rossman, ed., "The Molecular Replacement Method", *Int. Sci. Rev. Ser.*, No. 13, Gordon & Breach, New York (1972)).

An embodiment of the invention also includes, for example, a structure based drug design method for evaluating the potential of a candidate MEK1 inhibitor (e.g., an ATP competitive inhibitor) to associate with: a) a polypeptide or complex thereof wherein said polypeptide comprises a binding pocket defined by structure coordinates of amino acids 70-84; 93-98; 117-120; 128-129; 140-152; 193-197 and 205-208 according to any of Tables 2-4 and/or a hinge region defined by structural coordinates of amino acids E144, H145 and M146 according to Table 1 or amino acids E143, H144 and M145 according to Table 2, 3 or 4; or b) a homologue of said polypeptide of complex thereof, wherein said homologue comprises a binding pocket or hinge region comprising a three dimensional structure characterized by structural coordinates comprising a root mean square deviation of common residue backbone atoms or alpha carbon atoms of less than about 1.5 Å (e.g., about 1 Å, about 0.75 Å, about 0.5 Å, about 0.25 Å, about 0.1 Å) when superimposed on backbone atoms or alpha carbon atoms described by structural coordinates of any of Tables 1-4 comprising the steps of: (i) employing computational means to perform a fitting operation between the candidate and the binding pocket or hinge region of the molecule or molecular complex; and (ii) analyzing the results of said fitting operation to quantify the association between the candidate and the binding pocket or hinge region. In an embodiment of the invention, the MEK1/inhibitor complex identified by structure based drug design, as set forth above, is generated experimentally and crystallized (e.g., by a method set forth herein). The three-dimensional structure of the complex is then determined by any method known in the art, for example, as set forth herein. Any inhibitor observed to bind a MEK1 polypeptide of the invention can be, as discussed above, confirmed to inhibit the kinase activity of MEK1 (e.g., by a kinase assay as set forth herein). Identification of ATP competitive inhibitors that interact with the MEK1 hinge region or a homologue thereof are preferred.

Compound 2

Compound 2 can form salts which are also within the scope of this invention. Reference to compound 2 herein is understood to include reference to salts thereof, unless otherwise indicated. The term "salt(s)", as employed herein, includes acidic salts formed with inorganic and/or organic acids, as well as basic salts formed with inorganic and/or organic bases. Pharmaceutically acceptable (i.e., non-toxic, physiologically acceptable) salts are within the scope of the invention, although other salts are also useful. Salts of compound 2 may be formed, for example, by reacting compound 2 with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by S. Berge et al., Journal of Pharmaceutical Sciences (1977) 66(1) 1-19; P. Gould, International J. of Pharmaceutics (1986) 33 201-217; Anderson et al., The Practice of Medicinal Chemistry (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others. All such acid salts and base salts are intended to be pharmaceutically acceptable salts within the scope of the invention.

Compound 2 and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

The term "patient" or "subject" includes any organism, such as an animal, for example a mammal (e.g., a human).

Compound 2 has pharmacological properties; in particular, the compound is an inhibitor of MEK1 kinase. Compound 2 is useful in the therapy of proliferative diseases such as cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease. Many of these diseases and disorders are listed in U.S. Pat. No. 6,413,974, the disclosure of which is incorporated by reference herein.

More specifically, compound 2 can be useful in the treatment of a variety of cancers, including (but not limited to) the following: carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkeft's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Due to the key role of MEK1 in the regulation of cellular proliferation in general, inhibitors can act as reversible cytostatic agents which are useful in the treatment of any disease process which features abnormal cellular proliferation, e.g., benign prostate hyperplasia, familiar adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compound 2 is also useful in the treatment of Alzheimer's disease (see J. Biochem., (1995) 117, 741-749).

Compound 2 can induce or inhibit apoptosis. The apoptotic response is aberrant in a variety of human diseases. Compound 2, as modulators of apoptosis, is useful in the treatment of cancer (including but not limited to those types mentioned hereinabove), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compound 2, as inhibitors of the MEK1, can modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compound 2 is useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse. Compound 2 is also useful in inhibiting tumor angiogenesis and metastasis.

Another aspect of this invention is a method of treating a mammal (e.g., human) having a disease or condition associated with the MEK1 by administering a therapeutically effective amount of at least one compound of Formula 2, or a pharmaceutically acceptable salt or solvate of said compound to the mammal.

In an embodiment of the invention, a therapeutically effective dosage of compound 2 or a pharmaceutically acceptable salt or solvate of said compound is about 0.001 to 500 mg/kg of body weight/day (e.g., 0.01 to 25 mg/kg of body weight/day).

The term "in association" indicates that the components of the combinations of the invention can be formulated into a single composition for simultaneous delivery or formulated separately into two or more compositions (e.g., a kit). Furthermore, each component of a combination of the invention can be administered to a subject at a different time than when the other component is administered; for example, each administration may be given non-simultaneously (e.g., separately or sequentially) at several intervals over a given period of time. Moreover, the separate components may be administered to a subject by the same or by a different route (e.g., orally, intravenously, subcutaneously).

Compound 2 is useful in association (e.g., administered together or sequentially) with one or more of anti-cancer treatments such as radiation therapy, and/or one or more anti-cancer agents selected from the group consisting of cytostatic agents, cytotoxic agents (such as for example, but not limited to, DNA interactive agents (such as cisplatin or doxorubicin)); taxanes (e.g., taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methoxtrexate); alkylating agents (such as temozolomide (TEMODAR™ from Schering-Plough Corporation, Kenilworth, N.J.), cyclophosphamide); Farnesyl protein transferase inhibitors (such as, SARASAR™ (4-[2-[4-[(1-1R)-3,10-dibromo-8-chloro-6,11-dihydro-5H-benzo [5,6]cyclohepta[1,2-b]pyridin-11-yl-]-1-piperidinyl)-2-oxoethyl]-1-piperidinecarboxamide, or SCH 66336 from Schering-Plough Corporation, Kenilworth, N.J.), tipifarnib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa (from Astra Zeneca Pharmaceuticals, England), Tarceva (EGFR kinase inhibitors), antibodies to EGFR (e.g., C225), GLEEVEC™ (C-abl kinase inhibitor from Novartis Pharmaceuticals, East Hanover, N.J.); interferons such as, for example, intron (from Schering-Plough Corporation), Peg-Intron (from Schering-Plough Corporation); hormonal therapy combinations; aromatase combinations; ara-C, adriamycin, cytoxan, and gemcitabine.

Other anti-cancer (also known as anti-neoplastic) agents include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaeuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, or Hexamethylmelamine.

If formulated as a fixed dose, such combination products employ the compounds of this invention within the dosage range described herein and the other pharmaceutically active agent or treatment within its dosage range. For example, the scope of the present invention includes compound 2 in association with the CDC2 inhibitor olomucine (see J. Cell. Sci., (1995) 108, 2897). Compound 2 may also be administered sequentially with known anticancer or cytotoxic agents when a combination formulation is inappropriate. The invention is not limited in the sequence of administration; compound 2 may be administered either prior to or after administration of the known anticancer or cytotoxic agent. For example, the cytotoxic activity of the cyclin-dependent kinase inhibitor flavopiridol is affected by the sequence of administration with anticancer agents. Cancer Research, (1997) 57, 3375. Such techniques are within the skills of persons skilled in the art as well as attending physicians.

Accordingly, in an aspect, this invention includes combinations comprising an amount of compound 2, or a pharmaceutically acceptable salt or solvate thereof, and an amount of one or more anti-cancer treatments and/or anti-cancer agents listed above wherein the amounts of the compounds/treatments result in desired therapeutic effect.

This invention is also directed to pharmaceutical compositions which comprise compound 2 or a pharmaceutically acceptable salt or solvate of said compound and at least one pharmaceutically acceptable carrier.

For preparing pharmaceutical compositions from the compounds described by this invention, inert, pharmaceutically acceptable carriers can be either solid or liquid. Solid form preparations include, for example, powders, tablets, dispersible granules, capsules, cachets and suppositories. The powders and tablets may be comprised of, for example, from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in association with a pharmaceutically acceptable carrier, such as an inert compressed gas, e.g., nitrogen.

Also included are solid form preparations that are intended to be converted, shortly before use, to liquid form preparations for either oral or parenteral administration. Such liquid forms include solutions, suspensions and emulsions.

Compound 2 of the invention may also be deliverable transdermally. The transdermal compositions can take the form of creams, lotions, aerosols and/or emulsions and can be included in a transdermal patch of the matrix or reservoir type as are conventional in the art for this purpose.

Compound 2 of this invention may also be delivered subcutaneously. In an embodiment of the invention, compound 2 is administered orally or intravenously.

In an embodiment of the invention, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, e.g., from about 1 mg to about 50 mg, e.g., from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated.

Another aspect of this invention is a kit comprising a therapeutically effective amount of at least one compound of Formula 2, or a pharmaceutically acceptable salt or solvate of said compound and a pharmaceutically acceptable carrier, vehicle or diluent.

Yet another aspect of this invention is a kit comprising an amount of at least one compound of Formula 2, or a pharmaceutically acceptable salt or solvate of said compound and an amount of at least one anticancer therapy and/or anti-cancer agent listed above, wherein the amounts of the two or more ingredients result in desired therapeutic effect.

EXAMPLES

The following Examples are intended for exemplification of the present invention only and should not be construed to limit the scope of the invention. Any composition (e.g., crystal) or method disclosed in the Examples section forms part of the present invention.

Example 1

Domain Selection for MEK1 Constructs

Wild-type MEK1 has proven difficult to crystallize. This example describes the selection of the mutant MEK1 polypeptides of the invention that were used for the crystal studies set forth herein.

To chose a crystallizable domain of MEK1, the 3-dimensional structures of 20 distinct kinases were examined and divided into two classes: (A) CK2, CDK2, CDK6, ERK2, JNK & p38 have an insertion of –35 residues in the C-terminal domain and (B) PKA, calmodulin-dependent-kinase, CK1, LCK, HCK, SRC, ABL, PAK, titin kinase, twitchin kinase, FGFRTK, VEGFRTK, TGFβRTK and insulin-receptor-kinase lack this insertion. Using Clustal W, the sequences of each of these classes align well, corresponding to the structural alignment. In order to get correspondence of the sequence and structural alignments for the full 20 kinases, the –35 inserted residues must be deleted from the 6 kinases in class A.

MEK1 sequences from seven species and MEK2 sequences from five species were included in the sequence alignment to help illustrate conserved elements in the family. A Clustal W multi-sequence alignment was performed using the 7 MEK1, 5 MEK2 and the 20 distinct kinases of known structure.

From the multi-sequence analysis, the canonical kinase domain was deduced to be (55-369) MEK1. However, the construct MEK1 (55-369) was found to be completely insoluble (see Cha et al., J. Biol. Chem. 276:48494-48501 (2001)).

During purification, partial proteolysis was observed between the two serines in the sequence 236LS/SY, which is an auto-phosphorylation sequence. Large residues from the CK2 sequence were selected to replace the serines, SS->NK and to avoid phosphorylation the change Y->F was made. The triple mutant 237SSY->237NKF was observed to be resistant to proteolytic degradation and was the basis of subsequent work.

Limited tryptic and GluC digestion experimentally defined domain boundaries of MEK1 that were amenable to crystallization. Both enzymes trimmed MEK1 near the nuclear export sequence at position 35 but did not cut MEK1 at the C-terminus. Initial clones for wild-type MEK1 (2-393), and for N-terminal deletion mutants: (35-393)MEK1 and (55-393)MEK1 were constructed. MEK1 (35-393) includes a previously defined negative regulatory region which spans position 44-51 (Mansour et al., Science 265: 966-970 (1994)).

Though the canonical kinase domain (55-369) was observed to be highly insoluble, the N-terminal truncation mutant 55-393 (mentioned above), comprising residues C-terminal residues 370-393 was observed to be highly soluble. A final construct comprising a larger C-terminal domain—35-383 MEK1[237SSY->NKF]—was constructed and determined to be highly soluble.

Example 2

The Cloning of MEM N35 NKF Construct

Human MEK1 was cloned by PCR utilizing cDNA derived from human brain (Clonetech). Full length MEK1 was subcloned from pCR2.1 TOPO TA cloning vector (Invitrogen cat #K4500-01) utilizing BamH1 into pBluBacHis2 vector (Invitrogen Cat # V375-20) for baculovirus construction. The final construct was verified by sequence analysis. Three PCR primers, fTOPOI: 5ATCCCAACGACCGAAAACCTG-TATTTTCAGGGCatgcccaagaagaagccgacgcccatcca gc3' (SEQ ID NO: 3); fTOPPII: 5'CACCATGTCGTACTACCAT-CACCATC ACCATCACGATTACGATATCCCAACGAC-CGAAAACCTGTATTTTCAGGGC3' (SEQ ID NO: 4) and rTOPO: 5TTAGACGCCAGCAGCATGGGTTGGTGT-GCTGG3' (SEQ ID NO: 5) were used sequentially to incorporate a TEV-cleavable, N-terminal His6 tag through 2 rounds of PCR amplification. Purified PCR product from the first round was used as the template for the second round of amplification. The final PCR product was incorporated into the pENTR/D-TOPO vector following the TOPO cloning instruction manual. Two PCR primers then were used to delete the N-terminal 35 amino acids fN35: 5'GCTCTAGCTCCTCCAGCTTCTTGCCCTGAAAATA CAGG3' (SEQ ID NO: 6) and rN35: 5'CCTG-TATTTTCAGGGCAAGAAGCTGGAGGAGCTAGAGC3' (SEQ ID NO: 7), and two PCR primers fNKF: 5'GGAGGC-CCCTTAACAAATTTGGAATGGACAGC-CGACCTCCC3' (SEQ ID NO: 8) and rNKF: 5'GGGAG-GTCGGCTGTCCATTCCAAATTTGTTAAGGGGCCTCC3' (SEQ ID NO: 9) were used to incorporate the NKF mutation via the Quick Change method. The final construct was verified by sequence analysis. The insert was then subcloned into the pDEST8 vector using the Gateway LR clonase reaction following the instruction manual.

Example 3

Production of Recombinant Baculoviruses (Sf9) MEK1 N35 NKF

Recombinant baculovirus was produced by utilizing the Bac-to-Bac baculovirus expression system manual (Gibco BRL, Rockville, Md., USA; SF900-II) and following the protocol for transposition, isolation of recombinant bacmid DNA, transfection of Sf9 cells with recombinant bacmid DNA and harvesting/storage of recombinant baculovirus. Recombinant virus was then plaque purified according to the Bac-to-Bac baculovirus expression system manual and amplified by the infection of suspension cultures using a multiplicity of infection of 0.05.

Example 4

Expression and Recovery of Baculovirus Recombinant MEK1 N35 NKF (High-Five)

*Spodoptera frugiperda* (Sf9) and *Tridchopfusia ni* (High Five™ BTI-TN-5B1-4; Invitrogen, Carlsbad, Calif., USA) cells were grown in suspension at 27° C. in serum free media (SF900-II or Express Five; Gibco BRL, Rockville, Md., USA). Multiplicity of infection (MOI), cell type and time course of expression were all studied to obtain optimal protein expression yields of soluble MEK1 protein. A MOI of 5 with High-Five cells with an infection period of 48 hrs was optimal for protein expression yielding approximately 30 mg/L.

Example 5

Amino Acid Sequence of MEK1 N35 NKF

The sequence of this MEK1 N35 NKF construct expressed in High Five cells was as follows:

```
                                                                (SEQ ID NO: 1)
  1  MGYYHHHHHH DYDIPTTENL YFQGKKLEEL ELDEQQRKRL EAFLTQKQKV GELKDDDFEK   60

61  ISELGAGNGG VVFKVSHKPS GLVMARKLIH LEIKPAIRNQ IIRELQVLHE CNSPYIVGFY  120

121  GAFYSDGEIS ICMEHMDGGS LDQVLKKAGR IPEQILGKVS IAVIKGLTYL REKHKIMHRD  180

181  VKPSNILVNS RGEIKLCDFG VSGQLIDSMA NSFVGTRSYM SPERLQGTHY SVQSDIWSMG  240

241  LSLVEMAVGR YPIPPPDAKE LELMFGCQVE GDAAETPPRP RTPGRPLNKF GMDSRPPMAI  300

301  FELLDYIVNE PPPKLPSGVF SLEFQDFVNK CLIKNPAERA DLKQLMVHAF IKRSDAEEVD  360

361  FAGWLCSTIG LNQPSTPTHA AGV
```

Number of amino acids: 383
The molecular weight was deduced to be 42997.5 Daltons.

Example 6

Purification of MEK1 N35 NKF

The infected High Five cells were lysed in a microfluidizer in a lysis buffer (20 mM Tris pH 8.5, 10% glycerol, 5 mM β-mercaptoethanol, 1× protease inhibitor cocktail III (Calbiochem). The lysate was centrifuged at 100,000×g for 1 hour at 4° C. The supernatant was applied to a Q-Sepharose Fast Flow column (Amersham Biosciences) equilibrated in 20 mM Tris pH 8.5, 10% glycerol, 5 mM β-mercaptoethanol. The column was washed with 20 mM Tris pH 8.5, 10% glycerol, 5 mM β-mercaptoethanol, and protein was eluted with an elution buffer (20 mM Tris pH 8.5, 10% glycerol, 5 mM β-mercaptoethanol, 250 mM NaCl) over 10 column volumes. MEK1 protein eluted at around 125 mM NaCl. Appropriate fractions were pooled and applied to a Ni-NTA column (Qiagen) equilibrated in 20 mM Tris pH 8.0, 500 mM NaCl, 10% glycerol, and 5 mM β-mercaptoethanol. Protein was eluted with 20 mM Tris pH 8.0, 500 mM NaCl, 10% glycerol, 5 mM β-mercaptoethanol, 150 mM imidazole over 20 column volumes. Appropriate fractions were pooled and TEV protease (Invitrogen) was added at 200 Units/mg of MEK1 and allowed to incubate overnight at 4° C. to eliminate the His-tag. The cleaved protein was applied to a second Ni-NTA column (Qiagen) which was equilibrated as described above. Appropriate fractions were pooled, diluted to ~2 mg/ml and dialyzed against 50 mM Tris pH 7.8, 300 mM NaCl, 10% glycerol, 0.5 mM MnCl₂, 5 mM DTT for 4 hours at 4'C. Lambda phosphatase (Calbiochem) was added to the dialyzing protein at 1:450 molar ratio to remove the adventitious phosphorylation that occurs during expression. The de-phosphorylation reaction was allowed to continue in the dialysis tubing overnight at 4° C. LC-MS was used to confirm that MEK1 was completely de-phosphorylated under these conditions. The protein was concentrated to ~5 mg/ml and applied to a Superdex 75 (Amersham Biosciences) column equilibrated in 20 mM HEPES pH 7.5, 300 mM NaCl, 1% glycerol, 2 mM DTT, and 1 mM TCEP. Fractions containing MEK1 protein were pooled and concentrated to ~15 mg/ml.

Example 7

Preparation of MEK1 N35 NKF Ternary Complex (cpd.1 & ATPγS)

15 ul of a 50 mM ATPγS solution (2-fold molar excess) in the presence of 1.5 μl of (4-fold molar excess) 1M magnesium acetate stock solution was added to MEK1 N35 NFK solution (1 ml) from example 6. Compound 1 was titrated in 50 μM increments until a 1.5-fold molar excess was reached. The resulting MEK1 N35 NFK ternary complex was incubated on ice for 10 minutes than passed through a 1 μm spin filter.

Example 8

Crystallization of MEK1 N35 NKF Ternary Complex

Using a hanging-drop vapor diffusion method, the MEK1 N35 NFK ternary complex as described in example 7 (0.5 ul; 19.2 mg/ml) in 20 mM HEPES, pH 7.5, 300 mM sodium chloride, 2 mM DTT, 1 mM TCEP, 1% glycerol buffer was mixed with an equal volume of precipitant solution containing 90 mM TRIS, pH 8.5, 18% PEG 4000, 0.18 M calcium chloride and 3% DMSO as an additive component placed on the underside of a Teflon coated cover slip and sealed in close proximity to 100 μl of the precipitant solution. Crystallization plates were incubated at 4° C.; egg-shaped crystals (50×50× 150 microns) grew to full size in 5-7 days. Three additional additives: 3% 1, 8-Diamino-octane, 3% Trimethylamine N-oxide, and 3% 2,2,2,-Trifluoroethanol were found to also enhance the quality and size of the resulting crystals.

Example 9

Photomicrograph of MEK1 N35 NKF Ternary Complex Crystals

As set forth above, the crystallization conditions were as follows: Protein concentration 19.2 mg/ml, 90 mM TRIS, pH 8.5 18% PEG 4000, 0.18 M CaCl₂, 3% DMSO, 4° C. A photomicrograph of the crystal obtained under these conditions was taken (FIG. 1).

Example 10

Crystallographic Analysis of MEK1 N35 NKF Ternary Complex

Prior to data collection, crystals were washed with the reservoir solution of the crystallization setup and transferred into the same solution with 20% glycerol added. The crystals were then flash-cooled in a nitrogen stream at 95 K or in liquid nitrogen, X-ray diffraction was collected using a Rigaku generator equipped with a Raxis 4 detector. Data were integrated and scaled using the HKL package.

Data collection statistics:

| | |
|---|---|
| Resolution | 23 – 3.4 Å |
| No. of collected reflections | 323582 |
| No. of unique reflections (F >= 0) | 5874 |
| R-sym | 24.4% |
| Percent of theoretical (I/s > −3) | 98% |
| Unit Cell | a = 77.3 Å, b = 77.3 Å, c = 221.9 Å, $\alpha = 90°, \beta = 90°, \gamma = 120°$ |
| Space Group | $P 6_1 2 2$ (Number 78) |
| Asymmetric unit | 1 molecule |

The coordinates of the MEK1 N35 NKF-cpd.1-ATPγS ternary complex are set forth below in Table 1.

Example 11

The Cloning of MEK1 N35 NKF Cdel383 Construct

The MEK1 N35 NKF construct in pENTR/D-TOPO vector was used as a template for the generation of the MEK1 N35 NKF Cdel383 construct. Two PCR primers fCdel383:

```
fCdel383:
                                          (SEQ ID NO: 10)
5' GCAGGTTGGCTCTGCTCCACCATCGGCCTTAACCAGTAAAAGGGTGGG
CGCGCCGACCCAGC3'
and
rCdel383:
                                          (SEQ ID NO: 11)
5'GCTGGGTCGGCGCGCCCACCCTTTTACTGGTTAAGGCCGATGGTGGAGC
AGAGCCAACCTGC3'
``` were used to delete the C-terminal 10 amino acids, via the Quick Change method.

Example 12

Production of Recombinant Baculoviruses (Sf9) MEK1 N35 NKF Cdel 383

Recombinant baculovirus was produced by utilizing the Bac-to-Bac baculovirus expression system manual (Gibco BRL, Rockville, Md., USA; SF900-II) and following the protocol for transposition, isolation of recombinant bacmid DNA, transfection of Sf9 cells with recombinant bacmid DNA and harvesting/storage of recombinant baculovirus. Recombinant virus was then plaque purified according to the Bac-to-Bac baculovirus expression system manual and amplified by the infection of suspension cultures using a multiplicity of infection of 0.05.

Example 13

Expression and Recovery of baculovirus Recombinant MEK1 N35 NKF Cdel 383 (Hi-Five)

*Spodoptera frugiperda* (Sf9) and *Tridchoplusia ni*(High Five™ BTI-TN-581-4; Invitrogen, Carlsbad, Calif.) cells were grown in suspension at 27° C. in serum free media (SF900-II or Express Five; Gibco BRL, Rockville, Md., USA). Multiplicity of infection (MOD, cell type and time course of expression were all studied to obtain optimal protein expression yields of soluble MEK1 protein. A MOI of 5 with High-Five cells with an infection period of 48 hrs was optimal for protein expression yielding approximately 30 mg/L.

Example 14

Amino Acid Sequence of MEK1 N35 NKF Cdel 383

```
                                                    (SEQ ID NO: 2)
  1   MGYYHHHHHH DYDIPTTENL YFQGKKLEEL ELDEQQRKRL EAFLTQKQKV GELKDDDFEK    60
 61   ISELGAGNGG VVFKVSHKPS GLVMARKLIH LEIKPAIRNQ IIRELQVLHE CNSPYIVGFY   120
121   GAFYSDGEIS ICMEHMDGGS LDQVLKKAGR IPEQILGKVS IAVIKGLTYL REKHKIMHRD   180
181   VKPSNILVNS RGEIKLCDFG VSGQLIDSMA NSFVGTRSYM SPERLQGTHY SVQSDIWSMG   240
241   LSLVEMAVGR YPIPPPDAKE LELMFGCQVE GDAAETPPRP RTPGRPLSSY GMDSRPPMAI   300
301   FELLDYIVNE PPPKLPSGVF SLEFQDFVNK CLIKNPAERA DLKQLMVHAF IKRSDAEEVD   360
361   FAGWLCSTIG LNQ
```

Number of amino acids: 373
The molecular weight was deduced to be 42079.4 Daltons.

Example 15

Purification of MEK1 N35 NKF Cdel 383

The infected High Five cells were lysed in a microfluidizer in a lysis buffer (20 mM Tris pH 8.5, 10% glycerol, 5 mM β-mercaptoethanol, 1× protease inhibitor cocktail III (Calbiochem; San Diego, Calif.). The lysate was centrifuged at 100,000×g for 1 hour at 4° C. The supernatant was applied to a Q-Sepharose Fast Flow column (Amersham Biosciences) equilibrated in 20 mM Tris pH 8.5, 10% glycerol, 5 mM β-mercaptoethanol. The column was washed with 20 mM Tris pH 8.5, 10% glycerol, 5 mM 3-mercaptoethanol, and protein was eluted with an elution buffer (20 mM Tris pH 8.5, 10% glycerol, 5 mM β-mercaptoethanol, 250 mM NaCl) over 10 column volumes. MEK1 protein eluted at around 125 mM NaCl. Appropriate fractions were pooled and applied to a Ni-NTA column (Qiagen) equilibrated in 20 mM Tris pH 8.0, 500 mM NaCl, 10% glycerol, and 5 mM β-mercaptoethanol. Protein was eluted with 20 mM Tris pH 8.0, 500 mM NaCl, 10% glycerol, 5 mM β-mercaptoethanol, 150 mM imidazole over 20 column volumes. Appropriate fractions were pooled and TEV protease (Invitrogen) was added at 200 Units/mg of MEK1 and allowed to incubate overnight at 4° C. to eliminate the His-tag. The cleaved protein was applied to a second Ni-NTA column (Qiagen) which was equilibrated as described above. Appropriate fractions were pooled, diluted to ~2 mg/ml and dialyzed against 50 mM Tris pH 7.8, 300 mM NaCl, 10% glycerol, 0.5 mM MnCl2, 5 mM DTT for 4 hours at 4° C. Lambda phosphatase (Calbiochem) was added to the dialyzing protein at 1:450 molar ratio to remove the adventitious phosphorylation that occurs during expression. The de-phosphorylation reaction was allowed to continue in the dialysis tubing overnight at 4° C. LC-MS was used to confirm that MEK1 was completely de-phosphorylated under these conditions. The protein was concentrated to ~5 mg/ml and applied to a Superdex 75 (Amersham Biosciences) column equilibrated in 20 mM HEPES pH 7.5, 300 mM NaCl, 1% glycerol, 2 mM DTT, and 1 mM TCEP. Fractions containing MEK1 protein were pooled and concentrated to ~10 mg/ml.

Example 16

Preparation of MEK1 N35 NKF Cdel 383 Ternary Complex (Cpd. 1 & ATPγS)

15 μl of a 50 mM ATPγS solution (2-fold molar excess) in the presence of 1.5 μl of (4-fold molar excess) 1M magnesium acetate stock solution was added to the MEK1 N35 NKF Cdel 383 solution (1 ml) as described in example 7. Compound 1 was titrated in 50 μM increments until a 1.5-fold molar excess was reached. The resulting MEK1 N35 NKF Cdel 383 ternary complex was incubated on ice for 10 minutes and filtered using a 1 μm spin filter.

Example 17

Crystallization of MEK1 N35 NKF Cdel 383 Ternary Complex

Using a hanging-drop vapor diffusion method, the MEK1 N35 NKF Cdel 383 ternary complex as described in example 16 (1 μl; 0.28 mM) in 20 mM HEPES, pH 7.5, 300 mM sodium chloride, 2 mM DTT, 1 mM TCEP, 1% glycerol buffer was mixed with an equal volume of precipitant solution containing 90 mM TRIS pH 8.5, 18% PEG 4000, 0.18 M calcium chloride and 3% DMSO placed on the underside of a siliconized Teflon slip cover and sealed in dose proximity to 100 μL of the precipitant solution. Crystallization plates were incubated at 4° C.; hexagonal rod crystals (75×75×250 microns) grew within 18-24 hours.

Example 18

Photomicrograph of MEK1 N35 NKF Cdel 383 Ternary Complex Crystals

Figure 2:
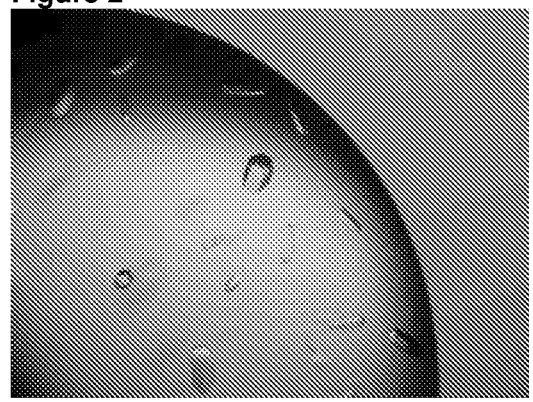
FIG. 2. Photomicrograph of MEK1 N35 NKF Cdel 383 ternary complex crystals.

As stated above, the crystallization conditions were as follows: protein concentration 0.28 mM, 90 mM TRIS, pH 8.5, 18% PEG 4000, 0.18 M $CaCl_2$. 3% DMSO, 4° C. A photomicrograph of the crystals obtained was taken (FIG. 2).

Example 19

Crystallographic Analysis of MEK1 N35 NKF Cdel 383 Ternary Complex

Prior to data collection, crystals were washed with the reservoir solution of the crystallization setup and transferred into the same solution with 20% glycerol added. The crystals were then flash-cooled in a nitrogen stream at 95 K or in liquid nitrogen. X-ray diffraction was collected using a Rigaku generator equipped with a Raxis 4 detector. Data were integrated and scaled using the HKL package.

| Data collection statistics: | |
| --- | --- |
| Resolution | 32.0 – 2.2 Å |
| No. of collected reflections | 583534 |
| No. of unique reflections (F >= 0) | 20338 |
| R-sym | 8.1% |
| Percent of theoretical (I/s > –3). | 97.9% |
| Unit Cell | a = 77.1 Å, b = 77.1 Å, c = 221.7 Å, α = β = 90°, γ = 120° |
| Space Group | P 6₁ 2 2 (Number 78) |
| Asymmetric unit | 1 molecule |

The coordinates of the MEK1 N35 NKF Cdel-cpd.1-ATPγS ternary complex are set forth below in Table 2.

Example 20

MEK1 N35 NKF Cdel 383 Ternary Complex Structure Determination

The crystal structure was solved using molecular replacement. Refinement was done using the program BUSTER.

| | |
| --- | --- |
| Theoretical number of reflections | 20334 |
| Resolution Limits | 32.0 – 2.2 Å |
| Number of unobserved reflections | 393 (1.9%) |
| Number of reflections in test set | 1012 (5.0%) |
| Number of protein residues | 349 |
| Number of solvent atoms | 80 |
| R-factor | 0.215 |
| R-free | 0.246 |
| RMSD bond length | 0.011 Å |
| RMSD bond angles | 1.054° |

Example 21

Preparation of MEK1 N35 NKF Cdel 383 Binary Complex 15 ul of a 50 mM ATP-γS solution (2-fold molar excess) in the presence of 1.5 ul of (4-fold molar excess) 1M magnesium acetate stock solution was added to the MEK1N35NKFCdel383 solution (1 ml) as described in example 6. The resulting MEK1N35NKFCdel383 binary complex was incubated on ice for 10 minutes and filtered using a 1 μm spin filter.

Example 22

Crystallization and Soaking of MEK1 N35 NKF Cdel 383 Binary Complex

Using a hanging-drop vapor diffusion method, The resulting MEK1 N35 NKF Cdel383 binary complex as described in example 21 (1 μl; 0.28 mM) in 20 mM HEPES, pH 7.5, 300 mM sodium chloride, 2 mM DTT, 1 mM TCEP, 1% glycerol buffer was mixed with an equal volume of precipitant solution containing 90 mM TRIS pH 8.5, 18% PEG 4000, 0.18 M calcium chloride, 3% DMSO placed on the underside of a siliconized Teflon slip cover and sealed in close proximity to 100 μL of the precipitant solution. Crystallization plates were incubated at 4° C.; hexagonal rod crystals (75×75×250 microns) grew within 18-24 hours.

To a drop of MEK1 N35 NKF Cdel 383/ATP-γS binary crystals described above was added 0.1 ul of 100 mM compound 1 in DMSO solution. The drop was subsequently incubated at 4° C. for 13 days. A MEK1 N35 NKF Cdel 383/ATP-γS/cpd.1 ternary complex crystal was thereby generated.

Example 23

Photomicrograph of MEK1 N35 NKF Cdel 383 Binary Complex Crystals

Figure 3:
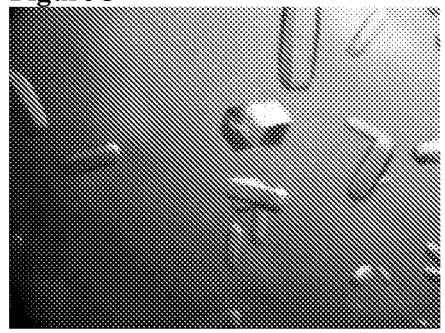
FIG. 3. Photomicrograph of MEK1 N35 NKF Cdel 383 binary complex crystals.

As stated above, the crystallization conditions were as follows: protein concentration 0.28 mM, 90 mM IRIS, pH 8.5, 18% PEG 4000, 0.18 M $CaCl_2$, DMSO, 4° C. A photomicrograph of the crystals obtained was taken (FIG. 3).

Example 24

Crystallographic Analysis of MEK1 N35 NKF Cdel 383 Binary Complex

Prior to data collection, crystals were washed with the reservoir solution of the crystallization setup and transferred into the same solution with 20% glycerol added. The crystals were then flash-cooled in a nitrogen stream at 95 K or in liquid nitrogen. X-ray diffraction was collected using a Rigaku generator equipped with a Raxis 4 detector. Data were integrated and scaled using the HKL package.

| Data collection statistics: | |
|---|---|
| Resolution | 39.0 – 2.45 Å |
| No. of collected reflections | 1087533 |
| No. of unique reflections (F >= 0) | 14882 |
| R-sym | 12.5% |
| Percent of theoretical (l/s > –3) | 97.7% |
| Unit Cell | a = 77.2 Å, b = 77.2 Å, c = 222.2 Å, α = β = 90° γ = 120° |
| Space Group | P 6₁ 2 2 (Number 78) |
| Asymmetric unit | 1 molecule |

The coordinates of the MEK1 N35 NKF Cdel-ATPγS binary complex are set forth below in Table 3.

Example 25

MEK1 N35 NKF Cdel383 Binary Complex Structure Determination

The crystal structure was solved using molecular replacement. Refinement was done using the program BUSTER.

| | |
|---|---|
| Theoretical number of reflections | 14882 |
| Resolution Limits | 39.0 – 2.45 Å |
| Number of unobserved reflections | 403 (2.6%) |
| Number of reflections in test set | 741 (5.0%) |
| Number of protein residues | 349 |
| R-factor | 0.245 |
| R-free | 0.286 |
| RMSD bond length | 0.009 Å |
| RMSD bond angles | 1.141° |

Example 26

Preparation of MEK1 N35 NKF Cdel 383 Binary-cpd.2 Complex by Soaking and Crystallographic Analysis To a drop of MEK1 N35 NKF Cdel 383 binary crystals as described in example 21 was added 0.1 ul of 100 mM compound 2 in DMSO solution. The drop was subsequently incubated at 4° C. for 13 days. Prior to data collection, a soaked crystal was washed with the reservoir solution of the crystallization setup and transferred into the same solution with 20% glycerol added. The crystals were then flash-cooled in a nitrogen stream at 95 K or in liquid nitrogen. X-ray diffraction was collected using a Rigaku generator equipped with a Raxis 4 detector. Data were integrated and scaled using the HKL package.

| Data Collection Statistics: | |
|---|---|
| Resolution | 38.0 – 2.55 Å |
| No. of collected reflections | 643654 |
| No. of unique reflections (F >= 0) | 13285 |
| R-sym | 9.2% |
| Percent of theoretical (l/s > –3) | 98.92% |
| Unit Cell | a = 76.8 Å, b = 76.8 Å, c = 222.4 Å, α = β = 90°, γ = 120° |
| Space Group | P 6₁ 2 2 (Number 78) |
| Asymmetric unit | 1 molecule |

A similar soaking procedure was carried out with

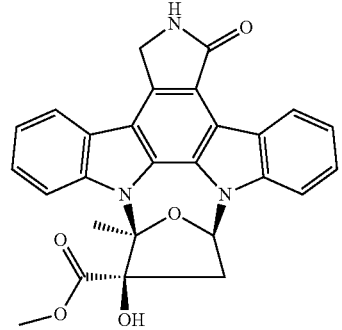 [SMILES: COC(=O)[C@@]1(O)C[C@H]2O[C@]1(C)n1c3ccccc3c3c4c(c5c6ccccc6n2c5c31)C(=O)NC4]

in place of compound 2 to generate a soaked MEK1 N35 NKF Cdel 383 binary—

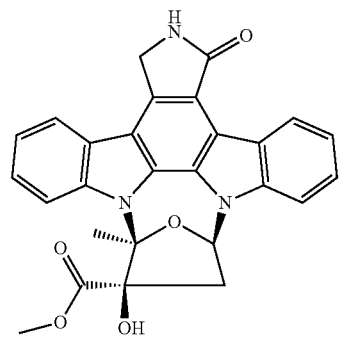 [SMILES: COC(=O)[C@@]1(O)C[C@H]2O[C@]1(C)n1c3ccccc3c3c4c(c5c6ccccc6n2c5c31)C(=O)NC4]

crystalline complex (lacking ATPγS). Soluble, non-crystalline complexes including these molecules are also within the scope of the present invention.

Example 27

MEK1 N35 NKF Cdel 383 Binary-cpd.2 Complex Structure Determination (Soaking)

The crystal structure was solved using molecular replacement. Refinement was done using the program BUSTER.

| | |
|---|---|
| Theoretical number of reflections | 13285 |
| Resolution Limits | 38.0 – 2.55 Å |
| Number of unobserved reflections | 167 (1.26%) |
| Number of reflections in test set | 658 (5.0%) |
| Number of protein residues | 349 |
| R-factor | 0.252 |
| R-free | 0.281 |
| RMSD bond length | 0.008 Å |
| RMSD bond angles | 0.968° |

The coordinates of the MEK1 N35 NKF Cdel-cpd.2 binary complex are set forth below in Table 4.

Example 28

Preparation of Compound 2

A compound represented by structural formula 2 can be synthesized by a method as set forth in this example.

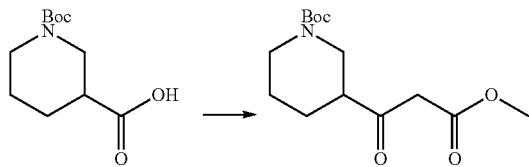 [SMILES: CC(C)(C)OC(=O)N1CCCC(C(=O)O)C1 ; COC(=O)CC(=O)C1CCCN(C(=O)OC(C)(C)C)C1]

$SOCl_2$ (18.5 mL) was added slowly under $N_2$ to a stirred mixture of the acid (50.0 g, 218 mmol) and pyridine (44.0 mL) in anhydrous $CH_2Cl_2$ (60 mL). The mixture was stirred at 25° C. for 20 min, then Meldrum's acid (35.0 g, 243 mmol) and DMAP (66.6 g, 546 mmol) were added and the mixture was stirred under $N_2$ for 1 hr. Then $Et_2O$ (2 L) was added, the mixture was washed with 1 M HCl (3×500 mL), brine (500 mL), and the organic layer was dried over $Na_2SO_4$, filtered, and the solvent was evaporated. The residue was dissolved in MeOH (580 mL), and the mixture was refluxed for 4 hr. The solvent was evaporated and the residue was purified by column chromatography on silica gel with 10:1 $CH_2Cl_2$/EtOAc as eluent. Pale yellow oil (26.5 g, 43%) was obtained.

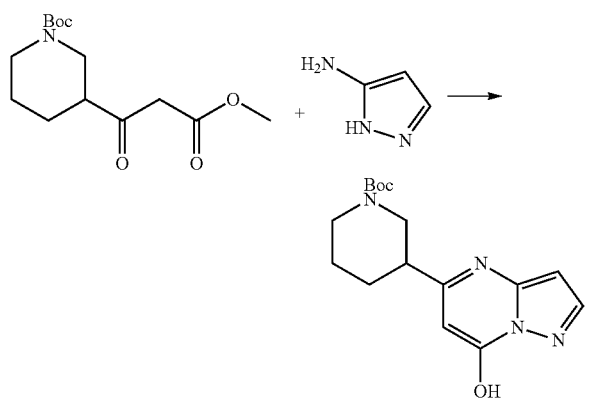

A mixture of the β-ketoester from Preparative Example 10 (20.0 g, 70.1 mmol) and 3-aminopyrazole (5.40 g, 65.0 mmol) in anhydrous toluene (60 mL) was stirred and refluxed under $N_2$ for 24 hr. The solvent was evaporated and the residue was purified by column chromatography on silica gel with 20:1 $CH_2Cl_2$/MeOH as eluent. White solid (15.0 g, 73%) was obtained. LC-MS: 319 [M+H].

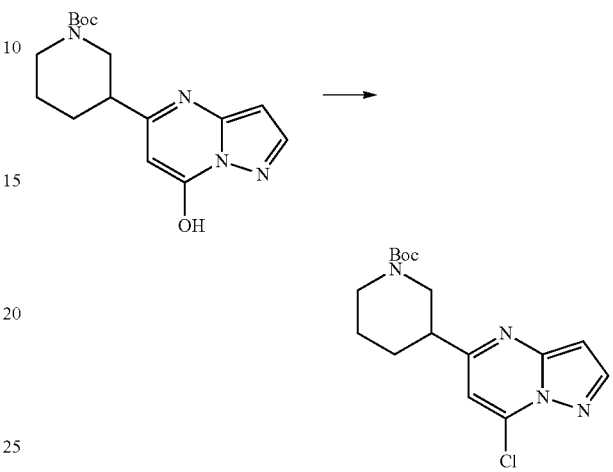

A mixture of the product from Preparative Example 20 (12.50 g, 39.3 mmol), N,N-dimethylaniline (15.5 mL), and $POCl_3$ (125 mL) was stirred at 25° C. for 4 days. Excess of $POCl_3$ was evaporated and the residue was poured into saturated aqueous $NaNCO_3$ (600 mL). The mixture was extracted with $CH_2Cl_2$ (3×200 mL), the combined extracts were dried over $Na_2SO_4$, filtered, and the solvent was evaporated. The residue was purified by column chromatography on silica gel with 8:1 $CH_2Cl_2$/EtOAc as eluent. Pale yellow wax (9.41 g, 71%) was obtained. LC-MS: 337 [M+].

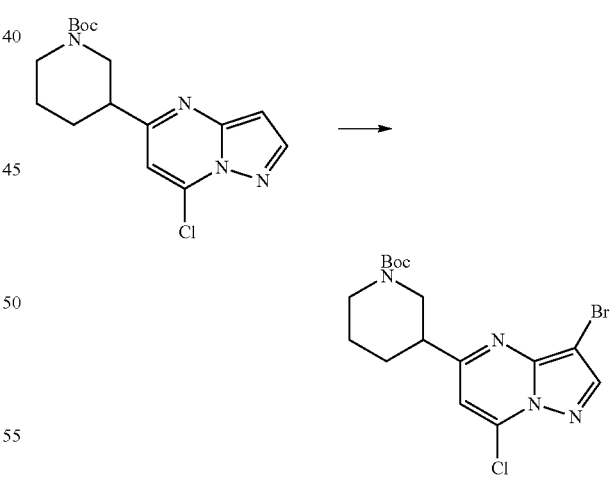

A solution of NBS (4.03 g, 22.7 mmol) in anhydrous $CH_3CN$ (40 mL) was added under $N_2$ to a stirred solution of the product from Preparative Example 30 (7.63 g, 22.7 mmol) in anhydrous $CH_3CN$ (60 mL) and $CH_2Cl_2$ (20 mL). The mixture was stirred for 2 hr, the solvents were evaporated, and the residue was purified by column chromatography on silica gel with 20:1 $CH_2Cl_2$/EtOAc as eluent. Pale yellow solid foam (9.20 g, 97%) was obtained. LC-MS: 417 [M+H].

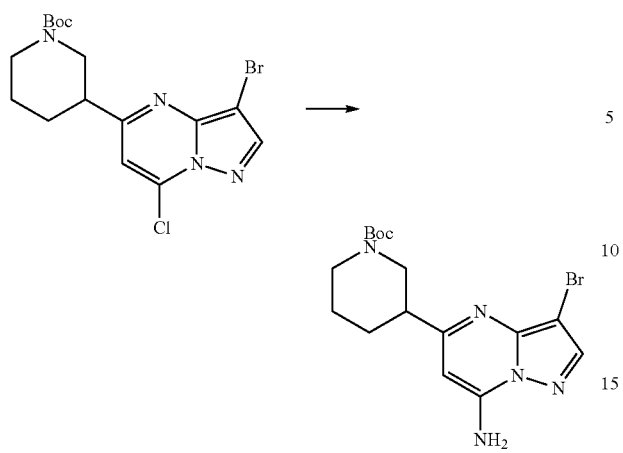

A mixture of the product from Preparative Example 40, 2.0 M $NH_3$ in 2-propanol, and concentrated aqueous $NH_4OH$ is stirred in a closed pressure vessel at 50° C. for 2 days. The solvents are evaporated and the residue purified by column chromatography on silica gel.

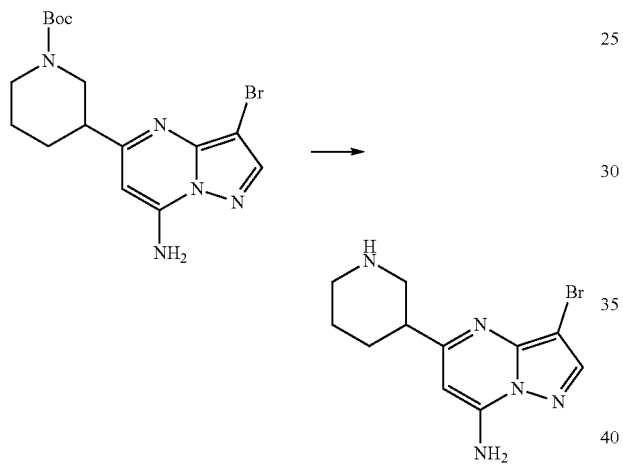

TEA is added under $N_2$ to a stirred solution of the product from Preparative Example 50 in $CH_2Cl_2$. The mixture is stirred for 1 hr, the solvent was evaporated, and the residue was mixed with solid $Na_2CO_3$ and 10:1 $CH_2Cl_2$/MeOH. The mixture is stirred under $N_2$ for 10 min, the solution was withdrawn and loaded onto a silica gel preparative TLC plate, which is then developed with 10:1 $CH_2Cl_2$/7N $NH_3$ in MeOH.

Example 29

Kinase Assays

A candidate that is identified to bind to a MEK1 polypeptide of the present invention by a method set forth herein can be confirmed to be a MEK1 kinase inhibitor by any of several MEK1 kinase assays known in the art. An example of an assay which can be used for this purpose is set forth in this example.

In an embodiment of the invention, the kinase activity of MEK1 in the presence of an inhibitor identified by a process as set forth herein is performed using a Biotinylated, 6-Histidine tagged fusion protein of kinase-inactive ERK2 (Biotin-His6-ERK2(K52R)) as the substrate. MEK kinase activity is assayed in the presence of activated MEK1 polypeptide (25 ng) in 20 mM HEPES (N-2-hydroxyethyl-piperazine-N'-2-ethanesulfonic acid) pH 7.5, mM $MgCl_2$, 0.2% Octyl-β-D-Glucopyranoside, 1 mM Dithiothreitol and one of several concentrations of candidate MEK1 inhibitor. The reaction is started with the addition of 2 μM ATP, with 0.1 μCi [$\gamma$-$^{33}$P] ATP and 1.4 μg Biotin-H6-ERK2($K_{52}$R). The reactions are incubated at room temperature for 60 minutes, then quenched with 10 μl 50 mM EDTA/10 mM HEPES pH 7.5 solution. The stopped reactions are transferred to a Streptavidin coated FlashPlate (NEN) and incubated one hour at room temperature to allow the Biotin-His6-ERK2(K52R) to bind to the plate. The plate is then washed 3 times with Phosphate Buffered Saline and read on a Packard Top Count NXT microplate scintillation counter. (The $K_i$ and $IC_{50}$ of a candidate inhibitor can be determined using commonly methods known in the art.

TABLE 1

Structural Coordinate of MEK1/N35/NKF (corresponding to amino acids 24, 383 of SEQ ID NO: 1) -compound 1-ATPγS Ternary Complex.

|  | A | B | C | D | E | F | G | H | I | J |
|---|---|---|---|---|---|---|---|---|---|---|
| ATOM | 1 | N | GLU | A | 62 | 12.940 | 67.410 | 47.451 | 1.00 | 28.03 |
| ATOM | 2 | CA | GLU | A | 62 | 12.043 | 66.230 | 47.367 | 1.00 | 26.21 |
| ATOM | 3 | C | GLU | A | 62 | 10.597 | 66.703 | 47.477 | 1.00 | 28.46 |
| ATOM | 4 | O | GLU | A | 62 | 10.321 | 67.591 | 48.274 | 1.00 | 37.72 |
| ATOM | 5 | CB | GLU | A | 62 | 12.418 | 65.207 | 48.451 | 1.00 | 23.90 |
| ATOM | 6 | CG | GLU | A | 62 | 11.357 | 64.202 | 48.778 | 1.00 | 20.44 |
| ATOM | 7 | CD | GLU | A | 62 | 11.724 | 62.786 | 48.290 | 1.00 | 31.76 |
| ATOM | 8 | OE1 | GLU | A | 62 | 12.349 | 62.022 | 49.092 | 1.00 | 26.74 |
| ATOM | 9 | OE2 | GLU | A | 62 | 11.388 | 62.415 | 47.097 | 1.00 | 32.03 |
| ATOM | 10 | N | LEU | A | 63 | 9.660 | 66.119 | 45.734 | 1.00 | 25.92 |
| ATOM | 11 | CA | LEU | A | 63 | 8.265 | 66.557 | 46.868 | 1.00 | 24.72 |
| ATOM | 12 | C | LEU | A | 63 | 7.532 | 65.822 | 47.999 | 1.00 | 30.28 |
| ATOM | 13 | O | LEU | A | 63 | 7.437 | 64.596 | 47.986 | 1.00 | 32.99 |
| ATOM | 14 | CB | LEU | A | 63 | 7.516 | 66.369 | 45.561 | 1.00 | 27.15 |
| ATOM | 15 | CG | LEU | A | 63 | 7.092 | 67.660 | 44.866 | 1.00 | 26.66 |
| ATOM | 16 | CD1 | LEU | A | 63 | 8.308 | 68.522 | 44.615 | 1.00 | 20.37 |
| ATOM | 17 | CD2 | LEU | A | 63 | 6.416 | 67.333 | 43.559 | 1.00 | 19.88 |
| ATOM | 18 | N | LYS | A | 64 | 7.032 | 66.587 | 48.979 | 1.00 | 34.73 |
| ATOM | 19 | CA | LYS | A | 64 | 6.314 | 66.061 | 50.163 | 1.00 | 33.2e |
| ATOM | 20 | C | LYS | A | 64 | 4.852 | 66.527 | 50.234 | 1.00 | 31.88 |
| ATOM | 21 | O | LYS | A | 64 | 4.489 | 67.558 | 49.665 | 1.00 | 33.72 |
| ATOM | 22 | CB | LYS | A | 64 | 7.012 | 66.506 | 51.457 | 1.00 | 34.83 |

TABLE 1-continued

Structural Coordinate of MEK1/N35/NKF (corresponding to amino acids 24, 383 of SEQ ID NO: 1) -compound 1-ATPγS Ternary Complex.

| | A | B | C | D | E | F | G | H | I | J |
|---|---|---|---|---|---|---|---|---|---|---|
| ATOM | 23 | CG | LYS | A | 64 | 8.334 | 65.814 | 51.749 | 1.00 | 39.38 |
| ATOM | 24 | CD | LYS | A | 64 | 8.725 | 65.963 | 53.220 | 1.00 | 39.15 |
| ATOM | 25 | CE | LYS | A | 64 | 9.104 | 67.394 | 53.560 | 1.00 | 38.49 |
| ATOM | 26 | NZ | LYS | A | 64 | 8.074 | 68.056 | 54.409 | 1.00 | 28.65 |
| ATOM | 27 | N | ASP | A | 65 | 4.019 | 65.788 | 50.960 | 1.00 | 27.94 |
| ATOM | 28 | CA | ASP | A | 65 | 2.610 | 66.152 | 51.081 | 1.00 | 27.09 |
| ATOM | 29 | C | ASP | A | 65 | 2.401 | 67.490 | 51.799 | 1.00 | 30.39 |
| ATOM | 30 | O | ASP | A | 65 | 1.569 | 68.307 | 51.384 | 1.00 | 26.56 |
| ATOM | 31 | CB | ASP | A | 65 | 1.841 | 65.052 | 51.818 | 1.00 | 28.31 |
| ATOM | 32 | CG | ASP | A | 65 | 0.369 | 65.404 | 52.029 | 1.00 | 26.42 |
| ATOM | 33 | OD1 | ASP | A | 65 | −0.271 | 65.977 | 51.121 | 1.00 | 28.69 |
| ATOM | 34 | OD2 | ASP | A | 65 | −0.157 | 65.097 | 53.112 | 1.00 | 37.08 |
| ATOM | 35 | N | ASP | A | 66 | 3.168 | 57.716 | 52.866 | 1.00 | 32.95 |
| ATOM | 36 | CA | ASP | A | 66 | 3.059 | 68.942 | 53.650 | 1.00 | 36.90 |
| ATOM | 37 | C | ASP | A | 66 | 3.490 | 70.222 | 52.950 | 1.00 | 33.30 |
| ATOM | 38 | O | ASP | A | 66 | 2.918 | 71.285 | 53.190 | 1.00 | 32.78 |
| ATOM | 39 | CB | ASP | A | 66 | 3.835 | 68.814 | 54.980 | 1.00 | 41.11 |
| ATOM | 40 | CG | ASP | A | 66 | 4.796 | 67.639 | 54.992 | 1.00 | 55.14 |
| ATOM | 41 | OD1 | ASP | A | 66 | 4.465 | 65.567 | 54.429 | 1.00 | 61.63 |
| ATOM | 42 | OD2 | ASP | A | 66 | 5.890 | 67.789 | 55.580 | 1.00 | 60.93 |
| ATOM | 43 | N | ASP | A | 67 | 4.482 | 70.127 | 52.072 | 1.00 | 26.09 |
| ATOM | 44 | CA | ASP | A | 67 | 4.960 | 71.297 | 51.351 | 1.00 | 19.83 |
| ATOM | 45 | C | ASP | A | 67 | 4.004 | 71.869 | 50.303 | 1.00 | 20.71 |
| ATOM | 46 | O | ASP | A | 67 | 4.411 | 72.730 | 49.522 | 1.00 | 21.95 |
| ATOM | 47 | CB | ASP | A | 67 | 6.305 | 70.973 | 50.714 | 1.00 | 24.28 |
| ATOM | 48 | CG | ASP | A | 67 | 7.344 | 70.566 | 51.744 | 1.00 | 28.79 |
| ATOM | 49 | OD1 | ASP | A | 67 | 8.526 | 70.350 | 51.387 | 1.00 | 23.75 |
| ATOM | 50 | OD2 | ASP | A | 67 | 6.967 | 70.463 | 52.928 | 1.00 | 32.90 |
| ATOM | 51 | N | PHE | A | 68 | 2.744 | 71.419 | 50.302 | 1.00 | 18.17 |
| ATOM | 52 | CA | PHE | A | 68 | 1.734 | 71.881 | 49.331 | 1.00 | 16.87 |
| ATOM | 53 | C | PHE | A | 68 | 0.581 | 72.579 | 50.010 | 1.00 | 17.08 |
| ATOM | 54 | O | PHE | A | 68 | 0.318 | 72.325 | 51.168 | 1.00 | 17.48 |
| ATOM | 55 | CB | PHE | A | 68 | 1.120 | 70.698 | 48.549 | 1.00 | 14.94 |
| ATOM | 56 | CG | PHE | A | 68 | 2.003 | 70.157 | 47.474 | 1.00 | 9.98 |
| ATOM | 57 | CD1 | PHE | A | 68 | 2.142 | 70.834 | 46.282 | 1.00 | 7.20 |
| ATOM | 58 | CD2 | PHE | A | 68 | 2.771 | 69.020 | 47.699 | 1.00 | 7.78 |
| ATOM | 59 | CE1 | PHE | A | 68 | 3.045 | 70.398 | 45.331 | 1.00 | 11.25 |
| ATOM | 60 | CE2 | PHE | A | 68 | 3.682 | 68.573 | 46.751 | 1.00 | 7.34 |
| ATOM | 61 | CZ | PHE | A | 68 | 3.825 | 69.261 | 45.565 | 1.00 | 2.26 |
| ATOM | 62 | N | GLU | A | 69 | −0.136 | 73.417 | 49.270 | 1.00 | 20.41 |
| ATOM | 63 | CA | GLU | A | 69 | −1.306 | 74.114 | 49.803 | 1.00 | 25.72 |
| ATOM | 64 | C | GLU | A | 69 | −2.348 | 74.210 | 48.688 | 1.00 | 26.45 |
| ATOM | 65 | O | GLU | A | 69 | −2.058 | 74.677 | 47.582 | 1.00 | 24.10 |
| ATOM | 66 | CB | GLU | A | 69 | −0.916 | 75.519 | 50.302 | 1.00 | 33.73 |
| ATOM | 67 | CG | GLU | A | 69 | −2.082 | 76.485 | 50.521 | 1.00 | 38.77 |
| ATOM | 68 | CD | GLU | A | 69 | −2.027 | 77.702 | 49.590 | 1.00 | 50.74 |
| ATOM | 69 | OE1 | GLU | A | 69 | −0.919 | 78.054 | 49.120 | 1.00 | 52.97 |
| ATOM | 70 | OE2 | CLU | A | 69 | −3.092 | 78.311 | 49.329 | 1.00 | 54.17 |
| ATOM | 71 | N | LYS | A | 70 | −3.561 | 73.766 | 48.978 | 1.00 | 25.31 |
| ATOM | 72 | CA | LYS | A | 70 | −4.622 | 73.790 | 47.981 | 1.00 | 28.72 |
| ATOM | 73 | C | LYS | A | 70 | −4.978 | 75.209 | 47.568 | 1.00 | 28.88 |
| ATOM | 74 | O | LYS | A | 70 | −5.259 | 76.043 | 48.417 | 1.00 | 34.75 |
| ATOM | 75 | CB | LYS | A | 70 | −5.872 | 73.086 | 48.527 | 1.00 | 30.22 |
| ATOM | 76 | CG | LYS | A | 70 | −6.453 | 71.999 | 47.639 | 1.00 | 31.99 |
| ATOM | 77 | CD | LYS | A | 70 | −6.321 | 70.626 | 48.308 | 1.00 | 39.75 |
| ATOM | 78 | CE | LYS | A | 70 | −7.674 | 70.068 | 48.767 | 1.00 | 38.07 |
| ATOM | 79 | NZ | LYS | A | 70 | −8.793 | 71.047 | 48.584 | 1.00 | 38.98 |
| ATOM | 80 | N | ILE | A | 71 | −4.969 | 75.478 | 46.268 | 1.00 | 28.54 |
| ATOM | 81 | CA | ILE | A | 71 | −5.334 | 76.791 | 45.746 | 1.00 | 27.55 |
| ATOM | 82 | C | ILE | A | 71 | −6.775 | 76.709 | 45.246 | 1.00 | 35.03 |
| ATOM | 83 | O | ILE | A | 71 | −7.598 | 77.253 | 45.869 | 1.00 | 36.66 |
| ATOM | 84 | CB | ILE | A | 71 | −4.437 | 77.206 | 44.567 | 1.00 | 25.58 |
| ATOM | 85 | CG1 | ILE | A | 71 | −3.056 | 77.621 | 45.073 | 1.00 | 26.32 |
| ATOM | 86 | CG2 | ILE | A | 71 | −5.077 | 78.344 | 43.807 | 1.00 | 18.03 |
| ATOM | 87 | CD1 | ILE | A | 71 | −2.044 | 77.843 | 43.957 | 1.00 | 29.25 |
| ATOM | 88 | N | SER | A | 72 | −6.967 | 76.020 | 44.120 | 1.00 | 37.32 |
| ATOM | 89 | CA | SER | A | 72 | −8.292 | 75.843 | 43.532 | 1.00 | 38.96 |
| ATOM | 90 | C | SER | A | 72 | −8.472 | 74.469 | 42.873 | 1.00 | 37.81 |
| ATOM | 91 | O | SER | A | 72 | −7.513 | 73.720 | 42.681 | 1.00 | 42.52 |
| ATOM | 92 | CB | SER | A | 72 | −8.562 | 76.941 | 42.513 | 1.00 | 39.00 |
| ATOM | 93 | OG | SER | A | 72 | −8.216 | 76.504 | 41.219 | 1.00 | 49.36 |
| ATOM | 94 | N | GLU | A | 73 | −9.712 | 74.145 | 42.533 | 1.00 | 37.27 |
| ATOM | 95 | CA | GLU | A | 73 | −10.049 | 72.861 | 41.908 | 1.00 | 38.21 |
| ATOM | 96 | C | GLU | A | 73 | −9.990 | 72.935 | 40.375 | 1.00 | 34.77 |
| ATOM | 97 | O | GLU | A | 73 | −10.731 | 73.703 | 39.767 | 1.00 | 34.23 |

TABLE 1-continued

Structural Coordinate of MEK1/N35/NKF (corresponding to amino acids 24, 383 of SEQ ID NO: 1) -compound 1-ATPγS Ternary Complex.

| | A | B | C | D | E | F | G | H | I | J |
|---|---|---|---|---|---|---|---|---|---|---|
| ATOM | 98 | CB | GLU | A | 73 | −11.451 | 72.443 | 42.359 | 1.00 | 38.55 |
| ATOM | 99 | CG | GLU | A | 73 | −12.140 | 71.452 | 41.453 | 1.00 | 51.45 |
| ATOM | 100 | CD | GLU | A | 73 | −12.088 | 70.042 | 42.004 | 1.00 | 59.57 |
| ATOM | 101 | OE1 | GLU | A | 73 | −13.130 | 69.349 | 41.951 | 1.00 | 62.16 |
| ATOM | 102 | OE2 | GLU | A | 73 | −11.006 | 69.632 | 42.492 | 1.00 | 62.93 |
| ATOM | 103 | N | LEU | A | 74 | −9.124 | 72.127 | 39.757 | 1.00 | 31.51 |
| ATOM | 104 | CA | LEU | A | 74 | −8.976 | 72.136 | 38.297 | 1.00 | 31.56 |
| ATOM | 105 | C | LEU | A | 74 | −9.999 | 71.287 | 37.534 | 1.00 | 32.39 |
| ATOM | 106 | O | LEU | A | 74 | −10.337 | 71.594 | 36.398 | 1.00 | 30.93 |
| ATOM | 107 | CB | LEU | A | 74 | −7.562 | 71.692 | 37.916 | 1.00 | 28.71 |
| ATOM | 108 | CG | LEU | A | 74 | −6.471 | 72.739 | 38.132 | 1.00 | 18.35 |
| ATOM | 109 | CD1 | LEU | A | 74 | −5.098 | 72.116 | 38.008 | 1.00 | 12.11 |
| ATOM | 110 | CD2 | LEU | A | 74 | −6.667 | 73.855 | 37.119 | 1.00 | 20.69 |
| ATOM | 111 | N | GLY | A | 75 | −10.488 | 70.225 | 38.166 | 1.00 | 32.15 |
| ATOM | 112 | CA | GLY | A | 75 | −11.461 | 69.360 | 37.537 | 1.00 | 29.95 |
| ATOM | 113 | C | GLY | A | 75 | −11.469 | 68.031 | 38.260 | 1.00 | 37.04 |
| ATOM | 114 | O | GLY | A | 75 | −10.642 | 67.802 | 39.155 | 1.00 | 33.34 |
| ATOM | 115 | N | ALA | A | 76 | −12.409 | 67.161 | 37.888 | 1.00 | 41.76 |
| ATOM | 116 | CA | ALA | A | 76 | −12.523 | 65.829 | 38.484 | 1.00 | 44.64 |
| ATOM | 117 | C | ALA | A | 76 | −12.840 | 64.839 | 37.384 | 1.00 | 45.64 |
| ATOM | 118 | O | ALA | A | 76 | −13.500 | 65.190 | 36.406 | 1.00 | 45.75 |
| ATOM | 119 | CB | ALA | A | 76 | −13.625 | 65.800 | 39.527 | 1.00 | 44.36 |
| ATOM | 120 | N | GLY | A | 77 | −12.368 | 63.607 | 37.545 | 1.00 | 45.50 |
| ATOM | 121 | CA | GLY | A | 77 | −12.630 | 62.595 | 36.544 | 1.00 | 47.02 |
| ATOM | 122 | C | GLY | A | 77 | −13.213 | 61.343 | 37.154 | 1.00 | 49.91 |
| ATOM | 123 | O | GLY | A | 77 | −13.645 | 61.349 | 38.307 | 1.00 | 48.60 |
| ATOM | 124 | N | ASN | A | 78 | −13.243 | 60.273 | 36.370 | 1.00 | 54.23 |
| ATOM | 125 | CA | ASN | A | 78 | −13.751 | 58.984 | 36.830 | 1.00 | 58.29 |
| ATOM | 126 | C | ASN | A | 78 | −12.739 | 58.499 | 37.856 | 1.00 | 57.46 |
| ATOM | 127 | O | ASN | A | 78 | −12.109 | 57.447 | 37.703 | 1.00 | 54.87 |
| ATOM | 128 | CB | ASN | A | 78 | −13.845 | 57.990 | 35.668 | 1.00 | 63.20 |
| ATOM | 129 | CG | ASN | A | 78 | −15.273 | 57.749 | 35.223 | 1.00 | 68.90 |
| ATOM | 130 | OD1 | ASN | A | 78 | −15.811 | 58.481 | 34.385 | 1.00 | 72.57 |
| ATOM | 131 | ND2 | ASN | A | 78 | −15.899 | 56.714 | 35.780 | 1.00 | 71.42 |
| ATOM | 132 | N | GLY | A | 79 | −12.252 | 59.429 | 38.677 | 1.00 | 56.32 |
| ATOM | 133 | CA | GLY | A | 79 | −11.319 | 59.123 | 39.734 | 1.00 | 58.97 |
| ATOM | 134 | C | GLY | A | 79 | −10.633 | 60.407 | 40.145 | 1.00 | 58.89 |
| ATOM | 135 | O | GLY | A | 79 | −11.286 | 61.417 | 40.443 | 1.00 | 60.02 |
| ATOM | 136 | N | GLY | A | 80 | −9.308 | 60.370 | 40.140 | 1.00 | 58.02 |
| ATOM | 137 | CA | GLY | A | 80 | −8.527 | 61.529 | 40.522 | 1.00 | 54.94 |
| ATOM | 138 | C | GLY | A | 80 | −9.133 | 62.902 | 40.305 | 1.00 | 50.91 |
| ATOM | 139 | O | GLY | A | 80 | −9.792 | 63.183 | 39.301 | 1.00 | 48.55 |
| ATOM | 140 | N | VAL | A | 81 | −8.943 | 63.755 | 41.301 | 1.00 | 49.95 |
| ATOM | 141 | CA | VAL | A | 81 | −9.390 | 65.134 | 41.213 | 1.00 | 43.61 |
| ATOM | 142 | C | VAL | A | 81 | −6.026 | 65.321 | 41.167 | 1.00 | 38.35 |
| ATOM | 143 | O | VAL | A | 81 | −7.054 | 65.306 | 41.713 | 1.00 | 35.63 |
| ATOM | 144 | CB | VAL | A | 81 | −10.167 | 65.591 | 42.450 | 1.00 | 42.16 |
| ATOM | 145 | CG1 | VAL | A | 81 | −9.246 | 65.619 | 43.667 | 1.00 | 41.39 |
| ATOM | 146 | CG2 | VAL | A | 91 | −10.767 | 66.956 | 42.186 | 1.00 | 33.43 |
| ATOM | 147 | N | VAL | A | 82 | −7.964 | 66.957 | 40.499 | 1.00 | 32.69 |
| ATOM | 148 | CA | VAL | A | 82 | −6.685 | 67.620 | 40.387 | 1.00 | 29.90 |
| ATOM | 149 | C | VAL | A | 82 | −6.786 | 69.066 | 40.830 | 1.00 | 27.01 |
| ATOM | 150 | O | VAL | A | 82 | −7.593 | 69.857 | 40.323 | 1.00 | 20.80 |
| ATOM | 151 | CB | VAL | A | 82 | −6.137 | 67.484 | 38.930 | 1.00 | 33.36 |
| ATOM | 152 | CG1 | VAL | A | 82 | −7.265 | 67.687 | 37.931 | 1.00 | 37.10 |
| ATOM | 153 | CG2 | VAL | A | 82 | −4.990 | 68.455 | 38.678 | 1.00 | 20.97 |
| ATOM | 154 | N | PHE | A | 83 | −5.953 | 69.393 | 41.804 | 1.00 | 27.74 |
| ATOM | 155 | CA | PHE | A | 83 | −5.934 | 70.727 | 42.373 | 1.00 | 24.71 |
| ATOM | 156 | C | PHE | A | 83 | −4.815 | 71.595 | 41.845 | 1.00 | 22.84 |
| ATOM | 157 | O | PHE | A | 83 | −3.691 | 71.123 | 41.611 | 1.00 | 18.52 |
| ATOM | 158 | CB | PHE | A | 83 | −5.780 | 70.645 | 43.893 | 1.00 | 25.25 |
| ATOM | 159 | CG | PHE | A | 83 | −6.806 | 69.778 | 44.580 | 1.00 | 27.67 |
| ATOM | 160 | CD1 | PHE | A | 83 | −6.448 | 68.537 | 45.097 | 1.00 | 27.58 |
| ATOM | 161 | CD2 | PHE | A | 83 | −8.105 | 70.241 | 44.791 | 1.00 | 29.64 |
| ATOM | 162 | CE1 | PHE | A | 83 | −7.367 | 67.770 | 45.823 | 1.00 | 29.02 |
| ATOM | 163 | CE2 | PHE | A | 83 | −9.034 | 69.486 | 45.517 | 1.00 | 25.35 |
| ATOM | 164 | CZ | PHE | A | 83 | −8.663 | 68.252 | 46.035 | 1.00 | 28.45 |
| ATOM | 165 | N | LYS | A | 84 | −5.133 | 72.871 | 41.645 | 1.00 | 21.05 |
| ATOM | 166 | CA | LYS | A | 84 | −4.115 | 73.831 | 41.247 | 1.00 | 22.35 |
| ATOM | 167 | C | LYS | A | 84 | −3.497 | 74.103 | 42.614 | 1.00 | 25.67 |
| ATOM | 168 | O | LYS | A | 84 | −4.208 | 74.494 | 43.532 | 1.00 | 25.09 |
| ATOM | 169 | CB | LYS | A | 84 | −4.752 | 75.111 | 40.729 | 1.00 | 24.32 |
| ATOM | 170 | CG | LYS | A | 84 | −3.888 | 76.329 | 40.947 | 1.00 | 28.32 |
| ATOM | 171 | CD | LYS | A | 84 | −3.882 | 77.202 | 39.721 | 1.00 | 30.68 |
| ATOM | 172 | CE | LYS | A | 84 | −4.360 | 78.502 | 40.049 | 1.00 | 27.51 |

TABLE 1-continued

Structural Coordinate of MEK1/N35/NKF (corresponding to amino acids 24, 383 of SEQ ID NO: 1) -compound 1-ATPγS Ternary Complex.

| | A | B | C | D | E | F | G | H | I | J |
|---|---|---|---|---|---|---|---|---|---|---|
| ATOM | 173 | NZ | LYS | A | 84 | −3.458 | 79.613 | 39.416 | 1.00 | 33.78 |
| ATOM | 174 | N | VAL | A | 85 | −2.200 | 73.881 | 42.778 | 1.00 | 25.76 |
| ATOM | 175 | CA | VAL | A | 85 | −1.601 | 74.104 | 44.078 | 1.00 | 21.15 |
| ATOM | 176 | C | VAL | A | 85 | −0.286 | 74.850 | 44.075 | 1.00 | 24.40 |
| ATOM | 177 | O | VAL | A | 85 | 0.292 | 75.150 | 43.023 | 1.00 | 23.45 |
| ATOM | 178 | CB | VAL | A | 85 | −1.363 | 72.775 | 44.840 | 1.00 | 19.62 |
| ATOM | 179 | CG1 | VAL | A | 85 | −2.621 | 71.936 | 44.838 | 1.00 | 21.31 |
| ATOM | 180 | CG2 | VAL | A | 85 | −0.191 | 72.022 | 44.222 | 1.00 | 22.44 |
| ATOM | 181 | N | SER | A | 86 | 0.180 | 75.144 | 45.287 | 1.00 | 23.79 |
| ATOM | 182 | CA | SER | A | 86 | 1.438 | 75.839 | 45.477 | 1.00 | 19.49 |
| ATOM | 183 | C | SER | A | 86 | 2.407 | 74.949 | 46.223 | 1.00 | 10.40 |
| ATOM | 184 | O | SER | A | 86 | 2.059 | 74.341 | 47.234 | 1.00 | 13.63 |
| ATOM | 125 | CB | SER | A | 86 | 1.234 | 77.133 | 46.269 | 1.00 | 24.55 |
| ATOM | 186 | OG | SER | A | 86 | 2.115 | 78.148 | 45.811 | 1.00 | 27.54 |
| ATOM | 187 | N | HIS | A | 87 | 3.618 | 74.835 | 45.703 | 1.00 | 3.09 |
| ATOM | 188 | CA | HIS | A | 87 | 4.620 | 74.049 | 46.390 | 1.00 | 8.82 |
| ATOM | 189 | C | HIS | A | 87 | 5.360 | 75.108 | 47.245 | 1.00 | 12.24 |
| ATOM | 190 | O | HIS | A | 87 | 6.223 | 75.836 | 46.750 | 1.00 | 6.71 |
| ATOM | 191 | CB | HIS | A | 87 | 5.548 | 73.399 | 45.377 | 1.00 | 1.00 |
| ATOM | 192 | CG | HIS | A | 87 | 6.689 | 72.668 | 46.001 | 1.00 | 1.00 |
| ATOM | 193 | ND2 | HIS | A | 87 | 8.006 | 72.938 | 45.688 | 1.00 | 5.69 |
| ATOM | 194 | CD2 | HIS | A | 87 | 6.715 | 71.673 | 46.923 | 1.00 | 1.00 |
| ATOM | 195 | CE1 | HIS | A | 87 | 8.797 | 72.138 | 46.388 | 1.00 | 5.77 |
| ATOM | 196 | NE2 | HIS | A | 87 | 8.040 | 71.361 | 47.145 | 1.00 | 1.06 |
| ATOM | 197 | N | LYS | A | 88 | 5.000 | 75.196 | 48.522 | 1.00 | 13.02 |
| ATOM | 198 | CA | LYS | A | 88 | 5.573 | 76.202 | 49.423 | 1.00 | 17.36 |
| ATOM | 199 | C | LYS | A | 88 | 7.076 | 76.409 | 49.386 | 1.00 | 11.97 |
| ATOM | 200 | O | LYS | A | 88 | 7.541 | 77.523 | 49.262 | 1.00 | 13.23 |
| ATOM | 201 | CB | LYS | A | 88 | 5.124 | 75.934 | 50.858 | 1.00 | 20.83 |
| ATOM | 202 | CG | LYS | A | 88 | 3.678 | 76.350 | 51.102 | 1.00 | 28.26 |
| ATOM | 203 | CD | LYS | A | 88 | 3.221 | 75.984 | 52.508 | 1.00 | 28.97 |
| ATOM | 204 | CE | LYS | A | 88 | 3.276 | 74.487 | 52.749 | 1.00 | 29.54 |
| ATOM | 205 | NZ | LYS | A | 88 | 2.380 | 74.110 | 53.878 | 1.00 | 31.27 |
| ATOM | 206 | N | PRO | A | 89 | 7.856 | 75.341 | 49.475 | 1.00 | 9.96 |
| ATOM | 207 | CA | PRO | A | 89 | 9.299 | 75.568 | 49.441 | 1.00 | 7.23 |
| ATOM | 208 | C | PRO | A | 89 | 9.855 | 76.249 | 48.196 | 1.00 | 16.13 |
| ATOM | 209 | O | PRO | A | 89 | 10.908 | 76.900 | 48.257 | 1.00 | 23.86 |
| ATOM | 210 | CB | PRO | A | 89 | 9.893 | 74.175 | 49.630 | 1.00 | 5.49 |
| ATOM | 211 | CG | PRO | A | 89 | 8.764 | 73.350 | 50.235 | 1.00 | 1.00 |
| ATOM | 212 | CD | PRO | A | 89 | 7.514 | 73.921 | 49.638 | 1.00 | 8.19 |
| ATOM | 213 | N | SER | A | 90 | 9.357 | 76.146 | 47.082 | 1.00 | 16.18 |
| ATOM | 214 | CA | SER | A | 90 | 9.924 | 76.718 | 45.868 | 1.00 | 10.05 |
| ATOM | 215 | C | SER | A | 90 | 9.163 | 77.895 | 45.293 | 1.00 | 6.20 |
| ATOM | 215 | O | SER | A | 90 | 9.698 | 78.654 | 44.482 | 1.00 | 7.89 |
| ATOM | 217 | CB | SER | A | 90 | 10.065 | 75.623 | 44.799 | 1.00 | 10.78 |
| ATOM | 218 | OG | SER | A | 90 | 8.830 | 75.438 | 44.109 | 1.00 | 14.16 |
| ATOM | 219 | N | GLY | A | 91 | 7.914 | 78.047 | 45.701 | 1.00 | 7.82 |
| ATOM | 220 | CA | GLY | A | 91 | 7.099 | 79.132 | 45.177 | 1.00 | 10.07 |
| ATOM | 221 | C | GLY | A | 91 | 6.483 | 78.805 | 43.819 | 1.00 | 14.60 |
| ATOM | 222 | O | GLY | A | 91 | 5.726 | 79.600 | 43.255 | 1.00 | 16.52 |
| ATOM | 223 | N | LEU | A | 92 | 6.810 | 77.634 | 43.284 | 1.00 | 16.87 |
| ATOM | 224 | CA | LEU | A | 92 | 6.276 | 77.217 | 41.984 | 1.00 | 16.33 |
| ATOM | 225 | C | LEU | A | 92 | 4.819 | 76.830 | 42.076 | 1.00 | 10.17 |
| ATOM | 226 | O | LEU | A | 92 | 4.432 | 76.080 | 42.965 | 1.00 | 14.79 |
| ATOM | 227 | CB | LEU | A | 92 | 7.036 | 76.006 | 41.446 | 1.00 | 16.49 |
| ATOM | 228 | CG | LEU | A | 92 | 8.361 | 76.234 | 40.733 | 1.00 | 21.57 |
| ATOM | 229 | CD1 | LEU | A | 92 | 8.965 | 74.884 | 40.321 | 1.00 | 18.61 |
| ATOM | 230 | CD2 | LEU | A | 92 | 8.121 | 77.137 | 39.534 | 1.00 | 24.00 |
| ATOM | 231 | N | VAL | A | 93 | 4.005 | 77.355 | 41.174 | 1.00 | 15.27 |
| ATOM | 232 | CA | VAL | A | 93 | 2.606 | 76.972 | 41.145 | 1.00 | 19.62 |
| ATOM | 233 | C | VAL | A | 93 | 2.639 | 75.648 | 40.369 | 1.00 | 19.33 |
| ATOM | 234 | O | VAL | A | 93 | 3.328 | 75.546 | 39.367 | 1.00 | 13.93 |
| ATOM | 235 | CB | VAL | A | 93 | 1.781 | 77.996 | 40.389 | 1.00 | 24.85 |
| ATOM | 236 | CG1 | VAL | A | 93 | 0.425 | 77.416 | 40.048 | 1.00 | 25.78 |
| ATOM | 237 | CG2 | VAL | A | 93 | 1.625 | 79.234 | 41.239 | 1.00 | 23.46 |
| ATOM | 238 | N | MET | A | 94 | 1.942 | 74.627 | 40.847 | 1.00 | 20.57 |
| ATOM | 239 | CA | MET | A | 94 | 1.942 | 73.330 | 40.171 | 1.00 | 17.95 |
| ATOM | 240 | C | MET | A | 94 | 0.515 | 72.802 | 40.015 | 1.00 | 20.55 |
| ATOM | 241 | O | MET | A | 94 | −0.446 | 73.432 | 40.466 | 1.00 | 22.33 |
| ATOM | 242 | CB | MET | A | 94 | 2.792 | 72.318 | 40.972 | 1.00 | 13.01 |
| ATOM | 243 | CG | MET | A | 94 | 4.288 | 72.662 | 41.016 | 1.00 | 12.46 |
| ATOM | 244 | SD | MET | A | 94 | 5.442 | 71.507 | 41.899 | 1.00 | 20.14 |
| ATOM | 245 | CE | MET | A | 94 | 4.357 | 70.506 | 42.641 | 1.00 | 14.00 |
| ATOM | 246 | N | ALA | A | 95 | 0.370 | 71.666 | 39.334 | 1.00 | 21.22 |
| ATOM | 247 | CA | ALA | A | 95 | −0.939 | 71.034 | 39.177 | 1.00 | 15.39 |

TABLE 1-continued

Structural Coordinate of MEK1/N35/NKF (corresponding to amino acids 24, 383 of SEQ ID NO: 1) -compound 1-ATPγS Ternary Complex.

| A | B | C | D | E | F | G | H | I | J |
|---|---|---|---|---|---|---|---|---|---|
| ATOM | 248 | C | ALA | A | 95 | −0.709 | 69.739 | 39.913 | 1.00 | 11.16 |
| ATOM | 249 | O | ALA | A | 95 | 0.290 | 69.059 | 39.685 | 1.00 | 10.36 |
| ATOM | 250 | CB | ALA | A | 95 | −1.260 | 70.779 | 37.722 | 1.00 | 16.97 |
| ATOM | 251 | N | ARG | A | 96 | −1.607 | 69.424 | 40.831 | 1.00 | 10.86 |
| ATOM | 252 | CA | ARG | A | 96 | −1.454 | 68.230 | 41.639 | 1.00 | 15.30 |
| ATOM | 253 | C | ARG | A | 96 | −2.601 | 67.273 | 41.394 | 1.00 | 17.68 |
| ATOM | 254 | O | ARG | A | 96 | −3.763 | 67.622 | 41.628 | 1.00 | 13.31 |
| ATOM | 255 | CB | ARG | A | 96 | −1.409 | 68.593 | 43.123 | 1.00 | 10.74 |
| ATOM | 256 | CG | ARG | A | 96 | −0.782 | 67.522 | 43.995 | 1.00 | 13.38 |
| ATOM | 257 | CD | ARG | A | 96 | −1.303 | 67.569 | 45.424 | 1.00 | 9.56 |
| ATOM | 258 | NE | ARG | A | 96 | −0.663 | 66.525 | 46.231 | 1.00 | 12.31 |
| ATOM | 259 | CZ | ARG | A | 96 | −0.697 | 66.476 | 47.560 | 1.00 | 20.63 |
| ATOM | 260 | NH1 | ARG | A | 96 | −1.344 | 67.404 | 48.248 | 1.00 | 19.12 |
| ATOM | 261 | NH2 | ARG | A | 96 | −0.076 | 65.494 | 48.198 | 1.00 | 19.24 |
| ATOM | 262 | N | LYS | A | 97 | −2.259 | 66.072 | 40.927 | 1.00 | 12.88 |
| ATOM | 263 | CA | LYS | A | 97 | −3.261 | 65.056 | 40.649 | 1.00 | 12.90 |
| ATOM | 244 | C | LYS | A | 97 | −3.255 | 64.014 | 41.750 | 1.00 | 10.35 |
| ATOM | 265 | O | LYS | A | 97 | −2.201 | 63.467 | 42.100 | 1.00 | 5.88 |
| ATOM | 266 | CB | LYS | A | 97 | −2.986 | 64.371 | 39.306 | 1.00 | 14.50 |
| ATOM | 267 | CG | LYS | A | 97 | −4.206 | 63.451 | 38.755 | 1.00 | 19.32 |
| ATOM | 268 | CD | LYS | A | 97 | −3.838 | 62.375 | 38.035 | 1.00 | 20.95 |
| ATOM | 269 | CE | LYS | A | 97 | −3.724 | 62.620 | 36.529 | 1.00 | 21.39 |
| ATOM | 270 | NZ | LYS | A | 97 | −5.054 | 62.747 | 35.884 | 1.00 | 17.49 |
| ATOM | 271 | N | LEU | A | 98 | −4.439 | 63.755 | 42.300 | 1.00 | 10.40 |
| ATOM | 272 | CA | LEU | A | 98 | −4.583 | 62.761 | 43.362 | 1.00 | 18.06 |
| ATOM | 273 | C | LEU | A | 98 | −5.347 | 61.541 | 42.829 | 1.00 | 20.34 |
| ATOM | 274 | O | LEU | A | 98 | −6.488 | 61.667 | 42.381 | 1.00 | 16.59 |
| ATOM | 275 | CB | LEU | A | 98 | −5.364 | 63.345 | 44.556 | 1.00 | 18.48 |
| ATOM | 276 | CG | LEU | A | 98 | −4.781 | 64.419 | 45.490 | 1.00 | 20.58 |
| ATOM | 277 | CD1 | LEU | A | 98 | −3.278 | 64.248 | 45.674 | 1.00 | 17.70 |
| ATOM | 278 | CD2 | LEU | A | 98 | −5.105 | 65.778 | 44.912 | 1.00 | 19.25 |
| ATOM | 279 | N | ILE | A | 99 | −4.720 | 60.373 | 42.879 | 1.00 | 20.85 |
| ATOM | 280 | CA | ILE | A | 99 | −5.371 | 59.148 | 42.424 | 1.00 | 22.57 |
| ATOM | 281 | C | ILE | A | 99 | −5.527 | 58.292 | 43.658 | 1.00 | 23.36 |
| ATOM | 282 | O | ILE | A | 99 | −4.527 | 57.874 | 44.228 | 1.00 | 23.15 |
| ATOM | 283 | CB | ILE | A | 99 | −4.497 | 58.367 | 41.396 | 1.00 | 21.07 |
| ATOM | 284 | CG1 | ILE | A | 99 | −4.331 | 59.176 | 40.120 | 1.00 | 15.13 |
| ATOM | 285 | CG2 | ILE | A | 99 | −5.147 | 57.041 | 41.045 | 1.00 | 12.27 |
| ATOM | 286 | CD1 | ILE | A | 99 | −3.179 | 58.706 | 39.279 | 1.00 | 20.74 |
| ATOM | 287 | N | HIS | A | 100 | −6.760 | 58.026 | 44.068 | 1.00 | 28.19 |
| ATOM | 288 | CA | HIS | A | 100 | −6.976 | 57.222 | 45.259 | 1.00 | 38.68 |
| ATOM | 289 | C | HIS | A | 100 | −6.171 | 55.939 | 45.207 | 1.00 | 44.03 |
| ATOM | 290 | O | HIS | A | 100 | −4.965 | 55.962 | 45.453 | 1.00 | 51.48 |
| ATOM | 291 | CB | HIS | A | 100 | −8.451 | 56.884 | 45.448 | 1.00 | 48.27 |
| ATOM | 292 | CG | HIS | A | 100 | −8.786 | 56.403 | 46.831 | 1.00 | 57.92 |
| ATOM | 293 | ND1 | HIS | A | 100 | −9.109 | 57.263 | 47.862 | 1.00 | 61.52 |
| ATOM | 294 | CD2 | HIS | A | 100 | −8.860 | 55.153 | 47.351 | 1.00 | 61.56 |
| ATOM | 295 | CE1 | HIS | A | 100 | −9.366 | 56.560 | 48.953 | 1.00 | 62.93 |
| ATOM | 296 | NE2 | HIS | A | 100 | −9.222 | 55.279 | 48.670 | 1.00 | 61.73 |
| ATOM | 297 | N | LEU | A | 101 | −6.829 | 54.825 | 44.906 | 1.00 | 44.60 |
| ATOM | 298 | CA | LEU | A | 101 | −6.155 | 53.528 | 44.825 | 1.00 | 50.23 |
| ATOM | 299 | C | LEU | A | 101 | −5.981 | 52.796 | 46.157 | 1.00 | 54.39 |
| ATOM | 300 | O | LEU | A | 101 | −4.959 | 52.953 | 46.830 | 1.00 | 55.41 |
| ATOM | 301 | CB | LEU | A | 101 | −4.772 | 53.678 | 44.172 | 1.00 | 46.54 |
| ATOM | 302 | CG | LEU | A | 101 | −4.630 | 53.469 | 42.664 | 1.00 | 45.94 |
| ATOM | 303 | CD1 | LEU | A | 101 | −5.952 | 53.758 | 41.964 | 1.00 | 42.83 |
| ATOM | 304 | CD2 | LEU | A | 101 | −3.532 | 54.375 | 42.141 | 1.00 | 44.78 |
| ATOM | 305 | N | GLU | A | 102 | −6.972 | 51.992 | 46.538 | 1.00 | 59.17 |
| ATOM | 306 | CA | GLU | A | 102 | −6.881 | 51.214 | 47.770 | 1.00 | 62.37 |
| ATOM | 307 | C | GLU | A | 102 | −5.890 | 50.108 | 47.445 | 1.00 | 63.05 |
| ATOM | 308 | O | CLU | A | 102 | −6.278 | 49.016 | 47.022 | 1.00 | 61.68 |
| ATOM | 309 | CB | GLU | A | 102 | −8.231 | 50.591 | 48.114 | 1.00 | 66.19 |
| ATOM | 310 | CG | GLU | A | 102 | −9.194 | 51.509 | 48.830 | 1.00 | 69.48 |
| ATOM | 311 | CD | GLU | A | 102 | −10.620 | 50.986 | 48.778 | 1.00 | 73.92 |
| ATOM | 312 | OE1 | GLU | A | 102 | −11.551 | 51.758 | 49.092 | 1.00 | 75.92 |
| ATOM | 313 | OE2 | GLU | A | 102 | −10.809 | 49.798 | 48.420 | 1.00 | 75.32 |
| ATOM | 314 | N | ILE | A | 103 | −4.609 | 50.396 | 47.638 | 1.00 | 63.66 |
| ATOM | 315 | CA | ILE | A | 103 | −3.569 | 49.433 | 47.323 | 1.00 | 63.02 |
| ATOM | 316 | C | ILE | A | 103 | −2.514 | 49.276 | 48.421 | 1.00 | 62.06 |
| ATOM | 317 | O | ILE | A | 103 | −2.196 | 50.226 | 49.137 | 1.00 | 60.99 |
| ATOM | 318 | CB | ILE | A | 103 | −2.911 | 49.819 | 45.966 | 1.00 | 64.69 |
| ATOM | 319 | CC1 | ILE | A | 103 | −3.096 | 48.670 | 44.969 | 1.00 | 66.53 |
| ATOM | 320 | CG2 | ILE | A | 103 | −1.444 | 50.189 | 46.152 | 1.00 | 64.43 |
| ATOM | 321 | CD1 | ILE | A | 103 | −4.552 | 48.370 | 44.627 | 1.00 | 66.64 |
| ATOM | 322 | N | LYS | A | 104 | −1.726 | 48.254 | 48.093 | 1.00 | 61.54 |

TABLE 1-continued

Structural Coordinate of MEK1/N35/NKF (corresponding to amino acids 24, 383 of SEQ ID NO: 1) -compound 1-ATPγS Ternary Complex.

| | A | B | C | D | E | F | G | H | I | J |
|---|---|---|---|---|---|---|---|---|---|---|
| ATOM | 323 | CA | LYS | A | 104 | −0.679 | 47.919 | 49.051 | 1.00 | 60.52 |
| ATOM | 324 | CB | LYS | A | 104 | −0.492 | 46.413 | 49.121 | 1.00 | 58.91 |
| ATOM | 325 | C | LYS | A | 104 | 0.629 | 48.584 | 48.673 | 1.00 | 61.97 |
| ATOM | 326 | O | LYS | A | 104 | 0.992 | 48.655 | 47.499 | 1.00 | 60.13 |
| ATOM | 327 | N | PRO | A | 105 | 1.359 | 49.078 | 49.675 | 1.00 | 65.06 |
| ATOM | 328 | CA | PRO | A | 105 | 2.644 | 49.749 | 49.458 | 1.00 | 57.05 |
| ATOM | 329 | C | PRO | A | 105 | 3.551 | 49.093 | 48.414 | 1.00 | 62.23 |
| ATOM | 330 | O | PRO | A | 105 | 4.335 | 49.774 | 47.754 | 1.00 | 62.64 |
| ATOM | 331 | CB | PRO | A | 105 | 3.270 | 49.771 | 50.850 | 1.00 | 66.56 |
| ATOM | 332 | CG | PRO | A | 105 | 2.077 | 49.836 | 51.774 | 1.00 | 66.22 |
| ATOM | 333 | CD | PRO | A | 105 | 0.986 | 49.038 | 51.104 | 1.00 | 65.58 |
| ATOM | 334 | N | ALA | A | 106 | 3.434 | 47.779 | 48.259 | 1.00 | 58.75 |
| ATOM | 335 | CA | ALA | A | 106 | 4.264 | 47.058 | 47.300 | 1.00 | 58.46 |
| ATOM | 336 | C | ALA | A | 106 | 4.110 | 47.610 | 45.888 | 1.00 | 58.13 |
| ATOM | 337 | O | ALA | A | 106 | 5.089 | 47.981 | 45.239 | 1.00 | 58.54 |
| ATOM | 338 | CB | ALA | A | 106 | 3.919 | 45.572 | 47.320 | 1.00 | 60.71 |
| ATOM | 339 | N | ILE | A | 107 | 2.871 | 47.663 | 45.413 | 1.00 | 55.28 |
| ATOM | 340 | CA | ILE | A | 107 | 2.598 | 48.157 | 44.078 | 1.00 | 52.31 |
| ATOM | 341 | C | ILE | A | 107 | 2.651 | 49.674 | 44.051 | 1.00 | 50.31 |
| ATOM | 342 | O | ILE | A | 107 | 3.221 | 50.274 | 43.134 | 1.00 | 46.96 |
| ATOM | 343 | CB | ILE | A | 107 | 1.215 | 47.657 | 43.569 | 1.00 | 51.94 |
| ATOM | 344 | CG1 | ILE | A | 107 | 0.301 | 48.833 | 43.239 | 1.00 | 53.37 |
| ATOM | 345 | CG2 | ILE | A | 107 | 0.564 | 46.769 | 44.609 | 1.00 | 48.92 |
| ATOM | 346 | CD1 | ILE | A | 107 | −0.829 | 48.461 | 42.317 | 1.00 | 54.73 |
| ATOM | 347 | N | ARG | A | 108 | 2.048 | 50.290 | 45.058 | 1.00 | 49.04 |
| ATOM | 348 | CA | ARG | A | 108 | 2.041 | 51.739 | 45.148 | 1.00 | 50.88 |
| ATOM | 349 | C | ARG | A | 108 | 3.484 | 52.212 | 44.963 | 1.00 | 50.50 |
| ATOM | 350 | O | ARG | A | 108 | 3.748 | 53.277 | 44.408 | 1.00 | 50.31 |
| ATOM | 351 | CB | ARG | A | 108 | 1.453 | 52.165 | 46.507 | 1.00 | 53.74 |
| ATOM | 352 | CG | ARG | A | 108 | 2.097 | 53.360 | 47.203 | 1.00 | 56.24 |
| ATOM | 353 | CD | ARG | A | 108 | 2.878 | 52.911 | 48.434 | 1.00 | 62.62 |
| ATOM | 354 | NE | ARG | A | 108 | 2.140 | 53.036 | 49.695 | 1.00 | 69.85 |
| ATOM | 355 | CZ | ARG | A | 108 | 1.013 | 52.385 | 49.993 | 1.00 | 72.41 |
| ATOM | 356 | NH1 | ARG | A | 108 | 0.464 | 51.552 | 49.119 | 1.00 | 73.73 |
| ATOM | 357 | NH2 | ARG | A | 108 | 0.441 | 52.546 | 51.181 | 1.00 | 69.61 |
| ATOM | 358 | N | ASN | A | 109 | 4.425 | 51.389 | 45.392 | 1.00 | 50.46 |
| ATOM | 359 | CA | ASN | A | 109 | 5.821 | 51.761 | 45.251 | 1.00 | 52.25 |
| ATOM | 360 | C | ASN | A | 109 | 6.312 | 51.470 | 43.840 | 1.00 | 48.73 |
| ATOM | 361 | O | ASN | A | 109 | 7.301 | 52.045 | 43.382 | 1.00 | 48.58 |
| ATOM | 362 | CB | ASN | A | 109 | 6.657 | 51.027 | 46.299 | 1.00 | 56.94 |
| ATOM | 363 | CG | ASN | A | 109 | 6.752 | 51.806 | 47.602 | 1.00 | 61.09 |
| ATOM | 364 | OD1 | ASN | A | 109 | 7.593 | 52.696 | 47.743 | 1.00 | 63.41 |
| ATOM | 365 | ND2 | ASN | A | 109 | 5.878 | 51.487 | 48.554 | 1.00 | 60.81 |
| ATOM | 366 | N | GLN | A | 110 | 5.606 | 50.580 | 43.154 | 1.00 | 43.67 |
| ATOM | 367 | CA | GLN | A | 110 | 5.939 | 50.231 | 41.779 | 1.00 | 38.75 |
| ATOM | 368 | C | GLN | A | 110 | 5.528 | 51.412 | 40.914 | 1.00 | 33.27 |
| ATOM | 369 | O | GLN | A | 110 | 6.290 | 51.902 | 40.074 | 1.00 | 29.57 |
| ATOM | 370 | CB | GLN | A | 110 | 5.146 | 49.002 | 41.346 | 1.00 | 42.20 |
| ATOM | 371 | CG | GLN | A | 110 | 5.994 | 47.798 | 41.036 | 1.00 | 46.47 |
| ATOM | 372 | CD | GLN | A | 110 | 6.219 | 47.637 | 39.565 | 1.00 | 49.63 |
| ATOM | 373 | OE1 | GLN | A | 110 | 7.285 | 47.982 | 39.044 | 1.00 | 54.15 |
| ATOM | 374 | NE2 | GLN | A | 110 | 5.214 | 47.110 | 38.872 | 1.00 | 45.60 |
| ATOM | 375 | N | ILE | A | 111 | 4.299 | 51.859 | 41.141 | 1.00 | 28.70 |
| ATOM | 376 | CA | ILE | A | 111 | 3.729 | 52.975 | 40.410 | 1.00 | 25.95 |
| ATOM | 377 | C | ILE | A | 111 | 4.623 | 54.193 | 40.542 | 1.00 | 28.35 |
| ATOM | 378 | O | ILE | A | 111 | 5.064 | 54.778 | 39.544 | 1.00 | 26.58 |
| ATOM | 379 | CB | ILE | A | 111 | 2.323 | 53.282 | 40.943 | 1.00 | 22.15 |
| ATOM | 380 | CG1 | ILE | A | 111 | 1.436 | 52.068 | 40.671 | 1.00 | 19.12 |
| ATOM | 381 | CG2 | ILE | A | 111 | 1.773 | 54.560 | 40.312 | 1.00 | 23.20 |
| ATOM | 382 | CD1 | ILE | A | 111 | −0.010 | 52.265 | 40.973 | 1.00 | 18.46 |
| ATOM | 383 | N | ILE | A | 112 | 4.906 | 54.572 | 41.783 | 1.00 | 30.27 |
| ATOM | 384 | CA | ILE | A | 112 | 5.769 | 55.719 | 42.025 | 1.00 | 27.04 |
| ATOM | 385 | C | ILE | A | 112 | 7.076 | 55.464 | 41.286 | 1.00 | 22.92 |
| ATOM | 386 | O | ILE | A | 112 | 7.611 | 56.354 | 40.621 | 1.00 | 19.56 |
| ATOM | 387 | CB | ILE | A | 112 | 6.061 | 55.900 | 43.543 | 1.00 | 24.82 |
| ATOM | 388 | CG1 | ILE | A | 112 | 4.768 | 56.194 | 44.298 | 1.00 | 21.88 |
| ATOM | 389 | CG2 | ILE | A | 112 | 7.038 | 57.033 | 43.753 | 1.00 | 23.61 |
| ATOM | 390 | CD1 | ILE | A | 112 | 4.092 | 57.454 | 43.848 | 1.00 | 21.37 |
| ATOM | 391 | N | ARG | A | 113 | 7.572 | 54.233 | 41.397 | 1.00 | 24.68 |
| ATOM | 392 | CA | ARG | A | 113 | 8.827 | 53.844 | 40.761 | 1.00 | 32.12 |
| ATOM | 393 | C | ARG | A | 113 | 8.775 | 54.037 | 39.253 | 1.00 | 32.48 |
| ATOM | 394 | O | ARG | A | 113 | 9.687 | 54.605 | 38.651 | 1.00 | 31.61 |
| ATOM | 395 | CB | ARG | A | 113 | 9.142 | 52.380 | 41.087 | 1.00 | 40.11 |
| ATOM | 396 | CG | ARG | A | 113 | 10.500 | 51.890 | 40.573 | 1.00 | 47.47 |
| ATOM | 397 | CD | ARG | A | 113 | 10.621 | 50.359 | 40.667 | 1.00 | 53.84 |

TABLE 1-continued

Structural Coordinate of MEK1/N35/NKF (corresponding to amino acids 24, 383 of SEQ ID NO: 1) -compound 1-ATPγS Ternary Complex.

| | A | B | C | D | E | F | G | H | I | J |
|---|---|---|---|---|---|---|---|---|---|---|
| ATOM | 398 | NE | ARG | A | 113 | 9.978 | 49.647 | 39.558 | 1.00 | 60.99 |
| ATOM | 399 | CZ | ARG | A | 113 | 10.400 | 49.674 | 38.292 | 1.00 | 61.37 |
| ATOM | 400 | NH1 | ARG | A | 113 | 11.475 | 50.383 | 37.967 | 1.00 | 57.24 |
| ATOM | 401 | NH2 | AEG | A | 113 | 9.750 | 48.990 | 37.353 | 1.00 | 60.78 |
| ATOM | 402 | N | GLU | A | 114 | 7.698 | 53.563 | 38.641 | 1.00 | 32.96 |
| ATOM | 403 | CA | GLU | A | 114 | 7.552 | 53.686 | 37.203 | 1.00 | 32.82 |
| ATOM | 404 | C | GLU | A | 114 | 7.257 | 55.128 | 36.791 | 1.00 | 29.09 |
| ATOM | 405 | O | GLU | A | 114 | 7.623 | 55.552 | 35.694 | 1.00 | 31.16 |
| ATOM | 406 | CB | GLU | A | 114 | 6.434 | 52.762 | 36.713 | 1.00 | 35.46 |
| ATOM | 407 | CG | GLU | A | 114 | 6.780 | 51.276 | 36.748 | 1.00 | 32.07 |
| ATOM | 408 | CD | GLU | A | 114 | 5.548 | 50.389 | 36.575 | 1.00 | 33.44 |
| ATOM | 409 | OE1 | GLU | A | 114 | 5.682 | 49.148 | 36.661 | 1.00 | 26.76 |
| ATOM | 410 | OE2 | GLU | A | 114 | 4.445 | 50.938 | 36.356 | 1.00 | 32.15 |
| ATOM | 411 | N | LEU | A | 115 | 6.604 | 55.879 | 37.675 | 1.00 | 27.10 |
| ATOM | 412 | CA | LEU | A | 115 | 6.246 | 57.275 | 37.394 | 1.00 | 22.36 |
| ATOM | 413 | C | LEU | A | 115 | 7.469 | 58.173 | 37.263 | 1.00 | 17.92 |
| ATOM | 414 | O | LEU | A | 115 | 7.376 | 59.271 | 36.735 | 1.00 | 20.20 |
| ATOM | 415 | CB | LEU | A | 115 | 5.346 | 57.816 | 38.496 | 1.00 | 20.05 |
| ATOM | 416 | CG | LEU | A | 115 | 3.862 | 58.060 | 38.262 | 1.00 | 23.53 |
| ATOM | 417 | CD1 | LEU | A | 115 | 3.373 | 57.359 | 36.998 | 1.00 | 21.23 |
| ATOM | 418 | CD2 | LEU | A | 115 | 3.114 | 57.560 | 39.497 | 1.00 | 18.45 |
| ATOM | 419 | N | GLN | A | 116 | 8.613 | 57.696 | 37.737 | 1.00 | 22.74 |
| ATOM | 420 | CA | GLN | A | 116 | 9.864 | 58.459 | 37.667 | 1.00 | 24.78 |
| ATOM | 421 | C | GLN | A | 116 | 10.324 | 58.700 | 36.234 | 1.00 | 25.45 |
| ATOM | 422 | O | GLN | A | 116 | 11.097 | 59.628 | 35.963 | 1.00 | 25.15 |
| ATOM | 423 | CB | GLN | A | 116 | 10.971 | 57.737 | 38.446 | 1.00 | 28.20 |
| ATOM | 424 | CG | GLN | A | 116 | 10.715 | 57.643 | 39.945 | 1.00 | 26.03 |
| ATOM | 425 | CD | GLN | A | 116 | 10.050 | 58.897 | 40.494 | 1.00 | 28.65 |
| ATOM | 426 | OE1 | GLN | A | 116 | 9.010 | 58.831 | 41.159 | 1.00 | 26.29 |
| ATOM | 427 | NE2 | GLN | A | 116 | 10.648 | 60.048 | 40.208 | 1.00 | 29.16 |
| ATOM | 428 | N | VAL | A | 117 | 9.863 | 57.859 | 35.312 | 1.00 | 25.17 |
| ATOM | 429 | CA | VAL | A | 117 | 10.234 | 58.015 | 33.912 | 1.00 | 19.53 |
| ATOM | 430 | C | VAL | A | 117 | 9.818 | 59.396 | 33.420 | 1.00 | 15.32 |
| ATOM | 431 | O | VAL | A | 117 | 10.439 | 59.960 | 32.525 | 1.00 | 16.56 |
| ATOM | 432 | CB | VAL | A | 117 | 9.544 | 56.953 | 33.027 | 1.00 | 25.29 |
| ATOM | 433 | CG1 | VAL | A | 117 | 9.977 | 57.133 | 31.572 | 1.00 | 14.32 |
| ATOM | 434 | CG2 | VAL | A | 117 | 9.884 | 55.553 | 33.536 | 1.00 | 22.83 |
| ATOM | 435 | N | LEU | A | 118 | 6.766 | 59.946 | 34.012 | 1.00 | 15.33 |
| ATOM | 436 | CA | LEU | A | 118 | 8.283 | 61.251 | 33.604 | 1.00 | 17.15 |
| ATOM | 437 | C | LEU | A | 118 | 9.336 | 62.370 | 33.663 | 1.00 | 22.71 |
| ATOM | 438 | O | LEU | A | 118 | 9.242 | 63.351 | 32.921 | 1.00 | 26.93 |
| ATOM | 439 | CB | LEU | A | 118 | 7.031 | 61.600 | 34.416 | 1.00 | 15.11 |
| ATOM | 440 | CG | LEU | A | 118 | 5.842 | 60.711 | 34.018 | 1.00 | 14.00 |
| ATOM | 441 | CD1 | LEU | A | 118 | 4.633 | 60.981 | 34.919 | 1.00 | 14.63 |
| ATOM | 442 | CD2 | LEU | A | 118 | 5.482 | 60.931 | 32.558 | 1.00 | 9.57 |
| ATOM | 443 | N | HIS | A | 119 | 10.349 | 62.232 | 34.516 | 1.00 | 27.09 |
| ATOM | 444 | CA | HIS | A | 119 | 11.396 | 63.252 | 34.559 | 1.00 | 29.55 |
| ATOM | 445 | C | HIS | A | 119 | 12.154 | 63.291 | 33.259 | 1.00 | 31.74 |
| ATOM | 446 | O | HIS | A | 119 | 12.706 | 64.319 | 32.877 | 1.00 | 34.17 |
| ATOM | 447 | CB | HIS | A | 119 | 12.379 | 62.948 | 35.727 | 1.00 | 29.68 |
| ATOM | 448 | CG | HIS | A | 119 | 11.936 | 63.459 | 37.064 | 1.00 | 31.58 |
| ATOM | 449 | ND1 | HIS | A | 119 | 11.756 | 62.632 | 38.156 | 1.00 | 31.57 |
| ATOM | 450 | CD2 | HIS | A | 119 | 11.628 | 64.710 | 37.485 | 1.00 | 27.98 |
| ATOM | 451 | CE1 | HIS | A | 119 | 11.355 | 63.361 | 39.190 | 1.00 | 30.22 |
| ATOM | 452 | NE2 | HIS | A | 119 | 11.269 | 64.615 | 38.809 | 1.00 | 29.65 |
| ATOM | 453 | N | GLU | A | 120 | 12.162 | 62.160 | 32.557 | 1.00 | 35.07 |
| ATOM | 454 | CA | CLU | A | 120 | 12.845 | 62.026 | 31.269 | 1.00 | 37.51 |
| ATOM | 455 | C | GLU | A | 120 | 12.017 | 62.460 | 30.049 | 1.00 | 36.81 |
| ATOM | 456 | O | GLU | A | 120 | 12.545 | 62.516 | 28.934 | 1.00 | 35.68 |
| ATOM | 457 | CB | GLU | A | 120 | 13.298 | 60.574 | 31.066 | 1.00 | 42.16 |
| ATOM | 458 | CG | GLU | A | 120 | 14.538 | 60.182 | 31.840 | 1.00 | 49.57 |
| ATOM | 459 | CD | GLU | A | 120 | 14.733 | 61.019 | 33.090 | 1.00 | 57.79 |
| ATOM | 460 | OE1 | GLU | A | 120 | 14.567 | 60.474 | 34.202 | 1.00 | 62.52 |
| ATOM | 461 | OE2 | GLU | A | 120 | 15.056 | 62.221 | 32.958 | 1.00 | 62.85 |
| ATOM | 462 | N | CYS | A | 121 | 10.733 | 62.759 | 30.244 | 1.00 | 32.92 |
| ATOM | 463 | CA | CYS | A | 121 | 9.898 | 63.193 | 29.130 | 1.00 | 31.31 |
| ATOM | 464 | C | CYS | A | 121 | 9.896 | 64.712 | 29.013 | 1.00 | 33.30 |
| ATOM | 465 | O | CYS | A | 121 | 9.010 | 65.391 | 29.531 | 1.00 | 38.11 |
| ATOM | 466 | CB | CYS | A | 121 | 8.465 | 62.674 | 29.289 | 1.00 | 27.73 |
| ATOM | 467 | SG | CYS | A | 121 | 8.354 | 60.868 | 29.314 | 1.00 | 23.47 |
| ATOM | 468 | N | ASN | A | 122 | 10.507 | 65.239 | 28.335 | 1.00 | 34.97 |
| ATOM | 469 | CA | ASN | A | 122 | 11.031 | 66.675 | 28.125 | 1.00 | 35.34 |
| ATOM | 470 | C | ASN | A | 122 | 10.749 | 66.978 | 26.666 | 1.00 | 31.05 |
| ATOM | 471 | O | ASN | A | 122 | 11.443 | 66.482 | 25.776 | 1.00 | 32.36 |
| ATOM | 472 | CB | ASN | A | 122 | 12.444 | 67.165 | 28.494 | 1.00 | 38.97 |

TABLE 1-continued

Structural Coordinate of MEK1/N35/NKF (corresponding to amino acids 24, 383 of SEQ ID NO: 1) -compound 1-ATPγS Ternary Complex.

| | A | B | C | D | E | F | G | H | I | J |
|---|---|---|---|---|---|---|---|---|---|---|
| ATOM | 473 | CG | ASN | A | 122 | 13.107 | 66.307 | 29.558 | 1.00 | 44.55 |
| ATOM | 474 | OD1 | ASN | A | 122 | 12.533 | 66.056 | 30.618 | 1.00 | 45.39 |
| ATOM | 475 | ND2 | ASN | A | 122 | 14.327 | 65.853 | 29.280 | 1.00 | 49.17 |
| ATOM | 476 | N | SER | A | 123 | 9.727 | 67.783 | 26.410 | 1.00 | 26.32 |
| ATOM | 477 | CA | SER | A | 123 | 9.373 | 68.112 | 25.040 | 1.00 | 25.49 |
| ATOM | 478 | C | SER | A | 123 | 8.308 | 69.189 | 24.973 | 1.00 | 24.33 |
| ATOM | 479 | O | SER | A | 123 | 7.322 | 69.150 | 25.695 | 1.00 | 29.83 |
| ATOM | 480 | CB | SER | A | 123 | 8.866 | 66.864 | 24.305 | 1.00 | 23.27 |
| ATOM | 481 | OG | SER | A | 123 | 7.775 | 67.188 | 23.453 | 1.00 | 23.75 |
| ATOM | 482 | N | PRO | A | 124 | 8.491 | 70.160 | 24.077 | 1.00 | 23.95 |
| ATOM | 483 | CA | PRO | A | 124 | 7.546 | 71.263 | 23.898 | 1.00 | 22.67 |
| ATOM | 484 | C | PRO | A | 124 | 6.107 | 70.764 | 23.849 | 1.00 | 24.18 |
| ATOM | 485 | O | PRO | A | 124 | 5.176 | 71.511 | 24.138 | 1.00 | 27.51 |
| ATOM | 486 | CB | PRO | A | 124 | 7.943 | 71.871 | 22.560 | 1.00 | 18.59 |
| ATOM | 487 | CG | PRO | A | 124 | 9.320 | 71.432 | 22.310 | 1.00 | 17.03 |
| ATOM | 488 | CD | PRO | A | 124 | 9.645 | 70.255 | 23.171 | 1.00 | 18.47 |
| ATOM | 489 | N | TYR | A | 125 | 5.966 | 69.475 | 23.546 | 1.00 | 25.26 |
| ATOM | 490 | CA | TYR | A | 125 | 4.622 | 68.920 | 23.400 | 1.00 | 23.95 |
| ATOM | 491 | C | TYR | A | 125 | 4.116 | 68.061 | 24.552 | 1.00 | 23.69 |
| ATOM | 492 | O | TYR | A | 125 | 2.941 | 67.679 | 24.576 | 1.00 | 22.99 |
| ATOM | 493 | CB | TYR | A | 125 | 4.549 | 68.153 | 22.077 | 1.00 | 19.98 |
| ATOM | 494 | CG | TYR | A | 125 | 5.032 | 68.998 | 20.930 | 1.00 | 15.47 |
| ATOM | 495 | CD1 | TYR | A | 125 | 6.297 | 68.516 | 20.383 | 1.00 | 18.77 |
| ATOM | 496 | CD2 | TYR | A | 125 | 4.260 | 70.048 | 20.456 | 1.00 | 21.04 |
| ATOM | 497 | CE1 | TYR | A | 125 | 6.783 | 69.666 | 19.399 | 1.00 | 19.08 |
| ATOM | 498 | CE2 | TYR | A | 125 | 4.734 | 70.902 | 19.474 | 1.00 | 20.98 |
| ATOM | 499 | CZ | TYR | A | 125 | 5.991 | 70.707 | 18.955 | 1.00 | 20.25 |
| ATOM | 500 | OH | TYR | A | 125 | 6.442 | 71.566 | 17.990 | 1.00 | 30.10 |
| ATOM | 501 | N | ILE | A | 126 | 4.991 | 67.776 | 25.512 | 1.00 | 18.49 |
| ATOM | 502 | CA | ILE | A | 126 | 4.608 | 66.988 | 26.668 | 1.00 | 15.65 |
| ATOM | 503 | C | ILE | A | 126 | 4.560 | 67.853 | 27.913 | 1.00 | 15.16 |
| ATOM | 504 | O | ILE | A | 126 | 5.529 | 68.532 | 28.235 | 1.00 | 13.12 |
| ATOM | 505 | CB | ILE | A | 126 | 5.596 | 65.841 | 26.939 | 1.00 | 10.05 |
| ATOM | 506 | CG1 | ILE | A | 126 | 5.548 | 64.819 | 25.804 | 1.00 | 11.19 |
| ATOM | 507 | CG2 | ILE | A | 126 | 5.211 | 65.143 | 28.257 | 1.00 | 4.98 |
| ATOM | 508 | CD1 | ILE | A | 125 | 4.127 | 64.445 | 25.348 | 1.00 | 10.39 |
| ATOM | 509 | N | VAL | A | 127 | 3.435 | 67.818 | 28.616 | 1.00 | 15.09 |
| ATOM | 510 | CA | VAL | A | 127 | 3.284 | 68.597 | 29.843 | 1.00 | 17.56 |
| ATOM | 511 | C | VAL | A | 127 | 4.394 | 68.258 | 30.851 | 1.00 | 16.93 |
| ATOM | 512 | O | VAL | A | 127 | 4.550 | 67.106 | 31.262 | 1.00 | 14.33 |
| ATOM | 513 | CB | VAL | A | 127 | 1.888 | 68.354 | 30.485 | 1.00 | 19.36 |
| ATOM | 514 | CG1 | VAL | A | 127 | 1.818 | 68.996 | 31.873 | 1.00 | 12.30 |
| ATOM | 515 | CG2 | VAL | A | 127 | 0.792 | 68.936 | 29.579 | 1.00 | 10.43 |
| ATOM | 516 | N | GLY | A | 128 | 5.166 | 69.279 | 31.232 | 1.00 | 16.61 |
| ATOM | 517 | CA | GLY | A | 128 | 6.261 | 69.114 | 32.179 | 1.00 | 13.65 |
| ATOM | 518 | C | GLY | A | 128 | 5.812 | 68.459 | 33.464 | 1.00 | 15.36 |
| ATOM | 519 | O | GLY | A | 128 | 4.717 | 68.719 | 33.951 | 1.00 | 18.98 |
| ATOM | 520 | N | PHE | A | 129 | 6.664 | 67.607 | 34.014 | 1.00 | 12.19 |
| ATOM | 521 | CA | PHE | A | 129 | 6.349 | 66.884 | 35.230 | 1.00 | 14.51 |
| ATOM | 522 | C | PHE | A | 129 | 7.355 | 67.281 | 36.289 | 1.00 | 14.64 |
| ATOM | 523 | O | PHE | A | 129 | 8.531 | 67.502 | 35.974 | 1.00 | 13.69 |
| ATOM | 524 | CB | PHE | A | 129 | 6.423 | 65.382 | 34.938 | 1.00 | 12.98 |
| ATOM | 525 | CG | PHE | A | 129 | 6.652 | 64.501 | 36.157 | 1.00 | 10.19 |
| ATOM | 526 | CD1 | PHE | A | 129 | 7.923 | 64.021 | 36.452 | 1.00 | 6.81 |
| ATOM | 527 | CD2 | PHE | A | 129 | 5.574 | 64.001 | 36.874 | 1.00 | 4.56 |
| ATOM | 528 | CE1 | PHE | A | 129 | 8.117 | 63.033 | 37.427 | 1.00 | 7.30 |
| ATOM | 529 | CE2 | PHE | A | 129 | 5.744 | 63.012 | 37.853 | 1.00 | 6.96 |
| ATOM | 530 | CZ | PHE | A | 129 | 7.016 | 62.522 | 38.128 | 1.00 | 9.00 |
| ATOM | 531 | N | TYR | A | 130 | 6.891 | 67.367 | 37.538 | 1.00 | 17.94 |
| ATOM | 532 | CA | TYR | A | 130 | 7.761 | 67.761 | 38.663 | 1.00 | 20.42 |
| ATOM | 533 | C | TYR | A | 130 | 8.056 | 66.615 | 39.634 | 1.00 | 22.08 |
| ATOM | 534 | O | TYR | A | 130 | 9.129 | 66.577 | 40.239 | 1.00 | 30.72 |
| ATOM | 535 | CB | TYR | A | 130 | 7.151 | 68.940 | 39.440 | 1.00 | 12.37 |
| ATOM | 536 | CG | TYR | A | 130 | 7.040 | 70.228 | 38.651 | 1.00 | 9.17 |
| ATOM | 537 | CD1 | TYR | A | 130 | 8.174 | 70.859 | 38.134 | 1.00 | 18.25 |
| ATOM | 538 | CD2 | TYR | A | 130 | 5.802 | 70.796 | 38.395 | 1.00 | 7.43 |
| ATOM | 539 | CE1 | TYR | A | 130 | 8.074 | 72.034 | 37.365 | 1.00 | 15.28 |
| ATOM | 540 | CE2 | TYR | A | 130 | 5.682 | 71.967 | 37.632 | 1.00 | 11.22 |
| ATOM | 541 | CZ | TYR | A | 130 | 6.818 | 72.576 | 37.114 | 1.00 | 19.64 |
| ATOM | 542 | OH | TYR | A | 130 | 6.680 | 73.687 | 36.287 | 1.00 | 23.04 |
| ATOM | 543 | N | GLY | A | 131 | 7.111 | 65.691 | 39.798 | 1.00 | 19.61 |
| ATOM | 544 | CA | GLY | A | 131 | 7.341 | 64.562 | 40.683 | 1.00 | 10.95 |
| ATOM | 545 | C | GLY | A | 131 | 6.074 | 63.862 | 41.122 | 1.00 | 15.66 |
| ATOM | 546 | O | GLY | A | 131 | 4.977 | 64.419 | 41.051 | 1.00 | 16.77 |
| ATOM | 547 | N | ALA | A | 132 | 6.232 | 62.629 | 41.593 | 1.00 | 15.34 |

TABLE 1-continued

Structural Coordinate of MEK1/N35/NKF (corresponding to amino acids 24, 383 of SEQ ID NO: 1) -compound 1-ATPγS Ternary Complex.

| | A | B | C | D | E | F | G | H | I | J |
|---|---|---|---|---|---|---|---|---|---|---|
| ATOM | 548 | CA | ALA | A | 132 | 5.099 | 61.839 | 42.047 | 1.00 | 16.40 |
| ATOM | 549 | C | ALA | A | 132 | 5.421 | 61.188 | 43.370 | 1.00 | 16.63 |
| ATOM | 550 | O | ALA | A | 132 | 6.547 | 60.740 | 43.600 | 1.00 | 15.99 |
| ATOM | 551 | CB | ALA | A | 132 | 4.761 | 60.756 | 41.017 | 1.00 | 18.51 |
| ATOM | 552 | N | PHE | A | 133 | 4.424 | 61.120 | 44.238 | 1.00 | 12.39 |
| ATOM | 553 | CA | PHE | A | 133 | 4.622 | 60.499 | 45.535 | 1.00 | 21.90 |
| ATOM | 554 | C | PHE | A | 133 | 3.260 | 60.061 | 46.042 | 1.00 | 26.87 |
| ATOM | 555 | O | PHE | A | 133 | 2.234 | 60.517 | 45.534 | 1.00 | 28.86 |
| ATOM | 556 | CB | PHE | A | 133 | 5.275 | 61.499 | 46.513 | 1.00 | 18.74 |
| ATOM | 557 | CG | PHE | A | 133 | 4.490 | 62.766 | 46.696 | 1.00 | 8.69 |
| ATOM | 558 | CD1 | PHE | A | 133 | 3.457 | 62.829 | 47.615 | 1.00 | 10.75 |
| ATOM | 559 | CD2 | PHE | A | 133 | 4.750 | 63.876 | 45.907 | 1.00 | 9.01 |
| ATOM | 560 | CE1 | PHE | A | 133 | 2.678 | 63.991 | 47.747 | 1.00 | 13.73 |
| ATOM | 561 | CE2 | PHE | A | 133 | 3.978 | 65.043 | 46.026 | 1.00 | 14.68 |
| ATOM | 562 | CZ | PHE | A | 133 | 2.935 | 65.098 | 46.950 | 1.00 | 10.48 |
| ATOM | 563 | N | TYR | A | 134 | 3.252 | 59.172 | 47.027 | 1.00 | 33.65 |
| ATOM | 564 | CA | TYR | A | 134 | 1.998 | 58.673 | 47.584 | 1.00 | 44.09 |
| ATOM | 565 | C | TYR | A | 134 | 1.707 | 59.308 | 42.936 | 1.00 | 46.08 |
| ATOM | 566 | O | TYR | A | 134 | 2.490 | 59.149 | 49.873 | 1.00 | 47.50 |
| ATOM | 567 | CB | TYR | A | 134 | 2.057 | 57.151 | 47.740 | 1.00 | 46.97 |
| ATOM | 568 | CG | TYR | A | 134 | 0.826 | 56.564 | 48.399 | 1.00 | 56.67 |
| ATOM | 569 | CD1 | TYR | A | 134 | 0.912 | 55.512 | 49.633 | 1.00 | 57.03 |
| ATOM | 570 | CD2 | TYR | A | 134 | −0.435 | 56.694 | 47.804 | 1.00 | 59.12 |
| ATOM | 571 | CE1 | TYR | A | 134 | −0.227 | 55.406 | 50.255 | 1.00 | 60.64 |
| ATOM | 572 | CE2 | TYR | A | 134 | −1.579 | 56.151 | 48.421 | 1.00 | 60.55 |
| ATOM | 573 | CZ | TYR | A | 134 | −1.470 | 55.550 | 49.644 | 1.00 | 61.42 |
| ATOM | 574 | OH | TYR | A | 134 | −2.604 | 55.061 | 50.258 | 1.00 | 62.79 |
| ATOM | 575 | N | SER | A | 135 | 0.582 | 60.008 | 49.048 | 1.00 | 47.37 |
| ATOM | 576 | CA | SER | A | 135 | 0.240 | 60.650 | 50.309 | 1.00 | 48.72 |
| ATOM | 577 | C | SER | A | 135 | −1.100 | 60.266 | 50.907 | 1.00 | 49.13 |
| ATOM | 578 | O | SER | A | 135 | −2.159 | 60.567 | 50.353 | 1.00 | 48.45 |
| ATOM | 579 | CB | SER | A | 135 | 0.284 | 62.173 | 50.171 | 1.00 | 49.20 |
| ATOM | 580 | OG | SER | A | 135 | −0.393 | 62.784 | 51.257 | 1.00 | 41.28 |
| ATOM | 581 | N | ASP | A | 136 | −1.028 | 59.612 | 52.058 | 1.00 | 52.23 |
| ATOM | 582 | CA | ASP | A | 135 | −2.194 | 59.192 | 52.821 | 1.00 | 55.18 |
| ATOM | 583 | C | ASP | A | 136 | −3.417 | 58.856 | 51.984 | 1.00 | 52.82 |
| ATOM | 584 | O | ASP | A | 136 | −4.360 | 59.646 | 51.897 | 1.00 | 52.40 |
| ATOM | 585 | CB | ASP | A | 136 | −2.553 | 60.279 | 53.847 | 1.00 | 63.38 |
| ATOM | 586 | CG | ASP | A | 136 | −1.405 | 60.575 | 54.830 | 1.00 | 71.73 |
| ATOM | 587 | OD1 | ASP | A | 136 | −1.396 | 59.993 | 55.946 | 1.00 | 74.02 |
| ATOM | 588 | OD2 | ASP | A | 136 | −0.515 | 61.393 | 54.488 | 1.00 | 72.19 |
| ATOM | 589 | N | GLY | A | 137 | −3.475 | 57.601 | 51.551 | 1.00 | 50.78 |
| ATOM | 590 | CA | GLY | A | 137 | −4.535 | 57.085 | 50.703 | 1.00 | 50.37 |
| ATOM | 591 | C | GLY | A | 137 | −4.644 | 57.679 | 49.309 | 1.00 | 52.17 |
| ATOM | 592 | O | GLY | A | 137 | −5.710 | 57.607 | 48.686 | 1.00 | 52.29 |
| ATOM | 593 | N | GLU | A | 138 | −3.560 | 58.253 | 48.799 | 1.00 | 47.60 |
| ATOM | 594 | CA | GLU | A | 138 | −3.620 | 58.841 | 47.476 | 1.00 | 43.63 |
| ATOM | 595 | C | GLU | A | 138 | −2.288 | 59.129 | 46.831 | 1.00 | 40.55 |
| ATOM | 596 | O | GLU | A | 138 | −1.550 | 60.004 | 47.276 | 1.00 | 45.45 |
| ATOM | 597 | CB | GLU | A | 138 | −4.425 | 60.127 | 47.517 | 1.00 | 43.23 |
| ATOM | 598 | CG | GLU | A | 138 | −5.603 | 60.119 | 46.581 | 1.00 | 48.93 |
| ATOM | 599 | CD | GLU | A | 138 | −6.909 | 60.362 | 47.304 | 1.00 | 56.15 |
| ATOM | 600 | OE1 | GLU | A | 138 | −7.429 | 59.411 | 47.925 | 1.00 | 61.04 |
| ATOM | 601 | OE2 | GLU | A | 138 | −7.414 | 61.505 | 47.254 | 1.00 | 60.20 |
| ATOM | 602 | N | ILE | A | 139 | −1.988 | 58.390 | 45.769 | 1.00 | 37.79 |
| ATOM | 603 | CA | ILE | A | 139 | −0.758 | 58.605 | 45.034 | 1.00 | 32.36 |
| ATOM | 604 | C | ILE | A | 139 | −0.881 | 60.009 | 44.450 | 1.00 | 27.26 |
| ATOM | 605 | O | ILE | A | 139 | −1.947 | 60.399 | 43.976 | 1.00 | 30.25 |
| ATOM | 606 | CB | ILE | A | 139 | −0.597 | 57.593 | 43.895 | 1.00 | 27.82 |
| ATOM | 607 | CG1 | ILE | A | 139 | 0.638 | 57.948 | 43.072 | 1.00 | 30.64 |
| ATOM | 608 | CG2 | ILE | A | 139 | −1.839 | 57.587 | 43.022 | 1.00 | 33.34 |
| ATOM | 609 | CD1 | ILE | A | 139 | 0.375 | 58.923 | 41.948 | 1.00 | 29.55 |
| ATOM | 610 | N | SER | A | 140 | 0.212 | 60.758 | 44.481 | 1.00 | 20.21 |
| ATOM | 611 | CA | SER | A | 140 | 0.212 | 62.132 | 44.000 | 1.00 | 20.04 |
| ATOM | 612 | C | SER | A | 140 | 1.156 | 62.352 | 42.835 | 1.00 | 17.48 |
| ATOM | 613 | O | SER | A | 140 | 2.266 | 61.819 | 42.838 | 1.00 | 17.20 |
| ATOM | 614 | CB | SER | A | 140 | 0.629 | 63.071 | 45.151 | 1.00 | 21.77 |
| ATOM | 615 | OG | SER | A | 140 | −0.395 | 63.989 | 45.486 | 1.00 | 13.91 |
| ATOM | 616 | N | ILE | A | 141 | 0.719 | 63.152 | 41.855 | 1.00 | 13.87 |
| ATOM | 617 | CA | ILE | A | 141 | 1.540 | 63.503 | 40.679 | 1.00 | 16.20 |
| ATOM | 618 | C | ILE | A | 141 | 1.469 | 65.026 | 40.458 | 1.00 | 12.84 |
| ATOM | 619 | O | ILE | A | 141 | 0.378 | 65.608 | 40.387 | 1.00 | 14.10 |
| ATOM | 620 | CB | ILE | A | 141 | 1.054 | 62.779 | 39.355 | 1.00 | 14.97 |
| ATOM | 621 | CG1 | ILE | A | 141 | 1.198 | 61.258 | 39.489 | 1.00 | 21.22 |
| ATOM | 622 | CG2 | ILE | A | 141 | 1.891 | 63.230 | 38.167 | 1.00 | 8.79 |

TABLE 1-continued

Structural Coordinate of MEK1/N35/NKF (corresponding to amino acids 24, 383 of SEQ ID NO: 1) -compound 1-ATPγS Ternary Complex.

| | A | B | C | D | E | F | G | H | I | J |
|---|---|---|---|---|---|---|---|---|---|---|
| ATOM | 623 | CD1 | ILE | A | 141 | 0.597 | 60.464 | 38.309 | 1.00 | 16.94 |
| ATOM | 624 | N | CYS | A | 142 | 2.627 | 65.665 | 40.328 | 1.00 | 10.20 |
| ATOM | 625 | CA | CYS | A | 142 | 2.657 | 67.117 | 40.149 | 1.00 | 10.62 |
| ATOM | 626 | C | CYS | A | 142 | 3.276 | 67.540 | 38.816 | 1.00 | 14.88 |
| ATOM | 627 | O | CYS | A | 142 | 4.394 | 67.119 | 38.423 | 1.00 | 6.78 |
| ATOM | 628 | CB | CYS | A | 142 | 3.394 | 67.762 | 41.329 | 1.00 | 12.82 |
| ATOM | 629 | SG | CYS | A | 142 | 2.998 | 67.001 | 42.948 | 1.00 | 20.75 |
| ATOM | 630 | N | MET | A | 143 | 2.544 | 68.395 | 38.119 | 1.00 | 12.04 |
| ATOM | 631 | CA | MET | A | 143 | 2.985 | 68.834 | 36.823 | 1.00 | 14.02 |
| ATOM | 632 | C | MET | A | 143 | 2.910 | 70.329 | 36.594 | 1.00 | 16.64 |
| ATOM | 633 | O | MET | A | 143 | 2.326 | 72.093 | 37.378 | 1.00 | 19.21 |
| ATOM | 634 | CB | MET | A | 143 | 2.153 | 68.134 | 35.738 | 1.00 | 17.79 |
| ATOM | 635 | CG | MET | A | 143 | 1.154 | 67.091 | 36.237 | 1.00 | 25.34 |
| ATOM | 636 | SD | MET | A | 143 | −0.237 | 66.982 | 35.189 | 1.00 | 29.14 |
| ATOM | 637 | CE | MET | A | 143 | −1.519 | 66.245 | 36.363 | 1.00 | 19.57 |
| ATOM | 638 | N | GLU | A | 144 | 3.512 | 70.731 | 35.486 | 1.00 | 15.71 |
| ATOM | 639 | CA | GLU | A | 144 | 3.486 | 72.111 | 35.064 | 1.00 | 17.16 |
| ATOM | 640 | C | GLU | A | 144 | 2.004 | 72.445 | 34.992 | 1.00 | 20.70 |
| ATOM | 641 | O | GLU | A | 144 | 1.192 | 71.626 | 34.548 | 1.00 | 24.10 |
| ATOM | 642 | CB | GLU | A | 144 | 4.142 | 72.211 | 33.695 | 1.00 | 15.59 |
| ATOM | 643 | CG | GLU | A | 144 | 3.577 | 73.246 | 32.755 | 1.00 | 14.63 |
| ATOM | 644 | CD | GLU | A | 144 | 4.382 | 73.276 | 31.475 | 1.00 | 18.74 |
| ATOM | 645 | OE1 | GLU | A | 144 | 4.269 | 74.256 | 30.709 | 1.00 | 18.37 |
| ATOM | 646 | OE2 | GLU | A | 144 | 5.143 | 72.306 | 31.244 | 1.00 | 15.77 |
| ATOM | 647 | N | HIS | A | 145 | 1.644 | 73.625 | 35.472 | 1.00 | 22.19 |
| ATOM | 648 | CA | HIS | A | 145 | 0.259 | 74.051 | 35.455 | 1.00 | 15.99 |
| ATOM | 649 | C | HIS | A | 145 | 0.067 | 74.617 | 34.057 | 1.00 | 14.93 |
| ATOM | 650 | O | HIS | A | 145 | 0.947 | 75.285 | 33.534 | 1.00 | 17.75 |
| ATOM | 651 | CB | HIS | A | 145 | 0.034 | 75.105 | 36.553 | 1.00 | 16.29 |
| ATOM | 652 | CG | HIS | A | 145 | −1.212 | 75.917 | 36.378 | 1.00 | 19.09 |
| ATOM | 653 | ND1 | HIS | A | 145 | −2.465 | 75.439 | 36.693 | 1.00 | 23.92 |
| ATOM | 654 | CD2 | HIS | A | 145 | −1.400 | 77.156 | 35.867 | 1.00 | 18.53 |
| ATOM | 655 | CE1 | HIS | A | 145 | −3.373 | 76.347 | 36.380 | 1.00 | 17.96 |
| ATOM | 656 | NE2 | HIS | A | 145 | −2.752 | 77.397 | 35.876 | 1.00 | 12.39 |
| ATOM | 657 | N | MET | A | 146 | −1.060 | 74.321 | 33.425 | 1.00 | 14.86 |
| ATOM | 658 | CA | MET | A | 146 | −1.284 | 74.824 | 32.082 | 1.00 | 17.45 |
| ATOM | 659 | C | MET | A | 146 | −2.503 | 75.722 | 32.090 | 1.00 | 21.74 |
| ATOM | 660 | O | MET | A | 146 | −3.640 | 75.268 | 32.025 | 1.00 | 21.48 |
| ATOM | 662 | CB | MET | A | 146 | −1.458 | 73.657 | 31.097 | 1.00 | 18.67 |
| ATOM | 652 | CG | MET | A | 146 | −0.245 | 72.731 | 31.011 | 1.00 | 9.72 |
| ATOM | 663 | SD | MET | A | 146 | 1.165 | 73.392 | 30.043 | 1.00 | 17.17 |
| ATOM | 664 | CE | MET | A | 146 | 0.275 | 73.936 | 28.505 | 1.00 | 9.98 |
| ATOM | 665 | N | ASP | A | 147 | −2.306 | 76.888 | 32.646 | 1.00 | 25.53 |
| ATOM | 666 | CA | ASP | A | 147 | −3.334 | 77.905 | 32.810 | 1.00 | 30.59 |
| ATOM | 667 | C | ASP | A | 147 | −4.414 | 77.982 | 31.743 | 1.00 | 30.67 |
| ATOM | 668 | O | ASP | A | 147 | −5.464 | 78.581 | 31.974 | 1.00 | 31.44 |
| ATOM | 669 | CB | ASP | A | 147 | −2.663 | 79.275 | 32.966 | 1.00 | 38.86 |
| ATOM | 670 | CG | ASP | A | 147 | −1.876 | 79.687 | 31.741 | 1.00 | 41.29 |
| ATOM | 671 | OD1 | ASP | A | 147 | −1.534 | 80.883 | 31.640 | 1.00 | 42.35 |
| ATOM | 672 | OD2 | ASP | A | 147 | −1.600 | 78.822 | 30.882 | 1.00 | 43.11 |
| ATOM | 673 | N | GLY | A | 148 | −4.160 | 77.398 | 30.578 | 1.00 | 32.78 |
| ATOM | 674 | CA | GLY | A | 148 | −5.150 | 77.423 | 29.519 | 1.00 | 26.94 |
| ATOM | 675 | C | GLY | A | 148 | −6.169 | 76.320 | 29.737 | 1.00 | 26.92 |
| ATOM | 676 | O | GLY | A | 148 | −7.106 | 76.415 | 29.290 | 1.00 | 24.17 |
| ATOM | 677 | N | GLY | A | 149 | −5.756 | 75.274 | 30.448 | 1.00 | 26.07 |
| ATOM | 679 | CA | GLY | A | 149 | −6.553 | 74.131 | 30.676 | 1.00 | 26.57 |
| ATOM | 679 | C | GLY | A | 149 | −6.544 | 73.045 | 29.655 | 1.00 | 24.46 |
| ATOM | 680 | O | GLY | A | 149 | −5.568 | 72.964 | 28.893 | 1.00 | 23.13 |
| ATOM | 681 | N | SER | A | 150 | −7.553 | 72.181 | 29.634 | 1.00 | 20.10 |
| ATOM | 682 | CA | SER | A | 150 | −7.600 | 71.065 | 28.699 | 1.00 | 22.48 |
| ATOM | 683 | C | SER | A | 150 | −8.587 | 71.426 | 27.603 | 1.00 | 25.30 |
| ATOM | 684 | O | SER | A | 150 | −9.627 | 72.043 | 27.874 | 1.00 | 24.96 |
| ATOM | 685 | CB | SER | A | 150 | −8.061 | 69.803 | 29.412 | 1.00 | 19.17 |
| ATOM | 686 | OG | SER | A | 150 | −9.281 | 70.050 | 30.086 | 1.00 | 20.43 |
| ATOM | 687 | N | LEU | A | 151 | −8.280 | 71.021 | 26.375 | 1.00 | 23.37 |
| ATOM | 686 | CA | LEU | A | 151 | −9.127 | 71.354 | 25.235 | 1.00 | 21.64 |
| ATOM | 689 | C | LEU | A | 151 | −10.608 | 71.036 | 25.359 | 1.00 | 20.38 |
| ATOM | 690 | O | LEU | A | 151 | −11.412 | 71.656 | 24.681 | 1.00 | 21.59 |
| ATOM | 691 | CB | LEU | A | 151 | −8.553 | 70.751 | 23.955 | 1.00 | 16.06 |
| ATOM | 692 | CG | LEU | A | 151 | −7.263 | 71.428 | 23.458 | 1.00 | 17.32 |
| ATOM | 693 | CD1 | LEU | A | 151 | −6.872 | 70.898 | 22.075 | 1.00 | 17.19 |
| ATOM | 694 | CD2 | LEU | A | 151 | −7.456 | 72.942 | 23.416 | 1.00 | 16.11 |
| ATOM | 695 | N | ASP | A | 152 | −10.993 | 70.090 | 26.206 | 1.00 | 22.86 |
| ATOM | 696 | CA | ASP | A | 152 | −12.423 | 69.820 | 26.344 | 1.00 | 26.42 |
| ATOM | 697 | C | ASP | A | 152 | −13.073 | 71.045 | 26.989 | 1.00 | 27.30 |

TABLE 1-continued

Structural Coordinate of MEK1/N35/NKF (corresponding to amino acids 24, 383 of SEQ ID NO: 1) -compound 1-ATPγS Ternary Complex.

| | A | B | C | D | E | F | G | H | I | J |
|---|---|---|---|---|---|---|---|---|---|---|
| ATOM | 698 | O | ASP | A | 152 | −14.202 | 71.408 | 26.661 | 1.00 | 28.08 |
| ATOM | 699 | CB | ASP | A | 152 | −12.689 | 68.575 | 27.197 | 1.00 | 28.72 |
| ATOM | 700 | CG | ASP | A | 152 | −12.110 | 68.689 | 28.584 | 1.00 | 34.12 |
| ATOM | 701 | OD1 | ASP | A | 152 | −12.877 | 68.558 | 29.566 | 1.00 | 35.49 |
| ATOM | 702 | OD2 | ASP | A | 152 | −10.885 | 68.907 | 28.688 | 1.00 | 36.66 |
| ATOM | 703 | N | GLN | A | 153 | −12.359 | 71.689 | 27.904 | 1.00 | 27.94 |
| ATOM | 704 | CA | GLN | A | 153 | −12.897 | 72.889 | 28.536 | 1.00 | 31.58 |
| ATOM | 708 | C | GLN | A | 153 | −12.938 | 74.004 | 27.475 | 1.00 | 30.22 |
| ATOM | 706 | O | GLN | A | 153 | −13.976 | 74.628 | 27.256 | 1.00 | 29.34 |
| ATOM | 707 | CB | GLN | A | 153 | −12.028 | 73.318 | 29.731 | 1.00 | 31.94 |
| ATOM | 708 | CG | GLN | A | 153 | −11.277 | 72.185 | 30.436 | 1.00 | 37.31 |
| ATOM | 709 | CD | GLN | A | 153 | −10.540 | 72.645 | 31.698 | 1.00 | 38.91 |
| ATOM | 710 | OE1 | GLN | A | 153 | −9.300 | 72.630 | 31.769 | 1.00 | 33.30 |
| ATOM | 711 | NE2 | GLN | A | 153 | −11.302 | 73.052 | 32.698 | 1.00 | 40.65 |
| ATOM | 712 | N | VAL | A | 154 | −11.807 | 74.235 | 26.813 | 1.00 | 29.11 |
| ATOM | 713 | CA | VAL | A | 154 | −11.711 | 75.258 | 25.773 | 1.00 | 24.82 |
| ATOM | 714 | C | VAL | A | 154 | −12.799 | 05.077 | 24.711 | 1.00 | 30.19 |
| ATOM | 715 | O | VAL | A | 154 | −13.282 | 76.045 | 24.133 | 1.00 | 32.86 |
| ATOM | 716 | CB | VAL | A | 154 | −10.319 | 75.224 | 25.096 | 1.00 | 22.46 |
| ATOM | 717 | CG1 | VAL | A | 154 | −10.233 | 76.261 | 23.985 | 1.00 | 15.50 |
| ATOM | 718 | CG2 | VAL | A | 154 | −9.243 | 75.471 | 26.134 | 1.00 | 8.68 |
| ATOM | 719 | N | LEU | A | 155 | −13.190 | 73.832 | 24.460 | 1.00 | 33.07 |
| ATOM | 720 | CA | LEU | A | 155 | −14.223 | 73.537 | 23.474 | 1.00 | 30.20 |
| ATOM | 721 | C | LEU | A | 155 | −15.603 | 73.907 | 24.002 | 1.00 | 30.50 |
| ATOM | 722 | O | LEU | A | 155 | −16.462 | 74.347 | 23.243 | 1.00 | 34.91 |
| ATOM | 723 | CB | LEU | A | 155 | −14.203 | 72.049 | 23.116 | 1.00 | 30.99 |
| ATOM | 724 | CG | LEU | A | 155 | −14.874 | 71.561 | 21.824 | 1.00 | 29.65 |
| ATOM | 725 | CD1 | LEU | A | 155 | −16.327 | 71.296 | 22.097 | 1.00 | 31.20 |
| ATOM | 726 | CD2 | LEU | A | 155 | −14.712 | 72.582 | 20.711 | 1.00 | 26.00 |
| ATOM | 727 | N | LYS | A | 156 | −15.824 | 73.716 | 25.300 | 1.00 | 28.46 |
| ATOM | 728 | CA | LYS | A | 156 | −17.116 | 74.043 | 25.894 | 1.00 | 29.48 |
| ATOM | 729 | CB | LYS | A | 156 | −17.193 | 73.545 | 27.333 | 1.00 | 20.91 |
| ATOM | 730 | C | LYS | A | 156 | −17.308 | 75.551 | 25.848 | 1.00 | 34.24 |
| ATOM | 731 | O | LYS | A | 156 | −18.392 | 76.039 | 25.508 | 1.00 | 39.12 |
| ATOM | 732 | N | LYS | A | 150 | −16.249 | 76.290 | 26.171 | 1.00 | 35.95 |
| ATOM | 733 | CA | LYS | A | 157 | −16.300 | 77.746 | 26.163 | 1.00 | 35.68 |
| ATOM | 734 | CB | LYS | A | 157 | −15.337 | 78.314 | 27.210 | 1.00 | 29.27 |
| ATOM | 735 | C | LYS | A | 157 | −15.974 | 78.316 | 24.785 | 1.00 | 40.65 |
| ATOM | 736 | O | LYS | A | 157 | −15.614 | 79.483 | 24.665 | 1.00 | 44.71 |
| ATOM | 737 | N | ALA | A | 158 | −16.100 | 77.497 | 23.744 | 1.00 | 45.65 |
| ATOM | 738 | CA | ALA | A | 158 | −15.808 | 77.949 | 22.381 | 1.00 | 45.62 |
| ATOM | 739 | C | ALA | A | 158 | −16.686 | 77.293 | 21.326 | 1.00 | 47.53 |
| ATOM | 740 | O | ALA | A | 158 | −16.452 | 77.476 | 20.133 | 1.00 | 50.88 |
| ATOM | 741 | CB | ALA | A | 158 | −14.335 | 77.698 | 22.042 | 1.00 | 47.87 |
| ATOM | 742 | N | GLY | A | 159 | −17.686 | 75.527 | 21.762 | 1.00 | 46.73 |
| ATOM | 743 | CA | GLY | A | 159 | −18.574 | 75.856 | 20.823 | 1.00 | 46.87 |
| ATOM | 744 | C | GLY | A | 159 | −17.832 | 74.855 | 19.955 | 1.00 | 46.86 |
| ATOM | 745 | O | GLY | A | 159 | −17.867 | 73.648 | 20.211 | 1.00 | 45.56 |
| ATOM | 746 | N | ARG | A | 160 | −17.169 | 75.366 | 18.917 | 1.00 | 45.69 |
| ATOM | 747 | CA | ARG | A | 160 | −16.375 | 74.545 | 18.009 | 1.00 | 44.28 |
| ATOM | 748 | C | ARG | A | 160 | −15.090 | 75.313 | 17.746 | 1.00 | 39.43 |
| ATOM | 749 | O | ARG | A | 160 | −15.122 | 76.519 | 17.529 | 1.00 | 41.84 |
| ATOM | 750 | CB | ARG | A | 160 | −17.137 | 74.282 | 16.701 | 1.00 | 45.12 |
| ATOM | 751 | CG | ARG | A | 160 | −17.023 | 75.370 | 18.662 | 1.00 | 45.97 |
| ATOM | 752 | CD | ARG | A | 160 | −18.397 | 75.874 | 15.259 | 1.00 | 55.74 |
| ATOM | 753 | NE | ARG | A | 160 | −18.937 | 75.165 | 14.103 | 1.00 | 61.36 |
| ATOM | 754 | CZ | ARG | A | 160 | −18.907 | 75.629 | 12.854 | 1.00 | 66.31 |
| ATOM | 755 | NH1 | ARG | A | 160 | −18.361 | 76.814 | 12.588 | 1.00 | 62.96 |
| ATOM | 756 | NH2 | ARG | A | 160 | −19.423 | 74.904 | 11.866 | 1.00 | 65.23 |
| ATOM | 757 | N | ILE | A | 161 | −13.957 | 74.626 | 17.804 | 1.00 | 35.92 |
| ATOM | 758 | CA | ILE | A | 161 | −12.679 | 75.272 | 17.565 | 1.00 | 31.37 |
| ATOM | 759 | C | ILE | A | 161 | −12.464 | 75.362 | 16.054 | 1.00 | 35.54 |
| ATOM | 760 | O | ILE | A | 161 | −12.842 | 74.463 | 15.314 | 1.00 | 37.48 |
| ATOM | 761 | CB | ILE | A | 161 | −11.550 | 74.494 | 18.268 | 1.00 | 26.70 |
| ATOM | 762 | CG1 | ILE | A | 161 | −11.609 | 74.790 | 19.774 | 1.00 | 25.16 |
| ATOM | 763 | CG2 | ILE | A | 161 | −10.202 | 74.905 | 17.741 | 1.00 | 24.00 |
| ATOM | 764 | CD1 | ILE | A | 161 | −10.870 | 73.795 | 20.652 | 1.00 | 21.33 |
| ATOM | 765 | N | PRO | A | 162 | −11.891 | 76.477 | 15.574 | 1.00 | 37.44 |
| ATOM | 766 | CA | PRO | A | 162 | −11.623 | 76.716 | 14.149 | 1.00 | 35.38 |
| ATOM | 767 | C | PRO | A | 162 | −10.532 | 75.857 | 13.529 | 1.00 | 34.79 |
| ATOM | 768 | O | PRO | A | 162 | −9.524 | 75.537 | 14.168 | 1.00 | 37.94 |
| ATOM | 769 | CB | PRO | A | 162 | −11.263 | 78.199 | 14.079 | 1.00 | 34.53 |
| ATOM | 770 | CG | PRO | A | 162 | −11.522 | 78.755 | 15.452 | 1.00 | 37.13 |
| ATOM | 771 | CD | PRO | A | 162 | −11.461 | 77.611 | 16.404 | 1.00 | 39.70 |
| ATOM | 772 | N | GLU | A | 163 | −10.833 | 75.524 | 12.140 | 1.00 | 32.34 |

TABLE 1-continued

Structural Coordinate of MEK1/N35/NKF (corresponding to amino acids 24, 383 of SEQ ID NO: 1) -compound 1-ATPγS Ternary Complex.

| | A | B | C | D | E | F | G | H | I | J |
|---|---|---|---|---|---|---|---|---|---|---|
| ATOM | 773 | CA | GLU | A | 163 | −9.912 | 74.675 | 11.409 | 1.00 | 35.84 |
| ATOM | 774 | C | GLU | A | 163 | −8.456 | 75.119 | 11.487 | 1.00 | 36.46 |
| ATOM | 775 | O | GLU | A | 163 | −7.557 | 74.297 | 11.636 | 1.00 | 40.80 |
| ATOM | 776 | CB | GLU | A | 163 | −10.339 | 74.587 | 9.949 | 1.00 | 35.27 |
| ATOM | 777 | CG | GLU | A | 163 | −9.442 | 73.709 | 9.131 | 1.00 | 35.84 |
| ATOM | 778 | CD | GLU | A | 163 | −9.864 | 73.639 | 7.689 | 1.00 | 38.55 |
| ATOM | 779 | OE1 | GLU | A | 163 | −10.958 | 74.149 | 7.357 | 1.00 | 42.91 |
| ATOM | 780 | OE2 | GLU | A | 163 | −9.094 | 73.072 | 6.888 | 1.00 | 38.53 |
| ATOM | 781 | N | GLN | A | 164 | −8.214 | 76.418 | 11.388 | 1.00 | 36.63 |
| ATOM | 782 | CA | GLN | A | 164 | −6.846 | 76.909 | 11.442 | 1.00 | 37.30 |
| ATOM | 783 | C | GLN | A | 164 | −6.178 | 76.558 | 12.771 | 1.00 | 36.11 |
| ATOM | 784 | O | GLN | A | 164 | −5.021 | 76.126 | 12.805 | 1.00 | 35.86 |
| ATOM | 785 | CB | GLN | A | 164 | −6.828 | 78.420 | 11.212 | 1.00 | 39.53 |
| ATOM | 786 | CG | GLN | A | 164 | −5.789 | 78.866 | 10.203 | 1.00 | 43.05 |
| ATOM | 787 | CD | GLN | A | 164 | −6.387 | 79.141 | 8.841 | 1.00 | 49.30 |
| ATOM | 788 | OE1 | GLN | A | 164 | −7.253 | 80.006 | 8.693 | 1.00 | 47.73 |
| ATOM | 789 | NE2 | GLN | A | 164 | −5.932 | 78.402 | 7.830 | 1.00 | 48.05 |
| ATOM | 790 | N | ILE | A | 165 | −6.911 | 76.736 | 13.863 | 1.00 | 34.47 |
| ATOM | 791 | CA | ILE | A | 165 | −6.388 | 76.429 | 15.186 | 1.00 | 35.29 |
| ATOM | 792 | C | ILE | A | 165 | −6.384 | 74.252 | 15.832 | 1.00 | 32.10 |
| ATOM | 793 | O | ILE | A | 165 | −5.337 | 74.385 | 15.930 | 1.00 | 28.56 |
| ATOM | 794 | CB | ILE | A | 165 | −7.255 | 77.091 | 16.276 | 1.00 | 37.53 |
| ATOM | 795 | CG1 | ILE | A | 165 | −6.766 | 78.519 | 16.501 | 1.00 | 35.01 |
| ATOM | 796 | CG2 | ILE | A | 165 | −7.161 | 76.329 | 17.586 | 1.00 | 40.94 |
| ATOM | 797 | CD1 | ILE | A | 165 | −7.857 | 79.526 | 16.433 | 1.00 | 38.89 |
| ATOM | 798 | N | LEU | A | 166 | −7.326 | 74.194 | 14.914 | 1.00 | 33.23 |
| ATOM | 799 | CA | LEU | A | 166 | −7.299 | 72.744 | 15.018 | 1.00 | 30.09 |
| ATOM | 800 | C | LEU | A | 166 | −6.073 | 72.249 | 14.257 | 1.00 | 30.60 |
| ATOM | 801 | O | LEU | A | 166 | −5.580 | 71.149 | 14.500 | 1.00 | 32.76 |
| ATOM | 802 | CB | LEU | A | 166 | −8.574 | 72.145 | 14.426 | 1.00 | 28.10 |
| ATOM | 803 | CG | LEU | A | 166 | −9.782 | 72.301 | 15.353 | 1.00 | 27.13 |
| ATOM | 804 | CD1 | LEU | A | 166 | −10.960 | 71.453 | 14.844 | 1.00 | 20.97 |
| ATOM | 805 | CD2 | LEU | A | 166 | −9.363 | 71.901 | 16.774 | 1.00 | 19.88 |
| ATOM | 806 | N | GLY | A | 167 | −5.578 | 73.060 | 13.339 | 1.00 | 32.63 |
| ATOM | 807 | CA | GLY | A | 167 | −4.405 | 72.722 | 12.563 | 1.00 | 30.17 |
| ATOM | 808 | C | GLY | A | 167 | −3.154 | 72.753 | 13.422 | 1.00 | 30.43 |
| ATOM | 609 | O | GLY | A | 167 | −2.296 | 71.872 | 13.324 | 1.00 | 30.93 |
| ATOM | 810 | N | LYS | A | 168 | −3.046 | 73.772 | 14.268 | 1.00 | 31.57 |
| ATOM | 811 | CA | LYS | A | 168 | −1.896 | 73.898 | 15.156 | 1.00 | 30.89 |
| ATOM | 812 | CB | LYS | A | 168 | −1.877 | 75.276 | 15.807 | 1.00 | 27.56 |
| ATOM | 613 | C | LYS | A | 168 | −1.952 | 72.798 | 16.221 | 1.00 | 32.22 |
| ATOM | 814 | O | LYS | A | 168 | −0.912 | 72.258 | 16.623 | 1.00 | 35.68 |
| ATOM | 815 | N | VAL | A | 169 | −3.165 | 72.456 | 16.664 | 1.00 | 28.88 |
| ATOM | 816 | CA | VAL | A | 169 | −3.353 | 71.408 | 17.670 | 1.00 | 19.89 |
| ATOM | 617 | C | VAL | A | 169 | −2.815 | 70.089 | 17.127 | 1.00 | 21.63 |
| ATOM | 818 | O | VAL | A | 169 | −2.073 | 69.366 | 17.807 | 1.00 | 21.58 |
| ATOM | 819 | CB | VAL | A | 169 | −4.845 | 71.234 | 18.026 | 1.00 | 18.98 |
| ATOM | 820 | CG1 | VAL | A | 169 | −5.029 | 70.037 | 18.981 | 1.00 | 14.97 |
| ATOM | 821 | CG2 | VAL | A | 169 | −5.375 | 72.516 | 18.665 | 1.00 | 14.52 |
| ATOM | 822 | N | SER | A | 170 | −3.188 | 69.792 | 15.886 | 1.00 | 20.33 |
| ATOM | 823 | CA | SER | A | 170 | −2.752 | 68.570 | 15.230 | 1.00 | 17.37 |
| ATOM | 824 | C | SER | A | 170 | −1.229 | 68.501 | 15.219 | 1.00 | 17.09 |
| ATOM | 825 | O | SER | A | 170 | −0.657 | 67.499 | 15.629 | 1.00 | 20.61 |
| ATOM | 826 | CB | SER | A | 170 | −3.313 | 68.505 | 13.810 | 1.00 | 19.84 |
| ATOM | 827 | OG | SER | A | 170 | −4.733 | 68.533 | 13.823 | 1.00 | 19.10 |
| ATOM | 828 | N | ILE | A | 171 | −0.568 | 69.560 | 14.763 | 1.00 | 17.15 |
| ATOM | 829 | CA | ILE | A | 171 | 0.889 | 69.576 | 14.752 | 1.00 | 17.81 |
| ATOM | 830 | C | ILE | A | 171 | 1.422 | 69.204 | 16.148 | 1.00 | 17.91 |
| ATOM | 831 | O | ILE | A | 171 | 2.322 | 68.369 | 16.276 | 1.00 | 16.55 |
| ATOM | 832 | CB | ILE | A | 171 | 1.432 | 70.968 | 14.325 | 1.00 | 18.36 |
| ATOM | 833 | CG1 | ILE | A | 171 | 1.401 | 71.086 | 12.808 | 1.00 | 24.02 |
| ATOM | 834 | CG2 | ILE | A | 171 | 2.876 | 71.135 | 14.757 | 1.00 | 23.10 |
| ATOM | 835 | CD1 | ILE | A | 171 | 0.739 | 72.329 | 12.304 | 1.00 | 31.26 |
| ATOM | 836 | N | ALA | A | 172 | 0.838 | 69.800 | 17.190 | 1.00 | 15.52 |
| ATOM | 837 | CA | ALA | A | 172 | 1.249 | 69.527 | 18.575 | 1.00 | 15.61 |
| ATOM | 838 | C | ALA | A | 172 | 1.034 | 68.080 | 18.994 | 1.00 | 14.16 |
| ATOM | 839 | O | ALA | A | 172 | 1.949 | 67.443 | 19.528 | 1.00 | 12.15 |
| ATOM | 840 | CB | ALA | A | 172 | 0.499 | 70.451 | 19.535 | 1.00 | 18.77 |
| ATOM | 841 | N | VAL | A | 173 | −0.179 | 67.570 | 18.770 | 1.00 | 13.42 |
| ATOM | 842 | CA | VAL | A | 173 | −0.505 | 66.187 | 19.128 | 1.00 | 15.18 |
| ATOM | 843 | C | VAL | A | 173 | 0.438 | 65.216 | 18.429 | 1.00 | 17.01 |
| ATOM | 844 | O | VAL | A | 173 | 0.984 | 64.319 | 19.062 | 1.00 | 23.77 |
| ATOM | 845 | CB | VAL | A | 173 | −1.975 | 65.791 | 18.750 | 1.00 | 14.24 |
| ATOM | 846 | CG1 | VAL | A | 173 | −2.186 | 64.291 | 18.935 | 1.00 | 5.50 |
| ATOM | 847 | CG2 | VAL | A | 173 | −2.964 | 66.547 | 19.594 | 1.00 | 7.97 |

TABLE 1-continued

Structural Coordinate of MEK1/N35/NKF (corresponding to amino acids 24, 383 of SEQ ID NO: 1) -compound 1-ATPγS Ternary Complex.

| | A | B | C | D | E | F | G | H | I | J |
|---|---|---|---|---|---|---|---|---|---|---|
| ATOM | 848 | N | ILE | A | 174 | 0.634 | 65.388 | 17.128 | 1.00 | 19.25 |
| ATOM | 849 | CA | ILE | A | 174 | 1.521 | 64.488 | 16.400 | 1.00 | 21.80 |
| ATOM | 850 | C | ILE | A | 174 | 2.990 | 64.650 | 16.803 | 1.00 | 21.26 |
| ATOM | 851 | O | ILE | A | 174 | 3.664 | 63.659 | 17.038 | 1.00 | 21.58 |
| ATOM | 852 | CB | ILE | A | 174 | 1.373 | 64.641 | 14.865 | 1.00 | 25.48 |
| ATOM | 853 | CG1 | ILE | A | 174 | 2.598 | 64.064 | 14.160 | 1.00 | 32.34 |
| ATOM | 854 | CG2 | ILE | A | 174 | 1.239 | 66.078 | 14.499 | 1.00 | 31.40 |
| ATOM | 855 | CD1 | ILE | A | 174 | 2.416 | 62.629 | 13.686 | 1.00 | 41.26 |
| ATOM | 856 | N | LYS | A | 175 | 3.498 | 65.877 | 16.894 | 1.00 | 19.28 |
| ATOM | 857 | CA | LYS | A | 175 | 4.895 | 66.044 | 17.308 | 1.00 | 22.09 |
| ATOM | 858 | C | LYS | A | 175 | 5.060 | 65.390 | 18.681 | 1.00 | 19.31 |
| ATOM | 859 | O | LYS | A | 176 | 6.114 | 64.839 | 19.013 | 1.00 | 17.73 |
| ATOM | 860 | CB | LYS | A | 175 | 5.262 | 67.523 | 17.391 | 1.00 | 24.23 |
| ATOM | 861 | CG | LYS | A | 175 | 5.107 | 68.252 | 16.063 | 1.00 | 27.00 |
| ATOM | 862 | CD | LYS | A | 175 | 6.432 | 68.455 | 15.364 | 1.00 | 24.86 |
| ATOM | 663 | CE | LYS | A | 175 | 6.914 | 69.890 | 15.515 | 1.00 | 35.11 |
| ATOM | 864 | NZ | LYS | A | 175 | 6.920 | 70.633 | 14.222 | 1.00 | 31.01 |
| ATOM | 865 | N | GLY | A | 176 | 3.989 | 65.449 | 19.469 | 1.00 | 18.02 |
| ATOM | 866 | CA | GLY | A | 176 | 3.992 | 64.854 | 20.795 | 1.00 | 14.51 |
| ATOM | 867 | C | GLY | A | 176 | 4.023 | 63.334 | 20.806 | 1.00 | 14.32 |
| ATOM | 868 | O | GLY | A | 176 | 4.889 | 62.720 | 21.445 | 1.00 | 12.68 |
| ATOM | 869 | N | LEU | A | 177 | 3.075 | 62.710 | 20.109 | 1.00 | 13.29 |
| ATOM | 870 | CA | LEU | A | 177 | 3.038 | 61.252 | 20.059 | 1.00 | 11.02 |
| ATOM | 871 | C | LEU | A | 177 | 4.321 | 60.664 | 19.469 | 1.00 | 12.05 |
| ATOM | 872 | O | LEU | A | 177 | 4.794 | 59.622 | 19.940 | 1.00 | 14.19 |
| ATOM | 873 | CB | LEU | A | 177 | 1.819 | 60.783 | 19.264 | 1.00 | 5.55 |
| ATOM | 874 | CG | LEU | A | 177 | 0.503 | 61.029 | 19.988 | 1.00 | 4.04 |
| ATOM | 875 | CD1 | LEU | A | 177 | −0.624 | 61.254 | 19.005 | 1.00 | 13.14 |
| ATOM | 876 | CD2 | LEU | A | 177 | 0.210 | 59.844 | 20.845 | 1.00 | 13.50 |
| ATOM | 877 | N | THR | A | 178 | 4.918 | 61.326 | 18.470 | 1.00 | 18.26 |
| ATOM | 372 | CA | THR | A | 178 | 6.137 | 60.762 | 17.884 | 1.00 | 20.52 |
| ATOM | 879 | C | THR | A | 178 | 7.351 | 60.894 | 18.804 | 1.00 | 23.30 |
| ATOM | 880 | O | THR | A | 178 | 8.269 | 60.060 | 18.750 | 1.00 | 21.43 |
| ATOM | 881 | CB | THR | A | 178 | 6.439 | 61.323 | 16.442 | 1.00 | 17.29 |
| ATOM | 882 | OG1 | THR | A | 178 | 7.805 | 61.733 | 16.342 | 1.00 | 22.66 |
| ATOM | 883 | CG2 | THR | A | 178 | 5.561 | 62.461 | 16.103 | 1.00 | 17.00 |
| ATOM | 884 | N | TYR | A | 179 | 7.354 | 61.917 | 19.665 | 1.00 | 24.20 |
| ATOM | 885 | CA | TYR | A | 179 | 8.454 | 62.076 | 20.615 | 1.00 | 17.23 |
| ATOM | 886 | C | TYR | A | 179 | 8.369 | 60.937 | 21.629 | 1.00 | 17.06 |
| ATOM | 887 | O | TYR | A | 179 | 9.362 | 60.267 | 21.913 | 1.00 | 16.76 |
| ATOM | 888 | CB | TYR | A | 179 | 8.364 | 53.410 | 21.359 | 1.00 | 21.87 |
| ATOM | 889 | CG | TYR | A | 179 | 9.236 | 63.440 | 22.595 | 1.00 | 22.98 |
| ATOM | 890 | CD1 | TYR | A | 179 | 10.576 | 63.810 | 22.519 | 1.00 | 20.65 |
| ATOM | 891 | CD2 | TYR | A | 179 | 8.738 | 63.025 | 23.830 | 1.00 | 22.75 |
| ATOM | 892 | CE1 | TYR | A | 179 | 11.397 | 63.762 | 23.636 | 1.00 | 22.93 |
| ATOM | 893 | CE2 | TYR | A | 179 | 9.552 | 62.974 | 24.951 | 1.00 | 28.14 |
| ATOM | 894 | CZ | TYR | A | 179 | 10.880 | 63.341 | 24.847 | 1.00 | 26.95 |
| ATOM | 895 | OH | TYR | A | 179 | 11.681 | 63.286 | 25.959 | 1.00 | 32.49 |
| ATOM | 896 | N | LEU | A | 180 | 7.170 | 60.712 | 22.162 | 1.00 | 16.69 |
| ATOM | 897 | CA | LEU | A | 180 | 6.963 | 59.660 | 23.149 | 1.00 | 18.83 |
| ATOM | 898 | C | LEU | A | 180 | 7.325 | 58.300 | 22.562 | 1.00 | 24.40 |
| ATOM | 899 | O | LEU | A | 180 | 8.024 | 57.498 | 23.192 | 1.00 | 26.33 |
| ATOM | 900 | CB | LEU | A | 180 | 5.501 | 59.657 | 23.629 | 1.00 | 21.53 |
| ATOM | 901 | CG | LEU | A | 180 | 5.032 | 60.716 | 24.644 | 1.00 | 21.20 |
| ATOM | 902 | CD1 | LEU | A | 180 | 3.525 | 60.668 | 24.746 | 1.00 | 8.96 |
| ATOM | 903 | CD2 | LEU | A | 180 | 5.652 | 60.458 | 26.013 | 1.00 | 15.59 |
| ATOM | 904 | N | ARG | A | 181 | 6.847 | 58.043 | 21.347 | 1.00 | 23.85 |
| ATOM | 905 | CA | ARG | A | 181 | 7.116 | 56.779 | 20.674 | 1.00 | 26.96 |
| ATOM | 906 | C | ARG | A | 181 | 8.600 | 56.613 | 20.284 | 1.00 | 29.51 |
| ATOM | 907 | O | ARG | A | 181 | 9.215 | 55.571 | 20.565 | 1.00 | 24.95 |
| ATOM | 908 | CB | ARG | A | 181 | 6.186 | 56.657 | 19.442 | 1.00 | 31.64 |
| ATOM | 909 | CG | ARG | A | 181 | 6.746 | 55.917 | 18.240 | 1.00 | 29.36 |
| ATOM | 910 | CD | ARG | A | 181 | 5.837 | 54.787 | 17.801 | 1.00 | 37.78 |
| ATOM | 911 | NE | ARG | A | 181 | 6.586 | 53.538 | 17.747 | 1.00 | 43.86 |
| ATOM | 912 | CZ | ARG | A | 181 | 6.895 | 52.800 | 18.811 | 1.00 | 47.64 |
| ATOM | 913 | NH1 | ARG | A | 181 | 6.513 | 53.181 | 20.025 | 1.00 | 51.77 |
| ATOM | 914 | NH2 | ARG | A | 181 | 7.623 | 51.702 | 18.666 | 1.00 | 48.00 |
| ATOM | 915 | N | GLU | A | 182 | 9.185 | 57.637 | 19.667 | 1.00 | 28.25 |
| ATOM | 916 | CA | GLU | A | 182 | 10.579 | 57.559 | 19.246 | 1.00 | 32.29 |
| ATOM | 917 | C | GLU | A | 182 | 11.579 | 57.667 | 20.403 | 1.00 | 36.52 |
| ATOM | 918 | O | GLU | A | 182 | 12.534 | 56.893 | 20.490 | 1.00 | 37.51 |
| ATOM | 919 | CB | GLU | A | 182 | 10.868 | 58.649 | 18.214 | 1.00 | 39.69 |
| ATOM | 920 | CC | GLU | A | 182 | 10.972 | 58.150 | 16.769 | 1.00 | 47.59 |
| ATOM | 921 | CD | GLU | A | 182 | 10.460 | 59.166 | 15.751 | 1.00 | 54.53 |
| ATOM | 922 | OE1 | GLU | A | 182 | 9.533 | 58.821 | 14.981 | 1.00 | 59.11 |

TABLE 1-continued

Structural Coordinate of MEK1/N35/NKF (corresponding to amino acids 24, 383 of SEQ ID NO: 1) -compound 1-ATPγS Ternary Complex.

| | A | B | C | D | E | F | G | H | I | J |
|---|---|---|---|---|---|---|---|---|---|---|
| ATOM | 923 | OE2 | GLU | A | 182 | 10.981 | 60.307 | 15.717 | 1.00 | 55.59 |
| ATOM | 924 | N | LYS | A | 183 | 11.354 | 58.617 | 21.302 | 1.00 | 34.85 |
| ATOM | 925 | CA | LYS | A | 183 | 12.267 | 58.802 | 22.410 | 1.00 | 31.76 |
| ATOM | 926 | C | LYS | A | 183 | 12.057 | 57.875 | 23.593 | 1.00 | 31.00 |
| ATOM | 927 | O | LYS | A | 183 | 12.998 | 57.601 | 24.324 | 1.00 | 34.57 |
| ATOM | 928 | CB | LYS | A | 183 | 12.205 | 60.253 | 22.875 | 1.00 | 31.46 |
| ATOM | 929 | CG | LYS | A | 183 | 12.649 | 61.239 | 21.807 | 1.00 | 34.29 |
| ATOM | 930 | CD | LYS | A | 183 | 13.908 | 60.759 | 21.095 | 1.00 | 38.20 |
| ATOM | 931 | CE | LYS | A | 183 | 14.730 | 61.922 | 20.559 | 1.00 | 38.45 |
| ATOM | 932 | NZ | LYS | A | 183 | 13.831 | 62.850 | 19.769 | 1.00 | 41.41 |
| ATOM | 933 | N | HIS | A | 184 | 10.844 | 57.373 | 23.734 | 1.00 | 33.70 |
| ATOM | 934 | CA | HIS | A | 184 | 10.577 | 56.498 | 24.926 | 1.00 | 29.58 |
| ATOM | 935 | C | HIS | A | 184 | 9.890 | 55.173 | 24.632 | 1.00 | 27.54 |
| ATOM | 936 | O | HIS | A | 184 | 9.577 | 54.378 | 25.483 | 1.00 | 23.78 |
| ATOM | 937 | CB | HIS | A | 184 | 9.790 | 57.288 | 25.976 | 1.00 | 29.02 |
| ATOM | 938 | CG | HIS | A | 184 | 10.494 | 58.533 | 26.420 | 1.00 | 31.48 |
| ATOM | 939 | ND1 | HIS | A | 184 | 11.536 | 58.516 | 27.326 | 1.00 | 25.12 |
| ATOM | 940 | CD2 | HIS | A | 184 | 10.379 | 59.818 | 26.001 | 1.00 | 30.21 |
| ATOM | 941 | CE1 | HIS | A | 184 | 12.033 | 59.734 | 27.441 | 1.00 | 19.96 |
| ATOM | 942 | NE2 | HIS | A | 184 | 11.351 | 60.544 | 26.648 | 1.00 | 19.98 |
| ATOM | 943 | N | LYS | A | 185 | 9.796 | 54.892 | 23.320 | 1.00 | 29.94 |
| ATOM | 944 | CA | LYS | A | 185 | 9.190 | 53.638 | 22.911 | 1.00 | 25.67 |
| ATOM | 945 | C | LYS | A | 185 | 7.890 | 53.334 | 23.628 | 1.00 | 23.62 |
| ATOM | 946 | O | LYS | A | 185 | 7.695 | 52.210 | 24.077 | 1.00 | 26.79 |
| ATOM | 947 | CB | LYS | A | 185 | 10.178 | 52.490 | 23.150 | 1.00 | 27.19 |
| ATOM | 948 | CG | LYS | A | 185 | 11.531 | 52.654 | 22.435 | 1.00 | 36.23 |
| ATOM | 949 | CD | LYS | A | 185 | 12.291 | 51.326 | 22.277 | 1.00 | 36.43 |
| ATOM | 950 | CE | LYS | A | 185 | 13.059 | 51.267 | 20.953 | 1.00 | 42.84 |
| ATOM | 951 | NZ | LYS | A | 185 | 14.269 | 52.150 | 20.924 | 1.00 | 41.69 |
| ATOM | 952 | N | ILE | A | 186 | 6.990 | 54.314 | 23.735 | 1.00 | 22.46 |
| ATOM | 953 | CA | ILE | A | 186 | 5.709 | 54.071 | 24.405 | 1.00 | 22.53 |
| ATOM | 954 | C | ILE | A | 186 | 4.540 | 54.777 | 23.720 | 1.00 | 23.99 |
| ATOM | 955 | O | ILE | A | 186 | 4.721 | 55.824 | 23.092 | 1.00 | 20.57 |
| ATOM | 956 | CB | ILE | A | 186 | 5.728 | 54.506 | 25.922 | 1.00 | 27.19 |
| ATOM | 957 | CG1 | ILE | A | 186 | 5.423 | 56.001 | 26.070 | 1.00 | 24.94 |
| ATOM | 958 | CG2 | ILE | A | 186 | 7.076 | 54.208 | 26.549 | 1.00 | 23.58 |
| ATOM | 959 | CD1 | ILE | A | 186 | 6.433 | 56.898 | 25.415 | 1.00 | 28.89 |
| ATOM | 960 | N | MET | A | 187 | 3.348 | 54.187 | 23.825 | 1.00 | 20.86 |
| ATOM | 961 | CA | MET | A | 187 | 2.164 | 54.794 | 23.243 | 1.00 | 14.33 |
| ATOM | 962 | C | MET | A | 187 | 1.408 | 55.593 | 24.306 | 1.00 | 16.97 |
| ATOM | 963 | O | MET | A | 187 | 1.516 | 55.348 | 25.507 | 1.00 | 15.96 |
| ATOM | 964 | CB | MET | A | 187 | 1.247 | 53.727 | 22.617 | 1.00 | 18.58 |
| ATOM | 965 | CG | MET | A | 187 | 0.657 | 52.690 | 23.574 | 1.00 | 16.74 |
| ATOM | 966 | SD | MET | A | 187 | −0.722 | 51.650 | 22.859 | 1.00 | 15.64 |
| ATOM | 967 | CE | MET | A | 187 | −1.869 | 52.922 | 22.193 | 1.00 | 1.00 |
| ATOM | 968 | N | HIS | A | 188 | 0.644 | 86.569 | 23.870 | 1.00 | 14.62 |
| ATOM | 969 | CA | HIS | A | 188 | −0.097 | 57.369 | 24.809 | 1.00 | 10.78 |
| ATOM | 970 | C | HIS | A | 188 | −1.138 | 56.519 | 25.529 | 1.00 | 13.41 |
| ATOM | 971 | O | HIS | A | 188 | −1.022 | 56.252 | 26.727 | 1.00 | 12.76 |
| ATOM | 972 | CB | HIS | A | 188 | −0.761 | 58.509 | 24.072 | 1.00 | 7.01 |
| ATOM | 973 | CG | HIS | A | 188 | −1.215 | 59.596 | 24.979 | 1.00 | 19.48 |
| ATOM | 974 | NDI | HIS | A | 188 | −2.266 | 59.432 | 25.857 | 1.00 | 22.43 |
| ATOM | 975 | CD2 | HIS | A | 188 | −0.782 | 60.869 | 25.133 | 1.00 | 7.48 |
| ATOM | 976 | CE1 | HIS | A | 188 | −2.464 | 60.561 | 26.513 | 1.00 | 10.95 |
| ATOM | 977 | NE2 | HIS | A | 188 | −1.577 | 61.448 | 26.090 | 1.00 | 19.02 |
| ATOM | 978 | N | ARG | A | 189 | −2.139 | 56.080 | 24.773 | 1.00 | 4.98 |
| ATOM | 979 | CA | ARG | A | 189 | −3.205 | 55.231 | 25.259 | 1.00 | 1.00 |
| ATOM | 980 | C | ARG | A | 189 | −4.383 | 55.951 | 25.774 | 1.00 | 1.00 |
| ATOM | 981 | O | ARG | A | 189 | −5.309 | 55.310 | 26.213 | 1.00 | −4.19 |
| ATOM | 982 | CB | ARG | A | 189 | −2.720 | 54.284 | 26.337 | 1.00 | 1.00 |
| ATOM | 983 | CG | ARG | A | 189 | −1.507 | 53.529 | 25.886 | 1.00 | 9.33 |
| ATOM | 984 | CD | ARG | A | 189 | −0.859 | 52.801 | 27.025 | 1.00 | 21.68 |
| ATOM | 985 | NE | ARG | A | 189 | −1.282 | 51.414 | 27.036 | 1.00 | 26.56 |
| ATOM | 986 | CZ | ARG | A | 189 | −2.527 | 51.041 | 27.303 | 1.00 | 35.81 |
| ATOM | 987 | NH1 | ARG | A | 189 | −3.440 | 51.961 | 27.577 | 1.00 | 41.96 |
| ATOM | 988 | NH2 | ARG | A | 189 | −2.865 | 49.759 | 27.297 | 1.00 | 37.90 |
| ATOM | 989 | N | ASP | A | 190 | −4.371 | 57.278 | 25.729 | 1.00 | 9.10 |
| ATOM | 990 | CA | ASP | A | 190 | −5.516 | 58.024 | 26.248 | 1.00 | 6.50 |
| ATOM | 991 | C | ASP | A | 190 | −5.598 | 59.437 | 25.699 | 1.00 | 7.95 |
| ATOM | 992 | O | ASP | A | 190 | −5.799 | 60.392 | 26.448 | 1.00 | 11.22 |
| ATOM | 993 | CB | ASP | A | 190 | −5.473 | 58.058 | 27.784 | 1.00 | 6.98 |
| ATOM | 994 | CG | ASP | A | 190 | −6.825 | 58.454 | 28.419 | 1.00 | 15.04 |
| ATOM | 995 | OD1 | ASP | A | 190 | −7.874 | 58.430 | 27.731 | 1.00 | 17.20 |
| ATOM | 996 | OD2 | ASP | A | 190 | −6.835 | 58.796 | 29.629 | 1.00 | 22.60 |
| ATOM | 997 | N | VAL | A | 191 | −5.454 | 59.581 | 24.386 | 1.00 | 6.04 |

TABLE 1-continued

Structural Coordinate of MEK1/N35/NKF (corresponding to amino acids 24, 383 of SEQ ID NO: 1) -compound 1-ATPγS Ternary Complex.

| A | B | C | D | E | F | G | H | I | J |
|---|---|---|---|---|---|---|---|---|---|
| ATOM | 998 | CA | VAL | A | 191 | −5.567 | 60.903 | 23.829 | 1.00 | 7.99 |
| ATOM | 999 | C | VAL | A | 191 | −7.028 | 61.213 | 23.509 | 1.00 | 10.60 |
| ATOM | 1000 | O | VAL | A | 191 | −7.794 | 60.371 | 23.158 | 1.00 | 16.67 |
| ATOM | 1001 | CB | VAL | A | 191 | −4.729 | 61.088 | 22.524 | 1.00 | 7.90 |
| ATOM | 1002 | CG1 | VAL | A | 191 | −3.990 | 59.819 | 22.186 | 1.00 | 10.45 |
| ATOM | 1003 | CG2 | VAL | A | 191 | −5.596 | 61.587 | 21.389 | 1.00 | 8.16 |
| ATOM | 1004 | N | LYS | A | 192 | −7.407 | 62.426 | 23.999 | 1.00 | 15.69 |
| ATOM | 1005 | CA | LYS | A | 192 | −8.760 | 62.944 | 23.872 | 1.00 | 10.37 |
| ATOM | 1006 | C | LYS | A | 192 | −8.635 | 64.404 | 24.241 | 1.00 | 13.21 |
| ATOM | 1007 | O | LYS | A | 192 | −7.645 | 64.798 | 24.820 | 1.00 | 17.39 |
| ATOM | 1008 | CB | LYS | A | 192 | −9.695 | 62.236 | 24.826 | 1.00 | 9.57 |
| ATOM | 1009 | CG | LYS | A | 192 | −9.089 | 61.877 | 26.158 | 1.00 | 13.00 |
| ATOM | 1010 | CD | LYS | A | 192 | −10.190 | 61.502 | 27.134 | 1.00 | 4.26 |
| ATOM | 1011 | CE | LYS | A | 192 | −9.696 | 60.480 | 28.107 | 1.00 | 14.42 |
| ATOM | 1012 | NZ | LYS | A | 192 | −10.306 | 60.658 | 29.454 | 1.00 | 14.54 |
| ATOM | 1013 | N | PRO | A | 193 | −9.640 | 65.226 | 23.934 | 1.00 | 14.53 |
| ATOM | 1014 | CA | PRO | A | 193 | −9.535 | 66.653 | 24.273 | 1.00 | 15.55 |
| ATOM | 1015 | C | PRO | A | 193 | −9.030 | 67.005 | 25.691 | 1.00 | 21.41 |
| ATOM | 1016 | O | PRO | A | 193 | −8.164 | 67.877 | 25.859 | 1.00 | 24.92 |
| ATOM | 1017 | CB | PRO | A | 193 | −10.949 | 67.186 | 24.019 | 1.00 | 14.07 |
| ATOM | 1018 | CG | PRO | A | 193 | −11.527 | 66.251 | 23.013 | 1.00 | 15.45 |
| ATOM | 1019 | CD | PRO | A | 193 | −10.936 | 64.896 | 23.316 | 1.00 | 13.08 |
| ATOM | 1020 | N | SER | A | 194 | −9.556 | 66.327 | 26.707 | 1.00 | 17.12 |
| ATOM | 1021 | CA | SER | A | 194 | −9.170 | 66.619 | 28.084 | 1.00 | 11.99 |
| ATOM | 1022 | C | SER | A | 194 | −7.722 | 66.313 | 28.462 | 1.00 | 12.87 |
| ATOM | 1023 | O | SER | A | 194 | −7.259 | 66.758 | 29.512 | 1.00 | 15.78 |
| ATOM | 1024 | CB | SER | A | 194 | −10.099 | 65.888 | 29.046 | 1.00 | 2.95 |
| ATOM | 1025 | OG | SER | A | 194 | −9.735 | 64.525 | 29.109 | 1.00 | 4.10 |
| ATOM | 1026 | N | ASN | A | 195 | −7.004 | 65.544 | 27.649 | 1.00 | 13.19 |
| ATOM | 1027 | CA | ASN | A | 195 | −5.604 | 65.239 | 27.969 | 1.00 | 3.16 |
| ATOM | 1028 | C | ASN | A | 195 | −4.659 | 65.979 | 27.033 | 1.00 | 3.51 |
| ATOM | 1029 | O | ASN | A | 195 | −3.531 | 65.560 | 26.816 | 1.00 | 3.62 |
| ATOM | 1030 | CB | ASN | A | 195 | −5.345 | 63.725 | 27.940 | 1.00 | 7.29 |
| ATOM | 1031 | CG | ASN | A | 195 | −6.078 | 62.980 | 29.067 | 1.00 | 16.24 |
| ATOM | 1032 | OD1 | ASN | A | 195 | −6.705 | 63.609 | 29.918 | 1.00 | 22.53 |
| ATOM | 1033 | ND2 | ASN | A | 195 | −5.999 | 61.644 | 29.073 | 1.00 | 5.10 |
| ATOM | 1034 | N | ILE | A | 196 | −5.144 | 67.078 | 26.462 | 1.00 | 10.19 |
| ATOM | 1035 | CA | ILE | A | 196 | −4.345 | 67.935 | 25.587 | 1.00 | 11.06 |
| ATOM | 1036 | C | ILE | A | 196 | −4.429 | 69.291 | 26.296 | 1.00 | 14.37 |
| ATOM | 1037 | O | ILE | A | 196 | −5.478 | 69.943 | 26.302 | 1.00 | 11.81 |
| ATOM | 1038 | CB | ILE | A | 196 | −4.951 | 68.067 | 24.159 | 1.00 | 8.54 |
| ATOM | 1039 | CG1 | ILE | A | 196 | −5.146 | 66.681 | 23.531 | 1.00 | 13.43 |
| ATOM | 1040 | CG2 | ILE | A | 196 | −4.049 | 68.920 | 23.284 | 1.00 | 3.89 |
| ATOM | 1041 | CD1 | ILE | A | 196 | −5.747 | 66.709 | 22.132 | 1.00 | 9.24 |
| ATOM | 1042 | N | LEU | A | 197 | −3.331 | 69.706 | 26.909 | 1.00 | 13.27 |
| ATOM | 1043 | CA | LEU | A | 197 | −3.327 | 70.961 | 27.645 | 1.00 | 18.16 |
| ATOM | 1044 | C | LEU | A | 197 | −2.768 | 72.150 | 26.867 | 1.00 | 20.90 |
| ATOM | 1045 | O | LEU | A | 197 | −1.782 | 72.028 | 26.140 | 1.00 | 24.12 |
| ATOM | 1046 | CB | LEU | A | 197 | −2.537 | 70.767 | 28.931 | 1.00 | 9.76 |
| ATOM | 1047 | CG | LEU | A | 197 | −3.316 | 70.231 | 30.123 | 1.00 | 14.11 |
| ATOM | 1048 | CD1 | LEU | A | 197 | −4.468 | 69.396 | 29.668 | 1.00 | 10.30 |
| ATOM | 1049 | CD2 | LEU | A | 197 | −2.391 | 69.432 | 31.006 | 1.00 | 15.62 |
| ATOM | 1050 | N | VAL | A | 198 | −3.422 | 73.298 | 26.996 | 1.00 | 19.80 |
| ATOM | 1051 | CA | VAL | A | 198 | −2.937 | 74.503 | 26.328 | 1.00 | 25.06 |
| ATOM | 1052 | C | VAL | A | 198 | −2.563 | 75.594 | 27.362 | 1.00 | 25.90 |
| ATOM | 1053 | O | VAL | A | 198 | −2.758 | 75.414 | 28.566 | 1.00 | 22.42 |
| ATOM | 1054 | CB | VAL | A | 198 | −3.986 | 75.061 | 25.333 | 1.00 | 23.02 |
| ATOM | 1055 | CC1 | VAL | A | 198 | −4.088 | 74.141 | 24.130 | 1.00 | 25.99 |
| ATOM | 1056 | CG2 | VAL | A | 198 | −5.334 | 75.205 | 26.008 | 1.00 | 26.53 |
| ATOM | 1057 | N | ASN | A | 199 | −1.993 | 76.703 | 26.891 | 1.00 | 26.25 |
| ATOM | 1058 | CA | ASN | A | 199 | −1.515 | 77.796 | 27.779 | 1.00 | 23.88 |
| ATOM | 1059 | C | ASN | A | 199 | −1.535 | 79.153 | 27.075 | 1.00 | 29.40 |
| ATOM | 1060 | O | ASN | A | 199 | −1.406 | 79.232 | 25.853 | 1.00 | 24.22 |
| ATOM | 1061 | CB | ASN | A | 199 | −0.307 | 77.452 | 28.521 | 1.00 | 9.76 |
| ATOM | 1062 | CG | ASN | A | 199 | 0.943 | 77.663 | 27.675 | 1.00 | 16.12 |
| ATOM | 1063 | OD1 | ASN | A | 199 | 2.027 | 77.204 | 28.050 | 1.00 | 16.82 |
| ATOM | 1064 | ND2 | ASN | A | 199 | 0.812 | 78.347 | 26.550 | 1.00 | 10.04 |
| ATOM | 1065 | N | SER | A | 200 | −1.632 | 80.219 | 27.863 | 1.00 | 36.99 |
| ATOM | 1066 | CA | SER | A | 200 | −1.614 | 81.589 | 27.350 | 1.00 | 40.77 |
| ATOM | 1067 | C | SER | A | 200 | −0.458 | 81.877 | 26.401 | 1.00 | 42.42 |
| ATOM | 1068 | O | SER | A | 200 | −0.506 | 82.810 | 25.607 | 1.00 | 43.48 |
| ATOM | 1069 | CB | SER | A | 200 | −1.549 | 62.561 | 28.516 | 1.00 | 36.57 |
| ATOM | 1070 | OG | SER | A | 200 | −0.511 | 82.174 | 29.392 | 1.00 | 40.92 |
| ATOM | 1071 | N | ARG | A | 201 | 0.820 | 81.208 | 26.398 | 1.00 | 44.32 |
| ATOM | 1072 | CA | ARG | A | 201 | 1.988 | 81.346 | 25.549 | 1.00 | 43.41 |

TABLE 1-continued

Structural Coordinate of MEK1/N35/NKF (corresponding to amino acids 24, 383 of SEQ ID NO: 1) -compound 1-ATPγS Ternary Complex.

| | A | B | C | D | E | F | G | H | I | J |
|---|---|---|---|---|---|---|---|---|---|---|
| ATOM | 1073 | C | ARG | A | 201 | 1.780 | 80.725 | 24.177 | 1.00 | 43.74 |
| ATOM | 1074 | O | ARG | A | 201 | 2.651 | 80.815 | 23.320 | 1.00 | 48.13 |
| ATOM | 1075 | CB | ARG | A | 201 | 3.179 | 80.702 | 26.243 | 1.00 | 46.39 |
| ATOM | 1076 | CG | ARG | A | 201 | 2.972 | 80.550 | 27.745 | 1.00 | 55.29 |
| ATOM | 1077 | CD | ARG | A | 201 | 4.271 | 80.726 | 28.488 | 1.00 | 62.48 |
| ATOM | 1078 | NE | ARG | A | 201 | 5.353 | 79.986 | 27.845 | 1.00 | 69.50 |
| ATOM | 1079 | CZ | ARG | A | 201 | 5.844 | 78.841 | 28.305 | 1.00 | 75.38 |
| ATOM | 1080 | NH1 | ARG | A | 201 | 5.351 | 78.299 | 29.415 | 1.00 | 76.77 |
| ATOM | 1081 | NH2 | ARG | A | 201 | 6.829 | 78.233 | 27.650 | 1.00 | 76.77 |
| ATOM | 1082 | N | GLY | A | 202 | 0.626 | 80.101 | 23.961 | 1.00 | 41.65 |
| ATOM | 1083 | CA | GLY | A | 202 | 0.354 | 79.486 | 22.671 | 1.00 | 39.21 |
| ATOM | 1084 | C | GLY | A | 202 | 0.821 | 78.044 | 22.571 | 1.00 | 34.48 |
| ATOM | 1085 | O | GLY | A | 202 | 0.775 | 77.431 | 21.503 | 1.00 | 27.95 |
| ATOM | 1086 | N | GLU | A | 203 | 1.265 | 77.505 | 23.701 | 1.00 | 34.61 |
| ATOM | 1087 | CA | GLU | A | 203 | 1.747 | 76.135 | 23.770 | 1.00 | 34.41 |
| ATOM | 1088 | C | GLU | A | 203 | 0.594 | 75.115 | 23.869 | 1.00 | 32.38 |
| ATOM | 1089 | O | GLU | A | 203 | −0.457 | 75.378 | 24.456 | 1.00 | 29.49 |
| ATOM | 1090 | CB | GLU | A | 203 | 2.704 | 75.988 | 24.958 | 1.00 | 35.99 |
| ATOM | 1091 | CG | GLU | A | 203 | 4.163 | 76.308 | 24.637 | 1.00 | 38.65 |
| ATOM | 1092 | CD | GLU | A | 203 | 5.065 | 76.247 | 25.861 | 1.00 | 42.02 |
| ATOM | 1093 | OE1 | GLU | A | 203 | 4.638 | 76.717 | 26.934 | 1.00 | 42.72 |
| ATOM | 1094 | OE2 | GLU | A | 203 | 6.199 | 75.726 | 25.753 | 1.00 | 44.37 |
| ATOM | 1095 | N | ILE | A | 204 | 0.812 | 73.948 | 23.277 | 1.00 | 29.50 |
| ATOM | 1096 | CA | ILE | A | 204 | −0.184 | 72.884 | 23.264 | 1.00 | 23.36 |
| ATOM | 1097 | C | ILE | A | 204 | 0.547 | 71.620 | 23.637 | 1.00 | 19.48 |
| ATOM | 1098 | O | ILE | A | 204 | 1.433 | 71.190 | 22.908 | 1.00 | 18.22 |
| ATOM | 1099 | CB | ILE | A | 204 | −0.775 | 72.725 | 21.860 | 1.00 | 21.23 |
| ATOM | 1100 | CC1 | ILE | A | 204 | −1.297 | 74.079 | 21.361 | 1.00 | 20.55 |
| ATOM | 1101 | CG2 | ILE | A | 204 | −1.867 | 71.682 | 21.884 | 1.00 | 24.25 |
| ATOM | 1102 | CD1 | ILE | A | 204 | −1.979 | 74.031 | 19.991 | 1.00 | 23.30 |
| ATOM | 1103 | N | LYS | A | 205 | 0.183 | 71.020 | 24.767 | 1.00 | 17.60 |
| ATOM | 1104 | CA | LYS | A | 205 | 0.868 | 69.820 | 25.222 | 1.00 | 13.58 |
| ATOM | 1105 | C | LYS | A | 205 | −0.050 | 68.694 | 25.632 | 1.00 | 9.43 |
| ATOM | 1106 | O | LYS | A | 205 | −1.233 | 68.897 | 25.893 | 1.00 | 11.03 |
| ATOM | 1107 | CB | LYS | A | 205 | 1.787 | 70.153 | 26.395 | 1.00 | 20.21 |
| ATOM | 1108 | CG | LYS | A | 205 | 2.519 | 71.481 | 26.251 | 1.00 | 22.19 |
| ATOM | 1109 | CD | LYS | A | 205 | 3.617 | 71.618 | 27.318 | 1.00 | 28.07 |
| ATOM | 1110 | CE | LYS | A | 205 | 4.629 | 72.702 | 26.942 | 1.00 | 24.19 |
| ATOM | 1111 | NZ | LYS | A | 205 | 5.301 | 73.302 | 28.125 | 1.00 | 24.47 |
| ATOM | 1112 | N | LEU | A | 206 | 0.231 | 67.507 | 25.732 | 1.00 | 6.38 |
| ATOM | 1113 | CA | LEU | A | 206 | −0.197 | 66.301 | 26.104 | 1.00 | 10.11 |
| ATOM | 1114 | C | LEU | A | 206 | 0.141 | 65.877 | 27.513 | 1.00 | 9.98 |
| ATOM | 1115 | O | LEU | A | 206 | 1.305 | 65.915 | 27.915 | 1.00 | 11.25 |
| ATOM | 1116 | CB | LEU | A | 206 | 0.201 | 65.124 | 25.193 | 1.00 | 11.39 |
| ATOM | 1117 | CG | LEU | A | 206 | −0.442 | 64.733 | 23.867 | 1.00 | 7.60 |
| ATOM | 1118 | CD1 | LEU | A | 206 | −1.260 | 65.827 | 23.278 | 1.00 | 11.01 |
| ATOM | 1119 | CD2 | LEU | A | 206 | 0.655 | 64.373 | 22.941 | 1.00 | 1.68 |
| ATOM | 1120 | N | CYS | A | 206 | −0.865 | 65.425 | 28.245 | 1.00 | 4.73 |
| ATOM | 1121 | CA | CYS | A | 207 | −0.651 | 64.913 | 29.589 | 1.00 | 8.41 |
| ATOM | 1122 | C | CYS | A | 207 | −1.366 | 63.578 | 29.682 | 1.00 | 13.52 |
| ATOM | 1123 | O | CYS | A | 207 | −1.968 | 63.105 | 28.719 | 1.00 | 10.76 |
| ATOM | 1124 | CB | CYS | A | 207 | −1.267 | 65.835 | 30.630 | 1.00 | 6.53 |
| ATOM | 1125 | SG | CYS | A | 207 | −3.024 | 66.080 | 30.340 | 1.00 | 13.39 |
| ATOM | 1126 | N | ASP | A | 208 | −1.294 | 62.982 | 30.861 | 1.00 | 15.78 |
| ATOM | 1127 | CA | ASP | A | 208 | −1.973 | 61.736 | 31.143 | 1.00 | 17.32 |
| ATOM | 1128 | C | ASP | A | 208 | −1.711 | 60.540 | 30.221 | 1.00 | 18.84 |
| ATOM | 1129 | O | ASP | A | 208 | −2.647 | 59.806 | 29.899 | 1.00 | 18.11 |
| ATOM | 1130 | CB | ASP | A | 208 | −3.481 | 62.003 | 31.206 | 1.00 | 18.66 |
| ATOM | 1131 | CG | ASP | A | 208 | −3.873 | 62.871 | 32.385 | 1.00 | 22.68 |
| ATOM | 1132 | OD1 | ASP | A | 208 | −4.998 | 63.396 | 32.385 | 1.00 | 20.44 |
| ATOM | 1133 | OD2 | ASP | A | 208 | −3.061 | 63.032 | 33.315 | 1.00 | 26.55 |
| ATOM | 1134 | N | PHE | A | 209 | −0.467 | 60.329 | 29.800 | 1.00 | 14.63 |
| ATOM | 1135 | CA | PHE | A | 209 | −0.176 | 59.176 | 28.966 | 1.00 | 18.87 |
| ATOM | 1136 | C | PHE | A | 209 | 0.212 | 58.018 | 29.867 | 1.00 | 20.60 |
| ATOM | 1137 | O | PHE | A | 209 | 0.407 | 58.214 | 31.054 | 1.00 | 20.15 |
| ATOM | 1138 | CB | PHE | A | 209 | 0.926 | 59.465 | 27.953 | 1.00 | 17.74 |
| ATOM | 1139 | CG | PHE | A | 209 | 1.998 | 60.365 | 28.454 | 1.00 | 12.99 |
| ATOM | 1140 | CD1 | PHE | A | 209 | 1.873 | 61.744 | 28.322 | 1.00 | 17.78 |
| ATOM | 1141 | CD2 | PHE | A | 209 | 3.172 | 59.837 | 28.968 | 1.00 | 7.67 |
| ATOM | 1142 | CE1 | PHE | A | 209 | 2.907 | 62.587 | 28.690 | 1.00 | 13.83 |
| ATOM | 1143 | CE2 | PHE | A | 209 | 4.196 | 60.633 | 29.299 | 1.00 | 9.69 |
| ATOM | 1144 | CZ | PHE | A | 209 | 4.079 | 62.042 | 29.196 | 1.00 | 14.31 |
| ATOM | 1145 | N | GLY | A | 210 | 0.330 | 56.819 | 29.301 | 1.00 | 19.53 |
| ATOM | 1146 | CA | GLY | A | 210 | 0.635 | 55.646 | 30.098 | 1.00 | 17.23 |
| ATOM | 1147 | C | GLY | A | 210 | 2.088 | 55.267 | 30.263 | 1.00 | 23.73 |

TABLE 1-continued

Structural Coordinate of MEK1/N35/NKF (corresponding to amino acids 24, 383 of SEQ ID NO: 1) -compound 1-ATPγS Ternary Complex.

| A | B | C | D | E | F | G | H | I | J |
|---|---|---|---|---|---|---|---|---|---|
| ATOM | 1148 | O | GLY | A | 210 | 2.583 | 54.390 | 29.546 | 1.00 | 23.36 |
| ATOM | 1149 | N | VAL | A | 211 | 2.766 | 55.903 | 31.222 | 1.00 | 18.69 |
| ATOM | 1150 | CA | VAL | A | 211 | 4.175 | 55.624 | 31.486 | 1.00 | 15.92 |
| ATOM | 1151 | C | VAL | A | 211 | 4.343 | 54.460 | 32.456 | 1.00 | 18.33 |
| ATOM | 1152 | O | VAL | A | 211 | 5.406 | 53.844 | 32.513 | 1.00 | 23.10 |
| ATOM | 1153 | CB | VAL | A | 211 | 4.919 | 56.853 | 32.099 | 1.00 | 15.49 |
| ATOM | 1154 | CG1 | VAL | A | 211 | 5.258 | 57.856 | 31.015 | 1.00 | 20.17 |
| ATOM | 1155 | CG2 | VAL | A | 211 | 4.057 | 57.515 | 33.182 | 1.00 | 8.13 |
| ATOM | 1156 | N | SER | A | 212 | 3.300 | 54.158 | 33.219 | 1.00 | 16.14 |
| ATOM | 1157 | CA | SER | A | 212 | 3.400 | 53.084 | 34.192 | 1.00 | 16.89 |
| ATOM | 1158 | C | SER | A | 212 | 2.437 | 51.933 | 33.950 | 1.00 | 17.75 |
| ATOM | 1159 | O | SER | A | 212 | 1.210 | 52.084 | 34.035 | 1.00 | 11.52 |
| ATOM | 1160 | CB | SER | A | 212 | 3.200 | 53.645 | 35.612 | 1.00 | 22.55 |
| ATOM | 1161 | OG | SER | A | 212 | 2.661 | 52.692 | 36.524 | 1.00 | 14.76 |
| ATOM | 1162 | N | GLY | A | 213 | 3.002 | 50.772 | 33.650 | 1.00 | 18.52 |
| ATOM | 1163 | CA | GLY | A | 213 | 2.169 | 49.612 | 33.430 | 1.00 | 22.77 |
| ATOM | 1164 | C | GLY | A | 213 | 1.353 | 49.343 | 34.678 | 1.00 | 22.25 |
| ATOM | 1165 | O | GLY | A | 213 | 0.155 | 49.041 | 34.611 | 1.00 | 20.29 |
| ATOM | 1166 | N | GLN | A | 214 | 2.015 | 49.465 | 35.826 | 1.00 | 27.41 |
| ATOM | 1167 | CA | GLN | A | 214 | 1.371 | 49.232 | 37.114 | 1.00 | 25.26 |
| ATOM | 1168 | C | GLN | A | 214 | 0.242 | 50.229 | 37.331 | 1.00 | 24.17 |
| ATOM | 1169 | O | GLN | A | 214 | −0.783 | 49.887 | 37.920 | 1.00 | 24.74 |
| ATOM | 1170 | CB | GLN | A | 214 | 2.390 | 49.334 | 38.240 | 1.00 | 30.54 |
| ATOM | 1171 | CG | GLN | A | 214 | 2.430 | 48.128 | 39.161 | 1.00 | 32.29 |
| ATOM | 1172 | CD | GLN | A | 214 | 1.068 | 47.495 | 39.317 | 1.00 | 36.82 |
| ATOM | 1173 | OE1 | GLN | A | 214 | 0.067 | 40.190 | 39.500 | 1.00 | 39.11 |
| ATOM | 1174 | NE2 | GLN | A | 214 | 1.016 | 46.172 | 39.239 | 1.00 | 34.02 |
| ATOM | 1175 | N | LEU | A | 215 | 0.421 | 51.462 | 36.859 | 1.00 | 21.87 |
| ATOM | 1176 | CA | LEU | A | 215 | −0.637 | 82.447 | 37.013 | 1.00 | 22.64 |
| ATOM | 1177 | C | LEU | A | 215 | −1.792 | 52.021 | 36.112 | 1.00 | 25.00 |
| ATOM | 1178 | O | LEU | A | 215 | −2.929 | 51.900 | 36.578 | 1.00 | 23.14 |
| ATOM | 1179 | CB | LEU | A | 215 | −0.153 | 53.856 | 36.644 | 1.00 | 21.78 |
| ATOM | 1180 | CG | LEU | A | 215 | −1.039 | 54.950 | 37.248 | 1.00 | 22.99 |
| ATOM | 1181 | CD1 | LEU | A | 215 | −1.500 | 54.507 | 38.630 | 1.00 | 12.37 |
| ATOM | 1182 | CD2 | LEU | A | 215 | −0.285 | 56.257 | 37.339 | 1.00 | 21.05 |
| ATOM | 1183 | N | ILE | A | 216 | −1.489 | 51.766 | 34.833 | 1.00 | 25.13 |
| ATOM | 1184 | CA | ILE | A | 216 | −2.498 | 51.314 | 33.868 | 1.00 | 26.43 |
| ATOM | 1185 | C | ILE | A | 216 | −3.306 | 50.177 | 34.522 | 1.00 | 29.08 |
| ATOM | 1186 | O | ILE | A | 216 | −4.545 | 50.203 | 34.563 | 1.00 | 25.25 |
| ATOM | 1187 | CB | ILE | A | 216 | −1.846 | 50.754 | 32.572 | 1.00 | 24.55 |
| ATOM | 1188 | CG1 | ILE | A | 216 | −1.290 | 51.881 | 31.711 | 1.00 | 17.39 |
| ATOM | 1189 | CG2 | ILE | A | 216 | −2.887 | 50.022 | 31.739 | 1.00 | 24.26 |
| ATOM | 1190 | CD1 | ILE | A | 216 | −0.088 | 51.464 | 30.873 | 1.00 | 17.82 |
| ATOM | 1191 | N | ASP | A | 217 | −2.589 | 49.184 | 35.034 | 1.00 | 31.63 |
| ATOM | 1192 | CA | ASP | A | 217 | −3.222 | 48.049 | 35.684 | 1.00 | 37.82 |
| ATOM | 1193 | C | ASP | A | 217 | −4.168 | 48.528 | 36.771 | 1.00 | 38.70 |
| ATOM | 1194 | O | ASP | A | 217 | −5.383 | 48.396 | 36.642 | 1.00 | 36.98 |
| ATOM | 1195 | CB | ASP | A | 217 | −2.161 | 47.129 | 36.295 | 1.00 | 46.25 |
| ATOM | 1196 | CG | ASP | A | 217 | −1.600 | 46.139 | 35.289 | 1.00 | 56.08 |
| ATOM | 1197 | OD1 | ASP | A | 217 | −1.754 | 46.378 | 34.069 | 1.00 | 69.08 |
| ATOM | 1198 | OD2 | ASP | A | 217 | −1.004 | 45.121 | 35.715 | 1.00 | 60.98 |
| ATOM | 1199 | N | SER | A | 218 | −3.608 | 49.104 | 37.829 | 1.00 | 38.42 |
| ATOM | 1200 | CA | SER | A | 218 | −4.410 | 49.579 | 38.947 | 1.00 | 39.52 |
| ATOM | 1201 | C | SER | A | 218 | −5.500 | 50.553 | 38.578 | 1.00 | 41.42 |
| ATOM | 1202 | O | SER | A | 218 | −6.219 | 51.038 | 39.448 | 1.00 | 44.53 |
| ATOM | 1203 | CB | SER | A | 218 | −3.510 | 50.197 | 40.009 | 1.00 | 37.46 |
| ATOM | 1204 | OG | SER | A | 218 | −2.555 | 49.248 | 40.430 | 1.00 | 39.57 |
| ATOM | 1205 | N | MET | A | 219 | −5.651 | 50.863 | 37.302 | 1.00 | 46.31 |
| ATOM | 1206 | CA | MET | A | 219 | −6.719 | 51.762 | 36.896 | 1.00 | 53.76 |
| ATOM | 1207 | C | MET | A | 219 | −7.731 | 50.953 | 36.082 | 1.00 | 56.84 |
| ATOM | 1208 | O | MET | A | 219 | −8.157 | 51.363 | 35.003 | 1.00 | 60.21 |
| ATOM | 1209 | CB | MET | A | 219 | −6.165 | 52.931 | 36.068 | 1.00 | 54.06 |
| ATOM | 1210 | CG | MET | A | 219 | −4.905 | 53.579 | 36.640 | 1.00 | 55.99 |
| ATOM | 1211 | SD | MET | A | 219 | −5.081 | 55.303 | 37.181 | 1.00 | 54.86 |
| ATOM | 1212 | CE | MET | A | 219 | −6.131 | 55.068 | 38.631 | 1.00 | 46.80 |
| ATOM | 1213 | N | ALA | A | 220 | −8.109 | 49.797 | 36.621 | 1.00 | 59.86 |
| ATOM | 1214 | CA | ALA | A | 220 | −9.065 | 48.898 | 35.974 | 1.00 | 59.07 |
| ATOM | 1215 | C | ALA | A | 220 | −10.476 | 49.481 | 35.913 | 1.00 | 59.01 |
| ATOM | 1216 | O | ALA | A | 220 | −11.106 | 49.486 | 34.852 | 1.00 | 55.25 |
| ATOM | 1217 | CB | ALA | A | 220 | −9.093 | 47.561 | 36.710 | 1.00 | 57.22 |
| ATOM | 1218 | N | ASN | A | 221 | −10.960 | 49.974 | 37.052 | 1.00 | 60.48 |
| ATOM | 1219 | CA | ASN | A | 221 | −12.304 | 50.549 | 37.160 | 1.00 | 60.01 |
| ATOM | 1220 | C | ASN | A | 221 | −12.365 | 52.068 | 36.929 | 1.00 | 57.20 |
| ATOM | 1221 | O | ASN | A | 221 | −13.283 | 52.510 | 36.208 | 1.00 | 53.31 |
| ATOM | 1222 | CB | ASN | A | 221 | −12.503 | 50.210 | 38.537 | 1.00 | 59.42 |

TABLE 1-continued

Structural Coordinate of MEK1/N35/NKF (corresponding to amino acids 24, 383 of SEQ ID NO: 1) -compound 1-ATPγS Ternary Complex.

| | A | B | C | D | E | F | G | H | I | J |
|---|---|---|---|---|---|---|---|---|---|---|
| ATOM | 1223 | CG | ASN | A | 221 | −12.642 | 48.769 | 38.959 | 1.00 | 61.87 |
| ATOM | 1224 | OD1 | ASN | A | 221 | −11.650 | 48.144 | 38.557 | 1.00 | 58.70 |
| ATOM | 1225 | ND2 | ASN | A | 221 | −13.541 | 48.213 | 39.778 | 1.00 | 63.04 |
| ATOM | 1226 | N | SER | A | 222 | −11.346 | 53.157 | 37.210 | 1.00 | 57.70 |
| ATOM | 1227 | N | VAL | A | 224 | −13.882 | 55.228 | 31.393 | 1.00 | 73.05 |
| ATOM | 1228 | CA | VAL | A | 224 | −14.409 | 56.543 | 30.920 | 1.00 | 72.43 |
| ATOM | 1229 | C | VAL | A | 224 | −15.906 | 56.404 | 30.663 | 1.00 | 70.78 |
| ATOM | 1230 | O | VAL | A | 224 | −16.410 | 55.290 | 30.519 | 1.00 | 72.56 |
| ATOM | 1231 | CB | VAL | A | 224 | −13.669 | 57.005 | 29.618 | 1.00 | 73.49 |
| ATOM | 1232 | CG1 | VAL | A | 224 | −14.604 | 57.795 | 28.695 | 1.00 | 75.72 |
| ATOM | 1233 | CG2 | VAL | A | 224 | −12.467 | 57.858 | 29.939 | 1.00 | 71.02 |
| ATOM | 1234 | N | GLY | A | 225 | −16.616 | 57.528 | 30.626 | 1.00 | 69.28 |
| ATOM | 1235 | CA | GLY | A | 225 | −18.049 | 57.488 | 30.390 | 1.00 | 66.97 |
| ATOM | 1236 | C | CLY | A | 225 | −18.405 | 56.922 | 29.026 | 1.00 | 64.94 |
| ATOM | 1237 | O | GLY | A | 225 | −17.548 | 55.342 | 28.352 | 1.00 | 64.02 |
| ATOM | 1238 | N | THR | A | 226 | −19.672 | 57.081 | 28.631 | 1.00 | 61.39 |
| ATOM | 1239 | CA | THR | A | 226 | −20.161 | 56.607 | 27.336 | 1.00 | 54.72 |
| ATOM | 1240 | C | THR | A | 226 | −19.181 | 57.006 | 26.229 | 1.00 | 52.97 |
| ATOM | 1241 | O | THR | A | 226 | −18.343 | 56.206 | 25.810 | 1.00 | 55.32 |
| ATOM | 1242 | CB | THR | A | 226 | −21.538 | 57.220 | 26.997 | 1.00 | 55.83 |
| ATOM | 1243 | OG1 | THR | A | 226 | −22.116 | 57.775 | 28.181 | 1.00 | 49.67 |
| ATOM | 1244 | CG2 | THR | A | 226 | −22.479 | 56.156 | 26.403 | 1.00 | 53.80 |
| ATOM | 1245 | N | ARG | A | 227 | −19.292 | 58.244 | 25.757 | 1.00 | 43.94 |
| ATOM | 1246 | CA | ARG | A | 227 | −18.407 | 58.742 | 24.714 | 1.00 | 40.03 |
| ATOM | 1247 | C | ARG | A | 227 | −16.984 | 58.165 | 24.837 | 1.00 | 37.22 |
| ATOM | 1248 | O | ARG | A | 227 | −16.214 | 58.556 | 25.720 | 1.00 | 42.82 |
| ATOM | 1249 | CB | ARG | A | 227 | −18.379 | 60.271 | 24.773 | 1.00 | 39.52 |
| ATOM | 1250 | CG | ARG | A | 227 | −19.773 | 60.891 | 24.751 | 1.00 | 46.07 |
| ATOM | 1251 | CD | ARG | A | 227 | −19.882 | 62.091 | 25.679 | 1.00 | 52.06 |
| ATOM | 1252 | NE | ARG | A | 227 | −19.849 | 63.357 | 24.949 | 1.00 | 53.53 |
| ATOM | 1253 | CZ | ARG | A | 227 | −18.736 | 63.935 | 24.500 | 1.00 | 53.26 |
| ATOM | 1254 | NH1 | ARG | A | 227 | −17.558 | 63.359 | 24.704 | 1.00 | 54.16 |
| ATOM | 1255 | NH2 | ARG | A | 227 | −18.797 | 65.091 | 23.845 | 1.00 | 48.57 |
| ATOM | 1256 | N | SER | A | 228 | −16.650 | 57.224 | 23.955 | 1.00 | 27.69 |
| ATOM | 1257 | CA | SER | A | 228 | −15.331 | 56.588 | 23.946 | 1.00 | 21.04 |
| ATOM | 1258 | C | SER | A | 228 | −14.465 | 57.083 | 22.791 | 1.00 | 17.51 |
| ATOM | 1259 | O | SER | A | 228 | −14.970 | 57.453 | 21.740 | 1.00 | 18.61 |
| ATOM | 1260 | CB | SER | A | 228 | −15.471 | 55.068 | 23.847 | 1.00 | 16.43 |
| ATOM | 1261 | OG | SER | A | 228 | −14.236 | 54.432 | 24.114 | 1.00 | 17.59 |
| ATOM | 1252 | N | TYR | A | 229 | −13.155 | 57.111 | 22.996 | 1.00 | 18.98 |
| ATOM | 1263 | CA | TYR | A | 229 | −12.232 | 57.543 | 21.958 | 1.00 | 11.61 |
| ATOM | 1264 | C | TYR | A | 229 | −11.298 | 56.380 | 21.727 | 1.00 | 9.85 |
| ATOM | 1265 | O | TYR | A | 229 | −10.280 | 56.509 | 21.038 | 1.00 | 9.69 |
| ATOM | 1266 | CB | TYR | A | 229 | −11.442 | 58.785 | 22.382 | 1.00 | 8.85 |
| ATOM | 1267 | CG | TYR | A | 229 | −12.297 | 60.018 | 22.551 | 1.00 | 7.07 |
| ATOM | 1268 | CD1 | TYR | A | 229 | −12.462 | 60.926 | 21.518 | 1.00 | 6.82 |
| ATOM | 1269 | CD2 | TYR | A | 229 | −13.001 | 60.236 | 23.734 | 1.00 | 10.05 |
| ATOM | 1270 | CE1 | TYR | A | 229 | −13.321 | 62.022 | 21.652 | 1.00 | 11.84 |
| ATOM | 1271 | CE2 | TYR | A | 229 | −13.854 | 61.317 | 23.879 | 1.00 | 3.10 |
| ATOM | 1272 | CZ | TYR | A | 229 | −14.016 | 62.200 | 22.836 | 1.00 | 10.50 |
| ATOM | 1273 | OH | TYR | A | 229 | −14.917 | 63.224 | 22.974 | 1.00 | 13.64 |
| ATOM | 1274 | N | MET | A | 230 | −11.652 | 55.243 | 22.322 | 1.00 | 4.53 |
| ATOM | 1275 | CA | MET | A | 230 | −10.872 | 54.024 | 22.161 | 1.00 | 11.52 |
| ATOM | 1276 | C | MET | A | 230 | −10.972 | 53.492 | 20.719 | 1.00 | 14.18 |
| ATOM | 1277 | O | MET | A | 230 | −12.027 | 53.543 | 20.085 | 1.00 | 5.79 |
| ATOM | 1278 | CB | MET | A | 230 | −11.381 | 52.934 | 23.081 | 1.00 | 18.26 |
| ATOM | 1279 | CG | MET | A | 230 | −11.524 | 53.332 | 24.503 | 1.00 | 18.76 |
| ATOM | 1280 | SD | MET | A | 230 | −10.711 | 52.093 | 25.469 | 1.00 | 27.82 |
| ATOM | 1281 | CE | MET | A | 230 | −11.466 | 52.424 | 27.070 | 1.00 | 34.63 |
| ATOM | 1282 | N | SER | A | 231 | −9.863 | 52.970 | 20.220 | 1.00 | 11.84 |
| ATOM | 1283 | CA | SER | A | 231 | −9.836 | 52.429 | 18.881 | 1.00 | 13.96 |
| ATOM | 1284 | C | SER | A | 231 | −10.596 | 51.103 | 18.888 | 1.00 | 16.30 |
| ATOM | 1285 | O | SER | A | 231 | −10.750 | 50.447 | 19.936 | 1.00 | 14.37 |
| ATOM | 1286 | CB | SER | A | 231 | −8.288 | 52.206 | 18.418 | 1.00 | 5.81 |
| ATOM | 1287 | OG | SER | A | 231 | −7.869 | 51.006 | 18.960 | 1.00 | 5.77 |
| ATOM | 1288 | N | PRO | A | 232 | −11.103 | 50.702 | 17.713 | 1.00 | 16.03 |
| ATOM | 1289 | CA | PRO | A | 232 | −11.848 | 49.445 | 17.589 | 1.00 | 12.50 |
| ATOM | 1290 | C | PRO | A | 232 | −11.026 | 48.273 | 18.094 | 1.00 | 9.49 |
| ATOM | 1291 | O | PRO | A | 232 | −11.552 | 47.398 | 18.792 | 1.00 | 9.39 |
| ATOM | 1292 | CB | PRO | A | 232 | −12.141 | 49.342 | 16.101 | 1.00 | 16.44 |
| ATOM | 1293 | CG | PRO | A | 232 | −12.076 | 50.748 | 15.609 | 1.00 | 17.49 |
| ATOM | 1294 | CD | PRO | A | 232 | −11.024 | 51.424 | 16.434 | 1.00 | 16.19 |
| ATOM | 1295 | N | GLU | A | 233 | −9.735 | 48.261 | 17.764 | 1.00 | 2.58 |
| ATOM | 1296 | CA | GLU | A | 233 | −8.883 | 47.159 | 18.219 | 1.00 | 8.07 |
| ATOM | 1297 | C | GLU | A | 233 | −8.755 | 47.165 | 19.743 | 1.00 | 12.93 |

TABLE 1-continued

Structural Coordinate of MEK1/N35/NKF (corresponding to amino acids 24, 383 of SEQ ID NO: 1) -compound 1-ATPγS Ternary Complex.

| | A | B | C | D | E | F | G | H | I | J |
|---|---|---|---|---|---|---|---|---|---|---|
| ATOM | 1298 | O | GLU | A | 233 | −8.970 | 45.132 | 20.392 | 1.00 | 12.72 |
| ATOM | 1299 | CB | GLU | A | 233 | −7.493 | 47.189 | 17.529 | 1.00 | 4.71 |
| ATOM | 1300 | CG | GLU | A | 233 | −6.558 | 48.318 | 17.909 | 1.00 | 12.03 |
| ATOM | 1301 | CD | GLU | A | 233 | −6.659 | 49.492 | 16.955 | 1.00 | 22.82 |
| ATOM | 1302 | OE1 | GLU | A | 233 | −5.684 | 50.291 | 16.928 | 1.00 | 11.37 |
| ATOM | 1303 | OE2 | GLU | A | 233 | −7.709 | 49.613 | 16.247 | 1.00 | 10.91 |
| ATOM | 1304 | N | ARG | A | 234 | −8.434 | 48.329 | 20.318 | 1.00 | 13.03 |
| ATOM | 1305 | CA | ARG | A | 234 | −8.324 | 48.431 | 21.770 | 1.00 | 7.45 |
| ATOM | 1306 | C | ARG | A | 234 | −9.634 | 48.001 | 22.401 | 1.00 | 3.63 |
| ATOM | 1307 | O | ARG | A | 234 | −9.630 | 47.249 | 23.365 | 1.00 | 7.47 |
| ATOM | 1308 | CB | ARG | A | 234 | −7.995 | 49.854 | 22.206 | 1.00 | 9.92 |
| ATOM | 1309 | CG | ARG | A | 234 | −7.295 | 49.906 | 23.547 | 1.00 | 15.19 |
| ATOM | 1310 | CD | ARG | A | 234 | −7.151 | 51.322 | 24.072 | 1.00 | 12.50 |
| ATOM | 1311 | NE | ARG | A | 234 | −7.161 | 51.313 | 25.523 | 1.00 | 25.86 |
| ATOM | 1312 | CZ | ARG | A | 234 | −6.578 | 52.219 | 26.299 | 1.00 | 20.07 |
| ATOM | 1313 | NH1 | ARG | A | 234 | −5.916 | 53.247 | 25.779 | 1.00 | 13.56 |
| ATOM | 1314 | NH2 | ARG | A | 234 | −6.646 | 52.065 | 27.607 | 1.00 | 12.50 |
| ATOM | 1315 | N | LEU | A | 235 | −10.757 | 48.463 | 21.850 | 1.00 | 1.00 |
| ATOM | 1316 | CA | LEU | A | 235 | −12.067 | 48.088 | 22.378 | 1.00 | 6.12 |
| ATOM | 1317 | C | LEU | A | 235 | −12.322 | 46.567 | 22.351 | 1.00 | 13.38 |
| ATOM | 1318 | O | LEU | A | 235 | −13.054 | 46.039 | 23.189 | 1.00 | 15.84 |
| ATOM | 1319 | CB | LEU | A | 235 | −13.166 | 48.769 | 21.574 | 1.00 | 2.62 |
| ATOM | 1320 | CG | LEU | A | 235 | −13.538 | 50.230 | 21.800 | 1.00 | 14.11 |
| ATOM | 1321 | CD1 | LEU | A | 235 | −14.914 | 50.460 | 21.213 | 1.00 | 5.49 |
| ATOM | 1322 | CD2 | LEU | A | 235 | −13.541 | 50.573 | 23.291 | 1.00 | 11.85 |
| ATOM | 1323 | N | GLN | A | 236 | −11.710 | 45.858 | 21.401 | 1.00 | 15.05 |
| ATOM | 1324 | CA | GLN | A | 236 | −11.946 | 44.423 | 21.280 | 1.00 | 17.07 |
| ATOM | 1325 | C | GLN | A | 236 | −10.961 | 43.478 | 21.983 | 1.00 | 16.84 |
| ATOM | 1226 | O | GLN | A | 236 | −11.325 | 42.358 | 22.354 | 1.00 | 19.39 |
| ATOM | 1327 | CB | GLN | A | 236 | −12.082 | 44.056 | 19.790 | 1.00 | 18.30 |
| ATOM | 1328 | CG | GLN | A | 236 | −13.448 | 44.464 | 19.201 | 1.00 | 22.72 |
| ATOM | 1329 | CD | GLN | A | 236 | −13.455 | 44.652 | 17.670 | 1.00 | 31.91 |
| ATOM | 1330 | OE1 | GLN | A | 236 | −12.406 | 44.778 | 17.033 | 1.00 | 25.55 |
| ATOM | 1331 | NE2 | GLN | A | 236 | −14.655 | 44.681 | 17.085 | 1.00 | 32.13 |
| ATOM | 1332 | N | GLY | A | 237 | −9.722 | 43.900 | 22.186 | 1.00 | 13.06 |
| ATOM | 1333 | CA | GLY | A | 237 | −8.807 | 43.002 | 22.864 | 1.00 | 12.96 |
| ATOM | 1334 | C | GLY | A | 237 | −7.502 | 43.648 | 23.260 | 1.00 | 18.20 |
| ATOM | 1335 | O | GLY | A | 237 | −0.418 | 44.856 | 23.416 | 1.00 | 18.82 |
| ATOM | 1336 | N | THR | A | 238 | −6.483 | 42.814 | 23.409 | 1.00 | 24.69 |
| ATOM | 1337 | CA | THR | A | 238 | −5.136 | 43.229 | 23.786 | 1.00 | 27.84 |
| ATOM | 1338 | C | THR | A | 238 | −4.254 | 43.518 | 22.562 | 1.00 | 28.84 |
| ATOM | 1339 | O | THR | A | 238 | −3.078 | 43.865 | 22.703 | 1.00 | 29.67 |
| ATOM | 1340 | CB | THR | A | 238 | −4.435 | 42.101 | 24.580 | 1.00 | 31.65 |
| ATOM | 1341 | OG1 | THR | A | 238 | −4.049 | 41.060 | 23.667 | 1.00 | 36.43 |
| ATOM | 1342 | CG2 | THR | A | 238 | −5.370 | 41.497 | 25.630 | 1.00 | 29.39 |
| ATOM | 1343 | N | HIS | A | 239 | −4.798 | 43.360 | 21.362 | 1.00 | 28.94 |
| ATOM | 1344 | CA | HIS | A | 239 | −3.986 | 43.584 | 20.174 | 1.00 | 29.55 |
| ATOM | 1345 | C | HIS | A | 239 | −4.077 | 44.996 | 19.628 | 1.00 | 28.05 |
| ATOM | 1346 | O | HIS | A | 239 | −4.747 | 45.263 | 18.620 | 1.00 | 29.66 |
| ATOM | 1347 | CB | HIS | A | 239 | −4.335 | 42.568 | 19.086 | 1.00 | 30.81 |
| ATOM | 1348 | CG | HIS | A | 239 | −4.002 | 41.156 | 19.459 | 1.00 | 33.94 |
| ATOM | 1349 | ND1 | HIS | A | 239 | −4.953 | 40.251 | 19.881 | 1.00 | 36.18 |
| ATOM | 1350 | CD2 | HIS | A | 239 | −2.798 | 40.499 | 19.503 | 1.00 | 34.71 |
| ATOM | 1351 | CE1 | HIS | A | 239 | −4.369 | 39.103 | 20.174 | 1.00 | 32.97 |
| ATOM | 1252 | NE2 | HIS | A | 239 | −3.072 | 39.229 | 19.956 | 1.00 | 36.62 |
| ATOM | 1353 | N | TYR | A | 240 | −2.391 | 45.896 | 20.318 | 1.00 | 22.57 |
| ATOM | 1354 | CA | TYR | A | 240 | −3.336 | 47.286 | 19.923 | 1.00 | 20.14 |
| ATOM | 1355 | C | TYR | A | 240 | −2.040 | 47.844 | 20.482 | 1.00 | 19.73 |
| ATOM | 1356 | O | TYR | A | 240 | −1.405 | 47.222 | 21.346 | 1.00 | 15.28 |
| ATOM | 1357 | CB | TYR | A | 240 | −4.622 | 48.056 | 20.493 | 1.00 | 24.44 |
| ATOM | 1358 | CG | TYR | A | 240 | −4.408 | 48.269 | 21.976 | 1.00 | 31.08 |
| ATOM | 1359 | CD1 | TYR | A | 240 | −3.992 | 49.498 | 22.496 | 1.00 | 33.64 |
| ATOM | 1360 | CD2 | TYR | A | 240 | −4.663 | 47.228 | 22.862 | 1.00 | 31.36 |
| ATOM | 1361 | CE1 | TYR | A | 240 | −3.820 | 49.684 | 22.865 | 1.00 | 28.24 |
| ATOM | 1362 | CE2 | TYR | A | 240 | −4.508 | 47.396 | 24.226 | 1.00 | 32.79 |
| ATOM | 1363 | CZ | TYR | A | 240 | −4.087 | 48.627 | 24.720 | 1.00 | 33.22 |
| ATOM | 1364 | OH | TYR | A | 240 | −3.907 | 48.777 | 26.067 | 1.00 | 33.85 |
| ATOM | 1365 | N | SER | A | 241 | −1.647 | 49.010 | 19.975 | 1.00 | 14.20 |
| ATOM | 1366 | CA | SER | A | 241 | −0.442 | 49.690 | 20.412 | 1.00 | 6.35 |
| ATOM | 1367 | C | SER | A | 241 | −0.506 | 51.170 | 20.021 | 1.00 | 2.08 |
| ATOM | 1268 | O | SER | A | 241 | −1.582 | 51.772 | 20.056 | 1.00 | 2.96 |
| ATOM | 1369 | CB | SER | A | 241 | 0.786 | 49.017 | 19.802 | 1.00 | 11.60 |
| ATOM | 1370 | OG | SER | A | 241 | 1.960 | 49.780 | 20.037 | 1.00 | 21.68 |
| ATOM | 1371 | N | VAL | A | 242 | 0.278 | 51.587 | 18.833 | 1.00 | 2.29 |
| ATOM | 1372 | CA | VAL | A | 242 | 0.391 | 53.025 | 18.606 | 1.00 | 8.94 |

TABLE 1-continued

Structural Coordinate of MEK1/N35/NKF (corresponding to amino acids 24, 383 of SEQ ID NO: 1) -compound 1-ATPγS Ternary Complex.

| | A | B | C | D | E | F | G | H | I | J |
|---|---|---|---|---|---|---|---|---|---|---|
| ATOM | 1373 | C | VAL | A | 242 | −0.536 | 53.651 | 17.571 | 1.00 | 15.31 |
| ATOM | 1374 | O | VAL | A | 242 | −0.836 | 54.856 | 17.648 | 1.00 | 15.12 |
| ATOM | 1375 | CB | VAL | A | 242 | 1.825 | 53.392 | 18.259 | 1.00 | 17.11 |
| ATOM | 1376 | CG1 | VAL | A | 242 | 2.758 | 52.850 | 19.332 | 1.00 | 16.09 |
| ATOM | 1377 | CG2 | VAL | A | 242 | 2.178 | 52.831 | 16.894 | 1.00 | 17.52 |
| ATOM | 1378 | N | GLN | A | 243 | −0.978 | 52.853 | 16.597 | 1.00 | 13.56 |
| ATOM | 1379 | CA | GLN | A | 243 | −1.889 | 53.342 | 15.570 | 1.00 | 6.91 |
| ATOM | 1380 | C | GLN | A | 243 | −3.189 | 53.776 | 16.236 | 1.00 | 4.90 |
| ATOM | 1381 | O | GLN | A | 243 | −3.867 | 54.686 | 15.770 | 1.00 | 13.17 |
| ATOM | 1382 | CB | GLN | A | 243 | −2.183 | 52.231 | 14.547 | 1.00 | 18.34 |
| ATOM | 1383 | CG | GLN | A | 243 | −1.292 | 52.227 | 13.298 | 1.00 | 13.69 |
| ATOM | 1384 | CD | GLN | A | 243 | −1.018 | 53.611 | 12.756 | 1.00 | 15.91 |
| ATOM | 1385 | OE1 | GLN | A | 243 | −0.023 | 54.285 | 13.203 | 1.00 | 21.34 |
| ATOM | 1386 | NE2 | GLN | A | 243 | −1.877 | 54.086 | 11.858 | 1.00 | 20.85 |
| ATOM | 1387 | N | SEP | A | 244 | −3.551 | 53.096 | 17.320 | 1.00 | 6.15 |
| ATOM | 1388 | CA | SER | A | 244 | −4.763 | 53.412 | 18.071 | 1.00 | 4.95 |
| ATOM | 1389 | C | SER | A | 244 | −4.849 | 54.887 | 18.527 | 1.00 | 10.20 |
| ATOM | 1390 | O | SER | A | 244 | −5.952 | 55.438 | 18.667 | 1.00 | 11.43 |
| ATOM | 1391 | CB | SER | A | 244 | −4.860 | 52.501 | 19.279 | 1.00 | 3.14 |
| ATOM | 1392 | OG | SER | A | 244 | −6.182 | 52.510 | 19.770 | 1.00 | 18.08 |
| ATOM | 1393 | N | ASP | A | 245 | −2.690 | 55.524 | 18.739 | 1.00 | 8.16 |
| ATOM | 1394 | CA | ASP | A | 245 | −3.659 | 56.919 | 19.157 | 1.00 | 12.93 |
| ATOM | 1395 | C | ASP | A | 245 | −4.115 | 57.826 | 18.016 | 1.00 | 18.15 |
| ATOM | 1396 | O | ASP | A | 245 | −4.715 | 58.891 | 18.258 | 1.00 | 18.63 |
| ATOM | 1397 | CB | ASP | A | 245 | −2.241 | 57.347 | 19.593 | 1.00 | 16.81 |
| ATOM | 1398 | CG | ASP | A | 245 | −1.808 | 56.758 | 20.951 | 1.00 | 16.67 |
| ATOM | 1399 | OD1 | ASP | A | 245 | −0.587 | 56.538 | 21.121 | 1.00 | 11.97 |
| ATOM | 1400 | OD2 | ASP | A | 245 | −2.666 | 56.509 | 21.839 | 1.00 | 12.98 |
| ATOM | 1401 | N | ILE | A | 246 | −3.836 | 57.408 | 16.775 | 1.00 | 17.55 |
| ATOM | 1402 | CA | ILE | A | 246 | −4.209 | 58.204 | 15.604 | 1.00 | 13.94 |
| ATOM | 1403 | C | ILE | A | 246 | −5.709 | 58.355 | 15.511 | 1.00 | 11.92 |
| ATOM | 1404 | O | ILE | A | 246 | −6.208 | 59.454 | 15.236 | 1.00 | 10.02 |
| ATOM | 1405 | CB | ILE | A | 246 | −3.690 | 57.585 | 14.266 | 1.00 | 19.52 |
| ATOM | 1406 | CG1 | ILE | A | 246 | −2.165 | 57.550 | 14.269 | 1.00 | 13.12 |
| ATOM | 1407 | CD2 | ILE | A | 246 | −4.169 | 58.434 | 13.065 | 1.00 | 13.77 |
| ATOM | 1408 | CD1 | ILE | A | 246 | −1.539 | 58.911 | 14.456 | 1.00 | 17.58 |
| ATOM | 1409 | N | TRP | A | 247 | −5.426 | 57.254 | 15.737 | 1.00 | 15.90 |
| ATOM | 1410 | CA | TRP | A | 247 | −7.893 | 57.272 | 15.685 | 1.00 | 15.15 |
| ATOM | 1411 | C | TRP | A | 247 | −8.416 | 58.300 | 16.712 | 1.00 | 17.52 |
| ATOM | 1412 | O | TRP | A | 247 | −9.204 | 59.214 | 16.374 | 1.00 | 11.79 |
| ATOM | 1413 | CB | TRP | A | 247 | −8.455 | 55.864 | 15.988 | 1.00 | 14.62 |
| ATOM | 1414 | CG | TRP | A | 247 | −9.951 | 55.839 | 16.231 | 1.00 | 17.81 |
| ATOM | 1415 | CD1 | TRP | A | 247 | −10.506 | 56.140 | 17.398 | 1.00 | 21.33 |
| ATOM | 1416 | CD2 | TRP | A | 247 | −10.969 | 55.581 | 15.261 | 1.00 | 24.47 |
| ATOM | 1417 | NE1 | TRP | A | 247 | −11.970 | 56.096 | 17.207 | 1.00 | 20.95 |
| ATOM | 1418 | CE2 | TRP | A | 247 | −12.219 | 55.756 | 15.905 | 1.00 | 28.03 |
| ATOM | 1419 | CE3 | TRP | A | 247 | −10.951 | 55.222 | 13.904 | 1.00 | 22.49 |
| ATOM | 1420 | CZ2 | TRP | A | 247 | −13.440 | 55.583 | 15.232 | 1.00 | 31.67 |
| ATOM | 1421 | CZ3 | TRP | A | 247 | −12.161 | 55.057 | 13.238 | 1.00 | 25.52 |
| ATOM | 1422 | CH2 | TRP | A | 247 | −13.388 | 55.238 | 13.900 | 1.00 | 24.32 |
| ATOM | 1423 | N | SER | A | 248 | −7.952 | 58.162 | 17.957 | 1.00 | 13.59 |
| ATOM | 1424 | CA | SER | A | 248 | −8.365 | 59.069 | 19.040 | 1.00 | 11.50 |
| ATOM | 1425 | C | SER | A | 248 | −8.140 | 60.519 | 18.634 | 1.00 | 9.87 |
| ATOM | 1426 | O | SER | A | 248 | −9.010 | 61.379 | 18.812 | 1.00 | 6.56 |
| ATOM | 1427 | CB | SER | A | 248 | −7.577 | 58.777 | 20.327 | 1.00 | 8.79 |
| ATOM | 1428 | OG | SER | A | 248 | −7.657 | 57.409 | 20.710 | 1.00 | 10.37 |
| ATOM | 1429 | N | MET | A | 249 | −6.971 | 60.800 | 18.076 | 1.00 | 4.51 |
| ATOM | 1430 | CA | MET | A | 249 | −6.695 | 62.162 | 17.665 | 1.00 | 7.99 |
| ATOM | 1431 | C | MET | A | 249 | −7.707 | 62.597 | 16.631 | 1.00 | 9.96 |
| ATOM | 1432 | O | MET | A | 249 | −8.232 | 63.703 | 16.705 | 1.00 | 20.20 |
| ATOM | 1433 | CB | MET | A | 249 | −5.287 | 62.283 | 17.093 | 1.00 | 10.52 |
| ATOM | 1434 | CG | MET | A | 249 | −4.995 | 63.633 | 16.470 | 1.00 | 18.01 |
| ATOM | 1435 | SD | MET | A | 249 | −3.294 | 63.694 | 15.882 | 1.00 | 25.60 |
| ATOM | 1436 | CE | MET | A | 249 | −3.492 | 62.846 | 14.283 | 1.00 | 23.08 |
| ATOM | 1437 | N | GLY | A | 250 | −7.998 | 61.718 | 15.670 | 1.00 | 13.00 |
| ATOM | 1438 | CA | GLY | A | 250 | −8.948 | 62.057 | 14.620 | 1.00 | 7.94 |
| ATOM | 1439 | C | GLY | A | 250 | −10.354 | 62.303 | 15.116 | 1.00 | 9.43 |
| ATOM | 1440 | O | GLY | A | 250 | −11.024 | 63.247 | 14.677 | 1.00 | 11.01 |
| ATOM | 1441 | N | LEU | A | 251 | −10.814 | 61.435 | 16.013 | 1.00 | 11.75 |
| ATOM | 1442 | CA | LEU | A | 251 | −12.149 | 61.575 | 16.587 | 1.00 | 12.10 |
| ATOM | 1443 | C | LEU | A | 251 | −12.203 | 62.901 | 17.382 | 1.00 | 15.74 |
| ATOM | 1444 | O | LEU | A | 251 | −13.172 | 63.665 | 17.277 | 1.00 | 14.37 |
| ATOM | 1445 | CB | LEU | A | 251 | −12.439 | 60.367 | 17.488 | 1.00 | 10.07 |
| ATOM | 1446 | CG | LEU | A | 251 | −13.858 | 59.808 | 17.652 | 1.00 | 17.78 |
| ATOM | 1447 | CD1 | LEU | A | 251 | −14.247 | 59.899 | 19.104 | 1.00 | 7.26 |

TABLE 1-continued

Structural Coordinate of MEK1/N35/NKF (corresponding to amino acids 24, 383 of SEQ ID NO: 1) -compound 1-ATPγS Ternary Complex.

| A | B | C | D | E | F | G | H | I | J |
|---|---|---|---|---|---|---|---|---|---|
| ATOM | 1448 | CD2 | LEU | A | 251 | −14.868 | 60.557 | 16.790 | 1.00 | 11.79 |
| ATOM | 1449 | N | SER | A | 252 | −11.138 | 63.192 | 18.136 | 1.00 | 13.46 |
| ATOM | 1450 | CA | SER | A | 252 | −11.060 | 64.422 | 18.944 | 1.00 | 18.14 |
| ATOM | 1451 | C | SER | A | 252 | −11.135 | 65.683 | 18.097 | 1.00 | 17.41 |
| ATOM | 1452 | O | SER | A | 252 | −11.825 | 66.627 | 18.460 | 1.00 | 19.27 |
| ATOM | 1453 | CB | SER | A | 252 | −9.768 | 64.447 | 19.775 | 1.00 | 9.91 |
| ATOM | 1454 | OG | SER | A | 252 | −9.750 | 63.359 | 20.687 | 1.00 | 8.34 |
| ATOM | 1455 | N | LEU | A | 253 | −10.424 | 65.696 | 16.970 | 1.00 | 19.18 |
| ATOM | 1456 | CA | LEU | A | 253 | −10.432 | 66.849 | 16.062 | 1.00 | 18.31 |
| ATOM | 1457 | C | LEU | A | 253 | −11.790 | 67.075 | 15.405 | 1.00 | 19.03 |
| ATOM | 1458 | O | LEU | A | 253 | −12.163 | 68.205 | 15.120 | 1.00 | 22.36 |
| ATOM | 1459 | CB | LEU | A | 253 | −9.396 | 66.668 | 14.962 | 1.00 | 19.05 |
| ATOM | 1460 | CG | LEU | A | 253 | −7.947 | 66.985 | 15.282 | 1.00 | 14.67 |
| ATOM | 1461 | CD1 | LEU | A | 253 | −7.066 | 66.438 | 14.166 | 1.00 | 12.71 |
| ATOM | 1462 | CD2 | LEU | A | 253 | −7.778 | 68.489 | 15.433 | 1.00 | 18.22 |
| ATOM | 1463 | N | VAL | A | 254 | −12.524 | 65.998 | 15.138 | 1.00 | 25.00 |
| ATOM | 1464 | CA | VAL | A | 254 | −13.845 | 66.131 | 14.526 | 1.00 | 25.23 |
| ATOM | 1465 | C | VAL | A | 254 | −14.799 | 66.694 | 15.576 | 1.00 | 26.73 |
| ATOM | 1466 | O | VAL | A | 254 | −15.680 | 67.496 | 15.260 | 1.00 | 28.21 |
| ATOM | 1467 | CB | VAL | A | 254 | −14.395 | 64.755 | 14.028 | 1.00 | 26.92 |
| ATOM | 1468 | CG1 | VAL | A | 254 | −15.883 | 64.887 | 13.736 | 1.00 | 25.06 |
| ATOM | 1469 | CG2 | VAL | A | 254 | −13.628 | 64.299 | 12.783 | 1.00 | 22.80 |
| ATOM | 1470 | N | GLU | A | 255 | −14.628 | 66.264 | 16.226 | 1.00 | 27.36 |
| ATOM | 1471 | CA | GLU | A | 255 | −15.474 | 66.757 | 17.920 | 1.00 | 23.68 |
| ATOM | 1472 | C | GLU | A | 255 | −15.282 | 68.264 | 18.119 | 1.00 | 24.91 |
| ATOM | 1473 | O | GLU | A | 255 | −16.255 | 69.027 | 18.150 | 1.00 | 20.96 |
| ATOM | 1474 | CB | GLU | A | 255 | −15.155 | 66.048 | 19.240 | 1.00 | 14.74 |
| ATOM | 1475 | CG | GLU | A | 255 | −15.884 | 66.670 | 20.408 | 1.00 | 15.04 |
| ATOM | 1476 | CD | GLU | A | 255 | −15.768 | 65.868 | 21.677 | 1.00 | 21.02 |
| ATOM | 1477 | OE1 | GLU | A | 255 | −16.519 | 66.166 | 22.627 | 1.00 | 22.66 |
| ATOM | 1478 | OE2 | GLU | A | 255 | −14.937 | 64.942 | 21.735 | 1.00 | 20.57 |
| ATOM | 1479 | N | MET | A | 256 | −14.020 | 68.683 | 18.253 | 1.00 | 24.35 |
| ATOM | 1480 | CA | MET | A | 256 | −13.694 | 70.088 | 18.462 | 1.00 | 25.34 |
| ATOM | 1481 | C | MET | A | 256 | −14.119 | 70.979 | 17.297 | 1.00 | 28.72 |
| ATOM | 1482 | O | MET | A | 256 | −14.443 | 72.148 | 17.484 | 1.00 | 29.34 |
| ATOM | 1483 | CB | MET | A | 256 | −12.192 | 70.236 | 18.715 | 1.00 | 26.97 |
| ATOM | 1484 | CG | MET | A | 256 | −11.716 | 69.502 | 19.962 | 1.00 | 26.86 |
| ATOM | 1485 | SD | MET | A | 256 | −10.012 | 69.864 | 20.407 | 1.00 | 28.01 |
| ATOM | 1486 | CE | MET | A | 256 | −9.107 | 68.604 | 19.489 | 1.00 | 25.72 |
| ATOM | 1487 | N | ALA | A | 257 | −14.118 | 70.417 | 16.093 | 1.00 | 33.65 |
| ATOM | 1488 | CA | ALA | A | 257 | −14.508 | 71.157 | 14.897 | 1.00 | 32.34 |
| ATOM | 1489 | C | ALA | A | 257 | −16.031 | 71.324 | 14.785 | 1.00 | 32.79 |
| ATOM | 1490 | O | ALA | A | 257 | −16.500 | 72.336 | 14.270 | 1.00 | 35.14 |
| ATOM | 1491 | CB | ALA | A | 257 | −13.554 | 70.457 | 13.653 | 1.00 | 31.98 |
| ATOM | 1492 | N | VAL | A | 258 | −16.801 | 70.344 | 15.265 | 1.00 | 30.48 |
| ATOM | 1493 | CA | VAL | A | 258 | −18.259 | 70.432 | 15.193 | 1.00 | 31.53 |
| ATOM | 1494 | C | VAL | A | 258 | −18.908 | 70.857 | 16.511 | 1.00 | −34.51 |
| ATOM | 1495 | O | VAL | A | 258 | −20.099 | 71.164 | 16.562 | 1.00 | 36.30 |
| ATOM | 1496 | CB | VAL | A | 258 | −18.878 | 69.102 | 14.734 | 1.00 | 29.13 |
| ATOM | 1497 | CG1 | VAL | A | 258 | −18.213 | 68.647 | 13.449 | 1.00 | 26.45 |
| ATOM | 1498 | CG2 | VAL | A | 258 | −18.728 | 68.055 | 15.814 | 1.00 | 31.99 |
| ATOM | 1499 | N | GLY | A | 259 | −18.118 | 70.885 | 17.577 | 1.00 | 35.42 |
| ATOM | 1500 | CA | GLY | A | 259 | −18.643 | 71.292 | 18.865 | 1.00 | 32.33 |
| ATOM | 1501 | C | GLY | A | 259 | −19.520 | 70.263 | 19.539 | 1.00 | 30.18 |
| ATOM | 1502 | O | GLY | A | 259 | −20.454 | 70.617 | 20.241 | 1.00 | 32.70 |
| ATOM | 1503 | N | ARG | A | 260 | −19.222 | 68.987 | 19.340 | 1.00 | 33.31 |
| ATOM | 1504 | CA | ARG | A | 260 | −20.018 | 67.936 | 19.956 | 1.00 | 33.81 |
| ATOM | 1505 | C | ARG | A | 260 | −19.453 | 66.560 | 19.603 | 1.00 | 32.35 |
| ATOM | 1506 | O | ARG | A | 260 | −19.051 | 66.336 | 18.465 | 1.00 | 32.71 |
| ATOM | 1507 | CB | ARG | A | 260 | −21.462 | 68.075 | 19.475 | 1.00 | 41.22 |
| ATOM | 1508 | CG | ARG | A | 260 | −22.343 | 66.871 | 19.673 | 1.00 | 44.46 |
| ATOM | 1509 | CD | ARG | A | 260 | −23.362 | 66.770 | 18.542 | 1.00 | 46.16 |
| ATOM | 1510 | NE | ARG | A | 260 | −23.067 | 65.631 | 17.677 | 1.00 | 54.94 |
| ATOM | 1511 | CZ | ARG | A | 260 | −23.930 | 65.080 | 16.830 | 1.00 | 54.19 |
| ATOM | 1512 | NH1 | ARG | A | 260 | −25.165 | 65.555 | 16.716 | 1.00 | 55.11 |
| ATOM | 1513 | NH2 | ARG | A | 260 | −23.554 | 64.043 | 16.096 | 1.00 | 55.19 |
| ATOM | 1514 | N | TYR | A | 261 | −19.393 | 65.662 | 20.581 | 1.00 | 29.73 |
| ATOM | 1515 | CA | TYR | A | 261 | −18.890 | 64.311 | 20.340 | 1.00 | 26.56 |
| ATOM | 1516 | C | TYR | A | 261 | −19.621 | 63.857 | 19.077 | 1.00 | 28.46 |
| ATOM | 1517 | O | TYR | A | 261 | −20.844 | 63.779 | 19.051 | 1.00 | 26.56 |
| ATOM | 1518 | CB | TYR | A | 261 | −19.223 | 63.417 | 21.525 | 1.00 | 20.44 |
| ATOM | 1519 | CG | TYR | A | 261 | −18.714 | 62.010 | 21.393 | 1.00 | 16.63 |
| ATOM | 1520 | CD1 | TYR | A | 261 | −17.358 | 61.725 | 21.466 | 1.00 | 12.74 |
| ATOM | 1521 | CD2 | TYR | A | 261 | −19.600 | 60.952 | 21.209 | 1.00 | 15.49 |
| ATOM | 1522 | CE1 | TYR | A | 261 | −16.892 | 60.414 | 21.360 | 1.00 | 13.47 |

TABLE 1-continued

Structural Coordinate of MEK1/N35/NKF (corresponding to amino acids 24, 383 of SEQ ID NO: 1) -compound 1-ATPγS Ternary Complex.

| | A | B | C | D | E | F | G | H | I | J |
|---|---|---|---|---|---|---|---|---|---|---|
| ATOM | 1523 | CE2 | TYR | A | 261 | −19.153 | 59.648 | 21.101 | 1.00 | 12.90 |
| ATOM | 1524 | CZ | TYR | A | 261 | −17.799 | 59.381 | 21.177 | 1.00 | 15.15 |
| ATOM | 1525 | OH | TYR | A | 261 | −17.375 | 58.076 | 21.075 | 1.00 | 9.75 |
| ATOM | 1526 | N | PRO | A | 262 | −18.869 | 63.533 | 18.022 | 1.00 | 29.32 |
| ATOM | 1527 | CA | PRO | A | 262 | −19.347 | 63.105 | 16.704 | 1.00 | 32.21 |
| ATOM | 1528 | C | PRO | A | 262 | −19.980 | 61.726 | 16.455 | 1.00 | 34.38 |
| ATOM | 1529 | O | PRO | A | 262 | −20.149 | 61.331 | 15.300 | 1.00 | 34.69 |
| ATOM | 1530 | CB | PRO | A | 262 | −18.124 | 63.321 | 15.824 | 1.00 | 29.71 |
| ATOM | 1531 | CG | PRO | A | 262 | −17.014 | 62.963 | 16.716 | 1.00 | 30.68 |
| ATOM | 1532 | CD | PRO | A | 262 | −17.400 | 63.500 | 18.082 | 1.00 | 29.38 |
| ATOM | 1533 | N | ILE | A | 263 | −20.083 | 61.326 | 18.194 | 1.00 | 33.38 |
| ATOM | 1534 | CA | ILE | A | 263 | −20.946 | 59.683 | 17.309 | 1.00 | 32.69 |
| ATOM | 1535 | C | ILE | A | 263 | −22.204 | 59.630 | 18.157 | 1.00 | 33.42 |
| ATOM | 1536 | O | ILE | A | 263 | −22.145 | 59.797 | 19.372 | 1.00 | 34.18 |
| ATOM | 1537 | CB | ILE | A | 263 | −19.998 | 58.529 | 17.700 | 1.00 | 31.58 |
| ATOM | 1538 | CC1 | ILE | A | 263 | −18.636 | 58.456 | 16.713 | 1.00 | 31.35 |
| ATOM | 1539 | CG2 | ILE | A | 263 | −20.735 | 57.213 | 17.646 | 1.00 | 30.37 |
| ATOM | 1540 | CD1 | ILE | A | 263 | −17.916 | 57.406 | 17.055 | 1.00 | 32.09 |
| ATOM | 1541 | N | PRO | A | 264 | −23.365 | 59.390 | 17.531 | 1.00 | 35.35 |
| ATOM | 1542 | CA | PRO | A | 264 | −23.590 | 59.162 | 16.100 | 1.00 | 36.67 |
| ATOM | 1543 | C | PRO | A | 264 | −23.430 | 60.426 | 15.284 | 1.00 | 35.40 |
| ATOM | 1544 | O | PRO | A | 264 | −23.621 | 61.526 | 15.794 | 1.00 | 35.56 |
| ATOM | 1545 | CB | PRO | A | 264 | −25.021 | 58.659 | 16.052 | 1.00 | 35.46 |
| ATOM | 1546 | CG | PRO | A | 264 | −25.666 | 59.391 | 17.171 | 1.00 | 36.75 |
| ATOM | 1547 | CD | PRO | A | 264 | −24.639 | 59.405 | 18.270 | 1.00 | 34.29 |
| ATOM | 1548 | N | PRO | A | 265 | −23.097 | 60.284 | 13.995 | 1.00 | 36.51 |
| ATOM | 1549 | CA | PRO | A | 265 | −22.916 | 61.431 | 13.104 | 1.00 | 37.50 |
| ATOM | 1550 | C | PRO | A | 265 | −24.013 | 62.469 | 13.283 | 1.00 | 39.18 |
| ATOM | 1551 | O | PRO | A | 265 | −25.160 | 62.134 | 13.577 | 1.00 | 32.26 |
| ATOM | 1552 | CB | PRO | A | 265 | −22.930 | 60.914 | 11.708 | 1.00 | 36.47 |
| ATOM | 1553 | CG | PRO | A | 265 | −23.331 | 59.370 | 11.905 | 1.00 | 38.04 |
| ATOM | 1554 | CD | PRO | A | 265 | −22.887 | 59.023 | 13.279 | 1.00 | 37.36 |
| ATOM | 1555 | N | PRO | A | 266 | −23.665 | 63.750 | 13.127 | 1.00 | 44.06 |
| ATOM | 1556 | CA | PRO | A | 266 | −24.672 | 64.800 | 13.284 | 1.00 | 48.47 |
| ATOM | 1557 | C | PRO | A | 266 | −25.816 | 64.562 | 12.314 | 1.00 | 51.74 |
| ATOM | 1558 | O | PRO | A | 266 | −25.516 | 64.188 | 11.156 | 1.00 | 51.24 |
| ATOM | 1559 | CB | PRO | A | 266 | −23.907 | 66.086 | 12.974 | 1.00 | 50.13 |
| ATOM | 1560 | CG | PRO | A | 266 | −22.459 | 65.734 | 13.196 | 1.00 | 51.79 |
| ATOM | 1561 | CD | PRO | A | 266 | −22.336 | 64.295 | 12.802 | 1.00 | 47.28 |
| ATOM | 1562 | N | ASP | A | 267 | −27.045 | 64.374 | 12.771 | 1.00 | 52.60 |
| ATOM | 1563 | N | PRO | A | 307 | −28.979 | 60.710 | 23.903 | 1.00 | 65.09 |
| ATOM | 1564 | CA | PRO | A | 307 | −29.002 | 59.318 | 24.425 | 1.00 | 64.51 |
| ATOM | 1565 | C | PRO | A | 307 | −27.775 | 58.466 | 24.050 | 1.00 | 61.30 |
| ATOM | 1566 | O | PRO | A | 307 | −26.668 | 58.983 | 23.893 | 1.00 | 62.13 |
| ATOM | 1567 | CB | PRO | A | 307 | −30.290 | 58.661 | 23.938 | 1.00 | 63.24 |
| ATOM | 1568 | CG | PRO | A | 307 | −31.188 | 59.869 | 23.597 | 1.00 | 64.01 |
| ATOM | 1569 | CD | PRO | A | 307 | −30.330 | 61.154 | 23.504 | 1.00 | 65.27 |
| ATOM | 1570 | N | MET | A | 308 | −27.993 | 57.158 | 23.925 | 1.00 | 57.23 |
| ATOM | 1571 | CA | MET | A | 308 | −26.958 | 56.176 | 23.588 | 1.00 | 48.66 |
| ATOM | 1572 | C | MET | A | 308 | −26.084 | 55.767 | 24.778 | 1.00 | 43.01 |
| ATOM | 1573 | O | MET | A | 308 | −25.212 | 56.516 | 25.227 | 1.00 | 45.77 |
| ATOM | 1574 | CB | MET | A | 308 | −26.075 | 56.675 | 22.449 | 1.00 | 49.51 |
| ATOM | 1575 | CG | MET | A | 308 | −25.288 | 55.561 | 21.784 | 1.00 | 55.77 |
| ATOM | 1576 | SD | MET | A | 308 | −25.344 | 55.652 | 19.986 | 1.00 | 62.75 |
| ATOM | 1577 | CE | MET | A | 308 | −26.483 | 54.349 | 19.570 | 1.00 | 53.22 |
| ATOM | 1578 | N | ALA | A | 309 | −26.338 | 54.563 | 25.285 | 1.00 | 32.29 |
| ATOM | 1579 | CA | ALA | A | 309 | −25.595 | 54.027 | 26.408 | 1.00 | 19.70 |
| ATOM | 1580 | C | ALA | A | 309 | −24.164 | 53.771 | 25.990 | 1.00 | 18.92 |
| ATOM | 1581 | O | ALA | A | 309 | −23.823 | 53.860 | 24.815 | 1.00 | 21.47 |
| ATOM | 1582 | CB | ALA | A | 309 | −26.229 | 52.736 | 26.877 | 1.00 | 19.24 |
| ATOM | 1583 | N | ILE | A | 310 | −23.320 | 53.431 | 26.950 | 1.00 | 21.32 |
| ATOM | 1584 | CA | ILE | A | 310 | −21.926 | 53.179 | 26.645 | 1.00 | 20.61 |
| ATOM | 1585 | C | ILE | A | 310 | −21.780 | 52.016 | 25.668 | 1.00 | 24.69 |
| ATOM | 1586 | O | ILE | A | 310 | −21.140 | 52.150 | 24.622 | 1.00 | 23.49 |
| ATOM | 1587 | CB | ILE | A | 310 | −21.145 | 52.910 | 27.932 | 1.00 | 18.38 |
| ATOM | 1588 | CG1 | ILE | A | 310 | −21.160 | 54.179 | 28.802 | 1.00 | 25.45 |
| ATOM | 1589 | CG2 | ILE | A | 310 | −19.731 | 52.513 | 27.601 | 1.00 | 16.27 |
| ATOM | 1590 | CD1 | ILE | A | 310 | −20.720 | 53.985 | 30.246 | 1.00 | 22.44 |
| ATOM | 1591 | N | PHE | A | 311 | −22.369 | 50.672 | 26.000 | 1.00 | 27.31 |
| ATOM | 1592 | CA | PHE | A | 311 | −22.291 | 49.734 | 25.097 | 1.00 | 25.27 |
| ATOM | 1593 | C | PHE | A | 311 | −23.030 | 50.090 | 23.801 | 1.00 | 23.26 |
| ATOM | 1594 | O | PHE | A | 311 | −22.543 | 49.838 | 22.699 | 1.00 | 19.03 |
| ATOM | 1595 | CB | PHE | A | 311 | −22.914 | 48.436 | 25.727 | 1.00 | 29.96 |
| ATOM | 1596 | CG | PHE | A | 311 | −22.876 | 47.289 | 24.824 | 1.00 | 30.78 |
| ATOM | 1597 | CD1 | PHE | A | 311 | −21.795 | 46.426 | 24.852 | 1.00 | 30.28 |

TABLE 1-continued

Structural Coordinate of MEK1/N35/NKF (corresponding to amino acids 24, 383 of SEQ ID NO: 1) -compound 1-ATPγS Ternary Complex.

| | A | B | C | D | E | F | G | H | I | J |
|---|---|---|---|---|---|---|---|---|---|---|
| ATOM | 1598 | CD2 | PHE | A | 311 | −23.885 | 47.071 | 23.896 | 1.00 | 29.13 |
| ATOM | 1599 | CE1 | PHE | A | 311 | −21.715 | 45.372 | 23.966 | 1.00 | 32.78 |
| ATOM | 1600 | CE2 | PHE | A | 311 | −23.811 | 46.020 | 23.007 | 1.00 | 32.18 |
| ATOM | 1601 | CZ | PHE | A | 311 | −22.722 | 45.166 | 23.041 | 1.00 | 31.76 |
| ATOM | 1602 | N | GLU | A | 312 | −24.209 | 50.688 | 23.936 | 1.00 | 17.24 |
| ATOM | 1603 | CA | GLU | A | 312 | −24.982 | 51.083 | 22.770 | 1.00 | 23.14 |
| ATOM | 1604 | C | GLU | A | 312 | −24.147 | 51.872 | 21.752 | 1.00 | 26.51 |
| ATOM | 1605 | O | GLU | A | 312 | −24.271 | 51.674 | 20.550 | 1.00 | 27.72 |
| ATOM | 1606 | CB | GLU | A | 312 | −26.183 | 51.916 | 23.211 | 1.00 | 22.31 |
| ATOM | 1607 | CG | GLU | A | 312 | −27.056 | 52.359 | 22.061 | 1.00 | 32.19 |
| ATOM | 1608 | CD | GLU | A | 312 | −28.357 | 53.013 | 22.513 | 1.00 | 43.74 |
| ATOM | 1609 | OE1 | GLU | A | 312 | −29.385 | 52.838 | 21.816 | 1.00 | 47.50 |
| ATOM | 1610 | OE2 | GLU | A | 312 | −28.360 | 53.703 | 23.560 | 1.00 | 45.51 |
| ATOM | 1611 | N | LEU | A | 313 | −23.290 | 52.768 | 22.234 | 1.00 | 29.43 |
| ATOM | 1612 | CA | LEU | A | 313 | −22.457 | 53.587 | 21.354 | 1.00 | 23.91 |
| ATOM | 1613 | C | LEU | A | 313 | −21.292 | 52.806 | 20.731 | 1.00 | 24.29 |
| ATOM | 1614 | O | LEU | A | 313 | −20.995 | 52.943 | 19.535 | 1.00 | 19.89 |
| ATOM | 1615 | CB | LEU | A | 313 | −21.908 | 54.790 | 22.147 | 1.00 | 24.50 |
| ATOM | 1616 | CG | LEU | A | 313 | −21.357 | 56.046 | 21.454 | 1.00 | 19.51 |
| ATOM | 1617 | CD1 | LEU | A | 313 | −19.882 | 55.874 | 21.203 | 1.00 | 21.95 |
| ATOM | 1618 | CD2 | LEU | A | 313 | −22.063 | 56.285 | 20.143 | 1.00 | 26.43 |
| ATOM | 1619 | N | LEU | A | 314 | −20.636 | 51.985 | 21.546 | 1.00 | 21.51 |
| ATOM | 1620 | CA | LEU | A | 314 | −19.477 | 51.223 | 21.099 | 1.00 | 23.89 |
| ATOM | 1621 | C | LEU | A | 314 | −19.795 | 50.107 | 20.105 | 1.00 | 29.16 |
| ATOM | 1622 | O | LEU | A | 314 | −18.985 | 49.800 | 19.219 | 1.00 | 23.78 |
| ATOM | 1523 | CB | LEU | A | 314 | −18.739 | 50.668 | 22.312 | 1.00 | 20.26 |
| ATOM | 1624 | CG | LEU | A | 314 | −17.556 | 51.526 | 22.787 | 1.00 | 27.81 |
| ATOM | 1625 | CD1 | LEU | A | 314 | −17.917 | 52.999 | 22.741 | 1.00 | 20.24 |
| ATOM | 1626 | CD2 | LEU | A | 314 | −17.152 | 51.113 | 24.188 | 1.00 | 18.09 |
| ATOM | 1627 | N | ASP | A | 315 | −21.074 | 49.773 | 19.793 | 1.00 | 33.42 |
| ATOM | 1628 | CA | ASP | A | 315 | −21.378 | 48.979 | 18.610 | 1.00 | 33.48 |
| ATOM | 1629 | C | ASP | A | 315 | −21.336 | 49.896 | 17.400 | 1.00 | 29.94 |
| ATOM | 1630 | O | ASP | A | 315 | −20.965 | 49.476 | 16.308 | 1.00 | 31.00 |
| ATOM | 1631 | CB | ASP | A | 315 | −22.759 | 48.334 | 18.738 | 1.00 | 38.85 |
| ATOM | 1632 | CG | ASP | A | 315 | −23.112 | 47.471 | 17.538 | 1.00 | 46.48 |
| ATOM | 1633 | OD1 | ASP | A | 315 | −22.283 | 46.624 | 17.123 | 1.00 | 46.46 |
| ATOM | 1634 | OD2 | ASP | A | 315 | −24.230 | 47.646 | 17.008 | 1.00 | 52.20 |
| ATOM | 1635 | N | TYR | A | 316 | −21.692 | 51.155 | 17.612 | 1.00 | 24.48 |
| ATOM | 1636 | CA | TYR | A | 316 | −21.676 | 52.124 | 16.537 | 1.00 | 25.94 |
| ATOM | 1637 | C | TYR | A | 316 | −20.267 | 52.507 | 16.082 | 1.00 | 28.29 |
| ATOM | 1638 | O | TYR | A | 316 | −20.030 | 52.736 | 14.896 | 1.00 | 30.62 |
| ATOM | 1639 | CB | TYR | A | 316 | −22.416 | 53.395 | 16.949 | 1.00 | 27.97 |
| ATOM | 1640 | CG | TYR | A | 316 | −22.757 | 54.258 | 15.762 | 1.00 | 37.03 |
| ATOM | 1641 | CD1 | TYR | A | 316 | −21.758 | 54.936 | 15.049 | 1.00 | 38.41 |
| ATOM | 1642 | CD2 | TYR | A | 316 | −24.071 | 54.347 | 15.306 | 1.00 | 40.18 |
| ATOM | 1643 | CE1 | TYR | A | 316 | −22.064 | 55.677 | 13.903 | 1.00 | 39.43 |
| ATOM | 1644 | CE2 | TYR | A | 316 | −24.388 | 55.083 | 14.166 | 1.00 | 43.05 |
| ATOM | 1645 | CZ | TYR | A | 316 | −23.384 | 55.743 | 13.468 | 1.00 | 44.43 |
| ATOM | 1646 | OH | TYR | A | 316 | −23.709 | 56.440 | 12.328 | 1.00 | 48.33 |
| ATOM | 1647 | N | ILE | A | 317 | −19.316 | 52.594 | 16.999 | 1.00 | 25.68 |
| ATOM | 1648 | CA | ILE | A | 317 | −17.993 | 52.980 | 16.554 | 1.00 | 19.28 |
| ATOM | 1649 | C | ILE | A | 317 | −17.296 | 51.803 | 15.879 | 1.00 | 21.49 |
| ATOM | 1650 | O | ILE | A | 317 | −16.550 | 51.994 | 14.521 | 1.00 | 22.54 |
| ATOM | 1651 | CB | ILE | A | 317 | −17.114 | 53.577 | 17.724 | 1.00 | 18.71 |
| ATOM | 1652 | CG1 | ILE | A | 317 | −16.120 | 52.542 | 18.223 | 1.00 | 9.61 |
| ATOM | 1653 | CG2 | ILE | A | 317 | −17.986 | 54.046 | 18.889 | 1.00 | 23.94 |
| ATOM | 1654 | CD1 | ILE | A | 317 | −14.762 | 52.765 | 17.699 | 1.00 | 9.51 |
| ATOM | 1655 | N | VAL | A | 318 | −17.542 | 50.584 | 16.347 | 1.00 | 22.76 |
| ATOM | 1656 | CA | VAL | A | 318 | −16.875 | 49.447 | 15.730 | 1.00 | 26.45 |
| ATOM | 1657 | C | VAL | A | 318 | −17.597 | 48.889 | 14.507 | 1.00 | 31.54 |
| ATOM | 1658 | O | VAL | A | 318 | −16.945 | 48.465 | 13.559 | 1.00 | 30.25 |
| ATOM | 1659 | CB | VAL | A | 318 | −15.633 | 48.266 | 16.727 | 1.00 | 25.44 |
| ATOM | 1660 | CG1 | VAL | A | 318 | −16.512 | 48.775 | 18.144 | 1.00 | 27.71 |
| ATOM | 1661 | CG2 | VAL | A | 318 | −17.738 | 47.244 | 16.614 | 1.00 | 25.81 |
| ATOM | 1662 | N | ASN | A | 319 | −18.930 | 48.901 | 14.525 | 1.00 | 33.02 |
| ATOM | 1663 | CA | ASN | A | 319 | −19.723 | 48.354 | 13.417 | 1.00 | 33.39 |
| ATOM | 1664 | C | ASN | A | 319 | −20.506 | 49.356 | 12.569 | 1.00 | 37.02 |
| ATOM | 1665 | O | ASN | A | 319 | −21.558 | 49.022 | 12.022 | 1.00 | 40.88 |
| ATOM | 1666 | CB | ASN | A | 319 | −20.696 | 47.303 | 13.942 | 1.00 | 25.22 |
| ATOM | 1667 | CG | ASN | A | 319 | −19.996 | 46.052 | 14.370 | 1.00 | 30.51 |
| ATOM | 1668 | OD1 | ASN | A | 319 | −20.403 | 45.387 | 15.326 | 1.00 | 31.40 |
| ATOM | 1669 | ND2 | ASN | A | 319 | −18.923 | 45.717 | 13.670 | 1.00 | 31.28 |
| ATOM | 1670 | N | GLU | A | 320 | −20.009 | 50.579 | 12.465 | 1.00 | 36.63 |
| ATOM | 1671 | CA | GLU | A | 320 | −20.664 | 51.585 | 11.644 | 1.00 | 33.11 |
| ATOM | 1672 | C | GLU | A | 320 | −19.545 | 52.374 | 11.005 | 1.00 | 35.79 |

TABLE 1-continued

Structural Coordinate of MEK1/N35/NKF (corresponding to amino acids 24, 383 of SEQ ID NO: 1) -compound 1-ATPγS Ternary Complex.

| | A | B | C | D | E | F | G | H | I | J |
|---|---|---|---|---|---|---|---|---|---|---|
| ATOM | 1673 | O | GLU | A | 320 | −18.377 | 52.101 | 11.246 | 1.00 | 34.22 |
| ATOM | 1674 | CB | GLU | A | 320 | −21.544 | 52.498 | 12.486 | 1.00 | 25.71 |
| ATOM | 1675 | CG | GLU | A | 320 | −22.798 | 51.842 | 13.005 | 1.00 | 35.24 |
| ATOM | 1676 | CD | GLU | A | 320 | −23.810 | 51.554 | 11.916 | 1.00 | 41.36 |
| ATOM | 1677 | OE1 | GLU | A | 320 | −23.649 | 52.084 | 10.796 | 1.00 | 40.25 |
| ATOM | 1678 | OE2 | GLU | A | 320 | −24.767 | 50.797 | 12.190 | 1.00 | 42.46 |
| ATOM | 1679 | N | PRO | A | 321 | −19.875 | 53.452 | 10.128 | 1.00 | 40.79 |
| ATOM | 1680 | CA | PRO | A | 321 | −18.807 | 54.136 | 9.554 | 1.00 | 41.65 |
| ATOM | 1681 | C | PRO | A | 321 | −18.240 | 55.205 | 10.466 | 1.00 | 40.06 |
| ATOM | 1682 | O | PRO | A | 321 | −18.961 | 55.805 | 11.255 | 1.00 | 43.82 |
| ATOM | 1683 | CB | PRO | A | 321 | −19.482 | 54.738 | 8.329 | 1.00 | 42.29 |
| ATOM | 1684 | CG | PRO | A | 321 | −20.906 | 54.944 | 8.772 | 1.00 | 44.16 |
| ATOM | 1685 | CD | PRO | A | 321 | −21.216 | 53.851 | 9.790 | 1.00 | 45.10 |
| ATOM | 1686 | N | PRO | A | 322 | −16.934 | 55.454 | 10.366 | 1.00 | 36.15 |
| ATOM | 1687 | CA | PRO | A | 322 | −16.320 | 56.474 | 11.211 | 1.00 | 36.97 |
| ATOM | 1688 | C | PRO | A | 322 | −16.904 | 57.832 | 10.855 | 1.00 | 35.95 |
| ATOM | 1689 | O | PRO | A | 322 | −17.417 | 58.009 | 9.760 | 1.00 | 34.07 |
| ATOM | 1690 | CB | PRO | A | 322 | −14.840 | 56.384 | 10.853 | 1.00 | 36.52 |
| ATOM | 1691 | CG | PRO | A | 322 | −14.835 | 55.823 | 9.476 | 1.00 | 36.70 |
| ATOM | 1692 | CD | PRO | A | 322 | −15.953 | 54.826 | 9.471 | 1.00 | 35.69 |
| ATOM | 1693 | N | PRO | A | 323 | −16.868 | 58.796 | 11.789 | 1.00 | 34.57 |
| ATOM | 1694 | CA | PRO | A | 323 | −17.403 | 60.135 | 11.510 | 1.00 | 34.83 |
| ATOM | 1695 | C | PRO | A | 323 | −16.607 | 60.730 | 10.346 | 1.00 | 36.97 |
| ATOM | 1696 | O | PRO | A | 323 | −15.586 | 60.161 | 9.949 | 1.00 | 37.11 |
| ATOM | 1697 | CB | PRO | A | 323 | −17.189 | 60.889 | 12.820 | 1.00 | 33.19 |
| ATOM | 1698 | CG | PRO | A | 323 | −17.066 | 59.817 | 13.848 | 1.00 | 35.15 |
| ATOM | 1699 | CD | PRO | A | 323 | −16.362 | 58.688 | 13.162 | 1.00 | 34.44 |
| ATOM | 1700 | N | LYS | A | 324 | −17.034 | 61.873 | 9.813 | 1.00 | 38.65 |
| ATOM | 1701 | CA | LYS | A | 324 | −16.332 | 62.410 | 8.653 | 1.00 | 44.36 |
| ATOM | 1702 | C | LYS | A | 324 | −16.006 | 63.890 | 8.574 | 1.00 | 45.09 |
| ATOM | 1703 | O | LYS | A | 324 | −15.005 | 64.257 | 7.946 | 1.00 | 49.78 |
| ATOM | 1704 | CB | LYS | A | 324 | −17.096 | 52.020 | 7.376 | 1.00 | 46.69 |
| ATOM | 1705 | CG | LYS | A | 324 | −16.714 | 60.658 | 6.791 | 1.00 | 53.88 |
| ATOM | 1706 | CD | LYS | A | 324 | −16.842 | 60.633 | 5.264 | 1.00 | 58.03 |
| ATOM | 1707 | CE | LYS | A | 324 | −18.219 | 60.141 | 4.809 | 1.00 | 60.47 |
| ATOM | 1708 | NZ | LYS | A | 324 | −19.349 | 60.935 | 5.380 | 1.00 | 54.66 |
| ATOM | 1709 | N | LEU | A | 325 | −16.732 | 64.824 | 9.304 | 1.00 | 43.22 |
| ATOM | 1710 | CA | LEU | A | 325 | −16.537 | 66.283 | 9.272 | 1.00 | 45.81 |
| ATOM | 1711 | C | LEU | A | 325 | −17.379 | 66.843 | 8.117 | 1.00 | 49.22 |
| ATOM | 1712 | O | LEU | A | 325 | −17.138 | 66.511 | 6.952 | 1.00 | 52.12 |
| ATOM | 1713 | CB | LEU | A | 325 | −15.056 | 66.638 | 9.047 | 1.00 | 39.14 |
| ATOM | 1714 | CG | LEU | A | 325 | −14.455 | 67.922 | 9.615 | 1.00 | 38.72 |
| ATOM | 1715 | CD1 | LEU | A | 325 | −14.707 | 67.977 | 11.109 | 1.00 | 37.31 |
| ATOM | 1716 | CD2 | LEU | A | 325 | −12.953 | 67.962 | 9.327 | 1.00 | 31.46 |
| ATOM | 1717 | N | PRO | A | 326 | −18.360 | 67.693 | 8.418 | 1.00 | 50.07 |
| ATOM | 1718 | CA | PRO | A | 326 | −19.221 | 68.265 | 7.359 | 1.00 | 51.46 |
| ATOM | 1719 | C | PRO | A | 326 | −18.390 | 66.796 | 6.199 | 1.00 | 52.63 |
| ATOM | 1720 | O | PRO | A | 326 | −17.216 | 69.112 | 6.367 | 1.00 | 54.24 |
| ATOM | 1721 | CB | PRO | A | 326 | −19.990 | 69.387 | 8.064 | 1.00 | 50.91 |
| ATOM | 1722 | CG | PRO | A | 326 | −19.333 | 69.549 | 9.404 | 1.00 | 50.63 |
| ATOM | 1723 | CD | PRO | A | 326 | −18.774 | 68.201 | 9.741 | 1.00 | 50.81 |
| ATOM | 3724 | N | SER | A | 327 | −18.992 | 68.890 | 5.020 | 1.00 | 54.72 |
| ATOM | 1725 | CA | SER | A | 327 | −18.259 | 69.404 | 3.874 | 1.00 | 54.52 |
| ATOM | 1726 | C | SER | A | 327 | −18.636 | 70.844 | 3.566 | 1.00 | 53.41 |
| ATOM | 1727 | O | SER | A | 327 | −19.668 | 71.353 | 4.022 | 1.00 | 49.00 |
| ATOM | 1728 | CB | SER | A | 327 | −18.498 | 68.539 | 2.634 | 1.00 | 55.05 |
| ATOM | 1729 | OG | SER | A | 327 | −17.642 | 68.950 | 1.578 | 1.00 | 53.99 |
| ATOM | 1730 | N | GLY | A | 328 | −17.783 | 71.499 | 2.789 | 1.00 | 53.66 |
| ATOM | 1731 | CA | GLY | A | 328 | −18.033 | 72.877 | 2.421 | 1.00 | 56.94 |
| ATOM | 1732 | C | GLY | A | 328 | −17.764 | 73.838 | 3.558 | 1.00 | 57.41 |
| ATOM | 1733 | O | GLY | A | 328 | −17.424 | 75.000 | 3.329 | 1.00 | 59.46 |
| ATOM | 1734 | N | VAL | A | 329 | −17.925 | 73.354 | 4.787 | 1.00 | 56.20 |
| ATOM | 1735 | CA | VAL | A | 329 | −17.682 | 74.171 | 5.969 | 1.00 | 52.30 |
| ATOM | 1736 | C | VAL | A | 329 | −16.195 | 74.073 | 6.339 | 1.00 | 51.10 |
| ATOM | 1737 | O | VAL | A | 329 | −15.653 | 74.955 | 7.012 | 1.00 | 50.96 |
| ATOM | 1738 | CB | VAL | A | 329 | −18.545 | 73.696 | 7.171 | 1.00 | 52.02 |
| ATOM | 1739 | CG1 | VAL | A | 329 | −18.566 | 74.769 | 8.244 | 1.00 | 49.49 |
| ATOM | 1740 | CG2 | VAL | A | 329 | −19.964 | 73.369 | 6.711 | 1.00 | 49.32 |
| ATOM | 1741 | N | PHE | A | 330 | −15.549 | 73.001 | 5.882 | 1.00 | 47.04 |
| ATOM | 1742 | CA | PHE | A | 330 | −14.132 | 72.759 | 6.152 | 1.00 | 44.27 |
| ATOM | 1743 | C | PHE | A | 330 | −13.355 | 72.401 | 4.892 | 1.00 | 44.37 |
| ATOM | 1744 | O | PHE | A | 330 | −13.841 | 71.660 | 4.032 | 1.00 | 42.88 |
| ATOM | 1745 | CB | PHE | A | 330 | −13.959 | 71.618 | 7.161 | 1.00 | 39.38 |
| ATOM | 1746 | CG | PHE | A | 330 | −14.573 | 71.890 | 8.491 | 1.00 | 34.06 |
| ATOM | 1747 | CD1 | PHE | A | 330 | −13.901 | 72.652 | 9.435 | 1.00 | 26.26 |

TABLE 1-continued

Structural Coordinate of MEK1/N35/NKF (corresponding to amino acids 24, 383 of SEQ ID NO: 1) -compound 1-ATPγS Ternary Complex.

| | A | B | C | D | E | F | G | H | I | J |
|---|---|---|---|---|---|---|---|---|---|---|
| ATOM | 2748 | CD2 | PHE | A | 330 | −15.839 | 71.395 | 8.794 | 1.00 | 31.05 |
| ATOM | 1749 | CE1 | PHE | A | 330 | −14.485 | 72.917 | 10.671 | 1.00 | 29.71 |
| ATOM | 1750 | CE2 | PHE | A | 330 | −16.431 | 71.654 | 10.031 | 1.00 | 29.80 |
| ATOM | 1751 | CZ | PHE | A | 330 | −15.756 | 72.416 | 10.972 | 1.00 | 24.30 |
| ATOM | 1752 | N | SER | A | 331 | −12.131 | 72.914 | 4.812 | 1.00 | 44.31 |
| ATOM | 1753 | CA | SER | A | 331 | −11.250 | 72.673 | 3.682 | 1.00 | 42.02 |
| ATOM | 1754 | C | SER | A | 331 | −11.127 | 71.190 | 3.353 | 1.00 | 42.62 |
| ATOM | 1755 | O | SER | A | 331 | −11.247 | 70.335 | 4.225 | 1.00 | 43.55 |
| ATOM | 1756 | CB | SER | A | 331 | −9.865 | 73.240 | 3.972 | 1.00 | 40.13 |
| ATOM | 1757 | OG | SER | A | 331 | −8.911 | 72.198 | 4.028 | 1.00 | 42.50 |
| ATOM | 1758 | N | LEU | A | 332 | −10.887 | 70.903 | 2.080 | 1.00 | 43.03 |
| ATOM | 1759 | CA | LEU | A | 332 | −10.740 | 69.538 | 1.608 | 1.00 | 43.70 |
| ATOM | 1760 | C | LEU | A | 332 | −9.545 | 68.899 | 2.296 | 1.00 | 44.35 |
| ATOM | 1761 | O | LEU | A | 332 | −9.576 | 67.710 | 2.616 | 1.00 | 45.21 |
| ATOM | 1762 | CB | LEU | A | 332 | −10.528 | 69.524 | 0.089 | 1.00 | 44.08 |
| ATOM | 1763 | CG | LEU | A | 332 | −11.712 | 69.393 | −0.882 | 1.00 | 44.77 |
| ATOM | 1764 | CD1 | LEU | A | 332 | −11.629 | 68.029 | −1.542 | 1.00 | 43.67 |
| ATOM | 1765 | CD2 | LEU | A | 332 | −13.055 | 69.574 | −0.180 | 1.00 | 42.40 |
| ATOM | 1766 | N | GLU | A | 333 | −8.495 | 69.693 | 2.515 | 1.00 | 43.47 |
| ATOM | 1767 | CA | GLU | A | 333 | −7.273 | 69.217 | 3.168 | 1.00 | 44.27 |
| ATOM | 1768 | C | GLU | A | 333 | −7.568 | 68.638 | 4.551 | 1.00 | 44.90 |
| ATOM | 1769 | O | GLU | A | 333 | −7.181 | 67.507 | 4.860 | 1.00 | 42.45 |
| ATOM | 1770 | CB | GLU | A | 333 | −6.278 | 70.362 | 3.321 | 1.00 | 46.83 |
| ATOM | 1771 | CG | GLU | A | 333 | −5.034 | 70.216 | 2.471 | 1.00 | 56.47 |
| ATOM | 1772 | CD | GLU | A | 333 | −4.811 | 77.418 | 1.565 | 1.00 | 61.64 |
| ATOM | 1773 | OE1 | GLU | A | 333 | −3.665 | 71.606 | 1.087 | 1.00 | 63.78 |
| ATOM | 1774 | OE2 | GLU | A | 333 | −5.787 | 72.170 | 1.334 | 1.00 | 61.66 |
| ATOM | 1775 | N | PHE | A | 334 | −8.235 | 69.434 | 5.381 | 1.00 | 43.71 |
| ATOM | 1776 | CA | PHE | A | 334 | −8.603 | 69.027 | 5.730 | 1.00 | 42.62 |
| ATOM | 1777 | C | PHE | A | 334 | −9.446 | 67.756 | 6.654 | 1.00 | 44.19 |
| ATOM | 1778 | O | PHE | A | 334 | −9.180 | 66.782 | 7.350 | 1.00 | 49.41 |
| ATOM | 1779 | CB | PHE | A | 334 | −9.394 | 70.153 | 7.406 | 1.00 | 41.89 |
| ATOM | 1780 | CG | PHE | A | 334 | −9.711 | 69.910 | 8.859 | 1.00 | 39.29 |
| ATOM | 1781 | CD1 | PHE | A | 334 | −8.980 | 69.003 | 9.614 | 1.00 | 39.69 |
| ATOM | 1782 | CD2 | PHE | A | 334 | −10.742 | 70.615 | 9.475 | 1.00 | 38.19 |
| ATOM | 1783 | CE1 | PHE | A | 334 | −9.273 | 68.806 | 10.953 | 1.00 | 39.69 |
| ATOM | 1784 | CE2 | PHE | A | 334 | −11.040 | 70.424 | 10.811 | 1.00 | 35.73 |
| ATOM | 1785 | CZ | PHE | A | 334 | −10.306 | 69.518 | 11.554 | 1.00 | 39.02 |
| ATOM | 1786 | N | GLN | A | 335 | −10.456 | 67.758 | 5.792 | 1.00 | 40.70 |
| ATOM | 1787 | CA | GLN | A | 335 | −11.311 | 66.592 | 5.661 | 1.00 | 38.96 |
| ATOM | 1788 | C | GLN | A | 335 | −10.501 | 65.314 | 5.410 | 1.00 | 38.54 |
| ATOM | 1789 | O | GLN | A | 335 | −10.724 | 64.295 | 6.073 | 1.00 | 36.94 |
| ATOM | 1790 | CB | GLN | A | 335 | −12.334 | 66.829 | 4.545 | 1.00 | 40.63 |
| ATOM | 1791 | CG | GLN | A | 335 | −13.257 | 68.023 | 4.813 | 1.00 | 40.03 |
| ATOM | 1792 | CD | GLN | A | 335 | −14.396 | 68.137 | 3.808 | 1.00 | 40.97 |
| ATOM | 1793 | OE1 | GLN | A | 335 | −14.730 | 69.233 | 3.345 | 1.00 | 40.86 |
| ATOM | 1794 | NE2 | GLN | A | 335 | −14.996 | 67.005 | 3.469 | 1.00 | 36.03 |
| ATOM | 1795 | N | ASP | A | 336 | −9.556 | 65.371 | 4.473 | 1.00 | 38.02 |
| ATOM | 1796 | CA | ASP | A | 336 | −8.715 | 64.211 | 4.155 | 1.00 | 38.81 |
| ATOM | 1797 | C | ASP | A | 336 | −7.931 | 63.778 | 5.382 | 1.00 | 37.31 |
| ATOM | 1798 | O | ASP | A | 336 | −7.910 | 62.597 | 5.733 | 1.00 | 41.15 |
| ATOM | 1799 | CB | ASP | A | 336 | −7.725 | 64.537 | 3.021 | 1.00 | 43.06 |
| ATOM | 1800 | CG | ASP | A | 336 | −6.986 | 63.299 | 2.501 | 1.00 | 43.28 |
| ATOM | 1801 | OD1 | ASP | A | 336 | −7.654 | 62.374 | 1.989 | 1.00 | 39.54 |
| ATOM | 1802 | OD2 | ASP | A | 336 | −5.739 | 63.246 | 2.603 | 1.00 | 42.70 |
| ATOM | 1803 | N | PHE | A | 337 | −7.280 | 64.743 | 6.028 | 1.00 | 33.36 |
| ATOM | 1804 | CA | PHE | A | 337 | −6.491 | 64.474 | 7.227 | 1.00 | 31.84 |
| ATOM | 1805 | C | PHE | A | 337 | −7.304 | 63.670 | 8.252 | 1.00 | 28.10 |
| ATOM | 1806 | O | PHE | A | 337 | −6.901 | 62.582 | 8.657 | 1.00 | 25.73 |
| ATOM | 1807 | CB | PHE | A | 337 | −6.014 | 65.792 | 7.843 | 1.00 | 28.41 |
| ATOM | 1808 | CG | PHE | A | 337 | −5.097 | 65.616 | 9.011 | 1.00 | 32.15 |
| ATOM | 1809 | CD1 | PHE | A | 337 | −5.575 | 65.753 | 10.317 | 1.00 | 31.68 |
| ATOM | 1810 | CD2 | PHE | A | 337 | −3.760 | 65.300 | 8.816 | 1.00 | 30.96 |
| ATOM | 1811 | CE1 | PHE | A | 337 | −4.736 | 65.576 | 11.408 | 1.00 | 32.28 |
| ATOM | 1812 | CE2 | PHE | A | 337 | −2.907 | 65.119 | 9.905 | 1.00 | 32.34 |
| ATOM | 1813 | CZ | PHE | A | 337 | −3.398 | 65.258 | 11.205 | 1.00 | 34.20 |
| ATOM | 1814 | N | VAL | A | 338 | −8.450 | 64.214 | 8.652 | 1.00 | 26.17 |
| ATOM | 1815 | CA | VAL | A | 338 | −9.327 | 63.568 | 9.616 | 1.00 | 24.52 |
| ATOM | 1816 | C | VAL | A | 338 | −9.675 | 62.186 | 9.107 | 1.00 | 27.76 |
| ATOM | 1817 | O | VAL | A | 338 | −9.601 | 61.195 | 9.841 | 1.00 | 30.23 |
| ATOM | 1818 | CB | VAL | A | 338 | −10.633 | 64.353 | 9.777 | 1.00 | 23.80 |
| ATOM | 1819 | CG1 | VAL | A | 338 | −11.742 | 63.430 | 10.234 | 1.00 | 30.94 |
| ATOM | 1820 | CG2 | VAL | A | 338 | −10.438 | 65.479 | 10.759 | 1.00 | 25.08 |
| ATOM | 1821 | N | ASN | A | 339 | −10.052 | 62.126 | 7.836 | 1.00 | 29.15 |
| ATOM | 1822 | CA | ASN | A | 339 | −10.434 | 60.870 | 7.227 | 1.00 | 28.27 |

TABLE 1-continued

Structural Coordinate of MEK1/N35/NKF (corresponding to amino acids 24, 383 of SEQ ID NO: 1) -compound 1-ATPγS Ternary Complex.

| | A | B | C | D | E | F | G | H | I | J |
|---|---|---|---|---|---|---|---|---|---|---|
| ATOM | 1823 | C | ASN | A | 339 | −9.328 | 59.815 | 7.236 | 1.00 | 26.42 |
| ATOM | 1824 | O | ASN | A | 339 | −9.612 | 68.617 | 7.361 | 1.00 | 27.22 |
| ATOM | 1825 | CB | ASN | A | 339 | −10.938 | 61.126 | 5.809 | 1.00 | 35.10 |
| ATOM | 1826 | CG | ASN | A | 339 | −12.421 | 61.453 | 5.776 | 1.00 | 41.02 |
| ATOM | 1827 | OD1 | ASN | A | 339 | −12.836 | 62.567 | 6.120 | 1.00 | 46.01 |
| ATOM | 1828 | ND2 | ASN | A | 339 | −13.234 | 60.476 | 5.375 | 1.00 | 44.68 |
| ATOM | 1829 | N | LYS | A | 340 | −8.139 | 60.129 | 7.011 | 1.00 | 23.28 |
| ATOM | 1830 | CA | LYS | A | 340 | −7.017 | 59.194 | 7.022 | 1.00 | 23.48 |
| ATOM | 1831 | C | LYS | A | 340 | −6.748 | 58.632 | 8.422 | 1.00 | 23.77 |
| ATOM | 1832 | O | LYS | A | 340 | −6.103 | 57.585 | 8.573 | 1.00 | 21.60 |
| ATOM | 1833 | CB | LYS | A | 240 | −5.760 | 59.388 | 6.497 | 1.00 | 28.68 |
| ATOM | 1834 | CG | LYS | A | 340 | −5.921 | 60.499 | 5.117 | 1.00 | 26.60 |
| ATOM | 1835 | CD | LYS | A | 340 | −4.611 | 60.442 | 4.333 | 1.00 | 37.57 |
| ATOM | 1836 | CE | LYS | A | 340 | −4.672 | 59.429 | 3.188 | 1.00 | 41.31 |
| ATOM | 1637 | NZ | LYS | A | 340 | −5.724 | 59.780 | 2.190 | 1.00 | 39.04 |
| ATOM | 1838 | N | CYS | A | 341 | −7.246 | 59.342 | 9.432 | 1.00 | 21.69 |
| ATOM | 1839 | CA | CYS | A | 341 | −7.090 | 58.952 | 10.631 | 1.00 | 25.76 |
| ATOM | 1840 | C | CYS | A | 341 | −8.236 | 58.049 | 11.233 | 1.00 | 26.90 |
| ATOM | 1841 | O | CYS | A | 341 | −8.067 | 57.146 | 12.049 | 1.00 | 25.45 |
| ATOM | 1842 | CB | CYS | A | 341 | −7.143 | 60.178 | 11.756 | 1.00 | 22.44 |
| ATOM | 1843 | SG | CYS | A | 341 | −5.858 | 61.391 | 11.554 | 1.00 | 21.34 |
| ATOM | 1844 | N | LEU | A | 342 | −9.412 | 58.314 | 10.664 | 1.00 | 26.83 |
| ATOM | 1845 | CA | LEU | A | 342 | −10.609 | 57.559 | 11.008 | 1.00 | 22.24 |
| ATOM | 1846 | C | LEU | A | 342 | −10.884 | 56.323 | 10.164 | 1.00 | 26.89 |
| ATOM | 1847 | O | LEU | A | 342 | −12.032 | 55.885 | 10.038 | 1.00 | 27.72 |
| ATOM | 1848 | CB | LEU | A | 342 | −11.809 | 58.511 | 11.029 | 1.00 | 17.16 |
| ATOM | 1849 | CG | LEU | A | 342 | −11.636 | 59.620 | 12.096 | 1.00 | 18.71 |
| ATOM | 1850 | CD1 | LEU | A | 342 | −12.796 | 60.613 | 12.071 | 1.00 | 15.80 |
| ATOM | 1851 | CD2 | LEU | A | 342 | −11.540 | 58.967 | 13.475 | 1.00 | 7.33 |
| ATOM | 1852 | N | ILE | A | 343 | −9.819 | 55.753 | 9.599 | 1.00 | 26.64 |
| ATOM | 1853 | CA | ILE | A | 343 | −9.912 | 54.538 | 8.794 | 1.00 | 24.35 |
| ATOM | 1854 | C | ILE | A | 343 | −10.004 | 53.379 | 9.783 | 1.00 | 26.29 |
| ATOM | 1855 | O | ILE | A | 343 | −9.062 | 53.106 | 10.522 | 1.00 | 25.94 |
| ATOM | 1856 | CB | ILE | A | 343 | −8.651 | 54.325 | 7.920 | 1.00 | 26.61 |
| ATOM | 1857 | CG1 | ILE | A | 343 | −8.690 | 55.239 | 6.694 | 1.00 | 29.30 |
| ATOM | 1858 | CG2 | ILE | A | 343 | −8.570 | 52.882 | 7.468 | 1.00 | 25.17 |
| ATOM | 1859 | CD1 | ILE | A | 343 | −7.376 | 55.296 | 5.942 | 1.00 | 32.35 |
| ATOM | 1860 | N | LYS | A | 344 | −11.135 | 52.691 | 9.793 | 1.00 | 24.72 |
| ATOM | 1861 | CA | LYS | A | 344 | −11.324 | 51.585 | 10.712 | 1.00 | 24.40 |
| ATOM | 1862 | C | LYS | A | 344 | −10.166 | 50.601 | 10.830 | 1.00 | 24.06 |
| ATOM | 1863 | O | LYS | A | 344 | −9.872 | 50.130 | 11.925 | 1.00 | 29.34 |
| ATOM | 1864 | CB | LYS | A | 344 | −12.587 | 50.831 | 10.348 | 1.00 | 21.72 |
| ATOM | 1865 | CG | LYS | A | 344 | −13.805 | 51.310 | 11.086 | 1.00 | 25.93 |
| ATOM | 1866 | CD | LYS | A | 344 | −14.477 | 50.134 | 11.773 | 1.00 | 22.29 |
| ATOM | 1867 | CE | LYS | A | 344 | −15.947 | 50.115 | 11.433 | 1.00 | 27.12 |
| ATOM | 1866 | NZ | LYS | A | 344 | −16.436 | 51.495 | 11.269 | 1.00 | 27.32 |
| ATOM | 1869 | N | ASN | A | 345 | −9.504 | 50.273 | 9.729 | 1.00 | 23.75 |
| ATOM | 1870 | CA | ASN | A | 345 | −8.404 | 49.313 | 9.805 | 1.00 | 20.16 |
| ATOM | 1871 | C | ASN | A | 345 | −7.086 | 49.969 | 10.206 | 1.00 | 19.86 |
| ATOM | 1872 | O | ASN | A | 345 | −6.597 | 50.882 | 9.527 | 1.00 | 22.22 |
| ATOM | 1873 | CB | ASN | A | 345 | −8.230 | 48.585 | 8.480 | 1.00 | 16.87 |
| ATOM | 1874 | CG | ASN | A | 345 | −7.263 | 47.441 | 8.590 | 1.00 | 18.21 |
| ATOM | 1875 | OD1 | ASN | A | 345 | −7.668 | 46.295 | 8.721 | 1.00 | 28.21 |
| ATOM | 1876 | ND2 | ASN | A | 345 | −5.975 | 47.744 | 8.560 | 1.00 | 21.14 |
| ATOM | 1677 | N | PRO | A | 346 | −6.469 | 49.473 | 11.293 | 1.00 | 16.28 |
| ATOM | 1878 | CA | PRO | A | 346 | −5.198 | 49.979 | 11.847 | 1.00 | 17.23 |
| ATOM | 1879 | C | PRO | A | 346 | −4.029 | 50.055 | 10.870 | 1.00 | 18.68 |
| ATOM | 1880 | O | PRO | A | 346 | −3.377 | 51.099 | 10.752 | 1.00 | 15.58 |
| ATOM | 1881 | CB | PRO | A | 346 | −4.897 | 49.037 | 13.021 | 1.00 | 15.88 |
| ATOM | 1882 | CG | PRO | A | 346 | −6.175 | 48.340 | 13.320 | 1.00 | 15.67 |
| ATOM | 1883 | CD | PRO | A | 346 | −6.989 | 48.318 | 12.042 | 1.00 | 13.71 |
| ATOM | 1884 | N | ALA | A | 347 | −3.768 | 48.947 | 10.177 | 1.00 | 20.95 |
| ATOM | 1885 | CA | ALA | A | 347 | −2.670 | 48.870 | 9.208 | 1.00 | 16.75 |
| ATOM | 1886 | C | ALA | A | 347 | −2.936 | 49.806 | 8.029 | 1.00 | 15.22 |
| ATOM | 1887 | O | ALA | A | 347 | −2.031 | 50.477 | 7.509 | 1.00 | 14.33 |
| ATOM | 1888 | CB | ALA | A | 347 | −2.511 | 47.446 | 8.739 | 1.00 | 14.19 |
| ATOM | 1889 | N | GLU | A | 346 | −4.190 | 49.886 | 7.631 | 1.00 | 15.51 |
| ATOM | 1890 | CA | GLU | A | 348 | −4.546 | 50.766 | 6.534 | 1.00 | 19.61 |
| ATOM | 1891 | CB | GLU | A | 348 | −5.959 | 50.445 | 6.035 | 1.00 | 18.97 |
| ATOM | 1892 | C | GLU | A | 348 | −4.458 | 52.213 | 7.009 | 1.00 | 21.39 |
| ATOM | 1893 | O | GLU | A | 348 | −3.875 | 53.060 | 6.336 | 1.00 | 27.15 |
| ATOM | 1894 | N | ARG | A | 349 | −5.039 | 52.490 | 8.173 | 1.00 | 20.69 |
| ATOM | 1895 | CA | ARG | A | 349 | −5.027 | 53.838 | 3.746 | 1.00 | 17.92 |
| ATOM | 1896 | C | ARG | A | 349 | −3.654 | 54.460 | 8.637 | 1.00 | 7.78 |
| ATOM | 1897 | O | ARG | A | 349 | −2.649 | 53.765 | 8.765 | 1.00 | 12.41 |

TABLE 1-continued

Structural Coordinate of MEK1/N35/NKF (corresponding to amino acids 24, 383 of SEQ ID NO: 1) -compound 1-ATPγS Ternary Complex.

| A | B | C | D | E | F | G | H | I | J |
|---|---|---|---|---|---|---|---|---|---|
| ATOM | 1898 | CB | ARG | A | 349 | −5.415 | 53.773 | 10.224 | 1.00 | 20.98 |
| ATOM | 1899 | CG | ARG | A | 349 | −5.710 | 55.118 | 10.874 | 1.30 | 17.06 |
| ATOM | 1900 | CD | ARG | A | 349 | −6.733 | 54.931 | 12.000 | 1.00 | 14.66 |
| ATOM | 1901 | NE | ARG | A | 349 | −6.288 | 53.989 | 13.018 | 1.00 | 6.25 |
| ATOM | 1902 | CZ | ARG | A | 349 | −7.049 | 53.037 | 13.535 | 1.00 | 12.99 |
| ATOM | 1903 | NH1 | ARG | A | 349 | −8.293 | 52.895 | 13.122 | 1.00 | 16.90 |
| ATOM | 1904 | NH2 | ARG | A | 349 | −6.578 | 52.245 | 14.488 | 1.00 | 17.23 |
| ATOM | 1905 | N | ALA | A | 350 | −3.600 | 55.762 | 8.389 | 1.00 | 6.21 |
| ATOM | 1906 | CA | ALA | A | 350 | −2.309 | 86.442 | 8.319 | 1.00 | 9.41 |
| ATOM | 1907 | C | ALA | A | 350 | −1.609 | 56.336 | 9.667 | 1.00 | 15.70 |
| ATOM | 1908 | O | ALA | A | 350 | −2.242 | 56.119 | 13.711 | 1.00 | 13.12 |
| ATOM | 1909 | CB | ALA | A | 350 | −2.491 | 57.908 | 7.968 | 1.00 | 6.10 |
| ATOM | 1910 | N | ASP | A | 351 | −0.297 | 56.497 | 9.639 | 1.00 | 15.82 |
| ATOM | 1911 | CA | ASP | A | 351 | 0.498 | 56.440 | 10.842 | 1.90 | 21.67 |
| ATOM | 1912 | C | ASP | A | 351 | 1.177 | 57.812 | 11.031 | 1.00 | 24.56 |
| ATOM | 1913 | O | ASP | A | 351 | 1.020 | 58.706 | 10.194 | 1.00 | 29.51 |
| ATOM | 1914 | CB | ASP | A | 351 | 1.519 | 55.303 | 10.727 | 1.00 | 18.58 |
| ATOM | 1915 | CG | ASP | A | 351 | 2.700 | 55.668 | 9.851 | 1.00 | 20.97 |
| ATOM | 1916 | OD1 | ASP | A | 351 | 2.579 | 56.613 | 9.035 | 1.00 | 16.93 |
| ATOM | 1917 | OD2 | ASP | A | 351 | 3.755 | 55.008 | 9.986 | 1.00 | 23.35 |
| ATOM | 1918 | N | LEU | A | 352 | 1.922 | 57.973 | 12.121 | 1.00 | 24.09 |
| ATOM | 1919 | CA | LEU | A | 352 | 2.590 | 59.241 | 12.438 | 1.00 | 23.69 |
| ATOM | 1920 | C | LEU | A | 352 | 3.457 | 59.795 | 11.310 | 1.00 | 21.24 |
| ATOM | 1921 | O | LEU | A | 352 | 3.360 | 60.975 | 10.973 | 1.00 | 23.54 |
| ATOM | 1922 | CB | LEU | A | 352 | 3.436 | 59.081 | 13.718 | 1.00 | 17.72 |
| ATOM | 1923 | CG | LEU | A | 352 | 2.856 | 59.475 | 15.084 | 1.00 | 14.59 |
| ATOM | 1924 | CD1 | LEU | A | 352 | 1.413 | 59.786 | 14.971 | 1.00 | 10.57 |
| ATOM | 1925 | CD2 | LEU | A | 352 | 3.071 | 58.361 | 16.082 | 1.00 | 14.58 |
| ATOM | 1926 | N | LYS | A | 353 | 4.301 | 58.948 | 10.733 | 1.00 | 22.47 |
| ATOM | 1927 | CA | LYS | A | 353 | 5.193 | 59.336 | 9.640 | 1.00 | 26.48 |
| ATOM | 1928 | C | LYS | A | 353 | 4.473 | 60.059 | 8.511 | 1.00 | 27.20 |
| ATOM | 1929 | O | LYS | A | 353 | 4.901 | 61.120 | 8.055 | 1.90 | 21.83 |
| ATOM | 1930 | CB | LYS | A | 353 | 5.863 | 58.096 | 9.050 | 1.00 | 32.21 |
| ATOM | 1931 | CG | LYS | A | 353 | 7.319 | 57.912 | 9.450 | 1.00 | 45.37 |
| ATOM | 1932 | CD | LYS | A | 353 | 7.549 | 56.584 | 10.193 | 1.00 | 55.46 |
| ATOM | 1933 | CE | LYS | A | 353 | 7.614 | 55.382 | 9.241 | 1.00 | 56.01 |
| ATOM | 1934 | NZ | LYS | A | 353 | 7.202 | 54.101 | 9.911 | 1.00 | 57.64 |
| ATOM | 1935 | N | GLN | A | 354 | 3.378 | 59.462 | 8.054 | 1.00 | 28.69 |
| ATOM | 1936 | CA | GLN | A | 354 | 2.609 | 60.025 | 6.958 | 1.00 | 29.15 |
| ATOM | 1937 | C | GLN | A | 354 | 1.833 | 61.270 | 7.325 | 1.00 | 31.90 |
| ATOM | 1938 | O | GLN | A | 354 | 1.912 | 62.277 | 6.623 | 1.00 | 34.48 |
| ATOM | 1939 | CB | GLN | A | 354 | 1.664 | 58.975 | 6.398 | 1.00 | 26.68 |
| ATOM | 1940 | CG | GLN | A | 354 | 2.379 | 57.740 | 5.872 | 1.00 | 29.55 |
| ATOM | 1941 | CD | GLN | A | 354 | 1.415 | 56.611 | 5.586 | 1.00 | 28.22 |
| ATOM | 1942 | OE1 | GLN | A | 354 | 0.254 | 56.676 | 5.975 | 1.09 | 34.18 |
| ATOM | 1943 | NE2 | GLN | A | 354 | 1.885 | 55.572 | 4.905 | 1.00 | 33.76 |
| ATOM | 1944 | N | LEU | A | 355 | 1.078 | 61.211 | 8.416 | 1.00 | 32.07 |
| ATOM | 1945 | CA | LEU | A | 355 | 0.310 | 62.381 | 8.831 | 1.00 | 28.51 |
| ATOM | 1945 | C | LEU | A | 355 | 1.264 | 63.576 | 8.928 | 1.00 | 29.22 |
| ATOM | 1947 | O | LEU | A | 355 | 0.875 | 64.706 | 2.636 | 1.00 | 24.91 |
| ATOM | 1948 | CB | LEU | A | 355 | −0.371 | 62.134 | 10.186 | 1.00 | 27.44 |
| ATOM | 1949 | CG | LEU | A | 355 | −1.501 | 61.101 | 10.276 | 1.00 | 28.08 |
| ATOM | 1950 | CD1 | LEU | A | 355 | −1.976 | 61.000 | 11.721 | 1.00 | 24.11 |
| ATOM | 1951 | CD2 | LEU | A | 355 | −2.657 | 61.498 | 9.367 | 1.00 | 20.45 |
| ATOM | 1952 | N | MET | A | 356 | 2.512 | 63.322 | 9.322 | 1.00 | 31.07 |
| ATOM | 1953 | CA | MET | A | 356 | 3.500 | 64.396 | 9.451 | 1.00 | 37.13 |
| ATOM | 1954 | C | MET | A | 356 | 3.764 | 65.079 | 8.118 | 1.00 | 38.03 |
| ATOM | 1955 | O | MET | A | 356 | 4.056 | 66.273 | 8.073 | 1.00 | 41.67 |
| ATOM | 1956 | CB | MET | A | 356 | 4.835 | 63.865 | 9.993 | 1.00 | 39.54 |
| ATOM | 1957 | CG | MET | A | 356 | 4.945 | 63.819 | 11.517 | 1.00 | 49.00 |
| ATOM | 1958 | SD | MET | A | 356 | 5.656 | 65.295 | 12.314 | 1.00 | 53.92 |
| ATOM | 1959 | CE | MET | A | 356 | 4.721 | 66.612 | 11.503 | 1.00 | 47.94 |
| ATOM | 1960 | N | VAL | A | 357 | 3.680 | 64.323 | 7.033 | 1.00 | 36.93 |
| ATOM | 1961 | CA | VAL | A | 357 | 3.929 | 64.892 | 5.719 | 1.00 | 36.19 |
| ATOM | 1962 | C | VAL | A | 357 | 2.639 | 65.162 | 4.965 | 1.00 | 39.27 |
| ATOM | 1963 | O | VAL | A | 357 | 2.677 | 65.482 | 3.779 | 1.00 | 40.56 |
| ATOM | 1964 | CB | VAL | A | 357 | 4.824 | 63.965 | 4.867 | 1.00 | 36.30 |
| ATOM | 1965 | CG1 | VAL | A | 357 | 6.084 | 63.616 | 5.641 | 1.00 | 28.89 |
| ATOM | 1966 | CG2 | VAL | A | 357 | 4.060 | 62.698 | 4.475 | 1.00 | 33.20 |
| ATOM | 1967 | N | HIS | A | 358 | 1.501 | 65.042 | 5.650 | 1.00 | 38.28 |
| ATOM | 1968 | CA | HIS | A | 358 | 0.199 | 65.273 | 5.024 | 1.00 | 32.30 |
| ATOM | 1969 | C | HIS | A | 358 | 0.000 | 66.734 | 4.675 | 1.00 | 36.28 |
| ATOM | 1970 | O | HIS | A | 358 | 0.495 | 67.622 | 5.362 | 1.00 | 36.14 |
| ATOM | 1971 | CB | HIS | A | 358 | −0.931 | 64.820 | 5.946 | 1.00 | 26.95 |
| ATOM | 1972 | CG | HIS | A | 358 | −2.278 | 64.773 | 5.288 | 1.00 | 22.17 |

TABLE 1-continued

Structural Coordinate of MEK1/N35/NKF (corresponding to amino acids 24, 383 of SEQ ID NO: 1) -compound 1-ATPγS Ternary Complex.

| | A | B | C | D | E | F | G | H | I | J |
|---|---|---|---|---|---|---|---|---|---|---|
| ATOM | 1973 | ND1 | HIS | A | 359 | −3.046 | 65.901 | 5.080 | 1.00 | 19.46 |
| ATOM | 1974 | CD2 | HIS | A | 358 | −3.013 | 63.730 | 4.838 | 1.00 | 12.82 |
| ATOM | 1975 | CE1 | HIS | A | 358 | −4.198 | 65.552 | 4.534 | 1.00 | 19.53 |
| ATOM | 1976 | NE2 | HIS | A | 358 | −4.200 | 64.239 | 4.377 | 1.00 | 20.08 |
| ATOM | 1977 | N | ALA | A | 359 | −0.738 | 66.970 | 3.599 | 1.00 | 39.27 |
| ATOM | 1979 | CA | ALA | A | 359 | −0.993 | 68.324 | 3.136 | 1.00 | 40.52 |
| ATOM | 1979 | C | ALA | A | 359 | −1.546 | 69.225 | 4.222 | 1.00 | 42.82 |
| ATOM | 1980 | O | ALA | A | 359 | −1.062 | 70.342 | 4.408 | 1.00 | 46.44 |
| ATOM | 1981 | CB | ALA | A | 359 | −1.951 | 68.299 | 1.960 | 1.00 | 40.31 |
| ATOM | 1982 | N | PHE | A | 360 | −2.560 | 68.746 | 4.937 | 1.00 | 42.80 |
| ATOM | 1983 | CA | PHE | A | 360 | −3.182 | 69.559 | 5.976 | 1.00 | 41.30 |
| ATOM | 1984 | C | PHE | A | 360 | −2.199 | 70.181 | 6.957 | 1.00 | 36.01 |
| ATOM | 1985 | O | PHE | A | 360 | −2.283 | 71.371 | 7.255 | 1.00 | 36.96 |
| ATOM | 1986 | CB | PHE | A | 360 | −4.223 | 68.750 | 6.753 | 1.00 | 41.54 |
| ATOM | 1937 | CG | PHE | A | 360 | −4.868 | 69.523 | 7.864 | 1.00 | 41.26 |
| ATOM | 1988 | CD1 | PHE | A | 360 | −5.768 | 70.551 | 7.581 | 1.00 | 44.60 |
| ATOM | 1989 | CD2 | PHE | A | 360 | −4.551 | 69.256 | 9.195 | 1.00 | 39.00 |
| ATOM | 1990 | CE1 | PHE | A | 360 | −6.344 | 71.306 | 8.605 | 1.00 | 42.18 |
| ATOM | 1991 | CE2 | PHE | A | 360 | −5.118 | 70.002 | 10.226 | 1.00 | 38.72 |
| ATOM | 1992 | CZ | PHE | A | 360 | −6.017 | 71.031 | 9.930 | 1.00 | 40.54 |
| ATOM | 1993 | N | ILE | A | 351 | −1.269 | 69.399 | 7.472 | 1.00 | 34.40 |
| ATOM | 1994 | CA | ILE | A | 361 | −0.339 | 69.979 | 8.410 | 1.00 | 34.72 |
| ATOM | 1995 | C | ILE | A | 361 | 0.708 | 70.806 | 7.686 | 1.00 | 36.39 |
| ATOM | 1996 | O | ILE | A | 361 | 1.086 | 71.870 | 8.170 | 1.00 | 42.25 |
| ATOM | 1997 | CB | ILE | A | 361 | 0.319 | 68.911 | 9.332 | 1.00 | 34.20 |
| ATOM | 1998 | CG1 | ILE | A | 361 | 1.480 | 68.235 | 8.627 | 1.00 | 32.14 |
| ATOM | 1999 | CG2 | ILE | A | 361 | −0.722 | 67.911 | 9.794 | 1.00 | 33.00 |
| ATOM | 2000 | CD1 | ILE | A | 361 | 2.777 | 68.476 | 9.341 | 1.00 | 33.06 |
| ATOM | 2001 | N | LYS | A | 362 | 1.165 | 70.352 | 6.517 | 1.00 | 37.29 |
| ATOM | 2002 | CA | LYS | A | 362 | 2.161 | 71.112 | 5.747 | 1.00 | 33.35 |
| ATOM | 2003 | C | LYS | A | 362 | 1.624 | 72.514 | 5.480 | 1.00 | 31.71 |
| ATOM | 2004 | O | LYS | A | 362 | 2.337 | 73.503 | 5.634 | 1.00 | 29.19 |
| ATOM | 2005 | CB | LYS | A | 362 | 2.478 | 70.409 | 4.425 | 1.00 | 34.07 |
| ATOM | 2006 | CG | LYS | A | 362 | 3.415 | 69.219 | 4.573 | 1.00 | 36.58 |
| ATOM | 2007 | CD | LYS | A | 362 | 4.231 | 68.992 | 3.311 | 1.00 | 43.23 |
| ATOM | 2008 | CE | LYS | A | 362 | 5.666 | 68.560 | 3.638 | 1.00 | 48.51 |
| ATOM | 2009 | NZ | LYS | A | 362 | 6.732 | 69.524 | 3.132 | 1.00 | 46.38 |
| ATOM | 2010 | N | ARG | A | 363 | 0.361 | 72.590 | 5.075 | 1.00 | 22.76 |
| ATOM | 2011 | CA | ARG | A | 363 | −0.279 | 73.873 | 4.829 | 1.00 | 36.19 |
| ATOM | 2012 | C | ARG | A | 363 | −0.639 | 74.473 | 6.180 | 1.00 | 33.31 |
| ATOM | 2013 | O | ARG | A | 363 | −0.994 | 75.645 | 6.272 | 1.00 | 39.69 |
| ATOM | 2014 | CB | ARG | A | 363 | −1.562 | 73.706 | 3.999 | 1.00 | 37.74 |
| ATOM | 2015 | CG | ARG | A | 363 | −2.463 | 74.958 | 3.984 | 1.00 | 40.97 |
| ATOM | 2016 | CD | ARG | A | 363 | −3.971 | 74.638 | 3.980 | 1.00 | 43.17 |
| ATOM | 2017 | NE | ARG | A | 363 | −4.581 | 74.736 | 5.309 | 1.00 | 45.24 |
| ATOM | 2018 | CZ | ARG | A | 363 | −5.764 | 74.216 | 5.636 | 1.00 | 44.99 |
| ATOM | 2019 | NH1 | ARG | A | 363 | −6.473 | 73.559 | 4.728 | 1.00 | 45.04 |
| ATOM | 2020 | NH2 | ARG | A | 363 | −6.232 | 74.339 | 6.871 | 1.00 | 42.98 |
| ATOM | 2021 | N | SER | A | 364 | −0.543 | 73.664 | 7.232 | 1.00 | 41.94 |
| ATOM | 2022 | CA | SER | A | 364 | −0.884 | 74.125 | 8.574 | 1.00 | 44.68 |
| ATOM | 2023 | C | SER | A | 364 | 0.274 | 74.720 | 9.373 | 1.00 | 44.51 |
| ATOM | 2024 | O | SER | A | 364 | 0.154 | 75.820 | 9.905 | 1.00 | 44.42 |
| ATOM | 2025 | CB | SER | A | 364 | −1.530 | 72.993 | 9.370 | 1.00 | 42.64 |
| ATOM | 2026 | OG | SER | A | 364 | −2.297 | 73.521 | 10.428 | 1.00 | 42.96 |
| ATOM | 2027 | N | ASP | A | 365 | 1.393 | 74.006 | 9.473 | 1.00 | 46.88 |
| ATOM | 2028 | CA | ASP | A | 365 | 2.525 | 74.547 | 10.220 | 1.00 | 51.48 |
| ATOM | 2029 | C | ASP | A | 365 | 3.240 | 75.596 | 9.387 | 1.00 | 53.14 |
| ATOM | 2030 | O | ASP | A | 365 | 4.372 | 75.980 | 9.678 | 1.00 | 53.14 |
| ATOM | 2031 | CB | ASP | A | 365 | 3.513 | 73.444 | 10.638 | 1.00 | 51.70 |
| ATOM | 2032 | CG | ASP | A | 365 | 3.935 | 72.566 | 9.490 | 1.00 | 50.62 |
| ATOM | 2033 | OD1 | ASP | A | 365 | 3.307 | 72.658 | 8.416 | 1.00 | 52.17 |
| ATOM | 2034 | OD2 | ASP | A | 365 | 4.893 | 71.780 | 9.664 | 1.00 | 46.70 |
| ATOM | 2035 | N | ALA | A | 366 | 2.560 | 76.051 | 8.343 | 1.00 | 56.72 |
| ATOM | 2036 | CA | ALA | A | 366 | 3.083 | 77.074 | 7.458 | 1.00 | 57.10 |
| ATOM | 2037 | C | ALA | A | 366 | 2.042 | 78.179 | 7.412 | 1.00 | 59.35 |
| ATOM | 2038 | O | ALA | A | 366 | 1.864 | 78.832 | 6.389 | 1.00 | 63.04 |
| ATOM | 2039 | CB | ALA | A | 366 | 3.308 | 76.503 | 6.072 | 1.00 | 55.61 |
| ATOM | 2040 | N | GLU | A | 367 | 1.348 | 78.378 | 8.527 | 1.00 | 60.82 |
| ATOM | 2041 | CA | GLU | A | 367 | 0.314 | 79.399 | 8.609 | 1.00 | 61.72 |
| ATOM | 2042 | C | GLU | A | 367 | 0.671 | 80.477 | 9.627 | 1.00 | 62.67 |
| ATOM | 2043 | O | GLU | A | 367 | 1.685 | 80.373 | 10.312 | 1.00 | 61.46 |
| ATOM | 2044 | CB | GLU | A | 367 | −1.027 | 78.751 | 8.961 | 1.00 | 64.20 |
| ATOM | 2045 | CG | GLU | A | 367 | −1.915 | 78.474 | 7.750 | 1.00 | 69.00 |
| ATOM | 2046 | CD | GLU | A | 367 | −2.928 | 77.354 | 7.984 | 1.00 | 73.74 |
| ATOM | 2047 | OE1 | GLU | A | 367 | −3.008 | 76.826 | 9.116 | 1.00 | 76.77 |

TABLE 1-continued

Structural Coordinate of MEK1/N35/NKF (corresponding to amino acids 24, 383 of SEQ ID NO: 1) -compound 1-ATPγS Ternary Complex.

| | A | B | C | D | E | F | G | H | I | J |
|---|---|---|---|---|---|---|---|---|---|---|
| ATOM | 2048 | OE2 | GLU | A | 367 | −3.647 | 77.002 | 7.024 | 1.00 | 75.15 |
| ATOM | 2049 | N | GLU | A | 368 | −0.176 | 81.502 | 9.722 | 1.00 | 9.722 |
| ATOM | 2050 | CA | GLU | A | 368 | 0.035 | 82.633 | 10.626 | 1.00 | 67.48 |
| ATOM | 2051 | C | GLU | A | 368 | −0.467 | 82.454 | 12.067 | 1.00 | 69.16 |
| ATOM | 2052 | O | GLU | A | 368 | 0.331 | 82.158 | 12.960 | 1.00 | 70.91 |
| ATOM | 2053 | CB | GLU | A | 368 | −0.594 | 83.899 | 10.020 | 1.00 | 71.00 |
| ATOM | 2054 | CG | GLU | A | 368 | 0.343 | 84.694 | 9.093 | 1.00 | 75.97 |
| ATOM | 2055 | CD | GLU | A | 368 | −0.373 | 85.335 | 7.895 | 1.00 | 76.77 |
| ATOM | 2056 | OE1 | GLU | A | 368 | 0.215 | 85.357 | 6.786 | 1.00 | 76.77 |
| ATOM | 2057 | OE2 | GLU | A | 368 | −1.518 | 85.816 | 8.060 | 1.00 | 76.77 |
| ATOM | 2058 | N | VAL | A | 369 | −1.772 | 82.638 | 12.286 | 1.00 | 68.33 |
| ATOM | 2059 | CA | VAL | A | 369 | −2.422 | 82.532 | 13.615 | 1.00 | 66.88 |
| ATOM | 2060 | C | VAL | A | 369 | −1.519 | 82.311 | 14.830 | 1.00 | 64.85 |
| ATOM | 2061 | O | VAL | A | 369 | −0.774 | 81.333 | 14.894 | 1.00 | 63.15 |
| ATOM | 2062 | CB | VAL | A | 369 | −3.507 | 81.433 | 13.638 | 1.00 | 66.81 |
| ATOM | 2063 | CG1 | VAL | A | 369 | −4.656 | 81.816 | 12.706 | 1.00 | 66.26 |
| ATOM | 2064 | CG2 | VAL | A | 369 | −2.900 | 80.089 | 13.264 | 1.00 | 61.40 |
| ATOM | 2065 | N | ASP | A | 370 | −1.614 | 83.213 | 15.805 | 1.00 | 63.73 |
| ATOM | 2066 | CA | ASP | A | 370 | −0.783 | 83.134 | 17.008 | 1.00 | 66.12 |
| ATOM | 2067 | C | ASP | A | 370 | −1.274 | 82.117 | 18.030 | 1.00 | 64.72 |
| ATOM | 2068 | O | ASP | A | 370 | −0.530 | 81.720 | 18.939 | 1.00 | 66.39 |
| ATOM | 2069 | CB | ASP | A | 370 | −0.682 | 84.518 | 17.674 | 1.00 | 66.32 |
| ATOM | 2070 | CG | ASP | A | 370 | −1.942 | 84.901 | 18.430 | 1.00 | 67.73 |
| ATOM | 2071 | OD1 | ASP | A | 370 | −1.883 | 85.885 | 19.202 | 1.00 | 65.69 |
| ATOM | 2072 | OD2 | ASP | A | 370 | −2.985 | 84.229 | 13.253 | 1.00 | 68.04 |
| ATOM | 2073 | N | PHE | A | 371 | −2.520 | 81.690 | 17.864 | 1.00 | 59.14 |
| ATOM | 2074 | CA | PHE | A | 371 | −3.129 | 80.736 | 18.778 | 1.00 | 53.87 |
| ATOM | 2075 | C | PHE | A | 371 | −3.197 | 81.359 | 20.157 | 1.00 | 50.88 |
| ATOM | 2076 | O | PHE | A | 371 | −4.287 | 31.628 | 20.669 | 1.00 | 48.84 |
| ATOM | 2077 | CB | PHE | A | 371 | −2.321 | 79.443 | 18.861 | 1.00 | 48.42 |
| ATOM | 2078 | CG | PHE | A | 371 | −2.924 | 78.440 | 19.782 | 1.00 | 44.83 |
| ATOM | 2079 | CD1 | PHE | A | 371 | −2.420 | 78.266 | 21.063 | 1.00 | 45.11 |
| ATOM | 2080 | CD2 | PHE | A | 371 | −4.055 | 77.729 | 19.401 | 1.00 | 43.24 |
| ATOM | 2081 | CE1 | PHE | A | 371 | −3.041 | 77.400 | 21.961 | 1.00 | 43.17 |
| ATOM | 2082 | CE2 | PHE | A | 371 | −4.680 | 76.863 | 20.238 | 1.00 | 44.90 |
| ATOM | 2083 | CZ | PHE | A | 371 | −4.175 | 76.699 | 21.572 | 1.00 | 42.52 |
| ATOM | 2084 | N | ALA | A | 372 | −2.024 | 81.587 | 20.746 | 1.00 | 47.94 |
| ATOM | 2085 | CA | ALA | A | 372 | −1.905 | 82.192 | 22.059 | 1.00 | 45.39 |
| ATOM | 2086 | C | ALA | A | 372 | −2.929 | 83.307 | 22.250 | 1.00 | 45.44 |
| ATOM | 2087 | O | ALA | A | 372 | −3.486 | 83.484 | 23.332 | 1.00 | 47.00 |
| ATOM | 2088 | CB | ALA | A | 372 | −0.505 | 82.734 | 22.256 | 1.00 | 44.48 |
| ATOM | 2089 | N | GLY | A | 373 | −3.176 | 84.058 | 21.181 | 1.00 | 45.75 |
| ATOM | 2390 | CA | GLY | A | 373 | −4.136 | 85.141 | 21.249 | 1.00 | 44.66 |
| ATOM | 2091 | C | GLY | A | 373 | −5.567 | 84.645 | 21.228 | 1.00 | 46.58 |
| ATOM | 2092 | O | GLY | A | 373 | −6.381 | 85.029 | 22.074 | 1.00 | 46.98 |
| ATOM | 2093 | N | TRP | A | 374 | −5.876 | 83.783 | 20.261 | 1.00 | 46.70 |
| ATOM | 2094 | CA | TRP | A | 374 | −7.221 | 83.234 | 20.130 | 1.00 | 45.33 |
| ATOM | 2095 | C | TRP | A | 374 | −7.675 | 82.538 | 21.417 | 1.00 | 45.68 |
| ATOM | 2096 | O | TRP | A | 374 | −8.651 | 82.604 | 21.782 | 1.00 | 45.67 |
| ATOM | 2097 | CB | TRP | A | 374 | −7.281 | 82.255 | 18.954 | 1.00 | 41.02 |
| ATOM | 2098 | CG | TRP | A | 374 | −8.525 | 81.456 | 18.941 | 1.00 | 41.06 |
| ATOM | 2099 | CD1 | TRP | A | 374 | −9.706 | 81.790 | 18.354 | 1.00 | 39.92 |
| ATOM | 2100 | CD2 | TRP | A | 374 | −8.743 | 80.202 | 19.597 | 1.00 | 42.91 |
| ATOM | 2101 | NE1 | TRP | A | 374 | −10.651 | 80.828 | 18.606 | 1.00 | 38.27 |
| ATOM | 2102 | CE2 | TRP | A | 374 | −10.085 | 79.839 | 19.369 | 1.00 | 44.86 |
| ATOM | 2103 | CE3 | TRP | A | 374 | −7.931 | 79.348 | 20.361 | 1.00 | 40.55 |
| ATOM | 2104 | CZ2 | TRP | A | 374 | −10.639 | 78.655 | 19.879 | 1.00 | 42.33 |
| ATOM | 2105 | CZ3 | TRP | A | 374 | −8.481 | 78.174 | 20.867 | 1.00 | 39.52 |
| ATOM | 2106 | CH2 | TRP | A | 374 | −9.821 | 77.841 | 20.622 | 1.00 | 41.43 |
| ATOM | 2107 | N | LEU | A | 375 | −6.738 | 81.878 | 22.097 | 1.00 | 42.95 |
| ATOM | 2108 | CA | LEU | A | 375 | −7.036 | 81.174 | 23.341 | 1.00 | 41.42 |
| ATOM | 2109 | C | LEU | A | 375 | −7.601 | 82.156 | 24.356 | 1.00 | 44.84 |
| ATOM | 2110 | O | LEU | A | 375 | −8.787 | 82.117 | 24.676 | 1.00 | 46.61 |
| ATOM | 2111 | CB | LEU | A | 375 | −5.764 | 80.528 | 23.907 | 1.00 | 36.17 |
| ATOM | 2112 | CG | LEU | A | 375 | −5.817 | 79.160 | 24.593 | 1.00 | 29.33 |
| ATOM | 2113 | CD1 | LEU | A | 375 | −4.508 | 78.918 | 25.292 | 1.00 | 26.36 |
| ATOM | 2114 | CD2 | LEU | A | 375 | −6.945 | 79.093 | 25.586 | 1.00 | 27.64 |
| ATOM | 2115 | N | CYS | A | 376 | −6.743 | 83.044 | 24.851 | 1.00 | 47.62 |
| ATOM | 2116 | CA | CYS | A | 376 | −7.142 | 34.039 | 25.838 | 1.00 | 48.88 |
| ATOM | 2117 | C | CYS | A | 376 | −8.426 | 84.771 | 25.466 | 1.00 | 47.94 |
| ATOM | 2118 | O | CYS | A | 376 | −9.257 | 85.058 | 26.327 | 1.00 | 47.20 |
| ATOM | 2119 | CB | CYS | A | 376 | −6.005 | 85.024 | 26.044 | 1.00 | 50.29 |
| ATOM | 2120 | SG | CYS | A | 376 | −4.439 | 84.174 | 26.290 | 1.00 | 58.98 |
| ATOM | 2121 | N | SER | A | 377 | −8.594 | 85.073 | 24.187 | 1.00 | 47.38 |
| ATOM | 2122 | CA | SER | A | 377 | −9.809 | 85.739 | 23.743 | 1.00 | 49.18 |

TABLE 1-continued

Structural Coordinate of MEK1/N35/NKF (corresponding to amino acids 24, 383 of SEQ ID NO: 1) -compound 1-ATPγS Ternary Complex.

| | A | B | C | D | E | F | G | H | I | J |
|---|---|---|---|---|---|---|---|---|---|---|
| ATOM | 2123 | C | SER | A | 377 | −11.00 | 84.881 | 24.160 | 1.00 | 49.87 |
| ATOM | 2124 | O | SER | A | 377 | −11.903 | 85.345 | 24.854 | 1.00 | 51.63 |
| ATOM | 2125 | CB | SER | A | 377 | −9.812 | 85.883 | 22.223 | 1.00 | 49.86 |
| ATOM | 2126 | OG | SER | A | 377 | −9.123 | 87.047 | 21.816 | 1.00 | 52.08 |
| ATOM | 2127 | N | THR | A | 378 | −10.979 | 83.622 | 23.734 | 1.00 | 49.22 |
| ATOM | 2128 | CA | THR | A | 378 | −12.044 | 82.671 | 24.027 | 1.00 | 47.64 |
| ATOM | 2129 | C | THR | A | 378 | −12.031 | 82.179 | 25.472 | 1.00 | 49.13 |
| ATOM | 2130 | O | THR | A | 378 | −13.041 | 82.244 | 26.170 | 1.00 | 46.46 |
| ATOM | 2131 | CB | THR | A | 378 | −11.949 | 81.445 | 23.104 | 1.00 | 45.88 |
| ATOM | 2132 | OG1 | THR | A | 378 | −11.187 | 81.778 | 21.940 | 1.00 | 45.49 |
| ATOM | 2133 | CG2 | THR | A | 378 | −13.328 | 80.992 | 22.632 | 1.00 | 43.26 |
| ATOM | 2134 | N | ILE | A | 379 | −10.885 | 81.669 | 25.910 | 1.00 | 53.40 |
| ATOM | 2135 | CA | ILE | A | 379 | −10.727 | 81.157 | 27.270 | 1.00 | 56.16 |
| ATOM | 2136 | C | ILE | A | 379 | −10.876 | 82.288 | 28.236 | 1.00 | 59.83 |
| ATOM | 2137 | O | ILE | A | 379 | −11.090 | 82.049 | 29.472 | 1.00 | 62.28 |
| ATOM | 2138 | CB | ILE | A | 379 | −9.237 | 80.499 | 27.446 | 1.00 | 54.13 |
| ATOM | 2139 | CG1 | ILE | A | 379 | −9.228 | 79.818 | 28.803 | 1.00 | 50.70 |
| ATOM | 2140 | CG2 | ILE | A | 379 | −8.254 | 81.547 | 27.355 | 1.00 | 57.43 |
| ATOM | 2141 | CD1 | ILE | A | 379 | −7.831 | 79.309 | 29.103 | 1.00 | 49.28 |
| ATOM | 2142 | N | GLY | A | 380 | −10.766 | 83.525 | 27.808 | 1.00 | 62.15 |
| ATOM | 2143 | CA | GLY | A | 380 | −10.887 | 84.668 | 28.690 | 1.00 | 61.36 |
| ATOM | 2144 | C | CLY | A | 380 | −9.650 | 84.862 | 29.547 | 1.00 | 63.54 |
| ATOM | 2145 | O | GLY | A | 380 | −9.754 | 85.048 | 30.756 | 1.00 | 61.23 |
| ATOM | 2145 | N | LEU | A | 381 | −8.477 | 84.809 | 28.926 | 1.00 | 66.75 |
| ATOM | 2147 | CA | LEU | A | 381 | −7.224 | 84.991 | 29.652 | 1.30 | 69.61 |
| ATOM | 2148 | C | LEU | A | 381 | −6.675 | 66.389 | 29.378 | 1.00 | 72.24 |
| ATOM | 2149 | O | LEU | A | 381 | −5.508 | 86.682 | 29.648 | 1.00 | 71.50 |
| ATOM | 2150 | CB | LEU | A | 381 | −6.206 | 83.929 | 29.219 | 1.00 | 70.68 |
| ATOM | 2151 | CG | LEU | A | 381 | −6.216 | 82.609 | 29.997 | 1.00 | 70.44 |
| ATOM | 2152 | CD1 | LEU | A | 381 | −5.306 | 81.602 | 29.306 | 1.00 | 70.05 |
| ATOM | 2153 | CD2 | LEU | A | 381 | −5.762 | 82.851 | 31.431 | 1.00 | 68.57 |
| ATOM | 2154 | N | ASN | A | 382 | −7.539 | 87.249 | 28.843 | 1.00 | 75.49 |
| ATOM | 2155 | CA | ASN | A | 382 | −7.183 | 88.628 | 28.521 | 1.00 | 76.77 |
| ATOM | 2156 | CB | ASN | A | 382 | −7.275 | 88.851 | 27.005 | 1.00 | 75.92 |
| ATOM | 2157 | C | ASN | A | 382 | −8.099 | 89.609 | 29.262 | 1.00 | 76.77 |
| ATOM | 2158 | O | ASN | A | 382 | −8.574 | 89.260 | 30.366 | 1.00 | 75.18 |
| ATOM | 2159 | N | GLN | A | 383 | −8.328 | 90.720 | 28.727 | 1.00 | 76.77 |
| END | | | | | | | | | | |

In each of tables 1-4, the columns, marked A-J, indicate the following data:
A: atom number
B: atom identity
C: amino acid identity
D: polypeptide chain
E: MEK1 residue number
F: X coordinate
G: Y coordinate
H: Z coordinate
I: occupancy factor
J: temperature factor

TABLE 2

Structural Coordinate of MEK1/N35/NKFCdel(corresponding to amino acids 24-373 of SEQ ID NO: 2)-compound 1-ATPγS Ternary Complex.

| ATOM | 1 | N | GLU | A | 38 | 11.151 | 66.442 | 12.859 | 1.00 | 71.47 |
|---|---|---|---|---|---|---|---|---|---|---|
| ATOM | 2 | CA | GLU | A | 38 | 9.979 | 66.846 | 13.630 | 1.00 | 71.26 |
| ATOM | 3 | C | GLU | A | 38 | 10.272 | 66.918 | 15.126 | 1.00 | 74.81 |
| ATOM | 4 | O | GLU | A | 38 | 9.437 | 67.372 | 15.905 | 1.00 | 74.50 |
| ATOM | 5 | CB | GLU | A | 38 | 8.797 | 65.898 | 13.364 | 1.00 | 72.56 |
| ATOM | 6 | CG | GLU | A | 38 | 9.092 | 64.428 | 13.649 | 1.00 | 80.22 |
| ATOM | 7 | CD | GLU | A | 38 | 9.300 | 63.613 | 12.378 | 1.00 | 91.57 |
| ATOM | 8 | OE1 | GLU | A | 38 | 8.602 | 62.586 | 12.202 | 1.00 | 75.81 |
| ATOM | 9 | OE2 | GLU | A | 38 | 10.166 | 63.993 | 11.559 | 1.00 | 82.37 |
| ATOM | 10 | N | LEU | A | 39 | 11.465 | 66.477 | 15.521 | 1.00 | 71.20 |
| ATOM | 11 | CA | LEU | A | 39 | 11.858 | 66.495 | 16.929 | 1.00 | 70.68 |
| ATOM | 12 | C | LEU | A | 39 | 12.911 | 67.569 | 17.241 | 1.00 | 73.80 |
| ATOM | 13 | O | LEU | A | 39 | 13.365 | 67.693 | 18.382 | 1.00 | 72.92 |
| ATOM | 14 | CB | LEU | A | 39 | 12.318 | 65.108 | 17.392 | 1.00 | 70.67 |
| ATOM | 15 | CC | LEU | A | 39 | 11.204 | 64.052 | 17.541 | 1.00 | 75.24 |
| ATOM | 16 | CD1 | LEU | A | 39 | 11.738 | 62.721 | 18.044 | 1.00 | 75.17 |
| ATOM | 17 | CD2 | LEU | A | 39 | 10.075 | 64.548 | 18.439 | 1.00 | 77.96 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 18 | N | GLU | A | 40 | 13.272 | 68.359 | 16.227 | 1.00 | 70.35 |
|---|---|---|---|---|---|---|---|---|---|---|
| ATOM | 19 | CA | GLU | A | 40 | 14.228 | 69.455 | 16.404 | 1.00 | 69.93 |
| ATOM | 20 | C | GLU | A | 40 | 13.529 | 70.622 | 17.097 | 1.00 | 72.11 |
| ATOM | 21 | O | GLU | A | 40 | 12.436 | 71.023 | 16.701 | 1.00 | 71.83 |
| ATOM | 22 | CB | GLU | A | 40 | 14.775 | 69.926 | 15.057 | 1.00 | 71.49 |
| ATOM | 23 | CG | GLU | A | 40 | 15.051 | 68.827 | 14.059 | 1.00 | 83.83 |
| ATOM | 24 | CD | GLU | A | 40 | 15.611 | 69.367 | 12.753 | 1.00 | 107.19 |
| ATOM | 25 | OE1 | GLU | A | 40 | 15.046 | 70.349 | 12.224 | 1.00 | 104.41 |
| ATOM | 26 | OE2 | GLU | A | 40 | 16.632 | 68.829 | 12.272 | 1.00 | 101.92 |
| ATOM | 27 | N | LEU | A | 41 | 14.166 | 71.171 | 18.119 | 1.00 | 67.32 |
| ATOM | 28 | CA | LEU | A | 41 | 13.576 | 72.256 | 18.887 | 1.00 | 66.62 |
| ATOM | 29 | C | LEU | A | 41 | 13.832 | 73.646 | 18.328 | 1.00 | 69.24 |
| ATOM | 30 | O | LEU | A | 41 | 14.865 | 73.910 | 17.722 | 1.00 | 68.43 |
| ATOM | 31 | CB | LEU | A | 41 | 14.035 | 72.190 | 20.342 | 1.00 | 66.65 |
| ATOM | 32 | CG | LEU | A | 41 | 13.683 | 70.913 | 21.110 | 1.00 | 71.10 |
| ATOM | 33 | CD1 | LEU | A | 41 | 13.207 | 71.256 | 22.505 | 1.00 | 70.93 |
| ATOM | 34 | CD2 | LEU | A | 41 | 12.628 | 70.112 | 20.355 | 1.00 | 73.92 |
| ATOM | 35 | N | ASP | A | 42 | 12.884 | 74.538 | 18.572 | 1.00 | 65.54 |
| ATOM | 36 | CA | ASP | A | 42 | 13.002 | 75.927 | 18.171 | 1.00 | 65.17 |
| ATOM | 37 | C | ASP | A | 42 | 13.993 | 76.571 | 19.130 | 1.00 | 66.66 |
| ATOM | 38 | O | ASP | A | 42 | 14.371 | 75.966 | 20.134 | 1.00 | 66.35 |
| ATOM | 39 | CB | ASP | A | 42 | 11.643 | 76.613 | 18.331 | 1.00 | 67.35 |
| ATOM | 40 | CC | ASP | A | 42 | 11.496 | 77.821 | 17.463 | 1.00 | 80.52 |
| ATOM | 41 | OD1 | ASP | A | 42 | 10.378 | 76.044 | 16.953 | 1.00 | 81.98 |
| ATOM | 42 | OD2 | ASP | A | 42 | 12.483 | 78.583 | 17.333 | 1.00 | 88.08 |
| ATOM | 43 | N | GLU | A | 43 | 14.400 | 77.797 | 18.841 | 1.00 | 61.22 |
| ATOM | 44 | CA | GLU | A | 43 | 15.297 | 78.504 | 19.734 | 1.00 | 60.20 |
| ATOM | 45 | C | GLU | A | 43 | 14.512 | 76.834 | 20.997 | 1.00 | 61.29 |
| ATOM | 46 | O | GLU | A | 43 | 14.939 | 78.530 | 22.106 | 1.00 | 60.78 |
| ATOM | 47 | CB | GLU | A | 43 | 15.802 | 79.796 | 19.077 | 1.00 | 61.67 |
| ATOM | 48 | CG | GLU | A | 43 | 17.201 | 79.685 | 18.485 | 1.00 | 73.53 |
| ATOM | 49 | CD | GLU | A | 43 | 17.983 | 80.991 | 18.570 | 1.00 | 94.40 |
| ATOM | 50 | OE1 | GLU | A | 43 | 17.412 | 82.003 | 19.036 | 1.00 | 88.83 |
| ATOM | 51 | OE2 | GLU | A | 43 | 19.166 | 81.003 | 18.158 | 1.00 | 84.50 |
| ATOM | 52 | N | GLN | A | 44 | 13.338 | 79.418 | 20.804 | 1.00 | 56.05 |
| ATOM | 53 | CA | GLN | A | 44 | 12.456 | 79.783 | 21.900 | 1.00 | 55.32 |
| ATOM | 54 | C | GLN | A | 44 | 11.917 | 78.559 | 22.643 | 1.00 | 56.71 |
| ATOM | 55 | O | GLN | A | 44 | 11.570 | 78.645 | 23.821 | 1.00 | 56.32 |
| ATOM | 56 | CB | GLN | A | 44 | 11.304 | 80.646 | 21.379 | 1.00 | 56.67 |
| ATOM | 57 | CG | GLN | A | 44 | 10.175 | 80.842 | 22.365 | 1.00 | 67.37 |
| ATOM | 58 | CD | GLN | A | 44 | 8.844 | 81.063 | 21.680 | 1.00 | 80.20 |
| ATOM | 59 | OE1 | GLN | A | 44 | 8.362 | 80.205 | 20.940 | 1.00 | 75.96 |
| ATOM | 60 | NE2 | GLN | A | 44 | 8.247 | 82.226 | 21.907 | 1.00 | 69.26 |
| ATOM | 61 | N | GLN | A | 45 | 11.863 | 77.422 | 21.956 | 1.00 | 51.49 |
| ATOM | 62 | CA | GLN | A | 45 | 11.397 | 76.177 | 22.570 | 1.00 | 50.73 |
| ATOM | 63 | C | GLN | A | 45 | 12.516 | 75.582 | 23.424 | 1.00 | 55.52 |
| ATOM | 64 | O | GLN | A | 45 | 12.302 | 75.188 | 24.578 | 1.00 | 54.87 |
| ATOM | 65 | CD | GLN | A | 45 | 11.016 | 75.156 | 21.489 | 1.00 | 51.58 |
| ATOM | 66 | CG | GLN | A | 45 | 9.735 | 75.450 | 20.734 | 1.00 | 57.34 |
| ATOM | 67 | CD | GLN | A | 45 | 9.303 | 74.277 | 19.860 | 1.00 | 69.17 |
| ATOM | 68 | OE1 | GLN | A | 45 | 10.141 | 73.526 | 19.342 | 1.00 | 61.68 |
| ATOM | 69 | NE2 | GLN | A | 45 | 7.993 | 74.101 | 19.703 | 1.00 | 59.07 |
| ATOM | 70 | N | ARG | A | 46 | 13.701 | 75.476 | 22.824 | 1.00 | 52.52 |
| ATOM | 71 | CA | ARG | A | 46 | 14.865 | 74.920 | 23.494 | 1.00 | 52.19 |
| ATOM | 72 | C | ARG | A | 46 | 15.150 | 75.702 | 24.764 | 1.00 | 54.56 |
| ATOM | 73 | O | ARG | A | 46 | 15.510 | 75.133 | 25.788 | 1.00 | 53.31 |
| ATOM | 74 | CB | ARG | A | 46 | 16.078 | 74.976 | 22.561 | 1.00 | 53.75 |
| ATOM | 75 | CC | ARG | A | 46 | 17.149 | 73.956 | 22.878 | 1.00 | 67.01 |
| ATOM | 76 | CD | ARG | A | 46 | 18.506 | 74.621 | 23.082 | 1.00 | 82.90 |
| ATOM | 77 | NE | ARG | A | 46 | 18.793 | 74.864 | 24.493 | 1.00 | 94.74 |
| ATOM | 78 | CZ | ARG | A | 49 | 18.636 | 73.960 | 25.458 | 1.00 | 108.67 |
| ATOM | 79 | NH1 | ARG | A | 46 | 18.194 | 72.741 | 25.166 | 1.00 | 96.82 |
| ATOM | 80 | NH2 | ARG | A | 46 | 18.917 | 74.276 | 26.715 | 1.00 | 93.20 |
| ATOM | 81 | N | LYS | A | 47 | 14.942 | 77.009 | 24.691 | 1.00 | 51.41 |
| ATOM | 82 | CA | LYS | A | 47 | 15.164 | 77.890 | 25.820 | 1.00 | 51.49 |
| ATOM | 83 | C | LYS | A | 47 | 14.115 | 77.684 | 26.930 | 1.00 | 55.15 |
| ATOM | 84 | O | LYS | A | 47 | 14.453 | 77.634 | 28.117 | 1.00 | 54.30 |
| ATOM | 85 | CB | LYS | A | 47 | 15.169 | 79.345 | 25.357 | 1.00 | 54.27 |
| ATOM | 86 | CG | LYS | A | 47 | 14.263 | 80.252 | 26.146 | 1.00 | 70.16 |
| ATOM | 87 | CD | LYS | A | 47 | 13.868 | 81.474 | 25.307 | 1.00 | 82.24 |
| ATOM | 88 | CE | LYS | A | 47 | 15.125 | 82.291 | 24.927 | 1.00 | 94.63 |
| ATOM | 89 | NZ | LYS | A | 47 | 14.770 | 83.513 | 24.241 | 1.00 | 105.34 |
| ATOM | 90 | N | ARG | A | 48 | 12.849 | 77.562 | 26.531 | 1.00 | 51.89 |
| ATOM | 91 | CA | ARG | A | 48 | 11.758 | 77.340 | 27.473 | 1.00 | 51.48 |
| ATOM | 92 | C | ARG | A | 48 | 11.968 | 76.026 | 28.213 | 1.00 | 54.44 |
| ATOM | 93 | O | ARG | A | 48 | 11.679 | 75.920 | 29.405 | 1.00 | 53.22 |
| ATOM | 94 | CB | ARG | A | 48 | 10.417 | 77.289 | 26.736 | 1.00 | 52.21 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 95 | CG | ARG | A | 48 | 9.871 | 78.648 | 26.291 | 1.00 | 61.13 |
|---|---|---|---|---|---|---|---|---|---|---|
| ATOM | 96 | CD | ARG | A | 48 | 8.427 | 78.496 | 25.803 | 1.00 | 68.19 |
| ATOM | 97 | NE | ARG | A | 48 | 7.834 | 79.754 | 25.352 | 1.00 | 71.56 |
| ATOM | 98 | CZ | ARG | A | 48 | 7.064 | 79.870 | 24.272 | 1.00 | 78.89 |
| ATOM | 99 | NH1 | ARG | A | 48 | 6.816 | 78.813 | 23.511 | 1.00 | 61.26 |
| ATOM | 100 | NH2 | ARG | A | 48 | 6.552 | 81.044 | 23.946 | 1.00 | 64.80 |
| ATOM | 101 | N | LEU | A | 49 | 12.458 | 75.019 | 27.494 | 1.00 | 51.59 |
| ATOM | 102 | CA | LEU | A | 49 | 12.703 | 73.708 | 28.084 | 1.00 | 51.83 |
| ATOM | 103 | C | LEU | A | 49 | 13.874 | 73.774 | 29.056 | 1.00 | 56.66 |
| ATOM | 104 | O | LEU | A | 49 | 13.923 | 73.039 | 30.045 | 1.00 | 55.69 |
| ATOM | 105 | CB | LEU | A | 49 | 12.984 | 72.672 | 26.996 | 1.00 | 51.84 |
| ATOM | 106 | CG | LEU | A | 49 | 12.388 | 71.273 | 27.192 | 1.00 | 56.92 |
| ATOM | 107 | CD1 | LEU | A | 49 | 12.060 | 70.998 | 28.665 | 1.00 | 57.19 |
| ATOM | 108 | CD2 | LEU | A | 49 | 11.146 | 71.086 | 26.319 | 1.00 | 58.69 |
| ATOM | 109 | N | GLU | A | 50 | 14.828 | 74.648 | 28.750 | 1.00 | 53.99 |
| ATOM | 110 | CA | GLU | A | 50 | 16.008 | 74.820 | 29.584 | 1.00 | 53.94 |
| ATOM | 111 | C | GLU | A | 50 | 15.600 | 75.440 | 30.901 | 1.00 | 55.79 |
| ATOM | 112 | O | GLU | A | 50 | 16.088 | 75.052 | 31.959 | 1.00 | 55.15 |
| ATOM | 113 | CB | GLU | A | 50 | 17.038 | 75.711 | 28.873 | 1.00 | 55.44 |
| ATOM | 114 | CG | GLU | A | 50 | 18.385 | 75.802 | 29.599 | 1.00 | 69.06 |
| ATOM | 115 | CD | GLU | A | 50 | 19.471 | 76.430 | 28.731 | 1.00 | 94.86 |
| ATOM | 116 | OE1 | GLU | A | 50 | 19.291 | 76.505 | 27.498 | 1.00 | 89.67 |
| ATOM | 117 | OE2 | GLU | A | 50 | 20.511 | 76.849 | 29.294 | 1.00 | 91.35 |
| ATOM | 118 | N | ALA | A | 51 | 14.659 | 76.378 | 30.831 | 1.00 | 51.27 |
| ATOM | 119 | CA | ALA | A | 51 | 14.162 | 77.060 | 32.014 | 1.00 | 50.34 |
| ATOM | 120 | C | ALA | A | 51 | 13.363 | 76.131 | 32.933 | 1.00 | 52.94 |
| ATOM | 121 | O | ALA | A | 51 | 13.541 | 76.156 | 34.156 | 1.00 | 53.23 |
| ATOM | 122 | CB | ALA | A | 51 | 13.331 | 78.260 | 31.615 | 1.00 | 51.19 |
| ATOM | 123 | N | PHE | A | 52 | 12.491 | 75.304 | 32.350 | 1.00 | 46.97 |
| ATOM | 124 | CA | PHE | A | 52 | 11.691 | 74.383 | 33.154 | 1.00 | 45.85 |
| ATOM | 125 | C | PHE | A | 52 | 12.575 | 73.415 | 33.909 | 1.00 | 49.71 |
| ATOM | 126 | O | PHE | A | 52 | 12.297 | 73.072 | 35.055 | 1.00 | 49.15 |
| ATOM | 127 | CB | PHE | A | 52 | 10.664 | 73.602 | 32.305 | 1.00 | 46.55 |
| ATOM | 128 | CG | PHE | A | 52 | 9.900 | 72.559 | 33.091 | 1.00 | 46.83 |
| ATOM | 129 | CD1 | PHE | A | 52 | 8.785 | 72.913 | 33.845 | 1.00 | 48.58 |
| ATOM | 130 | CD2 | PHE | A | 52 | 10.334 | 71.241 | 33.126 | 1.00 | 48.60 |
| ATOM | 131 | CE1 | PHE | A | 52 | 8.102 | 71.967 | 34.591 | 1.00 | 49.11 |
| ATOM | 132 | CE2 | PHE | A | 52 | 9.645 | 70.282 | 33.865 | 1.00 | 50.89 |
| ATOM | 133 | CZ | PHE | A | 52 | 8.533 | 70.648 | 34.605 | 1.00 | 48.55 |
| ATOM | 134 | N | LEU | A | 53 | 13.630 | 72.961 | 33.252 | 1.00 | 47.11 |
| ATOM | 135 | CA | LEU | A | 53 | 14.563 | 72.021 | 33.871 | 1.00 | 47.57 |
| ATOM | 136 | C | LEU | A | 53 | 15.323 | 72.695 | 35.012 | 1.00 | 51.93 |
| ATOM | 137 | O | LEU | A | 53 | 15.353 | 72.194 | 36.132 | 1.00 | 51.14 |
| ATOM | 138 | CB | LEU | A | 53 | 15.530 | 71.474 | 32.825 | 1.00 | 47.70 |
| ATOM | 139 | CG | LEU | A | 53 | 14.863 | 70.618 | 31.745 | 1.00 | 52.34 |
| ATOM | 140 | CD1 | LEU | A | 53 | 15.838 | 70.308 | 30.608 | 1.00 | 52.65 |
| ATOM | 141 | CD2 | LEU | A | 53 | 14.322 | 69.334 | 32.362 | 1.00 | 53.88 |
| ATOM | 142 | N | THR | A | 54 | 15.886 | 73.863 | 34.723 | 1.00 | 49.89 |
| ATOM | 143 | CA | THR | A | 54 | 16.624 | 74.637 | 35.707 | 1.00 | 50.39 |
| ATOM | 144 | C | THR | A | 54 | 15.797 | 74.854 | 36.973 | 1.00 | 55.48 |
| ATOM | 145 | O | THR | A | 54 | 16.302 | 74.688 | 38.085 | 1.00 | 55.34 |
| ATOM | 146 | CB | THR | A | 54 | 17.057 | 75.991 | 35.130 | 1.00 | 58.56 |
| ATOM | 147 | OG1 | THR | A | 54 | 17.811 | 75.775 | 33.928 | 1.00 | 58.22 |
| ATOM | 148 | CG2 | THR | A | 54 | 17.912 | 76.759 | 36.134 | 1.00 | 57.48 |
| ATOM | 149 | N | GLN | A | 55 | 14.525 | 75.222 | 36.805 | 1.00 | 52.17 |
| ATOM | 150 | CA | GLN | A | 55 | 13.638 | 75.415 | 37.951 | 1.00 | 52.08 |
| ATOM | 151 | C | GLN | A | 55 | 13.452 | 74.068 | 38.620 | 1.00 | 56.67 |
| ATOM | 152 | O | GLN | A | 55 | 13.582 | 73.938 | 39.836 | 1.00 | 56.46 |
| ATOM | 153 | CB | GLN | A | 55 | 12.270 | 75.953 | 37.511 | 1.00 | 53.44 |
| ATOM | 154 | CG | GLN | A | 55 | 12.286 | 77.361 | 36.943 | 1.00 | 67.64 |
| ATOM | 155 | CD | GLN | A | 55 | 10.879 | 77.919 | 36.725 | 1.00 | 87.49 |
| ATOM | 156 | OE1 | GLN | A | 55 | 10.073 | 77.348 | 35.976 | 1.00 | 79.95 |
| ATOM | 157 | NE2 | GLN | A | 53 | 10.572 | 79.031 | 37.398 | 1.00 | 79.82 |
| ATOM | 158 | N | LYS | A | 56 | 13.164 | 73.060 | 37.806 | 1.00 | 53.32 |
| ATOM | 159 | CA | LYS | A | 56 | 12.960 | 71.706 | 38.291 | 1.00 | 33.07 |
| ATOM | 160 | C | LYS | A | 56 | 14.093 | 71.268 | 39.215 | 1.00 | 56.76 |
| ATOM | 161 | O | LYS | A | 56 | 13.860 | 70.660 | 40.250 | 1.00 | 56.30 |
| ATOM | 162 | CB | LYS | A | 56 | 12.849 | 70.737 | 37.109 | 1.00 | 55.01 |
| ATOM | 163 | CG | LYS | A | 56 | 12.519 | 69.314 | 37.507 | 1.00 | 60.46 |
| ATOM | 164 | CD | LYS | A | 56 | 12.046 | 68.505 | 36.309 | 1.00 | 65.81 |
| ATOM | 165 | CE | LYS | A | 56 | 11.570 | 67.123 | 36.732 | 1.00 | 70.78 |
| ATOM | 166 | NZ | LYS | A | 56 | 10.773 | 66.467 | 35.659 | 1.00 | 76.04 |
| ATOM | 167 | N | GLN | A | 57 | 15.317 | 71.583 | 38.825 | 1.00 | 54.16 |
| ATOM | 168 | CA | GLN | A | 57 | 16.498 | 71.192 | 39.589 | 1.00 | 54.49 |
| ATOM | 169 | C | GLN | A | 57 | 16.493 | 71.690 | 41.033 | 1.00 | 58.36 |
| ATOM | 170 | O | GLN | A | 57 | 17.030 | 71.039 | 41.919 | 1.00 | 58.16 |
| ATOM | 171 | CB | GLN | A | 57 | 17.763 | 71.665 | 38.880 | 1.00 | 55.99 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 172 | CG | GLN | A | 57 | 18.891 | 70.659 | 38.889 | 1.00 | 72.53 |
|---|---|---|---|---|---|---|---|---|---|---|
| ATOM | 173 | CD | GLN | A | 57 | 20.110 | 71.157 | 38.135 | 1.00 | 94.24 |
| ATOM | 174 | OE1 | GLN | A | 57 | 20.041 | 72.161 | 37.417 | 1.00 | 87.23 |
| ATOM | 175 | NE2 | GLN | A | 57 | 21.238 | 70.467 | 38.303 | 1.00 | 88.51 |
| ATOM | 176 | N | LYS | A | 58 | 15.898 | 72.853 | 41.259 | 1.00 | 54.90 |
| ATOM | 177 | CA | LYS | A | 58 | 15.862 | 73.439 | 42.594 | 1.00 | 54.65 |
| ATOM | 178 | C | LYS | A | 58 | 14.871 | 72.750 | 43.532 | 1.00 | 59.30 |
| ATOM | 179 | O | LYS | A | 58 | 14.981 | 72.856 | 44.759 | 1.00 | 58.24 |
| ATOM | 180 | CB | LYS | A | 58 | 15.554 | 74.932 | 42.507 | 1.00 | 56.49 |
| ATOM | 181 | CG | LYS | A | 58 | 16.509 | 75.704 | 41.602 | 1.00 | 60.63 |
| ATOM | 192 | CD | LYS | A | 58 | 15.996 | 77.120 | 41.343 | 1.00 | 64.90 |
| ATOM | 183 | CE | LYS | A | 58 | 16.982 | 77.922 | 40.505 | 1.00 | 69.91 |
| ATOM | 184 | NZ | LYS | A | 58 | 16.847 | 79.391 | 40.724 | 1.00 | 72.05 |
| ATOM | 185 | N | VAL | A | 59 | 13.907 | 72.045 | 42.950 | 1.00 | 57.03 |
| ATOM | 186 | CA | VAL | A | 59 | 12.903 | 71.326 | 43.732 | 1.00 | 57.20 |
| ATOM | 187 | C | VAL | A | 59 | 13.519 | 70.062 | 44.326 | 1.00 | 62.57 |
| ATOM | 188 | O | VAL | A | 59 | 14.247 | 69.331 | 43.646 | 1.00 | 62.63 |
| ATOM | 189 | CB | VAL | A | 59 | 11.670 | 70.942 | 42.853 | 1.00 | 60.88 |
| ATOM | 190 | CG1 | VAL | A | 59 | 10.546 | 70.371 | 43.712 | 1.00 | 60.57 |
| ATOM | 191 | CG2 | VAL | A | 59 | 11.176 | 72.148 | 42.066 | 1.00 | 60.75 |
| ATOM | 192 | N | GLY | A | 60 | 13.260 | 69.819 | 45.598 | 1.00 | 59.49 |
| ATOM | 193 | CA | GLY | A | 60 | 13.813 | 68.642 | 46.249 | 1.00 | 59.85 |
| ATOM | 194 | C | GLY | A | 60 | 12.864 | 67.478 | 46.072 | 1.00 | 64.54 |
| ATOM | 195 | O | GLY | A | 60 | 12.342 | 67.255 | 44.982 | 1.00 | 64.49 |
| ATOM | 196 | N | GLU | A | 61 | 12.627 | 66.747 | 47.154 | 1.00 | 61.48 |
| ATOM | 197 | CA | GLU | A | 61 | 11.695 | 65.632 | 47.133 | 1.00 | 61.14 |
| ATOM | 198 | C | GLU | A | 61 | 10.316 | 66.159 | 47.522 | 1.00 | 64.20 |
| ATOM | 199 | O | GLU | A | 61 | 10.192 | 66.959 | 48.446 | 1.00 | 63.59 |
| ATOM | 200 | CB | GLU | A | 61 | 12.142 | 64.546 | 48.107 | 1.00 | 62.63 |
| ATOM | 201 | CG | GLU | A | 61 | 11.822 | 63.136 | 47.647 | 1.00 | 73.54 |
| ATOM | 202 | CD | GLU | A | 61 | 13.073 | 62.302 | 47.425 | 1.00 | 92.51 |
| ATOM | 203 | OE1 | GLU | A | 61 | 14.180 | 62.885 | 47.394 | 1.00 | 90.34 |
| ATOM | 204 | OE2 | GLU | A | 61 | 12.951 | 61.054 | 47.283 | 1.00 | 80.04 |
| ATOM | 205 | N | LEU | A | 62 | 9.291 | 65.742 | 46.786 | 1.00 | 60.20 |
| ATOM | 206 | CA | LEU | A | 62 | 7.926 | 66.206 | 47.032 | 1.00 | 59.49 |
| ATOM | 207 | C | LEU | A | 62 | 7.334 | 65.589 | 48.290 | 1.00 | 62.74 |
| ATOM | 208 | O | LEU | A | 52 | 7.367 | 64.380 | 48.469 | 1.00 | 62.60 |
| ATOM | 209 | CB | LEU | A | 62 | 7.026 | 65.920 | 45.816 | 1.00 | 59.26 |
| ATOM | 210 | CG | LEU | A | 62 | 6.903 | 67.036 | 44.764 | 1.00 | 63.47 |
| ATOM | 211 | CD1 | LEU | A | 62 | 8.118 | 57.946 | 44.750 | 1.00 | 63.22 |
| ATOM | 212 | CD2 | LEU | A | 62 | 6.642 | 66.467 | 43.381 | 1.00 | 65.13 |
| ATOM | 213 | N | LYS | A | 63 | 6.796 | 66.439 | 45.161 | 1.00 | 58.64 |
| ATOM | 214 | CA | LYS | A | 63 | 6.195 | 65.994 | 50.415 | 1.00 | 58.08 |
| ATOM | 215 | C | LYS | A | 63 | 4.797 | 66.581 | 50.525 | 1.00 | 60.41 |
| ATOM | 216 | O | LYS | A | 63 | 4.893 | 67.763 | 50.235 | 1.00 | 59.38 |
| ATOM | 217 | CB | LYS | A | 63 | 7.043 | 66.461 | 51.611 | 1.00 | 60.60 |
| ATOM | 218 | CG | LYS | A | 63 | 8.212 | 65.647 | 51.838 | 1.00 | 77.25 |
| ATOM | 219 | CD | LYS | A | 63 | 8.762 | 65.718 | 53.293 | 1.00 | 88.58 |
| ATOM | 220 | CE | LYS | A | 63 | 8.940 | 64.326 | 53.898 | 1.00 | 99.95 |
| ATOM | 221 | NZ | LYS | A | 63 | 8.928 | 64.351 | 55.392 | 1.00 | 109.42 |
| ATOM | 222 | N | ASP | A | 64 | 3.838 | 65.754 | 50.941 | 1.00 | 56.62 |
| ATOM | 223 | CA | ASP | A | 64 | 2.443 | 66.181 | 51.043 | 1.00 | 56.50 |
| ATOM | 224 | C | ASP | A | 64 | 2.251 | 67.535 | 51.720 | 1.00 | 59.47 |
| ATOM | 225 | O | ASP | A | 64 | 1.646 | 68.446 | 51.148 | 1.00 | 58.11 |
| ATOM | 226 | CB | ASP | A | 64 | 1.580 | 65.118 | 51.741 | 1.00 | 58.61 |
| ATOM | 227 | CG | ASP | A | 64 | 0.086 | 65.478 | 51.735 | 1.00 | 72.35 |
| ATOM | 228 | OD1 | ASP | A | 64 | −0.279 | 66.510 | 51.127 | 1.00 | 73.31 |
| ATOM | 229 | OD2 | ASP | A | 64 | −0.717 | 64.740 | 52.346 | 1.00 | 79.53 |
| ATOM | 230 | N | ASP | A | 65 | 2.731 | 67.651 | 52.952 | 1.00 | 55.71 |
| ATOM | 231 | CA | ASP | A | 65 | 2.558 | 68.874 | 53.718 | 1.00 | 55.14 |
| ATOM | 232 | C | ASP | A | 65 | 3.328 | 70.040 | 53.114 | 1.00 | 58.45 |
| ATOM | 233 | O | ASP | A | 65 | 3.276 | 71.154 | 53.616 | 1.00 | 58.17 |
| ATOM | 234 | CB | ASP | A | 65 | 2.931 | 68.645 | 55.185 | 1.00 | 57.00 |
| ATOM | 235 | CG | ASP | A | 65 | 2.642 | 67.226 | 55.638 | 1.00 | 67.37 |
| ATOM | 236 | OD1 | ASP | A | 65 | 1.450 | 66.863 | 55.771 | 1.00 | 67.17 |
| ATOM | 237 | OD2 | ASP | A | 65 | 3.605 | 66.443 | 55.775 | 1.00 | 76.33 |
| ATOM | 238 | N | ASP | A | 66 | 4.001 | 69.787 | 51.998 | 1.00 | 54.77 |
| ATOM | 239 | CA | ASP | A | 66 | 4.761 | 70.831 | 51.315 | 1.00 | 54.36 |
| ATOM | 240 | C | ASP | A | 66 | 3.879 | 71.638 | 50.362 | 1.00 | 55.88 |
| ATOM | 241 | O | ASP | A | 66 | 4.344 | 72.591 | 49.720 | 1.00 | 54.92 |
| ATOM | 242 | CB | ASP | A | 66 | 5.922 | 70.208 | 50.535 | 1.00 | 57.02 |
| ATOM | 243 | CG | ASP | A | 66 | 7.214 | 70.144 | 51.351 | 1.00 | 71.35 |
| ATOM | 244 | OD1 | ASP | A | 66 | 7.263 | 70.746 | 52.455 | 1.00 | 71.32 |
| ATOM | 245 | OD2 | ASP | A | 66 | 8.177 | 69.499 | 50.882 | 1.00 | 77.25 |
| ATOM | 246 | N | PHE | A | 67 | 2.607 | 71.261 | 50.276 | 1.00 | 51.34 |
| ATOM | 247 | CA | PHE | A | 67 | 1.678 | 71.904 | 49.343 | 1.00 | 50.36 |
| ATOM | 248 | C | PHE | A | 67 | 0.521 | 72.678 | 49.961 | 1.00 | 53.90 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 249 | O | PHE | A | 67 | −0.071 | 72.264 | 50.957 | 1.00 | 52.58 |
| --- | --- | --- | --- | --- | --- | --- | --- | --- | --- | --- |
| ATOM | 250 | CB | PHE | A | 67 | 1.109 | 70.871 | 48.369 | 1.00 | 51.39 |
| ATOM | 251 | CG | PHE | A | 67 | 2.139 | 70.239 | 47.492 | 1.00 | 52.36 |
| ATOM | 252 | CD1 | PHE | A | 67 | 2.639 | 70.916 | 46.392 | 1.00 | 54.62 |
| ATOM | 253 | CD2 | PHE | A | 67 | 2.610 | 68.963 | 47.762 | 1.00 | 54.03 |
| ATOM | 254 | CE1 | PHE | A | 67 | 3.595 | 70.338 | 45.592 | 1.00 | 55.20 |
| ATOM | 255 | CE2 | PHE | A | 67 | 3.562 | 68.382 | 46.956 | 1.00 | 56.28 |
| ATOM | 256 | CZ | PHE | A | 67 | 4.054 | 69.068 | 45.873 | 1.00 | 54.15 |
| ATOM | 257 | N | GLU | A | 68 | 0.161 | 73.762 | 49.290 | 1.00 | 50.93 |
| ATOM | 258 | CA | GLU | A | 68 | −0.989 | 74.568 | 49.645 | 1.00 | 51.27 |
| ATOM | 259 | C | GLU | A | 68 | −1.935 | 74.541 | 48.424 | 1.00 | 56.40 |
| ATOM | 260 | O | GLU | A | 68 | −1.540 | 74.911 | 47.321 | 1.00 | 56.15 |
| ATOM | 261 | CB | GLU | A | 68 | −0.554 | 76.007 | 49.925 | 1.00 | 52.56 |
| ATOM | 262 | CG | GLU | A | 68 | −1.521 | 76.793 | 50.775 | 1.00 | 65.06 |
| ATOM | 263 | CD | GLU | A | 68 | −1.350 | 78.295 | 50.616 | 1.00 | 92.76 |
| ATOM | 264 | OE1 | GLU | A | 68 | −0.287 | 78.729 | 50.111 | 1.00 | 83.73 |
| ATOM | 265 | OE2 | GLU | A | 68 | −2.283 | 79.040 | 50.991 | 1.00 | 91.17 |
| ATOM | 266 | N | LYS | A | 69 | −3.155 | 74.053 | 48.623 | 1.00 | 53.57 |
| ATOM | 267 | CA | LYS | A | 69 | −4.143 | 73.988 | 47.549 | 1.00 | 53.70 |
| ATOM | 268 | C | LYS | A | 69 | −4.631 | 75.394 | 47.193 | 1.00 | 57.76 |
| ATOM | 269 | O | LYS | A | 69 | −4.879 | 76.210 | 48.078 | 1.00 | 57.38 |
| ATOM | 270 | CB | LYS | A | 69 | −5.323 | 73.108 | 47.973 | 1.00 | 56.10 |
| ATOM | 271 | CG | LYS | A | 69 | −6.498 | 72.118 | 47.009 | 1.00 | 71.86 |
| ATOM | 272 | CD | LYS | A | 69 | −7.621 | 72.218 | 47.506 | 1.00 | 82.45 |
| ATOM | 273 | CE | LYS | A | 69 | −8.989 | 72.811 | 47.193 | 1.00 | 95.67 |
| ATOM | 274 | NZ | LYS | A | 69 | −10.094 | 72.020 | 47.816 | 1.00 | 104.79 |
| ATOM | 275 | N | ILE | A | 70 | −4.722 | 75.688 | 45.896 | 1.00 | 54.36 |
| ATOM | 276 | CA | ILE | A | 70 | −5.183 | 77.001 | 45.443 | 1.00 | 54.13 |
| ATOM | 277 | C | ILE | A | 70 | −6.599 | 76.921 | 44.880 | 1.00 | 58.49 |
| ATOM | 278 | O | ILE | A | 70 | −7.365 | 77.574 | 44.964 | 1.00 | 59.71 |
| ATOM | 279 | CB | ILE | A | 70 | −4.283 | 77.585 | 44.358 | 1.00 | 57.17 |
| ATOM | 280 | CG1 | ILE | A | 70 | −2.835 | 77.682 | 44.834 | 1.00 | 57.03 |
| ATOM | 281 | CG2 | ILE | A | 70 | −4.798 | 78.958 | 43.921 | 1.00 | 58.42 |
| ATOM | 282 | CD1 | ILE | A | 70 | −1.390 | 78.223 | 43.775 | 1.00 | 52.96 |
| ATOM | 283 | N | SER | A | 71 | −6.921 | 75.796 | 44.265 | 1.00 | 54.70 |
| ATOM | 284 | CA | SER | A | 71 | −8.244 | 75.603 | 43.678 | 1.00 | 54.05 |
| ATOM | 285 | C | SER | A | 71 | −8.312 | 74.282 | 42.943 | 1.00 | 57.67 |
| ATOM | 286 | O | SER | A | 71 | −7.286 | 73.676 | 42.640 | 1.00 | 57.37 |
| ATOM | 287 | CB | SER | A | 71 | −8.592 | 76.746 | 42.723 | 1.00 | 56.66 |
| ATOM | 288 | OG | SER | A | 71 | −7.465 | 77.159 | 41.973 | 1.00 | 62.55 |
| ATOM | 289 | N | GLU | A | 72 | −9.525 | 73.830 | 42.665 | 1.00 | 54.04 |
| ATOM | 290 | CA | GLU | A | 72 | −9.722 | 72.580 | 41.952 | 1.00 | 53.48 |
| ATOM | 291 | C | GLU | A | 72 | −9.705 | 72.831 | 40.448 | 1.00 | 55.39 |
| ATOM | 292 | O | GLU | A | 72 | −10.418 | 73.697 | 39.954 | 1.00 | 54.01 |
| ATOM | 293 | CB | GLU | A | 72 | −11.034 | 71.927 | 42.368 | 1.00 | 55.03 |
| ATOM | 294 | CG | GLU | A | 72 | −10.994 | 70.405 | 42.350 | 1.00 | 67.69 |
| ATOM | 295 | CD | GLU | A | 72 | −12.044 | 69.767 | 43.242 | 1.00 | 89.57 |
| ATOM | 296 | OE1 | GLU | A | 72 | −12.560 | 70.497 | 44.136 | 1.00 | 83.97 |
| ATOM | 297 | OE2 | GLU | A | 72 | −12.349 | 68.590 | 43.058 | 1.00 | 84.34 |
| ATOM | 298 | N | LEU | A | 73 | −8.858 | 72.095 | 39.732 | 1.00 | 51.15 |
| ATOM | 299 | CA | LEU | A | 73 | −6.751 | 72.254 | 38.279 | 1.00 | 50.83 |
| ATOM | 300 | C | LEU | A | 73 | −9.713 | 71.327 | 37.532 | 1.00 | 56.67 |
| ATOM | 301 | O | LEU | A | 73 | −9.931 | 71.489 | 36.334 | 1.00 | 56.84 |
| ATOM | 302 | CB | LEU | A | 73 | −7.315 | 72.016 | 37.804 | 1.00 | 50.19 |
| ATOM | 303 | CG | LEU | A | 73 | −6.271 | 73.035 | 38.282 | 1.00 | 53.78 |
| ATOM | 304 | CD1 | LEU | A | 73 | −4.869 | 72.559 | 37.969 | 1.00 | 52.96 |
| ATOM | 305 | CD2 | LEU | A | 73 | −6.535 | 74.401 | 37.664 | 1.00 | 56.11 |
| ATOM | 306 | N | GLY | A | 74 | −10.270 | 70.352 | 38.246 | 1.00 | 54.08 |
| ATOM | 307 | CA | GLY | A | 74 | −11.205 | 69.407 | 37.660 | 1.00 | 54.67 |
| ATOM | 308 | C | GLY | A | 74 | −11.002 | 68.012 | 38.235 | 1.00 | 61.20 |
| ATOM | 309 | O | GLY | A | 74 | −10.197 | 67.816 | 39.158 | 1.00 | 61.09 |
| ATOM | 310 | N | ALA | A | 75 | −11.716 | 67.040 | 37.678 | 1.00 | 59.00 |
| ATOM | 311 | CA | ALA | A | 75 | −11.612 | 65.663 | 38.139 | 1.00 | 59.55 |
| ATOM | 312 | C | ALA | A | 75 | −12.138 | 64.687 | 37.106 | 1.00 | 64.83 |
| ATOM | 313 | O | ALA | A | 75 | −13.017 | 65.012 | 36.319 | 1.00 | 64.68 |
| ATOM | 314 | CB | ALA | A | 75 | −12.356 | 65.487 | 39.456 | 1.00 | 60.31 |
| ATOM | 315 | N | GLY | A | 76 | −11.601 | 63.479 | 37.123 | 1.00 | 62.65 |
| ATOM | 316 | CA | GLY | A | 76 | −12.040 | 62.442 | 36.222 | 1.00 | 63.16 |
| ATOM | 317 | C | GLY | A | 76 | −12.873 | 61.455 | 37.020 | 1.00 | 69.19 |
| ATOM | 318 | O | GLY | A | 76 | −13.351 | 61.772 | 38.113 | 1.00 | 69.35 |
| ATOM | 319 | N | ASN | A | 77 | −13.019 | 60.250 | 36.492 | 1.00 | 66.29 |
| ATOM | 320 | CA | ASN | A | 77 | −13.799 | 59.222 | 37.154 | 1.00 | 66.48 |
| ATOM | 321 | C | ASN | A | 77 | −12.932 | 58.375 | 38.076 | 1.00 | 71.09 |
| ATOM | 322 | O | ASN | A | 77 | −12.958 | 57.141 | 38.019 | 1.00 | 71.21 |
| ATOM | 323 | CB | ASN | A | 77 | −14.506 | 58.351 | 36.117 | 1.00 | 67.89 |
| ATOM | 324 | CG | ASN | A | 77 | −15.378 | 59.167 | 35.174 | 1.00 | 93.31 |
| ATOM | 325 | OD1 | ASN | A | 77 | −15.236 | 59.087 | 33.955 | 1.00 | 89.21 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 326 | ND2 | ASN | A | 77 | −16.242 | 60.005 | 35.743 | 1.00 | 84.25 |
|---|---|---|---|---|---|---|---|---|---|---|
| ATOM | 327 | N | GLY | A | 78 | −12.172 | 59.045 | 38.935 | 1.00 | 67.17 |
| ATOM | 328 | CA | GLY | A | 78 | −13.301 | 58.356 | 39.878 | 1.00 | 66.51 |
| ATOM | 329 | C | GLY | A | 78 | −9.998 | 59.110 | 40.077 | 1.00 | 68.27 |
| ATOM | 330 | O | GLY | A | 78 | −8.957 | 58.510 | 40.343 | 1.00 | 68.07 |
| ATOM | 331 | N | GLY | A | 79 | −10.063 | 60.429 | 39.955 | 1.00 | 63.03 |
| ATOM | 332 | CA | GLY | A | 79 | −8.890 | 61.272 | 40.129 | 1.00 | 61.63 |
| ATOM | 333 | C | GLY | A | 79 | −9.273 | 62.745 | 40.120 | 1.00 | 62.16 |
| ATOM | 334 | O | GLY | A | 79 | −10.093 | 63.179 | 39.317 | 1.00 | 62.00 |
| ATOM | 335 | N | VAL | A | 80 | −8.682 | 53.507 | 41.031 | 1.00 | 55.63 |
| ATOM | 336 | CA | VAL | A | 80 | −8.953 | 64.933 | 41.113 | 1.00 | 53.59 |
| ATOM | 337 | C | VAL | A | 80 | −7.656 | 65.664 | 40.827 | 1.00 | 53.85 |
| ATOM | 338 | O | VAL | A | 80 | −6.569 | 65.113 | 41.026 | 1.00 | 53.30 |
| ATOM | 339 | CE | VAL | A | 80 | −9.449 | 65.328 | 42.512 | 1.00 | 57.25 |
| ATOM | 340 | CG1 | VAL | A | 80 | −9.959 | 66.756 | 42.523 | 1.00 | 56.77 |
| ATOM | 341 | CG2 | VAL | A | 80 | −10.515 | 64.350 | 42.983 | 1.90 | 57.19 |
| ATOM | 342 | N | VAL | A | 81 | −7.767 | 66.894 | 40.335 | 1.00 | 47.51 |
| ATOM | 343 | CA | VAL | A | 81 | −5.591 | 67.695 | 40.036 | 1.00 | 45.52 |
| ATOM | 344 | C | VAL | A | 81 | −6.717 | 69.072 | 40.651 | 1.00 | 46.51 |
| ATOM | 345 | O | VAL | A | 81 | −7.703 | 69.772 | 40.436 | 1.00 | 45.51 |
| ATOM | 346 | CB | VAL | A | 81 | −6.324 | 67.813 | 38.503 | 1.00 | 48.91 |
| ATOM | 347 | CG1 | VAL | A | 81 | −5.039 | 68.597 | 38.247 | 1.00 | 48.34 |
| ATOM | 348 | CO2 | VAL | A | 81 | −6.231 | 66.427 | 37.862 | 1.00 | 48.78 |
| ATOM | 349 | N | PHE | A | 82 | −5.709 | 69.455 | 41.425 | 1.00 | 42.84 |
| ATOM | 350 | CA | PHE | A | 82 | −5.698 | 70.760 | 42.078 | 1.00 | 41.96 |
| ATOM | 351 | C | PRE | A | 82 | −4.591 | 71.660 | 41.567 | 1.00 | 43.01 |
| ATOM | 352 | O | PHE | A | 82 | −3.503 | 71.205 | 41.253 | 1.00 | 42.62 |
| ATOM | 353 | CB | PHE | A | 82 | −5.537 | 70.595 | 43.601 | 1.00 | 43.97 |
| ATOM | 354 | CG | PHE | A | 82 | −6.756 | 70.043 | 44.284 | 1.00 | 45.99 |
| ATOM | 355 | CO1 | PHE | A | 82 | −6.951 | 68.678 | 44.380 | 1.00 | 49.15 |
| ATOM | 356 | OD2 | PHE | A | 82 | −7.715 | 70.894 | 44.822 | 1.00 | 48.15 |
| ATOM | 357 | OE1 | PHE | A | 82 | −8.080 | 68.166 | 45.006 | 1.00 | 50.14 |
| ATOM | 358 | CE2 | PHE | A | 82 | −8.851 | 70.387 | 45.439 | 1.00 | 50.93 |
| ATOM | 359 | CZ | PHE | A | 82 | −9.030 | 69.025 | 45.534 | 1.00 | 49.08 |
| ATOM | 360 | N | LYS | A | 83 | −4.856 | 72.950 | 41.544 | 1.00 | 38.85 |
| ATOM | 361 | CA | LYS | A | 83 | −3.820 | 73.918 | 41.245 | 1.00 | 39.03 |
| ATOM | 362 | C | LYS | A | 83 | −3.195 | 74.195 | 42.628 | 1.00 | 45.02 |
| ATOM | 363 | O | LYS | A | 83 | −3.878 | 74.683 | 43.533 | 1.00 | 45.41 |
| ATOM | 364 | CB | LYS | A | 83 | −4.424 | 75.204 | 40.685 | 1.00 | 40.16 |
| ATOM | 365 | CG | LYS | A | 83 | −3.394 | 76.283 | 40.388 | 1.00 | 44.84 |
| ATOM | 366 | CO | LYS | A | 83 | −4.064 | 77.598 | 40.050 | 1.00 | 51.85 |
| ATOM | 367 | CE | LYS | A | 83 | −3.058 | 78.613 | 39.555 | 1.00 | 56.51 |
| ATOM | 368 | NZ | LYS | A | 83 | −3.672 | 79.962 | 39.407 | 1.00 | 62.92 |
| ATOM | 369 | N | VAL | A | 84 | −1.938 | 73.795 | 42.813 | 1.00 | 41.30 |
| ATOM | 370 | CA | VAL | A | 84 | −1.272 | 73.933 | 44.115 | 1.00 | 40.08 |
| ATOM | 371 | C | VAL | A | 84 | −0.027 | 74.794 | 44.073 | 1.00 | 44.31 |
| ATOM | 372 | O | VAL | A | 84 | 0.614 | 74.954 | 43.028 | 1.00 | 43.05 |
| ATOM | 373 | CB | VAL | A | 84 | −0.816 | 72.554 | 44.660 | 1.00 | 42.76 |
| ATOM | 374 | CG1 | VAL | A | 84 | −1.998 | 71.643 | 44.900 | 1.00 | 42.17 |
| ATOM | 375 | CG2 | VAL | A | 84 | 0.180 | 71.916 | 43.703 | 1.00 | 42.22 |
| ATOM | 376 | N | SER | A | 85 | 0.359 | 75.285 | 45.242 | 1.00 | 41.89 |
| ATOM | 377 | CA | SER | A | 85 | 1.601 | 76.021 | 45.378 | 1.00 | 41.78 |
| ATOM | 378 | C | SER | A | 85 | 2.560 | 75.147 | 46.163 | 1.00 | 44.85 |
| ATOM | 379 | O | SER | A | 85 | 2.199 | 74.604 | 47.210 | 1.00 | 43.95 |
| ATOM | 380 | CB | SER | A | 85 | 1.384 | 77.332 | 46.141 | 1.00 | 45.56 |
| ATOM | 381 | OG | SER | A | 85 | 2.630 | 77.857 | 46.593 | 1.00 | 51.12 |
| ATOM | 382 | N | HIS | A | 86 | 3.764 | 74.967 | 45.640 | 1.00 | 41.50 |
| ATOM | 383 | CA | HIS | A | 86 | 4.775 | 74.218 | 46.365 | 1.00 | 41.09 |
| ATOM | 384 | C | HIS | A | 86 | 5.511 | 75.240 | 47.246 | 1.00 | 46.14 |
| ATOM | 385 | O | HIS | A | 86 | 6.361 | 76.001 | 46.767 | 1.00 | 45.93 |
| ATOM | 386 | CB | HIS | A | 86 | 5.748 | 73.532 | 45.421 | 1.00 | 41.60 |
| ATOM | 387 | CG | HIS | A | 86 | 6.683 | 72.596 | 46.115 | 1.00 | 44.78 |
| ATOM | 388 | ND1 | HIS | A | 86 | 8.039 | 72.830 | 46.205 | 1.00 | 46.56 |
| ATOM | 389 | CD2 | HIS | A | 86 | 6.446 | 71.470 | 46.827 | 1.00 | 46.13 |
| ATOM | 390 | CE1 | HIS | A | 86 | 8.601 | 71.865 | 45.909 | 1.00 | 45.95 |
| ATOM | 391 | NE2 | HIS | A | 66 | 7.658 | 71.023 | 47.292 | 1.00 | 46.31 |
| ATOM | 392 | N | LYS | A | 87 | 5.104 | 75.304 | 48.508 | 1.00 | 43.26 |
| ATOM | 393 | CA | LYS | A | 87 | 5.617 | 76.293 | 49.458 | 1.00 | 43.38 |
| ATOM | 394 | C | LYS | A | 87 | 7.106 | 76.589 | 49.400 | 1.00 | 48.21 |
| ATOM | 395 | O | LYS | A | 87 | 7.510 | 77.742 | 49.232 | 1.00 | 48.16 |
| ATOM | 396 | CB | LYS | A | 87 | 5.200 | 75.938 | 50.885 | 1.00 | 45.13 |
| ATOM | 397 | CG | LYS | A | 87 | 3.697 | 76.031 | 51.125 | 1.00 | 59.88 |
| ATOM | 398 | CD | LYS | A | 87 | 3.200 | 74.852 | 51.980 | 1.00 | 68.23 |
| ATOM | 399 | CE | LYS | A | 87 | 2.192 | 75.293 | 53.002 | 1.00 | 74.50 |
| ATOM | 400 | NZ | LYS | A | 87 | 1.531 | 74.125 | 53.651 | 1.00 | 83.18 |
| ATOM | 401 | N | PRO | A | 88 | 7.924 | 75.562 | 45.599 | 1.00 | 45.00 |
| ATOM | 402 | CA | PRO | A | 88 | 9.361 | 75.742 | 49.650 | 1.00 | 44.30 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 403 | C | PRO | A | 88 | 9.912 | 76.459 | 48.436 | 1.00 | 47.89 |
|---|---|---|---|---|---|---|---|---|---|---|
| ATOM | 404 | O | PRO | A | 88 | 10.538 | 77.519 | 48.556 | 1.00 | 47.01 |
| ATOM | 405 | CB | PRO | A | 88 | 9.883 | 74.313 | 49.709 | 1.00 | 45.59 |
| ATOM | 406 | CG | PRO | A | 88 | 8.508 | 73.571 | 50.406 | 1.00 | 49.92 |
| ATOM | 407 | CD | PRO | A | 88 | 7.529 | 74.184 | 49.955 | 1.00 | 45.51 |
| ATOM | 408 | N | SER | A | 89 | 9.700 | 75.859 | 47.269 | 1.00 | 44.44 |
| ATOM | 409 | CA | SER | A | 89 | 10.197 | 76.394 | 46.007 | 1.00 | 43.79 |
| ATOM | 410 | C | SER | A | 89 | 9.389 | 77.589 | 45.540 | 1.00 | 47.52 |
| ATOM | 411 | O | SER | A | 89 | 9.841 | 78.362 | 44.703 | 1.00 | 46.89 |
| ATOM | 412 | CB | SER | A | 89 | 10.134 | 75.300 | 44.931 | 1.00 | 47.67 |
| ATOM | 413 | OG | SER | A | 89 | 8.903 | 74.588 | 45.007 | 1.00 | 54.30 |
| ATOM | 414 | N | GLY | A | 90 | 8.158 | 77.699 | 46.031 | 1.00 | 45.42 |
| ATOM | 415 | CA | GLY | A | 90 | 7.271 | 78.785 | 45.604 | 1.00 | 45.56 |
| ATOM | 416 | C | GLY | A | 90 | 6.706 | 78.553 | 44.175 | 1.00 | 49.86 |
| ATOM | 417 | O | GLY | A | 90 | 6.058 | 79.434 | 43.604 | 1.00 | 49.21 |
| ATOM | 418 | N | LEU | A | 91 | 6.941 | 77.368 | 43.614 | 1.00 | 46.88 |
| ATOM | 419 | CA | LEU | A | 91 | 6.434 | 77.050 | 42.263 | 1.00 | 46.99 |
| ATOM | 420 | C | LEU | A | 91 | 4.968 | 76.601 | 42.305 | 1.00 | 49.83 |
| ATOM | 421 | O | LEU | A | 91 | 4.583 | 75.797 | 43.151 | 1.00 | 49.55 |
| ATOM | 422 | CB | LEU | A | 91 | 7.260 | 75.929 | 41.622 | 1.00 | 47.07 |
| ATOM | 423 | CG | LEU | A | 91 | 8.720 | 76.143 | 41.211 | 1.00 | 51.69 |
| ATOM | 424 | CD1 | LEU | A | 91 | 9.379 | 74.793 | 41.036 | 1.00 | 52.06 |
| ATOM | 425 | CD2 | LEU | A | 91 | 8.835 | 76.950 | 39.929 | 1.00 | 52.54 |
| ATOM | 426 | N | VAL | A | 92 | 4.163 | 77.100 | 41.375 | 1.00 | 46.00 |
| ATOM | 427 | CA | VAL | A | 92 | 2.777 | 76.667 | 41.271 | 1.00 | 45.49 |
| ATOM | 428 | C | VAL | A | 92 | 2.769 | 75.379 | 40.431 | 1.00 | 47.14 |
| ATOM | 429 | O | VAL | A | 92 | 3.499 | 75.267 | 39.468 | 1.00 | 45.80 |
| ATOM | 430 | CB | VAL | A | 92 | 1.884 | 77.739 | 40.600 | 1.00 | 49.66 |
| ATOM | 431 | CG1 | VAL | A | 92 | 0.539 | 77.139 | 40.168 | 1.00 | 49.31 |
| ATOM | 432 | CG2 | VAL | A | 92 | 1.657 | 78.894 | 41.549 | 1.00 | 49.79 |
| ATOM | 433 | N | MET | A | 93 | 1.989 | 74.390 | 40.858 | 1.00 | 42.77 |
| ATOM | 434 | CA | MET | A | 93 | 1.913 | 73.118 | 40.148 | 1.00 | 41.64 |
| ATOM | 435 | C | MET | A | 93 | 0.491 | 72.637 | 39.994 | 1.00 | 43.77 |
| ATOM | 436 | O | MET | A | 93 | −0.419 | 73.094 | 40.690 | 1.00 | 42.43 |
| ATOM | 437 | CB | MET | A | 93 | 2.687 | 72.035 | 40.902 | 1.00 | 43.58 |
| ATOM | 438 | CG | MET | A | 93 | 4.186 | 72.293 | 41.047 | 1.00 | 46.81 |
| ATOM | 439 | SD | MET | A | 93 | 4.908 | 71.048 | 42.112 | 1.00 | 50.38 |
| ATOM | 440 | CE | MET | A | 93 | 6.702 | 71.513 | 42.045 | 1.00 | 46.93 |
| ATOM | 441 | N | ALA | A | 94 | 0.330 | 71.639 | 39.132 | 1.00 | 40.18 |
| ATOM | 442 | CA | ALA | A | 94 | −0.934 | 70.962 | 38.952 | 1.00 | 40.22 |
| ATOM | 443 | C | ALA | A | 94 | −0.745 | 69.629 | 39.652 | 1.00 | 43.40 |
| ATOM | 444 | O | ALA | A | 94 | 0.131 | 68.849 | 39.280 | 1.00 | 42.72 |
| ATOM | 445 | CB | ALA | A | 94 | −1.216 | 70.738 | 37.440 | 1.00 | 41.03 |
| ATOM | 446 | N | ARG | A | 95 | −1.518 | 69.390 | 40.703 | 1.00 | 39.77 |
| ATOM | 447 | CA | ARG | A | 95 | −1.380 | 68.151 | 41.457 | 1.00 | 39.25 |
| ATOM | 448 | C | ARG | A | 95 | −2.572 | 67.234 | 41.283 | 1.00 | 44.29 |
| ATOM | 449 | O | ARG | A | 95 | −3.702 | 67.588 | 41.626 | 1.00 | 43.93 |
| ATOM | 450 | CB | ARG | A | 95 | −1.138 | 68.449 | 42.943 | 1.00 | 37.69 |
| ATOM | 451 | CG | ARG | A | 95 | −1.343 | 67.247 | 43.878 | 1.00 | 40.83 |
| ATOM | 452 | CD | ARG | A | 95 | −0.985 | 67.613 | 45.326 | 1.00 | 40.74 |
| ATOM | 453 | NE | ARG | A | 95 | −0.842 | 66.443 | 46.181 | 1.03 | 53.26 |
| ATOM | 454 | CZ | ARG | A | 95 | −0.855 | 66.479 | 47.515 | 1.00 | 66.15 |
| ATOM | 455 | NH1 | ARG | A | 95 | −1.013 | 67.630 | 48.153 | 1.00 | 52.85 |
| ATOM | 456 | NH2 | ARG | A | 95 | −0.708 | 65.366 | 48.212 | 1.00 | 51.47 |
| ATOM | 457 | N | LYS | A | 96 | −2.312 | 66.047 | 40.750 | 1.00 | 42.33 |
| ATOM | 458 | CA | LYS | A | 96 | −3.352 | 65.051 | 40.550 | 1.00 | 43.00 |
| ATOM | 459 | C | LYS | A | 96 | −3.264 | 63.967 | 41.627 | 1.00 | 49.05 |
| ATOM | 460 | O | LYS | A | 96 | −2.190 | 63.429 | 41.900 | 1.00 | 47.43 |
| ATOM | 461 | CH | LYS | A | 96 | −3.237 | 64.424 | 39.149 | 1.00 | 44.21 |
| ATOM | 462 | CC | LYS | A | 96 | −4.111 | 63.185 | 38.941 | 1.00 | 48.45 |
| ATOM | 463 | CD | LYS | A | 96 | −3.920 | 62.593 | 37.544 | 1.00 | 55.17 |
| ATOM | 464 | CE | LYS | A | 56 | −5.013 | 63.051 | 36.577 | 1.00 | 58.25 |
| ATOM | 465 | NE | LYS | A | 96 | −4.825 | 62.476 | 35.156 | 1.00 | 56.38 |
| ATOM | 466 | N | LEU | A | 97 | −4.406 | 63.641 | 42.220 | 1.00 | 49.53 |
| ATOM | 467 | CA | LEU | A | 97 | −4.460 | 62.634 | 43.268 | 1.00 | 50.80 |
| ATOM | 468 | C | LEU | A | 97 | −5.328 | 61.447 | 42.885 | 1.00 | 58.90 |
| ATOM | 469 | O | LEU | A | 97 | −6.495 | 61.607 | 42.555 | 1.00 | 57.90 |
| ATOM | 470 | CB | LEU | A | 97 | −4.981 | 63.251 | 44.566 | 1.00 | 50.71 |
| ATOM | 471 | CC | LEU | A | 97 | −4.239 | 64.486 | 45.069 | 1.00 | 55.32 |
| ATOM | 472 | CD1 | LEU | A | 97 | −5.041 | 65.757 | 44.778 | 1.00 | 54.76 |
| ATOM | 473 | CD2 | LEU | A | 97 | −3.952 | 64.348 | 46.562 | 1.00 | 58.25 |
| ATOM | 474 | N | ILE | A | 98 | −4.757 | 60.252 | 42.973 | 1.00 | 59.52 |
| ATOM | 475 | CA | ILE | A | 98 | −5.493 | 59.030 | 42.668 | 1.00 | 61.19 |
| ATOM | 476 | C | ILE | A | 98 | −5.511 | 58.119 | 43.903 | 1.00 | 69.28 |
| ATOM | 477 | O | ILE | A | 98 | −4.503 | 57.493 | 44.238 | 1.00 | 68.88 |
| ATOM | 478 | CB | ILE | A | 98 | −4.883 | 58.281 | 41.462 | 1.00 | 64.20 |
| ATOM | 479 | CG1 | ILE | A | 98 | −4.806 | 59.213 | 40.248 | 1.00 | 64.72 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 480 | CG2 | ILE | A | 98 | −5.711 | 57.051 | 41.122 | 1.00 | 64.58 |
|---|---|---|---|---|---|---|---|---|---|---|
| ATOM | 481 | CD1 | ILE | A | 98 | −3.476 | 59.173 | 39.528 | 1.00 | 71.59 |
| ATOM | 482 | N | HIS | A | 99 | −6.650 | 58.080 | 44.590 | 1.00 | 69.01 |
| ATOM | 483 | CA | HIS | A | 99 | −6.787 | 57.277 | 45.804 | 1.00 | 70.49 |
| ATOM | 484 | C | HIS | A | 99 | −6.705 | 55.771 | 45.543 | 1.00 | 76.02 |
| ATOM | 485 | O | HIS | A | 99 | −7.270 | 54.971 | 46.289 | 1.00 | 76.36 |
| ATOM | 486 | CB | HIS | A | 99 | −8.094 | 57.630 | 46.550 | 1.00 | 71.81 |
| ATOM | 487 | CG | HIS | A | 99 | −8.041 | 57.361 | 48.023 | 1.00 | 75.67 |
| ATOM | 488 | ND1 | HIS | A | 99 | −7.907 | 56.091 | 48.542 | 1.00 | 77.65 |
| ATOM | 489 | CD2 | HIS | A | 99 | −8.101 | 58.198 | 49.087 | 1.00 | 77.66 |
| ATOM | 490 | CE1 | HIS | A | 99 | −7.884 | 56.156 | 49.862 | 1.00 | 77.12 |
| ATOM | 491 | NE2 | HIS | A | 99 | −8.002 | 57.423 | 50.218 | 1.00 | 77.45 |
| ATOM | 492 | N | LEU | A | 100 | −5.971 | 55.392 | 44.502 | 1.00 | 72.85 |
| ATOM | 493 | CA | LEU | A | 100 | −5.801 | 53.987 | 44.153 | 1.00 | 72.65 |
| ATOM | 494 | C | ASN | A | 108 | 6.855 | 52.274 | 43.921 | 1.00 | 70.27 |
| ATOM | 495 | O | ASN | A | 108 | 7.989 | 52.154 | 43.446 | 1.00 | 69.82 |
| ATOM | 496 | N | GLN | A | 109 | 5.957 | 51.293 | 43.907 | 1.00 | 66.56 |
| ATOM | 497 | CA | GLN | A | 109 | 5.674 | 50.525 | 42.696 | 1.00 | 66.18 |
| ATOM | 498 | C | GLN | A | 109 | 5.426 | 51.450 | 41.502 | 1.00 | 69.26 |
| ATOM | 499 | O | GLN | A | 109 | 6.289 | 51.628 | 40.638 | 1.00 | 68.23 |
| ATOM | 500 | CS | GLN | A | 109 | 4.463 | 49.625 | 42.915 | 1.00 | 67.57 |
| ATOM | 501 | CC | GLN | A | 109 | 3.678 | 49.938 | 44.179 | 1.00 | 86.30 |
| ATOM | 502 | CD | GLN | A | 109 | 2.680 | 48.854 | 44.522 | 1.00 | 109.60 |
| ATOM | 503 | OE1 | GLN | A | 109 | 1.722 | 48.621 | 43.784 | 1.00 | 106.27 |
| ATOM | 504 | NE2 | GLN | A | 109 | 2.914 | 48.162 | 45.633 | 1.00 | 101.55 |
| ATOM | 505 | N | ILE | A | 110 | 4.235 | 52.029 | 41.453 | 1.00 | 65.59 |
| ATOM, | 505 | CA | ILE | A | 110 | 3.906 | 52.947 | 40.383 | 1.00 | 64.93 |
| ATOM | 507 | C | ILE | A | 110 | 4.901 | 54.105 | 40.428 | 1.00 | 67.50 |
| ATOM | 508 | O | ILE | A | 110 | 5.390 | 54.561 | 39.389 | 1.00 | 67.15 |
| ATOM | 509 | CB | ILE | A | 110 | 2.470 | 53.471 | 40.517 | 1.00 | 67.98 |
| ATOM | 510 | CG1 | ILE | A | 110 | 1.477 | 52.301 | 40.477 | 1.00 | 68.14 |
| ATOM | 511 | CG2 | ILE | A | 110 | 2.168 | 54.474 | 39.412 | 1.00 | 68.83 |
| ATOM | 512 | CD1 | ILE | A | 110 | 0.369 | 52.399 | 41.496 | 1.00 | 72.66 |
| ATOM | 513 | N | ILE | A | 111 | 5.249 | 54.529 | 41.643 | 1.00 | 52.88 |
| ATOM | 514 | CA | ILE | A | 111 | 6.216 | 55.607 | 41.840 | 1.00 | 61.96 |
| ATOM | 515 | C | ILE | A | 111 | 7.518 | 55.355 | 41.074 | 1.00 | 64.67 |
| ATOM | 516 | O | IDE | A | 111 | 8.056 | 56.258 | 40.439 | 1.00 | 64.37 |
| ATOM | 517 | CB | ILE | A | 111 | 6.527 | 55.828 | 43.339 | 1.00 | 64.66 |
| ATOM | 518 | CG1 | ILE | A | 111 | 5.241 | 56.105 | 44.111 | 1.00 | 64.94 |
| ATOM | 519 | CG2 | ILE | A | 111 | 7.491 | 56.981 | 43.521 | 1.00 | 64.83 |
| ATOM | 520 | CD1 | ILE | A | 111 | 4.080 | 56.511 | 42.236 | 1.00 | 71.45 |
| ATOM | 521 | N | ARG | A | 112 | 8.018 | 54.124 | 41.138 | 1.00 | 60.56 |
| ATOM | 522 | CA | ARG | A | 112 | 9.252 | 53.749 | 40.434 | 1.00 | 60.01 |
| ATOM | 523 | C | ARG | A | 112 | 9.075 | 53.932 | 38.918 | 1.00 | 61.95 |
| ATOM | 524 | O | ARG | A | 112 | 9.936 | 84.496 | 38.234 | 1.00 | 60.73 |
| ATOM | 525 | CB | ARG | A | 112 | 9.607 | 52.280 | 40.727 | 1.00 | 61.23 |
| ATOM | 526 | CG | ARG | A | 112 | 10.387 | 52.058 | 42.018 | 1.00 | 75.25 |
| ATOM | 527 | CD | ARG | A | 112 | 10.686 | 50.572 | 42.242 | 1.00 | 86.86 |
| ATOM | 828 | NE | ARG | A | 112 | 12.120 | 50.320 | 42.367 | 1.00 | 99.93 |
| ATOM | 529 | CZ | ARG | A | 112 | 12.772 | 49.362 | 41.711 | 1.00 | 117.35 |
| ATOM | 530 | NH1 | ARG | A | 112 | 12.115 | 48.556 | 40.886 | 1.00 | 106.81 |
| ATOM | 531 | NH2 | ARG | A | 112 | 14.079 | 49.204 | 41.885 | 1.00 | 103.98 |
| ATOM | 532 | N | GLU | A | 113 | 7.969 | 53.410 | 38.400 | 1.00 | 57.61 |
| ATOM | 533 | CA | GLU | A | 113 | 7.672 | 53.513 | 36.978 | 1.00 | 56.88 |
| ATOM | 534 | C | GLU | A | 113 | 7.501 | 54.985 | 36.571 | 1.00 | 58.03 |
| ATOM | 535 | O | GLU | A | 113 | 8.172 | 55.470 | 35.656 | 1.00 | 57.43 |
| ATOM | 536 | CB | GLU | A | 113 | 6.411 | 52.714 | 36.641 | 1.00 | 58.32 |
| ATOM | 537 | CG | GLU | A | 113 | 6.682 | 51.273 | 36.237 | 1.00 | 70.27 |
| ATOM | 538 | CD | GLU | A | 113 | 5.465 | 50.380 | 36.402 | 1.00 | 93.71 |
| ATOM | 539 | OE1 | GLU | A | 113 | 4.347 | 50.914 | 36.566 | 1.00 | 86.59 |
| ATOM | 540 | OE2 | GLU | A | 113 | 5.632 | 49.141 | 36.364 | 1.00 | 90.93 |
| ATOM | 541 | N | LEU | A | 114 | 6.623 | 55.691 | 37.282 | 1.00 | 52.34 |
| ATOM | 542 | CA | LEU | A | 114 | 6.354 | 57.105 | 37.008 | 1.00 | 50.90 |
| ATOM | 543 | C | LEU | A | 114 | 7.622 | 57.960 | 36.917 | 1.00 | 54.43 |
| ATOM | 544 | O | LEU | A | 114 | 7.622 | 59.029 | 36.290 | 1.00 | 54.17 |
| ATOM | 545 | CB | LEU | A | 114 | 5.416 | 57.677 | 38.064 | 1.00 | 50.31 |
| ATOM | 546 | CG | LEU | A | 114 | 4.021 | 57.066 | 38.100 | 1.00 | 54.45 |
| ATOM | 547 | CD1 | LEU | A | 114 | 3.421 | 57.197 | 39.485 | 1.00 | 54.77 |
| ATOM | 548 | CD2 | LEU | A | 114 | 3.123 | 57.711 | 37.043 | 1.00 | 55.40 |
| ATOM | 549 | N | GLN | A | 115 | 8.698 | 57.498 | 37.547 | 1.00 | 49.94 |
| ATOM | 550 | CA | GLN | A | 115 | 9.948 | 58.257 | 37.565 | 1.00 | 49.30 |
| ATOM | 551 | C | GLN | A | 115 | 10.522 | 58.502 | 36.177 | 1.00 | 52.16 |
| ATOM | 552 | O | GLN | A | 115 | 11.423 | 59.320 | 36.012 | 1.00 | 51.78 |
| ATOM | 553 | CB | GLN | A | 115 | 10.987 | 57.586 | 38.475 | 1.00 | 50.79 |
| ATOM | 554 | CG | GLN | A | 115 | 10.540 | 57.437 | 39.921 | 1.00 | 56.57 |
| ATOM | 555 | CD | GLN | A | 115 | 10.234 | 58.766 | 40.567 | 1.00 | 71.57 |
| ATOM | 556 | OE1 | GLN | A | 115 | 10.977 | 59.734 | 40.404 | 1.00 | 66.84 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 557 | NE2 | GLN | A | 115 | 9.128 | 58.827 | 41.303 | 1.00 | 61.16 |
|---|---|---|---|---|---|---|---|---|---|---|
| ATOM | 558 | N | VAL | A | 116 | 10.004 | 57.793 | 35.181 | 1.00 | 48.21 |
| ATOM | 559 | CA | VAL | A | 116 | 10.476 | 57.956 | 33.802 | 1.00 | 47.63 |
| ATOM | 560 | C | VAL | A | 116 | 10.082 | 59.314 | 33.199 | 1.00 | 49.84 |
| ATOM | 561 | O | VAL | A | 116 | 10.698 | 59.777 | 32.235 | 1.00 | 48.76 |
| ATOM | 562 | CB | VAL | A | 116 | 9.951 | 56.833 | 32.886 | 1.00 | 51.75 |
| ATOM | 563 | CG1 | VAL | A | 116 | 10.731 | 56.807 | 31.575 | 1.00 | 51.20 |
| ATOM | 564 | CG2 | VAL | A | 116 | 10.046 | 55.504 | 33.590 | 1.00 | 51.86 |
| ATOM | 565 | N | LEU | A | 117 | 9.065 | 59.943 | 33.789 | 1.00 | 45.80 |
| ATOM | 566 | CA | LEU | A | 117 | 8.572 | 61.244 | 33.335 | 1.00 | 45.18 |
| ATOM | 567 | C | LEU | A | 117 | 9.622 | 62.329 | 33.465 | 1.00 | 49.20 |
| ATOM | 568 | O | LEU | A | 117 | 9.517 | 63.379 | 32.835 | 1.00 | 47.79 |
| ATOM | 569 | CB | LEU | A | 117 | 7.303 | 61.640 | 34.107 | 1.00 | 44.76 |
| ATOM | 570 | CG | LEU | A | 117 | 6.098 | 60.718 | 33.909 | 1.00 | 48.47 |
| ATOM | 571 | CD1 | LEU | A | 117 | 5.042 | 60.979 | 34.954 | 1.00 | 47.90 |
| ATOM | 572 | CD2 | LEU | A | 117 | 5.529 | 60.888 | 32.495 | 1.00 | 49.89 |
| ATOM | 573 | N | HIS | A | 118 | 10.638 | 62.074 | 34.289 | 1.00 | 46.44 |
| ATOM | 574 | CA | HIS | A | 118 | 11.726 | 63.036 | 34.478 | 1.00 | 45.98 |
| ATOM | 575 | C | HIS | A | 118 | 12.575 | 63.069 | 33.219 | 1.00 | 50.81 |
| ATOM | 576 | O | HIS | A | 118 | 13.314 | 64.013 | 32.980 | 1.00 | 50.41 |
| ATOM | 577 | CB | HIS | A | 118 | 12.606 | 62.628 | 35.688 | 1.00 | 46.50 |
| ATOM | 578 | CG | HIS | A | 118 | 12.035 | 63.025 | 37.016 | 1.00 | 49.63 |
| ATOM | 579 | ND1 | HIS | A | 118 | 11.683 | 62.103 | 37.982 | 1.00 | 51.38 |
| ATOM | 580 | CD2 | HIS | A | 118 | 11.755 | 64.243 | 37.540 | 1.00 | 50.55 |
| ATOM | 581 | CE1 | HIS | A | 118 | 11.212 | 62.739 | 39.041 | 1.00 | 50.19 |
| ATOM | 582 | NE2 | HIS | A | 118 | 11.239 | 64.037 | 38.797 | 1.00 | 50.15 |
| ATOM | 583 | N | GLU | A | 119 | 12.447 | 62.025 | 32.407 | 1.00 | 48.36 |
| ATOM | 584 | CA | GLU | A | 119 | 13.203 | 61.917 | 31.164 | 1.00 | 48.39 |
| ATOM | 585 | C | GLU | A | 119 | 12.389 | 62.398 | 29.944 | 1.00 | 51.49 |
| ATOM | 586 | O | GLU | A | 119 | 12.929 | 62.552 | 28.848 | 1.00 | 51.08 |
| ATOM | 587 | CB | GLU | A | 119 | 13.668 | 60.471 | 30.961 | 1.00 | 49.86 |
| ATOM | 588 | CG | GLU | A | 119 | 14.284 | 59.848 | 32.210 | 1.00 | 63.13 |
| ATOM | 589 | CD | GLU | A | 119 | 14.625 | 58.370 | 32.033 | 1.00 | 90.64 |
| ATOM | 590 | OE1 | GLU | A | 119 | 14.308 | 57.737 | 30.963 | 1.00 | 87.20 |
| ATOM | 591 | OE2 | GLU | A | 119 | 15.227 | 57.785 | 32.961 | 1.00 | 86.97 |
| ATOM | 592 | N | CYS | A | 120 | 11.101 | 62.651 | 30.149 | 1.00 | 47.36 |
| ATOM | 593 | CA | CYS | A | 120 | 10.228 | 63.135 | 29.063 | 1.00 | 45.40 |
| ATOM | 594 | C | CYS | A | 120 | 10.259 | 64.632 | 28.980 | 1.00 | 49.30 |
| ATOM | 595 | O | CYS | A | 120 | 9.454 | 65.305 | 29.607 | 1.00 | 49.60 |
| ATOM | 596 | CB | CYS | A | 120 | 8.801 | 62.702 | 29.307 | 1.00 | 46.43 |
| ATOM | 597 | SG | CYS | A | 120 | 8.620 | 60.923 | 29.474 | 1.00 | 50.32 |
| ATOM | 598 | N | ASN | A | 121 | 11.175 | 65.158 | 28.189 | 1.00 | 44.91 |
| ATOM | 599 | CA | ASN | A | 121 | 11.330 | 66.597 | 28.058 | 1.00 | 43.99 |
| ATOM | 600 | C | ASN | A | 121 | 11.091 | 67.041 | 26.635 | 1.00 | 44.34 |
| ATOM | 601 | O | ASN | A | 121 | 11.904 | 66.810 | 25.759 | 1.00 | 43.55 |
| ATOM | 602 | CB | ASN | A | 121 | 12.716 | 67.017 | 28.542 | 1.00 | 47.26 |
| ATOM | 603 | CG | ASN | A | 121 | 13.039 | 66.452 | 29.918 | 1.00 | 75.03 |
| ATOM | 604 | OD1 | ASN | A | 121 | 12.450 | 66.865 | 30.919 | 1.00 | 70.43 |
| ATOM | 605 | ND2 | ASN | A | 121 | 13.871 | 65.414 | 29.953 | 1.00 | 66.55 |
| ATOM | 606 | N | SER | A | 122 | 9.931 | 67.636 | 26.409 | 1.00 | 39.22 |
| ATOM | 607 | CA | SER | A | 122 | 9.526 | 68.059 | 25.081 | 1.00 | 37.77 |
| ATOM | 608 | C | SER | A | 122 | 8.517 | 69.190 | 25.184 | 1.00 | 39.24 |
| ATOM | 609 | O | SER | A | 122 | 7.730 | 69.254 | 26.128 | 1.00 | 38.53 |
| ATOM | 610 | CB | SER | A | 122 | 8.899 | 66.873 | 24.331 | 1.00 | 41.01 |
| ATOM | 611 | OG | SER | A | 122 | 8.121 | 67.313 | 23.237 | 1.00 | 50.29 |
| ATOM | 612 | N | PRO | A | 123 | 8.529 | 70.076 | 24.201 | 1.00 | 34.82 |
| ATOM | 613 | CA | PRO | A | 123 | 7.587 | 71.190 | 24.183 | 1.00 | 33.77 |
| ATOM: | 614 | C | PRO | A | 123 | 6.155 | 70.688 | 23.988 | 1.00 | 35.43 |
| ATOM | 615 | O | PRO | A | 123 | 5.205 | 71.4.51 | 24.110 | 1.00 | 34.02 |
| ATOM | 616 | CB | PRO | A | 123 | 8.019 | 72.012 | 22.949 | 1.00 | 35.60 |
| ATOM | 617 | CG | PRO | A | 123 | 9.408 | 71.520 | 22.602 | 1.00 | 39.84 |
| ATOM | 618 | CD | PRO | A | 123 | 9.498 | 70.119 | 23.087 | 1.00 | 35.07 |
| ATOM | 619 | N | TYR | A | 124 | 6.017 | 69.408 | 23.644 | 1.00 | 32.12 |
| ATOM | 620 | CA | TYR | A | 124 | 4.705 | 68.824 | 23.374 | 1.00 | 31.85 |
| ATOM | 621 | C | TYR | A | 124 | 4.269 | 67.878 | 24.447 | 1.00 | 36.25 |
| ATOM | 622 | O | TYR | A | 124 | 3.272 | 67.170 | 24.297 | 1.00 | 36.29 |
| ATOM | 623 | CB | TYR | A | 124 | 4.688 | 68.133 | 22.003 | 1.00 | 32.15 |
| ATOM | 624 | CG | TYR | A | 124 | 5.236 | 69.017 | 20.918 | 1.00 | 32.54 |
| ATOM | 625 | CD1 | TYR | A | 124 | 4.561 | 70.154 | 20.526 | 1.00 | 34.26 |
| ATOM | 626 | CD2 | TYR | A | 124 | 6.502 | 68.789 | 20.383 | 1.00 | 33.13 |
| ATOM | 627 | CE1 | TYR | A | 124 | 5.089 | 70.999 | 19.581 | 1.00 | 34.96 |
| ATOM | 628 | CE2 | TYR | A | 124 | 7.027 | 69.617 | 19.439 | 1.00 | 33.49 |
| ATOM | 629 | CZ | TYR | A | 124 | 6.236 | 70.729 | 19.053 | 1.00 | 40.28 |
| ATOM | 630 | OH | TYR | A | 124 | 6.887 | 71.576 | 18.134 | 1.00 | 42.88 |
| ATOM | 631 | N | ILE | A | 125 | 4.996 | 67.889 | 25.558 | 1.00 | 32.51 |
| ATOM | 632 | CA | ILE | A | 125 | 4.678 | 67.025 | 26.695 | 1.00 | 31.51 |
| ATOM | 633 | C | ILE | A | 125 | 4.589 | 67.857 | 27.961 | 1.00 | 36.57 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 634 | O | ILE | A | 125 | 5.424 | 68.723 | 28.198 | 1.00 | 35.99 |
|------|-----|-----|-----|---|-----|-------|--------|--------|------|-------|
| ATOM | 635 | CB | ILE | A | 125 | 5.766 | 65.931 | 26.904 | 1.00 | 33.73 |
| ATOM | 636 | CG1 | ILE | A | 125 | 5.869 | 65.008 | 25.669 | 1.00 | 33.43 |
| ATOM | 637 | CG2 | ILE | A | 125 | 5.462 | 65.126 | 28.163 | 1.00 | 34.20 |
| ATOM | 638 | CD1 | ILE | A | 125 | 4.543 | 64.568 | 25.098 | 1.00 | 38.55 |
| ATOM | 639 | N | VAL | A | 126 | 3.549 | 67.620 | 28.753 | 1.00 | 34.41 |
| ATOM | 640 | CA | VAL | A | 126 | 3.351 | 68.366 | 29.994 | 1.00 | 34.70 |
| ATOM | 641 | C | VAL | A | 126 | 4.521 | 68.063 | 30.955 | 1.00 | 40.63 |
| ATOM | 642 | O | VAL | A | 126 | 4.842 | 66.897 | 31.195 | 1.00 | 40.30 |
| ATOM | 643 | CB | VAL | A | 126 | 2.011 | 67.950 | 30.684 | 1.00 | 38.08 |
| ATOM | 644 | CG1 | VAL | A | 126 | 2.003 | 68.345 | 32.143 | 1.00 | 37.40 |
| ATOM | 645 | CG2 | VAL | A | 126 | 0.798 | 68.538 | 29.938 | 1.00 | 37.85 |
| ATOM | 646 | N | GLY | A | 127 | 5.134 | 69.116 | 31.491 | 1.00 | 38.38 |
| ATOM | 647 | CA | GLY | A | 127 | 6.266 | 68.974 | 32.430 | 1.00 | 38.45 |
| ATOM | 648 | C | GLY | A | 127 | 5.898 | 68.243 | 33.722 | 1.00 | 42.49 |
| ATOM | 649 | O | GLY | A | 127 | 4.624 | 68.448 | 34.282 | 1.00 | 42.43 |
| ATOM | 650 | N | PHE | A | 128 | 6.826 | 67.418 | 34.203 | 1.00 | 39.12 |
| ATOM | 651 | CA | PHE | A | 128 | 6.636 | 66.606 | 35.408 | 1.00 | 39.01 |
| ATOM | 652 | C | PHE | A | 128 | 7.547 | 67.090 | 36.545 | 1.00 | 44.65 |
| ATOM | 653 | O | PHE | A | 128 | 8.745 | 67.302 | 36.349 | 1.00 | 44.02 |
| ATOM | 654 | CB | PHE | A | 128 | 6.557 | 65.136 | 35.058 | 1.00 | 40.69 |
| ATOM | 655 | CG | PHE | A | 128 | 6.955 | 64.194 | 36.229 | 1.00 | 42.19 |
| ATOM | 656 | CD1 | PHE | A | 128 | 5.780 | 63.877 | 36.883 | 1.00 | 45.30 |
| ATOM | 657 | CD2 | PHE | A | 128 | 8.123 | 63.524 | 36.594 | 1.00 | 44.63 |
| ATOM | 658 | CE1 | PHE | A | 128 | 5.775 | 62.969 | 37.930 | 1.00 | 46.36 |
| ATOM | 659 | CE2 | PHE | A | 128 | 8.126 | 62.616 | 37.631 | 1.00 | 47.55 |
| ATOM | 660 | CZ | PHE | A | 128 | 6.954 | 62.336 | 38.302 | 1.00 | 46.13 |
| ATOM | 661 | N | TYR | A | 129 | 6.984 | 67.230 | 37.739 | 1.00 | 42.34 |
| ATOM | 662 | CA | TYR | A | 129 | 7.773 | 67.642 | 38.897 | 1.00 | 42.42 |
| ATOM | 663 | C | TYR | A | 129 | 8.155 | 66.464 | 39.787 | 1.00 | 48.96 |
| ATOM | 664 | O | TYR | A | 129 | 9.295 | 66.367 | 40.244 | 1.00 | 49.29 |
| ATOM | 665 | CB | TYR | A | 129 | 7.053 | 68.719 | 39.692 | 1.00 | 42.35 |
| ATOM | 666 | CG | TYR | A | 129 | 7.217 | 70.061 | 39.069 | 1.00 | 42.74 |
| ATOM | 667 | CD1 | TYR | A | 129 | 8.476 | 70.590 | 38.875 | 1.00 | 44.30 |
| ATOM | 668 | CD2 | TYR | A | 129 | 6.122 | 70.758 | 38.572 | 1.00 | 43.13 |
| ATOM | 669 | OE1 | TYR | A | 129 | 6.650 | 71.798 | 38.267 | 1.00 | 44.97 |
| ATOM | 670 | CE2 | TYR | A | 129 | 6.286 | 71.976 | 37.970 | 1.00 | 44.18 |
| ATOM | 671 | CZ | TYR | A | 129 | 7.559 | 72.492 | 37.814 | 1.00 | 51.17 |
| ATOM | 672 | OH | TYR | A | 129 | 7.745 | 73.710 | 37.198 | 1.00 | 52.35 |
| ATOM | 673 | N | GLY | A | 130 | 7.217 | 65.549 | 40.003 | 1.00 | 46.04 |
| ATOM | 674 | CA | GLY | A | 130 | 7.497 | 64.381 | 40.830 | 1.00 | 46.08 |
| ATOM | 675 | C | GLY | A | 130 | 6.226 | 63.632 | 41.192 | 1.00 | 50.62 |
| ATOM | 676 | O | GLY | A | 130 | 5.120 | 64.072 | 40.87.6 | 1.00 | 49.50 |
| ATOM | 677 | N | ALA | A | 131 | 6.403 | 62.488 | 41.848 | 1.00 | 48.50 |
| ATOM | 678 | CA | ALA | A | 131 | 5.292 | 61.644 | 42.274 | 1.00 | 49.21 |
| ATOM | 679 | C | ALA | A | 131 | 5.595 | 61.028 | 43.643 | 1.00 | 55.41 |
| ATOM | 680 | O | ALA | A | 131 | 6.708 | 60.566 | 43.896 | 1.00 | 55.14 |
| ATOM | 681 | CB | ALA | A | 131 | 5.041 | 60.539 | 41.243 | 1.00 | 49.77 |
| ATOM | 682 | N | PHE | A | 132 | 4.596 | 61.010 | 44.512 | 1.00 | 53.35 |
| ATOM | 683 | CA | PHE | A | 132 | 4.758 | 60.439 | 45.837 | 1.00 | 53.84 |
| ATOM | 684 | C | PHE | A | 132 | 2.430 | 59.876 | 46.293 | 1.00 | 61.83 |
| ATOM | 685 | O | PHE | A | 132 | 2.381 | 60.201 | 45.728 | 1.00 | 61.53 |
| ATOM | 686 | CB | PHE | A | 132 | 5.257 | 61.501 | 46.829 | 1.00 | 54.84 |
| ATOM | 687 | CG | PHE | A | 132 | 4.371 | 62.709 | 46.918 | 1.00 | 55.48 |
| ATOM | 688 | CD1 | PHE | A | 132 | 4.552 | 63.782 | 46.064 | 1.00 | 57.76 |
| ATOM | 689 | CD2 | PHE | A | 132 | 3.340 | 62.762 | 47.841 | 1.00 | 57.07 |
| ATOM | 690 | CE1 | PHE | A | 132 | 3.734 | 64.885 | 46.138 | 1.00 | 58.13 |
| ATOM | 691 | CE2 | PHE | A | 132 | 2.526 | 63.871 | 47.922 | 1.00 | 59.31 |
| ATOM | 692 | CZ | PHE | A | 132 | 2.730 | 64.935 | 47.072 | 1.00 | 57.20 |
| ATOM | 693 | N | TYR | A | 133 | 3.476 | 59.017 | 47.305 | 1.00 | 60.80 |
| ATOM | 694 | CA | TYR | A | 133 | 2.267 | 58.398 | 47.830 | 1.00 | 61.84 |
| ATOM | 695 | C | TYR | A | 133 | 1.993 | 58.894 | 49.242 | 1.00 | 66.74 |
| ATOM | 696 | O | TYR | A | 133 | 2.922 | 59.190 | 49.996 | 1.00 | 66.21 |
| ATOM | 697 | CE | TYR | A | 133 | 2.413 | 56.876 | 47.819 | 1.00 | 63.68 |
| ATOM | 698 | CG | TYR | A | 133 | 1.175 | 56.121 | 48.237 | 1.00 | 66.33 |
| ATOM | 699 | CD1 | TYR | A | 133 | 0.685 | 56.208 | 49.536 | 1.00 | 68.60 |
| ATOM | 700 | CD2 | TYR | A | 133 | 0.527 | 55.274 | 47.346 | 1.00 | 67.43 |
| ATOM | 701 | CE1 | TYR | A | 133 | −0.432 | 55.479 | 49.927 | 1.00 | 70.23 |
| ATOM | 702 | CE2 | TYR | A | 133 | −0.585 | 54.550 | 47.720 | 1.00 | 68.45 |
| ATOM | 703 | CZ | TYR | A | 133 | −1.064 | 54.655 | 49.011 | 1.00 | 77.03 |
| ATOM | 704 | OH | TYR | A | 133 | −2.164 | 53.910 | 49.375 | 1.00 | 78.72 |
| ATOM | 705 | N | SER | A | 134 | 0.718 | 59.006 | 49.590 | 1.00 | 64.57 |
| ATOM | 706 | CA | SER | A | 134 | 0.328 | 59.500 | 50.899 | 1.00 | 65.24 |
| ATOM | 707 | C | SER | A | 134 | −1.179 | 59.456 | 51.054 | 1.00 | 71.77 |
| ATOM | 708 | O | SER | A | 134 | −1.914 | 59.538 | 50.071 | 1.00 | 72.09 |
| ATOM | 709 | CB | SER | A | 134 | 0.827 | 60.934 | 51.088 | 1.00 | 65.83 |
| ATOM | 710 | OG | SER | A | 134 | −0.059 | 61.674 | 51.908 | 1.00 | 79.12 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 711 | N | ASP | A | 135 | −1.643 | 59.331 | 52.294 | 1.00 | 69.39 |
|---|---|---|---|---|---|---|---|---|---|---|
| ATOM | 712 | CA | ASP | A | 135 | −3.073 | 59.281 | 52.565 | 1.00 | 69.55 |
| ATOM | 713 | C | ASP | A | 135 | −3.739 | 58.189 | 51.708 | 1.00 | 72.90 |
| ATOM | 714 | O | ASP | A | 135 | −4.942 | 58.232 | 51.431 | 1.00 | 72.74 |
| ATOM | 715 | CB | ASP | A | 135 | −3.709 | 60.653 | 52.300 | 1.00 | 71.83 |
| ATOM | 716 | CG | ASP | A | 135 | −5.178 | 60.702 | 52.682 | 1.00 | 86.76 |
| ATOM | 717 | OD1 | ASP | A | 135 | −5.480 | 60.947 | 53.875 | 1.00 | 88.12 |
| ATOM | 718 | OD2 | ASP | A | 135 | −6.030 | 60.451 | 51.794 | 1.00 | 93.17 |
| ATOM | 719 | N | GLY | A | 136 | −2.943 | 57.211 | 51.293 | 1.00 | 68.57 |
| ATOM | 720 | CA | GLY | A | 136 | −3.449 | 56.101 | 50.506 | 1.00 | 67.85 |
| ATOM | 721 | C | GLY | A | 136 | −3.645 | 56.463 | 49.038 | 1.00 | 70.79 |
| ATOM | 722 | O | GLY | A | 136 | −3.982 | 55.601 | 48.216 | 1.00 | 70.55 |
| ATOM | 723 | N | GLU | A | 137 | −3.434 | 57.734 | 48.706 | 1.00 | 65.62 |
| ATOM | 724 | CA | GLU | A | 137 | −3.610 | 58.195 | 47.336 | 1.00 | 64.27 |
| ATOM | 725 | C | GLU | A | 137 | −2.287 | 58.589 | 46.686 | 1.00 | 65.60 |
| ATOM | 726 | O | GLU | A | 137 | −1.418 | 59.186 | 47.329 | 1.00 | 65.58 |
| ATOM | 727 | CB | GLU | A | 137 | −4.604 | 59.360 | 47.283 | 1.00 | 65.51 |
| ATOM | 728 | CG | GLU | A | 137 | −4.348 | 60.440 | 48.310 | 1.00 | 74.65 |
| ATOM | 729 | CD | GLU | A | 137 | −5.433 | 61.490 | 48.320 | 1.00 | 91.48 |
| ATOM | 730 | OE1 | GLU | A | 137 | −6.450 | 61.295 | 47.627 | 1.00 | 82.91 |
| ATOM | 731 | OE2 | GLU | A | 137 | −5.274 | 62.509 | 49.026 | 1.00 | 85.26 |
| ATOM | 732 | N | ILE | A | 138 | −2.134 | 58.249 | 45.408 | 1.00 | 58.97 |
| ATOM | 733 | CA | ILE | A | 138 | −0.919 | 58.587 | 44.682 | 1.00 | 57.28 |
| ATOM | 734 | C | ILE | A | 138 | −0.957 | 60.045 | 44.250 | 1.00 | 57.15 |
| ATOM | 735 | O | ILE | A | 138 | −2.031 | 60.604 | 44.004 | 1.00 | 56.89 |
| ATOM | 736 | CB | ILE | A | 138 | −0.703 | 57.680 | 43.461 | 1.00 | 60.47 |
| ATOM | 737 | CG1 | ILE | A | 138 | −0.424 | 56.245 | 43.912 | 1.00 | 61.09 |
| ATOM | 738 | CG2 | ILE | A | 138 | 0.450 | 58.188 | 42.617 | 1.00 | 61.10 |
| ATOM | 739 | CD1 | ILE | A | 138 | 0.531 | 55.496 | 43.001 | 1.00 | 69.83 |
| ATOM | 740 | N | SER | A | 139 | 0.213 | 60.674 | 44.216 | 1.00 | 50.20 |
| ATOM | 741 | CA | SER | A | 139 | 0.316 | 62.078 | 43.839 | 1.00 | 48.27 |
| ATOM | 742 | C | SER | A | 139 | 1.243 | 62.247 | 42.636 | 1.00 | 48.99 |
| ATOM | 743 | O | SER | A | 139 | 2.379 | 61.763 | 42.635 | 1.00 | 48.04 |
| ATOM | 744 | CB | SER | A | 139 | 0.833 | 62.924 | 45.026 | 1.00 | 51.10 |
| ATOM | 745 | OG | SER | A | 139 | −0.156 | 63.842 | 45.504 | 1.00 | 55.23 |
| ATOM | 746 | N | ILE | A | 140 | 0.747 | 62.925 | 41.605 | 1.00 | 43.60 |
| ATOM | 747 | CA | ILE | A | 140 | 1.548 | 63.226 | 40.432 | 1.00 | 42.39 |
| ATOM | 748 | C | ILE | A | 140 | 1.481 | 64.722 | 40.212 | 1.00 | 45.48 |
| ATOM | 749 | O | ILE | A | 140 | 0.401 | 65.290 | 40.024 | 1.00 | 44.30 |
| ATOM | 750 | CB | ILE | A | 140 | 1.059 | 62.475 | 39.170 | 1.00 | 45.22 |
| ATOM | 751 | CG1 | ILE | A | 140 | 1.021 | 60.972 | 39.430 | 1.00 | 45.94 |
| ATOM | 752 | CG2 | ILE | A | 140 | 1.979 | 62.752 | 38.004 | 1.00 | 44.14 |
| ATOM | 753 | CD1 | ILE | A | 140 | 0.659 | 60.137 | 38.189 | 1.00 | 52.48 |
| ATOM | 754 | N | CYS | A | 141 | 2.633 | 65.365 | 40.312 | 1.00 | 42.45 |
| ATOM | 755 | CA | CYS | A | 141 | 2.719 | 66.808 | 40.195 | 1.00 | 41.58 |
| ATOM | 756 | C | CYS | A | 141 | 3.326 | 67.180 | 38.901 | 1.00 | 42.65 |
| ATOM | 757 | O | CYS | A | 141 | 4.343 | 66.630 | 38.494 | 1.00 | 42.28 |
| ATOM | 758 | CB | CYS | A | 141 | 3.531 | 67.389 | 41.348 | 1.00 | 42.31 |
| ATOM | 759 | SG | CYS | A | 141 | 2.842 | 66.957 | 42.967 | 1.00 | 46.63 |
| ATOM | 760 | N | MET | A | 142 | 2.701 | 68.122 | 38.226 | 1.00 | 36.40 |
| ATOM | 761 | CA | MET | A | 142 | 3.170 | 63.483 | 36.940 | 1.00 | 35.61 |
| ATOM | 762 | C | MET | A | 142 | 3.109 | 69.959 | 36.700 | 1.00 | 39.09 |
| ATOM | 763 | O | MET | A | 142 | 2.639 | 70.742 | 37.538 | 1.00 | 39.11 |
| ATOM | 764 | CE | MET | A | 142 | 2.360 | 67.720 | 35.864 | 1.00 | 37.66 |
| ATOM | 765 | CG | MET | A | 142 | 0.849 | 67.895 | 36.034 | 1.00 | 40.66 |
| ATOM | 766 | SD | MET | A | 142 | −0.151 | 66.689 | 35.007 | 1.00 | 43.56 |
| ATOM | 767 | CE | MET | A | 142 | −1.438 | 66.228 | 36.249 | 1.00 | 40.23 |
| ATOM | 768 | N | GLU | A | 143 | 3.601 | 70.365 | 35.541 | 1.00 | 34.78 |
| ATOM | 769 | CA | GLU | A | 143 | 3.553 | 71.733 | 35.117 | 1.00 | 34.21 |
| ATOM | 770 | C | GLU | A | 143 | 2.071 | 72.158 | 35.078 | 1.00 | 39.67 |
| ATOM | 771 | O | GLU | A | 143 | 1.181 | 71.358 | 34.653 | 1.00 | 39.25 |
| ATOM | 772 | CB | GLU | A | 143 | 4.169 | 71.823 | 33.729 | 1.00 | 35.35 |
| ATOM | 773 | CG | GLU | A | 143 | 3.966 | 73.117 | 33.014 | 1.00 | 42.71 |
| ATOM | 774 | CD | GLU | A | 143 | 4.452 | 73.051 | 31.594 | 1.00 | 48.44 |
| ATOM | 775 | OE1 | GLU | A | 143 | 4.820 | 71.948 | 31.136 | 1.00 | 39.76 |
| ATOM | 776 | OE2 | GLU | A | 143 | 4.455 | 74.090 | 30.929 | 1.00 | 45.53 |
| ATOM | 777 | N | HIS | A | 144 | 1.793 | 73.374 | 35.545 | 1.00 | 35.00 |
| ATOM | 778 | CA | HIS | A | 144 | 0.437 | 73.877 | 35.544 | 1.00 | 34.22 |
| ATOM | 779 | C | HIS | A | 144 | 0.189 | 74.548 | 34.204 | 1.00 | 36.94 |
| ATOM | 780 | O | HIS | A | 144 | 0.950 | 75.436 | 33.788 | 1.00 | 38.03 |
| ATOM | 781 | CB | HIS | A | 144 | 0.186 | 74.882 | 36.719 | 1.00 | 34.36 |
| ATOM | 782 | CG | HIS | A | 144 | −1.080 | 75.686 | 36.571 | 1.00 | 37.13 |
| ATOM | 783 | ND1 | HIS | A | 144 | −2.338 | 75.127 | 36.673 | 1.00 | 38.54 |
| ATOM | 784 | CD2 | HIS | A | 144 | −1.275 | 76.999 | 36.306 | 1.00 | 38.24 |
| ATOM | 785 | CE1 | HIS | A | 144 | −3.252 | 76.062 | 36.490 | 1.00 | 37.46 |
| ATOM | 786 | NE2 | HIS | A | 144 | −2.634 | 77.208 | 36.265 | 1.00 | 37.82 |
| ATOM | 787 | N | MET | A | 145 | −0.832 | 74.084 | 33.499 | 1.00 | 30.64 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 788 | CA | MET | A | 145 | −1.177 | 74.657 | 32.196 | 1.00 | 30.00 |
|---|---|---|---|---|---|---|---|---|---|---|
| ATOM | 789 | C | MET | A | 145 | −2.423 | 75.506 | 32.389 | 1.00 | 36.02 |
| ATOM | 790 | O | MET | A | 145 | −3.512 | 74.984 | 32.637 | 1.00 | 35.96 |
| ATOM | 791 | CB | MET | A | 145 | −1.411 | 73.547 | 31.164 | 1.00 | 31.59 |
| ATOM | 792 | CG | MET | A | 145 | −0.201 | 72.622 | 30.964 | 1.00 | 33.70 |
| ATOM | 793 | SD | MET | A | 145 | 1.097 | 73.408 | 29.974 | 1.00 | 37.21 |
| ATOM | 794 | CE | MET | A | 145 | 0.292 | 73.463 | 28.246 | 1.00 | 33.23 |
| ATOM | 795 | N | ASP | A | 146 | −2.232 | 76.824 | 32.376 | 1.00 | 34.11 |
| ATOM | 796 | CA | ASP | A | 146 | −3.296 | 77.775 | 32.687 | 1.00 | 34.28 |
| ATOM | 797 | C | ASP | A | 146 | −4.439 | 77.858 | 31.682 | 1.00 | 38.13 |
| ATOM | 798 | O | ASP | A | 146 | −5.466 | 78.477 | 31.964 | 1.00 | 37.87 |
| ATOM | 799 | CB | ASP | A | 146 | −2.718 | 79.163 | 32.964 | 1.00 | 35.92 |
| ATOM | 800 | CG | ASP | A | 146 | −2.038 | 79.761 | 31.756 | 1.00 | 45.46 |
| ATOM | 801 | OD1 | ASP | A | 146 | −1.947 | 79.077 | 30.720 | 1.00 | 45.45 |
| ATOM | 802 | OD2 | ASP | A | 146 | −1.609 | 80.932 | 31.834 | 1.00 | 51.52 |
| ATOM | 803 | N | GLY | A | 147 | −4.270 | 77.243 | 30.519 | 1.00 | 33.36 |
| ATOM | 804 | CA | GLY | A | 147 | −5.325 | 77.264 | 29.510 | 1.00 | 32.44 |
| ATOM | 805 | C | GLY | A | 147 | −6.292 | 76.104 | 29.732 | 1.00 | 35.57 |
| ATOM | 806 | O | GLY | A | 147 | −7.332 | 76.019 | 29.081 | 1.00 | 35.05 |
| ATOM | 807 | N | GLY | A | 148 | −5.924 | 75.196 | 30.638 | 1.00 | 31.65 |
| ATOM | 808 | CA | GLY | A | 148 | −6.747 | 74.022 | 30.951 | 1.00 | 31.04 |
| ATOM | 809 | C | GLY | A | 148 | −6.661 | 72.964 | 29.832 | 1.00 | 34.50 |
| ATOM | 810 | O | GLY | A | 148 | −5.720 | 72.969 | 29.032 | 1.00 | 33.20 |
| ATOM | 811 | N | SER | A | 149 | −7.643 | 72.063 | 29.789 | 1.00 | 30.59 |
| ATOM | 812 | CA | SER | A | 149 | −7.693 | 71.038 | 28.743 | 1.00 | 30.39 |
| ATOM | 813 | C | SER | A | 149 | −8.552 | 71.494 | 27.527 | 1.00 | 33.24 |
| ATOM | 814 | O | SER | A | 149 | −9.281 | 72.499 | 27.602 | 1.00 | 31.44 |
| ATOM | 815 | CB | SER. | A | 149 | −8.194 | 69.712 | 29.308 | 1.00 | 33.60 |
| ATOM | 816 | OG | SER | A | 149 | −9.370 | 69.900 | 30.072 | 1.00 | 43.68 |
| ATOM | 817 | N | LEU | A | 150 | −8.407 | 70.785 | 26.403 | 1.00 | 29.51 |
| ATOM | 813 | CA | LEU | A | 150 | −9.119 | 71.133 | 25.166 | 1.00 | 28.78 |
| ATOM | 819 | C | LEU | A | 150 | −10.608 | 70.848 | 25.238 | 1.00 | 33.56 |
| ATOM | 820 | O | LEU | A | 150 | −11.386 | 71.424 | 24.487 | 1.00 | 32.42 |
| ATOM | 821 | CB | LEU | A | 150 | −8.471 | 70.469 | 23.934 | 1.00 | 28.25 |
| ATOM | 822 | CG | LEU | A | 150 | −7.274 | 71.24.2 | 23.351 | 1.00 | 32.35 |
| ATOM | 823 | CD1 | LEU | A | 150 | −6.840 | 70.694 | 21.988 | 1.00 | 31.53 |
| ATOM | 824 | CO2 | LEU | A | 150 | −7.569 | 72.748 | 23.259 | 1.00 | 34.35 |
| ATOM | 825 | N | ASP | A | 151 | −11.012 | 69.972 | 26.162 | 1.00 | 31.81 |
| ATOM | 826 | CA | ASP | A | 151 | −12.423 | 69.724 | 26.374 | 1.00 | 32.40 |
| ATOM | 827 | C | ASP | A | 151 | −13.006 | 70.941 | 27.093 | 1.00 | 36.08 |
| ATOM | 828 | O | ASP | A | 151 | −14.095 | 71.405 | 26.765 | 1.00 | 35.15 |
| ATOM | 829 | CB | ASP | A | 151 | −12.659 | 68.444 | 27.190 | 1.00 | 34.83 |
| ATOM | 830 | CG | ASP | A | 151 | −11.994 | 68.483 | 28.552 | 1.00 | 48.34 |
| ATOM | 831 | OD1 | ASP | A | 151 | −12.702 | 68.320 | 29.566 | 1.00 | 43.46 |
| ATOM | 832 | OD2 | ASP | A | 151 | −10.753 | 68.575 | 28.604 | 1.00 | 57.90 |
| ATOM | 833 | N | GLN | A | 152 | −12.232 | 71.499 | 28.020 | 1.00 | 33.38 |
| ATOM | 834 | CA | GLN | A | 152 | −12.659 | 72.701 | 28.745 | 1.00 | 32.90 |
| ATOM | 835 | C | GLN | A | 152 | −12.686 | 73.888 | 27.782 | 1.00 | 34.75 |
| ATOM | 836 | O | GLN | A | 152 | −13.627 | 74.698 | 27.785 | 1.00 | 35.30 |
| ATOM | 837 | CB | GLN | A | 152 | −11.710 | 72.984 | 29.923 | 1.00 | 34.29 |
| ATOM | 838 | CG | GLN | A | 152 | −11.779 | 71.967 | 31.053 | 1.00 | 35.90 |
| ATOM | 839 | CD | GLN | A | 152 | −10.712 | 72.204 | 32.139 | 1.00 | 53.57 |
| ATOM | 840 | OE1 | GLN | A | 152 | −9.529 | 72.447 | 31.843 | 1.00 | 41.46 |
| ATOM | 841 | NE2 | GLN | A | 152 | −11.120 | 72.086 | 33.394 | 1.00 | 51.55 |
| ATOM | 842 | N | VAL | A | 153 | −11.671 | 73.967 | 26.924 | 1.00 | 29.66 |
| ATOM | 843 | CA | VAL | A | 153 | −11.587 | 75.029 | 25.917 | 1.00 | 28.47 |
| ATOM | 844 | C | VAL | A | 153 | −12.763 | 74.953 | 24.924 | 1.00 | 33.52 |
| ATOM | 845 | O | VAL | A | 153 | −13.391 | 75.968 | 24.604 | 1.00 | 32.52 |
| ATOM | 846 | CB | VAL | A | 153 | −10.253 | 74.948 | 25.131 | 1.00 | 32.44 |
| ATOM | 847 | CG1 | VAL | A | 153 | −10.268 | 75.929 | 23.927 | 1.00 | 31.72 |
| ATOM | 848 | CG2 | VAL | A | 153 | −9.061 | 75.246 | 26.072 | 1.00 | 32.06 |
| ATOM | 849 | N | LEU | A | 154 | −13.038 | 73.748 | 24.429 | 1.00 | 31.24 |
| ATOM | 850 | CA | LEU | A | 154 | −14.147 | 73.524 | 23.486 | 1.00 | 31.41 |
| ATOM | 851 | C | LEU | A | 154 | −15.506 | 73.991 | 24.067 | 1.00 | 37.12 |
| ATOM | 852 | O | LEU | A | 154 | −16.262 | 74.693 | 23.405 | 1.00 | 36.45 |
| ATOM | 853 | CB | LEU | A | 154 | −14.235 | 72.038 | 23.136 | 1.00 | 31.08 |
| ATOM | 854 | CG | LEU | A | 154 | −15.275 | 71.636 | 22.096 | 1.00 | 35.29 |
| ATOM | 855 | CD1 | LEU | A | 154 | −15.009 | 72.347 | 20.776 | 1.00 | 35.01 |
| ATOM | 856 | CD2 | LEU | A | 154 | −15.299 | 70.106 | 21.913 | 1.00 | 36.52 |
| ATOM | 857 | N | LYS | A | 155 | −15.815 | 73.533 | 25.282 | 1.00 | 35.14 |
| ATOM | 858 | CA | LYS | A | 155 | −17.057 | 73.888 | 25.972 | 1.00 | 35.99 |
| ATOM | 859 | C | LYS | A | 155 | −17.262 | 75.391 | 25.922 | 1.00 | 42.43 |
| ATOM | 860 | O | LYS | A | 155 | −18.371 | 75.884 | 25.672 | 1.00 | 43.00 |
| ATOM | 861 | CB | LYS | A | 155 | −16.979 | 73.450 | 27.438 | 1.00 | 38.79 |
| ATOM | 862 | CG | LYS | A | 155 | −17.879 | 72.308 | 27.802 | 1.00 | 60.03 |
| ATOM | 863 | CD | LYS | A | 155 | −17.441 | 71.674 | 29.114 | 1.00 | 72.91 |
| ATOM | 864 | CE | LYS | A | 155 | −17.686 | 70.168 | 29.110 | 1.00 | 88.91 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 865 | NZ | LYS | A | 155 | −18.553 | 69.736 | 30.250 | 1.00 | 99.25 |
|------|-----|-----|-----|---|-----|---------|--------|--------|------|-------|
| ATOM | 866 | N | LYS | A | 156 | −16.169 | 76.113 | 26.151 | 1.00 | 39.61 |
| ATOM | 867 | CA | LYS | A | 156 | −16.153 | 77.577 | 26.151 | 1.00 | 38.73 |
| ATOM | 868 | C | LYS | A | 156 | −16.306 | 78.148 | 24.760 | 1.00 | 40.97 |
| ATOM | 869 | O | LYS | A | 156 | −17.092 | 79.062 | 24.542 | 1.00 | 40.82 |
| ATOM | 870 | CB | LYS | A | 156 | −14.822 | 73.077 | 26.750 | 1.00 | 41.18 |
| ATOM | 871 | CG | LYS | A | 156 | −14.895 | 79.452 | 27.356 | 1.00 | 56.91 |
| ATOM | 872 | CD | LYS | A | 156 | −14.679 | 79.402 | 28.853 | 1.00 | 64.59 |
| ATOM | 873 | CE | LYS | A | 156 | −14.800 | 80.790 | 29.469 | 1.00 | 75.51 |
| ATOM | 874 | NZ | LYS | A | 156 | −13.859 | 80.980 | 30.610 | 1.00 | 85.01 |
| ATOM | 875 | N | ALA | A | 157 | −15.518 | 77.633 | 23.819 | 1.00 | 35.59 |
| ATOM | 876 | CA | ALA | A | 157 | −15.516 | 78.156 | 22.459 | 1.00 | 34.03 |
| ATOM | 877 | C | ALA | A | 157 | −16.739 | 77.802 | 21.604 | 1.00 | 35.42 |
| ATOM | 878 | O | ALA | A | 157 | −17.072 | 78.527 | 20.678 | 1.00 | 33.60 |
| ATOM | 879 | CB | ALA | A | 157 | −14.232 | 77.755 | 21.737 | 1.00 | 34.37 |
| ATOM | 880 | N | GLY | A | 158 | −17.354 | 76.658 | 21.876 | 1.00 | 31.75 |
| ATOM | 881 | CA | GLY | A | 158 | −18.464 | 76.173 | 21.051 | 1.00 | 31.72 |
| ATOM | 882 | C | GLY | A | 158 | −17.846 | 75.166 | 20.064 | 1.00 | 36.08 |
| ATOM | 833 | O | GLY | A | 158 | −18.025 | 73.958 | 20.191 | 1.00 | 37.65 |
| ATOM | 884 | N | ARG | A | 159 | −17.072 | 75.680 | 19.128 | 1.00 | 31.21 |
| ATOM | 885 | CA | ARG | A | 159 | −16.300 | 74.858 | 18.189 | 1.00 | 30.50 |
| ATOM | 886 | C | ARG | A | 159 | −15.002 | 75.558 | 17.890 | 1.00 | 32.67 |
| ATOM | 887 | O | ARG | A | 159 | −14.937 | 76.804 | 18.011 | 1.00 | 30.88 |
| ATOM | 888 | CB | ARG | A | 159 | −17.076 | 74.534 | 16.902 | 1.00 | 30.08 |
| ATOM | 889 | CG | ARG | A | 159 | −17.410 | 75.707 | 16.042 | 1.00 | 35.69 |
| ATOM | 890 | CD | ARG | A | 159 | −18.399 | 75.273 | 14.960 | 1.00 | 41.83 |
| ATOM | 891 | NE | ARG | A | 159 | −18.659 | 76.336 | 13.985 | 1.00 | 39.93 |
| ATOM | 892 | CZ | ARG | A | 159 | −19.671 | 76.770 | 13.686 | 1.00 | 51.17 |
| ATOM | 893 | NH1 | ARG | A | 159 | −20.925 | 76.235 | 14.280 | 1.00 | 47.55 |
| ATOM | 894 | NH2 | ARG | A | 159 | −20.034 | 77.724 | 12.791 | 1.00 | 38.32 |
| ATOM | 895 | N | ILE | A | 160 | −13.949 | 74.826 | 17.604 | 1.00 | 28.72 |
| ATOM | 896 | CA | ILE | A | 160 | −12.614 | 75.382 | 17.384 | 1.00 | 27.42 |
| ATOM | 897 | C | ILE | A | 160 | −12.264 | 75.468 | 15.896 | 1.00 | 32.05 |
| ATOM | 898 | O | ILE | A | 160 | −12.434 | 74.498 | 15.148 | 1.00 | 30.84 |
| ATOM | 899 | CB | ILE | A | 160 | −11.560 | 74.549 | 18.172 | 1.00 | 29.58 |
| ATOM | 900 | CG1 | ILE | A | 160 | −11.963 | 74.490 | 19.664 | 1.00 | 28.83 |
| ATOM | 901 | CG2 | ILE | A | 160 | −10.170 | 75.128 | 17.992 | 1.00 | 29.71 |
| ATOM | 902 | CD1 | ILE | A | 160 | −11.075 | 73.569 | 20.544 | 1.00 | 28.36 |
| ATOM | 903 | N | PRO | A | 161 | −11.794 | 76.644 | 15.465 | 1.00 | 28.54 |
| ATOM | 904 | CA | PRO | A | 161 | −11.497 | 76.889 | 14.036 | 1.00 | 26.92 |
| ATOM | 905 | C | PRO | A | 161 | −10.440 | 75.937 | 13.472 | 1.00 | 29.06 |
| ATOM | 906 | O | PRO | A | 161 | −9.541 | 75.521 | 14.172 | 1.00 | 29.17 |
| ATOM | 907 | CB | PRO | A | 161 | −10.966 | 78.341 | 14.027 | 1.00 | 28.31 |
| ATOM | 908 | CG | PRO | A | 161 | −11.419 | 78.927 | 15.352 | 1.00 | 32.56 |
| ATOM | 909 | CD | PRO | A | 161 | −11.384 | 77.772 | 16.311 | 1.00 | 28.33 |
| ATOM | 910 | N | GLU | A | 162 | −10.584 | 75.598 | 12.194 | 1.00 | 25.23 |
| ATOM | 911 | CA | GLU | A | 162 | −9.676 | 74.694 | 11.496 | 1.00 | 24.24 |
| ATOM | 912 | C | GLU | A | 162 | −8.192 | 75.046 | 11.668 | 1.00 | 28.61 |
| ATOM | 913 | O | GLU | A | 162 | −7.370 | 74.173 | 11.929 | 1.00 | 28.78 |
| ATOM | 914 | CB | GLU | A | 162 | −10.035 | 74.644 | 10.004 | 1.00 | 25.25 |
| ATOM | 915 | CG | GLU | A | 162 | −8.959 | 74.017 | 9.130 | 1.00 | 33.47 |
| ATOM | 916 | CD | GLU | A | 162 | −9.457 | 73.674 | 7.747 | 1.00 | 38.51 |
| ATOM | 917 | OE1 | GLU | A | 162 | −10.678 | 73.723 | 7.522 | 1.00 | 28.97 |
| ATOM | 918 | OE2 | GLU | A | 162 | −8.621 | 73.415 | 6.871 | 1.00 | 33.16 |
| ATOM | 919 | N | GLN | A | 163 | −7.840 | 76.314 | 11.480 | 1.00 | 26.44 |
| ATOM | 920 | CA | GLN | A | 163 | −6.433 | 76.724 | 11.595 | 1.00 | 27.23 |
| ATOM | 921 | C | GLN | A | 163 | −5.915 | 76.494 | 12.984 | 1.00 | 31.72 |
| ATOM | 922 | O | GLN | A | 163 | −4.741 | 76.135 | 13.173 | 1.00 | 32.09 |
| ATOM | 923 | CB | GLN | A | 163 | −6.236 | 78.190 | 11.193 | 1.00 | 29.17 |
| ATOM | 924 | CG | GLN | A | 163 | −6.341 | 78.435 | 9.687 | 1.00 | 34.22 |
| ATOM | 925 | CD | GLN | A | 163 | −5.857 | 79.819 | 9.306 | 1.00 | 44.36 |
| ATOM | 926 | OE1 | GLN | A | 163 | −5.684 | 80.674 | 10.160 | 1.00 | 40.53 |
| ATOM | 927 | NE2 | GLN | A | 163 | −5.607 | 80.019 | 8.035 | 1.00 | 36.16 |
| ATOM | 928 | N | ILE | A | 164 | −6.784 | 76.666 | 13.977 | 1.00 | 26.85 |
| ATOM | 929 | CA | ILE | A | 164 | −6.363 | 76.398 | 15.343 | 1.00 | 25.43 |
| ATOM | 930 | C | ILE | A | 164 | −6.160 | 74.902 | 15.480 | 1.00 | 27.59 |
| ATOM | 931 | O | ILE | A | 164 | −5.205 | 74.447 | 16.109 | 1.00 | 27.47 |
| ATOM | 932 | CB | ILE | A | 164 | −7.380 | 76.267 | 16.371 | 1.00 | 28.21 |
| ATOM | 933 | CG1 | ILE | A | 164 | −7.507 | 78.399 | 16.336 | 1.00 | 28.25 |
| ATOM | 934 | CG2 | ILE | A | 164 | −7.005 | 76.324 | 17.778 | 1.00 | 28.74 |
| ATOM | 935 | CD1 | ILE | A | 164 | −6.254 | 79.144 | 16.833 | 1.00 | 32.23 |
| ATOM | 936 | N | LEU | A | 165 | −7.042 | 74.132 | 14.847 | 1.00 | 22.50 |
| ATOM | 937 | CA | LEU | A | 165 | −6.929 | 72.660 | 14.894 | 1.00 | 22.42 |
| ATOM | 938 | C | LEU | A | 165 | −5.699 | 72.139 | 14.126 | 1.00 | 26.23 |
| ATOM | 939 | O | LEU | A | 165 | −5.190 | 71.067 | 14.414 | 1.00 | 25.77 |
| ATOM | 940 | CB | LEU | A | 165 | −8.228 | 72.000 | 14.437 | 1.00 | 22.36 |
| ATOM | 941 | CG | LEU | A | 165 | −9.412 | 72.239 | 15.400 | 1.00 | 25.97 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 942 | CD1 | LEU | A | 165 | −10.676 | 71.581 | 14.889 | 1.00 | 26.34 |
|---|---|---|---|---|---|---|---|---|---|---|
| ATOM | 943 | CD2 | LEU | A | 166 | −9.072 | 71.724 | 16.846 | 1.00 | 26.63 |
| ATOM | 944 | N | GLY | A | 166 | −5.190 | 72.952 | 13.202 | 1.00 | 24.87 |
| ATOM | 945 | CA | GLY | A | 166 | −3.955 | 72.635 | 12.474 | 1.00 | 25.00 |
| ATOM | 946 | C | GLY | A | 166 | −2.755 | 72.675 | 13.439 | 1.00 | 30.03 |
| ATOM | 947 | O | GLY | A | 166 | −1.910 | 71.778 | 13.417 | 1.00 | 30.25 |
| ATOM | 948 | N | LYS | A | 167 | −2.710 | 73.673 | 14.326 | 1.00 | 26.89 |
| ATOM | 949 | CA | LYS | A | 167 | −1.624 | 73.733 | 15.337 | 1.00 | 27.08 |
| ATOM | 950 | C | LYS | A | 167 | −1.787 | 72.616 | 16.359 | 1.00 | 29.23 |
| ATOM | 951 | O | LYS | A | 167 | −0.814 | 71.999 | 16.795 | 1.00 | 30.05 |
| ATOM | 952 | CB | LYS | A | 167 | −1.601 | 75.102 | 16.060 | 1.00 | 29.84 |
| ATOM | 953 | CG | LYS | A | 167 | −1.334 | 76.275 | 15.142 | 1.00 | 39.22 |
| ATOM | 954 | CD | LYS | A | 167 | −0.032 | 76.088 | 14.369 | 1.00 | 48.58 |
| ATOM | 955 | CE | LYS | A | 167 | 0.121 | 77.154 | 13.269 | 1.00 | 52.34 |
| ATOM | 956 | NZ | LYS | A | 167 | 1.324 | 76.931 | 12.425 | 1.00 | 54.69 |
| ATOM | 957 | N | VAL | A | 168 | −3.027 | 72.352 | 16.751 | 1.00 | 24.07 |
| ATOM | 958 | CA | VAL | A | 168 | −3.293 | 71.268 | 17.693 | 1.00 | 22.47 |
| ATOM | 959 | C | VAL | A | 168 | −2.838 | 69.919 | 17.084 | 1.00 | 26.56 |
| ATOM | 960 | O | VAL | A | 168 | −2.232 | 69.110 | 17.757 | 1.00 | 27.06 |
| ATOM | 961 | CB | VAL | A | 168 | −4.816 | 71.190 | 18.056 | 1.00 | 24.94 |
| ATOM | 962 | CG1 | VAL | A | 168 | −5.108 | 69.947 | 18.852 | 1.00 | 24.15 |
| ATOM | 963 | CG2 | VAL | A | 168 | −5.279 | 72.480 | 18.824 | 1.00 | 23.74 |
| ATOM | 964 | N | SER | A | 169 | −3.124 | 69.718 | 15.804 | 1.00 | 23.86 |
| ATOM | 965 | CA | SER | A | 169 | −2.730 | 68.482 | 15.088 | 1.00 | 23.84 |
| ATOM | 966 | C | SER | A | 169 | −1.220 | 68.314 | 15.085 | 1.00 | 27.80 |
| ATOM | 967 | O | SER | A | 169 | −0.706 | 67.221 | 15.342 | 1.00 | 27.49 |
| ATOM | 968 | CB | SER | A | 169 | −3.229 | 68.523 | 13.633 | 1.00 | 24.75 |
| ATOM | 969 | OG | SER | A | 169 | −4.632 | 68.46.9 | 13.570 | 1.00 | 29.49 |
| ATOM | 970 | N | ILE | A | 170 | −0.511 | 69.394 | 14.754 | 1.00 | 24.28 |
| ATOM | 971 | CA | ILE | A | 170 | 0.950 | 69.372 | 14.727 | 1.00 | 24.68 |
| ATOM | 972 | C | ILE | A | 170 | 1.519 | 68.913 | 16.102 | 1.00 | 30.29 |
| ATOM | 973 | O | ILE | A | 170 | 2.383 | 68.040 | 16.172 | 1.00 | 31.21 |
| ATOM | 974 | CB | ILE | A | 170 | 1.516 | 70.773 | 14.361 | 1.00 | 28.00 |
| ATOM | 975 | CG1 | ILE | A | 170 | 1.312 | 71.057 | 12.876 | 1.00 | 28.41 |
| ATOM | 976 | CG2 | ILE | A | 170 | 3.019 | 70.893 | 14.746 | 1.00 | 28.95 |
| ATOM | 977 | CD1 | ILE | A | 170 | 1.562 | 72.518 | 12.496 | 1.00 | 35.07 |
| ATOM | 978 | N | ALA | A | 171 | 1.001 | 69.502 | 17.179 | 1.00 | 26.18 |
| ATOM | 979 | CA | ALA | A | 171 | 1.457 | 69.229 | 18.539 | 1.00 | 25.26 |
| ATOM | 980 | C | ALA | A | 171 | 1.229 | 67.792 | 18.973 | 1.00 | 31.52 |
| ATOM | 981 | O | ALA | A | 171 | 2.103 | 67.155 | 19.603 | 1.00 | 29.89 |
| ATOM | 982 | CB | ALA | A | 171 | 0.780 | 70.188 | 19.514 | 1.00 | 25.72 |
| ATOM | 983 | N | VAL | A | 172 | 0.039 | 67.286 | 18.687 | 1.00 | 29.42 |
| ATOM | 984 | CA | VAL | A | 172 | −0.282 | 65.926. | 19.033 | 1.00 | 28.86 |
| ATOM | 985 | C | VAL | A | 172 | 0.646 | 64.958 | 18.299 | 1.00 | 34.69 |
| ATOM | 986 | O | VAL | A | 172 | 1.224 | 64.069 | 18.913 | 1.00 | 36.18 |
| ATOM | 987 | CB | VAL | A | 172 | −1.741 | 65.598 | 18.720 | 1.00 | 31.75 |
| ATOM | 988 | CG1 | VAL | A | 172 | −2.026 | 64.101 | 18.972 | 1.00 | 31.04 |
| ATOM | 989 | CG2 | VAL | A | 172 | −2.679 | 66.498 | 19.573 | 1.00 | 30.92 |
| ATOM | 990 | N | ILE | A | 173 | 0.791 | 55.131 | 16.988 | 1.00 | 31.26 |
| ATOM | 991 | CA | ILE | A | 173 | 1.647 | 64.248 | 16.214 | 1.00 | 31.50 |
| ATOM | 992 | C | ILE | A | 173 | 3.107 | 64.316 | 16.702 | 1.00 | 36.09 |
| ATOM | 993 | O | ILE | A | 173 | 3.785 | 63.302 | 16.752 | 1.00 | 35.53 |
| ATOM | 994 | CB | ILE | A | 173 | 1.621 | 64.569 | 14.708 | 1.00 | 34.79 |
| ATOM | 995 | CG1 | ILE | A | 173 | 0.295 | 64.136 | 14.076 | 1.00 | 35.01 |
| ATOM | 996 | CG2 | ILE | A | 173 | 2.765 | 63.841 | 14.006 | 1.00 | 37.69 |
| ATOM | 997 | CD1 | ILE | A | 173 | −0.005 | 64.866 | 12.744 | 1.00 | 39.46 |
| ATOM | 998 | N | LYS | A | 174 | 3.589 | 65.522 | 17.002 | 1.00 | 32.10 |
| ATOM | 999 | CA | LYS | A | 174 | 4.974 | 65.687 | 17.475 | 1.00 | 32.23 |
| ATOM | 1000 | C | LYS | A | 174 | 5.133 | 65.113 | 18.862 | 1.00 | 36.81 |
| ATOM | 1001 | O | LYS | A | 174 | 6.213 | 64.429 | 19.144 | 1.00 | 36.10 |
| ATOM | 1002 | CB | LYS | A | 174 | 5.410 | 67.153 | 17.434 | 1.00 | 34.05 |
| ATOM | 1003 | CG | LYS | A | 174 | 5.580 | 67.680 | 16.027 | 1.00 | 33.11 |
| ATOM | 1004 | CD | LYS | A | 174 | 6.372 | 68.953 | 16.004 | 1.00 | 33.65 |
| ATOM | 1005 | CE | LYS | A | 174 | 6.424 | 69.528 | 14.621 | 1.00 | 43.36 |
| ATOM | 1006 | NZ | LYS | A | 174 | 7.393 | 70.656 | 14.539 | 1.00 | 53.94 |
| ATOM | 1007 | N | GLY | A | 175 | 4.125 | 65.326 | 19.709 | 1.00 | 33.81 |
| ATOM | 1008 | CA | GLY | A | 175 | 4.128 | 64.763 | 21.051 | 1.00 | 33.74 |
| ATOM | 1009 | C | GLY | A | 175 | 4.141 | 63.225 | 21.001 | 1.00 | 38.15 |
| ATOM | 1010 | O | GLY | A | 175 | 4.888 | 62.572 | 21.746 | 1.00 | 39.00 |
| ATOM | 1011 | N | LEU | A | 176 | 3.310 | 62.658 | 20.133 | 1.00 | 33.24 |
| ATOM | 1012 | CA | LEU | A | 176 | 3.246 | 61.199 | 19.949 | 1.00 | 32.87 |
| ATOM | 1013 | C | LEU | A | 176 | 4.564 | 60.669 | 19.338 | 1.00 | 38.82 |
| ATOM | 1014 | O | LEU | A | 176 | 5.053 | 59.616 | 19.716 | 1.00 | 38.51 |
| ATOM | 1015 | CB | LEU | A | 176 | 2.061 | 60.817 | 19.047 | 1.00 | 32.30 |
| ATOM | 1016 | CG | LEU | A | 176 | 0.630 | 60.947 | 19.618 | 1.00 | 35.72 |
| ATOM | 1017 | CD1 | LEU | A | 176 | −0.424 | 60.445 | 18.559 | 1.00 | 33.90 |
| ATOM | 1018 | CD2 | LEU | A | 176 | 0.511 | 60.164 | 20.918 | 1.00 | 37.48 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 1019 | N   | THR | A | 177  | 5.126  | 61.411 | 18.394 | 1.00 | 37.37  |
|------|------|-----|-----|---|------|--------|--------|--------|------|--------|
| ATOM | 1020 | CA  | THR | A | 177  | 6.393  | 61.025 | 17.778 | 1.00 | 38.00  |
| ATOM | 1021 | C   | THR | A | 177  | 7.495  | 61.001 | 18.843 | 1.00 | 43.86  |
| ATOM | 1022 | O   | THR | A | 177  | 8.338  | 60.110 | 18.860 | 1.00 | 43.84  |
| ATOM | 1023 | CB  | THR | A | 177  | 6.804  | 62.012 | 16.679 | 1.00 | 43.68  |
| ATOM | 1024 | OG1 | THR | A | 177  | 5.804  | 62.025 | 15.653 | 1.00 | 44.93  |
| ATOM | 1025 | CG2 | THR | A | 177  | 8.185  | 61.602 | 16.054 | 1.00 | 39.12  |
| ATOM | 1026 | N   | TYR | A | 178  | 7.477  | 61.988 | 19.730 | 1.00 | 41.14  |
| ATOM | 1027 | CA  | TYR | A | 178  | 8.478  | 62.079 | 20.779 | 1.00 | 41.45  |
| ATOM | 1028 | C   | TYR | A | 178  | 8.401  | 60.898 | 21.741 | 1.00 | 45.76  |
| ATOM | 1029 | O   | TYR | A | 178  | 9.390  | 60.222 | 21.982 | 1.00 | 45.74  |
| ATOM | 1030 | CB  | TYR | A | 178  | 8.353  | 63.397 | 21.542 | 1.00 | 42.61  |
| ATOM | 1031 | CG  | TYR | A | 178  | 9.199  | 63.423 | 22.788 | 1.00 | 44.33  |
| ATOM | 1032 | CD1 | TYR | A | 178  | 8.694  | 62.992 | 23.995 | 1.00 | 46.20  |
| ATOM | 1033 | CD2 | TYR | A | 178  | 10.533 | 63.815 | 22.740 | 1.00 | 45.02  |
| ATOM | 1034 | CE1 | TYR | A | 178  | 9.475  | 62.981 | 25.131 | 1.00 | 47.44  |
| ATOM | 1035 | CE2 | TYR | A | 178  | 11.315 | 63.818 | 23.884 | 1.00 | 45.69  |
| ATOM | 1036 | CZ  | TYR | A | 178  | 10.786 | 63.386 | 25.062 | 1.00 | 52.82  |
| ATOM | 1037 | OH  | TYR | A | 178  | 11.556 | 63.372 | 26.188 | 1.00 | 57.37  |
| ATOM | 1038 | N   | LEU | A | 179  | 7.221  | 60.655 | 22.292 | 1.00 | 42.46  |
| ATOM | 1039 | CA  | LEU | A | 179  | 7.039  | 59.543 | 23.219 | 1.00 | 42.54  |
| ATOM | 1040 | C   | LEU | A | 179  | 7.531  | 58.233 | 22.619 | 1.00 | 49.79  |
| ATOM | 1041 | O   | LEU | A | 179  | 8.164  | 57.420 | 23.303 | 1.00 | 49.04  |
| ATOM | 1042 | CB  | LEU | A | 179  | 5.584  | 59.413 | 23.627 | 1.00 | 42.01  |
| ATOM | 1043 | CG  | LEU | A | 179  | 5.028  | 60.537 | 24.508 | 1.00 | 46.28  |
| ATOM | 1044 | CD1 | LEU | A | 179  | 3.531  | 60.517 | 24.512 | 1.00 | 46.00  |
| ATOM | 1045 | CD2 | LEU | A | 179  | 5.570  | 60.447 | 25.937 | 1.00 | 48.89  |
| ATOM | 1046 | N   | ARG | A | 180  | 7.225  | 58.026 | 21.341 | 1.00 | 48.77  |
| ATOM | 1047 | CA  | ARG | A | 180  | 7.611  | 56.805 | 20.636 | 1.00 | 49.26  |
| ATOM | 1048 | C   | ARG | A | 180  | 9.115  | 56.736 | 20.391 | 1.00 | 53.43  |
| ATOM | 1049 | O   | ARG | A | 180  | 9.778  | 55.792 | 20.804 | 1.00 | 54.18  |
| ATOM | 1050 | CB  | ARG | A | 180  | 6.873  | 56.707 | 19.308 | 1.00 | 50.74  |
| ATOM | 1051 | CG  | ARG | A | 180  | 7.052  | 55.383 | 18.603 | 1.00 | 63.75  |
| ATOM | 1052 | CD  | ARG | A | 180  | 6.316  | 55.372 | 17.281 | 1.00 | 77.03  |
| ATOM | 1053 | NE  | ARG | A | 180  | 6.732  | 56.476 | 16.421 | 1.00 | 87.31  |
| ATOM | 1054 | CZ  | ARG | A | 180  | 6.957  | 56.358 | 15.116 | 1.00 | 98.76  |
| ATOM | 1055 | NH1 | ARG | A | 180  | 6.813  | 55.178 | 14.526 | 1.00 | 83.85  |
| ATOM | 1056 | NH2 | ARG | A | 180  | 7.330  | 57.416 | 14.404 | 1.00 | 82.89  |
| ATOM | 1057 | N   | GLU | A | 181  | 9.639  | 57.736 | 19.702 | 1.00 | 49.05  |
| ATOM | 1058 | CA  | GLU | A | 181  | 11.049 | 57.786 | 19.373 | 1.00 | 48.37  |
| ATOM | 1059 | C   | GLU | A | 181  | 11.952 | 57.723 | 20.594 | 1.00 | 52.58  |
| ATOM | 1060 | O   | GLU | A | 181  | 12.813 | 56.836 | 20.702 | 1.00 | 52.18  |
| ATOM | 1061 | CB  | GLU | A | 181  | 11.360 | 59.044 | 18.570 | 1.00 | 49.50  |
| ATOM | 1062 | CG  | GLU | A | 181  | 10.892 | 58.984 | 17.137 | 1.00 | 59.76  |
| ATOM | 1063 | CD  | GLU | A | 181  | 1.1141 | 57.628 | 16.502 | 1.00 | 80.18  |
| ATOM | 1064 | OE1 | GLU | A | 181  | 10.294 | 56.723 | 16.671 | 1.00 | 71.86  |
| ATOM | 1065 | OE2 | GLU | A | 181  | 12.195 | 57.464 | 15.847 | 1.00 | 70.10  |
| ATOM | 1066 | N   | LYS | A | 182  | 11.783 | 58.685 | 21.497 | 1.00 | 48.08  |
| ATOM | 1067 | CA  | LYS | A | 182  | 12.644 | 58.790 | 22.664 | 1.00 | 47.13  |
| ATOM | 1068 | C   | LYS | A | 182  | 12.428 | 57.770 | 23.757 | 1.00 | 51.69  |
| ATOM | 1069 | O   | LYS | A | 182  | 13.378 | 57.395 | 24.441 | 1.00 | 52.25  |
| ATOM | 1070 | CB  | LYS | A | 182  | 12.603 | 60.203 | 23.245 | 1.00 | 48.98  |
| ATOM | 1071 | CG  | LYS | A | 182  | 12.886 | 61.296 | 22.228 | 1.00 | 58.87  |
| ATOM | 1072 | CD  | LYS | A | 182  | 13.910 | 60.853 | 21.205 | 1.00 | 68.31  |
| ATOM | 1073 | CE  | LYS | A | 182  | 15.328 | 61.165 | 21.670 | 1.00 | 79.79  |
| ATOM | 1074 | NZ  | LYS | A | 182  | 16.323 | 60.186 | 21.139 | 1.00 | 88.95  |
| ATOM | 1075 | N   | HIS | A | 183  | 11.186 | 57.339 | 23.959 | 1.00 | 47.72  |
| ATOM | 1075 | CA  | HIS | A | 183  | 10.894 | 56.421 | 25.055 | 1.00 | 47.45  |
| ATOM | 1077 | C   | HIS | A | 183  | 10.227 | 55.112 | 24.675 | 1.00 | 52.40  |
| ATOM | 1078 | O   | HIS | A | 183  | 9.869  | 54.32:7| 25.854 | 1.00 | 51.52  |
| ATOM | 1079 | CB  | HIS | A | 183  | 10.081 | 57.141 | 26.144 | 1.00 | 48.22  |
| ATOM | 1080 | CG  | HIS | A | 183  | 10.654 | 58.465 | 26.540 | 1.00 | 51.27  |
| ATOM | 1081 | ND1 | HIS | A | 183  | 11.530 | 58.610 | 27.594 | 1.00 | 52.89  |
| ATOM | 1082 | CD2 | HIS | A | 183  | 10.522 | 59.693 | 25.988 | 1.00 | 53.10  |
| ATOM | 1083 | CE1 | HIS | A | 183  | 11.900 | 59.874 | 27.685 | 1.00 | 52.47  |
| ATOM | 1084 | NE2 | HIS | A | 183  | 11.305 | 60.554 | 26.721 | 1.00 | 52.89  |
| ATOM | 1085 | N   | LYS | A | 184. | 10.059 | 54.883 | 23.373 | 1.00 | 50.38  |
| ATOM | 1086 | CA  | LYS | A | 184  | 9.417  | 53.666 | 22.867 | 1.00 | 51.42  |
| ATOM | 1087 | C   | LYS | A | 184  | 8.145  | 53.350 | 23.624 | 1.00 | 56.61  |
| ATOM | 1088 | O   | LYS | A | 184  | 8.007  | 52.271 | 24.195 | 1.00 | 57.17  |
| ATOM | 1089 | CB  | LYS | A | 184  | 10.375 | 52.461 | 22.930 | 1.00 | 54.85  |
| ATOM | 1090 | CG  | LYS | A | 184  | 11.845 | 52.809 | 22.706 | 1.00 | 73.17  |
| ATOM | 1091 | CD  | LYS | A | 184  | 12.561 | 51.724 | 21.908 | 1.00 | 84.76  |
| ATOM | 1092 | CE  | LYS | A | 184  | 12.531 | 50.382 | 22.633 | 1.00 | 97.00  |
| ATOM | 1093 | NZ  | LYS | A | 184  | 13.120 | 49.284 | 21.804 | 1.00 | 106.37 |
| ATOM | 1094 | N   | ILE | A | 185  | 7.229  | 54.312 | 23.663 | 1.00 | 53.12  |
| ATOM | 1095 | CA  | ILE | A | 185  | 5.965  | 54.131 | 24.363 | 1.00 | 52.31  |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 1096 | C | ILE | A | 185 | 4.851 | 54.931 | 23.702 | 1.00 | 53.30 |
|------|------|------|-----|---|-----|--------|--------|--------|------|-------|
| ATOM | 1097 | O | ILE | A | 185 | 5.087 | 56.019 | 23.170 | 1.00 | 53.07 |
| ATOM | 1098 | CB | ILE | A | 185 | 6.084 | 54.531 | 25.824 | 1.00 | 55.61 |
| ATOM | 1099 | CG1 | ILE | A | 185 | 6.393 | 56.027 | 25.946 | 1.00 | 55.98 |
| ATOM | 1100 | CG2 | ILE | A | 185 | 7.160 | 53.699 | 26.505 | 1.00 | 56.50 |
| ATOM | 1101 | CD1 | ILE | A | 185 | 6.857 | 56.445 | 27.346 | 1.00 | 58.97 |
| ATOM | 1102 | N | MET | A | 186 | 3.641 | 54.375 | 23.719 | 1.00 | 46.79 |
| ATOM | 1103 | CA | MET | A | 186 | 2.498 | 55.025 | 23.110 | 1.00 | 45.29 |
| ATOM | 1104 | C | MET | A | 186 | 1.636. | 55.658 | 24.170 | 1.00 | 47.26 |
| ATOM | 1105 | O | MET | A | 186 | 1.695 | 55.274 | 25.346 | 1.00 | 47.21 |
| ATOM | 1106 | CB | MET | A | 186 | 1.688 | 54.041 | 22.255 | 1.00 | 47.44 |
| ATOM | 1107 | CG | MET | A | 186 | 0.989 | 52.935 | 23.023 | 1.00 | 50.59 |
| ATOM | 1108 | SD | MET | A | 186 | 0.026 | 51.809 | 21.927 | 1.00 | 54.10 |
| ATOM | 1109 | CE | MET | A | 186 | −1.608 | 52.659 | 21.933 | 1.00 | 50.32 |
| ATOM | 1110 | N | HIS | A | 187 | 0.860 | 56.658 | 23.769 | 1.00 | 40.91 |
| ATOM | 1111 | CA | HIS | A | 187 | 0.028 | 57.387 | 24.711 | 1.00 | 39.05 |
| ATOM | 1112 | C | HIS | A | 187 | −1.036 | 56.509 | 25.363 | 1.00 | 41.20 |
| ATOM | 1113 | O | HIS | A | 187 | −1.168 | 56.493 | 26.595 | 1.00 | 39.69 |
| ATOM | 1114 | CB | HIS | A | 187 | −0.625 | 58.610 | 24.024 | 1.00 | 38.94 |
| ATOM | 1115 | CG | HIS | A | 187 | −1.184 | 59.610 | 24.985 | 1.00 | 41.40 |
| ATOM | 1116 | ND1 | HIS | A | 187 | −2.213 | 59.312 | 25.851 | 1.00 | 42.69 |
| ATOM | 1117 | CD2 | HIS | A | 187 | −0.856 | 60.905 | 25.218 | 1.00 | 42.00 |
| ATOM | 1118 | CE1 | HIS | A | 187 | −2.488 | 60.379 | 26.584 | 1.00 | 41.73 |
| ATOM | 1119 | NE2 | HIS | A | 187 | −1.677 | 61.357 | 26.218 | 1.00 | 41.74 |
| ATOM | 1120 | N | ARG | A | 188 | −1.825 | 55.829 | 24.522 | 1.00 | 37.02 |
| ATOM | 1121 | CA | ARG | A | 188 | −2.935 | 54.938 | 24.974 | 1.00 | 36.30 |
| ATOM | 1122 | C | ARG | A | 188 | −4.184 | 55.664 | 25.390 | 1.00 | 40.37 |
| ATOM | 1123 | O | ARG | A | 188 | −5.243 | 55.043 | 25.502 | 1.00 | 39.96 |
| ATOM | 1124 | CB | ARG | A | 188 | −2.445 | 54.031 | 26.115 | 1.00 | 37.24 |
| ATOM | 1125 | CG | ARG | A | 188 | −1.555 | 52.882 | 25.689 | 1.00 | 46.38 |
| ATOM | 1126 | CD | ARG | A | 188 | −1.062 | 52.076 | 26.903 | 1.00 | 54.04 |
| ATOM | 1127 | NE | ARG | A | 188 | 0.222 | 51.422 | 26.627 | 1.00 | 63.45 |
| ATOM | 1128 | CZ | ARG | A | 188 | 0.351 | 50.290 | 25.938 | 1.00 | 74.87 |
| ATOM | 1129 | NH1 | ARG | A | 188 | −0.723 | 49.671 | 25.466 | 1.00 | 53.69 |
| ATOM | 1130 | NH2 | ARG | A | 188 | 1.552 | 49.772 | 25.730 | 1.00 | 65.85 |
| ATOM | 1131 | N | ASP | A | 189 | −4.095 | 56.965 | 25.661 | 1.00 | 35.99 |
| ATOM | 1132 | CA | ASP | A | 189 | −5.287 | 57.692 | 25.079 | 1.00 | 34.79 |
| ATOM | 1133 | C | ASP | A | 189 | −5.386 | 59.110 | 25.527 | 1.00 | 37.36 |
| ATOM | 1134 | O | ASP | A | 189 | −5.606 | 60.061 | 26.265 | 1.00 | 36.75 |
| ATOM | 1135 | CB | ASP | A | 189 | −5.455 | 57.656 | 27.611 | 1.00 | 35.64 |
| ATOM | 1136 | CG | ASP | A | 189 | −6.888 | 57.987 | 28.063 | 1.00 | 39.81 |
| ATOM | 1137 | OD1 | ASP | A | 189 | −7.837 | 57.783 | 27.282 | 1.00 | 37.95 |
| ATOM | 1138 | OD2 | ASP | A | 189 | −7.057 | 58.483 | 29.200 | 1.00 | 44.73 |
| ATOM | 1139 | N | VAL | A | 190 | −5.299 | 54.231 | 24.209 | 1.00 | 32.74 |
| ATOM | 1140 | CA | VAL | A | 190 | −5.463 | 60.515 | 23.563 | 1.00 | 31.25 |
| ATOM | 1141 | C | VAL | A | 190 | −6.941 | 60.892 | 23.577 | 1.00 | 34.54 |
| ATOM | 1142 | O | VAL | A | 190 | −7.808 | 60.063 | 23.288 | 1.00 | 33.71 |
| ATOM | 1143 | CB | VAL | A | 190 | −4.954 | 60.493 | 22.087 | 1.00 | 34.46 |
| ATOM | 1144 | CG1 | VAL | A | 190 | −5.315 | 61.802 | 21.364 | 1.00 | 33.35 |
| ATOM | 1145 | CG2 | VAL | A | 190 | −3.442 | 60.248 | 22.038 | 1.00 | 34.32 |
| ATOM | 1146 | N | LYS | A | 191 | −7.218 | 62.141 | 23.946 | 1.00 | 30.06 |
| ATOM | 1147 | CA | LYS | A | 191 | −8.574 | 62.678 | 23.962 | 1.00 | 28.85 |
| ATOM | 1148 | C | LYS | A | 191 | −8.477 | 64.140 | 24.371 | 1.00 | 33.58 |
| ATOM | 1149 | O | LYS | A | 191 | −7.431 | 64.583 | 24.836 | 1.00 | 34.07 |
| ATOM | 1150 | CB | LYS | A | 191 | −9.478 | 61.881 | 24.897 | 1.00 | 29.99 |
| ATOM | 1151 | CG | LYS | A | 191 | −9.065 | 61.918 | 26.365 | 1.00 | 31.44 |
| ATOM | 1152 | CD | LYS | A | 191 | −9.861 | 60.921 | 27.161 | 1.00 | 36.50 |
| ATOM | 1153 | CE | LYS | A | 191 | −9.794 | 61.197 | 28.648 | 1.00 | 43.47 |
| ATOM | 1154 | NZ | LYS | A | 191 | −10.123 | 59.984 | 29.426 | 1.00 | 52.01 |
| ATOM | 1155 | N | PRO | A | 192 | −9.530 | 64.909 | 24.143 | 1.00 | 30.66 |
| ATOM | 1156 | CA | PRO | A | 192 | −9.474 | 66.359 | 24.433 | 1.00 | 29.70 |
| ATOM | 1157 | C | PRO | A | 192 | −9.046 | 66.741 | 25.850 | 1.00 | 31.72 |
| ATOM | 1158 | O | PRO | A | 192 | −8.323 | 67.705 | 26.035 | 1.00 | 32.55 |
| ATOM | 1159 | CB | PRO | A | 192 | −10.892 | 66.847 | 24.121 | 1.00 | 31.08 |
| ATOM | 1160 | CG | PRO | A | 192 | −11.449 | 65.814 | 23.162 | 1.00 | 35.70 |
| ATOM | 1161 | CD | PRO | A | 192 | −10.839 | 64.504 | 23.580 | 1.00 | 31.05 |
| ATOM | 1162 | N | SER | A | 193 | −9.483 | 65.984 | 26.848 | 1.00 | 27.88 |
| ATOM | 1163 | CA | SER | A | 193 | −9.124 | 66.296 | 28.229 | 1.00 | 27.48 |
| ATOM | 1164 | C | SER | A | 193 | −7.662 | 65.953 | 28.556 | 1.00 | 32.42 |
| ATOM | 1165 | O | SER | A | 193 | −7.166 | 66.273 | 29.650 | 1.00 | 30.99 |
| ATOM | 1166 | CB | SER | A | 193 | −10.105 | 65.638 | 29.228 | 1.00 | 29.74 |
| ATOM | 1167 | OG | SER | A | 193 | −9.817 | 64.269 | 29.431 | 1.00 | 31.19 |
| ATOM | 1168 | N | ASN | A | 194 | −6.967 | 65.325 | 27.595 | 1.00 | 29.51 |
| ATOM | 1169 | CA | ASN | A | 194 | −5.559 | 64.942 | 27.792 | 1.00 | 28.95 |
| ATOM | 1170 | C | ASN | A | 194 | −4.600 | 65.748 | 26.931 | 1.00 | 31.70 |
| ATOM | 1171 | O | ASN | A | 194 | −3.416 | 65.441 | 26.837 | 1.00 | 31.39 |
| ATOM | 1172 | CB | ASN | A | 194 | −5.356 | 63.430 | 27.640 | 1.00 | 29.30 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 1173 | CC | ASN | A | 194 | −5.915 | 62.651 | 28.825 | 1.00 | 43.62 |
|---|---|---|---|---|---|---|---|---|---|---|
| ATOM | 1174 | OD1 | ASN | A | 194 | −6.294 | 63.246 | 29.837 | 1.00 | 32.55 |
| ATOM | 1175 | ND2 | ASN | A | 194 | −6.019 | 61.326 | 28.686 | 1.00 | 31.52 |
| ATOM | 1176 | N | ILE | A | 195 | −5.132 | 66.794 | 26.314 | 1.00 | 27.16 |
| ATOM | 1177 | CA | ILE | A | 195 | −4.339 | 67.742 | 25.563 | 1.00 | 26.39 |
| ATOM | 1178 | C | ILE | A | 195 | −4.497 | 69.079 | 26.280 | 1.00 | 30.55 |
| ATOM | 1179 | O | ILE | A | 195 | −5.603 | 69.618 | 26.368 | 1.00 | 30.29 |
| ATOM | 1180 | CB | ILE | A | 195 | −4.841 | 67.880 | 24.109 | 1.00 | 28.81 |
| ATOM | 1181 | CG1 | ILE | A | 195 | −4.916 | 66.498 | 23.438 | 1.00 | 28.51 |
| ATOM | 1182 | CG2 | ILE | A | 195 | −3.945 | 68.813 | 23.326 | 1.00 | 28.01 |
| ATOM | 1183 | CD1 | ILE | A | 195 | −5.743 | 66.433 | 22.151 | 1.00 | 29.33 |
| ATOM | 1184 | N | LEU | A | 196 | −3.400 | 69.592 | 26.829 | 1.00 | 28.59 |
| ATOM | 1185 | CA | LEU | A | 196 | −3.425 | 70.849 | 27.615 | 1.00 | 28.18 |
| ATOM | 1186 | C | LEU | A | 196 | −2.793 | 72.001 | 26.896 | 1.00 | 31.40 |
| ATOM | 1187 | O | LEU | A | 196 | −1.899 | 71.813 | 26.086 | 1.00 | 30.46 |
| ATOM | 1168 | CB | LEU | A | 196 | −2.764 | 70.659 | 28.988 | 1.00 | 28.17 |
| ATOM | 1189 | CG | LEU | A | 196 | −3.176 | 69.429 | 29.788 | 1.00 | 33.14 |
| ATOM | 1190 | CD1 | LEU | A | 196 | −2.545 | 69.472 | 31.185 | 1.00 | 33.61 |
| ATOM | 1191 | CD2 | LEU | A | 196 | −4.711 | 69.310 | 29.878 | 1.00 | 33.60 |
| ATOM | 1192 | N | VAL | A | 197 | −3.287 | 73.205 | 27.190 | 1.00 | 27.99 |
| ATOM | 1193 | CA | VAL | A | 197 | −2.831 | 74.431 | 26.534 | 1.00 | 28.13 |
| ATOM | 1194 | C | VAL | A | 197 | −2.551 | 75.553 | 27.564 | 1.00 | 33.06 |
| ATOM | 1195 | O | VAL | A | 19.7 | −2.980 | 75.478 | 23.717 | 1.00 | 32.45 |
| ATOM | 1196 | CB | VAL | A | 197 | −3.874 | 74.919 | 25.456 | 1.00 | 32.34 |
| ATOM | 1197 | CG1 | VAL | A | 197 | −4.014 | 73.877 | 24.329 | 1.00 | 32.14 |
| ATOM | 1198 | CG2 | VAL | A | 197 | −5.246 | 75.185 | 26.099 | 1.00 | 31.87 |
| ATOM | 1199 | N | ASN | A | 198 | −1.760 | 76.541 | 27.177 | 1.00 | 30.82 |
| ATOM | 1200 | CA | ASN | A | 198 | −1.425 | 77.617 | 28.114 | 1.00 | 30.80 |
| ATOM | 1201 | C | ASN | A | 198 | −1.382 | 78.960 | 27.433 | 1.00 | 34.26 |
| ATOM | 1202 | O | ASN | A | 198 | −1.385 | 79.039 | 26.211 | 1.00 | 32.21 |
| ATOM | 1203 | CB | ASN | A | 198 | −0.111 | 77.321 | 28.888 | 1.00 | 30.02 |
| ATOM | 1204 | CG | ASN | A | 198 | 1.126 | 77.327 | 27.994 | 1.00 | 42.37 |
| ATOM | 1205 | OD1 | ASN | A | 198 | 1.165 | 77.982 | 26.959 | 1.00 | 39.43 |
| ATOM | 1206 | ND2 | ASN | A | 198 | 2.161 | 76.633 | 28.432 | 1.00 | 39.20 |
| ATOM | 1207 | N | SER | A | 199 | −1.333 | 80.026 | 28.229 | 1.00 | 32.55 |
| ATOM | 1208 | CA | SER | A | 199 | −1.326 | 81.392 | 27.687 | 1.00 | 32.79 |
| ATOM | 1209 | C | SER | A | 199 | −0.122 | 81.713 | 26.803 | 1.00 | 38.55 |
| ATOM | 1210 | O | SER | A | 199 | −0.153 | 82.671 | 26.057 | 1.00 | 38.67 |
| ATOM | 1211 | CB | SER | A | 199 | −1.478 | 82.430 | 28.802 | 1.00 | 36.41 |
| ATOM | 1212 | OG | SER | A | 199 | −0.570 | 82.178 | 29.867 | 1.00 | 45.99 |
| ATOM | 1213 | N | ARG | A | 200 | 0.932 | 80.909 | 26.876 | 1.00 | 36.53 |
| ATOM | 1214 | CA | ARG | A | 200 | 2.093 | 81.134 | 26.000 | 1.00 | 36.86 |
| ATOM | 1215 | C | ARG | A | 200 | 1.831 | 88.571 | 24.585 | 1.00 | 39.52 |
| ATOM | 1216 | O | ARG | A | 200 | 2.594 | 80.828 | 23.650 | 1.00 | 38.97 |
| ATOM | 1217 | CB | ARG | A | 200 | 3.347 | 80.503 | 26.587 | 1.00 | 37.93 |
| ATOM | 1218 | CG | ARG | A | 200 | 3.885 | 81.237 | 27.771 | 1.00 | 50.46 |
| ATOM | 1219 | CD | ARG | A | 200 | 5.074 | 80.529 | 28.334 | 1.00 | 62.70 |
| ATOM | 1220 | NE | ARG | A | 200 | 6.043 | 81.468 | 28.882 | 1.00 | 73.77 |
| ATOM | 1221 | CZ | ARG | A | 200 | 7.241 | 81.118 | 29.327 | 1.00 | 86.34 |
| ATOM | 1222 | NH1 | ARG | A | 200 | 7.617 | 79.844 | 29.289 | 1.00 | 68.09 |
| ATOM | 1223 | NH2 | ARG | A | 200 | 8.061 | 82.038 | 29.815 | 1.00 | 75.00 |
| ATOM | 1224 | N | GLY | A | 201 | 0.763 | 79.785 | 24.448 | 1.00 | 34.32 |
| ATOM | 1225 | CA | GLY | A | 201 | 0.408 | 79.207 | 23.150 | 1.00 | 33.57 |
| ATOM | 1226 | C | GLY | A | 201 | 0.977 | 77.801 | 22.970 | 1.00 | 35.65 |
| ATOM | 1227 | O | GLY | A | 201 | 1.062 | 77.295 | 21.856 | 1.00 | 35.59 |
| ATOM | 1228 | N | GLU | A | 202 | 1.337 | 77.161 | 24.072 | 1.00 | 30.45 |
| ATOM | 1229 | CA | GLU | A | 202 | 1.870 | 75.808 | 23.999 | 1.00 | 29.82 |
| ATOM | 1230 | C | GLU | A | 202 | 0.726 | 74.806 | 24.058 | 1.00 | 32.98 |
| ATOM | 1231 | O | GLU | A | 202 | −0.336 | 75.093 | 24.613 | 1.00 | 30.11 |
| ATOM | 1232 | CB | GLU | A | 202 | 2.880 | 75.546 | 25.124 | 1.00 | 30.44 |
| ATOM | 1233 | CG | GLU | A | 202 | 4.024 | 76.545 | 25.129 | 1.00 | 37.82 |
| ATOM | 1234 | CD | GLU | A | 202 | 5.034 | 76.271 | 26.233 | 1.00 | 49.43 |
| ATOM | 1235 | OE1 | GLU | A | 202 | 4.638 | 76.225 | 27.421 | 1.00 | 36.18 |
| ATOM | 1236 | OE2 | GLU | A | 202 | 6.216 | 76.082 | 25.903 | 1.00 | 50.68 |
| ATOM | 1237 | N | ILE | A | 203 | 0.951 | 73.658 | 23.432 | 1.00 | 31.00 |
| ATOM | 1238 | CA | ILE | A | 203 | −0.030 | 72.581 | 23.339 | 1.00 | 30.51 |
| ATOM | 1239 | C | ILE | A | 203 | 0.723 | 71.302 | 23.682 | 1.00 | 32.75 |
| ATOM | 1240 | O | ILE | A | 203 | 1.740 | 71.015 | 23.073 | 1.00 | 32.65 |
| ATOM | 1241 | CB | ILE | A | 203 | −0.600 | 72.522 | 21.679 | 1.00 | 33.10 |
| ATOM | 1242 | CG1 | ILE | A | 203 | −1.125 | 73.922 | 21.479 | 1.00 | 33.02 |
| ATOM | 1243 | CG2 | ILE | A | 203 | −1.684 | 71.448 | 21.746 | 1.00 | 31.97 |
| ATOM | 1244 | CD1 | ILE | A | 203 | −1.493 | 74.057 | 19.999 | 1.00 | 32.51 |
| ATOM | 1245 | N | LYS | A | 204 | 0.288 | 70.604 | 24.738 | 1.00 | 28.31 |
| ATOM | 1246 | CA | LYS | A | 204 | 1.027 | 69.441 | 25.253 | 1.00 | 28.01 |
| ATOM | 1247 | C | LYS | A | 204 | 0.160 | 68.311 | 25.701 | 1.00 | 32.56 |
| ATOM | 1248 | O | LYS | A | 204 | −0.900 | 68.525 | 26.271 | 1.00 | 32.29 |
| ATOM | 1249 | CB | LYS | A | 204 | 1.910 | 69.856 | 26.449 | 1.00 | 29.78 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 1250 | CG | LYS | A | 204 | 2.721 | 71.126 | 26.214 | 1.00 | 38.47 |
|---|---|---|---|---|---|---|---|---|---|---|
| ATOM | 1251 | CD | LYS | A | 204 | 3.603 | 71.443 | 27.413 | 1.00 | 39.97 |
| ATOM | 1252 | CE | LYS | A | 204 | 4.445 | 72.673 | 27.162 | 1.00 | 39.62 |
| ATOM | 1253 | NZ | LYS | A | 204 | 5.365 | 72.948 | 28.319 | 1.00 | 46.59 |
| ATOM | 1254 | N | LEU | A | 205 | 0.681 | 67.096 | 25.559 | 1.00 | 29.67 |
| ATOM | 1255 | CA | LEU | A | 205 | −0.036 | 65.895 | 25.969 | 1.00 | 29.10 |
| ATOM | 1256 | C | LEU | A | 205 | 0.289 | 65.507 | 27.402 | 1.00 | 35.15 |
| ATOM | 1257 | O | LEU | A | 205 | 1.402 | 65.719 | 27.887 | 1.00 | 34.87 |
| ATOM | 1258 | CB | LEU | A | 205 | 0.347 | 64.730 | 25.059 | 1.00 | 28.89 |
| ATOM | 1259 | CG | LEU | A | 205 | 0.169 | 64.929 | 23.570 | 1.00 | 32.84 |
| ATOM | 1260 | CD1 | LEU | A | 205 | 0.795 | 63.742 | 22.811 | 1.00 | 32.52 |
| ATOM | 1261 | CD2 | LEU | A | 205 | −1.308 | 65.085 | 23.256 | 1.00 | 33.44 |
| ATOM | 1252 | N | CYS | A | 206 | −0.675 | 64.885 | 28.059 | 1.00 | 34.14 |
| ATOM | 1263 | CA | CYS | A | 206 | −0.486 | 64.412 | 29.412 | 1.00 | 35.16 |
| ATOM | 1264 | C | CYS | A | 206 | −1.213 | 63.082 | 29.579 | 1.00 | 38.96 |
| ATOM | 1265 | O | CYS | A | 206 | −1.857 | 62.591 | 28.638 | 1.00 | 37.59 |
| ATOM | 1266 | CB | CYS | A | 206 | −1.018 | 65.435 | 30.416 | 1.00 | 36.07 |
| ATOM | 1267 | SG | CYS | A | 206 | −2.839 | 65.538 | 30.490 | 1.00 | 40.38 |
| ATOM | 1268 | N | ASP | A | 207 | −1.089 | 62.492 | 30.760 | 1.00 | 35.92 |
| ATOM | 1269 | CA | ASP | A | 207 | −1.778 | 61.246 | 31.061 | 1.00 | 36.18 |
| ATOM | 1270 | C | ASP | A | 207 | −1.497 | 60.083 | 30.092 | 1.00 | 41.37 |
| ATOM | 1271 | O | ASP | A | 207 | −2.362 | 59.250 | 29.866 | 1.00 | 40.36 |
| ATOM | 1272 | CB | ASP | A | 207 | −3.290 | 51.489 | 31.186 | 1.00 | 37.56 |
| ATOM | 1273 | CG | ASP | A | 207 | −3.639 | 62.392 | 32.357 | 1.00 | 45.10 |
| ATOM | 1274 | OD1 | ASP | A | 207 | −2.699 | 62.906 | 33.005 | 1.00 | 46.10 |
| ATOM | 1275 | OD2 | ASP | A | 207 | −4.845 | 62.627 | 32.606 | 1.00 | 47.45 |
| ATOM | 1276 | N | PHE | A | 208 | −0.281 | 60.021 | 29.550 | 1.00 | 40.15 |
| ATOM | 1277 | CA | PHE | A | 208 | 0.100 | 58.906 | 28.687 | 1.00 | 41.33 |
| ATOM | 1278 | C | PHE | A | 208 | 0.585 | 57.733 | 29.570 | 1.00 | 50.26 |
| ATOM | 1279 | O | PHE | A | 208 | 0.923 | 57.928 | 30.740 | 1.00 | 49.46 |
| ATOM | 1280 | CB | PHE | A | 208 | 1.183 | 59.307 | 27.686 | 1.00 | 42.36 |
| ATOM | 1281 | CG | PHE | A | 208 | 2.186 | 60.275 | 28.228 | 1.00 | 43.26 |
| ATOM | 1282 | CD1 | PHE | A | 208 | 3.357 | 59.824 | 28.817 | 1.00 | 45.42 |
| ATOM | 1283 | CD2 | PHE | A | 208 | 1.976 | 61.645 | 28.120 | 1.00 | 44.33 |
| ATOM | 1284 | CE1 | PHE | A | 208 | 4.288 | 60.717 | 29.300 | 1.00 | 45.76 |
| ATOM | 1285 | CE2 | PHE | A | 208 | 2.910 | 62.544 | 28.600 | 1.00 | 46.52 |
| ATOM | 1286 | CZ | PHE | A | 208 | 4.067 | 62.084 | 29.181 | 1.00 | 44.55 |
| ATOM | 1287 | N | GLY | A | 209 | 0.589 | 56.526 | 29.007 | 1.00 | 50.61 |
| ATOM | 1288 | CA | GLY | A | 209 | 0.943 | 55.312 | 29.758 | 1.00 | 52.34 |
| ATOM | 1289 | C | GLY | A | 209 | 2.449 | 55.063 | 29.901 | 1.00 | 58.83 |
| ATOM | 1290 | O | GLY | A | 209 | 3.000 | 54.140 | 29.292 | 1.00 | 57.91 |
| ATOM | 1291 | N | VAL | A | 210 | 3.098 | 55.870 | 30.732 | 1.00 | 57.44 |
| ATOM | 1292 | CA | VAL | A | 210 | 4.526 | 55.734 | 30.978 | 1.00 | 58.38 |
| ATOM | 1293 | C | VAL | A | 210 | 4.756 | 54.695 | 32.076 | 1.00 | 64.19 |
| ATOM | 1294 | O | VAL | A | 210 | 5.858 | 54.180 | 32.235 | 1.00 | 64.05 |
| ATOM | 1295 | CB | VAL | A | 210 | 5.144 | 57.084 | 31.435 | 1.00 | 62.40 |
| ATOM | 1296 | CG1 | VAL | A | 210 | 4.901 | 57.301 | 32.907 | 1.00 | 62.04 |
| ATOM | 1297 | CG2 | VAL | A | 210 | 6.634 | 57.132 | 31.125 | 1.00 | 62.32 |
| ATOM | 1298 | N | SFR | A | 211 | 3.700 | 54.381 | 32.815 | 1.00 | 62.32 |
| ATOM | 1299 | CA | SER | A | 211 | 3.790 | 53.424 | 33.910 | 1.00 | 63.27 |
| ATOM | 1300 | C | SER | A | 211 | 3.553 | 51.975 | 33.479 | 1.00 | 69.46 |
| ATOM | 1301 | O | SER | A | 211 | 4.453 | 51.316 | 32.939 | 1.00 | 69.36 |
| ATOM | 1302 | CB | SER | A | 211 | 2.825 | 53.806 | 35.032 | 1.00 | 66.52 |
| ATOM | 1303 | OG | SER | A | 211 | 3.084 | 53.056 | 36.207 | 1.00 | 74.95 |
| ATOM | 1304 | N | GLY | A | 212 | 2.353 | 51.473 | 33.755 | 1.00 | 66.88 |
| ATOM | 1305 | CA | GLY | A | 212 | 2.003 | 50.096 | 33.432 | 1.00 | 57.19 |
| ATOM | 1306 | C | GLY | A | 212 | 1.194 | 49.512 | 34.575 | 1.00 | 72.37 |
| ATOM | 1307 | O | GLY | A | 212 | 0.047 | 49.101 | 34.392 | 1.00 | 71.80 |
| ATOM | 1308 | N | GLN | A | 213 | 1.782 | 49.514 | 35.767 | 1.00 | 70.36 |
| ATOM | 1309 | CA | GLN | A | 213 | 1.096 | 49.020 | 36.951 | 1.00 | 70.55 |
| ATOM | 1310 | C | GLN | A | 213 | −0.022 | 49.984 | 37.331 | 1.00 | 76.21 |
| ATOM | 1311 | O | GLN | A | 213 | −1.073 | 49.568 | 37.829 | 1.00 | 76.23 |
| ATOM | 1312 | CB | GLN | A | 213 | 2.078 | 48.851 | 38.114 | 1.00 | 72.31 |
| ATOM | 1313 | CG | GLN | A | 213 | 2.008 | 47.486 | 38.792 | 1.00 | 86.28 |
| ATOM | 1314 | CD | GLN | A | 213 | 0.724 | 47.291 | 39.586 | 1.00 | 106.04 |
| ATOM | 1315 | OE1 | GLN | A | 213 | 0.342 | 48.142 | 40.393 | 1.00 | 100.96 |
| ATOM | 1316 | NE2 | GLN | A | 213 | 0.057 | 46.161 | 39.356 | 1.00 | 42.65 |
| ATOM | 1317 | N | LEU | A | 214 | 0.203 | 51.271 | 37.074 | 1.00 | 73.50 |
| ATOM | 1318 | CA | LEU | A | 214 | −0.803 | 52.290 | 37.351 | 1.00 | 73.43 |
| ATOM | 1319 | C | LEU | A | 214 | −1.9.95 | 52.078 | 36.424 | 1.00 | 78.06 |
| ATOM | 1320 | O | LEU | A | 214 | −3.146 | 52.318 | 36.803 | 1.00 | 77.39 |
| ATOM | 1321 | CB | LEU | A | 214 | −0.219 | 53.589 | 37.146 | 1.00 | 73.34 |
| ATOM | 1322 | CG | LEU | A | 214 | −1.142 | 54.856 | 37.505 | 1.00 | 77.65 |
| ATOM | 1323 | CD1 | LEU | A | 214 | −1.642 | 54.719 | 38.936 | 1.00 | 77.79 |
| ATOM | 1324 | CD2 | LEU | A | 214 | −0.442 | 56.199 | 37.297 | 1.00 | 79.33 |
| ATOM | 1325 | N | ILE | A | 215 | −1.712 | 51.609 | 35.210 | 1.00 | 75.79 |
| ATOM | 1326 | CA | ILE | A | 215 | −2.759 | 51.341 | 34.231 | 1.00 | 76.34 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 1327 | C | ILE | A | 215 | −3.615 | 50.171 | 34.696 | 1.00 | 82.06 |
|---|---|---|---|---|---|---|---|---|---|---|
| ATOM | 1328 | O | ILE | A | 215 | −4.845 | 50.217 | 34.623 | 1.00 | 81.87 |
| ATOM | 1329 | CB | ILE | A | 215 | −2.174 | 50.995 | 32.846 | 1.00 | 79.49 |
| ATOM | 1330 | CG1 | ILE | A | 215 | −1.541 | 52.232 | 32.200 | 1.00 | 79.73 |
| ATOM | 1331 | CG2 | ILE | A | 215 | −3.259 | 50.408 | 31.942 | 1.00 | 80.26 |
| ATOM | 1332 | CD1 | ILE | A | 215 | −0.255 | 51.942 | 31.444 | 1.00 | 84.61 |
| ATOM | 1333 | N | ASP | A | 216 | −2.952 | 49.120 | 35.170 | 1.00 | 79.61 |
| ATOM | 1334 | CA | ASP | A | 216 | −3.643 | 47.933 | 35.660 | 1.00 | 79.62 |
| ATOM | 1335 | C | ASP | A | 216 | −4.311 | 48.227 | 36.996 | 1.00 | 83.92 |
| ATOM | 1336 | O | ASP | A | 216 | −5.489 | 47.923 | 37.197 | 1.00 | 83.64 |
| ATOM | 1337 | CB | ASP | A | 216 | −2.658 | 46.767 | 35.814 | 1.00 | 81.22 |
| ATOM | 1338 | CG | ASP | A | 216 | −1.723 | 46.631 | 34.624 | 1.00 | 89.59 |
| ATOM | 1339 | OD1 | ASP | A | 216 | −2.185 | 46.813 | 33.477 | 1.00 | 90.41 |
| ATOM | 1340 | OD2 | ASP | A | 216 | −0.529 | 46.331 | 34.834 | 1.00 | 93.42 |
| ATOM | 1341 | N | SER | A | 217 | −3.555 | 48.835 | 37.902 | 1.00 | 80.61 |
| ATOM | 1342 | CA | SER | A | 217 | −4.054 | 49.154 | 39.232 | 1.00 | 80.60 |
| ATOM | 1343 | C | SER | A | 217 | −5.263 | 50.079 | 39.222 | 1.00 | 85.16 |
| ATOM | 1344 | O | SER | A | 217 | −5.768 | 50.456 | 40.278 | 1.00 | 84.67 |
| ATOM | 1345 | CB | SER | A | 217 | −2.941 | 49.738 | 40.092 | 1.00 | 84.08 |
| ATOM | 1346 | OG | SER | A | 217 | −1.748 | 48.988 | 39.947 | 1.00 | 92.72 |
| ATOM | 1347 | N | MET | A | 218 | −5.733 | 50.435 | 38.029 | 1.00 | 82.43 |
| ATOM | 1348 | CA | MET | A | 218 | −6.900 | 51.306 | 37.899 | 1.00 | 82.24 |
| ATOM | 1349 | CB | MET | A | 218 | −6.490 | 52.682 | 37.369 | 1.00 | 84.65 |
| ATOM | 1350 | C | MET | A | 218 | −7.959 | 50.686 | 36.993 | 1.00 | 85.84 |
| ATOM | 1351 | O | MET | A | 218 | −7.636 | 49.952 | 36.054 | 1.00 | 85.56 |
| ATOM | 1352 | N | ALA | A | 219 | −9.223 | 50.998 | 37.265 | 1.00 | 81.99 |
| ATOM | 1353 | N | PHE | A | 222 | −12.863 | 52.641 | 39.824 | 1.00 | 78.17 |
| ATOM | 1354 | CA | PHE | A | 222 | −12.167 | 53.479 | 38.849 | 1.00 | 77.83 |
| ATOM | 1355 | C | PHE | A | 222 | −12.383 | 52.985 | 37.415 | 1.00 | 80.65 |
| ATOM | 1356 | O | PHE | A | 222 | −12.088 | 51.828 | 37.096 | 1.00 | 80.78 |
| ATOM | 1357 | CB | PHE | A | 222 | −10.669 | 53.542 | 39.165 | 1.00 | 79.64 |
| ATOM | 1358 | N | VAL | A | 223 | −12.884 | 53.871 | 36.553 | 1.00 | 75.60 |
| ATOM | 1359 | CA | VAL | A | 223 | −13.133 | 53.532 | 35.149 | 1.00 | 74.34 |
| ATOM | 1360 | C | VAL | A | 223 | −13.039 | 54.758 | 34.217 | 1.00 | 74.56 |
| ATOM | 1361 | O | VAL | A | 223 | −13.694 | 55.786 | 34.449 | 1.00 | 74.18 |
| ATOM | 1362 | CB | VAL | A | 223 | −14.512 | 52.845 | 34.963 | 1.00 | 78.40 |
| ATOM | 1363 | CG1 | VAL | A | 223 | −14.342 | 51.448 | 34.369 | 1.00 | 78.12 |
| ATOM | 1364 | CG2 | VAL | A | 223 | −15.264 | 52.783 | 36.289 | 1.00 | 78.16 |
| ATOM | 1365 | N | GLY | A | 224 | −12.228 | 54.632 | 33.164 | 1.00 | 67.59 |
| ATOM | 1366 | CA | GLY | A | 224 | −12.031 | 55.710 | 32.192 | 1.00 | 65.82 |
| ATOM | 1367 | C | GLY | A | 224 | −12.807 | 55.436 | 30.898 | 1.00 | 65.53 |
| ATOM | 1368 | O | GLY | A | 224 | −12.827 | 54.292 | 30.448 | 1.00 | 65.50 |
| ATOM | 1369 | N | THR | A | 225 | −13.379 | 56.485 | 30.309 | 1.00 | 58.19 |
| ATOM | 1370 | CA | THR | A | 225 | −14.177 | 56.344 | 29.091 | 1.00 | 56.05 |
| ATOM | 1371 | C | THR | A | 225 | −13.408 | 55.711 | 27.923 | 1.00 | 54.21 |
| ATOM | 1372 | O | THR | A | 225 | −12.255 | 56.057 | 27.666 | 1.00 | 52.90 |
| ATOM | 1373 | CB | THR | A | 225 | −14.798 | 57.696 | 28.642 | 1.00 | 64.96 |
| ATOM | 1374 | OG1 | THR | A | 225 | −15.855 | 57.459 | 27.701 | 1.00 | 65.16 |
| ATOM | 1375 | CG2 | THR | A | 225 | −13.744 | 58.586 | 27.995 | 1.00 | 63.72 |
| ATOM | 1376 | N | ARG | A | 226 | −14.064 | 54.778 | 27.226 | 1.00 | 46.95 |
| ATOM | 1377 | CA | ARG | A | 226 | −13.487 | 54.129 | 26.043 | 1.00 | 44.48 |
| ATOM | 1378 | C | ARG | A | 226 | −14.082 | 54.762 | 24.790 | 1.00 | 42.67 |
| ATOM | 1379 | O | ARG | A | 226 | −13.914 | 54.255 | 23.684 | 1.00 | 40.68 |
| ATOM | 1380 | CE | ARG | A | 226 | −13.809 | 52.629 | 26.025 | 1.00 | 43.80 |
| ATOM | 1381 | CG | ARG | A | 226 | −13.915 | 51.974 | 27.383 | 1.00 | 52.17 |
| ATOM | 1332 | CD | ARG | A | 226 | −13.900 | 50.451 | 27.233 | 1.00 | 54.51 |
| ATOM | 1383 | NE | ARG | A | 226 | −12.552 | 49.941 | 27.409 | 1.00 | 55.72 |
| ATOM | 1384 | CZ | ARG | A | 226 | −11.996 | 48.996 | 26.670 | 1.00 | 62.47 |
| ATOM | 1385 | NH1 | ARG | A | 226 | −12.682 | 48.404 | 25.696 | 1.00 | 41.49 |
| ATOM | 1386 | NH2 | ARG | A | 226 | −10.752 | 45.627 | 26.924 | 1.00 | 51.10 |
| ATOM | 1387 | N | SER | A | 227 | −14.803 | 55.852 | 24.979 | 1.00 | 37.33 |
| ATOM | 1388 | CA | SER | A | 227 | −15.475 | 56.521 | 23.871 | 1.00 | 36.12 |
| ATOM | 1389 | C | SER | A | 227 | −14.547 | 57.032 | 22.765 | 1.00 | 37.33 |
| ATOM | 1390 | O | SER | A | 227 | −15.003 | 57.279 | 21.651 | 1.00 | 35.87 |
| ATOM | 1391 | CB | SER | A | 227 | −16.419 | 57.613 | 24.377 | 1.00 | 38.29 |
| ATOM | 1392 | OG | SER | A | 227 | −15.707 | 58.780 | 24.705 | 1.00 | 47.24 |
| ATOM | 1393 | N | TYR | A | 228 | −13.234 | 57.104 | 23.040 | 1.00 | 32.68 |
| ATOM | 1394 | CA | TYR | A | 228 | −12.256 | 57.534 | 22.015 | 1.00 | 30.97 |
| ATOM | 1395 | C | TYR | A | 228 | −11.346 | 56.396 | 21.562 | 1.00 | 37.35 |
| ATOM | 1396 | O | TYR | A | 228 | −10.398 | 56.614 | 20.796 | 1.00 | 37.36 |
| ATOM | 1397 | CB | TYR | A | 228 | −11.402 | 58.716 | 22.514 | 1.00 | 30.08 |
| ATOM | 1398 | CG | TYR | A | 228 | −12.218 | 59.944 | 22.844 | 1.00 | 28.57 |
| ATOM | 1399 | CD1 | TYR | A | 228 | −12.509 | 60.895 | 21.869 | 1.00 | 28.54 |
| ATOM | 1400 | CD2 | TYR | A | 228 | −12.728 | 60.133 | 24.119 | 1.00 | 29.30 |
| ATOM | 1401 | CE1 | TYR | A | 228 | −13.297 | 61.995 | 22.153 | 1.00 | 27.01 |
| ATOM | 1402 | CE2 | TYR | A | 228 | −13.512 | 61.237 | 24.421 | 1.00 | 30.10 |
| ATOM | 1403 | CZ | TYR | A | 228 | −13.785 | 62.169 | 23.432 | 1.00 | 32.95 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 1404 | OH | TYR | A | 228 | −14.535 | 63.271 | 23.736 | 1.00 | 29.42 |
|---|---|---|---|---|---|---|---|---|---|---|
| ATOM | 1405 | N | MET | A | 229 | −11.640 | 55.180 | 22.017 | 1.00 | 34.82 |
| ATOM | 1406 | CA | MET | A | 229 | −10.835 | 54.013 | 21.653 | 1.00 | 35.21 |
| ATOM | 1407 | C | MET | A | 229 | −11.057 | 53.584 | 20.205 | 1.00 | 37.74 |
| ATOM | 1408 | O | MET | A | 229 | −12.170 | 53.633 | 19.701 | 1.00 | 36.90 |
| ATOM | 1409 | CB | MET | A | 229 | −11.139 | 52.850 | 22.588 | 1.00 | 38.44 |
| ATOM | 1410 | CG | MET | A | 229 | −10.603 | 53.054 | 23.981 | 1.00 | 43.70 |
| ATOM | 1411 | SD | MET | A | 229 | −10.428 | 51.509 | 24.871 | 1.00 | 49.14 |
| ATOM | 1412 | CE | MET | A | 229 | −9.909 | 52.154 | 26.498 | 1.00 | 45.88 |
| ATOM | 1413 | N | SER | A | 230 | −9.993 | 53.160 | 19.539 | 1.00 | 34.37 |
| ATOM | 1414 | CA | SER | A | 230 | −10.114 | 52.719 | 18.152 | 1.00 | 35.11 |
| ATOM | 1415 | C | SER | A | 230 | −10.927 | 51.428 | 18.091 | 1.00 | 39.92 |
| ATOM | 1416 | O | SER | A | 230 | −11.006 | 50.691 | 19.072 | 1.00 | 39.60 |
| ATOM | 1417 | CB | SER | A | 230 | −8.729 | 52.499 | 17.530 | 1.00 | 38.83 |
| ATOM | 1418 | OG | SER | A | 230 | −7.995 | 51.512 | 18.246 | 1.00 | 48.18 |
| ATOM | 1419 | N | PRO | A | 231 | −11.505 | 51.141 | 16.929 | 1.00 | 36.80 |
| ATOM | 1420 | CA | PRO | A | 231 | −12.276 | 49.901 | 16.745 | 1.00 | 35.85 |
| ATOM | 1421 | C | PRO | A | 231 | −11.422 | 48.651 | 17.052 | 1.00 | 39.50 |
| ATOM | 1422 | O | PRO | A | 231 | −11.885 | 47.727 | 17.696 | 1.00 | 36.98 |
| ATOM | 1423 | CB | PRO | A | 231 | −12.650 | 49.932 | 15.247 | 1.00 | 37.27 |
| ATOM | 1424 | CG | PRO | A | 231 | −12.341 | 51.346 | 14.780 | 1.00 | 41.37 |
| ATOM | 1425 | CD | PRO | A | 231 | −11.236 | 51.822 | 15.651 | 1.00 | 36.83 |
| ATOM | 1426 | N | GLU | A | 232 | −10.172 | 48.648 | 16.604 | 1.00 | 37.24 |
| ATOM | 1427 | CA | GLU | A | 232 | −9.291 | 47.511 | 16.838 | 1.00 | 37.76 |
| ATOM | 1428 | C | GLU | A | 232 | −9.043 | 47.271 | 18.327 | 1.00 | 45.46 |
| ATOM | 1429 | O | GLU | A | 232 | −8.968 | 46.123 | 18.767 | 1.00 | 44.87 |
| ATOM | 1430 | CB | GLU | A | 232 | −7.967 | 47.640 | 16.053 | 1.00 | 38.53 |
| ATOM | 1431 | CG | GLU | A | 232 | −6.957 | 48.640 | 16.639 | 1.00 | 44.10 |
| ATOM | 1432 | CD | GLU | A | 232 | −6.985 | 50.001 | 15.937 | 1.00 | 51.28 |
| ATOM | 1433 | OE1 | GLU | A | 232 | −8.009 | 50.332 | 15.318 | 1.00 | 29.96 |
| ATOM | 1434 | OE2 | GLU | A | 232 | −5.980 | 50.735 | 16.007 | 1.00 | 44.19 |
| ATOM | 1435 | N | ARG | A | 233 | −8.949 | 48.358 | 19.102 | 1.00 | 43.38 |
| ATOM | 1436 | CA | ARG | A | 233 | −8.749 | 48.257 | 20.552 | 1.00 | 43.35 |
| ATOM | 1437 | C | ARG | A | 233 | −10.021 | 47.800 | 21.247 | 1.00 | 47.40 |
| ATOM | 1438 | O | ARG | A | 233 | −9.974 | 47.072 | 22.243 | 1.00 | 46.20 |
| ATOM | 1439 | CB | ARG | A | 233 | −8.322 | 49.601 | 21.137 | 1.00 | 42.86 |
| ATOM | 1440 | CG | ARG | A | 233 | −6.823 | 49.771 | 21.205 | 1.00 | 50.67 |
| ATOM | 1441 | CD | ARG | A | 233 | −6.440 | 50.890 | 22.160 | 1.00 | 57.63 |
| ATOM | 1442 | NE | ARG | A | 233 | −6.588 | 50.493 | 23.558 | 1.00 | 59.57 |
| ATOM | 1443 | CZ | ARG | A | 233 | −6.216 | 51.286 | 24.585 | 1.00 | 69.16 |
| ATOM | 1444 | NH1 | ARG | A | 233 | −5.886 | 52.525 | 24.369 | 1.00 | 52.85 |
| ATOM | 1445 | NH2 | ARG | A | 233 | −6.467 | 50.842 | 25.826 | 1.00 | 52.70 |
| ATOM | 1446 | N | LEU | A | 234 | −11.160 | 48.256 | 20.737 | 1.00 | 44.85 |
| ATOM | 1447 | CA | LEU | A | 234 | −12.447 | 47.880 | 21.300 | 1.00 | 45.64 |
| ATOM | 1448 | C | LEU | A | 234 | −12.785 | 46.419 | 20.915 | 1.00 | 52.91 |
| ATOM | 1449 | O | LEU | A | 234 | −13.633 | 45.779 | 21.535 | 1.00 | 52.33 |
| ATOM | 1450 | CB | LEU | A | 234 | −13.542 | 48.826 | 20.782 | 1.00 | 45.43 |
| ATOM | 1451 | CG | LEU | A | 234 | −13.533 | 50.266 | 21.305 | 1.00 | 49.54 |
| ATOM | 1452 | CD1 | LEU | A | 234 | −14.682 | 51.051 | 20.711 | 1.00 | 49.16 |
| ATOM | 1453 | CD2 | LEU | A | 234 | −13.602 | 50.287 | 22.834 | 1.00 | 52.87 |
| ATOM | 1454 | N | GLN | A | 235 | −12.114 | 45.512 | 19.888 | 1.00 | 51.72 |
| ATOM | 1455 | CA | GLN | A | 235 | −12.374 | 44.565 | 19.398 | 1.00 | 52.72 |
| ATOM | 1456 | C | GLN | A | 235 | −11.426 | 43.516 | 19.982 | 1.00 | 60.13 |
| ATOM | 1457 | O | GLN | A | 235 | −11.466 | 42.356 | 19.597 | 1.00 | 59.38 |
| ATOM | 1458 | CB | GLN | A | 235 | −12.324 | 44.539 | 17.868 | 1.00 | 53.75 |
| ATOM | 1459 | CG | GLN | A | 235 | −13.687 | 44.555 | 17.197 | 1.00 | 69.87 |
| ATOM | 1460 | CD | GLN | A | 235 | −13.634 | 44.069 | 15.754 | 1.00 | 95.11 |
| ATOM | 1461 | OE1 | GLN | A | 235 | −12.564 | 44.017 | 15.140 | 1.00 | 91.03 |
| ATOM | 1462 | NE2 | GLN | A | 235 | −14.796 | 43.719 | 15.203 | 1.00 | 88.72 |
| ATOM | 1463 | N | GLY | A | 236 | −10.574 | 43.936 | 20.910 | 1.00 | 59.96 |
| ATOM | 1464 | CA | GLY | A | 236 | −9.639 | 43.019 | 21.555 | 1.00 | 61.15 |
| ATOM | 1465 | C | GLY | A | 236 | −8.354 | 42.834 | 20.751 | 1.00 | 68.92 |
| ATOM | 1466 | O | GLY | A | 236 | −7.333 | 42.403 | 21.290 | 1.00 | 69.16 |
| ATOM | 1467 | N | THR | A | 237 | −8.407 | 43.144 | 19.463 | 1.00 | 67.94 |
| ATOM | 1468 | CA | THR | A | 237 | −7.228 | 43.032 | 18.616 | 1.00 | 68.89 |
| ATOM | 1469 | C | THR | A | 237 | −6.137 | 43.936 | 19.183 | 1.00 | 75.83 |
| ATOM | 1470 | O | THR | A | 237 | −6.351 | 45.144 | 19.344 | 1.00 | 75.75 |
| ATOM | 1471 | CB | THR | A | 237 | −7.532 | 43.460 | 17.178 | 1.00 | 77.60 |
| ATOM | 1472 | OG1 | THR | A | 237 | −8.237 | 42.411 | 16.506 | 1.00 | 78.51 |
| ATOM | 1473 | CG2 | THR | A | 237 | −6.245 | 43.766 | 16.426 | 1.00 | 76.85 |
| ATOM | 1474 | N | HIS | A | 238 | −4.986 | 43.352 | 19.521 | 1.00 | 73.93 |
| ATOM | 1475 | CA | HIS | A | 238 | −3.887 | 44.130 | 20.097 | 1.00 | 74.36 |
| ATOM | 1476 | C | HIS | A | 229 | −3.575 | 45.370 | 19.264 | 1.00 | 76.04 |
| ATOM | 1477 | O | HIS | A | 238 | −3.492 | 45.311 | 18.031 | 1.00 | 75.72 |
| ATOM | 1478 | CB | HIS | A | 238 | −2.625 | 43.268 | 20.333 | 1.00 | 75.91 |
| ATOM | 1479 | CG | HIS | A | 238 | −1.960 | 43.530 | 21.651 | 1.00 | 80.14 |
| ATOM | 1480 | ND1 | HIS | A | 238 | −2.670 | 43.704 | 22.822 | 1.00 | 82.36 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 1481 | CD2 | HIS | A | 238 | −0.654 | 43.689 | 21.978 | 1.00 | 82.54 |
|------|------|-----|-----|---|-----|--------|--------|--------|------|-------|
| ATOM | 1482 | CE1 | HIS | A | 238 | −1.829 | 43.940 | 23.815 | 1.00 | 82.09 |
| ATOM | 1483 | NE2 | HIS | A | 238 | −0.599 | 43.935 | 23.330 | 1.00 | 82.40 |
| ATOM | 1484 | N | TYR | A | 239 | −3.460 | 46.503 | 19.944 | 1.00 | 70.51 |
| ATOM | 1485 | CA | TYR | A | 239 | −3.259 | 47.777 | 19.276 | 1.00 | 69.01 |
| ATOM | 1486 | C | TYR | A | 239 | −1.816 | 48.266 | 19.257 | 1.00 | 67.50 |
| ATOM | 1487 | O | TYR | A | 239 | −0.927 | 47.662 | 19.853 | 1.00 | 66.93 |
| ATOM | 1488 | CB | TYR | A | 239 | −4.144 | 48.832 | 19.928 | 1.00 | 70.69 |
| ATOM | 1489 | CG | TYR | A | 239 | −3.972 | 48.932 | 21.432 | 1.00 | 73.42 |
| ATOM | 1490 | CD1 | TYR | A | 239 | −4.546 | 47.991 | 22.284 | 1.00 | 75.70 |
| ATOM | 1491 | CD2 | TYR | A | 239 | −3.275 | 49.992 | 22.001 | 1.00 | 74.16 |
| ATOM | 1492 | CE1 | TYR | A | 239 | −4.409 | 48.096 | 23.659 | 1.00 | 76.81 |
| ATOM | 1493 | CE2 | TYR | A | 239 | −3.129 | 50.100 | 23.367 | 1.00 | 75.10 |
| ATOM | 1494 | CZ | TYR | A | 239 | −3.692 | 49.153 | 24.193 | 1.00 | 82.68 |
| ATOM | 1495 | OH | TYR | A | 239 | −3.538 | 49.271 | 25.553 | 1.00 | 83.99 |
| ATOM | 1496 | N | SER | A | 240 | −1.611 | 49.395 | 18.587 | 1.00 | 59.79 |
| ATOM | 1497 | CA | SER | A | 240 | −0.307 | 50.035 | 18.518 | 1.00 | 57.27 |
| ATOM | 1498 | C | SER | A | 240 | −0.505 | 51.546 | 18.566 | 1.00 | 55.43 |
| ATOM | 1499 | O | SER | A | 240 | −1.543 | 52.027 | 19.012 | 1.00 | 54.14 |
| ATOM | 1500 | CB | SER | A | 240. | 0.415 | 49.642 | 17.233 | 1.00 | 59.80 |
| ATOM | 1501 | OG | SER | A | 240 | 0.005 | 50.456 | 16.155 | 1.00 | 65.92 |
| ATOM | 1502 | N | VAL | A | 241 | 0.485 | 52.288 | 18.087 | 1.00 | 49.05 |
| ATOM | 1503 | CA | VAL | A | 241 | 0.385 | 53.736 | 18.048 | 1.00 | 47.75 |
| ATOM | 1504 | C | VAL | A | 241 | −0.740 | 54.145 | 17.106 | 1.00 | 47.36 |
| ATOM | 1505 | O | VAL | A | 241 | −1.328 | 55.217 | 17.257 | 1.00 | 46.67 |
| ATOM | 1506 | CB | VAL | A | 241 | 1.705 | 54.387 | 17.595 | 1.00 | 52.45 |
| ATOM | 1507 | CG1 | VAL | A | 241 | 1.684 | 55.909 | 17.889 | 1.00 | 52.31 |
| ATOM | 1508 | CH2 | VAL | A | 241 | 2.897 | 53.714 | 18.303 | 1.00 | 52.56 |
| ATOM | 1509 | N | GLN | A | 242 | −1.052 | 53.271 | 16.149 | 1.00 | 40.50 |
| ATOM | 1510 | CA | GLN | A | 242 | −2.118 | 53.539 | 15.194 | 1.00 | 38.87 |
| ATOM | 1511 | C | GLN | A | 242 | −3.403 | 53.901 | 15.938 | 1.00 | 40.18 |
| ATOM | 1512 | O | GLN | A | 242 | −4.141 | 54.775 | 15.514 | 1.00 | 39.96 |
| ATOM | 1513 | CB | GLN | A | 242 | −2.356 | 52.321 | 14.287 | 1.00 | 39.85 |
| ATOM | 1514 | CG | GLN | A | 242 | −1.248 | 52.065 | 13.274 | 1.00 | 45.36 |
| ATOM | 1515 | CD | GLN | A | 242 | −0.879 | 53.307 | 12.469 | 1.00 | 59.35 |
| ATOM | 1516 | OE1 | GLN | A | 242 | 0.027 | 54.053 | 12.838 | 1.00 | 51.36 |
| ATOM | 1517 | NE2 | GLN | A | 242 | −1.543 | 53.495 | 11.329 | 1.00 | 49.91 |
| ATOM | 1518 | N | SER | A | 243 | −3.654 | 53.219 | 17.052 | 1.00 | 34.99 |
| ATOM | 1519 | CA | SER | A | 243 | −4.835 | 53.475 | 17.867 | 1.00 | 33.85 |
| ATOM | 1520 | C | SER | A | 243 | −4.884 | 54.901 | 18.456 | 1.00 | 36.12 |
| ATOM | 1521 | O | SER | A | 243 | −5.962 | 55.438 | 18.698 | 1.00 | 35.52 |
| ATOM | 1522 | CB | SER | A | 243 | −4.945 | 52.438 | 18.963 | 1.00 | 37.92 |
| ATOM | 1523 | OG | SER | A | 243 | −4.323 | 51.246 | 18.546 | 1.00 | 51.67 |
| ATOM | 1524 | N | ASP | A | 244 | −3.715 | 55.504 | 18.669 | 1.00 | 31.88 |
| ATOM | 1525 | CA | ASP | A | 244 | −3.626 | 56.877 | 19.187 | 1.00 | 30.94 |
| ATOM | 1526 | C | ASP | A | 244 | −4.009 | 57.867 | 18.070 | 1.00 | 34.54 |
| ATOM | 1527 | O | ASP | A | 244 | −4.624 | 58.906 | 18.309 | 1.00 | 33.66 |
| ATOM | 1528 | CB | ASP | A | 244 | −2.197 | 57.162 | 19.674 | 1.00 | 31.88 |
| ATOM | 1529 | CG | ASP | A | 244 | −1.895 | 56.512 | 21.016 | 1.00 | 36.68 |
| ATOM | 1530 | OD1 | ASP | A | 244 | −2.849 | 56.143 | 21.745 | 1.00 | 35.28 |
| ATOM | 1531 | OD2 | ASP | A | 244 | −0.708 | 56.382 | 21.350 | 1.00 | 41.96 |
| ATOM | 1532 | N | ILE | A | 245 | −3.666 | 57.510 | 16.842 | 1.00 | 31.35 |
| ATOM | 1533 | CA | ILE | A | 245 | −3.976 | 58.340 | 15.688 | 1.00 | 30.40 |
| ATOM | 1534 | C | ILE | A | 245 | −5.483 | 58.407 | 15.452 | 1.00 | 32.16 |
| ATOM | 1535 | O | ILE | A | 245 | −6.035 | 59.463 | 15.110 | 1.00 | 31.42 |
| ATOM | 1536 | CB | ILE | A | 245 | −3.222 | 57.849 | 14.449 | 1.00 | 33.34 |
| ATOM | 1537 | CG1 | ILE | A | 245 | −1.738 | 58.314 | 14.544 | 1.00 | 33.05 |
| ATOM | 1538 | CG2 | ILE | A | 245 | −3.932 | 58.324 | 13.121 | 1.00 | 33.28 |
| ATOM | 1539 | CD1 | ILE | A | 245 | −0.801 | 57.603 | 13.595 | 1.00 | 33.32 |
| ATOM | 1540 | N | TRP | A | 246 | −6.158 | 57.301 | 15.714 | 1.00 | 28.46 |
| ATOM | 1541 | CA | TRP | A | 246 | −7.603 | 57.256 | 15.572 | 1.00 | 28.53 |
| ATOM | 1542 | C | TRP | A | 246 | −8.208 | 58.220 | 16.602 | 1.00 | 32.05 |
| ATOM | 1543 | O | TRP | A | 246 | −9.080 | 59.032 | 16.280 | 1.00 | 31.70 |
| ATOM | 1544 | CB | TRP | A | 246 | −8.128 | 55.827 | 15.829 | 1.00 | 27.72 |
| ATOM | 1545 | CG | TRP | A | 246 | −9.574 | 55.796 | 16.232 | 1.00 | 29.11 |
| ATOM | 1546 | CD1 | TRP | A | 246 | −10.095 | 56.086 | 17.471 | 1.00 | 32.27 |
| ATOM | 1547 | CD2 | TSP | A | 246 | −10.693 | 55.599 | 15.368 | 1.00 | 29.44 |
| ATOM | 1548 | NE1 | TRP | A | 246 | −11.467 | 36.038 | 17.431 | 1.00 | 31.92 |
| ATOM | 1549 | CE2 | TRP | A | 246 | −11.861 | 55.728 | 16.155 | 1.00 | 33.49 |
| ATOM | 1550 | CE3 | TRP | A | 246 | −10.826 | 55.258 | 14.015 | 1.00 | 30.85 |
| ATOM | 1551 | CZ2 | TRP | A | 246 | −13.135 | 55.569 | 15.629 | 1.00 | 32.92 |
| ATOM | 1552 | CZ3 | TRP | A | 246 | −12.102 | 55.107 | 13.494 | 1.00 | 32.55 |
| ATOM | 1553 | CH2 | TRP | A | 246 | −13.236 | 55.288 | 14.291 | 1.00 | 33.24 |
| ATOM | 1554 | N | SER | A | 247 | −7.763 | 58.085 | 17.852 | 1.00 | 28.17 |
| ATOM | 1555 | CA | SER | A | 247 | −8.271 | 58.910 | 18.955 | 1.00 | 27.59 |
| ATOM | 1556 | C | SER | A | 247 | −8.065 | 60.381 | 18.661 | 1.00 | 30.51 |
| ATOM | 1557 | O | SER | A | 247 | −8.915 | 61.215 | 18.991 | 1.00 | 30.51 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 1558 | CB  | SER | A | 247 | −7.578  | 58.525 | 20.269 | 1.00 | 29.89 |
|------|------|-----|-----|---|-----|---------|--------|--------|------|-------|
| ATOM | 1559 | OG  | SER | A | 247 | −7.830  | 57.158 | 20.536 | 1.00 | 35.32 |
| ATOM | 1560 | N   | MET | A | 248 | −6.936  | 60.700 | 18.040 | 1.00 | 26.41 |
| ATOM | 1561 | CA  | MET | A | 248 | −6.652  | 62.067 | 17.671 | 1.00 | 25.98 |
| ATOM | 1562 | C   | MET | A | 248 | −7.641  | 62.495 | 16.621 | 1.00 | 29.06 |
| ATOM | 1563 | O   | MET | A | 248 | −8.221  | 63.563 | 16.712 | 1.00 | 29.04 |
| ATOM | 1564 | CB  | MET | A | 248 | −5.230  | 62.225 | 17.122 | 1.00 | 27.89 |
| ATOM | 1565 | CG  | MET | A | 248 | −4.929  | 63.665 | 16.657 | 1.00 | 30.64 |
| ATOM | 1566 | SD  | MET | A | 248 | −3.339  | 63.842 | 15.852 | 1.00 | 34.02 |
| ATOM | 1567 | CE  | MET | A | 248 | −3.631  | 62.889 | 14.317 | 1.00 | 30.31 |
| ATOM | 1568 | N   | GLY | A | 249 | −7.826  | 61.655 | 15.606 | 1.00 | 25.78 |
| ATOM | 1569 | CA  | GLY | A | 249 | −8.757  | 61.973 | 14.521 | 1.00 | 25.42 |
| ATOM | 1570 | C   | GLY | A | 249 | −10.150 | 62.268 | 15.070 | 1.00 | 29.91 |
| ATOM | 1571 | O   | GLY | A | 249 | −10.793 | 63.246 | 14.681 | 1.00 | 30.39 |
| ATOM | 1572 | N   | LEU | A | 250 | −10.602 | 61.420 | 15.981 | 1.00 | 26.99 |
| ATOM | 1573 | CA  | LEU | A | 250 | −11.933 | 61.549 | 16.585 | 1.00 | 27.07 |
| ATOM | 1574 | C   | LEU | A | 250 | −12.033 | 62.815 | 17.442 | 1.00 | 29.50 |
| ATOM | 1575 | O   | LEU | A | 250 | −13.004 | 63.552 | 17.361 | 1.00 | 27.76 |
| ATOM | 1576 | CB  | LEU | A | 250 | −12.261 | 60.292 | 17.421 | 1.00 | 27.00 |
| ATOM | 1577 | CG  | LEU | A | 250 | −13.670 | 60.258 | 18.037 | 1.00 | 32.57 |
| ATOM | 1578 | CD1 | LEU | A | 250 | −14.707 | 60.568 | 16.973 | 1.00 | 33.97 |
| ATOM | 1579 | CD2 | LEU | A | 250 | −13.966 | 58.942 | 18.716 | 1.00 | 33.08 |
| ATOM | 1580 | N   | SER | A | 251 | −11.006 | 63.065 | 18.244 | 1.00 | 27.23 |
| ATOM | 1581 | CA  | SER | A | 251 | −10.952 | 64.284 | 19.078 | 1.00 | 26.54 |
| ATOM | 1582 | C   | SER | A | 251 | −10.960 | 65.534 | 18.192 | 1.00 | 29.01 |
| ATOM | 1583 | O   | SER | A | 251 | −11.556 | 66.554 | 18.550 | 1.00 | 27.52 |
| ATOM | 1584 | CB  | SER | A | 251 | −9.698  | 64.272 | 19.972 | 1.00 | 27.98 |
| ATOM | 1585 | OG  | SER | A | 251 | −9.671  | 63.087 | 20.759 | 1.00 | 32.73 |
| ATOM | 1586 | N   | LEU | A | 252 | −10.312 | 65.450 | 17.027 | 1.00 | 26.00 |
| ATOM | 1587 | CA  | LEU | A | 252 | −10.292 | 65.589 | 16.109 | 1.00 | 26.53 |
| ATOM | 1588 | C   | LEU | A | 252 | −11.683 | 66.903 | 15.537 | 1.00 | 30.23 |
| ATOM | 1589 | O   | LEU | A | 252 | −12.065 | 68.068 | 15.414 | 1.00 | 29.42 |
| ATOM | 1590 | CB  | LEU | A | 252 | −9.283  | 66.384 | 14.963 | 1.00 | 26.52 |
| ATOM | 1591 | CG  | LEU | A | 252 | −7.803  | 66.507 | 15.338 | 1.00 | 30.98 |
| ATOM | 1592 | CD1 | LEU | A | 252 | −6.892  | 66.046 | 14.172 | 1.00 | 30.25 |
| ATOM | 1593 | CD2 | LEU | A | 252 | −7.466  | 67.950 | 15.790 | 1.00 | 31.66 |
| ATOM | 1594 | N   | VAL | A | 253 | −12.423 | 65.872 | 15.152 | 1.00 | 27.03 |
| ATOM | 1595 | CA  | VAL | A | 253 | −13.766 | 66.101 | 14.587 | 1.00 | 26.19 |
| ATOM | 1596 | C   | VAL | A | 253 | −14.699 | 66.643 | 15.650 | 1.00 | 30.13 |
| ATOM | 1597 | O   | VAL | A | 253 | −15.451 | 67.578 | 15.403 | 1.00 | 31.28 |
| ATOM | 1598 | CB  | VAL | A | 253 | −14.353 | 64.831 | 13.959 | 1.00 | 29.46 |
| ATOM | 1599 | CG1 | VAL | A | 253 | −15.819 | 65.089 | 13.457 | 1.00 | 29.05 |
| ATOM | 1600 | CG2 | VAL | A | 253 | −13.462 | 64.346 | 12.825 | 1.00 | 28.45 |
| ATOM | 1601 | N   | GLU | A | 254 | −14.596 | 66.114 | 16.863 | 1.00 | 26.03 |
| ATOM | 1602 | CA  | GLU | A | 254 | −15.421 | 66.611 | 17.941 | 1.00 | 25.78 |
| ATOM | 1603 | C   | GLU | A | 254 | −15.183 | 68.104 | 18.153 | 1.00 | 31.56 |
| ATOM | 1604 | O   | GLU | A | 254 | −16.131 | 68.885 | 18.355 | 1.00 | 32.14 |
| ATOM | 1605 | CB  | GLU | A | 254 | −15.125 | 65.888 | 19.234 | 1.00 | 26.92 |
| ATOM | 1606 | CG  | GLU | A | 254 | −15.704 | 66.624 | 20.459 | 1.00 | 29.75 |
| ATOM | 1607 | CD  | GLU | A | 254 | −15.620 | 65.820 | 21.725 | 1.00 | 36.66 |
| ATOM | 1608 | OE1 | GLU | A | 254 | −15.090 | 64.700 | 21.686 | 1.00 | 36.73 |
| ATOM | 1609 | OE2 | GLU | A | 254 | −16.096 | 66.301 | 22.765 | 1.00 | 29.17 |
| ATOM | 1610 | N   | MET | A | 255 | −13.910 | 68.487 | 18.175 | 1.00 | 27.63 |
| ATOM | 1611 | CA  | MET | A | 255 | −13.518 | 69.874 | 18.395 | 1.00 | 27.41 |
| ATOM | 1612 | C   | MET | A | 255 | −13.949 | 70.793 | 17.246 | 1.00 | 29.26 |
| ATOM | 1613 | O   | MET | A | 255 | −14.322 | 71.938 | 17.473 | 1.00 | 27.94 |
| ATOM | 1614 | CB  | MET | A | 255 | −12.009 | 69.961 | 18.628 | 1.00 | 29.69 |
| ATOM | 1615 | CG  | MET | A | 255 | −11.576 | 69.397 | 19.994 | 1.00 | 33.36 |
| ATOM | 1616 | SD  | MET | A | 255 | −9.852  | 69.651 | 20.354 | 1.00 | 37.59 |
| ATOM | 1617 | CE  | MET | A | 255 | −9.111  | 68.408 | 19.265 | 1.00 | 33.60 |
| ATOM | 1618 | N   | ALA | A | 256 | −13.897 | 70.276 | 16.020 | 1.00 | 25.00 |
| ATOM | 1619 | CA  | ALA | A | 256 | −14.291 | 71.043 | 14.835 | 1.00 | 25.44 |
| ATOM | 1620 | C   | ALA | A | 256 | −15.820 | 71.212 | 14.743 | 1.00 | 30.83 |
| ATOM | 1621 | O   | ALA | A | 256 | −16.245 | 72.260 | 14.273 | 1.00 | 29.78 |
| ATOM | 1622 | CB  | ALA | A | 256 | −13.802 | 70.329 | 13.550 | 1.00 | 25.63 |
| ATOM | 1623 | N   | VAL | A | 257 | −16.620 | 70.325 | 15.124 | 1.00 | 29.53 |
| ATOM | 1624 | CA  | VAL | A | 257 | −18.06.8| 70.444 | 15.007 | 1.00 | 30.69 |
| ATOM | 1625 | C   | VAL | A | 257 | −18.766 | 70.850 | 16.294 | 1.00 | 35.95 |
| ATOM | 1626 | O   | VAL | A | 257 | −19.939 | 71.222 | 16.279 | 1.00 | 35.13 |
| ATOM | 1627 | CB  | VAL | A | 257 | −18.705 | 69.169 | 14.411 | 1.00 | 34.67 |
| ATOM | 1628 | CG1 | VAL | A | 257 | −17.972 | 68.769 | 13.127 | 1.00 | 34.21 |
| ATOM | 1629 | CG2 | VAL | A | 257 | −18.668 | 68.045 | 15.407 | 1.00 | 34.38 |
| ATOM | 1630 | N   | GLY | A | 258 | −18.025 | 70.801 | 17.405 | 1.00 | 33.58 |
| ATOM | 1631 | CA  | GLY | A | 258 | −18.563 | 71.251 | 18.688 | 1.00 | 33.74 |
| ATOM | 1632 | C   | GLY | A | 258 | −19.330 | 70.199 | 19.476 | 1.00 | 38.14 |
| ATOM | 1633 | O   | GLY | A | 258 | −20.055 | 70.526 | 20.405 | 1.00 | 36.93 |
| ATOM | 1634 | N   | ARG | A | 259 | −19.141 | 68.936 | 19.135 | 1.00 | 36.15 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 1635 | CA | ARG | A | 259 | −19.812 | 67.878 | 19.869 | 1.00 | 36.18 |
| --- | --- | --- | --- | --- | --- | --- | --- | --- | --- | --- |
| ATOM | 1636 | C | ARG | A | 259 | −19.217 | 66.525 | 19.542 | 1.00 | 38.38 |
| ATOM | 1637 | O | ARG | A | 259 | −18.666 | 66.329 | 18.457 | 1.00 | 36.60 |
| ATOM | 1638 | CB | ARG | A | 259 | −21.315 | 67.895 | 19.554 | 1.00 | 38.19 |
| ATOM | 1629 | CG | ARG | A | 259 | −21.924 | 66.531 | 19.383 | 1.00 | 49.32 |
| ATOM | 1640 | CD | ARG | A | 259. | −23.076 | 66.562 | 18.415 | 1.00 | 62.68 |
| ATOM | 1641 | NE | ARG | A | 259 | −22.901 | 65.572 | 17.359 | 1.00 | 74.91 |
| ATOM | 1642 | CZ | ARG | A | 259. | −23.803 | 64.659 | 17.035 | 1.00 | 85.18 |
| ATOM | 1643 | NH1 | ARG | A | 259. | −24.960 | 64.620 | 17.667 | 1.00 | 69.94 |
| ATOM | 1644 | NR2 | ARG | A | 259 | −23.552 | 63.796 | 16.068 | 1.00 | 76.65 |
| ATOM | 1645 | N | TYR | A | 260 | −19.307 | 65.592 | 20.490 | 1.00 | 35.77 |
| ATOM | 1646 | CA | TYR | A | 260 | −18.822 | 64.237 | 20.249 | 1.00 | 35.90 |
| ATOM | 1647 | C | TYR | A | 260. | −19.586 | 63.750 | 19.013 | 1.00 | 40.56 |
| ATOM | 1648 | O | TYR | A | 260 | −20.813 | 63.763 | 18.993 | 1.00 | 39.41 |
| ATOM | 1649 | CB | TYR | A | 260 | −19.094 | 63.348 | 21.458 | 1.00 | 36.83 |
| ATOM | 1650 | CG | TYR | A | 260 | −18.638 | 61.913 | 21.285 | 1.00 | 38.79 |
| ATOM | 1651 | CD1 | TYR | A | 260 | −17.290 | 61.574 | 21.346 | 1.00 | 39.93 |
| ATOM | 1652 | CD2 | TYR | A | 260 | −19.560 | 60.896 | 21.051 | 1.00 | 29.66 |
| ATOM | 1653 | CE1 | TYR | A | 260 | −16.879 | 60.261 | 21.190 | 1.00 | 38.61 |
| ATOM | 1654 | CE2 | TYR | A | 260 | −19.152 | 59.588 | 20.885 | 1.00 | 40.44 |
| ATOM | 1655 | CZ | TYR | A | 260 | −17.809 | 59.276 | 20.977 | 1.00 | 44.25 |
| ATOM | 1656 | OH | TYR | A | 260 | −17.410 | 57.961 | 20.840 | 1.00 | 41.29 |
| ATOM | 1657 | N | PRO | A | 261 | −18.840 | 63.408 | 17.964 | 1.00 | 39.07 |
| ATOM | 1658 | CA | PRO | A | 261 | −19.399 | 63.102 | 16.651 | 1.00 | 38.60 |
| ATOM | 1659 | C | PRO | A | 261 | −20.077 | 61.752 | 16.365 | 1.00 | 44.14 |
| ATOM | 1660 | O | PRO | A | 261 | −20.385 | 61.455 | 15.217 | 1.00 | 44.61 |
| ATOM | 1661 | CB | PRO | A | 261 | −18.206 | 63.304 | 15.726 | 1.00 | 39.80 |
| ATOM | 1662 | CG | PRO | A | 261 | −17.021 | 62.915 | 16.561 | 1.00 | 44.28 |
| ATOM | 1663 | CD | PRO | A | 261 | −17.386 | 63.156 | 18.014 | 1.00 | 39.82 |
| ATOM | 1664 | N | ILE | A | 262 | −20.306 | 60.942 | 17.383 | 1.00 | 41.56 |
| ATOM | 1665 | CA | ILE | A | 262 | −20.987 | 59.654 | 17.190 | 1.00 | 41.57 |
| ATOM | 1666 | C | ILE | A | 262 | −22.195 | 59.578 | 18.110 | 1.00 | 45.98 |
| ATOM | 1667 | O | ILE | A | 262 | −22.070 | 59.753 | 19.314 | 1.00 | 45.22 |
| ATOM | 1668 | CB | ILE | A | 262 | −20.070 | 58.453 | 17.518 | 1.00 | 44.60 |
| ATOM | 1669 | CG1 | ILE | A | 262 | −18.826 | 58.467 | 16.648 | 1.00 | 44.38 |
| ATOM | 1670 | CG2 | ILE | A | 262 | −20.819 | 57.146 | 17.312 | 1.00 | 45.37 |
| ATOM | 1671 | CD1 | ILE | A | 262 | −17.772 | 57.508 | 17.110 | 1.00 | 46.80 |
| ATOM | 1672 | N | PRO | A | 263 | −23.370 | 59.326 | 17.535 | 1.00 | 43.93 |
| ATOM | 1673 | CA | PRO | A | 263 | −23.499 | 59.119 | 16.103 | 1.00 | 43.68 |
| ATOM | 1674 | C | PRO | A | 263 | −23.433 | 60.454 | 15.266 | 1.00 | 48.14 |
| ATOM | 1675 | O | PRO | A | 263 | −23.609 | 61.505 | 15.962 | 1.00 | 46.93 |
| ATOM | 1676 | CB | PRO | A | 263 | −24.891 | 58.509 | 15.977 | 1.00 | 45.35 |
| ATOM | 1677 | CG | PRO | A | 263 | −25.683 | 59.147 | 17.109 | 1.00 | 49.50 |
| ATOM | 1678 | CD | PRO | A | 263 | −24.671 | 59.621 | 18.161 | 1.00 | 44.77 |
| ATOM | 1679 | N | PRO | A | 264 | −23.173 | 60.400 | 14.066 | 1.00 | 46.61 |
| ATOM | 1680 | CA | PRO | A | 264 | −23.042 | 61.612 | 13.252 | 1.00 | 46.86 |
| ATOM | 1681 | C | PRO | A | 254 | −24.264 | 52.538 | 13.279 | 1.00 | 53.95 |
| ATOM | 1682 | O | PRO | A | 264 | −25.401 | 62.083 | 13.399 | 1.00 | 53.34 |
| ATOM | 1683 | CB | PRO | A | 264 | −22.819 | 61.061 | 11.838 | 1.00 | 47.89 |
| ATOM | 1684 | CG | PRO | A | 264 | −23.286 | 59.700 | 11.864 | 1.00 | 51.83 |
| ATOM | 1685 | CD | PRO | A | 264 | −23.177 | 59.178 | 13.245 | 1.00 | 47.08 |
| ATOM | 1686 | N | PRO | A | 265 | −24.010 | 63.838 | 13.160 | 1.00 | 52.74 |
| ATOM | 1687 | CA | PRO | A | 265 | −25.073 | 64.850 | 13.132 | 1.00 | 53.09 |
| ATOM | 1688 | C | PRO | A | 265 | −25.841 | 64.772 | 11.806 | 1.00 | 60.33 |
| ATOM | 1689 | O | PRO | A | 265 | −25.285 | 64.400 | 10.777 | 1.00 | 59.31 |
| ATOM | 1690 | CB | PRO | A | 265 | −24.302 | 66.1.79 | 13.191 | 1.00 | 54.28 |
| ATOM | 1691 | CG | PRO | A | 265 | −22.954 | 65.830 | 13.751 | 1.00 | 58.50 |
| ATOM | 1692 | CD | PRO | A | 265 | −22.669 | 64.436 | 13.283 | 1.00 | 53.59 |
| ATOM | 1693 | N | ASP | A | 266 | −27.117 | 65.144 | 11.841 | 1.00 | 60.41 |
| ATOM | 1694 | CA | ASP | A | 266 | −27.963 | 65.110 | 10.651 | 1.00 | 61.49 |
| ATOM | 1695 | C | ASP | A | 266 | −27.787 | 66.366 | 9.821 | 1.00 | 66.58 |
| ATOM | 1696 | O | ASP | A | 266 | −27.154 | 67.330 | 10.261 | 1.00 | 66.08 |
| ATOM | 1697 | CB | ASP | A | 266 | −29.436 | 64.970 | 11.048 | 1.00 | 63.72 |
| ATOM | 1698 | CG | ASP | A | 266 | −29.690 | 63.751 | 11.907 | 1.00 | 78.58 |
| ATOM | 1699 | OD1 | ASP | A | 266 | −28.795 | 62.873 | 11.976 | 1.00 | 79.20 |
| ATOM | 1700 | OD2 | ASP | A | 266 | −30.776 | 63.676 | 12.525 | 1.00 | 86.02 |
| ATOM | 1701 | N | ALA | A | 267 | −28.366 | 66.363 | 8.625 | 1.00 | 63.90 |
| ATOM | 1702 | CA | ALA | A | 267 | −28.304 | 67.534 | 7.766 | 1.00 | 63.92 |
| ATOM | 1703 | C | ALA | A | 267 | −28.931 | 68.691 | 8.533 | 1.00 | 67.67 |
| ATOM | 1704 | O | ALA | A | 267 | −28.522 | 69.840 | 8.393 | 1.00 | 67.07 |
| ATOM | 1705 | CB | ALA | A | 267 | −29.063 | 67.278 | 6.464 | 1.00 | 64.69 |
| ATOM | 1706 | N | LYS | A | 268 | −29.900 | 68.355 | 9.384 | 1.00 | 64.48 |
| ATOM | 1707 | CA | LYS | A | 268 | −30.604 | 69.333 | 10.198 | 1.00 | 64.15 |
| ATOM | 1708 | C | LYS | A | 268 | −29.739 | 69.885 | 11.319 | 1.00 | 67.40 |
| ATOM | 1709 | O | LYS | A | 268 | −29.734 | 71.092 | 11.570 | 1.00 | 67.40 |
| ATOM | 1710 | CB | LYS | A | 268 | −31.880 | 68.725 | 10.770 | 1.00 | 67.32 |
| ATOM | 1711 | CG | LYS | A | 268 | −31.718 | 68.102 | 12.152 | 1.00 | 84.28 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 1712 | CD  | LYS | A | 268 | −32.990 | 67.365 | 12.573 | 1.00 | 94.08  |
|------|------|-----|-----|---|-----|---------|--------|--------|------|--------|
| ATOM | 1713 | CE  | LYS | A | 268 | −34.172 | 66.322 | 12.700 | 1.00 | 103.24 |
| ATOM | 1714 | NZ  | LYS | A | 268 | −35.413 | 67.771 | 12.083 | 1.00 | 111.76 |
| ATOM | 1715 | N   | GLU | A | 269 | −29.019 | 69.003 | 12.009 | 1.00 | 62.84  |
| ATOM | 1716 | CA  | GLU | A | 269 | −28.131 | 69.437 | 13.088 | 1.00 | 61.93  |
| ATOM | 1717 | C   | GLU | A | 269 | −26.991 | 70.251 | 12.479 | 1.00 | 63.49  |
| ATOM | 1718 | O   | GLU | A | 269 | −26.614 | 71.306 | 12.993 | 1.00 | 62.30  |
| ATOM | 1719 | CB  | GLU | A | 269 | −27.569 | 68.231 | 13.843 | 1.00 | 63.48  |
| ATOM | 1720 | CG  | GLU | A | 269 | −28.626 | 67.262 | 14.358 | 1.00 | 74.79  |
| ATOM | 1721 | CD  | GLU | A | 269 | −28.021 | 65.961 | 14.861 | 1.00 | 92.79  |
| ATOM | 1722 | OE1 | GLU | A | 269 | −27.204 | 66.017 | 15.808 | 1.00 | 88.58  |
| ATOM | 1723 | OE2 | GLU | A | 269 | −28.334 | 64.891 | 14.287 | 1.00 | 77.62  |
| ATOM | 1724 | N   | LEU | A | 270 | −26.471 | 69.758 | 11.361 | 1.00 | 58.98  |
| ATOM | 1725 | CA  | LEU | A | 270 | −25.404 | 70.428 | 10.638 | 1.00 | 58.49  |
| ATOM | 1726 | C   | LEU | A | 270 | −25.863 | 71.815 | 10.186 | 1.00 | 62.27  |
| ATOM | 1727 | O   | LEU | A | 270 | −25.095 | 72.782 | 10.223 | 1.00 | 61.09  |
| ATOM | 1728 | CB  | LEU | A | 270 | −24.986 | 69.589 | 9.435  | 1.00 | 58.44  |
| ATOM | 1729 | CG  | LEU | A | 270 | −24.163 | 68.353 | 9.793  | 1.00 | 62.55  |
| ATOM | 1730 | CD1 | LEU | A | 270 | −23.951 | 67.478 | 8.558  | 1.00 | 62.54  |
| ATOM | 1731 | CD2 | LEU | A | 270 | −22.836 | 68.778 | 10.401 | 1.00 | 64.10  |
| ATOM | 1732 | N   | GLU | A | 271 | −27.128 | 71.905 | 9.785  | 1.00 | 59.44  |
| ATOM | 1733 | CA  | GLU | A | 271 | −27.717 | 73.173 | 9.366  | 1.00 | 59.49  |
| ATOM | 1734 | C   | GLU | A | 271 | −27.735 | 74.136 | 10.556 | 1.00 | 62.32  |
| ATOM | 1735 | O   | GLU | A | 271 | −27.354 | 75.293 | 10.439 | 1.00 | 62.12  |
| ATOM | 1736 | CB  | GLU | A | 271 | −29.146 | 72.954 | 8.844  | 1.00 | 60.96  |
| ATOM | 1737 | CG  | GLU | A | 271 | −29.992 | 74.226 | 8.769  | 1.00 | 73.96  |
| ATOM | 1738 | CD  | GLU | A | 271 | −31.472 | 73.950 | 9.001  | 1.00 | 101.22 |
| ATOM | 1739 | OE1 | GLU | A | 271 | −32.099 | 73.290 | 8.150  | 1.00 | 98.41  |
| ATOM | 1740 | OE2 | GLU | A | 271 | −32.006 | 74.410 | 10.039 | 1.00 | 98.47  |
| ATOM | 1741 | N   | LEU | A | 272 | −28.160 | 73.637 | 11.703 | 1.00 | 58.03  |
| ATOM | 1742 | CA  | LEU | A | 272 | −28.199 | 74.447 | 12.907 | 1.00 | 57.77  |
| ATOM | 1743 | C   | LEU | A | 272 | −26.779 | 74.818 | 13.331 | 1.00 | 59.99  |
| ATOM | 1744 | O   | LEU | A | 272 | −26.511 | 75.960 | 13.706 | 1.00 | 59.33  |
| ATOM | 1745 | CB  | LEU | A | 272 | −28.891 | 73.679 | 14.035 | 1.00 | 58.10  |
| ATOM | 1746 | CG  | LEU | A | 272 | −30.163 | 72.928 | 13.634 | 1.00 | 63.45  |
| ATOM | 1747 | CD1 | LEU | A | 272 | −30.641 | 72.0.07| 14.762 | 1.00 | 63.53  |
| ATOM | 1748 | CD2 | LEU | A | 272 | −31.266 | 73.915 | 13.220 | 1.00 | 66.21  |
| ATOM | 1749 | N   | MET | A | 273 | −25.875 | 73.837 | 13.261 | 1.00 | 55.25  |
| ATOM | 1750 | CA  | MET | A | 273 | −24.476 | 74.019 | 13.651 | 1.00 | 53.69  |
| ATOM | 1751 | C   | MET | A | 273 | −23.723 | 75.038 | 12.787 | 1.00 | 55.73  |
| ATOM | 1752 | O   | MET | A | 273 | −23.147 | 75.987 | 13.307 | 1.00 | 55.38  |
| ATOM | 1753 | CB  | MET | A | 273 | −23.736 | 72.677 | 13.632 | 1.00 | 55.85  |
| ATOM | 1754 | CG  | MET | A | 273 | −24.264 | 71.650 | 14.623 | 1.00 | 59.42  |
| ATOM | 1755 | SD  | MET | A | 273 | −23.500 | 70.011 | 14.427 | 1.00 | 63.42  |
| ATOM | 1756 | CE  | MET | A | 273 | −22.468 | 69.922 | 15.906 | 1.00 | 59.92  |
| ATOM | 1757 | N   | PHE | A | 274 | −23.713 | 74.827 | 11.472 | 1.00 | 50.90  |
| ATOM | 1758 | CA  | PHE | A | 274 | −22.971 | 75.713 | 10.576 | 1.00 | 50.32  |
| ATOM | 1759 | C   | PHE | A | 274 | −23.824 | 76.546 | 9.627  | 1.00 | 57.45  |
| ATOM | 1760 | O   | PHE | A | 274 | −23.288 | 77.347 | 8.843  | 1.00 | 56.78  |
| ATOM | 1761 | CB  | PHE | A | 274 | −21.950 | 74.919 | 9.761  | 1.00 | 51.11  |
| ATOM | 1762 | CG  | PHE | A | 274 | −20.992 | 74.132 | 10.592 | 1.00 | 51.46  |
| ATOM | 1763 | CD1 | PHE | A | 274 | −21.342 | 72.885 | 11.086 | 1.00 | 54.02  |
| ATOM | 1764 | CD2 | PHE | A | 274 | −19.725 | 74.622 | 10.859 | 1.00 | 52.22  |
| ATOM | 1765 | CE1 | PHE | A | 274 | −20.450 | 72.152 | 11.845 | 1.00 | 54.29  |
| ATOM | 1766 | CE2 | PHE | A | 274 | −18.828 | 73.888 | 11.602 | 1.00 | 54.59  |
| ATOM | 1767 | CZ  | PHE | A | 274 | −19.187 | 72.656 | 12.096 | 1.00 | 52.63  |
| ATOM | 1768 | N   | GLY | A | 275 | −25.142 | 76.342 | 9.659  | 1.00 | 55.99  |
| ATOM | 1769 | CA  | GLY | A | 275 | −26.047 | 77.080 | 8.769  | 1.00 | 56.10  |
| ATOM | 1770 | C   | GLY | A | 275 | −25.828 | 76.677 | 7.311  | 1.00 | 60.59  |
| ATOM | 1771 | O   | GLY | A | 275 | −26.018 | 77.486 | 6.405  | 1.00 | 61.02  |
| ATOM | 1772 | N   | GYS | A | 276 | −25.293 | 75.475 | 7.104  | 1.00 | 56.87  |
| ATOM | 1773 | N   | PRO | A | 306 | −30.043 | 59.289 | 23.161 | 1.00 | 66.36  |
| ATOM | 1774 | CA  | PRO | A | 306 | −29.058 | 59.326 | 24.238 | 1.00 | 65.46  |
| ATOM | 1775 | C   | PRO | A | 306 | −28.332 | 57.989 | 24.345 | 1.00 | 68.29  |
| ATOM | 1776 | O   | PRO | A | 306 | −28.357 | 57.343 | 25.394 | 1.00 | 68.58  |
| ATOM | 1777 | CB  | PRO | A | 306 | −29.916 | 59.550 | 25.484 | 1.00 | 67.13  |
| ATOM | 1778 | CG  | PRO | A | 306 | −31.140 | 60.213 | 24.983 | 1.00 | 71.71  |
| ATOM | 1779 | CD  | PRO | A | 306 | −31.396 | 59.607 | 23.644 | 1.00 | 67.06  |
| ATOM | 1780 | N   | MET | A | 307 | −27.694 | 57.583 | 23.247 | 1.00 | 62.75  |
| ATOM | 1781 | CA  | MET | A | 307 | −26.963 | 56.314 | 23.160 | 1.00 | 61.62  |
| ATOM | 1782 | C   | MET | A | 307 | −26.172 | 55.925 | 24.415 | 1.00 | 63.02  |
| ATOM | 1783 | O   | MET | A | 307 | −25.235 | 56.618 | 24.810 | 1.00 | 62.32  |
| ATOM | 1784 | CB  | MET | A | 307 | −26.016 | 56.345 | 21.960 | 1.00 | 63.94  |
| ATOM | 1785 | CG  | MET | A | 307 | −26.242 | 55.246 | 20.952 | 1.00 | 67.38  |
| ATOM | 1786 | SD  | MET | A | 307 | −25.201 | 53.451 | 19.491 | 1.00 | 71.36  |
| ATOM | 1787 | CE  | MET | A | 307 | −24.735 | 53.790 | 19.187 | 1.00 | 67.99  |
| ATOM | 1788 | N   | ALA | A | 308 | −26.528 | 54.786 | 25.007 | 1.00 | 57.80  |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 1769 | CA  | ALA | A | 308 | −25.798 | 54.272 | 26.162 | 1.00 | 56.71 |
|------|------|-----|-----|---|-----|---------|--------|--------|------|-------|
| ATOM | 1790 | C   | ALA | A | 308 | −24.398 | 53.876 | 25.694 | 1.00 | 58.37 |
| ATOM | 1791 | O   | ALA | A | 308 | −24.201 | 53.548 | 24.523 | 1.00 | 57.57 |
| ATOM | 1792 | CB  | ALA | A | 308 | −26.522 | 53.072 | 26.756 | 1.00 | 57.42 |
| ATOM | 1793 | N   | ILE | A | 309 | −23.426 | 53.935 | 26.601 | 1.00 | 53.88 |
| ATOM | 1794 | CA  | ILE | A | 309 | −22.036 | 53.631 | 26.265 | 1.00 | 52.75 |
| ATOM | 1795 | C   | ILE | A | 309 | −21.855 | 52.334 | 25.469 | 1.00 | 52.93 |
| ATOM | 1796 | O   | ILE | A | 309 | −21.141 | 52.315 | 24.464 | 1.00 | 52.33 |
| ATOM | 1797 | CB  | ILE | A | 309 | −21.115 | 53.631 | 27.517 | 1.00 | 56.34 |
| ATOM | 1798 | CG1 | ILE | A | 309 | −20.528 | 55.023 | 27.743 | 1.00 | 57.29 |
| ATOM | 1799 | CG2 | ILE | A | 309 | −19.982 | 52.645 | 27.343 | 1.00 | 57.35 |
| ATOM | 1800 | CD1 | ILE | A | 309 | −19.806 | 55.182 | 29.090 | 1.00 | 70.09 |
| ATOM | 1801 | N   | PHE | A | 310 | −22.499 | 51.257 | 25.906 | 1.00 | 46.64 |
| ATOM | 1802 | CA  | PHE | A | 310 | −22.361 | 49.971 | 25.205 | 1.00 | 44.69 |
| ATOM | 1803 | C   | PHE | A | 310 | −22.802 | 50.047 | 23.744 | 1.00 | 46.18 |
| ATOM | 1804 | O   | PHE | A | 310 | −22.213 | 49.407 | 22.878 | 1.00 | 44.43 |
| ATOM | 1805 | CB  | PHE | A | 310 | −23.069 | 48.828 | 25.946 | 1.00 | 46.18 |
| ATOM | 1806 | CG  | PHE | A | 310 | −24.354 | 49.232 | 26.609 | 1.00 | 47.70 |
| ATOM | 1807 | CD1 | PHE | A | 310 | −25.567 | 49.078 | 25.952 | 1.00 | 51.45 |
| ATOM | 1808 | CD2 | PHE | A | 310 | −24.357 | 49.717 | 2.7.905 | 1.00 | 49.97 |
| ATOM | 1809 | CE1 | PHE | A | 310 | −26.761 | 49.436 | 26.564 | 1.00 | 52.42 |
| ATOM | 1810 | CE2 | PHE | A | 310 | −25.544 | 50.078 | 28.527 | 1.00 | 53.08 |
| ATOM | 1811 | CZ  | PHE | A | 310 | −26.752 | 49.929 | 27.854 | 1.00 | 51.29 |
| ATOM | 1812 | N   | GLU | A | 311 | −23.817 | 50.857 | 23.472 | 1.00 | 43.03 |
| ATOM | 1813 | CA  | GLU | A | 311 | −24.305 | 51.041 | 22.101 | 1.00 | 42.77 |
| ATOM | 1814 | C   | GLU | A | 311 | −23.200 | 51.875 | 21.322 | 1.00 | 45.59 |
| ATOM | 1815 | O   | GLU | A | 311 | −22.963 | 51.572 | 20.176 | 1.00 | 44.69 |
| ATOM | 1816 | CB  | GLU | A | 311 | −25.664 | 51.741 | 22.119 | 1.00 | 44.30 |
| ATOM | 1817 | CG  | GLU | A | 311 | −26.746 | 50.964 | 22.870 | 1.00 | 54.76 |
| ATOM | 1818 | CD  | GLU | A | 311 | −27.945 | 51.828 | 23.244 | 1.00 | 71.29 |
| ATOM | 1819 | OE1 | GLU | A | 311 | −27.795 | 53.065 | 23.306 | 1.00 | 62.64 |
| ATOM | 1820 | OE2 | GLU | A | 311 | −29.030 | 51.265 | 23.491 | 1.00 | 62.80 |
| ATOM | 1821 | N   | LEU | A | 312 | −22.793 | 52.908 | 21.976 | 1.00 | 42.45 |
| ATOM | 1822 | CA  | LEU | A | 312 | −21.797 | 53.768 | 21.383 | 1.00 | 42.51 |
| ATOM | 1823 | C   | LEU | A | 312 | −20.583 | 52.940 | 20.924 | 1.00 | 46.58 |
| ATOM | 1824 | O   | LEU | A | 312 | −20.150 | 53.029 | 19.771 | 1.00 | 46.36 |
| ATOM | 1825 | CB  | LEU | A | 312 | −21.368 | 54.814 | 22.412 | 1.00 | 42.78 |
| ATOM | 1826 | CG  | LEU | A | 312 | −20.790 | 56.116 | 21.887 | 1.00 | 47.55 |
| ATOM | 1827 | CD1 | LEU | A | 312 | −20.374 | 56.990 | 23.066 | 1.00 | 47.28 |
| ATOM | 1828 | CD2 | LEU | A | 312 | −19.610 | 55.823 | 20.981 | 1.00 | 50.44 |
| ATOM | 1829 | N   | LEU | A | 313 | −20.058 | 52.110 | 21.820 | 1.00 | 42.46 |
| ATOM | 1830 | CA  | LEU | A | 313 | −18.904 | 51.278 | 21.481 | 1.00 | 41.95 |
| ATOM | 1831 | C   | LEU | A | 313 | −19.233 | 50.306 | 20.345 | 1.00 | 44.63 |
| ATOM | 1832 | O   | LEU | A | 313 | −18.397 | 50.025 | 19.495 | 1.00 | 43.26 |
| ATOM | 1833 | CB  | LEU | A | 313 | −18.378 | 50.538 | 22.723 | 1.00 | 41.76 |
| ATOM | 1834 | CG  | LEU | A | 313 | −18.056 | 51.464 | 23.900 | 1.00 | 45.89 |
| ATOM | 1835 | CD1 | LEU | A | 313 | −17.488 | 50.699 | 25.073 | 1.00 | 45.61 |
| ATOM | 1836 | CD2 | LEU | A | 313 | −17.092 | 52.571 | 23.462 | 1.00 | 48.84 |
| ATOM | 1837 | N   | ASP | A | 314 | −20.462 | 49.812 | 20.329 | 1.00 | 42.55 |
| ATOM | 1838 | CA  | ASP | A | 314 | −20.900 | 48.920 | 19.261 | 1.00 | 42.99 |
| ATOM | 1839 | C   | ASP | A | 314 | −20.916 | 49.684 | 17.931 | 1.00 | 47.01 |
| ATOM | 1840 | O   | ASP | A | 314 | −20.417 | 49.199 | 16.920 | 1.00 | 47.11 |
| ATOM | 1841 | CB  | ASP | A | 314 | −22.288 | 48.372 | 19.562 | 1.00 | 45.41 |
| ATOM | 1842 | CG  | ASP | A | 314 | −22.696 | 47.275 | 18.602 | 1.00 | 60.70 |
| ATOM | 1843 | OD1 | ASP | A | 314 | −21.841 | 46.430 | 18.269 | 1.00 | 61.48 |
| ATOM | 1844 | OD2 | ASP | A | 314 | −23.865 | 47.271 | 18.163 | 1.00 | 70.17 |
| ATOM | 1845 | N   | TYR | A | 315 | −21.464 | 50.895 | 17.960 | 1.00 | 43.63 |
| ATOM | 1846 | CA  | TYR | A | 315 | −21.517 | 51.762 | 16.778 | 1.00 | 43.64 |
| ATOM | 1847 | C   | TYR | A | 315 | −20.119 | 51.954 | 16.208 | 1.00 | 46.45 |
| ATOM | 1848 | O   | TYR | A | 315 | −19.885 | 51.728 | 15.023 | 1.00 | 46.41 |
| ATOM | 1849 | CB  | TYR | A | 315 | −22.117 | 53.131 | 17.151 | 1.00 | 45.86 |
| ATOM | 1850 | CG  | TYR | A | 315 | −22.630 | 53.936 | 15.960 | 1.00 | 49.31 |
| ATOM | 1851 | CD1 | TYR | A | 315 | −21.780 | 54.766 | 15.234 | 1.00 | 51.35 |
| ATOM | 1852 | CD2 | TYR | A | 315 | −23.963 | 53.848 | 15.556 | 1.00 | 50.62 |
| ATOM | 1853 | CE1 | TYR | A | 315 | −22.236 | 55.486 | 14.141 | 1.00 | 52.66 |
| ATOM | 1854 | CE2 | TYR | A | 315 | −24.434 | 54.568 | 14.456 | 1.00 | 91.60 |
| ATOM | 1855 | CZ  | TYR | A | 315 | −23.569 | 55.388 | 13.759 | 1.00 | 59.64 |
| ATOM | 1856 | OH  | TYR | A | 315 | −24.030 | 56.107 | 12.669 | 1.00 | 60.21 |
| ATOM | 1857 | N   | ILE | A | 316 | −19.184 | 52.363 | 17.066 | 1.00 | 41.52 |
| ATOM | 1858 | CA  | ILE | A | 316 | −17.806 | 52.593 | 16.648 | 1.00 | 40.92 |
| ATOM | 1859 | C   | ILE | A | 316 | −17.229 | 51.358 | 15.964 | 1.00 | 44.59 |
| ATOM | 1860 | O   | ILE | A | 316 | −16.472 | 51.464 | 14.996 | 1.00 | 42.91 |
| ATOM | 1861 | CB  | ILE | A | 316 | −16.910 | 52.972 | 17.856 | 1.00 | 44.02 |
| ATOM | 1862 | CG1 | ILE | A | 316 | −17.305 | 54.359 | 15.400 | 1.00 | 44.48 |
| ATOM | 1863 | CG2 | ILE | A | 316 | −15.425 | 52.901 | 17.477 | 1.00 | 43.74 |
| ATOM | 1864 | CD1 | ILE | A | 316 | −16.822 | 54.635 | 19.814 | 1.00 | 47.18 |
| ATOM | 1865 | N   | VAL | A | 317 | −17.577 | 50.183 | 16.475 | 1.00 | 41.43 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 1866 | CA | VAL | A | 317 | −17.058 | 48.949 | 15.910 | 1.00 | 40.89 |
|---|---|---|---|---|---|---|---|---|---|---|
| ATOM | 1867 | C | VAL | A | 317 | −17.739 | 48.547 | 14.613 | 1.00 | 44.22 |
| ATOM | 1868 | O | VAL | A | 317 | −17.094 | 48.053 | 13.708 | 1.00 | 44.19 |
| ATOM | 1869 | CB | VAL | A | 317 | −17.151 | 47.757 | 16.918 | 1.00 | 44.34 |
| ATOM | 1870 | CG1 | VAL | A | 317 | −16.682 | 46.450 | 16.242 | 1.00 | 44.07 |
| ATOM | 1871 | CG2 | VAL | A | 317 | −16.308 | 48.039 | 18.156 | 1.00 | 43.79 |
| ATOM | 1872 | N | ASN | A | 318 | −19.045 | 48.757 | 14.529 | 1.00 | 40.40 |
| ATOM | 1873 | CA | ASN | A | 318 | −19.800 | 48.282 | 13.371 | 1.00 | 40.57 |
| ATOM | 1874 | C | ASN | A | 318 | −20.216 | 49.270 | 12.292 | 1.00 | 44.87 |
| ATOM | 1875 | O | ASN | A | 318 | −20.663 | 48.858 | 11.224 | 1.00 | 44.87 |
| ATOM | 1876 | CB | ASN | A | 318 | −20.988 | 47.435 | 13.823 | 1.00 | 39.31 |
| ATOM | 1877 | CG | ASN | A | 318 | −20.562 | 46.280 | 14.683 | 1.00 | 53.13 |
| ATOM | 1878 | OD1 | ASN | A | 318 | −19.736 | 45.463 | 14.268 | 1.00 | 51.50 |
| ATOM | 1879 | ND2 | ASN | A | 318 | −20.972 | 46.301 | 15.933 | 1.00 | 42.17 |
| ATOM | 1880 | N | GLU | A | 319 | −20.084 | 50.563 | 12.566 | 1.00 | 40.57 |
| ATOM | 1881 | CA | GLU | A | 319 | −20.462 | 51.579 | 11.595 | 1.00 | 39.79 |
| ATOM | 1882 | C | GLU | A | 319 | −19.237 | 52.212 | 10.954 | 1.00 | 43.04 |
| ATOM | 1883 | O | GLU | A | 319 | −18.118 | 52.041 | 11.434 | 1.00 | 41.89 |
| ATOM | 1854 | CB | GLU | A | 319 | −21.327 | 52.659 | 12.257 | 1.00 | 40.96 |
| ATOM | 1885 | CG | GLU | A | 319 | −22.703 | 52.159 | 12.706 | 1.00 | 49.50 |
| ATOM | 1886 | CD | GLU | A | 319 | −23.481 | 51.475 | 11.578 | 1.00 | 71.27 |
| ATOM | 1887 | OE1 | GLU | A | 319 | −23.642 | 52.086 | 10.501 | 1.00 | 65.80 |
| ATOM | 1888 | OE2 | GLU | A | 319 | −23.928 | 50.326 | 11.770 | 1.00 | 64.37 |
| ATOM | 1889 | N | PRO | A | 320 | −19.453 | 52.947 | 9.862 | 1.00 | 39.92 |
| ATOM | 1890 | CA | PRO | A | 320 | −18.355 | 53.657 | 9.201 | 1.00 | 38.89 |
| ATOM | 1891 | C | PRO | A | 320 | −17.930 | 54.815 | 10.108 | 1.00 | 39.68 |
| ATOM | 1892 | O | PRO | A | 320 | −18.745 | 55.360 | 10.861 | 1.00 | 38.12 |
| ATOM | 1893 | CB | PRO | A | 320 | −19.004 | 54.185 | 7.917 | 1.00 | 40.65 |
| ATOM | 1894 | CG | PRO | A | 320 | −20.125 | 53.209 | 7.649 | 1.00 | 45.36 |
| ATOM | 1895 | CD | PRO | A | 320 | −20.659 | 52.887 | 9.016 | 1.00 | 40.77 |
| ATOM | 1896 | N | PRO | A | 321 | −16.649 | 55.158 | 10.068 | 1.00 | 35.12 |
| ATOM | 1897 | CA | PRO | A | 321 | −16.109 | 56.207 | 10.939 | 1.00 | 34.70 |
| ATOM | 1898 | C | PRO | A | 321 | −16.728 | 57.601 | 10.686 | 1.00 | 38.34 |
| ATOM | 1899 | O | PRO | A | 321 | −17.194 | 57.899 | 9.595 | 1.00 | 36.95 |
| ATOM | 1900 | CB | PRO | A | 321 | −14.619 | 56.209 | 10.591 | 1.00 | 35.89 |
| ATOM | 1901 | CG | PRO | A | 321 | −14.572 | 55.771 | 9.174 | 1.00 | 40.30 |
| ATOM | 1902 | CD | PRO | A | 321 | −15.711 | 54.797 | 8.985 | 1.00 | 35.37 |
| ATOM | 1903 | N | PRO | A | 322 | −16.708 | 58.447 | 11.711 | 1.00 | 35.15 |
| ATOM | 1904 | CA | PRO | A | 322 | −17.221 | 59.810 | 11.578 | 1.00 | 34.54 |
| ATOM | 1905 | C | PRO | A | 322 | −16.390 | 50.583 | 10.549 | 1.00 | 36.66 |
| ATOM | 1906 | O | PRO | A | 322 | −15.270 | 60.190 | 10.193 | 1.00 | 35.07 |
| ATOM | 1907 | CB | PRO | A | 322 | −17.040 | 60.406 | 12.987 | 1.00 | 36.06 |
| ATOM | 1908 | CG | PRO | A | 322 | −16.099 | 59.490 | 13.678 | 1.00 | 40.17 |
| ATOM | 1909 | CD | PRO | A | 322 | −16.280 | 58.147 | 13.086 | 1.00 | 35.02 |
| ATOM | 1910 | N | LYS | A | 323 | −16.958 | 61.667 | 10.065 | 1.00 | 33.12 |
| ATOM | 1911 | CA | LYS | A | 323 | −16.328 | 62.472 | 9.038 | 1.00 | 33.60 |
| ATOM | 1912 | C | LYS | A | 323 | −16.685 | 63.935 | 9.297 | 1.00 | 37.57 |
| ATOM | 1913 | O | LYS | A | 323 | −17.763 | 64.212 | 9.810 | 1.00 | 37.81 |
| ATOM | 1914 | CB | LYS | A | 323 | −16.956 | 62.059 | 7.699 | 1.00 | 36.56 |
| ATOM | 1915 | CG | LYS | A | 323 | −16.117 | 62.255 | 6.493 | 1.00 | 57.81 |
| ATOM | 1916 | CD | LYS | A | 323 | −16.975 | 61.980 | 5.265 | 1.00 | 67.60 |
| ATOM | 1917 | CE | LYS | A | 323 | −18.323 | 61.394 | 5.679 | 1.00 | 72.41 |
| ATOM | 1918 | NZ | LYS | A | 323 | −19.471 | 62.120 | 5.063 | 1.00 | 79.18 |
| ATOM | 1919 | N | LEU | A | 324 | −15.830 | 64.868 | 8.866 | 1.00 | 32.78 |
| ATOM | 1920 | CA | LEU | A | 324 | −16.173 | 66.289 | 8.960 | 1.00 | 31.77 |
| ATOM | 1921 | C | LEU | A | 324 | −17.234 | 66.562 | 7.905 | 1.00 | 37.59 |
| ATOM | 1922 | O | LEU | A | 324 | −17.251 | 65.908 | 6.849 | 1.00 | 37.73 |
| ATOM | 1923 | CB | LEU | A | 324 | −14.930 | 67.176 | 8.639 | 1.00 | 31.06 |
| ATOM | 1924 | CG | LEU | A | 324 | −13.832 | 67.241 | 9.672 | 1.00 | 34.82 |
| ATOM | 1925 | CD1 | LEU | A | 324 | −12.614 | 67.968 | 9.100 | 1.00 | 34.02 |
| ATOM | 1926 | CD2 | LEU | A | 324 | −14.331 | 67.875 | 10.988 | 1.00 | 36.00 |
| ATOM | 1927 | N | PRO | A | 325 | −18.075 | 67.570 | 8.141 | 1.00 | 34.87 |
| ATOM | 1928 | CA | PRO | A | 325 | −19.073 | 67.952 | 7.152 | 1.00 | 34.21 |
| ATOM | 1929 | C | PRO | A | 325 | −18.352 | 68.637 | 5.991 | 1.00 | 38.30 |
| ATOM | 1930 | O | PRO | A | 325 | −17.382 | 69.376 | 6.193 | 1.00 | 37.32 |
| ATOM | 3931 | CB | PRO | A | 325 | −19.944 | 68.967 | 7.905 | 1.00 | 35.96 |
| ATOM | 1932 | CG | PRO | A | 325 | −19.163 | 69.313 | 9.150 | 1.00 | 40.54 |
| ATOM | 1933 | CD | PRO | A | 325 | −18.391 | 66.115 | 9.469 | 1.00 | 35.53 |
| ATOM | 1934 | N | SER | A | 326 | −18.805 | 68.376 | 4.777 | 1.00 | 36.40 |
| ATOM | 1935 | CA | SER | A | 326 | −18.173 | 68.962 | 3.605 | 1.00 | 36.90 |
| ATOM | 1936 | C | SER | A | 326 | −18.557 | 70.426 | 3.461 | 1.00 | 42.28 |
| ATOM | 1937 | O | SER | A | 226 | −19.500 | 70.892 | 4.094 | 1.00 | 42.77 |
| ATOM | 1938 | CB | SER | A | 326 | −18.554 | 68.183 | 2.348 | 1.00 | 40.98 |
| ATOM | 1939 | OG | SER | A | 326 | −19.892 | 68.429 | 1.986 | 1.00 | 50.24 |
| ATOM | 1940 | N | GLY | A | 327 | −17.807 | 71.156 | 2.648. | 1.00 | 39.14 |
| ATOM | 1941 | CA | GLY | A | 327 | −18.121 | 72.563 | 2.375 | 1.00 | 39.60 |
| ATOM | 1942 | C | GLY | A | 327 | −17.789 | 73.598 | 3.466 | 1.00 | 44.11 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 1943 | O | GLY | A | 327 | −17.784 | 74.797 | 3.195 | 1.00 | 45.55 |
|---|---|---|---|---|---|---|---|---|---|---|
| ATOM | 1944 | N | VAL | A | 328 | −17.535 | 73.153 | 4.690 | 1.00 | 38.22 |
| ATOM | 1945 | CA | VAL | A | 328 | −17.236 | 74.102 | 5.771 | 1.00 | 36.90 |
| ATOM | 1946 | C | VAL | A | 328 | −15.800 | 74.010 | 6.249 | 1.00 | 37.52 |
| ATOM | 1947 | O | VAL | A | 328 | −15.292 | 74.910 | 6.919 | 1.00 | 36.02 |
| ATOM | 1948 | CB | VAL | A | 328 | −18.234 | 73.991 | 6.946 | 1.00 | 40.77 |
| ATOM | 1949 | CG1 | VAL | A | 328 | −19.589 | 74.481 | 6.511 | 1.00 | 40.46 |
| ATOM | 1950 | CG2 | VAL | A | 328 | −18.327 | 72.568 | 7.441 | 1.00 | 40.61 |
| ATOM | 1951 | N | PHE | A | 329 | −15.135 | 72.921 | 5.862 | 1.00 | 31.60 |
| ATOM | 1952 | CA | PHE | A | 329 | −12.733 | 72.708 | 6.202 | 1.00 | 29.58 |
| ATOM | 1953 | C | PHE | A | 329 | −12.980 | 72.434 | 4.902 | 1.00 | 31.56 |
| ATOM | 1954 | O | PHE | A | 329 | −13.566 | 71.934 | 3.945 | 1.00 | 29.09 |
| ATOM | 1955 | CB | PHE | A | 329 | −13.613 | 71.513 | 7.149 | 1.00 | 30.71 |
| ATOM | 1956 | CG | PHE | A | 329 | −14.246 | 71.751 | 8.495 | 1.00 | 31.66 |
| ATOM | 1957 | CD1 | PHE | A | 329 | −13.597 | 72.523 | 9.453 | 1.00 | 33.13 |
| ATOM | 1958 | CD2 | PHE | A | 329 | −15.515 | 71.252 | 8.786 | 1.00 | 33.12 |
| ATOM | 1959 | CE1 | PHE | A | 329 | −14.170 | 72.763 | 10.677 | 1.00 | 33.81 |
| ATOM | 1960 | CE2 | PHE | A | 329 | −16.113 | 71.516 | 10.013 | 1.00 | 35.49 |
| ATOM | 1961 | CZ | PHE | A | 329 | −15.433 | 72.259 | 10.962 | 1.00 | 33.57 |
| ATOM | 1962 | N | SER | A | 330 | −11.679 | 72.735 | 4.876 | 1.00 | 26.61 |
| ATOM | 1963 | CA | SER | A | 330 | −10.894 | 72.490 | 3.679 | 1.00 | 24.60 |
| ATOM | 1964 | C | SER | A | 330 | −10.857 | 70.995 | 3.368 | 1.00 | 31.01 |
| ATOM | 1965 | O | SER | A | 330 | −11.039 | 70.160 | 4.248 | 1.00 | 30.95 |
| ATOM | 1966 | CB | SER | A | 330 | −9.473 | 73.057 | 3.798 | 1.00 | 23.12 |
| ATOM | 1967 | OG | SER | A | 330 | −8.667 | 72.262 | 4.659 | 1.00 | 27.45 |
| ATOM | 1968 | N | LEU | A | 331 | −10.664 | 70.668 | 2.100 | 1.00 | 28.50 |
| ATOM | 1969 | CA | LEU | A | 331 | −10.577 | 69.279 | 1.683 | 1.00 | 27.67 |
| ATOM | 1970 | C | LEU | A | 331 | −9.361 | 68.642 | 2.326 | 1.00 | 31.77 |
| ATOM | 1971 | O | LEU | A | 331 | −9.382 | 67.463 | 2.675 | 1.00 | 31.97 |
| ATOM | 1972 | CB | LEU | A | 331 | −10.478 | 69.199 | 0.168 | 1.00 | 27.84 |
| ATOM | 1973 | CG | LEU | A | 331 | −11.800 | 69.462 | −0.559 | 1.00 | 33.09 |
| ATOM | 1974 | CD1 | LEU | A | 331 | −11.648 | 69.210 | −2.054 | 1.00 | 33.00 |
| ATOM | 1975 | CD2 | LEU | A | 331 | −12.864 | 68.546 | 0.040 | 1.00 | 36.48 |
| ATOM | 1976 | N | GLU | A | 332 | −8.296 | 69.432 | 2.498 | 1.00 | 28.00 |
| ATOM | 1977 | CA | GLU | A | 332 | −7.060 | 68.935 | 3.136 | 1.00 | 27.28 |
| ATOM | 1978 | C | GLU | A | 332 | −7.278 | 68.529 | 4.576 | 1.00 | 30.11 |
| ATOM | 1979 | O | GLU | A | 332 | −6.782 | 67.471 | 5.019 | 1.00 | 30.82 |
| ATOM | 1980 | CB | GLU | A | 332 | −5.940 | 69.969 | 3.038 | 1.00 | 29.00 |
| ATOM | 1981 | CG | GLU | A | 332 | −5.441 | 70.144 | 1.598 | 1.00 | 38.55 |
| ATOM | 1982 | CD | GLU | A | 332 | −4.458 | 71.272 | 1.444 | 1.00 | 46.99 |
| ATOM | 1983 | OE1 | GLU | A | 332 | −4.484 | 72.197 | 2.273 | 1.00 | 41.37 |
| ATOM | 1984 | OE2 | GLU | A | 332 | −3.694 | 71.260 | 0.455 | 1.00 | 38.31 |
| ATOM | 1985 | N | PHE | A | 333 | −8.021 | 69.352 | 5.319 | 1.00 | 24.30 |
| ATOM | 1986 | CA | PHE | A | 333 | −8.341 | 69.012 | 6.723 | 1.00 | 23.92 |
| ATOM | 1987 | C | PHE | A | 333 | −9.222 | 67.756 | 6.733 | 1.00 | 27.77 |
| ATOM | 1988 | O | PHE | A | 333 | −8.987 | 66.836 | 7.503 | 1.00 | 27.02 |
| ATOM | 1989 | CB | PHE | A | 333 | −9.091 | 70.167 | 7.423 | 1.00 | 25.34 |
| ATOM | 1990 | CG | PHE | A | 333 | −9.321 | 69.936 | 8.903 | 1.00 | 26.39 |
| ATOM | 1991 | CD1 | PHE | A | 333 | −8.435 | 69.142 | 9.651 | 1.00 | 28.35 |
| ATOM | 1992 | CD2 | PHE | A | 333 | −10.405 | 70.523 | 9.554 | 1.00 | 27.27 |
| ATOM | 1993 | CE1 | PHE | A | 333 | −8.622 | 68.951 | 11.012 | 1.00 | 28.73 |
| ATOM | 1994 | CE2 | PHE | A | 333 | −10.617 | 70.318 | 10.907 | 1.00 | 29.37 |
| ATOM | 1995 | CZ | PHE | A | 333 | −9.723 | 69.538 | 11.643 | 1.00 | 27.96 |
| ATOM | 1996 | N | GLN | A | 334 | −10.211 | 67.715 | 5.841 | 1.00 | 25.99 |
| ATOM | 1997 | CA | GLN | A | 334 | −11.115 | 66.552 | 5.740 | 1.00 | 26.52 |
| ATOM | 1998 | C | GLN | A | 334 | −10.347 | 65.262 | 5.427 | 1.00 | 30.07 |
| ATOM | 1999 | O | GLN | A | 334 | −10.600 | 64.199 | 6.020 | 1.00 | 30.62 |
| ATOM | 2000 | CB | GLN | A | 334 | −12.179 | 66.784 | 4.652 | 1.00 | 27.69 |
| ATOM | 2001 | CG | GLN | A | 334 | −13.232 | 67.844 | 4.977 | 1.00 | 25.79 |
| ATOM | 2002 | CD | GLN | A | 334 | −14.139 | 68.144 | 3.765 | 1.00 | 31.23 |
| ATOM | 2003 | OE1 | GLN | A | 334 | −14.851 | 67.273 | 3.284 | 1.00 | 30.92 |
| ATOM | 2004 | NE2 | GLN | A | 334 | −14.039 | 69.350 | 3.232 | 1.00 | 23.72 |
| ATOM | 2005 | N | ASP | A | 335 | −9.428 | 65.350 | 4.483 | 1.00 | 26.02 |
| ATOM | 2006 | CA | ASP | A | 335 | −8.648 | 64.194 | 4.093 | 1.00 | 26.09 |
| ATOM | 2007 | C | ASP | A | 335 | −7.777 | 63.749 | 5.274 | 1.00 | 30.81 |
| ATOM | 2008 | O | ASP | A | 335 | −7.656 | 62.553 | 5.554 | 1.00 | 30.96 |
| ATOM | 2009 | CB | ASP | A | 335 | −7.786 | 64.522 | 2.872 | 1.00 | 27.46 |
| ATOM | 2010 | CG | ASP | A | 335 | −6.974 | 63.319 | 2.380 | 1.00 | 32.21 |
| ATOM | 2011 | OD1 | ASP | A | 335 | −7.592 | 62.349 | 1.873 | 1.00 | 31.78 |
| ATOM | 2012 | OD2 | ASP | A | 335 | −5.721 | 63.387 | 2.436 | 1.00 | 33.06 |
| ATOM | 2013 | N | PHE | A | 336 | −7.175 | 64.722 | 5.959 | 1.00 | 26.96 |
| ATOM | 2014 | CA | PHE | A | 336 | −6.342 | 64.448 | 7.132 | 1.00 | 26.35 |
| ATOM | 2015 | C | PHE | A | 336 | −7.114 | 63.640 | 8.176 | 1.00 | 27.67 |
| ATOM | 2016 | O | PHE | A | 336 | −6.651 | 62.619 | 8.637 | 1.00 | 27.52 |
| ATOM | 2017 | CB | PHE | A | 336 | −5.853 | 55.765 | 7.765 | 1.00 | 28.36 |
| ATOM | 2018 | CG | PHE | A | 336 | −4.995 | 65.565 | 8.990 | 1.00 | 30.33 |
| ATOM | 2019 | CD1 | PHE | A | 335 | −3.632 | 65.300 | 8.866 | 1.00 | 33.04 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 2020 | CD2 | PHE | A | 336 | −5.546 | 65.654 | 10.259 | 1.00 | 31.38 |
|---|---|---|---|---|---|---|---|---|---|---|
| ATOM | 2021 | CE1 | PHE | A | 336 | −2.843 | 65.115 | 9.987 | 1.00 | 33.46 |
| ATOM | 2022 | CE2 | PHE | A | 336 | −4.759 | 65.472 | 11.388 | 1.00 | 34.10 |
| ATOM | 2023 | CZ | PHE | A | 336 | −3.411 | 65.219 | 11.256 | 1.00 | 32.40 |
| ATOM | 2024 | N | VAL | A | 337 | −8.291 | 64.124 | 8.561 | 1.00 | 24.17 |
| ATOM | 2025 | CA | VAL | A | 337 | −9.085 | 63.414 | 9.547 | 1.00 | 25.29 |
| ATOM | 2026 | C | VAL | A | 337 | −9.518 | 62.052 | 9.018 | 1.00 | 29.79 |
| ATOM | 2027 | O | VAL | A | 337 | −9.539 | 61.091 | 9.757 | 1.00 | 27.98 |
| ATOM | 2028 | CB | VAL | A | 337 | −10.324 | 64.227 | 10.044 | 1.00 | 30.06 |
| ATOM | 2029 | CG1 | VAL | A | 337 | −9.887 | 65.549 | 10.707 | 1.00 | 29.67 |
| ATOM | 2030 | CG2 | VAL | A | 337 | −11.282 | 64.475 | 8.930 | 1.00 | 30.23 |
| ATOM | 2031 | N | ASN | A | 338 | −9.823 | 61.978 | 7.718 | 1.00 | 28.40 |
| ATOM | 2032 | CA | ASN | A | 338 | −10.230 | 60.712 | 7.087 | 1.00 | 28.63 |
| ATOM | 2033 | C | ASN | A | 338 | −9.147 | 59.652 | 7.210 | 1.00 | 32.34 |
| ATOM | 2034 | O | ASN | A | 338 | −9.431 | 58.493 | 7.555 | 1.00 | 31.89 |
| ATOM | 2035 | CB | ASN | A | 338 | −10.584 | 60.922 | 5.602 | 1.00 | 27.32 |
| ATOM | 2036 | CG | ASN | A | 338 | −11.990 | 61.482 | 5.417 | 1.00 | 37.97 |
| ATOM | 2037 | OD1 | ASN | A | 338 | −12.745 | 61.597 | 6.372 | 1.00 | 33.44 |
| ATOM | 2038 | ND2 | ASN | A | 338 | −12.346 | 61.794 | 4.193 | 1.00 | 27.86 |
| ATOM | 2039 | N | LYS | A | 339 | −7.907 | 60.041 | 6.944 | 1.00 | 27.59 |
| ATOM | 2040 | CA | LYS | A | 339 | −6.799 | 59.088 | 7.022 | 1.00 | 27.37 |
| ATOM | 2041 | C | LYS | A | 339 | −6.510 | 58.629 | 8.455 | 1.00 | 31.39 |
| ATOM | 2042 | O | LYS | A | 339 | −5.948 | 57.549 | 8.668 | 1.00 | 30.68 |
| ATOM | 2043 | CB | LYS | A | 339 | −5.544 | 59.669 | 6.369 | 1.00 | 29.65 |
| ATOM | 2044 | CG | LYS | A | 339 | −5.572 | 59.625 | 4.839 | 1.00 | 28.82 |
| ATOM | 2045 | CD | LYS | A | 339 | −4.441 | 60.467 | 4.252 | 1.00 | 37.12 |
| ATOM | 2046 | CE | LYS | A | 339 | −4.127 | 60.046 | 2.819 | 1.00 | 36.67 |
| ATOM | 2047 | NZ | LYS | A | 339 | −5.175 | 60.509 | 1.869 | 1.00 | 36.80 |
| ATOM | 2048 | N | CYS | A | 340 | −6.910 | 59.443 | 9.433 | 1.00 | 28.17 |
| ATOM | 2049 | CA | CYS | A | 340 | −6.694 | 59.106 | 10.845 | 1.00 | 28.24 |
| ATOM | 2050 | C | CYS | A | 340 | −7.781 | 58.154 | 11.286 | 1.00 | 32.62 |
| ATOM | 2051 | O | CYS | A | 340 | −7.627 | 57.431 | 12.258 | 1.00 | 31.48 |
| ATOM | 2052 | CB | CYS | A | 340 | −6.808 | 60.371 | 11.733 | 1.00 | 28.31 |
| ATOM | 2053 | SG | CYS | A | 340 | −5.410 | 61.517 | 11.689 | 1.00 | 31.92 |
| ATOM | 2054 | N | LEU | A | 341 | −8.926 | 58.255 | 10.628 | 1.00 | 30.59 |
| ATOM | 2055 | CA | LEU | A | 341 | −10.102 | 57.521 | 11.041 | 1.00 | 31.20 |
| ATOM | 2056 | C | LEU | A | 341 | −10.418 | 56.228 | 10.278 | 1.00 | 35.98 |
| ATOM | 2057 | O | LEU | A | 341 | −11.455 | 55.631 | 10.494 | 1.00 | 36.00 |
| ATOM | 2058 | CB | LEU | A | 341 | −11.310 | 58.450 | 11.068 | 1.00 | 30.96 |
| ATOM | 2059 | CG | LEU | A | 341 | −11.231 | 59.543 | 12.155 | 1.00 | 35.51 |
| ATOM | 2060 | CD1 | LEU | A | 341 | −12.466 | 60.441 | 12.134 | 1.00 | 35.08 |
| ATOM | 2061 | CD2 | LEU | A | 341 | −11.060 | 58.923 | 13.528 | 1.00 | 37.81 |
| ATOM | 2062 | N | ILE | A | 342 | −9.530 | 55.815 | 9.387 | 1.00 | 34.11 |
| ATOM | 2063 | CA | ILE | A | 342 | −9.734 | 54.565 | 8.650 | 1.00 | 35.01 |
| ATOM | 2064 | C | ILE | A | 342 | −9.748 | 53.418 | 9.681 | 1.00 | 41.39 |
| ATOM | 2065 | O | ILE | A | 342 | −8.825 | 53.285 | 10.470 | 1.00 | 41.24 |
| ATOM | 2066 | CB | ILE | A | 342 | −8.618 | 54.351 | 7.620 | 1.00 | 37.83 |
| ATOM | 2067 | CG1 | ILE | A | 342 | −8.830 | 55.279 | 6.416 | 1.00 | 27.19 |
| ATOM | 2068 | CG2 | ILE | A | 342 | −8.534 | 52.862 | 7.192 | 1.00 | 38.50 |
| ATOM | 2069 | CD1 | ILE | A | 342 | −7.588 | 55.618 | 5.688 | 1.00 | 40.07 |
| ATOM | 2070 | N | LYS | A | 343 | −10.851 | 52.677 | 9.736 | 1.00 | 39.60 |
| ATOM | 2071 | CA | LYS | A | 343 | −11.015 | 51.595 | 10.717 | 1.00 | 39.73 |
| ATOM | 2072 | C | LYS | A | 343 | −9.906 | 50.556 | 10.696 | 1.00 | 44.18 |
| ATOM | 2073 | O | LYS | A | 343 | −9.505 | 50.046 | 11.737 | 1.00 | 43.81 |
| ATOM | 2074 | CB | LYS | A | 343 | −12.369 | 50.927 | 10.558 | 1.00 | 42.27 |
| ATOM | 2075 | CG | LYS | A | 343 | −13.533 | 51.891 | 10.607 | 1.00 | 48.55 |
| ATOM | 2076 | CD | LYS | A | 343 | −14.533 | 51.478 | 11.665 | 1.00 | 51.80 |
| ATOM | 2077 | CE | LYS | A | 343 | −15.684 | 50.713 | 11.056 | 1.00 | 51.26 |
| ATOM | 2078 | NZ | LYS | A | 343 | −16.428 | 49.969 | 12.086 | 1.00 | 57.44 |
| ATOM | 2079 | N | ASN | A | 344 | −9.408 | 50.242 | 9.512 | 1.00 | 41.64 |
| ATOM | 2080 | CA | ASN | A | 344 | −8.313 | 49.284 | 9.385 | 1.00 | 41.45 |
| ATOM | 2081 | C | AEN | A | 344 | −6.995 | 49.970 | 9.760 | 1.00 | 43.89 |
| ATOM | 2082 | O | ASN | A | 344 | −6.499 | 50.816 | 9.018 | 1.00 | 43.59 |
| ATOM | 2083 | CB | ASN | A | 344 | −8.238 | 48.752 | 7.949 | 1.00 | 42.23 |
| ATOM | 2084 | CG | ASN | A | 344 | −7.166 | 47.701 | 7.777 | 1.00 | 63.68 |
| ATOM | 2085 | OD1 | ASN | A | 344 | −6.364 | 47.465 | 8.678 | 1.00 | 53.64 |
| ATOM | 2086 | ND2 | ASN | A | 344 | −7.135 | 47.073 | 6.606 | 1.00 | 57.56 |
| ATOM | 2087 | N | PRO | A | 345 | −6.428 | 49.593 | 10.901 | 1.00 | 39.46 |
| ATOM | 2088 | CA | PRO | A | 345 | −5.204 | 50.226 | 11.386 | 1.00 | 39.26 |
| ATOM | 2089 | C | PRO | A | 345 | −4.048 | 50.170 | 10.402 | 1.00 | 45.38 |
| ATOM | 2090 | O | PRO | A | 345 | −3.154 | 51.021 | 10.443 | 1.00 | 44.10 |
| ATOM | 2091 | CB | PRO | A | 345 | −4.867 | 49.432 | 12.680 | 1.00 | 40.47 |
| ATOM | 2092 | CG | PRO | A | 345 | −5.859 | 48.286 | 12.727 | 1.00 | 44.59 |
| ATOM | 2093 | CD | PRO | A | 345 | −7.040 | 48.728 | 11.923 | 1.00 | 39.86 |
| ATOM | 2094 | N | ALA | A | 346 | −4.049 | 49.151 | 9.535 | 1.00 | 43.85 |
| ATOM | 2095 | CA | ALA | A | 346 | −2.980 | 48.979 | 8.546 | 1.00 | 43.74 |
| ATOM | 2096 | C | ALA | A | 346 | −3.069 | 50.012 | 7.425 | 1.00 | 46.66 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 2097 | O | ALA | A | 346 | −2.052 | 50.463 | 6.897 | 1.00 | 46.97 |
|---|---|---|---|---|---|---|---|---|---|---|
| ATOM | 2098 | CB | ALA | A | 345 | −3.008 | 47.565 | 7.972 | 1.00 | 44.71 |
| ATOM | 2099 | N | GLU | A | 347 | −4.292 | 50.394 | 7.076 | 1.00 | 41.94 |
| ATOM | 2100 | CA | GLU | A | 347 | −4.514 | 51.372 | 6.017 | 1.00 | 40.97 |
| ATOM | 2101 | C | GLU | A | 347 | −4.501 | 52.801 | 6.596 | 1.00 | 42.16 |
| ATOM | 2102 | O | GLU | A | 347 | −4.085 | 53.739 | 5.932 | 1.00 | 40.74 |
| ATOM | 2103 | CB | GLU | A | 347 | −5.836 | 51.081 | 5.296 | 1.00 | 42.54 |
| ATOM | 2104 | CG | GLU | A | 347 | −5.725 | 49.987 | 4.242 | 1.00 | 55.16 |
| ATOM | 2105 | CD | GLU | A | 347 | −4.430 | 50.073 | 3.447 | 1.00 | 74.37 |
| ATOM | 2106 | OE1 | GLU | A | 347 | −4.238 | 51.080 | 2.730 | 1.00 | 67.13 |
| ATOM | 2107 | OE2 | GLU | A | 347 | −3.593 | 49.149 | 3.564 | 1.00 | 66.32 |
| ATOM | 2108 | N | ARG | A | 348 | −4.940 | 52.934 | 7.848 | 1.00 | 37.66 |
| ATOM | 2109 | CA | ARG | A | 348 | −4.913 | 54.212 | 8.566 | 1.00 | 36.75 |
| ATOM | 2110 | C | ARG | A | 348 | −3.498 | 54.776 | 8.470 | 1.00 | 41.20 |
| ATOM | 2111 | O | ARG | A | 348 | −2.529 | 54.032 | 8.546 | 1.00 | 41.88 |
| ATOM | 2112 | CB | ARG | A | 348 | −5.263 | 53.966 | 10.042 | 1.00 | 34.15 |
| ATOM | 2113 | CG | ARG | A | 348 | −5.359 | 55.209 | 10.899 | 1.00 | 34.44 |
| ATOM | 2114 | CD | ARG | A | 348 | −5.726 | 54.852 | 12.338 | 1.00 | 34.00 |
| ATOM | 2115 | NE | ARG | A | 348 | −6.909 | 53.982 | 12.414 | 1.00 | 35.16 |
| ATOM | 2116 | CZ | ARG | A | 348 | −7.072 | 53.025 | 13.328 | 1.00 | 46.14 |
| ATOM | 2117 | NH1 | ARG | A | 348 | −6.145 | 52.841 | 14.263 | 1.00 | 33.01 |
| ATOM | 2118 | NH2 | ARG | A | 348 | −8.162 | 52.267 | 13.323 | 1.00 | 32.43 |
| ATOM | 2119 | N | ALA | A | 349 | −3.370 | 56.064 | 8.287 | 1.00 | 37.20 |
| ATOM | 2120 | CA | ALA | A | 349 | −2.039 | 56.686 | 8.179 | 1.00 | 36.49 |
| ATOM | 2121 | C | ALA | A | 349 | −1.228 | 56.559 | 9.474 | 1.00 | 39.33 |
| ATOM | 2122 | O | ALA | A | 349 | −1.794 | 56.423 | 10.565 | 1.00 | 38.24 |
| ATOM | 2123 | CB | ALA | A | 349 | −2.139 | 58.146 | 7.741 | 1.00 | 37.24 |
| ATOM | 2124 | N | ASP | A | 350 | 0.097 | 56.587 | 9.347 | 1.00 | 35.64 |
| ATOM | 2125 | CA | ASP | A | 350 | 0.966 | 56.513 | 10.520 | 1.00 | 35.83 |
| ATOM | 2126 | C | ASP | A | 350 | 1.556 | 57.892 | 10.836 | 1.00 | 38.79 |
| ATOM | 2127 | O | ASP | A | 350 | 1.326 | 58.848 | 10.097 | 1.00 | 38.55 |
| ATOM | 2128 | CB | ASP | A | 350 | 2.066 | 55.434 | 10.360 | 1.00 | 37.60 |
| ATOM | 2129 | CG | ASP | A | 350 | 3.030 | 55.725 | 9.215 | 1.00 | 48.16 |
| ATOM | 2130 | OD1 | ASP | A | 350 | 3.044 | 56.860 | 8.708 | 1.00 | 47.70 |
| ATOM | 2131 | OD2 | ASP | A | 350 | 3.793 | 54.806 | 8.833 | 1.00 | 56.18 |
| ATOM | 2132 | N | LEU | A | 351 | 2.264 | 58.002 | 11.955 | 1.00 | 34.11 |
| ATOM | 2133 | CA | LEU | A | 351 | 2.834 | 59.286 | 12.364 | 1.00 | 33.95 |
| ATOM | 2134 | C | LEU | A | 351 | 3.722 | 59.907 | 11.309 | 1.00 | 38.84 |
| ATOM | 2135 | O | LEU | A | 351 | 3.692 | 61.125 | 11.093 | 1.00 | 39.22 |
| ATOM | 2136 | CB | LEU | A | 351 | 3.585 | 59.166 | 13.702 | 1.00 | 33.75 |
| ATOM | 2137 | CG | LEU | A | 351 | 2.735 | 58.919 | 14.958 | 1.00 | 38.08 |
| ATOM | 2138 | CD1 | LEU | A | 351 | 3.611 | 58.519 | 16.137 | 1.00 | 38.20 |
| ATOM | 2139 | CD2 | LEU | A | 351 | 1.884 | 60.147 | 15.306 | 1.00 | 38.11 |
| ATOM | 2140 | N | LYS | A | 352 | 4.520 | 59.076 | 10.650 | 1.00 | 36.22 |
| ATOM | 2141 | CA | LYS | A | 352 | 5.437 | 59.560 | 9.606 | 1.00 | 35.76 |
| ATOM | 2142 | C | LYS | A | 352 | 4.671 | 60.151 | 8.447 | 1.00 | 37.55 |
| ATOM | 2143 | O | LYS | A | 352 | 5.030 | 61.191 | 7.918 | 1.00 | 37.07 |
| ATOM | 2144 | CB | LYS | A | 352 | 6.319 | 58.410 | 9.102 | 1.00 | 39.45 |
| ATOM | 2145 | CG | LYS | A | 352 | 7.273 | 58.791 | 7.993 | 1.00 | 56.87 |
| ATOM | 2146 | CD | LYS | A | 352 | 8.661 | 58.190 | 8.242 | 1.00 | 68.69 |
| ATOM | 2147 | CE | LYS | A | 352 | 9.582 | 58.400 | 7.057 | 1.00 | 77.61 |
| ATOM | 2148 | NZ | LYS | A | 352 | 10.302 | 59.700 | 7.146 | 1.00 | 88.34 |
| ATOM | 2149 | N | GLN | A | 353 | 3.609 | 59.476 | 8.038 | 1.00 | 33.86 |
| ATOM | 2150 | CA | GLN | A | 353 | 2.819 | 59.955 | 6.906 | 1.00 | 33.54 |
| ATOM | 2151 | C | GLN | A | 353 | 2.061 | 61.245 | 7.275 | 1.00 | 36.10 |
| ATOM | 2152 | O | GLN | A | 353 | 1.992 | 62.189 | 6.489 | 1.00 | 35.26 |
| ATOM | 2153 | CB | GLN | A | 353 | 1.854 | 58.867 | 6.438 | 1.00 | 34.74 |
| ATOM | 2154 | CG | GLN | A | 353 | 2.560 | 57.561 | 6.041 | 1.00 | 45.86 |
| ATOM | 2155 | CD | GLN | A | 353 | 1.593 | 56.408 | 5.800 | 1.00 | 62.98 |
| ATOM | 2156 | OE1 | GLN | A | 353 | 0.505 | 56.368 | 6.362 | 1.00 | 55.37 |
| ATOM | 2157 | NE2 | GLN | A | 353 | 2.004 | 55.457 | 4.971 | 1.00 | 61.58 |
| ATOM | 2158 | N | LEU | A | 354 | 1.526 | 61.279 | 8.491 | 1.00 | 32.23 |
| ATOM | 2159 | CA | LEU | A | 354 | 0.785 | 62.458 | 8.980 | 1.00 | 31.60 |
| ATOM | 2160 | C | LEU | A | 354 | 1.660 | 63.679 | 9.032 | 1.00 | 34.51 |
| ATOM | 2161 | O | LEU | A | 354 | 1.263 | 64.741 | 8.594 | 1.00 | 33.34 |
| ATOM | 2162 | CB | LEU | A | 354 | 0.188 | 62.173 | 10.345 | 1.00 | 31.29 |
| ATOM | 2163 | CG | LEU | A | 354 | −0.977 | 61.194 | 10.251 | 1.00 | 35.33 |
| ATOM | 2164 | CD1 | LEU | A | 354 | −1.534 | 60.864 | 11.640 | 1.00 | 34.91 |
| ATOM | 2165 | CD2 | LEU | A | 354 | −2.075 | 61.769 | 9.332 | 1.00 | 36.32 |
| ATOM | 2166 | N | MET | A | 355 | 2.888 | 63.502 | 9.502 | 1.00 | 33.82 |
| ATOM | 2167 | CA | MET | A | 355 | 3.845 | 64.605 | 9.610 | 1.00 | 34.83 |
| ATOM | 2168 | C | MET | A | 355 | 4.054 | 65.341 | 8.290 | 1.00 | 36.88 |
| ATOM | 2169 | O | MET | A | 355 | 4.3.62 | 66.532 | 8.275 | 1.00 | 36.04 |
| ATOM | 2170 | CB | MET | A | 355 | 5.189 | 64.103 | 10.154 | 1.00 | 38.16 |
| ATOM | 2171 | CG | MET | A | 355 | 5.388 | 64.326 | 11.667 | 1.00 | 43.32 |
| ATOM | 2172 | SD | MET | A | 355 | 5.398 | 66.080 | 12.133 | 1.00 | 48.91 |
| ATOM | 2173 | CE | MET | A | 355 | 3.798 | 66.313 | 12.705 | 1.00 | 46.14 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 2174 | N   | VAL | A | 356 | 3.899  | 64.630 | 7.180  | 1.00 | 32.88 |
|------|------|-----|-----|---|-----|--------|--------|--------|------|-------|
| ATOM | 2175 | CA  | VAL | A | 355 | 4.054  | 65.251 | 5.876  | 1.00 | 32.76 |
| ATOM | 2176 | C   | VAL | A | 356 | 2.735  | 65.374 | 5.110  | 1.00 | 34.11 |
| ATOM | 2177 | O   | VAL | A | 356 | 2.714  | 65.756 | 3.945  | 1.00 | 32.61 |
| ATOM | 2178 | CB  | VAL | A | 356 | 5.133  | 64.571 | 5.039  | 1.00 | 37.75 |
| ATOM | 2179 | CG1 | VAL | A | 356 | 6.524  | 64.840 | 5.664  | 1.00 | 37.83 |
| ATOM | 2180 | CG2 | VAL | A | 356 | 4.860  | 63.052 | 4.922  | 1.00 | 37.35 |
| ATOM | 2181 | N   | HIS | A | 357 | 1.623  | 65.104 | 5.791  | 1.00 | 29.28 |
| ATOM | 2182 | CA  | HIS | A | 357 | 0.326  | 65.263 | 5.147  | 1.00 | 27.92 |
| ATOM | 2183 | C   | HIS | A | 357 | 0.140  | 66.732 | 4.718  | 1.00 | 31.01 |
| ATOM | 2184 | O   | HIS | A | 357 | 0.618  | 67.648 | 5.386  | 1.00 | 30.34 |
| ATOM | 2185 | CB  | HIS | A | 357 | −0.804 | 64.836 | 6.090  | 1.00 | 28.13 |
| ATOM | 2186 | CG  | HIS | A | 357 | −2.145 | 64.829 | 5.441  | 1.00 | 31.16 |
| ATOM | 2187 | ND1 | HIS | A | 357 | −2.857 | 65.988 | 5.192  | 1.00 | 31.95 |
| ATOM | 2188 | CD2 | HIS | A | 357 | −2.872 | 63.815 | 4.909  | 1.00 | 32.33 |
| ATOM | 2189 | CE1 | HIS | A | 357 | −3.974 | 65.681 | 4.558  | 1.00 | 31.29 |
| ATOM | 2190 | NE2 | HIS | A | 357 | −4.017 | 64.369 | 4.390  | 1.00 | 31.70 |
| ATOM | 2191 | N   | ALA | A | 358 | −0.551 | 66.946 | 3.603  | 1.00 | 27.16 |
| ATOM | 2192 | CA  | ALA | A | 358 | −0.800 | 68.295 | 3.092  | 1.00 | 26.83 |
| ATOM | 2193 | C   | ALA | A | 358 | −1.333 | 69.262 | 4.165  | 1.00 | 31.83 |
| ATOM | 2194 | O   | ALA | A | 358 | −0.991 | 70.451 | 4.170  | 1.00 | 31.68 |
| ATOM | 2195 | CB  | ALA | A | 358 | −1.749 | 68.244 | 1.936  | 1.00 | 27.36 |
| ATOM | 2196 | N   | PHE | A | 359 | −2.226 | 68.768 | 5.019  | 1.00 | 27.79 |
| ATOM | 2197 | CA  | PHE | A | 359 | −2.833 | 69.612 | 6.056  | 1.00 | 26.85 |
| ATOM | 2198 | C   | PHE | A | 359 | −1.801 | 70.061 | 7.106  | 1.00 | 32.35 |
| ATOM | 2199 | O   | PHE | A | 359 | −1.810 | 71.202 | 7.560  | 1.00 | 30.27 |
| ATOM | 2200 | CB  | PHE | A | 359 | −3.984 | 68.875 | 6.734  | 1.00 | 27.94 |
| ATOM | 2201 | CG  | PHE | A | 359 | −4.596 | 69.631 | 7.888  | 1.00 | 28.04 |
| ATOM | 2202 | CD1 | PHE | A | 359 | −5.221 | 70.840 | 7.681  | 1.00 | 30.15 |
| ATOM | 2203 | CD2 | PHE | A | 359 | −4.540 | 69.124 | 9.177  | 1.00 | 29.15 |
| ATOM | 2204 | CE1 | PHE | A | 359 | −5.792 | 71.525 | 8.734  | 1.00 | 30.51 |
| ATOM | 2205 | CE2 | PHE | A | 359 | −5.104 | 69.807 | 10.218 | 1.00 | 31.51 |
| ATOM | 2206 | CZ  | PHE | A | 359 | −5.717 | 71.020 | 9.993  | 1.00 | 28.76 |
| ATOM | 2207 | N   | ILE | A | 360 | −0.917 | 69.148 | 7.485  | 1.00 | 30.94 |
| ATOM | 2208 | CA  | ILE | A | 360 | 0.114  | 69.446 | 8.463  | 1.00 | 30.45 |
| ATOM | 2209 | C   | ILE | A | 360 | 1.132  | 70.449 | 7.883  | 1.00 | 36.72 |
| ATOM | 2210 | O   | ILE | A | 360 | 1.453  | 71.473 | 8.506  | 1.00 | 37.01 |
| ATOM | 2211 | CB  | ILE | A | 360 | 0.802  | 68.144 | 8.928  | 1.00 | 32.90 |
| ATOM | 2212 | CH1 | ILE | A | 360 | −0.207 | 67.267 | 9.677  | 1.00 | 32.49 |
| ATOM | 2213 | CG2 | ILE | A | 360 | 2.034  | 68.443 | 9.796  | 1.00 | 33.19 |
| ATOM | 2214 | CD1 | ILE | A | 360 | −0.983 | 68.023 | 10.778 | 1.00 | 30.76 |
| ATOM | 2215 | N   | LYS | A | 361 | 1.587  | 70.176 | 6.668  | 1.00 | 33.66 |
| ATOM | 2216 | CA  | LYS | A | 361 | 2.522  | 71.049 | 5.990  | 1.00 | 33.64 |
| ATOM | 2217 | C   | LYS | A | 361 | 1.950  | 72.450 | 5.800  | 1.00 | 37.50 |
| ATOM | 2218 | O   | LYS | A | 361 | 2.646  | 73.446 | 6.039  | 1.00 | 37.47 |
| ATOM | 2219 | CB  | LYS | A | 361 | 2.954  | 70.443 | 4.655  | 1.00 | 36.32 |
| ATOM | 2220 | CG  | LYS | A | 361 | 4.096  | 69.443 | 4.794  | 1.00 | 51.98 |
| ATOM | 2221 | CD  | LYS | A | 361 | 3.929  | 68.266 | 3.857  | 1.00 | 63.28 |
| ATOM | 2222 | CE  | LYS | A | 361 | 3.567  | 68.713 | 2.448  | 1.00 | 75.48 |
| ATOM | 2223 | NZ  | LYS | A | 361 | 3.909  | 67.668 | 1.447  | 1.00 | 85.72 |
| ATOM | 2224 | N   | ARG | A | 362 | 0.690  | 72.540 | 5.372  | 1.00 | 32.63 |
| ATOM | 2225 | CA  | ARG | A | 362 | 0.040  | 73.863 | 5.232  | 1.00 | 31.96 |
| ATOM | 2226 | C   | ARG | A | 362 | −0.064 | 74.550 | 6.617  | 1.00 | 35.03 |
| ATOM | 2227 | O   | ARG | A | 362 | 0.331  | 75.702 | 6.790  | 1.00 | 34.72 |
| ATOM | 2228 | CB  | ARG | A | 362 | −1.361 | 73.718 | 4.629  | 1.00 | 30.62 |
| ATOM | 2229 | CG  | ARG | A | 362 | −2.072 | 75.353 | 4.341  | 1.00 | 33.57 |
| ATOM | 2230 | CD  | ARG | A | 362 | −3.583 | 74.858 | 4.118  | 1.00 | 38.78 |
| ATOM | 2231 | NE  | ARG | A | 362 | −4.367 | 74.836 | 5.376  | 1.00 | 33.99 |
| ATOM | 2232 | CZ  | ARG | A | 362 | −5.534 | 74.206 | 5.520  | 1.00 | 44.26 |
| ATOM | 2233 | NH1 | ARG | A | 362 | −6.058 | 73.534 | 4.503  | 1.00 | 31.69 |
| ATOM | 2234 | NH2 | ARG | A | 362 | −6.187 | 74.255 | 6.675  | 1.00 | 31.58 |
| ATOM | 2235 | N   | SER | A | 363 | −0.588 | 73.821 | 7.599  | 1.00 | 30.47 |
| ATOM | 2236 | CA  | SER | A | 363 | −0.750 | 74.369 | 8.945  | 1.00 | 30.07 |
| ATOM | 2237 | C   | SER | A | 363 | 0.578  | 74.862 | 9.535  | 1.00 | 36.06 |
| ATOM | 2238 | O   | SER | A | 363 | 0.663  | 75.959 | 14.080 | 1.00 | 34.89 |
| ATOM | 2239 | CB  | SER | A | 363 | −1.408 | 73.325 | 9.868  | 1.00 | 31.36 |
| ATOM | 2240 | OG  | SER | A | 363 | −2.778 | 73.145 | 9.524  | 1.00 | 35.29 |
| ATOM | 2241 | N   | ASP | A | 364 | 1.613  | 74.043 | 9.407  | 1.00 | 34.95 |
| ATOM | 2242 | CA  | ASP | A | 364 | 2.932  | 74.382 | 9.929  | 1.00 | 35.73 |
| ATOM | 2243 | C   | ASP | A | 364 | 3.462  | 75.701 | 9.372  | 1.00 | 41.56 |
| ATOM | 2244 | O   | ASP | A | 364 | 4.194  | 76.411 | 10.046 | 1.00 | 40.90 |
| ATOM | 2245 | CB  | ASP | A | 364 | 3.931  | 73.253 | 9.626  | 1.00 | 37.90 |
| ATOM | 2246 | CG  | ASP | A | 364 | 4.981  | 73.089 | 10.718 | 1.00 | 52.59 |
| ATOM | 2247 | OD1 | ASP | A | 364 | 4.955  | 73.877 | 11.693 | 1.00 | 55.51 |
| ATOM | 2248 | OD2 | ASP | A | 364 | 5.788  | 72.136 | 10.636 | 1.00 | 56.27 |
| ATOM | 2249 | N   | ALA | A | 365 | 3.099  | 76.016 | 8.131  | 1.00 | 39.67 |
| ATOM | 2250 | CA  | ALA | A | 365 | 3.572  | 77.238 | 7.490  | 1.00 | 40.44 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 2251 | C | ALA | A | 365 | 2.695 | 78.456 | 7.782 | 1.00 | 46.20 |
|---|---|---|---|---|---|---|---|---|---|---|
| ATOM | 2252 | O | ALA | A | 365 | 3.106 | 79.587 | 7.546 | 1.00 | 46.56 |
| ATOM | 2253 | CB | ALA | A | 365 | 3.731 | 77.028 | 5.974 | 1.00 | 41.24 |
| ATOM | 2254 | N | GLU | A | 366 | 1.486 | 78.226 | 8.294 | 1.00 | 42.84 |
| ATOM | 2255 | CA | GLU | A | 366 | 0.583 | 79.329 | 8.624 | 1.00 | 42.41 |
| ATOM | 2256 | C | GLU | A | 366 | 1.057 | 80.051 | 9.886 | 1.00 | 47.12 |
| ATOM | 2257 | O | GLU | A | 366 | 1.539 | 79.430 | 10.825 | 1.00 | 46.41 |
| ATOM | 2258 | CB | GLU | A | 366 | −0.831 | 78.812 | 8.873 | 1.00 | 43.36 |
| ATOM | 2259 | CG | GLU | A | 366 | −1.632 | 78.538 | 7.641 | 1.00 | 45.65 |
| ATOM | 2260 | CD | GLU | A | 366 | −2.776 | 77.587 | 7.908 | 1.00 | 47.57 |
| ATOM | 2261 | OE1 | GLU | A | 366 | −2.990 | 77.202 | 9.083 | 1.00 | 37.93 |
| ATOM | 2262 | OE2 | GLU | A | 366 | −3.451 | 77.209 | 6.950 | 1.00 | 34.94 |
| ATOM | 2263 | N | GLU | A | 367 | 0.893 | 81.361 | 9.909 | 1.00 | 45.83 |
| ATOM | 2264 | CA | GLU | A | 367 | 1.246 | 82.142 | 11.089 | 1.00 | 46.77 |
| ATOM | 2265 | C | GLU | A | 367 | −0.025 | 82.270 | 11.882 | 1.00 | 50.64 |
| ATOM | 2266 | O | GLU | A | 367 | −0.884 | 83.087 | 11.555 | 1.00 | 51.21 |
| ATOM | 2267 | CB | GLU | A | 367 | 1.754 | 83.540 | 10.692 | 1.00 | 48.58 |
| ATOM | 2268 | CG | GLU | A | 367 | 2.391 | 84.334 | 11.649 | 1.00 | 62.50 |
| ATOM | 2269 | CD | GLU | A | 367 | 2.075 | 85.826 | 11.785 | 1.00 | 93.32 |
| ATOM | 2270 | OE1 | GLU | A | 367 | 1.012 | 86.230 | 12.312 | 1.00 | 93.08 |
| ATOM | 2271 | OE2 | GLU | A | 367 | 2.883 | 86.595 | 11.201 | 1.00 | 88.74 |
| ATOM | 2272 | N | VAL | A | 368 | −0.198 | 81.387 | 12.859 | 1.00 | 46.08 |
| ATOM | 2273 | CA | VAL | A | 368 | −1.414 | 81.379 | 13.658 | 1.00 | 45.39 |
| ATOM | 2274 | C | VAL | A | 365 | −1.105 | 81.779 | 15.083 | 1.00 | 46.99 |
| ATOM | 2275 | O | VAL | A | 368 | −0.239 | 81.189 | 15.727 | 1.00 | 45.14 |
| ATOM | 2276 | CB | VAL | A | 368 | −2.072 | 79.985 | 13.658 | 1.00 | 49.55 |
| ATOM | 2277 | CG1 | VAL | A | 368 | −3.402 | 80.023 | 14.395 | 1.00 | 49.37 |
| ATOM | 2278 | CG2 | VAL | A | 368 | −2.255 | 79.489 | 12.248 | 1.00 | 49.42 |
| ATOM | 2279 | N | ASP | A | 359 | −1.792 | 82.805 | 15.574 | 1.00 | 42.81 |
| ATOM | 2280 | CA | ASP | A | 369 | −1.569 | 83.250 | 16.942 | 1.00 | 42.07 |
| ATOM | 2281 | C | ASP | A | 369 | −2.467 | 82.449 | 17.867 | 1.00 | 43.01 |
| ATOM | 2282 | O | ASP | A | 369 | −3.564 | 82.878 | 18.198 | 1.00 | 42.39 |
| ATOM | 2283 | CB | ASP | A | 369 | −1.874 | 84.735 | 17.090 | 1.00 | 44.32 |
| ATOM | 2284 | CG | ASP | A | 369 | −1.731 | 85.210 | 18.519 | 1.00 | 54.17 |
| ATOM | 2285 | OD1 | ASP | A | 369 | −0.770 | 84.777 | 19.120 | 1.00 | 52.94 |
| ATOM | 2286 | OD2 | ASP | A | 369 | −2.51.9 | 85.952 | 12.999 | 1.00 | 64.17 |
| ATOM | 2287 | N | PHE | A | 370 | −2.009 | 21.269 | 18.256 | 1.00 | 37.69 |
| ATOM | 2288 | CA | PHE | A | 373 | −2.815 | 80.401 | 19.103 | 1.00 | 35.98 |
| ATOM | 2289 | C | PHE | A | 370 | −3.065 | 80.998 | 20.469 | 1.00 | 37.78 |
| ATOM | 2290 | O | PHE | A | 370 | −4.187 | 80.968 | 20.973 | 1.00 | 35.97 |
| ATOM | 2291 | CB | PHE | A | 370 | −2.190 | 79.009 | 19.245 | 1.00 | 36.86 |
| ATOM | 2292 | CG | PHE | A | 370 | −2.915 | 78.116 | 20.224 | 1.00 | 37.28 |
| ATOM | 2293 | CD1 | PHE | A | 370 | −4.229 | 77.744 | 20.000 | 1.00 | 40.25 |
| ATOM | 2294 | CD2 | PHE | A | 370. | −2.300 | 77.676 | 21.373 | 1.00 | 38.05 |
| ATOM | 2295 | CE1 | PHE | A | 370 | −4.896 | 76.932 | 20.900 | 1.00 | 40.52 |
| ATOM | 2296 | CE2 | PHE | A | 370 | −2.962 | 76.858 | 22.259 | 1.00 | 40.30 |
| ATOM | 2297 | CZ | PHE | A | 370 | −4.261 | 76.489 | 22.020 | 1.00 | 38.23 |
| ATOM | 2298 | N | ALA | A | 371 | −2.004 | 81.494 | 21.093 | 1.00 | 35.92 |
| ATOM | 2299 | CA | ALA | A | 371 | −2.117 | 82.086 | 22.430 | 1.00 | 36.20 |
| ATOM | 2300 | C | ALA | A | 371 | −3.174 | 83.179 | 22.457 | 1.00 | 39.93 |
| ATOM | 2301 | O | ALA | A | 371 | −4.017 | 83.217 | 23.356 | 1.00 | 41.31 |
| ATOM | 2302 | CB | ALA | A | 371 | −0.747 | 82.628 | 22.907 | 1.00 | 37.21 |
| ATOM | 2303 | N | GLY | A | 372 | −3.160 | 84.038 | 21.442 | 1.00 | 36.63 |
| ATOM | 2304 | CA | GLY | A | 372 | −4.134 | 85.139 | 21.345 | 1.00 | 36.17 |
| ATOM | 2305 | C | GLY | A | 372 | −5.555 | 84.618 | 21.186 | 1.00 | 39.13 |
| ATOM | 2306 | O | GLY | A | 372 | −6.475 | 85.055 | 21.897 | 1.00 | 39.59 |
| ATOM | 2307 | N | TRP | A | 373 | −5.748 | 83.698 | 20.238 | 1.00 | 32.69 |
| ATOM | 2308 | CA | TRP | A | 373 | −7.068 | 83.117 | 20.022 | 1.00 | 30.86 |
| ATOM | 2309 | C | TRP | A | 373 | −7.548 | 82.476 | 21.303 | 1.00 | 33.87 |
| ATOM | 2310 | O | TRP | A | 373 | −8.710 | 82.600 | 21.675 | 1.00 | 33.68 |
| ATOM | 2311 | CB | TRP | A | 373 | −7.033 | 82.063 | 18.908 | 1.00 | 28.64 |
| ATOM | 2312 | CG | TRP | A | 373 | −8.326 | 81.285 | 18.805 | 1.00 | 28.82 |
| ATOM | 2313 | CD1 | TRP | A | 373 | −9.418 | 81.597 | 18.033 | 1.00 | 31.62 |
| ATOM | 2314 | CD2 | TRP | A | 373 | −8.671 | 80.092 | 19.527 | 1.00 | 27.95 |
| ATOM | 2315 | NE1 | TRP | A | 373 | −10.416 | 80.667 | 18.230 | 1.00 | 30.93 |
| ATOM | 2316 | CE2 | TRP | A | 373 | −9.987 | 79.738 | 19.147 | 1.00 | 32.21 |
| ATOM | 2317 | CE3 | TRP | A | 373 | −8.021 | 79.321 | 20.497 | 1.00 | 28.68 |
| ATOM | 2318 | CZ2 | TRP | A | 373 | −10.653 | 78.629 | 19.695 | 1.00 | 31.13 |
| ATOM | 2319 | CZ3 | TRP | A | 373 | −8.664 | 78.205 | 21.009 | 1.00 | 29.76 |
| ATOM | 2320 | CH2 | TRP | A | 373 | −9.974 | 77.884 | 20.631 | 1.00 | 30.49 |
| ATOM | 2321 | N | LEU | A | 374 | −6.649 | 81.747 | 21.957 | 1.00 | 30.06 |
| ATOM | 2322 | CA | LEU | A | 374 | −6.976 | 81.034 | 23.176 | 1.00 | 29.19 |
| ATOM | 2323 | C | LEU | A | 374 | −7.372 | 81.973 | 24.310 | 1.00 | 35.36 |
| ATOM | 2324 | O | LEU | A | 374 | −8.393 | 81.770 | 24.956 | 1.00 | 34.84 |
| ATOM | 2325 | CB | LEU | A | 374 | −5.803 | 80.148 | 23.621 | 1.00 | 28.66 |
| ATOM | 2326 | CG | LEU | A | 374 | −6.032 | 79.430 | 24.961 | 1.00 | 32.17 |
| ATOM | 2327 | CD1 | LEU | A | 374 | −7.024 | 78.314 | 24.787 | 1.00 | 31.31 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 2328 | CD2 | LEU | A | 374 | −4.706 | 78.910 | 25.584 | 1.00 | 33.89 |
|---|---|---|---|---|---|---|---|---|---|---|
| ATOM | 2329 | N | CYS | A | 375 | −6.540 | 82.981 | 24.574 | 1.00 | 33.59 |
| ATOM | 2330 | CA | CYS | A | 375 | −6.809 | 83.918 | 25.669 | 1.00 | 34.34 |
| ATOM | 2331 | C | CYS | A | 375 | −8.120 | 84.649 | 25.514 | 1.00 | 36.34 |
| ATOM | 2332 | O | CYS | A | 375 | −8.862 | 84.801 | 26.470 | 1.00 | 35.60 |
| ATOM | 2333 | CB | CYS | A | 375 | −5.664 | 84.912 | 25.820 | 1.00 | 35.36 |
| ATOM | 2334 | SG | CYS | A | 375 | −4.145 | 84.097 | 26.378 | 1.00 | 39.65 |
| ATOM | 2335 | N | SER | A | 376 | −8.399 | 85.108 | 24.299 | 1.00 | 31.43 |
| ATOM | 2336 | CA | SER | A | 376 | −9.638 | 85.822 | 24.032 | 1.00 | 31.06 |
| ATOM | 2337 | C | SER | A | 376 | −10.857 | 84.884 | 24.054 | 1.00 | 34.85 |
| ATOM | 2338 | O | SER | A | 376 | −11.958 | 85.286 | 24.427 | 1.00 | 33.78 |
| ATOM | 2339 | CB | SER | A | 376 | −9.554 | 86.567 | 22.698 | 1.00 | 33.39 |
| ATOM | 2340 | OG | SER | A | 376 | −9.418 | 85.662 | 21.626 | 1.00 | 44.30 |
| ATOM | 2341 | N | THR | A | 377 | −10.634 | 83.627 | 23.678 | 1.00 | 30.94 |
| ATOM | 2342 | CA | THR | A | 377 | −11.700 | 82.627 | 23.627 | 1.00 | 30.21 |
| ATOM | 2343 | C | THR | A | 377 | −12.142 | 82.136 | 25.013 | 1.00 | 35.45 |
| ATOM | 2344 | O | THR | A | 377 | −13.313 | 81.888 | 25.242 | 1.00 | 34.76 |
| ATOM | 2345 | CB | THR | A | 377 | −11.245 | 81.385 | 22.857 | 1.00 | 35.17 |
| ATOM | 2346 | OG1 | THR | A | 377 | −11.231 | 81.670 | 21.464 | 1.00 | 29.13 |
| ATOM | 2347 | CG2 | THR | A | 377 | −12.176 | 80.206 | 23.132 | 1.00 | 36.31 |
| ATOM | 2348 | N | ILE | A | 378 | −11.195 | 82.063 | 25.926 | 1.00 | 32.84 |
| ATOM | 2349 | CA | ILE | A | 378 | −11.548 | 81.640 | 27.262 | 1.00 | 33.55 |
| ATOM | 2350 | C | ILE | A | 378 | −11.541 | 82.791 | 28.258 | 1.00 | 38.76 |
| ATOM | 2351 | O | ILE | A | 378 | −11.792 | 82.595 | 29.433 | 1.00 | 37.38 |
| ATOM | 2352 | CB | ILE | A | 378 | −10.708 | 80.428 | 27.753 | 1.00 | 35.70 |
| ATOM | 2353 | CG1 | ILE | A | 378 | −9.244 | 80.823 | 27.951 | 1.00 | 35.60 |
| ATOM | 2354 | CG2 | ILE | A | 378 | −10.814 | 79.282 | 26.753 | 1.00 | 35.88 |
| ATOM | 2355 | CD1 | ILE | A | 378 | −8.447 | 79.818 | 28.799 | 1.00 | 38.76 |
| ATOM | 2356 | N | GLY | A | 379 | −11.289 | 83.997 | 27.763 | 1.00 | 38.23 |
| ATOM | 2357 | CA | GLY | A | 379 | −11.296 | 85.184 | 28.612 | 1.00 | 39.66 |
| ATOM | 2358 | C | GLY | A | 379 | −10.172 | 85.106 | 29.628 | 1.00 | 48.17 |
| ATOM | 2359 | O | GLY | A | 379 | −10.393 | 85.254 | 30.826 | 1.00 | 47.55 |
| ATOM | 2360 | N | LEU | A | 380 | −8.963 | 84.846 | 29.141 | 1.00 | 48.58 |
| ATOM | 2361 | CA | LEU | A | 380 | −7.805 | 84.726 | 30.005 | 1.00 | 50.34 |
| ATOM | 2362 | C | LEU | A | 380 | −7.116 | 86.065 | 30.182 | 1.00 | 58.57 |
| ATOM | 2363 | O | LEU | A | 380 | −6.733 | 86.722 | 29.210 | 1.00 | 58.74 |
| ATOM | 2364 | CB | LEU | A | 380 | −6.826 | 83.695 | 29.447 | 1.00 | 50.50 |
| ATOM | 2365 | CG | LEU | A | 380 | −6.444 | 82.585 | 30.429 | 1.00 | 55.14 |
| ATOM | 2366 | CD1 | LEU | A | 380 | −5.547 | 81.545 | 29.769 | 1.00 | 54.69 |
| ATOM | 2367 | CD2 | LEU | A | 380 | −5.771 | 83.190 | 31.654 | 1.00 | 58.66 |
| ATOM | 2368 | N | ASN | A | 381 | −6.973 | 86.477 | 31.446 | 1.00 | 57.47 |
| ATOM | 2369 | CA | ASN | A | 381 | −6.335 | 87.747 | 31.780 | 1.00 | 58.33 |
| ATOM | 2370 | C | ASN | A | 381 | −5.003 | 87.522 | 32.478 | 1.00 | 64.77 |
| ATOM | 2371 | O | ASN | A | 381 | −4.814 | 86.4.96 | 33.145 | 1.00 | 64.63 |
| ATOM | 2372 | CB | ASN | A | 381 | −7.248 | 88.577 | 32.682 | 1.00 | 59.09 |
| ATOM | 2373 | CG | ASN | A | 381 | −8.452 | 89.114 | 31.949 | 1.00 | 81.90 |
| ATOM | 2374 | CD1 | ASN | A | 381 | −8.322 | 89.744 | 30.895 | 1.00 | 76.05 |
| ATOM | 2375 | ND2 | ASN | A | 381 | −9.640 | 88.826 | 32.473 | 1.00 | 72.34 |
| ATOM | 2376 | N | GLN | A | 382 | −4.240 | 88.606 | 32.597 | 1.00 | 62.34 |
| TER | 2377 | | GLN | A | 382 | | | | | |
| ATOM | 2378 | OW | WAT | W | 1 | −4.624 | 75.081 | 9.034 | 1.00 | 27.68 |
| ATOM | 2379 | OW | WAT | W | 2 | −2.577 | 76.231 | 11.416 | 1.00 | 29.05 |
| ATOM | 2380 | OW | WAT | W | 3 | −3.742 | 69.081 | −1.006 | 1.00 | 30.37 |
| ATOM | 2381 | OW | WAT | W | 4 | −14.964 | 74.471 | 13.770 | 1.00 | 31.93 |
| ATOM | 2382 | OW | WAT | W | 5 | −11.919 | 57.539 | 7.244 | 1.00 | 31.88 |
| ATOM | 2383 | OW | WAT | W | 6 | −11.116 | 72.975 | 0.157 | 1.00 | 34.55 |
| ATOM | 2384 | OW | WAT | W | 7 | −13.659 | 59.717 | 7.931 | 1.00 | 29.70 |
| ATOM | 2385 | OW | WAT | W | 8 | −15.768 | 70.359 | 1.074 | 1.00 | 37.39 |
| ATOM | 2386 | OW | WAT | W | 9 | 3.702 | 73.039 | 22.508 | 1.00 | 36.83 |
| ATOM | 2387 | OW | WAT | W | 10 | −8.014 | 61.681 | −0.933 | 1.00 | 39.30 |
| ATOM | 2388 | OW | WAT | W | 11 | −11.273 | 56.557 | 25.382 | 1.00 | 38.77 |
| ATOM | 2389 | OW | WAT | W | 12 | −5.122 | 56.773 | 22.513 | 1.00 | 34.68 |
| ATOM | 2390 | OW | WAT | W | 13 | −11.739 | 64.136 | 26.992 | 1.00 | 37.17 |
| ATOM | 2391 | OW | WAT | W | 14 | 0.443 | 78.008 | 32.084 | 1.00 | 40.11 |
| ATOM | 2392 | OW | WAT | W | 15 | −15.623 | 64.996 | 5.192 | 1.00 | 43.40 |
| ATOM | 2393 | OW | WAT | W | 16 | 2.238 | 53.070 | 26.823 | 1.00 | 57.67 |
| ATOM | 2394 | OW | WAT | W | 17 | −13.635 | 55.899 | 19.258 | 1.00 | 37.89 |
| ATOM | 2395 | OW | WAT | W | 18 | −4.575 | 74.107 | 0.759 | 1.00 | 37.31 |
| ATOM | 2396 | OW | WAT | W | 19 | 6.331 | 61.007 | 12.977 | 1.00 | 55.43 |
| ATOM | 2397 | OW | WAT | W | 20 | −12.774 | 76.436 | 10.591 | 1.00 | 32.37 |
| ATOM | 2398 | OW | WAT | W | 21 | −16.438 | 53.903 | 28.861 | 1.00 | 37.30 |
| ATOM | 2399 | OW | WAT | W | 22 | −13.743 | 86.024 | 26.513 | 1.00 | 32.43 |
| ATOM | 2400 | OW | WAT | W | 23 | −9.971 | 61.068 | 2.309 | 1.00 | 30.02 |
| ATOM | 2401 | OW | WAT | W | 24 | 0.848 | 81.061 | 19.815 | 1.00 | 43.98 |
| ATOM | 2402 | OW | WAT | W | 25 | −14.485 | 67.474 | 24.615 | 1.00 | 37.16 |
| ATOM | 2403 | OW | WAT | W | 26 | −15.104 | 69.736 | 25.760 | 1.00 | 30.79 |
| ATOM | 2404 | OW | WAT | W | 27 | 9.647 | 67.025 | 20.957 | 1.00 | 42.41 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 2405 | OW | WAT | W | 28 | −2.745 | 69.882 | 47.685 | 1.00 | 40.30 |
|---|---|---|---|---|---|---|---|---|---|---|
| ATOM | 2406 | OW | WAT | W | 29 | 5.706 | 56.554 | 11.512 | 1.00 | 45.72 |
| ATOM | 2407 | OW | WAT | W | 30 | −7.561 | 54.142 | 20.853 | 1.00 | 33.21 |
| ATOM | 2408 | OW | WAT | W | 31 | −13.489 | 64.239 | 6.990 | 1.00 | 35.53 |
| ATOM | 2409 | OW | WAT | W | 32 | −2.256 | 56.573 | 28.890 | 1.00 | 51.35 |
| ATOM | 2410 | OW | WAT | W | 33 | −12.567 | 75.838 | 7.931 | 1.00 | 35.03 |
| ATOM | 2411 | OW | MAT | W | 34 | −1.230 | 72.376 | 0.289 | 1.00 | 33.27 |
| ATOM | 2412 | OW | MAT | W | 35 | −18.950 | 72.658 | 22.382 | 1.00 | 45.98 |
| ATOM | 2413 | OW | MAT | W | 36 | −13.377 | 31.955 | 19.898 | 1.00 | 36.43 |
| ATOM | 2414 | OW | MAT | W | 37 | −12.793 | 52.525 | 7.544 | 1.00 | 39.83 |
| ATOM | 2415 | OW | MAT | W | 38 | 0.083 | 71.523 | 1.897 | 1.00 | 40.55 |
| ATOM | 2416 | OW | MAT | W | 39 | −8.845 | 57.963 | 24.752 | 1.00 | 34.15 |
| ATOM | 2417 | OW | MAT | W | 40 | −7.698 | 74.969 | 0.939 | 1.00 | 39.78 |
| ATOM | 2418 | OW | MAT | W | 41 | 7.596 | 71.335 | 27.791 | 1.00 | 46.01 |
| ATOM | 2419 | OW | MAT | W | 42 | 0.606 | 52.047 | 6.698 | 1.00 | 68.67 |
| ATOM | 2420 | OW | MAT | W | 43 | −16.485 | 53.782 | 13.115 | 1.00 | 38.71 |
| ATOM | 2421 | OW | MAT | W | 44. | 5.553 | 73.417 | 6.486 | 1.00 | 41.45 |
| ATOM | 2422 | OW | MAT | W | 45 | 7.623 | 75.582 | 24.046 | 1.00 | 42.35 |
| ATOM | 2423 | OW | MAT | W | 46 | −15.108 | 63.029 | 3.481 | 1.00 | 37.31 |
| ATOM | 2424 | OW | MAT | W | 47 | −18.182 | 68.179 | 22.755 | 1.00 | 41.92 |
| ATOM | 2425 | OW | MAT | W | 48 | −1.567 | 57.544 | 4.781 | 1.00 | 55.51 |
| ATOM | 2426 | OW | MAT | W | 49 | 5.270 | 54.963 | 7.087 | 1.00 | 58.04 |
| ATOM | 2427 | OW | MAT | W | 50 | −18.114 | 70.616 | 24.150 | 1.00 | 49.89 |
| ATOM | 2428 | OW | MAT | W | 51 | 9.645 | 74.346 | 24.716 | 1.00 | 38.07 |
| ATOM | 2429 | OW | MAT | W | 52 | −2.407 | 49.867 | 15.654 | 1.00 | 50.52 |
| ATOM | 2430 | OW | MAT | W | 53 | −23.191 | 78.787 | 12.861 | 1.00 | 53.87 |
| ATOM | 2431 | OW | MAT | W | 54 | −16.398 | 66.547 | 1.241 | 1.00 | 35.37 |
| ATOM | 2432 | OW | MAT | W | 55 | −7.301 | 55.4.28 | 23.272 | 1.00 | 44.58 |
| ATOM | 2433 | OW | MAT | W | 56 | −20.130 | 65.504 | 10.826 | 1.00 | 62.25 |
| ATOM | 2434 | OW | MAT | W | 57 | −9.620 | 75.975 | 30.030 | 1.00 | 44.26 |
| ATOM | 2435 | OW | MAT | W | 58 | −1.101 | 64.720 | 1.776 | 1.00 | 36.60 |
| ATOM | 2436 | OW | MAT | W | 59 | −14.826 | 83.968 | 26.930 | 1.00 | 42.76 |
| ATOM | 2437 | OW | MAT | W | 60 | 5.708 | 74.961 | 21.589 | 1.00 | 44.72 |
| ATOM | 2438 | OW | MAT | W | 61 | −10.828 | 50.524 | 6.804 | 1.00 | 44.09 |
| ATOM | 2439 | OW | MAT | W | 62 | −0.626 | 71.455 | −2.363 | 1.00 | 40.36 |
| ATOM | 2440 | OW | MAT | W | 63 | 3.044 | 75.866 | 31.540 | 1.00 | 45.03 |
| ATOM | 2441 | OW | MAT | W | 64 | −15.437 | 60.223 | 3.728 | 1.00 | 45.44 |
| ATOM | 2442 | OW | MAT | W | 55 | 8.940 | 61.511 | 42.174 | 1.00 | 59.50 |
| ATOM | 2443 | OW | MAT | W | 66 | −16.614 | 63.941 | 1.497 | 1.00 | 49.11 |
| ATOM | 2444 | OW | MAT | W | 67 | −19.852 | 61.372 | 10.416 | 1.00 | 48.85 |
| ATOM | 2445 | OW | MAT | W | 68 | −15.672 | 51.995 | 6.737 | 1.00 | 54.00 |
| ATOM | 2446 | OW | MAT | W | 69 | −23.534 | 50.004 | 8.328 | 1.00 | 62.07 |
| ATOM | 2447 | OW | MAT | W | 70 | 7.642 | 62.190 | 8.434 | 1.00 | 50.04 |
| ATOM | 2448 | OW | MAT | W | 71 | −15.960 | 68.780 | 44.824 | 1.00 | 62.11 |
| ATOM | 2449 | OW | MAT | W | 501 | −7.359 | 61.090 | 31.982 | 1.00 | 36.24 |
| ATOM | 2450 | OW | MAT | W | 502 | −6.203 | 65.450 | 32.091 | 1.00 | 37.46 |
| ATOM | 2451 | OW | MAT | W | 503 | −3.790 | 65.392 | 33.857 | 1.00 | 45.57 |
| ATOM | 2452 | OW | MAT | W | 504 | −11.919 | 68.273 | 31.788 | 1.00 | 44.80 |
| ATOM | 2453 | OW | WAT | W | 505 | −7.520 | 72.809 | 34.057 | 1.00 | 42.61 |
| ATOM | 2454 | OW | WAT | W | 901 | −18.486 | 78.358 | 18.478 | 0.50 | 34.54 |
| ATOM | 2455 | OW | WAT | W | 902 | −20.684 | 77.106 | 18.477 | 0.50 | 46.09 |
| ATOM | 2456 | OW | WAT | W | 903 | −7.421 | 66.578 | 0.296 | 0.50 | 24.89 |
| ATOM | 2457 | OW | WAT | W | 904 | −4.836 | 67.095 | −0.600 | 0.50 | 20.53 |
| ATOM | 2458 | C01 | SCE | Z | 1 | 0.248 | 60.985 | 33.956 | 1.00 | 38.12 |
| ATOM | 2459 | C02 | SOH | Z | 1 | 1.117 | 60.767 | 32.881 | 1.00 | 35.30 |
| ATOM | 2460 | C03 | SCH | Z | 1 | 1.973 | 61.759 | 32.424 | 1.00 | 36.46 |
| ATOM | 2461 | C04 | SCH | Z | 1 | 1.924 | 63.030 | 32.990 | 1.00 | 37.97 |
| ATOM | 2462 | C05 | SCH | Z | 1 | 1.037 | 63.306 | 34.032 | 1.00 | 39.21 |
| ATOM | 2463 | C06 | SCH | Z | 1 | 0.218 | 62.286 | 34.520 | 1.00 | 39.40 |
| ATOM | 2464 | N07 | SCH | Z | 1 | −0.593 | 59.962 | 34.455 | 1.00 | 41.43 |
| ATOM | 2465 | C08 | SCH | Z | 1 | −0.807 | 58.612 | 34.081 | 1.00 | 44.00 |
| ATOM | 2466 | C09 | SCH | Z | 1 | −2.123 | 58.154 | 33.881 | 1.00 | 46.76 |
| ATOM | 2467 | C10 | SCH | Z | 1 | −2.402 | 56.826 | 33.502 | 1.00 | 41.31 |
| ATOM | 2468 | C11 | SCH | Z | 1 | −1.358 | 55.933 | 33.295 | 1.00 | 45.40 |
| ATOM | 2469 | C12 | SCH | Z | 1 | −0.055 | 56.376 | 33.485 | 1.00 | 47.54 |
| ATOM | 2470 | C13 | SCH | Z | 1 | 0.221 | 57.688 | 33.873 | 1.00 | 46.85 |
| ATOM | 2471 | C14 | SCH | Z | 1 | −3.231 | 59.068 | 34.167 | 1.00 | 50.08 |
| ATOM | 2472 | N15 | SCH | Z | 1 | 4.441 | 58.731 | 33.628 | 1.00 | 53.33 |
| ATOM | 2473 | O16 | SCH | Z | 1 | −3.021 | 60.031 | 34.898 | 1.00 | 50.32 |
| ATOM | 2474 | O17 | SCH | Z | 1 | −5.503 | 59.651 | 33.782 | 1.00 | 56.97 |
| ATOM | 2475 | C18 | SCH | Z | 1 | −5.768 | 99.848 | 35.183 | 1.00 | 60.39 |
| ATOM | 2476 | C19 | SCH | Z | 1 | −7.246 | 60.141 | 35.358 | 1.00 | 62.23 |
| ATOM | 2477 | C20 | SCH | Z | 1 | −7.924 | 59.037 | 36.162 | 1.00 | 63.76 |
| ATOM | 2478 | O21 | SCH | Z | 1 | −7.880 | 60.195 | 34.068 | 1.00 | 62.27 |
| ATOM | 2479 | O22 | SCH | Z | 1 | −9.272 | 58.901 | 35.699 | 1.00 | 64.75 |
| ATOM | 2480 | I23 | SCH | Z | 1 | 3.170 | 64.505 | 32.262 | 1.00 | 41.66 |
| ATOM | 2481 | CL24 | SCR | Z | 1 | −0.862 | 62.667 | 35.820 | 1.00 | 41.85 |

TABLE 2-continued

Structural Coordinate of MEK1/N35/NKFCdel(corresponding to amino acids 24-373 of SEQ ID NO: 2)-compound 1-ATPγS Ternary Complex.

| ATOM | 2482 | F25 | SCH | Z | 1 | 1.509 | 58.023 | 34.034 | 1.00 | 48.39 |
|---|---|---|---|---|---|---|---|---|---|---|
| ATOM | 2483 | F26 | SCR | Z | 1 | 0.948 | 55.529 | 33.267 | 1.00 | 50.88 |
| ATOM | 2484 | PG | AGS | Z | 2 | −10.915 | 60.811 | 32.987 | 1.00 | 63.04 |
| ATOM | 2485 | S1G | AGS | Z | 2 | −12.339 | 60.025 | 32.561 | 1.00 | 70.14 |
| ATOM | 2486 | O2G | AGS | Z | 2 | −9.797 | 60.430 | 32.041 | 1.00 | 61.31 |
| ATOM | 2487 | O3G | AGS | Z | 2 | −10.513 | 60.504 | 34.506 | 1.00 | 63.60 |
| ATOM | 2488 | PB | AGS | Z | 2 | −10.232 | 63.584 | 32.898 | 1.00 | 48.34 |
| ATOM | 2489 | O1B | AGS | Z | 2 | −9.044 | 63.367 | 31.978 | 1.00 | 44.81 |
| ATOM | 2490 | O2B | AGS | Z | 2 | −10.911 | 64.870 | 32.526 | 1.00 | 48.17 |
| ATOM | 2491 | O3B | AGS | Z | 2 | −11.244 | 62.368 | 32.871 | 1.00 | 56.01 |
| ATOM | 2492 | PA | AGS | Z | 2 | −6.349 | 63.982 | 35.069 | 1.00 | 45.11 |
| ATOM | 2493 | O1A | AGS | Z | 2 | −8.225 | 63.477 | 36.481 | 1.00 | 48.51 |
| ATOM | 2494 | O2A | AGS | Z | 2 | −7.222 | 63.411 | 34.292 | 1.00 | 45.50 |
| ATOM | 2495 | O3A | AGS | Z | 2 | −9.769 | 63.706 | 34.438 | 1.00 | 48.80 |
| ATOM | 2496 | O5* | AGS | Z | 2 | −8.184 | 65.547 | 35.048 | 1.00 | 41.41 |
| ATOM | 2497 | C5* | AGS | Z | 2 | −9.234 | 66.395 | 35.556 | 1.00 | 41.72 |
| ATOM | 2498 | C4* | AGS | Z | 2 | −9.043 | 67.753 | 34.875 | 1.00 | 42.34 |
| ATOM | 2499 | O4* | AGS | Z | 2 | −7.892 | 68.468 | 35.433 | 1.00 | 40.38 |
| ATOM | 2500 | C3* | AGS | Z | 2 | −8.720 | 67.679 | 33.390 | 1.00 | 43.20 |
| ATOM | 2501 | O3* | AGS | Z | 2 | −9.925 | 67.477 | 32.654 | 1.00 | 46.68 |
| ATOM | 2502 | C2* | AGS | Z | 2 | −7.934 | 68.981 | 33.146 | 1.00 | 41.16 |
| ATOM | 2503 | O2* | AGS | Z | 2 | −8.804 | 70.028 | 32.765 | 1.00 | 45.58 |
| ATOM | 2504 | C1* | AGS | Z | 2 | −7.320 | 69.361 | 34.514 | 1.00 | 39.19 |
| ATOM | 2505 | N9 | AGS | Z | 2 | −5.849 | 69.222 | 34.538 | 1.00 | 35.77 |
| ATOM | 2506 | C8 | AGS | Z | 2 | −5.110 | 68.063 | 34.574 | 1.00 | 34.60 |
| ATOM | 2507 | N7 | AGS | Z | 2 | −3.761 | 68.278 | 34.486 | 1.00 | 35.25 |
| ATOM | 2508 | C5 | AGS | Z | 2 | −3.615 | 69.666 | 34.394 | 1.00 | 32.84 |
| ATOM | 2509 | C6 | AGS | Z | 2 | −2.445 | 70.482 | 34.310 | 1.00 | 33.19 |
| ATOM | 2510 | N6 | AGS | Z | 2 | −1.220 | 70.154 | 34.258 | 1.00 | 33.65 |
| ATOM | 2511 | N1 | AGS | Z | 2 | −2.787 | 71.799 | 34.247 | 1.00 | 33.38 |
| ATOM | 2512 | C2 | AGS | Z | 2 | −4.074 | 72.328 | 34.226 | 1.00 | 34.07 |
| ATOM | 2513 | N3 | AGS | Z | 2 | −5.162 | 71.586 | 34.332 | 1.00 | 32.84 |
| ATOM | 2514 | C4 | AGS | Z | 2 | −4.900 | 70.261 | 34.414 | 1.00 | 32.95 |
| TER | 2515 | | AGS | Z | 2 | | | | | |
| ATOM | 2516 | MC+2 | MG | Z | 3 | −6.773 | 63.248 | 31.971 | 1.00 | 25.75 |
| TER | 2517 | | MG | Z | 3 | | | | | |
| END | | | | | | | | | | |

TABLE 3

Structural Coordinate of MEK1/N35/NKFCdel (corresponding to amino acids 24-373 of SEQ ID NO: 2)-ATPγS Binary Complex.

| ATOM | 1 | N | GLU | A | 38 | 11.237 | 65.467 | 13.135 | 1.00 | 88.80 |
|---|---|---|---|---|---|---|---|---|---|---|
| ATOM | 2 | CA | GLU | A | 38 | 10.153 | 66.289 | 13.663 | 1.00 | 88.50 |
| ATOM | 3 | C | GLU | A | 38 | 10.352 | 66.568 | 15.147 | 1.00 | 91.34 |
| ATOM | 4 | O | GLU | A | 38 | 9.598 | 67.330 | 15.751 | 1.00 | 90.72 |
| ATOM | 5 | CB | GLU | A | 39 | 8.795 | 65.612 | 13.426 | 1.00 | 89.84 |
| ATOM | 6 | CG | GLU | A | 38 | 8.798 | 64.106 | 13.639 | 1.00 | 99.63 |
| ATOM | 7 | CD | GLU | A | 38 | 9.084 | 63.332 | 12.362 | 1.00 | 118.09 |
| ATOM | 8 | OE1 | GLU | A | 38 | 8.189 | 62.594 | 11.897 | 1.00 | 102.03 |
| ATOM | 9 | OE2 | GLU | A | 38 | 10.210 | 63.447 | 11.835 | 1.00 | 113.34 |
| ATOM | 10 | N | LEU | A | 39 | 11.375 | 65.948 | 15.727 | 1.00 | 87.45 |
| ATOM | 11 | CA | LEU | A | 39 | 11.684 | 66.134 | 17.142 | 1.00 | 65.90 |
| ATOM | 12 | C | LEU | A | 39 | 12.767 | 67.198 | 17.352 | 1.00 | 90.27 |
| ATOM | 13 | O | LEU | A | 39 | 13.338 | 67.316 | 18.440 | 1.00 | 89.67 |
| ATOM | 14 | CB | LEU | A | 39 | 12.081 | 64.801 | 17.795 | 1.00 | 86.89 |
| ATOM | 15 | CG | LEU | A | 39 | 11.000 | 63.706 | 17.774 | 1.00 | 91.43 |
| ATOM | 16 | CD1 | LEU | A | 39 | 11.347 | 62.545 | 18.699 | 1.00 | 91.37 |
| ATOM | 17 | CD2 | LEU | A | 39 | 9.616 | 64.274 | 18.110 | 1.00 | 93.64 |
| ATOM | 18 | N | GLU | A | 40 | 13.029 | 67.978 | 16.305 | 1.00 | 86.64 |
| ATOM | 19 | CA | GLU | A | 40 | 14.006 | 69.061 | 16.377 | 1.00 | 86.37 |
| ATOM | 20 | C | GLU | A | 40 | 13.411 | 70.192 | 17.214 | 1.00 | 88.29 |
| ATOM | 21 | O | GLU | A | 40 | 12.214 | 70.481 | 17.118 | 1.00 | 88.25 |
| ATOM | 22 | CB | GLU | A | 40 | 14.347 | 69.570 | 14.973 | 1.00 | 87.97 |
| ATOM | 23 | CG | GLU | A | 40 | 15.477 | 68.815 | 14.287 | 1.00 | 100.54 |
| ATOM | 24 | CD | GLU | A | 40 | 15.553 | 69.109 | 12.796 | 1.00 | 125.63 |
| ATOM | 25 | OE1 | GLU | A | 40 | 14.732 | 69.913 | 12.302 | 1.00 | 121.03 |
| ATOM | 26 | OE2 | GLU | A | 40 | 16.439 | 68.543 | 12.120 | 1.00 | 121.70 |
| ATOM | 27 | N | LEU | A | 41 | 14.238 | 70.816 | 18.045 | 1.00 | 82.50 |
| ATOM | 28 | CA | LEU | A | 41 | 13.762 | 71.867 | 18.930 | 1.00 | 81.07 |
| ATOM | 29 | C | LEU | A | 41 | 14.057 | 73.282 | 18.453 | 1.00 | 82.46 |
| ATOM | 30 | O | LEU | A | 41 | 15.172 | 73.601 | 18.052 | 1.00 | 81.68 |
| ATOM | 31 | CB | LEU | A | 41 | 14.303 | 71.663 | 20.345 | 1.00 | 81.02 |

TABLE 3-continued

Structural Coordinate of MEK1/N35/NKFCdel (corresponding to amino acids 24-373 of SEQ ID NO: 2)-ATPγS Binary Complex.

| | | | | | | | | | |
|---|---|---|---|---|---|---|---|---|---|
| ATOM | 32 | CG | LEU | A | 41 | 13.537 | 70.667 | 21.215 | 1.00 | 85.49 |
| ATOM | 33 | CD1 | LEU | A | 41 | 13.163 | 71.298 | 22.545 | 1.00 | 85.57 |
| ATOM | 34 | CD2 | LEU | A | 41 | 12.301 | 70.165 | 20.488 | 1.00 | 87.93 |
| ATOM | 35 | N | ASP | A | 42 | 13.045 | 74.133 | 18.530 | 1.00 | 77.53 |
| ATOM | 36 | CA | ASP | A | 42 | 13.195 | 75.526 | 18.169 | 1.00 | 76.52 |
| ATOM | 37 | C | ASP | A | 42 | 14.164 | 76.158 | 19.158 | 1.00 | 77.60 |
| ATOM | 38 | O | ASP | A | 42 | 14.590 | 75.514 | 20.119 | 1.00 | 76.66 |
| ATOM | 39 | CB | ASP | A | 42 | 11.841 | 76.235 | 18.262 | 1.00 | 78.54 |
| ATOM | 40 | CG | ASP | A | 42 | 11.741 | 77.415 | 17.330 | 1.00 | 90.83 |
| ATOM | 41 | OD1 | ASP | A | 42 | 10.843 | 77.408 | 16.461 | 1.00 | 91.56 |
| ATOM | 42 | OD2 | ASP | A | 42 | 12.570 | 78.346 | 17.455 | 1.00 | 97.95 |
| ATOM | 43 | N | GLU | A | 43 | 14.497 | 77.422 | 18.931 | 1.00 | 72.29 |
| ATOM | 44 | CA | GLU | A | 43 | 15.392 | 78.140 | 19.825 | 1.00 | 71.12 |
| ATOM | 45 | C | GLU | A | 43 | 14.636 | 78.539 | 21.091 | 1.00 | 71.37 |
| ATOM | 46 | O | GLU | A | 43 | 15.105 | 78.311 | 22.201 | 1.00 | 70.09 |
| ATOM | 47 | CB | GLU | A | 43 | 15.961 | 79.382 | 19.131 | 1.00 | 72.63 |
| ATOM | 48 | CG | GLU | A | 43 | 17.386 | 79.210 | 18.626 | 1.00 | 84.55 |
| ATOM | 49 | CD | GLU | A | 43 | 18.196 | 80.496 | 18.698 | 1.00 | 107.21 |
| ATOM | 50 | OE1 | GLU | A | 43 | 17.639 | 81.532 | 19.128 | 1.00 | 105.33 |
| ATOM | 51 | OE2 | GLU | A | 43 | 19.392 | 80.466 | 18.329 | 1.00 | 98.51 |
| ATOM | 52 | N | GLN | A | 44 | 13.452 | 79.112 | 20.907 | 1.00 | 66.25 |
| ATOM | 53 | CA | GLN | A | 44 | 12.617 | 79.523 | 22.025 | 1.00 | 65.54 |
| ATOM | 54 | C | GLN | A | 44 | 12.123 | 78.295 | 22.773 | 1.00 | 67.92 |
| ATOM | 55 | O | GLN | A | 44 | 11.885 | 78.339 | 23.980 | 1.00 | 67.38 |
| ATOM | 56 | CB | GLN | A | 44 | 11.428 | 80.347 | 21.530 | 1.00 | 66.93 |
| ATOM | 57 | CG | GLN | A | 44 | 10.224 | 80.298 | 22.446 | 1.00 | 81.44 |
| ATOM | 58 | CD | GLN | A | 44 | 8.986 | 80.900 | 21.813 | 1.00 | 97.65 |
| ATOM | 59 | OE1 | GLN | A | 44 | 8.291 | 80.246 | 21.032 | 1.00 | 91.57 |
| ATOM | 60 | NE2 | GLN | A | 44 | 8.697 | 82.153 | 22.154 | 1.00 | 88.69 |
| ATOM | 61 | N | GLN | A | 45 | 11.981 | 77.195 | 22.047 | 1.00 | 63.28 |
| ATOM | 62 | CA | GLN | A | 45 | 11.549 | 75.947 | 22.641 | 1.00 | 62.43 |
| ATOM | 63 | C | GLN | A | 45 | 12.651 | 75.417 | 23.545 | 1.00 | 66.05 |
| ATOM | 64 | O | GLN | A | 45 | 12.428 | 75.163 | 24.726 | 1.00 | 65.74 |
| ATOM | 65 | CB | GLN | A | 45 | 11.247 | 74.921 | 21.551 | 1.00 | 63.53 |
| ATOM | 66 | CG | GLN | A | 45 | 9.858 | 75.034 | 20.938 | 1.00 | 68.54 |
| ATOM | 67 | CD | GLN | A | 45 | 9.547 | 73.876 | 20.006 | 1.00 | 77.29 |
| ATOM | 68 | OE1 | GLN | A | 45 | 10.444 | 73.319 | 19.369 | 1.00 | 68.67 |
| ATOM | 69 | NE2 | GLN | A | 45 | 8.277 | 73.501 | 19.931 | 1.00 | 68.21 |
| ATOM | 70 | N | ARG | A | 46 | 13.842 | 75.252 | 22.973 | 1.00 | 62.19 |
| ATOM | 71 | CA | ARG | A | 46 | 15.000 | 74.736 | 23.702 | 1.00 | 61.63 |
| ATOM | 72 | C | ARG | A | 46 | 15.287 | 75.523 | 24.971 | 1.00 | 64.18 |
| ATOM | 73 | O | ARG | A | 46 | 15.647 | 74.952 | 25.999 | 1.00 | 63.67 |
| ATOM | 74 | CB | ARG | A | 46 | 16.241 | 74.732 | 22.803 | 1.00 | 61.97 |
| ATOM | 75 | CG | ARG | A | 46 | 17.281 | 73.708 | 23.206 | 1.00 | 74.65 |
| ATOM | 76 | CD | ARG | A | 46 | 18.658 | 74.341 | 23.387 | 1.00 | 87.34 |
| ATOM | 77 | NE | ARG | A | 46 | 19.030 | 74.478 | 24.795 | 1.00 | 95.70 |
| ATOM | 78 | CZ | ARG | A | 46 | 18.893 | 73.520 | 25.708 | 1.00 | 110.85 |
| ATOM | 79 | NH1 | ARG | A | 46 | 18.383 | 72.340 | 25.374 | 1.00 | 97.35 |
| ATOM | 80 | NH2 | ARG | A | 46 | 19.258 | 73.747 | 26.961 | 1.00 | 99.53 |
| ATOM | 81 | N | LYS | A | 47 | 15.143 | 76.837 | 24.888 | 1.00 | 60.06 |
| ATOM | 82 | CA | LYS | A | 47 | 15.380 | 77.699 | 26.031 | 1.00 | 59.74 |
| ATOM | 83 | C | LYS | A | 47 | 14.330 | 77.462 | 27.120 | 1.00 | 63.78 |
| ATOM | 84 | O | LYS | A | 47 | 14.642 | 77.486 | 28.309 | 1.00 | 63.75 |
| ATOM | 85 | CB | LYS | A | 47 | 15.392 | 79.169 | 25.597 | 1.00 | 61.94 |
| ATOM | 86 | CG | LYS | A | 47 | 14.563 | 80.090 | 26.471 | 1.00 | 74.94 |
| ATOM | 87 | CD | LYS | A | 47 | 13.696 | 81.024 | 25.627 | 1.00 | 84.73 |
| ATOM | 88 | CE | LYS | A | 47 | 14.527 | 81.775 | 24.590 | 1.00 | 94.02 |
| ATOM | 89 | NZ | LYS | A | 47 | 13.830 | 83.001 | 24.092 | 1.00 | 100.80 |
| ATOM | 90 | N | ARG | A | 48 | 13.091 | 77.216 | 26.704 | 1.00 | 60.11 |
| ATOM | 91 | CA | ARG | A | 48 | 12.000 | 76.965 | 27.642 | 1.00 | 59.81 |
| ATOM | 92 | C | ARG | A | 48 | 12.162 | 75.623 | 28.367 | 1.00 | 63.62 |
| ATOM | 93 | O | ARG | A | 48 | 11.817 | 75.493 | 29.548 | 1.00 | 63.26 |
| ATOM | 94 | CB | ARG | A | 48 | 10.656 | 77.020 | 26.925 | 1.00 | 59.80 |
| ATOM | 95 | CG | ARG | A | 48 | 10.069 | 78.420 | 26.807 | 1.00 | 69.22 |
| ATOM | 96 | CD | ARG | A | 48 | 8.668 | 78.382 | 26.233 | 1.00 | 78.57 |
| ATOM | 97 | NE | ARG | A | 48 | 8.219 | 79.698 | 25.795 | 1.00 | 89.53 |
| ATOM | 98 | CZ | ARG | A | 48 | 7.700 | 79.949 | 24.600 | 1.00 | 103.86 |
| ATOM | 99 | NH1 | ARG | A | 48 | 7.566 | 78.971 | 23.717 | 1.00 | 91.94 |
| ATOM | 100 | NH2 | ARG | A | 48 | 7.314 | 81.178 | 24.287 | 1.00 | 90.91 |
| ATOM | 101 | N | LEU | A | 49 | 12.693 | 74.633 | 27.659 | 1.00 | 59.61 |
| ATOM | 102 | CA | LEU | A | 49 | 12.922 | 73.313 | 28.235 | 1.00 | 59.26 |
| ATOM | 103 | C | LEU | A | 49 | 14.045 | 73.397 | 29.265 | 1.00 | 63.05 |
| ATOM | 104 | O | LEU | A | 49 | 13.983 | 72.787 | 30.334 | 1.00 | 62.63 |
| ATOM | 105 | CB | LEU | A | 49 | 13.307 | 72.324 | 27.136 | 1.00 | 59.37 |
| ATOM | 106 | CG | LEU | A | 49 | 12.740 | 70.911 | 27.252 | 1.00 | 64.42 |
| ATOM | 107 | CD1 | LEU | A | 49 | 12.291 | 70.618 | 28.685 | 1.00 | 64.64 |
| ATOM | 108 | CD2 | LEU | A | 49 | 11.600 | 70.703 | 26.267 | 1.00 | 66.64 |

TABLE 3-continued

Structural Coordinate of MEK1/N35/NKFCdel (corresponding to amino acids 24-373 of SEQ ID NO: 2)-ATPγS Binary Complex.

| | | | | | | | | | |
|---|---|---|---|---|---|---|---|---|---|
| ATOM | 109 | N | GLU | A | 50 | 15.071 | 74.167 | 28.930 | 1.00 | 59.50 |
| ATOM | 110 | CA | GLU | A | 50 | 16.209 | 74.361 | 29.810 | 1.00 | 59.12 |
| ATOM | 111 | C | GLU | A | 50 | 15.745 | 75.005 | 31.113 | 1.00 | 60.51 |
| ATOM | 112 | O | GLU | A | 50 | 16.051 | 74.525 | 32.207 | 1.00 | 59.92 |
| ATOM | 113 | CB | GLU | A | 50 | 17.224 | 75.274 | 29.127 | 1.00 | 60.81 |
| ATOM | 114 | CG | GLU | A | 50 | 18.670 | 74.986 | 29.461 | 1.00 | 73.47 |
| ATOM | 115 | CD | GLU | A | 50 | 19.615 | 75.958 | 28.772 | 1.00 | 98.72 |
| ATOM | 116 | OE1 | GLU | A | 50 | 19.683 | 75.933 | 27.524 | 1.00 | 85.73 |
| ATOM | 117 | OE2 | GLU | A | 50 | 20.245 | 76.782 | 29.473 | 1.00 | 98.75 |
| ATOM | 118 | N | ALA | A | 51 | 14.993 | 76.093 | 30.980 | 1.00 | 55.29 |
| ATOM | 119 | CA | ALA | A | 51 | 14.481 | 76.836 | 32.132 | 1.00 | 54.03 |
| ATOM | 120 | C | ALA | A | 51 | 13.607 | 75.980 | 33.037 | 1.00 | 55.66 |
| ATOM | 121 | O | ALA | A | 51 | 13.629 | 76.139 | 34.254 | 1.00 | 56.01 |
| ATOM | 122 | CB | ALA | A | 51 | 13.722 | 78.070 | 31.675 | 1.00 | 54.47 |
| ATOM | 123 | N | PHE | A | 52 | 12.845 | 75.064 | 32.444 | 1.00 | 49.53 |
| ATOM | 124 | CA | PHE | A | 52 | 11.971 | 74.200 | 33.228 | 1.00 | 48.27 |
| ATOM | 125 | C | PHE | A | 52 | 12.740 | 73.206 | 34.088 | 1.00 | 52.84 |
| ATOM | 126 | O | PHE | A | 52 | 12.381 | 72.967 | 35.238 | 1.00 | 51.77 |
| ATOM | 127 | CB | PHE | A | 52 | 10.973 | 73.462 | 32.341 | 1.00 | 48.87 |
| ATOM | 128 | CG | PHE | A | 52 | 10.095 | 72.506 | 33.094 | 1.00 | 48.93 |
| ATOM | 129 | CD1 | PHE | A | 52 | 8.998 | 72.968 | 33.813 | 1.00 | 50.24 |
| ATOM | 130 | CD2 | PHE | A | 52 | 10.387 | 71.150 | 33.122 | 1.00 | 49.89 |
| ATOM | 131 | CE1 | PHE | A | 52 | 8.192 | 72.099 | 34.506 | 1.00 | 50.42 |
| ATOM | 132 | CE2 | PEE | A | 52 | 9.581 | 70.274 | 33.819 | 1.00 | 52.17 |
| ATOM | 133 | CZ | SHE | A | 52 | 8.482 | 70.752 | 34.515 | 1.00 | 49.93 |
| ATOM | 134 | N | LEU | A | 53 | 13.787 | 72.621 | 33.519 | 1.00 | 51.13 |
| ATOM | 135 | CA | LEU | A | 53 | 14.613 | 71.652 | 34.245 | 1.00 | 51.55 |
| ATOM | 136 | C | LEU | A | 53 | 15.409 | 72.341 | 35.337 | 1.00 | 56.39 |
| ATOM | 137 | O | LEU | A | 53 | 15.551 | 71.822 | 36.443 | 1.00 | 55.83 |
| ATOM | 138 | CB | LEU | A | 53 | 15.555 | 70.935 | 33.293 | 1.00 | 51.59 |
| ATOM | 139 | CG | LEU | A | 53 | 14.873 | 69.937 | 32.369 | 1.00 | 56.33 |
| ATOM | 140 | CD1 | LEU | A | 53 | 15.615 | 69.839 | 31.048 | 1.00 | 56.35 |
| ATOM | 141 | CD2 | LEU | A | 53 | 14.773 | 68.578 | 33.047 | 1.00 | 58.93 |
| ATOM | 142 | N | THE | A | 54 | 15.931 | 73.517 | 35.024 | 1.00 | 53.69 |
| ATOM | 143 | CA | THR | A | 54 | 16.682 | 74.280 | 36.004 | 1.00 | 53.92 |
| ATOM | 144 | C | THR | A | 54 | 15.802 | 74.492 | 37.235 | 1.00 | 58.73 |
| ATOM | 145 | O | THE | A | 54 | 16.241 | 74.287 | 38.364 | 1.00 | 58.82 |
| ATOM | 146 | CB | THR | A | 54 | 17.112 | 75.645 | 35.441 | 1.00 | 59.69 |
| ATOM | 147 | OG1 | THE | A | 54 | 17.787 | 75.456 | 34.191 | 1.00 | 57.99 |
| ATOM | 148 | OG2 | THR | A | 54 | 18.038 | 76.353 | 36.409 | 1.00 | 56.90 |
| ATOM | 149 | N | GLN | A | 55 | 14.545 | 74.874 | 37.006 | 1.00 | 54.94 |
| ATOM | 150 | CA | GLN | A | 55 | 13.607 | 75.084 | 38.105 | 1.00 | 54.44 |
| ATOM | 151 | C | GLN | A | 55 | 13.343 | 73.770 | 38.845 | 1.00 | 57.83 |
| ATOM | 152 | O | GLN | A | 55 | 13.507 | 73.693 | 40.057 | 1.00 | 57.68 |
| ATOM | 153 | CB | GLN | A | 55 | 12.293 | 75.691 | 37.601 | 1.00 | 55.66 |
| ATOM | 154 | CG | GLN | A | 55 | 12.446 | 77.052 | 36.934 | 1.00 | 75.41 |
| ATOM | 155 | CD | GLN | A | 55 | 11.102 | 77.705 | 36.610 | 1.00 | 103.98 |
| ATOM | 156 | OE1 | GLN | A | 55 | 10.259 | 77.119 | 35.919 | 1.00 | 100.16 |
| ATOM | 157 | NE2 | GLN | A | 55 | 10.902 | 78.926 | 37.102 | 1.00 | 98.92 |
| ATOM | 158 | N | LYS | A | 56 | 12.968 | 72.734 | 38.100 | 1.00 | 54.03 |
| ATOM | 159 | CA | LYS | A | 56 | 12.698 | 71.417 | 38.682 | 1.00 | 53.55 |
| ATOM | 160 | C | LYS | A | 56 | 13.930 | 70.882 | 39.410 | 1.00 | 58.27 |
| ATOM | 161 | O | LYS | A | 56 | 13.845 | 69.944 | 40.198 | 1.00 | 58.33 |
| ATOM | 162 | CB | LYS | A | 56 | 12.261 | 70.436 | 37.593 | 1.00 | 55.32 |
| ATOM | 163 | CG | LYS | A | 56 | 12.617 | 68.992 | 37.873 | 1.00 | 62.95 |
| ATOM | 164 | CD | LYS | A | 56 | 11.509 | 68.057 | 37.409 | 1.00 | 69.51 |
| ATOM | 165 | CE | LYS | A | 56 | 12.006 | 66.630 | 37.246 | 1.00 | 74.10 |
| ATOM | 166 | NZ | LYS | A | 56 | 11.270 | 65.920 | 36.165 | 1.00 | 81.95 |
| ATOM | 167 | N | GLN | A | 57 | 15.075 | 71.492 | 39.141 | 1.00 | 55.10 |
| ATOM | 168 | CA | GLN | A | 57 | 16.325 | 71.095 | 39.768 | 1.00 | 55.03 |
| ATOM | 169 | C | GLN | A | 57 | 16.381 | 71.633 | 41.204 | 1.00 | 58.20 |
| ATOM | 170 | O | GLN | A | 57 | 16.800 | 70.935 | 42.118 | 1.00 | 57.42 |
| ATOM | 171 | CB | GLN | A | 57 | 17.512 | 71.625 | 38.957 | 1.00 | 56.61 |
| ATOM | 172 | CG | GLN | A | 57 | 18.578 | 70.583 | 38.644 | 1.00 | 76.82 |
| ATOM | 173 | CD | GLN | A | 57 | 18.039 | 69.416 | 37.830 | 1.00 | 100.63 |
| ATOM | 174 | OE1 | GLN | A | 57 | 18.721 | 68.406 | 37.646 | 1.00 | 98.78 |
| ATOM | 175 | NE2 | GLN | A | 57 | 16.815 | 69.557 | 37.331 | 1.00 | 91.54 |
| ATOM | 176 | N | LYS | A | 58 | 15.931 | 72.875 | 41.383 | 1.00 | 54.27 |
| ATOM | 177 | CA | LYS | A | 58 | 15.911 | 73.514 | 42.689 | 1.00 | 53.89 |
| ATOM | 178 | C | LYS | A | 58 | 14.938 | 72.846 | 43.663 | 1.00 | 58.58 |
| ATOM | 179 | O | LYS | A | 58 | 15.126 | 72.887 | 44.881 | 1.00 | 57.85 |
| ATOM | 180 | CB | LYS | A | 58 | 15.564 | 74.996 | 42.550 | 1.00 | 55.86 |
| ATOM | 181 | CG | LYS | A | 58 | 16.534 | 75.779 | 41.665 | 1.00 | 62.70 |
| ATOM | 182 | CD | LYS | A | 58 | 15.985 | 77.169 | 41.328 | 1.00 | 69.03 |
| ATOM | 183 | CE | LYS | A | 58 | 16.979 | 77.956 | 40.482 | 1.00 | 78.12 |
| ATOM | 184 | NZ | LYS | A | 58 | 16.988 | 79.418 | 40.810 | 1.00 | 82.80 |
| ATOM | 185 | N | VAL | A | 59 | 13.893 | 72.225 | 43.120 | 1.00 | 56.06 |

TABLE 3-continued

Structural Coordinate of MEK1/N35/NKFCdel (corresponding to amino acids 24-373 of SEQ ID NO: 2)-ATPγS Binary Complex.

| ATOM | 186 | CA | VAL | A | 59 | 12.903 | 71.536 | 43.945 | 1.00 | 55.92 |
| ATOM | 187 | C | VAL | A | 59 | 13.513 | 70.233 | 44.436 | 1.00 | 60.13 |
| ATOM | 188 | O | VAL | A | 59 | 14.315 | 69.606 | 43.735 | 1.00 | 60.35 |
| ATOM | 189 | CB | VAL | A | 59 | 11.601 | 71.244 | 43.141 | 1.00 | 59.87 |
| ATOM | 190 | CG1 | VAL | A | 59 | 10.486 | 70.790 | 44.076 | 1.00 | 59.65 |
| ATOM | 191 | CG2 | VAL | A | 59 | 11.161 | 72.466 | 42.356 | 1.00 | 59.81 |
| ATOM | 192 | N | GLY | A | 60 | 13.180 | 69.844 | 45.651 | 1.00 | 56.15 |
| ATOM | 193 | CA | GLY | A | 60 | 13.733 | 68.617 | 46.200 | 1.00 | 56.20 |
| ATOM | 194 | C | GLY | A | 60 | 12.704 | 67.516 | 46.114 | 1.00 | 61.18 |
| ATOM | 195 | O | GLY | A | 60 | 11.966 | 67.421 | 45.130 | 1.00 | 61.14 |
| ATOM | 196 | N | GLU | A | 61 | 12.653 | 66.684 | 47.146 | 1.00 | 57.92 |
| ATOM | 197 | CA | GLU | A | 61 | 11.674 | 65.621 | 47.209 | 1.00 | 57.86 |
| ATOM | 198 | C | GLU | A | 61 | 10.334 | 66.258 | 47.554 | 1.00 | 60.64 |
| ATOM | 199 | O | GLU | A | 61 | 10.268 | 67.159 | 48.393 | 1.00 | 60.53 |
| ATOM | 200 | CB | GLU | A | 61 | 12.068 | 64.600 | 48.276 | 1.00 | 59.42 |
| ATOM | 201 | CG | GLU | A | 61 | 11.671 | 63.177 | 47.937 | 1.00 | 73.65 |
| ATOM | 202 | CD | GLU | A | 61 | 12.746 | 62.442 | 47.156 | 1.00 | 99.64 |
| ATOM | 203 | OE1 | GLU | A | 61 | 13.507 | 63.107 | 46.419 | 1.00 | 98.16 |
| ATOM | 204 | OE2 | GLU | A | 61 | 12.824 | 61.197 | 47.271 | 1.00 | 93.51 |
| ATOM | 205 | N | LEU | A | 62 | 9.277 | 65.829 | 46.875 | 1.00 | 55.82 |
| ATOM | 206 | CA | LEU | A | 62 | 7.956 | 66.399 | 47.101 | 1.00 | 54.82 |
| ATOM | 207 | C | LEU | A | 62 | 7.301 | 65.808 | 48.335 | 1.00 | 57.10 |
| ATOM | 208 | O | LEU | A | 62 | 7.297 | 64.599 | 48.525 | 1.00 | 56.48 |
| ATOM | 209 | CB | LEU | A | 62 | 7.071 | 66.225 | 45.865 | 1.00 | 54.75 |
| ATOM | 210 | CG | LEU | A | 62 | 7.609 | 66.895 | 44.591 | 1.00 | 59.05 |
| ATOM | 211 | CD1 | LEU | A | 62 | 6.618 | 66.791 | 43.434 | 1.00 | 58.82 |
| ATOM | 212 | CD2 | LEU | A | 62 | 7.982 | 68.345 | 44.856 | 1.00 | 60.69 |
| ATOM | 213 | N | LYS | A | 63 | 6.769 | 66.676 | 49.186 | 1.00 | 53.03 |
| ATOM | 214 | CA | LYS | A | 63 | 6.131 | 66.241 | 50.429 | 1.00 | 52.36 |
| ATOM | 215 | C | LYS | A | 63 | 4.740 | 66.840 | 50.563 | 1.00 | 54.26 |
| ATOM | 216 | O | LYS | A | 63 | 4.527 | 68.011 | 50.252 | 1.00 | 53.53 |
| ATOM | 217 | CB | LYS | A | 63 | 6.993 | 66.631 | 51.637 | 1.00 | 54.84 |
| ATOM | 218 | CG | LYS | A | 63 | 8.372 | 65.988 | 51.645 | 1.00 | 69.91 |
| ATOM | 219 | CD | LYS | A | 63 | 8.879 | 65.773 | 53.060 | 1.00 | 81.08 |
| ATOM | 220 | CE | LYS | A | 63 | 9.316 | 64.328 | 53.279 | 1.00 | 90.79 |
| ATOM | 221 | NZ | LYS | A | 63 | 9.676 | 64.063 | 54.702 | 1.00 | 99.66 |
| ATOM | 222 | N | ASP | A | 64 | 3.798 | 66.026 | 51.023 | 1.00 | 49.71 |
| ATOM | 223 | CA | ASP | A | 64 | 2.412 | 66.452 | 51.182 | 1.00 | 49.37 |
| ATOM | 224 | C | ASP | A | 64 | 2.270 | 67.803 | 51.873 | 1.00 | 52.19 |
| ATOM | 225 | O | ASP | A | 64 | 1.710 | 68.747 | 51.306 | 1.00 | 51.16 |
| ATOM | 226 | CB | ASP | A | 64 | 1.612 | 65.399 | 51.955 | 1.00 | 51.28 |
| ATOM | 227 | CG | ASP | A | 64 | 0.202 | 65.856 | 52.275 | 1.00 | 63.90 |
| ATOM | 228 | OD1 | ASP | A | 64 | −0.593 | 66.043 | 51.333 | 1.00 | 65.29 |
| ATOM | 229 | OD2 | ASP | A | 64 | −0.110 | 66.036 | 53.470 | 1.00 | 72.24 |
| ATOM | 230 | N | ASP | A | 65 | 2.747 | 67.874 | 53.112 | 1.00 | 47.78 |
| ATOM | 231 | CA | ASP | A | 65 | 2.618 | 69.080 | 53.914 | 1.00 | 47.13 |
| ATOM | 232 | C | ASP | A | 65 | 3.279 | 70.330 | 53.286 | 1.00 | 49.75 |
| ATOM | 233 | O | ASP | A | 65 | 3.039 | 71.447 | 53.736 | 1.00 | 49.05 |
| ATOM | 234 | CB | ASP | A | 65 | 3.115 | 68.839 | 55.360 | 1.00 | 49.26 |
| ATOM | 235 | CG | ASP | A | 65 | 2.266 | 67.788 | 56.132 | 1.00 | 61.44 |
| ATOM | 236 | OD1 | ASP | A | 65 | 1.380 | 67.133 | 55.519 | 1.00 | 61.23 |
| ATOM | 237 | OD2 | ASP | A | 65 | 2.503 | 67.615 | 57.359 | 1.00 | 71.25 |
| ATOM | 238 | N | ASP | A | 66 | 4.067 | 70.142 | 52.227 | 1.00 | 45.54 |
| ATOM | 239 | CA | ASP | A | 66 | 4.725 | 71.273 | 51.557 | 1.00 | 45.21 |
| ATOM | 240 | C | ASP | A | 66 | 3.827 | 71.940 | 50.512 | 1.00 | 49.34 |
| ATOM | 241 | O | ASP | A | 66 | 4.234 | 72.898 | 49.842 | 1.00 | 48.47 |
| ATOM | 242 | CB | ASP | A | 66 | 6.026 | 70.827 | 50.897 | 1.00 | 47.47 |
| ATOM | 243 | CG | ASP | A | 66 | 7.141 | 70.581 | 51.903 | 1.00 | 59.55 |
| ATOM | 244 | OD1 | ASP | A | 66 | 7.179 | 71.281 | 52.939 | 1.00 | 60.26 |
| ATOM | 245 | OD2 | ASP | A | 66 | 7.986 | 69.696 | 51.650 | 1.00 | 65.13 |
| ATOM | 246 | N | PHE | A | 67 | 2.609 | 71.425 | 50.368 | 1.00 | 45.66 |
| ATOM | 247 | CA | PHE | A | 67 | 1.674 | 71.939 | 49.379 | 1.00 | 44.35 |
| ATOM | 248 | C | PHE | A | 67 | 0.535 | 72.733 | 49.982 | 1.00 | 47.94 |
| ATOM | 249 | O | PEE | A | 67 | 0.089 | 72.463 | 51.090 | 1.00 | 46.77 |
| ATOM | 250 | CB | PHE | A | 67 | 1.135 | 70.800 | 48.507 | 1.00 | 45.26 |
| ATOM | 251 | CG | PHE | A | 67 | 2.136 | 70.275 | 47.527 | 1.00 | 45.79 |
| ATOM | 252 | CD1 | PHE | A | 67 | 2.339 | 70.912 | 45.319 | 1.00 | 47.94 |
| ATOM | 253 | CD2 | PHE | A | 67 | 2.915 | 69.182 | 47.838 | 1.00 | 47.15 |
| ATOM | 254 | CE1 | PHE | A | 67 | 3.287 | 70.454 | 45.438 | 1.00 | 48.53 |
| ATOM | 255 | CE2 | PHE | A | 67 | 3.870 | 68.727 | 46.962 | 1.00 | 49.59 |
| ATOM | 256 | CZ | PHE | A | 67 | 4.055 | 69.358 | 45.763 | 1.00 | 47.60 |
| ATOM | 257 | N | GLU | A | 68 | 0.066 | 73.713 | 49.224 | 1.00 | 45.69 |
| ATOM | 258 | CA | GLU | A | 68 | −1.029 | 74.571 | 49.633 | 1.00 | 45.71 |
| ATOM | 259 | C | GLU | A | 68 | −1.990 | 74.688 | 46.437 | 1.00 | 49.76 |
| ATOM | 260 | O | GLU | A | 68 | −1.589 | 75.109 | 47.347 | 1.00 | 49.04 |
| ATOM | 261 | CB | GLU | A | 68 | −0.477 | 75.949 | 50.023 | 1.00 | 47.07 |
| ATOM | 262 | CG | GLU | A | 68 | −1.509 | 76.942 | 50.511 | 1.00 | 59.43 |

TABLE 3-continued

Structural Coordinate of MEK1/N35/NKFCdel (corresponding to amino acids 24-373 of SEQ ID NO: 2)-ATPγS Binary Complex.

| ATOM | 263 | CD  | GLU | A | 68 | −1.021  | 78.383 | 50.400 | 1.00 | 88.13  |
|------|-----|-----|-----|---|----|---------|--------|--------|------|--------|
| ATOM | 264 | OE1 | GLU | A | 68 | 0.213   | 78.605 | 50.426 | 1.00 | 76.75  |
| ATOM | 265 | OE2 | GLU | A | 68 | −1.870  | 79.291 | 50.266 | 1.00 | 89.20  |
| ATOM | 266 | N   | LYS | A | 69 | −3.237  | 74.261 | 48.631 | 1.00 | 46.48  |
| ATOM | 267 | CA  | LYS | A | 69 | −4.230  | 74.287 | 47.563 | 1.00 | 46.99  |
| ATOM | 268 | C   | LYS | A | 69 | −4.671  | 75.702 | 47.192 | 1.00 | 52.61  |
| ATOM | 269 | O   | LYS | A | 69 | −4.935  | 76.537 | 48.062 | 1.00 | 52.73  |
| ATOM | 270 | CB  | LYS | A | 69 | −5.445  | 73.435 | 47.932 | 1.00 | 49.46  |
| ATOM | 271 | CG  | LYS | A | 69 | −6.579  | 73.526 | 46.930 | 1.00 | 65.02  |
| ATOM | 272 | CD  | LYS | A | 69 | −7.746  | 72.633 | 47.335 | 1.00 | 74.94  |
| ATOM | 273 | CE  | LYS | A | 69 | −9.066  | 73.146 | 46.767 | 1.00 | 82.52  |
| ATOM | 274 | NZ  | LYS | A | 69 | −10.221 | 72.301 | 47.193 | 1.00 | 88.63  |
| ATOM | 275 | N   | ILE | A | 70 | −4.740  | 75.967 | 45.893 | 1.00 | 49.32  |
| ATOM | 276 | CA  | ILE | A | 70 | −5.151  | 77.274 | 45.402 | 1.00 | 49.03  |
| ATOM | 277 | C   | ILE | A | 70 | −6.572  | 77.195 | 44.880 | 1.00 | 54.06  |
| ATOM | 278 | O   | ILE | A | 70 | −7.437  | 77.955 | 45.296 | 1.00 | 54.85  |
| ATOM | 279 | CB  | ILE | A | 70 | −4.245  | 77.763 | 44.263 | 1.00 | 51.81  |
| ATOM | 280 | CG1 | ILE | A | 70 | −2.809  | 77.933 | 44.752 | 1.00 | 51.56  |
| ATOM | 281 | CG2 | ILE | A | 70 | −4.775  | 79.068 | 43.687 | 1.00 | 52.99  |
| ATOM | 282 | CD1 | ILE | A | 70 | −1.910  | 78.612 | 43.752 | 1.00 | 52.79  |
| ATOM | 283 | N   | SER | A | 71 | −6.809  | 76.261 | 43.975 | 1.00 | 50.28  |
| ATOM | 284 | CA  | SER | A | 71 | −8.128  | 76.076 | 43.406 | 1.00 | 50.24  |
| ATOM | 285 | C   | SER | A | 71 | −8.232  | 74.710 | 42.764 | 1.00 | 55.45  |
| ATOM | 286 | O   | SER | A | 71 | −7.242  | 73.977 | 42.666 | 1.00 | 55.08  |
| ATOM | 287 | CB  | SER | A | 71 | −8.419  | 77.160 | 42.367 | 1.00 | 53.17  |
| ATOM | 288 | OG  | SER | A | 71 | −7.354  | 77.271 | 41.432 | 1.00 | 60.02  |
| ATOM | 289 | N   | GLU | A | 72 | −9.433  | 74.370 | 42.323 | 1.00 | 53.13  |
| ATOM | 290 | CA  | GLU | A | 73 | −9.678  | 73.095 | 41.669 | 1.00 | 53.62  |
| ATOM | 291 | C   | GLU | A | 72 | −9.562  | 73.277 | 40.164 | 1.00 | 57.70  |
| ATOM | 292 | O   | GLU | A | 72 | −10.178 | 74.171 | 39.598 | 1.00 | 57.44  |
| ATOM | 293 | CB  | GLU | A | 72 | −11.066 | 72.570 | 42.034 | 1.00 | 55.21  |
| ATOM | 294 | OG  | GLU | A | 72 | −11.055 | 71.190 | 42.670 | 1.00 | 68.51  |
| ATOM | 295 | CD  | GLU | A | 72 | −12.091 | 71.045 | 43.775 | 1.00 | 90.12  |
| ATOM | 296 | OE1 | GLU | A | 72 | −12.607 | 72.079 | 44.250 | 1.00 | 82.31  |
| ATOM | 297 | OE2 | GLU | A | 72 | −12.385 | 69.897 | 44.170 | 1.00 | 85.74  |
| ATOM | 298 | N   | LEU | A | 73 | −8.746  | 72.442 | 39.526 | 1.00 | 54.70  |
| ATOM | 299 | CA  | LEU | A | 73 | −8.518  | 73.531 | 38.080 | 1.00 | 54.63  |
| ATOM | 300 | C   | LEU | A | 73 | −9.501  | 71.699 | 37.276 | 1.00 | 60.43  |
| ATOM | 301 | O   | LEU | A | 73 | −9.829  | 72.036 | 36.146 | 1.00 | 60.50  |
| ATOM | 302 | CB  | LEU | A | 73 | −7.096  | 72.101 | 37.737 | 1.00 | 54.38  |
| ATOM | 303 | CG  | LEU | A | 73 | −5.982  | 73.060 | 38.142 | 1.00 | 58.31  |
| ATOM | 304 | CD1 | LEU | A | 73 | −4.632  | 72.469 | 37.794 | 1.00 | 58.13  |
| ATOM | 305 | CD2 | LEU | A | 73 | −6.178  | 74.400 | 37.474 | 1.00 | 59.76  |
| ATOM | 306 | N   | GLY | A | 74 | −9.943  | 70.594 | 37.847 | 1.00 | 58.51  |
| ATOM | 307 | CA  | GLY | A | 74 | −10.869 | 69.717 | 37.162 | 1.00 | 59.58  |
| ATOM | 308 | C   | GLY | A | 74 | −10.870 | 68.355 | 37.822 | 1.00 | 66.53  |
| ATOM | 309 | O   | GLY | A | 74 | −10.102 | 68.107 | 38.756 | 1.00 | 66.15  |
| ATOM | 310 | N   | ALA | A | 75 | −11.729 | 67.466 | 37.334 | 1.00 | 65.14  |
| ATOM | 311 | CA  | ALA | A | 75 | −11.828 | 66.134 | 37.905 | 1.00 | 66.06  |
| ATOM | 312 | C   | ALA | A | 75 | −12.073 | 65.057 | 36.862 | 1.00 | 71.96  |
| ATOM | 313 | O   | ALA | A | 75 | −12.410 | 65.348 | 35.710 | 1.00 | 71.94  |
| ATOM | 314 | CB  | ALA | A | 75 | −12.911 | 66.097 | 38.973 | 1.00 | 66.81  |
| ATOM | 315 | N   | GLY | A | 76 | −11.909 | 63.808 | 37.281 | 1.00 | 69.54  |
| ATOM | 316 | CA  | GLY | A | 76 | −12.124 | 62.663 | 36.418 | 1.00 | 69.93  |
| ATOM | 317 | C   | GLY | A | 76 | −12.929 | 61.628 | 37.185 | 1.00 | 75.90  |
| ATOM | 318 | O   | GLY | A | 76 | −13.450 | 61.916 | 38.265 | 1.00 | 75.72  |
| ATOM | 319 | N   | ASN | A | 77 | −13.015 | 50.419 | 36.637 | 1.00 | 73.74  |
| ATOM | 320 | CA  | ASN | A | 77 | −13.777 | 59.333 | 37.257 | 1.00 | 74.06  |
| ATOM | 321 | C   | ASN | A | 77 | −13.037 | 58.643 | 38.417 | 1.00 | 78.60  |
| ATOM | 322 | O   | ASN | A | 77 | −13.129 | 57.417 | 38.593 | 1.00 | 78.46  |
| ATOM | 323 | CB  | ASN | A | 77 | −14.193 | 58.301 | 36.200 | 1.00 | 75.16  |
| ATOM | 324 | CG  | ASN | A | 77 | −14.768 | 58.945 | 34.947 | 1.00 | 101.10 |
| ATOM | 325 | OD1 | ASN | A | 77 | −15.445 | 59.976 | 35.016 | 1.00 | 95.52  |
| ATOM | 326 | NO2 | ASN | A | 77 | −14.505 | 58.335 | 33.794 | 1.00 | 92.98  |
| ATOM | 327 | N   | CLY | A | 78 | −12.331 | 59.430 | 39.221 | 1.00 | 74.93  |
| ATOM | 328 | CA  | CLY | A | 78 | −11.597 | 58.890 | 40.374 | 1.00 | 74.33  |
| ATOM | 329 | C   | GLY | A | 78 | −10.198 | 59.488 | 40.456 | 1.00 | 76.46  |
| ATOM | 330 | O   | GLY | A | 78 | −9.208  | 58.765 | 40.481 | 1.00 | 76.65  |
| ATOM | 331 | N   | GLY | A | 79 | −10.132 | 60.814 | 40.426 | 1.00 | 70.79  |
| ATOM | 332 | CA  | GLY | A | 79 | −8.860  | 61.526 | 40.479 | 1.00 | 69.29  |
| ATOM | 333 | C   | GLY | A | 79 | −9.098  | 63.021 | 40.247 | 1.00 | 69.97  |
| ATOM | 334 | O   | GLY | A | 79 | −9.444  | 63.456 | 39.143 | 1.00 | 69.20  |
| ATOM | 335 | N   | VAL | A | 80 | −8.943  | 63.794 | 41.311 | 1.00 | 63.87  |
| ATOM | 336 | CA  | VAL | A | 80 | −9.142  | 65.225 | 41.242 | 1.00 | 62.08  |
| ATOM | 337 | C   | VAL | A | 80 | −7.809  | 65.910 | 40.994 | 1.00 | 60.29  |
| ATOM | 338 | O   | VAL | A | 80 | −6.752  | 65.364 | 41.318 | 1.00 | 59.54  |
| ATOM | 339 | CB  | VAL | A | 80 | −9.754  | 65.753 | 42.545 | 1.00 | 66.76  |

TABLE 3-continued

Structural Coordinate of MEK1/N35/NKFCdel (corresponding to amino acids 24-373 of SEQ ID NO: 2)-ATPγS Binary Complex.

| ATOM | 340 | CG1 | VAL | A | 80 | −10.386 | 67.136 | 42.327 | 1.00 | 66.69 |
|---|---|---|---|---|---|---|---|---|---|---|
| ATOM | 341 | CG2 | VAL | A | 80 | −10.789 | 64.756 | 43.082 | 1.00 | 66.70 |
| ATOM | 342 | N | VAL | A | 81 | −7.859 | 67.092 | 40.387 | 1.00 | 52.52 |
| ATOM | 343 | CA | VAL | A | 81 | −6.648 | 67.845 | 40.110 | 1.00 | 50.30 |
| ATOM | 344 | C | VAL | A | 81 | −6.765 | 69.257 | 40.630 | 1.00 | 50.58 |
| ATOM | 345 | O | VAL | A | 81 | −7.680 | 69.996 | 40.269 | 1.00 | 49.16 |
| ATOM | 346 | CB | VAL | A | 81 | −6.281 | 67.853 | 38.603 | 1.00 | 53.36 |
| ATOM | 347 | CG1 | VAL | A | 81 | −4.956 | 68.587 | 38.385 | 1.00 | 52.57 |
| ATOM | 348 | CG2 | VAL | A | 81 | −6.197 | 66.433 | 38.071 | 1.00 | 53.11 |
| ATOM | 349 | N | PHE | A | 82 | −5.836 | 69.624 | 41.496 | 1.00 | 46.26 |
| ATOM | 350 | CA | PHE | A | 82 | −5.833 | 70.940 | 42.108 | 1.00 | 45.77 |
| ATOM | 351 | C | PHE | A | 82 | −4.686 | 71.807 | 41.610 | 1.00 | 47.34 |
| ATOM | 352 | O | PHE | A | 82 | −3.616 | 71.310 | 41.265 | 1.00 | 46.04 |
| ATOM | 353 | CB | PHE | A | 82 | −5.720 | 70.803 | 43.631 | 1.00 | 47.78 |
| ATOM | 354 | CG | PHE | A | 82 | −6.940 | 70.224 | 44.282 | 1.00 | 50.11 |
| ATOM | 355 | CD1 | PHE | A | 82 | −7.035 | 68.868 | 44.516 | 1.00 | 54.28 |
| ATOM | 356 | CD2 | PHE | A | 82 | −7.974 | 71.048 | 44.707 | 1.00 | 52.92 |
| ATOM | 357 | CE1 | PHE | A | 82 | −8.157 | 68.331 | 45.144 | 1.00 | 55.80 |
| ATOM | 358 | CE2 | PEE | A | 82 | −9.097 | 70.521 | 45.321 | 1.00 | 56.08 |
| ATOM | 359 | CZ | PHE | A | 82 | −9.188 | 69.163 | 45.543 | 1.00 | 54.46 |
| ATOM | 360 | N | LYS | A | 83 | −4.898 | 73.113 | 41.622 | 1.00 | 43.39 |
| ATOM | 361 | CA | LYS | A | 83 | −3.831 | 74.044 | 41.301 | 1.00 | 42.61 |
| ATOM | 362 | C | LYS | A | 83 | −3.225 | 74.362 | 42.654 | 1.00 | 44.84 |
| ATOM | 363 | O | LYS | A | 83 | −3.941 | 74.724 | 43.585 | 1.00 | 44.32 |
| ATOM | 364 | CB | LYS | A | 83 | −4.380 | 75.312 | 40.655 | 1.00 | 44.70 |
| ATOM | 365 | CG | LYS | A | 83 | −3.311 | 76.227 | 40.111 | 1.00 | 51.78 |
| ATOM | 366 | CD | LYS | A | 83 | −3.796 | 77.655 | 40.066 | 1.00 | 60.17 |
| ATOM | 367 | CE | LYS | A | 83 | −2.689 | 78.594 | 39.632 | 1.00 | 70.37 |
| ATOM | 368 | NZ | LYS | A | 93 | −3.236 | 79.882 | 39.118 | 1.00 | 82.16 |
| ATOM | 369 | N | VAL | A | 84 | −1.930 | 74.131 | 42.796 | 1.00 | 40.24 |
| ATOM | 370 | CA | VAL | A | 84 | −1.296 | 74.310 | 44.080 | 1.00 | 39.48 |
| ATOM | 371 | C | VAL | A | 84 | −0.044 | 75.149 | 44.052 | 1.00 | 43.70 |
| ATOM | 372 | O | VAL | A | 84 | 0.552 | 75.411 | 42.995 | 1.00 | 42.77 |
| ATOM | 373 | CB | VAL | A | 84 | −0.918 | 72.949 | 44.722 | 1.00 | 42.87 |
| ATOM | 374 | CG1 | VAL | A | 64 | −2.148 | 72.073 | 44.917 | 1.00 | 42.61 |
| ATOM | 375 | CG2 | VAL | A | 84 | 0.145 | 72.237 | 43.887 | 1.00 | 42.42 |
| ATOM | 376 | N | SER | A | 85 | 0.382 | 75.512 | 45.251 | 1.00 | 40.39 |
| ATOM | 377 | CA | SFR | A | 85 | 1.597 | 76.237 | 45.458 | 1.00 | 40.07 |
| ATOM | 378 | C | SER | A | 85 | 2.531 | 75.318 | 46.247 | 1.00 | 44.37 |
| ATOM | 379 | O | SER | A | 85 | 2.147 | 74.776 | 47.290 | 1.00 | 43.07 |
| ATOM | 380 | CB | SER | A | 85 | 1.310 | 77.496 | 46.275 | 1.00 | 42.88 |
| ATOM | 381 | OG | SER | A | 85 | 2.501 | 78.034 | 46.805 | 1.00 | 51.75 |
| ATOM | 382 | N | HIS | A | 86 | 3.727 | 75.087 | 45.721 | 1.00 | 42.51 |
| ATOM | 383 | CA | HIS | A | 86 | 4.716 | 74.312 | 46.448 | 1.00 | 43.33 |
| ATOM | 384 | C | HIS | A | 86 | 5.455 | 75.331 | 47.317 | 1.00 | 48.17 |
| ATOM | 385 | O | HIS | A | 86 | 6.368 | 76.021 | 46.844 | 1.00 | 47.35 |
| ATOM | 386 | CB | HIS | A | 86 | 5.697 | 73.626 | 45.508 | 1.00 | 44.29 |
| ATOM | 387 | CG | HIS | A | 86 | 6.683 | 72.754 | 46.216 | 1.00 | 47.68 |
| ATOM | 388 | ND1 | HIS | A | 86 | 8.038 | 73.005 | 46.212 | 1.00 | 49.52 |
| ATOM | 389 | CD2 | HIS | A | 86 | 6.504 | 71.666 | 47.002 | 1.00 | 49.21 |
| ATOM | 390 | CE1 | HIS | A | 86 | 8.654 | 72.095 | 46.947 | 1.00 | 48.74 |
| ATOM | 391 | NE2 | HIS | A | 86 | 7.745 | 71.274 | 47.440 | 1.00 | 49.01 |
| ATOM | 392 | N | LYS | A | 87 | 4.978 | 75.481 | 48.552 | 1.00 | 45.01 |
| ATOM | 393 | CA | LYS | A | 87 | 5.484 | 76.475 | 49.502 | 1.00 | 44.81 |
| ATOM | 394 | C | LYS | A | 87 | 6.976 | 76.790 | 49.445 | 1.00 | 49.01 |
| ATOM | 395 | O | LYS | A | 87 | 7.369 | 77.923 | 49.154 | 1.00 | 49.57 |
| ATOM | 396 | CB | LYS | A | 87 | 5.060 | 76.125 | 50.932 | 1.00 | 46.85 |
| ATOM | 397 | CG | LYS | A | 87 | 3.595 | 76.427 | 51.233 | 1.00 | 55.27 |
| ATOM | 398 | CD | LYS | A | 87 | 2.815 | 75.154 | 51.499 | 1.00 | 63.63 |
| ATOM | 399 | CE | LYS | A | 87 | 2.036 | 75.245 | 52.799 | 1.00 | 73.12 |
| ATOM | 400 | NZ | LYS | A | 87 | 2.709 | 74.497 | 53.902 | 1.00 | 80.83 |
| ATOM | 401 | N | PRO | A | 88 | 7.803 | 75.797 | 49.733 | 1.00 | 44.97 |
| ATOM | 402 | CA | PRO | A | 88 | 9.255 | 75.994 | 49.767 | 1.00 | 44.58 |
| ATOM | 403 | C | PRO | A | 88 | 9.821 | 76.665 | 48.510 | 1.00 | 49.49 |
| ATOM | 404 | O | PRO | A | 88 | 10.459 | 77.721 | 48.586 | 1.00 | 49.49 |
| ATOM | 405 | CB | PRO | A | 88 | 9.801 | 74.565 | 49.912 | 1.00 | 45.80 |
| ATOM | 406 | CG | PRO | A | 88 | 8.628 | 73.751 | 50.382 | 1.00 | 49.93 |
| ATOM | 407 | CD | PRO | A | 88 | 7.448 | 74.374 | 49.725 | 1.00 | 45.20 |
| ATOM | 408 | N | SER | A | 89 | 9.593 | 76.040 | 47.362 | 1.00 | 46.13 |
| ATOM | 409 | CA | SER | A | 89 | 10.096 | 76.543 | 46.090 | 1.00 | 45.61 |
| ATOM | 410 | C | SER | A | 89 | 9.346 | 77.771 | 45.587 | 1.00 | 48.69 |
| ATOM | 411 | O | SER | A | 89 | 9.880 | 78.543 | 44.808 | 1.00 | 48.38 |
| ATOM | 412 | CB | SER | A | 89 | 10.023 | 75.440 | 45.034 | 1.00 | 49.15 |
| ATOM | 413 | OG | SER | A | 89 | 8.672 | 75.137 | 44.725 | 1.00 | 56.83 |
| ATOM | 414 | N | GLY | A | 90 | 8.097 | 77.931 | 46.009 | 1.00 | 45.19 |
| ATOM | 415 | CA | GLY | A | 90 | 7.269 | 79.039 | 45.532 | 1.00 | 44.77 |
| ATOM | 416 | C | GLY | A | 90 | 6.643 | 78.689 | 44.161 | 1.00 | 48.28 |

TABLE 3-continued

Structural Coordinate of MEK1/N35/NKFCdel (corresponding to amino acids 24-373 of SEQ ID NO: 2)-ATPγS Binary Complex.

| ATOM | 417 | O   | GLY | A | 90  | 5.863  | 79.468 | 43.595 | 1.00 | 47.35 |
|------|-----|-----|-----|---|-----|--------|--------|--------|------|-------|
| ATOM | 418 | N   | LEU | A | 91  | 6.996  | 77.519 | 43.637 | 1.00 | 45.24 |
| ATOM | 419 | CA  | LEU | A | 91  | 6.466  | 77.059 | 42.343 | 1.00 | 44.99 |
| ATOM | 420 | C   | LEU | A | 91  | 4.987  | 76.706 | 42.440 | 1.00 | 47.71 |
| ATOM | 421 | O   | LEU | A | 91  | 4.547  | 76.081 | 43.405 | 1.00 | 46.57 |
| ATOM | 422 | CB  | LEU | A | 91  | 7.220  | 75.815 | 41.864 | 1.00 | 45.10 |
| ATOM | 423 | CG  | LEU | A | 91  | 8.627  | 75.939 | 41.267 | 1.00 | 50.01 |
| ATOM | 424 | CD1 | LEU | A | 91  | 8.896  | 74.750 | 40.370 | 1.00 | 50.15 |
| ATOM | 425 | CD2 | LEU | A | 91  | 8.822  | 77.248 | 40.503 | 1.00 | 51.82 |
| ATOM | 426 | N   | VAL | A | 92  | 4.236  | 77.082 | 41.416 | 1.00 | 44.23 |
| ATOM | 427 | CA  | VAL | A | 92  | 2.834  | 76.718 | 41.312 | 1.00 | 43.81 |
| ATOM | 428 | C   | VAL | A | 92  | 2.795  | 75.479 | 40.410 | 1.00 | 46.11 |
| ATOM | 429 | O   | VAL | A | 92  | 3.566  | 75.381 | 39.459 | 1.00 | 46.12 |
| ATOM | 430 | CB  | VAL | A | 92  | 2.008  | 77.836 | 40.661 | 1.00 | 47.91 |
| ATOM | 431 | CG1 | VAL | A | 92  | 0.633  | 77.333 | 40.285 | 1.00 | 47.81 |
| ATOM | 432 | CG2 | VAL | A | 92  | 1.899  | 79.021 | 41.595 | 1.00 | 47.79 |
| ATOM | 433 | N   | MET | A | 93  | 1.967  | 74.505 | 40.762 | 1.00 | 40.56 |
| ATOM | 434 | CA  | MET | A | 93  | 1.873  | 73.280 | 39.987 | 1.00 | 38.99 |
| ATOM | 435 | C   | MET | A | 93  | 0.453  | 72.790 | 39.918 | 1.00 | 41.70 |
| ATOM | 436 | O   | MET | A | 93  | −0.444 | 73.305 | 40.604 | 1.00 | 40.92 |
| ATOM | 437 | CB  | MET | A | 93  | 2.719  | 72.161 | 40.628 | 1.00 | 41.02 |
| ATOM | 438 | CG  | MET | A | 93  | 3.999  | 72.613 | 41.219 | 1.00 | 44.12 |
| ATOM | 439 | SD  | MET | A | 93  | 4.926  | 71.198 | 42.014 | 1.00 | 47.80 |
| ATOM | 440 | CE  | MET | A | 93  | 6.622  | 71.800 | 41.863 | 1.00 | 44.47 |
| ATOM | 441 | N   | ALA | A | 94  | 0.271  | 71.728 | 39.148 | 1.00 | 37.64 |
| ATOM | 442 | CA  | ALA | A | 94  | −0.996 | 71.036 | 39.073 | 1.00 | 37.27 |
| ATOM | 443 | C   | ALA | A | 94  | −0.746 | 69.748 | 39.825 | 1.00 | 40.99 |
| ATOM | 444 | O   | ALA | A | 94  | 0.256  | 69.079 | 39.600 | 1.00 | 40.04 |
| ATOM | 445 | CB  | ALA | A | 94  | −1.360 | 70.747 | 37.624 | 1.00 | 38.04 |
| ATOM | 446 | N   | ARG | A | 95  | −1.601 | 69.446 | 40.784 | 1.00 | 38.81 |
| ATOM | 447 | CA  | ARG | A | 95  | −1.422 | 68.252 | 41.594 | 1.00 | 38.80 |
| ATOM | 448 | C   | ARG | A | 95  | −2.567 | 67.287 | 41.372 | 1.00 | 43.55 |
| ATOM | 449 | O   | ARG | A | 95  | −3.715 | 67.597 | 41.680 | 1.00 | 43.26 |
| ATOM | 450 | CB  | ARG | A | 95  | −1.325 | 68.629 | 43.085 | 1.00 | 37.43 |
| ATOM | 451 | CG  | ARG | A | 95  | −1.010 | 67.453 | 44.050 | 1.00 | 40.99 |
| ATOM | 452 | CD  | ARG | A | 95  | −1.032 | 67.933 | 45.524 | 1.00 | 43.19 |
| ATOM | 453 | NE  | ARG | A | 95  | −0.801 | 66.845 | 46.489 | 1.00 | 46.69 |
| ATOM | 454 | CZ  | ARG | A | 95  | −0.922 | 66.976 | 47.815 | 1.00 | 59.60 |
| ATOM | 455 | NH1 | ARG | A | 95  | −1.294 | 68.133 | 48.345 | 1.00 | 43.11 |
| ATOM | 456 | NH2 | ARG | A | 95  | −0.693 | 65.940 | 48.614 | 1.00 | 49.01 |
| ATOM | 457 | N   | LYS | A | 96  | −2.255 | 66.119 | 40.831 | 1.00 | 41.36 |
| ATOM | 458 | CA  | LYS | A | 96  | −3.274 | 65.092 | 40.624 | 1.00 | 42.12 |
| ATOM | 459 | C   | LYS | A | 96  | −3.279 | 64.137 | 41.807 | 1.00 | 47.52 |
| ATOM | 460 | O   | LYS | A | 96  | −2.236 | 63.603 | 42.199 | 1.00 | 46.28 |
| ATOM | 461 | CB  | LYS | A | 96  | −3.040 | 64.327 | 39.323 | 1.00 | 44.23 |
| ATOM | 462 | CG  | LYS | A | 96  | −4.221 | 63.453 | 38.894 | 1.00 | 54.01 |
| ATOM | 463 | CD  | LYS | A | 96  | −3.991 | 62.869 | 37.500 | 1.00 | 59.57 |
| ATOM | 464 | CE  | LYS | A | 96  | −5.287 | 62.680 | 36.751 | 1.00 | 60.81 |
| ATOM | 465 | NZ  | LYS | A | 96  | −5.098 | 61.851 | 35.539 | 1.00 | 63.49 |
| ATOM | 466 | N   | LEU | A | 97  | −4.449 | 63.955 | 42.400 | 1.00 | 46.66 |
| ATOM | 467 | CA  | LEU | A | 97  | −4.578 | 63.079 | 43.550 | 1.00 | 47.96 |
| ATOM | 468 | C   | LEU | A | 97  | −5.430 | 61.874 | 43.228 | 1.00 | 55.33 |
| ATOM | 469 | O   | LEU | A | 97  | −6.615 | 62.001 | 42.926 | 1.00 | 54.75 |
| ATOM | 470 | CB  | LEU | A | 97  | −5.164 | 63.837 | 44.743 | 1.00 | 48.01 |
| ATOM | 471 | CG  | LEU | A | 97  | −4.385 | 65.083 | 45.170 | 1.00 | 53.09 |
| ATOM | 472 | CD1 | LEU | A | 97  | −5.315 | 66.284 | 45.339 | 1.00 | 53.13 |
| ATOM | 473 | CD2 | LEU | A | 97  | −3.610 | 64.808 | 46.453 | 1.00 | 55.88 |
| ATOM | 474 | N   | ILE | A | 98  | −4.818 | 60.701 | 43.283 | 1.00 | 55.10 |
| ATOM | 475 | CA  | ILE | A | 98  | −5.534 | 59.461 | 43.037 | 1.00 | 56.46 |
| ATOM | 476 | C   | ILE | A | 98  | −5.673 | 58.721 | 44.356 | 1.00 | 64.11 |
| ATOM | 477 | O   | ILE | A | 98  | −4.678 | 58.288 | 44.935 | 1.00 | 63.09 |
| ATOM | 478 | CB  | ILE | A | 98  | −4.783 | 58.554 | 42.047 | 1.00 | 59.35 |
| ATOM | 479 | CG1 | ILE | A | 98  | −4.525 | 59.286 | 40.731 | 1.00 | 59.59 |
| ATOM | 480 | CG2 | ILE | A | 98  | −5.565 | 57.282 | 41.798 | 1.00 | 60.00 |
| ATOM | 481 | CD1 | ILE | A | 98  | −3.289 | 58.797 | 40.000 | 1.00 | 65.00 |
| ATOM | 482 | N   | HIS | A | 99  | −6.900 | 58.608 | 44.853 | 1.00 | 64.29 |
| ATOM | 483 | CA  | HIS | A | 99  | −7.117 | 57.894 | 46.096 | 1.00 | 66.09 |
| ATOM | 484 | C   | HIS | A | 99  | −7.155 | 56.405 | 45.853 | 1.00 | 71.91 |
| ATOM | 485 | O   | HIS | A | 99  | −8.038 | 55.897 | 45.148 | 1.00 | 71.49 |
| ATOM | 486 | CB  | HIS | A | 99  | −8.396 | 58.331 | 46.807 | 1.00 | 67.40 |
| ATOM | 487 | CG  | HIS | A | 99  | −8.505 | 57.805 | 48.207 | 1.00 | 71.33 |
| ATOM | 488 | ND1 | HIS | A | 99  | −8.256 | 58.587 | 49.317 | 1.00 | 73.33 |
| ATOM | 489 | CD2 | HIS | A | 99  | −8.773 | 56.562 | 48.674 | 1.00 | 73.21 |
| ATOM | 490 | CE1 | HIS | A | 99  | −8.397 | 57.853 | 50.407 | 1.00 | 72.77 |
| ATOM | 491 | NE2 | HIS | A | 99  | −8.709 | 56.621 | 50.044 | 1.00 | 73.04 |
| ATOM | 492 | N   | LEU | A | 100 | −6.195 | 55.700 | 46.424 | 1.00 | 69.36 |
| ATOM | 493 | CA  | LEU | A | 100 | −6.136 | 54.273 | 46.269 | 1.00 | 69.47 |

TABLE 3-continued

Structural Coordinate of MEK1/N35/NKFCdel (corresponding to amino acids 24-373 of SEQ ID NO: 2)-ATPγS Binary Complex.

| ATOM | 494 | C | LEU | A | 100 | −5.759 | 53.618 | 47.587 | 1.00 | 72.05 |
|---|---|---|---|---|---|---|---|---|---|---|
| ATOM | 495 | O | LEU | A | 100 | −4.826 | 54.047 | 48.264 | 1.00 | 71.58 |
| ATOM | 496 | CB | LEU | A | 100 | −5.152 | 53.899 | 45.156 | 1.00 | 69.88 |
| ATOM | 497 | CG | LEU | A | 100 | −5.715 | 54.059 | 43.740 | 1.00 | 74.87 |
| ATOM. | 498 | CD1 | LEU | A | 100 | −4.638 | 53.907 | 42.702 | 1.00 | 75.16 |
| ATOM | 499 | CD2 | LEU | A | 100 | −6.788 | 53.017 | 43.537 | 1.00 | 77.41 |
| ATOM | 500 | N | GLU | A | 101 | −6.536 | 52.616 | 47.975 | 1.00 | 67.74 |
| ATOM | 501 | CA | GLU | A | 101 | −6.297 | 51.895 | 49.212 | 1.00 | 66.94 |
| ATOM | 502 | C | GLU | A | 101 | −5.574 | 50.601 | 48.896 | 1.00 | 70.57 |
| ATOM | 503 | O | GLU | A | 101 | −6.173 | 49.641 | 48.405 | 1.00 | 70.21 |
| ATOM | 504 | CB | GLU | A | 101 | −7.613 | 51.607 | 49.927 | 1.00 | 68.11 |
| ATOM | 505 | CG | GLU | A | 101 | −8.499 | 52.823 | 50.096 | 1.00 | 79.60 |
| ATOM | 506 | CD | GLU | A | 101 | −8.304 | 53.508 | 51.433 | 1.00 | 100.23 |
| ATOM | 507 | OE1 | GLU | A | 101 | −8.902 | 53.045 | 52.427 | 1.00 | 98.33 |
| ATOM | 508 | OE2 | GLU | A | 101 | −7.546 | 54.506 | 51.492 | 1.00 | 90.20 |
| ATOM | 509 | N | ILE | A | 102 | −4.267 | 50.597 | 49.126 | 1.00 | 67.43 |
| ATOM | 510 | CA | ILE | A | 102 | −3.457 | 49.427 | 48.846 | 1.00 | 67.73 |
| ATOM | 511 | C | ILE | A | 102 | −2.258 | 49.297 | 49.824 | 1.00 | 73.57 |
| ATOM | 512 | O | ILE | A | 102 | −2.155 | 50.098 | 50.751 | 1.00 | 73.54 |
| ATOM | 513 | CB | ILE | A | 102 | −2.923 | 49.440 | 47.407 | 1.00 | 70.85 |
| ATOM | 514 | CG1 | ILE | A | 102 | −3.689 | 50.462 | 46.572 | 1.00 | 71.05 |
| ATOM | 515 | CG2 | ILE | A | 102 | −3.045 | 48.058 | 46.783 | 1.00 | 71.85 |
| ATOM | 516 | CD1 | ILE | A | 102 | −4.219 | 49.911 | 45.264 | 1.00 | 77.53 |
| ATOM | 517 | N | LYS | A | 103 | −1.486 | 48.266 | 49.626 | 1.00 | 72.51 |
| ATOM | 518 | CA | LYS | A | 103 | −0.361 | 47.989 | 50.509 | 1.00 | 72.51 |
| ATOM | 519 | C | LYS | A | 103 | 0.877 | 48.810 | 50.159 | 1.00 | 76.53 |
| ATOM | 520 | O | LYS | A | 103 | 1.058 | 49.227 | 49.019 | 1.00 | 77.01 |
| ATOM | 521 | CB | LYS | A | 103 | −0.038 | 46.499 | 50.495 | 1.00 | 75.85 |
| ATOM | 522 | CG | LYS | A | 103 | −1.119 | 45.642 | 49.860 | 1.00 | 94.42 |
| ATOM | 523 | CD | LYS | A | 103 | −0.951 | 44.177 | 50.220 | 1.00 | 107.25 |
| ATOM | 524 | CE | LYS | A | 103 | −2.102 | 43.681 | 51.084 | 1.00 | 117.44 |
| ATOM | 525 | NZ | LYS | A | 103 | −2.032 | 42.213 | 51.315 | 1.00 | 124.08 |
| ATOM | 526 | N | PRO | A | 104 | 1.722 | 49.042 | 51.159 | 1.00 | 73.79 |
| ATOM | 527 | CA | PRO | A | 104 | 2.949 | 49.811 | 50.978 | 1.00 | 73.09 |
| ATOM | 528 | C | PRO | A | 104 | 3.787 | 49.249 | 49.841 | 1.00 | 77.39 |
| ATOM | 529 | O | PRO | A | 104 | 4.330 | 49.996 | 49.029 | 1.00 | 77.24 |
| ATOM | 530 | CB | PRO | A | 104 | 3.685 | 49.633 | 52.324 | 1.00 | 74.50 |
| ATOM | 531 | CG | PRO | A | 104 | 2.870 | 48.627 | 53.107 | 1.00 | 78.72 |
| ATOM | 532 | CD | PRO | A | 104 | 1.499 | 48.688 | 52.567 | 1.00 | 73.39 |
| ATOM | 533 | N | ALA | A | 105 | 3.898 | 47.927 | 49.796 | 1.00 | 75.03 |
| ATOM | 534 | CA | ALA | A | 105 | 4.639 | 47.265 | 48.739 | 1.00 | 75.11 |
| ATOM | 535 | C | ALA | A | 105 | 4.032 | 47.686 | 47.406 | 1.00 | 80.14 |
| ATOM | 536 | O | ALA | A | 105 | 4.726 | 48.214 | 46.536 | 1.00 | 80.02 |
| ATOM | 537 | CB | ALA | A | 105 | 4.557 | 45.764 | 48.904 | 1.00 | 75.76 |
| ATOM | 538 | N | ILE | A | 106 | 2.722 | 47.483 | 47.268 | 1.00 | 76.82 |
| ATOM | 539 | CA | ILE | A | 106 | 2.010 | 47.866 | 46.061 | 1.00 | 76.79 |
| ATOM | 540 | C | ILE | A | 106 | 2.295 | 49.330 | 45.713 | 1.00 | 78.22 |
| ATOM | 541 | O | ILE | A | 106 | 2.975 | 49.633 | 44.724 | 1.00 | 77.84 |
| ATOM | 542 | CB | ILE | A | 106 | 0.476 | 47.704 | 46.224 | 1.00 | 80.90 |
| ATOM | 543 | CG1 | ILE | A | 106 | 0.108 | 46.231 | 46.387 | 1.00 | 81.84 |
| ATOM | 544 | CG2 | ILE | A | 106 | −0.260 | 48.317 | 45.041 | 1.00 | 82.10 |
| ATOM | 545 | CD1 | ILE | A | 106 | −1.243 | 45.865 | 45.768 | 1.00 | 89.96 |
| ATOM | 546 | N | ARG | A | 107 | 1.760 | 50.234 | 46.533 | 1.00 | 72.72 |
| ATOM | 547 | CA | ARG | A | 107 | 1.911 | 51.665 | 46.308 | 1.00 | 71.63 |
| ATOM | 548 | C | ARG | A | 107 | 3.349 | 52.087 | 45.979 | 1.00 | 74.51 |
| ATOM | 549 | O | ARG | A | 107 | 3.571 | 52.964 | 45.133 | 1.00 | 72.76 |
| ATOM | 550 | CB | ARG | A | 107 | 1.403 | 52.450 | 47.521 | 1.00 | 71.16 |
| ATOM | 551 | CG | ARG | A | 107 | 2.479 | 53.204 | 48.268 | 1.00 | 81.38 |
| ATOM | 552 | CD | ARG | A | 107 | 2.130 | 53.365 | 49.736 | 1.00 | 92.32 |
| ATOM | 553 | NE | ARG | A | 107 | 3.320 | 53.530 | 50.573 | 1.00 | 101.91 |
| ATOM | 554 | CZ | ARG | A | 107 | 3.317 | 53.454 | 51.902 | 1.00 | 116.20 |
| ATOM | 555 | NH1 | ARG | A | 107 | 2.187 | 53.220 | 52.556 | 1.00 | 102.19 |
| ATOM | 556 | NH2 | ARG | A | 107 | 4.448 | 53.608 | 52.577 | 1.00 | 104.27 |
| ATOM | 557 | N | ASN | A | 108 | 4.317 | 51.483 | 46.652 | 1.00 | 71.33 |
| ATOM | 558 | CA | ASN | A | 108 | 5.721 | 51.847 | 46.442 | 1.00 | 70.99 |
| ATOM | 559 | C | ASN | A | 108 | 6.278 | 51.467 | 45.060 | 1.00 | 72.52 |
| ATOM | 560 | O | ASN | A | 108 | 7.380 | 51.883 | 44.690 | 1.00 | 71.66 |
| ATOM | 561 | CB | ASN | A | 108 | 6.609 | 51.318 | 47.576 | 1.00 | 72.72 |
| ATOM | 562 | CG | ASN | A | 108 | 6.612 | 52.237 | 48.795 | 1.00 | 96.36 |
| ATOM | 563 | OD1 | ASN | A | 108 | 7.074 | 53.379 | 48.728 | 1.00 | 93.42 |
| ATOM | 564 | ND2 | ASN | A | 108 | 6.114 | 51.733 | 49.916 | 1.00 | 87.85 |
| ATOM | 565 | N | GLN | A | 109 | 5.496 | 50.712 | 44.290 | 1.00 | 67.26 |
| ATOM | 566 | CA | GLN | A | 109 | 5.894 | 50.316 | 42.942 | 1.00 | 66.00 |
| ATOM | 567 | C | GLN | A | 109 | 5.429 | 51.359 | 41.938 | 1.00 | 67.49 |
| ATOM | 568 | O | GLN | A | 109 | 6.130 | 51.670 | 40.968 | 1.00 | 66.18 |
| ATOM | 569 | CB | GLN | A | 109 | 5.313 | 48.945 | 42.583 | 1.00 | 67.37 |
| ATOM | 570 | CG | GLN | A | 109 | 6.291 | 48.031 | 41.849 | 1.00 | 85.26 |

TABLE 3-continued

Structural Coordinate of MEK1/N35/NKFCdel (corresponding to amino acids 24-373 of SEQ ID NO: 2)-ATPγS Binary Complex.

| ATOM | 571 | CD | GLN | A | 109 | 5.603 | 46.913 | 41.102 | 1.00 | 113.16 |
|---|---|---|---|---|---|---|---|---|---|---|
| ATOM | 572 | OE1 | GLN | A | 109 | 5.712 | 45.743 | 41.460 | 1.00 | 112.08 |
| ATOM | 573 | NE2 | GLN | A | 109 | 4.894 | 47.256 | 40.021 | 1.00 | 105.49 |
| ATOM | 574 | N | ILE | A | 110 | 4.243 | 51.898 | 42.180 | 1.00 | 61.59 |
| ATOM | 575 | CA | ILE | A | 110 | 3.692 | 52.925 | 41.319 | 1.00 | 60.51 |
| ATOM | 576 | C | ILE | A | 110 | 4.658 | 54.114 | 41.295 | 1.00 | 61.99 |
| ATOM | 577 | O | ILE | A | 110 | 5.067 | 54.572 | 40.232 | 1.00 | 61.45 |
| ATOM | 578 | CB | ILE | A | 110 | 2.281 | 53.359 | 41.789 | 1.00 | 63.40 |
| ATOM | 579 | CG1 | ILE | A | 110 | 1.304 | 52.178 | 41.667 | 1.00 | 63.33 |
| ATOM | 580 | CG2 | ILE | A | 110 | 1.782 | 54.541 | 40.972 | 1.00 | 63.89 |
| ATOM | 581 | CD1 | ILE | A | 110 | 0.053 | 52.316 | 42.486 | 1.00 | 68.43 |
| ATOM | 582 | N | ILE | A | 111 | 5.092 | 54.547 | 42.471 | 1.00 | 57.23 |
| ATOM | 583 | CA | ILE | A | 111 | 6.042 | 55.649 | 42.565 | 1.00 | 56.82 |
| ATOM | 584 | C | ILE | A | 111 | 7.316 | 55.353 | 41.776 | 1.00 | 61.58 |
| ATOM | 585 | O | ILE | A | 111 | 7.917 | 56.250 | 41.181 | 1.00 | 61.05 |
| ATOM | 586 | CB | ILE | A | 111 | 6.374 | 55.988 | 44.022 | 1.00 | 59.36 |
| ATOM | 587 | CG1 | ILE | A | 111 | 5.154 | 56.602 | 44.696 | 1.00 | 59.69 |
| ATOM | 588 | CG2 | ILE | A | 111 | 7.546 | 56.940 | 44.097 | 1.00 | 59.55 |
| ATOM | 589 | CD1 | ILE | A | 111 | 4.195 | 57.264 | 43.720 | 1.00 | 66.02 |
| ATOM | 590 | N | ARG | A | 112 | 7.697 | 54.084 | 41.738 | 1.00 | 59.00 |
| ATOM | 591 | CA | ARG | A | 112 | 8.878 | 53.661 | 40.994 | 1.00 | 59.12 |
| ATOM | 592 | C | ARG | A | 112 | 8.645 | 53.791 | 39.483 | 1.00 | 62.26 |
| ATOM | 593 | O | ARG | A | 112 | 9.489 | 54.336 | 38.758 | 1.00 | 61.96 |
| ATOM | 594 | CB | ARG | A | 112 | 9.228 | 52.209 | 41.341 | 1.00 | 60.96 |
| ATOM | 595 | CG | ARG | A | 112 | 10.469 | 52.052 | 42.208 | 1.00 | 77.00 |
| ATOM | 596 | CD | ARG | A | 112 | 10.677 | 50.588 | 42.608 | 1.00 | 93.15 |
| ATOM | 597 | NE | ARG | A | 112 | 10.595 | 49.693 | 41.455 | 1.00 | 106.58 |
| ATOM | 598 | CZ | ARG | A | 112 | 10.691 | 48.368 | 41.526 | 1.00 | 125.06 |
| ATOM | 599 | NH1 | ARG | A | 112 | 10.867 | 47.774 | 42.698 | 1.00 | 115.82 |
| ATOM | 600 | NH2 | ARG | A | 112 | 10.606 | 47.638 | 40.422 | 1.00 | 112.74 |
| ATOM | 601 | N | GLU | A | 113 | 7.505 | 53.270 | 39.017 | 1.00 | 57.70 |
| ATOM | 602 | CA | GLU | A | 113 | 7.151 | 53.296 | 37.595 | 1.00 | 56.82 |
| ATOM | 603 | C | GLU | A | 113 | 6.854 | 54.707 | 37.059 | 1.00 | 59.02 |
| ATOM | 604 | O | GLU | A | 113 | 6.978 | 54.959 | 35.865 | 1.00 | 58.49 |
| ATOM | 605 | CB | GLU | A | 113 | 5.956 | 52.376 | 37.309 | 1.00 | 58.24 |
| ATOM | 606 | CG | GLU | A | 113 | 5.844 | 51.164 | 38.209 | 1.00 | 68.55 |
| ATOM | 607 | CD | GLU | A | 113 | 4.732 | 50.211 | 37.776 | 1.00 | 85.71 |
| ATOM | 608 | OE1 | GLU | A | 113 | 3.640 | 50.692 | 37.395 | 1.00 | 77.08 |
| ATOM | 609 | OE2 | GLU | A | 113 | 4.947 | 48.982 | 37.825 | 1.00 | 77.74 |
| ATOM | 610 | N | LEU | A | 113 | 6.431 | 55.611 | 37.936 | 1.00 | 53.89 |
| ATOM | 611 | CA | LEU | A | 114 | 6.132 | 56.977 | 37.516 | 1.00 | 52.90 |
| ATOM | 612 | C | LEU | A | 114 | 7.407 | 57.789 | 37.379 | 1.00 | 56.80 |
| ATOM | 613 | O | LEU | A | 114 | 7.418 | 58.841 | 36.729 | 1.00 | 56.28 |
| ATOM | 614 | CB | LEU | A | 114 | 5.186 | 57.645 | 38.504 | 1.00 | 52.64 |
| ATOM | 615 | CG | LEU | A | 114 | 3.868 | 56.907 | 38.682 | 1.00 | 56.55 |
| ATOM | 616 | CD1 | LEU | A | 114 | 3.148 | 57.377 | 39.935 | 1.00 | 56.39 |
| ATOM | 617 | CD2 | LEU | A | 114 | 3.005 | 57.086 | 37.443 | 1.00 | 57.76 |
| ATOM | 618 | N | GLN | A | 115 | 8.486 | 57.291 | 37.981 | 1.00 | 52.83 |
| ATOM | 619 | CA | GLN | A | 115 | 9.774 | 57.967 | 37.927 | 1.00 | 52.37 |
| ATOM | 620 | C | GLN | A | 115 | 10.269 | 58.104 | 36.491 | 1.00 | 55.50 |
| ATOM | 621 | O | GLN | A | 115 | 11.180 | 58.878 | 36.217 | 1.00 | 55.32 |
| ATOM | 622 | CB | GLN | A | 115 | 10.810 | 57.238 | 38.791 | 1.00 | 53.59 |
| ATOM | 623 | CG | GLN | A | 115 | 10.427 | 57.132 | 40.263 | 1.00 | 54.80 |
| ATOM | 624 | CD | GLN | A | 115 | 10.216 | 58.483 | 40.902 | 1.00 | 61.23 |
| ATOM | 625 | OE1 | GLN | A | 115 | 11.098 | 59.342 | 40.869 | 1.00 | 59.16 |
| ATOM | 626 | NE2 | GLN | A | 115 | 9.031 | 58.696 | 41.455 | 1.00 | 41.92 |
| ATOM | 627 | N | VAL | A | 116 | 9.657 | 57.355 | 35.579 | 1.00 | 51.56 |
| ATOM | 628 | CA | VAL | A | 116 | 10.005 | 57.428 | 34.158 | 1.00 | 51.35 |
| ATOM | 629 | C | VAL | A | 116 | 9.640 | 58.794 | 33.586 | 1.00 | 52.54 |
| ATOM | 630 | O | VAL | A | 116 | 10.222 | 59.242 | 32.599 | 1.00 | 51.86 |
| ATOM | 631 | CB | VAL | A | 116 | 9.249 | 56.367 | 33.342 | 1.00 | 56.11 |
| ATOM | 632 | CG1 | VAL | A | 116 | 9.941 | 56.138 | 32.004 | 1.00 | 56.23 |
| ATOM | 633 | CG2 | VAL | A | 116 | 9.155 | 55.080 | 34.121 | 1.00 | 56.24 |
| ATOM | 634 | N | LEU | A | 117 | 8.672 | 59.446 | 34.219 | 1.00 | 47.59 |
| ATOM | 635 | CA | LEU | A | 117 | 8.201 | 60.754 | 33.785 | 1.00 | 46.57 |
| ATOM | 636 | C | LEU | A | 117 | 9.276 | 61.818 | 33.873 | 1.00 | 50.07 |
| ATOM | 637 | O | LEU | A | 117 | 9.180 | 62.865 | 33.231 | 1.00 | 49.38 |
| ATOM | 638 | CB | LEU | A | 117 | 6.977 | 61.169 | 34.593 | 1.00 | 46.36 |
| ATOM | 639 | CG | LEU | A | 117 | 5.731 | 60.324 | 34.364 | 1.00 | 50.06 |
| ATOM | 640 | CD1 | LEU | A | 117 | 4.693 | 60.614 | 35.432 | 1.00 | 50.24 |
| ATOM | 641 | CD2 | LEU | A | 117 | 5.177 | 60.583 | 32.984 | 1.00 | 51.33 |
| ATOM | 642 | N | HIS | A | 118 | 10.301 | 61.561 | 34.670 | 1.00 | 47.18 |
| ATOM | 643 | CA | HIS | A | 118 | 11.396 | 62.515 | 34.811 | 1.00 | 47.41 |
| ATOM | 644 | C | HIS | A | 118 | 12.232 | 62.566 | 33.533 | 1.00 | 52.13 |
| ATOM | 645 | O | HIS | A | 118 | 12.989 | 63.511 | 33.314 | 1.00 | 51.97 |
| ATOM | 646 | CB | HIS | A | 118 | 12.289 | 62.147 | 36.008 | 1.00 | 48.10 |
| ATOM | 647 | CG | HIS | A | 118 | 11.707 | 62.526 | 37.334 | 1.00 | 51.12 |

TABLE 3-continued

Structural Coordinate of MEK1/N35/NKFCdel (corresponding to amino acids 24-373 of SEQ ID NO: 2)-ATPγS Binary Complex.

| ATOM | 648 | ND1 | HIS | A | 118 | 11.296 | 61.590 | 38.261 | 1.00 | 52.58 |
|---|---|---|---|---|---|---|---|---|---|---|
| ATOM | 649 | CD2 | HIS | A | 118 | 11.483 | 63.737 | 37.896 | 1.00 | 52.57 |
| ATOM | 650 | CE1 | HIS | A | 118 | 10.836 | 62.211 | 39.332 | 1.00 | 51.91 |
| ATOM | 651 | NE2 | HIS | A | 118 | 10.944 | 63.514 | 39.138 | 1.00 | 52.19 |
| ATOM | 652 | N | GLU | A | 119 | 12.067 | 61.552 | 32.685 | 1.00 | 48.86 |
| ATOM | 653 | CA | GLU | A | 119 | 12.813 | 61.457 | 31.435 | 1.00 | 48.84 |
| ATOM | 654 | C | GLU | A | 119 | 12.085 | 62.056 | 30.229 | 1.00 | 53.33 |
| ATOM | 655 | O | GLU | A | 119 | 12.709 | 62.362 | 29.212 | 1.00 | 52.81 |
| ATOM | 656 | CB | GLU | A | 119 | 13.161 | 59.998 | 31.141 | 1.00 | 50.25 |
| ATOM | 657 | CG | GLU | A | 119 | 14.024 | 59.327 | 32.205 | 1.00 | 62.42 |
| ATOM | 658 | CD | GLU | A | 119 | 13.956 | 57.806 | 32.131 | 1.00 | 86.20 |
| ATOM | 659 | OE1 | GLU | A | 119 | 14.395 | 57.236 | 31.106 | 1.00 | 73.89 |
| ATOM | 660 | OE2 | GLU | A | 119 | 13.446 | 57.183 | 33.090 | 1.00 | 84.10 |
| ATOM | 661 | N | CYS | A | 120 | 10.764 | 62.178 | 30.325 | 1.00 | 50.32 |
| ATOM | 662 | CA | CYS | A | 120 | 9.962 | 62.704 | 29.210 | 1.00 | 50.21 |
| ATOM | 663 | C | CYS | A | 120 | 10.052 | 64.211 | 29.105 | 1.00 | 52.71 |
| ATOM | 664 | O | CYS | A | 120 | 9.202 | 64.926 | 29.630 | 1.00 | 52.94 |
| ATOM | 665 | CB | CYS | A | 120 | 8.502 | 62.277 | 29.347 | 1.00 | 50.58 |
| ATOM | 666 | SG | CYS | A | 120 | 8.292 | 60.491 | 29.563 | 1.00 | 54.74 |
| ATOM | 667 | N | ASN | A | 121 | 11.064 | 64.689 | 28.397 | 1.00 | 47.69 |
| ATOM | 668 | CA | ASN | A | 121 | 11.270 | 66.124 | 28.230 | 1.00 | 47.26 |
| ATOM | 669 | C | ASN | A | 121 | 11.030 | 66.579 | 26.794 | 1.00 | 48.76 |
| ATOM | 670 | O | ASN | A | 121 | 11.838 | 66.317 | 25.901 | 1.00 | 48.20 |
| ATOM | 671 | CB | ASN | A | 121 | 12.675 | 66.512 | 28.696 | 1.00 | 50.37 |
| ATOM | 672 | CG | ASN | A | 121 | 12.992 | 65.972 | 30.089 | 1.00 | 75.62 |
| ATOM | 673 | OD1 | ASN | A | 121 | 12.250 | 66.219 | 31.044 | 1.00 | 64.39 |
| ATOM | 674 | ND2 | ASN | A | 121 | 14.059 | 65.176 | 30.191 | 1.00 | 68.30 |
| ATOM | 675 | N | SER | A | 122 | 9.907 | 67.256 | 26.577 | 1.00 | 43.39 |
| ATOM | 676 | CA | SER | A | 122 | 9.541 | 67.724 | 25.246 | 1.00 | 41.91 |
| ATOM | 677 | C | SER | A | 122 | 8.528 | 68.877 | 25.323 | 1.00 | 44.18 |
| ATOM | 678 | O | SER | A | 122 | 7.746 | 68.964 | 26.264 | 1.00 | 43.27 |
| ATOM | 679 | CB | SER | A | 122 | 8.995 | 66.551 | 24.409 | 1.00 | 43.95 |
| ATOM | 680 | OG | SER | A | 122 | 7.961 | 66.953 | 23.538 | 1.00 | 49.97 |
| ATOM | 681 | N | PRO | A | 123 | 8.580 | 69.778 | 24.345 | 1.00 | 40.17 |
| ATOM | 682 | CA | PRO | A | 123 | 7.669 | 70.919 | 24.300 | 1.00 | 39.21 |
| ATOM | 683 | C | PRO | A | 123 | 6.224 | 70.465 | 24.103 | 1.00 | 41.77 |
| ATOM | 684 | O | PRO | A | 123 | 5.293 | 71.268 | 24.206 | 1.00 | 41.64 |
| ATOM | 685 | CB | PRO | A | 123 | 8.137 | 71.694 | 23.053 | 1.00 | 41.09 |
| ATOM | 686 | CG | PRO | A | 123 | 9.503 | 71.158 | 22.737 | 1.00 | 45.37 |
| ATOM | 687 | CD | PRO | A | 123 | 9.492 | 69.747 | 23.189 | 1.00 | 40.61 |
| ATOM | 688 | N | TYR | A | 124 | 6.040 | 69.179 | 23.816 | 1.00 | 37.24 |
| ATOM | 689 | CA | TYR | A | 124 | 4.702 | 68.628 | 23.569 | 1.00 | 36.67 |
| ATOM | 690 | C | TYR | A | 124 | 4.249 | 67.687 | 24.659 | 1.00 | 41.42 |
| ATOM | 691 | O | TYR | A | 124 | 3.237 | 66.987 | 24.514 | 1.00 | 41.30 |
| ATOM | 692 | CB | TYR | A | 124 | 4.657 | 67.946 | 22.204 | 1.00 | 37.42 |
| ATOM | 693 | CG | TYR | A | 124 | 5.231 | 68.824 | 21.124 | 1.00 | 37.87 |
| ATOM | 694 | CD1 | TYR | A | 124 | 4.567 | 69.977 | 20.723 | 1.00 | 39.17 |
| ATOM | 695 | CD2 | TYR | A | 124 | 6.507 | 68.594 | 20.619 | 1.00 | 37.95 |
| ATOM | 696 | CE1 | TYR | A | 124 | 5.103 | 70.810 | 19.766 | 1.00 | 39.06 |
| ATOM | 697 | CE2 | TYR | A | 124 | 7.057 | 69.435 | 19.677 | 1.00 | 38.38 |
| ATOM | 698 | CZ | TYR | A | 124 | 6.355 | 70.553 | 19.265 | 1.00 | 45.52 |
| ATOM | 699 | OH | TYR | A | 124 | 6.903 | 71.411 | 18.337 | 1.00 | 47.09 |
| ATOM | 700 | N | ILE | A | 125 | 4.989 | 67.690 | 25.769 | 1.00 | 37.81 |
| ATOM | 701 | CA | ILE | A | 125 | 4.670 | 66.845 | 26.913 | 1.00 | 37.65 |
| ATOM | 702 | C | ILE | A | 125 | 4.612 | 67.719 | 28.158 | 1.00 | 43.81 |
| ATOM | 703 | O | ILE | A | 125 | 5.520 | 68.512 | 28.402 | 1.00 | 43.56 |
| ATOM | 704 | CB | ILE | A | 125 | 5.744 | 65.753 | 27.121 | 1.00 | 40.25 |
| ATOM | 705 | CG1 | ILE | A | 125 | 5.834 | 64.833 | 25.890 | 1.00 | 40.12 |
| ATOM | 706 | CG2 | ILE | A | 125 | 5.458 | 64.951 | 28.385 | 1.00 | 41.01 |
| ATOM | 707 | CD1 | ILE | A | 125 | 4.514 | 64.263 | 25.453 | 1.00 | 40.73 |
| ATOM | 708 | N | VAL | A | 126 | 3.530 | 67.611 | 28.928 | 1.00 | 41.82 |
| ATOM | 709 | CA | VAL | A | 126 | 3.408 | 68.423 | 30.133 | 1.00 | 42.51 |
| ATOM | 710 | C | VAL | A | 126 | 4.595 | 68.140 | 31.063 | 1.00 | 46.54 |
| ATOM | 711 | O | VAL | A | 126 | 5.025 | 66.996 | 31.200 | 1.00 | 45.10 |
| ATOM | 712 | CB | VAL | A | 126 | 2.077 | 68.163 | 30.890 | 1.00 | 46.85 |
| ATOM | 713 | CG1 | VAL | A | 126 | 1.799 | 69.287 | 31.871 | 1.00 | 46.53 |
| ATOM | 714 | CG2 | VAL | A | 126 | 0.925 | 68.018 | 29.909 | 1.00 | 46.80 |
| ATOM | 715 | N | GLY | A | 127 | 5.135 | 69.196 | 31.671 | 1.00 | 44.10 |
| ATOM | 716 | CA | GLY | A | 127 | 6.263 | 69.066 | 32.589 | 1.00 | 43.71 |
| ATOM | 717 | C | GLY | A | 127 | 5.878 | 68.229 | 33.804 | 1.00 | 47.33 |
| ATOM | 718 | O | GLY | A | 127 | 4.779 | 68.365 | 34.346 | 1.00 | 46.64 |
| ATOM | 719 | N | PHE | A | 128 | 6.784 | 67.351 | 34.218 | 1.00 | 43.59 |
| ATOM | 720 | CA | PHE | A | 128 | 6.558 | 66.490 | 35.380 | 1.00 | 42.86 |
| ATOM | 721 | C | PHE | A | 128 | 7.515 | 66.884 | 36.495 | 1.00 | 47.07 |
| ATOM | 722 | O | PHE | A | 128 | 8.725 | 66.967 | 36.281 | 1.00 | 46.77 |
| ATOM | 723 | CB | PHE | A | 128 | 6.779 | 65.025 | 34.996 | 1.00 | 44.16 |
| ATOM | 724 | CG | PHE | A | 128 | 6.739 | 64.072 | 36.158 | 1.00 | 45.61 |

TABLE 3-continued

Structural Coordinate of MEK1/N35/NKFCdel (corresponding to amino acids 24-373 of SEQ ID NO: 2)-ATPγS Binary Complex.

| | | | | | | | | | |
|---|---|---|---|---|---|---|---|---|---|
| ATOM | 725 | CD1 | PHE | A | 128 | 5.537 | 63.762 | 36.782 | 1.00 | 49.00 |
| ATOM | 726 | CD2 | PHE | A | 128 | 7.894 | 63.431 | 36.589 | 1.00 | 47.42 |
| ATOM | 727 | CE1 | PHE | A | 128 | 5.498 | 62.848 | 37.836 | 1.00 | 49.74 |
| ATOM | 728 | CE2 | PHE | A | 128 | 7.857 | 62.529 | 37.640 | 1.00 | 50.12 |
| ATOM | 729 | CZ | PHE | A | 128 | 6.660 | 62.239 | 38.263 | 1.00 | 48.38 |
| ATOM | 730 | N | TYR | A | 129 | 6.972 | 67.117 | 37.686 | 1.00 | 44.43 |
| ATOM | 731 | CA | TYR | A | 129 | 7.787 | 67.486 | 38.851 | 1.00 | 43.79 |
| ATOM | 732 | C | TYR | A | 129 | 8.154 | 66.286 | 39.709 | 1.00 | 49.78 |
| ATOM | 733 | O | TYR | A | 129 | 9.276 | 66.180 | 40.196 | 1.00 | 50.15 |
| ATOM | 734 | CB | TYR | A | 129 | 7.081 | 68.541 | 39.689 | 1.00 | 43.79 |
| ATOM | 735 | CG | TYR | A | 129 | 7.211 | 69.905 | 39.099 | 1.00 | 44.23 |
| ATOM | 736 | CD1 | TYR | A | 129 | 8.460 | 70.460 | 38.877 | 1.00 | 46.30 |
| ATOM | 737 | CD2 | TYR | A | 129 | 6.095 | 70.605 | 38.664 | 1.00 | 44.27 |
| ATOM | 738 | CE1 | TYR | A | 129 | 8.593 | 71.695 | 38.291 | 1.00 | 46.93 |
| ATOM | 739 | CE2 | TYR | A | 129 | 6.219 | 71.841 | 38.078 | 1.00 | 44.72 |
| ATOM | 740 | CZ | TYR | A | 129 | 7.473 | 72.377 | 37.884 | 1.00 | 50.88 |
| ATOM | 741 | OH | TYR | A | 129 | 7.611 | 73.610 | 37.297 | 1.00 | 51.44 |
| ATOM | 742 | N | GLY | A | 130 | 7.202 | 65.384 | 39.895 | 1.00 | 47.06 |
| ATOM | 743 | CA | GLY | A | 130 | 7.446 | 64.195 | 40.692 | 1.00 | 47.15 |
| ATOM | 744 | C | GLY | A | 130 | 6.140 | 63.591 | 41.166 | 1.00 | 51.79 |
| ATOM | 745 | O | GLY | A | 130 | 5.058 | 64.097 | 40.848 | 1.00 | 50.86 |
| ATOM | 746 | N | ALA | A | 131 | 6.248 | 62.506 | 41.929 | 1.00 | 49.48 |
| ATOM | 747 | CA | ALA | A | 131 | 5.082 | 61.809 | 42.455 | 1.00 | 49.81 |
| ATOM | 748 | C | ALA | A | 131 | 5.401 | 61.157 | 43.794 | 1.00 | 53.55 |
| ATOM | 749 | O | ALA | A | 131 | 6.511 | 60.668 | 44.016 | 1.00 | 53.41 |
| ATOM | 750 | CB | ALA | A | 131 | 4.592 | 60.760 | 41.455 | 1.00 | 50.77 |
| ATOM | 751 | N | PHE | A | 132 | 4.409 | 61.124 | 44.674 | 1.00 | 49.57 |
| ATOM | 752 | CA | PHE | A | 132 | 4.587 | 60.551 | 45.997 | 1.00 | 49.08 |
| ATOM | 753 | C | PHE | A | 132 | 3.258 | 60.050 | 46.544 | 1.00 | 54.20 |
| ATOM | 754 | O | PHE | A | 132 | 2.194 | 60.357 | 46.001 | 1.00 | 53.07 |
| ATOM | 755 | CB | PHE | A | 132 | 5.173 | 61.607 | 46.944 | 1.00 | 50.30 |
| ATOM | 756 | CG | PHE | A | 132 | 4.330 | 62.850 | 47.065 | 1.00 | 51.35 |
| ATOM | 757 | CD1 | PHE | A | 132 | 4.439 | 63.878 | 46.132 | 1.00 | 54.16 |
| ATOM | 758 | CD2 | PHE | A | 132 | 3.415 | 62.987 | 48.098 | 1.00 | 53.08 |
| ATOM | 759 | CE1 | PHE | A | 132 | 3.671 | 65.020 | 46.245 | 1.00 | 54.79 |
| ATOM | 760 | CE2 | PHE | A | 132 | 2.643 | 64.134 | 48.216 | 1.00 | 55.52 |
| ATOM | 761 | CZ | PHE | A | 132 | 2.770 | 65.148 | 47.292 | 1.00 | 53.59 |
| ATOM | 762 | N | TYR | A | 133 | 3.325 | 59.276 | 47.623 | 1.00 | 52.56 |
| ATOM | 763 | CA | TYR | A | 133 | 2.127 | 58.753 | 48.266 | 1.00 | 53.32 |
| ATOM | 764 | C | TYR | A | 133 | 1.929 | 59.416 | 49.621 | 1.00 | 58.10 |
| ATOM | 765 | O | TYR | A | 133 | 2.897 | 59.819 | 50.270 | 1.00 | 57.69 |
| ATOM | 766 | CB | TYR | A | 133 | 2.214 | 57.236 | 48.445 | 1.00 | 55.00 |
| ATOM | 767 | CG | TYR | A | 133 | 1.042 | 56.663 | 49.205 | 1.00 | 57.28 |
| ATOM | 768 | CD1 | TYR | A | 133 | 1.075 | 56.521 | 50.583 | 1.00 | 59.29 |
| ATOM | 769 | CD2 | TYR | A | 133 | −0.153 | 56.352 | 48.542 | 1.00 | 58.33 |
| ATOM | 770 | CE1 | TYR | A | 133 | −0.039 | 56.076 | 51.285 | 1.00 | 60.44 |
| ATOM | 771 | CE2 | TYR | A | 133 | −1.230 | 55.829 | 49.230 | 1.00 | 59.52 |
| ATOM | 772 | CZ | TYR | A | 133 | −1.186 | 55.719 | 50.600 | 1.00 | 69.38 |
| ATOM | 773 | OH | TYR | A | 133 | −2.250 | 55.192 | 51.273 | 1.00 | 73.84 |
| ATOM | 774 | N | SER | A | 134 | 0.682 | 59.532 | 50.055 | 1.00 | 55.13 |
| ATOM | 775 | CA | SER | A | 134 | 0.412 | 60.145 | 51.334 | 1.00 | 55.40 |
| ATOM | 776 | C | SER | A | 134 | −1.021 | 59.993 | 51.785 | 1.00 | 60.42 |
| ATOM | 777 | O | SER | A | 134 | −1.954 | 60.432 | 51.110 | 1.00 | 59.61 |
| ATOM | 778 | CB | SER | A | 134 | 0.821 | 61.622 | 51.326 | 1.00 | 59.40 |
| ATOM | 779 | OG | SER | A | 134 | 0.468 | 62.256 | 52.551 | 1.00 | 69.83 |
| ATOM | 780 | N | ASP | A | 135 | −1.183 | 59.382 | 52.948 | 1.00 | 58.60 |
| ATOM | 781 | CA | ASP | A | 135 | −2.480 | 59.192 | 53.571 | 1.00 | 59.21 |
| ATOM | 782 | C | ASP | A | 135 | −3.616 | 58.772 | 52.629 | 1.00 | 64.13 |
| ATOM | 783 | O | ASP | A | 135 | −4.631 | 59.464 | 52.500 | 1.00 | 63.53 |
| ATOM | 784 | CB | ASP | A | 135 | −2.853 | 60.403 | 54.427 | 1.00 | 61.52 |
| ATOM | 785 | CG | ASP | A | 135 | −2.071 | 60.450 | 55.755 | 1.00 | 74.92 |
| ATOM | 786 | OD1 | ASP | A | 135 | −2.093 | 61.506 | 56.423 | 1.00 | 76.12 |
| ATOM | 787 | OD2 | ASP | A | 135 | −1.401 | 59.440 | 56.096 | 1.00 | 80.38 |
| ATOM | 788 | N | GLY | A | 136 | −3.445 | 57.603 | 52.009 | 1.00 | 61.13 |
| ATOM | 789 | CA | GLY | A | 136 | −4.468 | 57.005 | 51.162 | 1.00 | 60.95 |
| ATOM | 790 | C | GLY | A | 136 | −4.607 | 57.575 | 49.759 | 1.00 | 64.42 |
| ATOM | 791 | O | GLY | A | 136 | −5.601 | 57.316 | 49.082 | 1.00 | 64.83 |
| ATOM | 792 | N | GLU | A | 137 | −3.622 | 58.330 | 49.299 | 1.00 | 59.33 |
| ATOM | 793 | CA | GLU | A | 137 | −3.712 | 58.881 | 47.955 | 1.00 | 58.24 |
| ATOM | 794 | C | GLU | A | 137 | −2.383 | 59.097 | 47.274 | 1.00 | 58.50 |
| ATOM | 795 | O | GLU | A | 137 | −1.388 | 59.442 | 47.913 | 1.00 | 57.81 |
| ATOM | 796 | CB | GLU | A | 137 | −4.534 | 60.167 | 47.938 | 1.00 | 59.80 |
| ATOM | 797 | CG | GLU | A | 137 | −4.123 | 61.171 | 48.986 | 1.00 | 72.29 |
| ATOM | 798 | CD | GLU | A | 137 | −5.137 | 62.270 | 49.153 | 1.00 | 92.13 |
| ATOM | 799 | OE1 | GLU | A | 137 | −6.194 | 62.208 | 48.489 | 1.00 | 84.42 |
| ATOM | 800 | OE2 | GLU | A | 137 | −4.877 | 63.201 | 49.941 | 1.00 | 87.23 |
| ATOM | 801 | N | ILE | A | 138 | −2.376 | 58.905 | 45.958 | 1.00 | 52.47 |

TABLE 3-continued

Structural Coordinate of MEK1/N35/NKFCdel (corresponding to amino acids 24-373 of SEQ ID NO: 2)-ATPγS Binary Complex.

| ATOM | 802 | CA  | ILE | A | 138 | −1.178 | 59.116 | 45.166 | 1.00 | 50.72 |
|------|-----|-----|-----|---|-----|--------|--------|--------|------|-------|
| ATOM | 803 | C   | ILE | A | 138 | −1.193 | 60.507 | 44.575 | 1.00 | 51.38 |
| ATOM | 804 | O   | ILE | A | 138 | −2.237 | 60.997 | 44.138 | 1.00 | 50.50 |
| ATOM | 805 | CB  | ILE | A | 138 | −1.068 | 58.112 | 44.027 | 1.00 | 53.50 |
| ATOM | 806 | CG1 | ILE | A | 138 | −0.862 | 56.706 | 44.583 | 1.00 | 53.99 |
| ATOM | 807 | CG2 | ILE | A | 138 | 0.086  | 58.484 | 43.122 | 1.00 | 53.75 |
| ATOM | 808 | CD1 | ILE | A | 138 | 0.582  | 56.276 | 44.598 | 1.00 | 61.13 |
| ATOM | 809 | N   | SER | A | 139 | −0.030 | 61.138 | 44.539 | 1.00 | 46.19 |
| ATOM | 810 | CA  | SER | A | 139 | 0.074  | 62.478 | 44.010 | 1.00 | 44.93 |
| ATOM | 811 | C   | SER | A | 139 | 1.003  | 62.542 | 42.818 | 1.00 | 47.92 |
| ATOM | 812 | O   | SER | A | 139 | 2.130  | 62.031 | 42.858 | 1.00 | 47.10 |
| ATOM | 813 | CB  | SER | A | 139 | 0.550  | 63.454 | 45.098 | 1.00 | 47.17 |
| ATOM | 814 | OG  | SER | A | 139 | −0.547 | 63.997 | 45.807 | 1.00 | 53.47 |
| ATOM | 815 | N   | ILE | A | 140 | 0.533  | 63.192 | 41.759 | 1.00 | 43.79 |
| ATOM | 816 | CA  | ILE | A | 140 | 1.338  | 63.406 | 40.568 | 1.00 | 43.06 |
| ATOM | 817 | C   | ILE | A | 140 | 1.356  | 64.899 | 40.318 | 1.00 | 45.06 |
| ATOM | 818 | O   | ILE | A | 140 | 0.322  | 65.513 | 40.066 | 1.00 | 43.65 |
| ATOM | 819 | CB  | ILE | A | 140 | 0.780  | 62.650 | 39.336 | 1.00 | 46.38 |
| ATOM | 820 | CG1 | ILE | A | 140 | 1.122  | 61.161 | 39.430 | 1.00 | 47.27 |
| ATOM | 821 | CG2 | ILE | A | 140 | 1.361  | 63.222 | 38.049 | 1.00 | 46.44 |
| ATOM | 822 | CD1 | ILE | A | 140 | −0.048 | 60.237 | 39.114 | 1.00 | 54.07 |
| ATOM | 823 | N   | CYS | A | 141 | 2.523  | 65.494 | 40.491 | 1.00 | 41.92 |
| ATOM | 824 | CA  | CYS | A | 141 | 2.673  | 66.931 | 40.350 | 1.00 | 41.37 |
| ATOM | 825 | C   | CYS | A | 141 | 3.306  | 67.246 | 39.037 | 1.00 | 44.11 |
| ATOM | 826 | O   | CYS | A | 141 | 4.328  | 66.673 | 38.673 | 1.00 | 43.30 |
| ATOM | 827 | CB  | CYS | A | 141 | 3.514  | 67.503 | 41.491 | 1.00 | 41.47 |
| ATOM | 828 | SG  | CYS | A | 141 | 2.917  | 67.011 | 43.134 | 1.00 | 45.33 |
| ATOM | 829 | N   | MET | A | 142 | 2.693  | 68.157 | 38.317 | 1.00 | 41.01 |
| ATOM | 830 | CA  | MET | A | 142 | 3.184  | 68.509 | 37.025 | 1.00 | 40.77 |
| ATOM | 831 | C   | MET | A | 142 | 3.114  | 69.995 | 36.811 | 1.00 | 44.64 |
| ATOM | 832 | O   | MET | A | 142 | 2.656  | 70.741 | 37.672 | 1.00 | 44.26 |
| ATOM | 833 | CB  | MET | A | 142 | 2.369  | 67.779 | 35.954 | 1.00 | 42.80 |
| ATOM | 834 | CG  | MET | A | 142 | 0.877  | 67.976 | 36.092 | 1.00 | 46.11 |
| ATOM | 835 | SD  | MET | A | 142 | −0.130 | 66.649 | 35.338 | 1.00 | 49.61 |
| ATOM | 836 | CE  | MET | A | 142 | −1.417 | 66.463 | 36.638 | 1.00 | 46.04 |
| ATOM | 837 | N   | GLU | A | 143 | 3.591  | 70.419 | 35.656 | 1.00 | 41.37 |
| ATOM | 838 | CA  | GLU | A | 143 | 3.551  | 71.805 | 35.280 | 1.00 | 40.86 |
| ATOM | 839 | C   | GLU | A | 143 | 2.076  | 72.195 | 35.161 | 1.00 | 43.89 |
| ATOM | 840 | O   | GLU | A | 143 | 1.234  | 71.375 | 34.782 | 1.00 | 43.80 |
| ATOM | 841 | CB  | GLU | A | 143 | 4.279  | 71.992 | 33.945 | 1.00 | 42.11 |
| ATOM | 842 | CG  | GLU | A | 143 | 3.706  | 73.050 | 33.054 | 1.00 | 49.11 |
| ATOM | 843 | CD  | GLU | A | 143 | 4.311  | 73.016 | 31.667 | 1.00 | 59.88 |
| ATOM | 844 | OE1 | GLU | A | 143 | 4.679  | 71.916 | 31.201 | 1.00 | 43.12 |
| ATOM | 845 | OE2 | GLU | A | 143 | 4.432  | 74.086 | 31.048 | 1.00 | 54.40 |
| ATOM | 846 | N   | HIS | A | 144 | 1.757  | 73.416 | 35.562 | 1.00 | 39.12 |
| ATOM | 847 | CA  | HIS | A | 144 | 0.388  | 73.888 | 35.508 | 1.00 | 38.36 |
| ATOM | 848 | C   | HIS | A | 144 | 0.113  | 74.585 | 34.166 | 1.00 | 41.61 |
| ATOM | 849 | O   | HIS | A | 144 | 0.808  | 75.529 | 33.796 | 1.00 | 41.90 |
| ATOM | 850 | CB  | HIS | A | 144 | 0.098  | 74.826 | 36.681 | 1.00 | 38.74 |
| ATOM | 851 | CG  | HIS | A | 144 | −1.086 | 75.715 | 36.465 | 1.00 | 42.25 |
| ATOM | 852 | ND1 | HIS | A | 144 | −2.385 | 75.276 | 36.618 | 1.00 | 44.04 |
| ATOM | 853 | CD2 | HIS | A | 144 | −1.169 | 77.020 | 36.116 | 1.00 | 43.89 |
| ATOM | 854 | CE1 | HIS | A | 144 | −3.216 | 76.273 | 36.377 | 1.00 | 43.31 |
| ATOM | 855 | NE2 | HIS | A | 144 | −2.504 | 77.339 | 36.059 | 1.00 | 43.63 |
| ATOM | 856 | N   | MET | A | 145 | −0.883 | 74.080 | 33.433 | 1.00 | 36.14 |
| ATOM | 857 | CA  | MET | A | 145 | −1.266 | 74.637 | 32.144 | 1.00 | 34.97 |
| ATOM | 858 | C   | MET | A | 145 | −2.480 | 75.551 | 32.333 | 1.00 | 40.53 |
| ATOM | 859 | O   | MET | A | 145 | −3.611 | 75.092 | 32.509 | 1.00 | 39.97 |
| ATOM | 860 | CB  | MET | A | 145 | −1.560 | 73.514 | 31.141 | 1.00 | 36.54 |
| ATOM | 861 | CG  | MET | A | 145 | −0.373 | 72.580 | 30.868 | 1.00 | 38.92 |
| ATOM | 862 | SD  | MET | A | 145 | 1.040  | 73.396 | 30.042 | 1.00 | 42.32 |
| ATOM | 863 | CE  | MET | A | 145 | 0.443  | 73.464 | 28.312 | 1.00 | 38.55 |
| ATOM | 864 | N   | ASP | A | 146 | −2.217 | 76.851 | 32.351 | 1.00 | 37.99 |
| ATOM | 865 | CA  | ASP | A | 146 | −3.246 | 77.860 | 32.640 | 1.00 | 37.56 |
| ATOM | 866 | C   | ASP | A | 146 | −4.436 | 77.871 | 31.680 | 1.00 | 40.10 |
| ATOM | 867 | O   | ASP | A | 146 | −5.485 | 78.440 | 31.985 | 1.00 | 39.53 |
| ATOM | 868 | CB  | ASP | A | 146 | −2.605 | 79.250 | 32.700 | 1.00 | 38.84 |
| ATOM | 869 | CG  | ASP | A | 146 | −1.977 | 79.646 | 31.394 | 1.00 | 46.28 |
| ATOM | 870 | OD1 | ASP | A | 146 | −1.945 | 78.804 | 30.459 | 1.00 | 45.95 |
| ATOM | 871 | OD2 | ASP | A | 146 | −1.546 | 80.806 | 31.278 | 1.00 | 51.89 |
| ATOM | 872 | N   | GLY | A | 147 | −4.272 | 77.259 | 30.515 | 1.00 | 35.63 |
| ATOM | 873 | CA  | GLY | A | 147 | −5.339 | 77.249 | 29.516 | 1.00 | 34.67 |
| ATOM | 874 | C   | GLY | A | 147 | −6.289 | 76.084 | 29.732 | 1.00 | 37.16 |
| ATOM | 875 | O   | GLY | A | 147 | −7.334 | 76.002 | 29.088 | 1.00 | 36.07 |
| ATOM | 876 | N   | GLY | A | 148 | −5.918 | 75.187 | 30.652 | 1.00 | 33.70 |
| ATOM | 877 | CA  | GLY | A | 148 | −6.728 | 74.015 | 30.978 | 1.00 | 32.98 |
| ATOM | 878 | C   | GLY | A | 148 | −6.627 | 72.966 | 29.868 | 1.00 | 36.75 |

TABLE 3-continued

Structural Coordinate of MEK1/N35/NKFCdel (corresponding to amino acids 24-373 of SEQ ID NO: 2)-ATPγS Binary Complex.

| ATOM | 879 | O | GLY | A | 148 | −5.662 | 72.956 | 29.094 | 1.00 | 36.57 |
|---|---|---|---|---|---|---|---|---|---|---|
| ATOM | 880 | N | SER | A | 149 | −7.642 | 72.110 | 29.782 | 1.00 | 32.82 |
| ATOM | 881 | CA | SER | A | 149 | −7.708 | 71.057 | 28.763 | 1.00 | 32.05 |
| ATOM | 882 | C | SER | A | 149 | −8.647 | 71.454 | 27.588 | 1.00 | 36.07 |
| ATOM | 883 | O | SER | A | 149 | −9.516 | 72.322 | 27.733 | 1.00 | 35.33 |
| ATOM | 884 | CB | SER | A | 149 | −8.174 | 69.751 | 29.396 | 1.00 | 33.58 |
| ATOM | 885 | OG | SER | A | 149 | −9.369 | 69.949 | 30.136 | 1.00 | 38.62 |
| ATOM | 886 | N | LEU | A | 150 | −8.467 | 70.810 | 26.437 | 1.00 | 32.55 |
| ATOM | 887 | CA | LEU | A | 150 | −9.244 | 71.137 | 25.239 | 1.00 | 32.31 |
| ATOM | 888 | C | LEU | A | 150 | −10.750 | 70.888 | 25.339 | 1.00 | 36.42 |
| ATOM | 889 | O | LEU | A | 150 | −11.534 | 71.520 | 24.634 | 1.00 | 35.66 |
| ATOM | 890 | CB | LEU | A | 150 | −8.634 | 70.506 | 23.984 | 1.00 | 32.30 |
| ATOM | 891 | CG | LEU | A | 150 | −7.369 | 71.198 | 23.442 | 1.00 | 36.21 |
| ATOM | 892 | CD1 | LEU | A | 150 | −7.008 | 70.655 | 22.075 | 1.00 | 35.91 |
| ATOM | 893 | CD2 | LEU | A | 150 | −7.556 | 72.714 | 23.382 | 1.00 | 37.50 |
| ATOM | 894 | N | ASP | A | 151 | −11.160 | 69.992 | 26.233 | 1.00 | 33.52 |
| ATOM | 895 | CA | ASP | A | 151 | −12.577 | 69.768 | 26.441 | 1.00 | 33.51 |
| ATOM | 896 | C | ASP | A | 151 | −13.161 | 71.014 | 27.074 | 1.00 | 36.74 |
| ATOM | 897 | O | ASP | A | 151 | −14.232 | 71.470 | 26.696 | 1.00 | 36.96 |
| ATOM | 898 | CB | ASP | A | 151 | −12.821 | 68.547 | 27.333 | 1.00 | 35.90 |
| ATOM | 899 | CG | ASP | A | 151 | −12.209 | 68.694 | 28.704 | 1.00 | 45.47 |
| ATOM | 900 | OD1 | ASP | A | 151 | −12.968 | 68.645 | 29.704 | 1.00 | 46.19 |
| ATOM | 901 | OD2 | ASP | A | 151 | −10.969 | 68.815 | 28.786 | 1.00 | 50.32 |
| ATOM | 902 | N | GLN | A | 152 | −12.409 | 71.613 | 27.987 | 1.00 | 33.29 |
| ATOM | 903 | CA | GLN | A | 152 | −12.843 | 72.844 | 28.646 | 1.00 | 32.60 |
| ATOM | 904 | C | GLN | A | 152 | −12.861 | 73.995 | 27.664 | 1.00 | 37.66 |
| ATOM | 905 | O | GLN | A | 152 | −13.781 | 74.817 | 27.664 | 1.00 | 38.61 |
| ATOM | 906 | CB | GLN | A | 152 | −11.928 | 73.178 | 29.825 | 1.00 | 33.34 |
| ATOM | 907 | CG | GLN | A | 152 | −11.983 | 72.156 | 30.963 | 1.00 | 33.39 |
| ATOM | 908 | CD | GLN | A | 152 | −10.850 | 72.350 | 31.994 | 1.00 | 50.32 |
| ATOM | 909 | OE1 | GLN | A | 152 | −9.703 | 72.686 | 31.643 | 1.00 | 43.09 |
| ATOM | 910 | NE2 | GLN | A | 152 | −11.159 | 72.089 | 33.249 | 1.00 | 40.91 |
| ATOM | 911 | N | VAL | A | 153 | −11.831 | 74.063 | 26.827 | 1.00 | 33.31 |
| ATOM | 912 | CA | VAL | A | 153 | −11.729 | 75.116 | 25.841 | 1.00 | 32.56 |
| ATOM | 913 | C | VAL | A | 153 | −12.864 | 74.997 | 24.837 | 1.00 | 37.28 |
| ATOM | 914 | O | VAL | A | 153 | −13.499 | 75.995 | 24.476 | 1.00 | 36.74 |
| ATOM | 915 | CB | VAL | A | 153 | −10.394 | 75.038 | 25.085 | 1.00 | 35.93 |
| ATOM | 916 | CG1 | VAL | A | 153 | −10.335 | 76.113 | 23.991 | 1.00 | 35.68 |
| ATOM | 917 | CG2 | VAL | A | 153 | −9.232 | 75.163 | 26.051 | 1.00 | 35.37 |
| ATOM | 918 | N | LEU | A | 154 | −13.086 | 73.779 | 24.350 | 1.00 | 34.14 |
| ATOM | 919 | CA | LEU | A | 154 | −14.161 | 73.526 | 23.386 | 1.00 | 34.15 |
| ATOM | 920 | C | LEU | A | 154 | −15.517 | 73.952 | 23.991 | 1.00 | 39.48 |
| ATOM | 921 | O | LEU | A | 154 | −16.288 | 74.669 | 23.368 | 1.00 | 38.45 |
| ATOM | 922 | CB | LEU | A | 154 | −14.184 | 72.042 | 22.993 | 1.00 | 33.79 |
| ATOM | 923 | CG | LEU | A | 154 | −15.326 | 71.621 | 22.070 | 1.00 | 37.51 |
| ATOM | 924 | CD1 | LEU | A | 154 | −15.278 | 72.417 | 20.792 | 1.00 | 37.43 |
| ATOM | 925 | CD2 | LEU | A | 154 | −15.312 | 70.121 | 21.800 | 1.00 | 37.47 |
| ATOM | 926 | N | LYS | A | 155 | −15.761 | 73.539 | 25.231 | 1.00 | 38.36 |
| ATOM | 927 | CA | LYS | A | 155 | −16.987 | 73.900 | 25.944 | 1.00 | 39.40 |
| ATOM | 928 | C | LYS | A | 155 | −17.203 | 75.411 | 25.925 | 1.00 | 44.71 |
| ATOM | 929 | O | LYS | A | 155 | −18.323 | 75.892 | 25.740 | 1.00 | 44.66 |
| ATOM | 930 | CB | LYS | A | 155 | −16.906 | 73.420 | 27.390 | 1.00 | 42.30 |
| ATOM | 931 | CG | LYS | A | 155 | −18.211 | 72.938 | 27.959 | 1.00 | 57.15 |
| ATOM | 932 | CD | LYS | A | 155 | −17.974 | 71.979 | 29.113 | 1.00 | 66.94 |
| ATOM | 933 | CE | LYS | A | 155 | −17.010 | 72.567 | 30.126 | 1.00 | 79.89 |
| ATOM | 934 | NZ | LYS | A | 155 | −16.227 | 71.509 | 30.834 | 1.00 | 90.98 |
| ATOM | 935 | N | LYS | A | 156 | −16.120 | 76.150 | 26.126 | 1.00 | 41.23 |
| ATOM | 936 | CA | LYS | A | 156 | −16.166 | 77.608 | 26.137 | 1.00 | 40.63 |
| ATOM | 937 | C | LYS | A | 156 | −16.353 | 78.189 | 24.729 | 1.00 | 44.10 |
| ATOM | 938 | O | LYS | A | 156 | −17.240 | 78.998 | 24.501 | 1.00 | 43.96 |
| ATOM | 939 | CB | LYS | A | 156 | −14.886 | 78.163 | 26.772 | 1.00 | 42.89 |
| ATOM | 940 | CG | LYS | A | 156 | −14.905 | 79.650 | 27.021 | 1.00 | 59.89 |
| ATOM | 941 | CD | LYS | A | 156 | −14.719 | 79.961 | 28.498 | 1.00 | 68.94 |
| ATOM | 942 | CE | LYS | A | 156 | −14.835 | 81.454 | 28.760 | 1.00 | 81.00 |
| ATOM | 943 | NZ | LYS | A | 156 | −14.067 | 81.870 | 29.968 | 1.00 | 92.98 |
| ATOM | 944 | N | ALA | A | 157 | −15.515 | 77.753 | 23.790 | 1.00 | 39.74 |
| ATOM | 945 | CA | ALA | A | 157 | −15.548 | 78.256 | 22.416 | 1.00 | 38.49 |
| ATOM | 946 | C | ALA | A | 157 | −16.761 | 77.818 | 21.580 | 1.00 | 41.26 |
| ATOM | 947 | O | ALA | A | 157 | −17.137 | 78.501 | 20.620 | 1.00 | 40.70 |
| ATOM | 948 | CB | ALA | A | 157 | −14.247 | 77.899 | 21.687 | 1.00 | 38.84 |
| ATOM | 949 | N | GLY | A | 158 | −17.345 | 76.673 | 21.909 | 1.00 | 37.14 |
| ATOM | 950 | CA | GLY | A | 158 | −18.469 | 76.139 | 21.129 | 1.00 | 36.96 |
| ATOM | 951 | C | GLY | A | 158 | −17.865 | 75.204 | 20.081 | 1.00 | 41.38 |
| ATOM | 952 | O | GLY | A | 158 | −18.104 | 74.007 | 20.083 | 1.00 | 42.77 |
| ATOM | 953 | N | ARG | A | 159 | −17.023 | 75.753 | 19.235 | 1.00 | 36.92 |
| ATOM | 954 | CA | ARG | A | 159 | −16.288 | 74.961 | 18.277 | 1.00 | 36.65 |
| ATOM | 955 | C | ARG | A | 159 | −14.970 | 75.655 | 17.943 | 1.00 | 39.24 |

TABLE 3-continued

Structural Coordinate of MEK1/N35/NKFCdel (corresponding to amino acids 24-373 of SEQ ID NO: 2)-ATPγS Binary Complex.

| ATOM | 956 | O | ARG | A | 159 | −14.872 | 76.874 | 18.013 | 1.00 | 39.10 |
|---|---|---|---|---|---|---|---|---|---|---|
| ATOM | 957 | CB | ARG | A | 159 | −17.124 | 74.621 | 17.031 | 1.00 | 37.51 |
| ATOM | 958 | CG | ARG | A | 159 | −17.322 | 75.742 | 16.048 | 1.00 | 46.30 |
| ATOM | 959 | CD | ARG | A | 159 | −18.203 | 75.265 | 14.884 | 1.00 | 51.91 |
| ATOM | 960 | NE | ARG | A | 159 | −18.501 | 76.341 | 13.941 | 1.00 | 53.90 |
| ATOM | 961 | CZ | ARG | A | 159 | −19.721 | 76.819 | 13.723 | 1.00 | 62.87 |
| ATOM | 962 | NH1 | ARG | A | 159 | −20.756 | 76.313 | 14.372 | 1.00 | 47.24 |
| ATOM | 963 | NH2 | ARG | A | 159 | −19.906 | 77.800 | 12.860 | 1.00 | 53.08 |
| ATOM | 964 | N | ILE | A | 160 | −13.946 | 74.859 | 17.668 | 1.00 | 34.28 |
| ATOM | 965 | CA | ILE | A | 160 | −12.609 | 75.359 | 17.403 | 1.00 | 33.32 |
| ATOM | 966 | C | ILE | A | 160 | −12.289 | 75.443 | 15.907 | 1.00 | 37.28 |
| ATOM | 967 | O | ILE | A | 160 | −12.519 | 74.484 | 15.151 | 1.00 | 36.77 |
| ATOM | 968 | CB | ILE | A | 160 | −11.573 | 74.493 | 18.138 | 1.00 | 36.08 |
| ATOM | 969 | CG1 | ILE | A | 160 | −11.992 | 74.346 | 19.628 | 1.00 | 36.19 |
| ATOM | 970 | CG2 | ILE | A | 160 | −10.174 | 75.065 | 17.975 | 1.00 | 35.96 |
| ATOM | 971 | CD1 | ILE | A | 160 | −10.896 | 73.862 | 20.556 | 1.00 | 38.32 |
| ATOM | 972 | N | PRO | A | 161 | −11.774 | 76.602 | 15.478 | 1.00 | 32.44 |
| ATOM | 973 | CA | PRO | A | 161 | −11.473 | 76.840 | 14.058 | 1.00 | 31.20 |
| ATOM | 974 | C | PRO | A | 161 | −10.402 | 75.910 | 13.494 | 1.00 | 34.35 |
| ATOM | 975 | O | PRO | A | 161 | −9.486 | 75.486 | 14.200 | 1.00 | 33.66 |
| ATOM | 976 | CB | PRO | A | 161 | −11.002 | 78.306 | 14.028 | 1.00 | 32.50 |
| ATOM | 977 | CG | PRO | A | 161 | −11.229 | 78.838 | 15.454 | 1.00 | 36.42 |
| ATOM | 978 | CD | PRO | A | 161 | −11.215 | 77.657 | 16.338 | 1.00 | 31.84 |
| ATOM | 979 | N | GLU | A | 162 | −10.539 | 75.599 | 12.215 | 1.00 | 31.29 |
| ATOM | 980 | CA | GLU | A | 162 | −9.625 | 74.700 | 11.520 | 1.00 | 31.45 |
| ATOM | 981 | C | GLU | A | 162 | −8.145 | 75.060 | 11.700 | 1.00 | 36.11 |
| ATOM | 982 | O | GLU | A | 162 | −7.316 | 74.186 | 11.947 | 1.00 | 36.02 |
| ATOM | 983 | CB | GLU | A | 162 | −9.973 | 74.650 | 10.035 | 1.00 | 32.70 |
| ATOM | 984 | CG | GLU | A | 162 | −9.174 | 73.641 | 9.248 | 1.00 | 42.08 |
| ATOM | 985 | CD | GLU | A | 162 | −9.584 | 73.590 | 7.789 | 1.00 | 51.46 |
| ATOM | 986 | OE1 | GLU | A | 162 | −10.786 | 73.796 | 7.495 | 1.00 | 41.25 |
| ATOM | 987 | OE2 | GLU | A | 162 | −8.703 | 73.381 | 6.937 | 1.00 | 39.17 |
| ATOM | 988 | N | GLN | A | 163 | −7.818 | 76.340 | 11.566 | 1.00 | 32.68 |
| ATOM | 989 | CA | GLN | A | 163 | −6.433 | 76.777 | 11.690 | 1.00 | 32.71 |
| ATOM | 990 | C | GLN | A | 163 | −5.869 | 76.489 | 13.060 | 1.00 | 36.07 |
| ATOM | 991 | O | GLN | A | 163 | −4.674 | 76.226 | 13.206 | 1.00 | 35.09 |
| ATOM | 992 | CB | GLN | A | 163 | −6.293 | 78.258 | 11.352 | 1.00 | 34.44 |
| ATOM | 993 | CG | GLN | A | 163 | −6.476 | 78.562 | 9.867 | 1.00 | 44.48 |
| ATOM | 994 | CD | GLN | A | 163 | −5.848 | 79.880 | 9.455 | 1.00 | 55.38 |
| ATOM | 995 | OE1 | GLN | A | 163 | −5.742 | 80.808 | 10.248 | 1.00 | 50.52 |
| ATOM | 996 | NE2 | GLN | A | 163 | −5.440 | 79.966 | 8.202 | 1.00 | 45.77 |
| ATOM | 997 | N | ILE | A | 164 | −6.731 | 76.550 | 14.069 | 1.00 | 32.65 |
| ATOM | 998 | CA | ILE | A | 164 | −6.323 | 76.259 | 15.444 | 1.00 | 31.80 |
| ATOM | 999 | C | ILE | A | 164 | −6.136 | 74.745 | 15.562 | 1.00 | 34.80 |
| ATOM | 1000 | O | ILE | A | 164 | −5.159 | 74.263 | 16.150 | 1.00 | 34.08 |
| ATOM | 1001 | CB | ILE | A | 164 | −7.410 | 76.730 | 16.469 | 1.00 | 34.51 |
| ATOM | 1002 | CG1 | ILE | A | 164 | −7.588 | 78.259 | 16.411 | 1.00 | 34.40 |
| ATOM | 1003 | CG2 | ILE | A | 164 | −7.056 | 76.287 | 17.877 | 1.00 | 34.35 |
| ATOM | 1004 | CD1 | ILE | A | 164 | −6.316 | 79.053 | 16.754 | 1.00 | 31.27 |
| ATOM | 1005 | N | LEU | A | 165 | −7.056 | 74.004 | 14.955 | 1.00 | 31.21 |
| ATOM | 1006 | CA | LEU | A | 165 | −6.993 | 72.537 | 14.959 | 1.00 | 30.87 |
| ATOM | 1007 | C | LEU | A | 165 | −5.770 | 72.039 | 14.193 | 1.00 | 34.16 |
| ATOM | 1008 | O | LEU | A | 165 | −5.235 | 70.986 | 14.496 | 1.00 | 32.53 |
| ATOM | 1009 | CB | LEU | A | 165 | −8.287 | 71.936 | 14.408 | 1.00 | 30.36 |
| ATOM | 1010 | CG | LEU | A | 165 | −9.476 | 72.143 | 15.352 | 1.00 | 33.55 |
| ATOM | 1011 | CD1 | LEU | A | 165 | −10.731 | 71.448 | 14.833 | 1.00 | 33.47 |
| ATOM | 1012 | CD2 | LEU | A | 165 | −9.119 | 71.650 | 16.743 | 1.00 | 33.52 |
| ATOM | 1013 | N | GLY | A | 166 | −5.295 | 72.850 | 13.249 | 1.00 | 31.50 |
| ATOM | 1014 | CA | GLY | A | 166 | −4.093 | 72.524 | 12.496 | 1.00 | 31.58 |
| ATOM | 1015 | C | GLY | A | 166 | −2.913 | 72.536 | 13.458 | 1.00 | 36.58 |
| ATOM | 1016 | O | GLY | A | 166 | −2.056 | 71.640 | 13.430 | 1.00 | 37.09 |
| ATOM | 1017 | N | LYS | A | 167 | −2.886 | 73.544 | 14.325 | 1.00 | 32.52 |
| ATOM | 1018 | CA | LYS | A | 167 | −1.825 | 73.680 | 15.328 | 1.00 | 32.54 |
| ATOM | 1019 | C | LYS | A | 167 | −1.910 | 72.549 | 16.339 | 1.00 | 35.59 |
| ATOM | 1020 | O | LYS | A | 167 | −0.897 | 71.973 | 16.736 | 1.00 | 36.00 |
| ATOM | 1021 | CB | LYS | A | 167 | −1.943 | 75.028 | 16.057 | 1.00 | 34.98 |
| ATOM | 1022 | CG | LYS | A | 167 | −1.393 | 76.211 | 15.279 | 1.00 | 42.93 |
| ATOM | 1023 | CD | LYS | A | 167 | −0.044 | 75.904 | 14.643 | 1.00 | 45.73 |
| ATOM | 1024 | CE | LYS | A | 167 | 0.209 | 76.830 | 13.444 | 1.00 | 54.67 |
| ATOM | 1025 | NZ | LYS | A | 167 | 1.593 | 76.717 | 12.903 | 1.00 | 61.73 |
| ATOM | 1026 | N | VAL | A | 168 | −3.122 | 72.251 | 16.772 | 1.00 | 30.43 |
| ATOM | 1027 | CA | VAL | A | 168 | −3.340 | 71.162 | 17.697 | 1.00 | 29.67 |
| ATOM | 1028 | C | VAL | A | 168 | −2.847 | 69.849 | 17.089 | 1.00 | 33.60 |
| ATOM | 1029 | O | VAL | A | 168 | −2.206 | 69.053 | 17.758 | 1.00 | 34.64 |
| ATOM | 1030 | CB | VAL | A | 168 | −4.842 | 71.007 | 18.039 | 1.00 | 32.67 |
| ATOM | 1031 | CG1 | VAL | A | 168 | −5.067 | 69.775 | 18.875 | 1.00 | 31.91 |
| ATOM | 1032 | CG2 | VAL | A | 168 | −5.363 | 72.262 | 18.754 | 1.00 | 32.46 |

TABLE 3-continued

Structural Coordinate of MEK1/N35/NKFCdel (corresponding to amino acids 24-373 of SEQ ID NO: 2)-ATPγS Binary Complex.

| ATOM | 1033 | N   | SER | A | 169 | −3.155 | 69.626 | 15.821 | 1.00 | 29.10 |
|------|------|-----|-----|---|-----|--------|--------|--------|------|-------|
| ATOM | 1034 | CA  | SER | A | 169 | −2.775 | 68.386 | 15.157 | 1.00 | 28.48 |
| ATOM | 1035 | C   | SER | A | 169 | −1.260 | 68.193 | 15.198 | 1.00 | 33.07 |
| ATOM | 1036 | O   | SER | A | 169 | −0.761 | 67.113 | 15.538 | 1.00 | 31.95 |
| ATOM | 1037 | CB  | SER | A | 169 | −3.280 | 68.381 | 13.707 | 1.00 | 30.26 |
| ATOM | 1038 | OG  | SER | A | 169 | −4.690 | 68.486 | 13.649 | 1.00 | 34.82 |
| ATOM | 1039 | N   | ILE | A | 170 | −0.535 | 69.241 | 14.842 | 1.00 | 30.41 |
| ATOM | 1040 | CA  | ILE | A | 170 | 0.907  | 69.201 | 14.832 | 1.00 | 30.84 |
| ATOM | 1041 | C   | ILE | A | 170 | 1.441  | 68.804 | 16.207 | 1.00 | 36.57 |
| ATOM | 1042 | O   | ILE | A | 170 | 2.379  | 68.005 | 16.315 | 1.00 | 36.18 |
| ATOM | 1043 | CB  | ILE | A | 170 | 1.492  | 70.575 | 14.461 | 1.00 | 34.17 |
| ATOM | 1044 | CG1 | ILE | A | 170 | 1.128  | 70.944 | 13.021 | 1.00 | 34.33 |
| ATOM | 1045 | CG2 | ILE | A | 170 | 2.997  | 70.586 | 14.644 | 1.00 | 35.76 |
| ATOM | 1046 | CD1 | ILE | A | 170 | 1.724  | 72.254 | 12.572 | 1.00 | 38.92 |
| ATOM | 1047 | N   | ALA | A | 171 | 0.866  | 69.402 | 17.251 | 1.00 | 33.98 |
| ATOM | 1049 | CA  | ALA | A | 171 | 1.308  | 69.171 | 18.621 | 1.00 | 33.66 |
| ATOM | 1049 | C   | ALA | A | 171 | 1.072  | 67.731 | 19.065 | 1.00 | 39.36 |
| ATOM | 1050 | O   | ALA | A | 171 | 1.935  | 67.104 | 19.675 | 1.00 | 39.76 |
| ATOM | 1051 | CB  | ALA | A | 171 | 0.632  | 70.143 | 19.562 | 1.00 | 34.11 |
| ATOM | 1052 | N   | VAL | A | 172 | −0.099 | 67.208 | 18.766 | 1.00 | 35.90 |
| ATOM | 1053 | CA  | VAL | A | 172 | −0.397 | 65.849 | 19.126 | 1.00 | 36.13 |
| ATOM | 1054 | C   | VAL | A | 172 | 0.483  | 64.867 | 18.348 | 1.00 | 42.01 |
| ATOM | 1055 | O   | VAL | A | 172 | 0.997  | 63.899 | 18.914 | 1.00 | 42.53 |
| ATOM | 1056 | CB  | VAL | A | 172 | −1.855 | 65.525 | 18.897 | 1.00 | 39.59 |
| ATOM | 1057 | CG1 | VAL | A | 172 | −2.117 | 64.047 | 19.209 | 1.00 | 39.12 |
| ATOM | 1058 | CG2 | VAL | A | 172 | −2.735 | 66.438 | 19.765 | 1.00 | 39.46 |
| ATOM | 1059 | N   | ILE | A | 173 | 0.645  | 65.106 | 17.051 | 1.00 | 38.58 |
| ATOM | 1060 | CA  | ILE | A | 173 | 1.467  | 64.225 | 16.244 | 1.00 | 38.47 |
| ATOM | 1061 | C   | ILE | A | 173 | 2.900  | 64.208 | 16.782 | 1.00 | 42.05 |
| ATOM | 1062 | O   | ILE | A | 173 | 3.523  | 63.153 | 16.863 | 1.00 | 41.56 |
| ATOM | 1063 | CB  | ILE | A | 173 | 1.518  | 64.657 | 14.768 | 1.00 | 41.34 |
| ATOM | 1064 | CG1 | ILE | A | 173 | 0.201  | 64.340 | 14.060 | 1.00 | 41.75 |
| ATOM | 1065 | CG2 | ILE | A | 173 | 2.642  | 63.933 | 14.062 | 1.00 | 42.52 |
| ATOM | 1066 | CD1 | ILE | A | 173 | 0.027  | 65.078 | 12.743 | 1.00 | 41.85 |
| ATOM | 1067 | N   | LYS | A | 174 | 3.423  | 65.391 | 17.104 | 1.00 | 38.05 |
| ATOM | 1068 | CA  | LYS | A | 174 | 4.799  | 65.522 | 17.574 | 1.00 | 37.85 |
| ATOM | 1069 | C   | LYS | A | 174 | 4.983  | 64.964 | 18.964 | 1.00 | 41.99 |
| ATOM | 1070 | O   | LYS | A | 174 | 6.050  | 64.465 | 19.301 | 1.00 | 40.88 |
| ATOM | 1071 | CB  | LYS | A | 174 | 5.270  | 66.971 | 17.511 | 1.00 | 39.44 |
| ATOM | 1072 | CG  | LYS | A | 174 | 5.651  | 67.425 | 16.127 | 1.00 | 43.97 |
| ATOM | 1073 | CD  | LYS | A | 174 | 6.330  | 68.788 | 16.154 | 1.00 | 46.42 |
| ATOM | 1074 | CE  | LYS | A | 174 | 6.645  | 69.256 | 14.746 | 1.00 | 51.29 |
| ATOM | 1075 | NZ  | LYS | A | 174 | 7.311  | 70.586 | 14.728 | 1.00 | 59.15 |
| ATOM | 1076 | N   | GLY | A | 175 | 3.932  | 65.045 | 19.769 | 1.00 | 39.80 |
| ATOM | 1077 | CA  | GLY | A | 175 | 3.964  | 64.519 | 21.123 | 1.00 | 39.81 |
| ATOM | 1078 | C   | GLY | A | 175 | 3.992  | 62.996 | 21.065 | 1.00 | 44.70 |
| ATOM | 1079 | O   | GLY | A | 175 | 4.784  | 62.354 | 21.755 | 1.00 | 45.16 |
| ATOM | 1080 | N   | LEU | A | 176 | 3.135  | 62.424 | 20.225 | 1.00 | 40.60 |
| ATOM | 1081 | CA  | LEU | A | 176 | 3.082  | 60.974 | 20.062 | 1.00 | 40.41 |
| ATOM | 1082 | C   | LEU | A | 176 | 4.389  | 60.456 | 19.459 | 1.00 | 46.63 |
| ATOM | 1083 | O   | LEU | A | 176 | 4.830  | 59.342 | 19.757 | 1.00 | 46.54 |
| ATOM | 1084 | CB  | LEU | A | 176 | 1.917  | 60.575 | 19.163 | 1.00 | 39.68 |
| ATOM | 1085 | CG  | LEU | A | 176 | 0.502  | 60.846 | 19.669 | 1.00 | 42.92 |
| ATOM | 1086 | CD1 | LEU | A | 176 | −0.534 | 60.500 | 18.571 | 1.00 | 42.64 |
| ATOM | 1087 | CD2 | LEU | A | 176 | 0.236  | 60.059 | 20.927 | 1.00 | 42.95 |
| ATOM | 1088 | N   | THR | A | 177 | 4.991  | 61.264 | 18.598 | 1.00 | 44.44 |
| ATOM | 1089 | CA  | THR | A | 177 | 6.232  | 60.891 | 17.934 | 1.00 | 44.75 |
| ATOM | 1090 | C   | THR | A | 177 | 7.407  | 60.895 | 18.898 | 1.00 | 49.46 |
| ATOM | 1091 | O   | THR | A | 177 | 8.346  | 60.120 | 18.745 | 1.00 | 49.49 |
| ATOM | 1092 | CB  | THR | A | 177 | 6.543  | 61.831 | 16.770 | 1.00 | 54.09 |
| ATOM | 1093 | OG1 | THR | A | 177 | 5.526  | 61.697 | 15.765 | 1.00 | 55.60 |
| ATOM | 1094 | CG2 | THR | A | 177 | 7.920  | 61.499 | 16.161 | 1.00 | 51.56 |
| ATOM | 1095 | N   | TYR | A | 178 | 7.353  | 61.777 | 19.887 | 1.00 | 45.90 |
| ATOM | 1096 | CA  | TYR | A | 178 | 8.419  | 61.874 | 20.857 | 1.00 | 45.44 |
| ATOM | 1097 | C   | TYR | A | 178 | 8.359  | 60.690 | 21.819 | 1.00 | 48.84 |
| ATOM | 1098 | O   | TYR | A | 178 | 9.387  | 60.121 | 22.188 | 1.00 | 48.37 |
| ATOM | 1099 | CB  | TYR | A | 178 | 8.336  | 63.189 | 21.631 | 1.00 | 46.53 |
| ATOM | 1100 | CG  | TYR | A | 178 | 9.214  | 63.194 | 22.861 | 1.00 | 48.50 |
| ATOM | 1101 | CD1 | TYR | A | 178 | 8.768  | 62.650 | 24.055 | 1.00 | 50.65 |
| ATOM | 1102 | CD2 | TYR | A | 178 | 10.518 | 63.676 | 22.807 | 1.00 | 49.11 |
| ATOM | 1103 | CE1 | TYR | A | 178 | 9.584  | 62.611 | 25.175 | 1.00 | 52.01 |
| ATOM | 1104 | CE2 | TYR | A | 178 | 11.337 | 63.650 | 23.924 | 1.00 | 49.79 |
| ATOM | 1105 | CZ  | TYR | A | 178 | 10.867 | 63.109 | 25.099 | 1.00 | 57.66 |
| ATOM | 1106 | OH  | TYR | A | 178 | 11.675 | 63.074 | 26.207 | 1.00 | 59.40 |
| ATOM | 1107 | N   | LEU | A | 179 | 7.148  | 60.316 | 22.208 | 1.00 | 44.58 |
| ATOM | 1108 | CA  | LEU | A | 179 | 6.961  | 59.196 | 23.112 | 1.00 | 44.57 |
| ATOM | 1109 | C   | LEU | A | 179 | 7.466  | 57.899 | 22.497 | 1.00 | 51.51 |

TABLE 3-continued

Structural Coordinate of MEK1/N35/NKFCdel (corresponding to amino acids 24-373 of SEQ ID NO: 2)-ATPγS Binary Complex.

| ATOM | 1110 | O   | LEU | A | 179 | 8.054  | 57.062 | 23.182 | 1.00 | 51.22  |
|------|------|-----|-----|---|-----|--------|--------|--------|------|--------|
| ATOM | 1111 | CB  | LEU | A | 179 | 5.492  | 59.068 | 23.505 | 1.00 | 44.16  |
| ATOM | 1112 | CG  | LEU | A | 179 | 5.010  | 60.217 | 24.395 | 1.00 | 48.28  |
| ATOM | 1113 | CD1 | LEU | A | 179 | 3.558  | 60.054 | 24.769 | 1.00 | 48.50  |
| ATOM | 1114 | CD2 | LEU | A | 179 | 5.879  | 60.333 | 25.643 | 1.00 | 49.44  |
| ATOM | 1115 | N   | ARG | A | 180 | 7.258  | 57.758 | 21.193 | 1.00 | 50.19  |
| ATOM | 1116 | CA  | ARG | A | 180 | 7.674  | 56.579 | 20.455 | 1.00 | 50.80  |
| ATOM | 1117 | C   | ARG | A | 180 | 9.191  | 56.530 | 20.241 | 1.00 | 55.94  |
| ATOM | 1118 | O   | ARG | A | 180 | 9.842  | 55.535 | 20.541 | 1.00 | 55.50  |
| ATOM | 1119 | CB  | ARG | A | 180 | 6.967  | 56.552 | 19.098 | 1.00 | 51.86  |
| ATOM | 1120 | CG  | ARG | A | 180 | 6.194  | 55.271 | 18.813 | 1.00 | 64.13  |
| ATOM | 1121 | CD  | ARG | A | 180 | 6.118  | 55.017 | 17.318 | 1.00 | 74.72  |
| ATOM | 1122 | NE  | ARG | A | 180 | 6.684  | 56.129 | 16.551 | 1.00 | 82.23  |
| ATOM | 1123 | CZ  | ARG | A | 180 | 6.983  | 56.070 | 15.257 | 1.00 | 94.42  |
| ATOM | 1124 | NH1 | ARG | A | 180 | 6.771  | 54.947 | 14.576 | 1.00 | 82.23  |
| ATOM | 1125 | NH2 | ARG | A | 180 | 7.502  | 57.129 | 14.643 | 1.00 | 75.18  |
| ATOM | 1126 | N   | GLU | A | 181 | 9.735  | 57.605 | 19.691 | 1.00 | 53.47  |
| ATOM | 1127 | CA  | GLU | A | 181 | 11.155 | 57.678 | 19.379 | 1.00 | 53.56  |
| ATOM | 1128 | C   | GLU | A | 181 | 12.056 | 57.605 | 20.599 | 1.00 | 57.26  |
| ATOM | 1129 | O   | GLU | A | 181 | 12.979 | 56.790 | 20.650 | 1.00 | 57.08  |
| ATOM | 1130 | CB  | GLU | A | 181 | 11.462 | 58.956 | 18.595 | 1.00 | 55.10  |
| ATOM | 1131 | CG  | GLU | A | 181 | 10.841 | 58.992 | 17.223 | 1.00 | 68.50  |
| ATOM | 1132 | CD  | GLU | A | 181 | 11.153 | 57.744 | 16.419 | 1.00 | 96.65  |
| ATOM | 1133 | OE1 | GLU | A | 181 | 10.219 | 56.951 | 16.159 | 1.00 | 94.99  |
| ATOM | 1134 | OE2 | GLU | A | 181 | 12.339 | 57.546 | 16.068 | 1.00 | 91.47  |
| ATOM | 1135 | N   | LYS | A | 182 | 11.820 | 58.496 | 21.558 | 1.00 | 52.84  |
| ATOM | 1136 | CA  | LYS | A | 182 | 12.669 | 58.588 | 22.735 | 1.00 | 51.94  |
| ATOM | 1137 | C   | LYS | A | 182 | 12.386 | 57.602 | 23.849 | 1.00 | 55.47  |
| ATOM | 1138 | O   | LYS | A | 182 | 13.267 | 57.316 | 24.654 | 1.00 | 55.55  |
| ATOM | 1139 | CB  | LYS | A | 182 | 12.673 | 60.014 | 23.281 | 1.00 | 54.15  |
| ATOM | 1140 | CG  | LYS | A | 182 | 13.076 | 61.069 | 22.256 | 1.00 | 66.05  |
| ATOM | 1141 | CD  | LYS | A | 182 | 14.505 | 60.862 | 21.799 | 1.00 | 77.82  |
| ATOM | 1142 | CE  | LYS | A | 182 | 14.933 | 61.932 | 20.807 | 1.00 | 93.36  |
| ATOM | 1143 | NZ  | LYS | A | 182 | 16.410 | 61.920 | 20.575 | 1.00 | 103.78 |
| ATOM | 1144 | N   | HIS | A | 183 | 11.166 | 57.090 | 23.921 | 1.00 | 51.26  |
| ATOM | 1145 | CA  | HIS | A | 183 | 10.816 | 56.195 | 25.016 | 1.00 | 50.74  |
| ATOM | 1146 | C   | HIS | A | 183 | 10.124 | 54.914 | 24.593 | 1.00 | 54.31  |
| ATOM | 1147 | O   | HIS | A | 183 | 9.774  | 54.083 | 25.438 | 1.00 | 52.81  |
| ATOM | 1148 | CB  | HIS | A | 183 | 9.982  | 56.954 | 26.078 | 1.00 | 51.49  |
| ATOM | 1149 | CG  | HIS | A | 183 | 10.568 | 58.276 | 26.463 | 1.00 | 54.72  |
| ATOM | 1150 | ND1 | HIS | A | 183 | 11.507 | 58.408 | 27.462 | 1.00 | 56.46  |
| ATOM | 1151 | CD2 | HIS | A | 183 | 10.407 | 59.511 | 25.933 | 1.00 | 56.55  |
| ATOM | 1152 | CE1 | HIS | A | 183 | 11.879 | 59.673 | 27.552 | 1.00 | 55.92  |
| ATOM | 1153 | NE2 | HIS | A | 183 | 11.232 | 60.363 | 26.631 | 1.00 | 56.37  |
| ATOM | 1154 | N   | LYS | A | 184 | 9.953  | 54.748 | 23.286 | 1.00 | 52.04  |
| ATOM | 1155 | CA  | LYS | A | 184 | 9.317  | 53.559 | 22.729 | 1.00 | 52.76  |
| ATOM | 1156 | C   | LYS | A | 184 | 8.036  | 53.234 | 23.451 | 1.00 | 57.54  |
| ATOM | 1157 | O   | LYS | A | 184 | 7.830  | 52.106 | 23.893 | 1.00 | 57.28  |
| ATOM | 1158 | CB  | LYS | A | 184 | 10.265 | 52.351 | 22.769 | 1.00 | 55.87  |
| ATOM | 1159 | CG  | LYS | A | 184 | 11.390 | 52.405 | 21.734 | 1.00 | 74.74  |
| ATOM | 1160 | CD  | LYS | A | 184 | 12.149 | 51.079 | 21.660 | 1.00 | 88.25  |
| ATOM | 1161 | CE  | LYS | A | 184 | 13.174 | 51.075 | 20.517 | 1.00 | 101.72 |
| ATOM | 1162 | NZ  | LYS | A | 184 | 13.294 | 49.735 | 19.851 | 1.00 | 109.61 |
| ATOM | 1163 | N   | ILE | A | 185 | 7.185  | 54.240 | 23.599 | 1.00 | 54.52  |
| ATOM | 1164 | CA  | ILE | A | 185 | 5.896  | 54.056 | 24.235 | 1.00 | 53.95  |
| ATOM | 1165 | C   | ILE | A | 185 | 4.810  | 54.856 | 23.540 | 1.00 | 55.99  |
| ATOM | 1166 | O   | ILE | A | 185 | 5.096  | 55.763 | 22.762 | 1.00 | 55.11  |
| ATOM | 1167 | CB  | ILE | A | 185 | 5.934  | 54.349 | 25.724 | 1.00 | 57.27  |
| ATOM | 1168 | CG1 | ILE | A | 185 | 6.385  | 55.787 | 25.987 | 1.00 | 57.67  |
| ATOM | 1169 | CG2 | ILE | A | 185 | 6.837  | 53.338 | 26.433 | 1.00 | 58.37  |
| ATOM | 1170 | CD1 | ILE | A | 185 | 6.509  | 56.121 | 27.474 | 1.00 | 61.27  |
| ATOM | 1171 | N   | MET | A | 186 | 3.566  | 54.463 | 23.767 | 1.00 | 51.75  |
| ATOM | 1172 | CA  | MET | A | 186 | 2.444  | 55.114 | 23.133 | 1.00 | 51.03  |
| ATOM | 1173 | C   | MET | A | 186 | 1.546  | 55.707 | 24.182 | 1.00 | 50.78  |
| ATOM | 1174 | O   | MET | A | 186 | 1.620  | 55.336 | 25.347 | 1.00 | 50.76  |
| ATOM | 1175 | CB  | MET | A | 186 | 1.679  | 54.129 | 22.263 | 1.00 | 54.00  |
| ATOM | 1176 | CG  | MET | A | 186 | 0.824  | 53.163 | 23.023 | 1.00 | 58.35  |
| ATOM | 1177 | SD  | MET | A | 186 | −0.026 | 52.048 | 21.890 | 1.00 | 63.39  |
| ATOM | 1178 | CE  | MET | A | 186 | −1.755 | 52.756 | 21.961 | 1.00 | 59.99  |
| ATOM | 1179 | N   | HIS | A | 187 | 0.720  | 56.662 | 23.784 | 1.00 | 43.67  |
| ATOM | 1180 | CA  | HIS | A | 187 | −0.151 | 57.324 | 24.745 | 1.00 | 41.38  |
| ATOM | 1181 | C   | HIS | A | 187 | −1.201 | 56.399 | 25.340 | 1.00 | 43.50  |
| ATOM | 1182 | O   | HIS | A | 187 | −1.254 | 56.221 | 26.554 | 1.00 | 42.07  |
| ATOM | 1183 | CB  | HIS | A | 187 | −0.810 | 58.573 | 24.137 | 1.00 | 40.80  |
| ATOM | 1184 | CG  | HIS | A | 187 | −1.328 | 59.532 | 25.160 | 1.00 | 43.03  |
| ATOM | 1185 | ND1 | HIS | A | 187 | −2.457 | 59.278 | 25.911 | 1.00 | 44.18  |
| ATOM | 1186 | CD2 | HIS | A | 187 | −0.854 | 60.728 | 25.584 | 1.00 | 43.71  |

TABLE 3-continued

Structural Coordinate of MEK1/N35/NKFCdel (corresponding to amino acids 24-373 of SEQ ID NO: 2)-ATPγS Binary Complex.

| ATOM | 1187 | CE1 | HIS | A | 187 | −2.672 | 60.292 | 26.731 | 1.00 | 43.16 |
|---|---|---|---|---|---|---|---|---|---|---|
| ATOM | 1188 | NE2 | HIS | A | 187 | −1.707 | 61.179 | 26.560 | 1.00 | 43.37 |
| ATOM | 1189 | N | ARG | A | 188 | −2.058 | 55.851 | 24.474 | 1.00 | 39.74 |
| ATOM | 1190 | CA | ARG | A | 188 | −3.140 | 54.936 | 24.874 | 1.00 | 39.28 |
| ATOM | 1191 | C | ARG | A | 188 | −4.388 | 55.631 | 25.366 | 1.00 | 42.30 |
| ATOM | 1192 | O | ARG | A | 188 | −5.429 | 55.012 | 25.506 | 1.00 | 42.44 |
| ATOM | 1193 | CB | ARG | A | 188 | −2.666 | 53.900 | 25.897 | 1.00 | 40.21 |
| ATOM | 1194 | CG | ARG | A | 188 | −2.047 | 52.661 | 25.274 | 1.00 | 54.29 |
| ATOM | 1195 | CD | ARG | A | 188 | −1.717 | 51.613 | 26.330 | 1.00 | 68.54 |
| ATOM | 1196 | NE | ARG | A | 188 | −0.278 | 51.403 | 26.450 | 1.00 | 79.47 |
| ATOM | 1197 | CZ | ARG | A | 188 | 0.365 | 50.346 | 25.968 | 1.00 | 93.79 |
| ATOM | 1198 | NH1 | ARG | A | 188 | −0.304 | 49.391 | 25.335 | 1.00 | 79.39 |
| ATOM | 1199 | NH2 | ARG | A | 188 | 1.678 | 50.245 | 26.120 | 1.00 | 82.59 |
| ATOM | 1200 | N | ASP | A | 189 | −4.292 | 56.922 | 25.637 | 1.00 | 38.34 |
| ATOM | 1201 | CA | ASP | A | 189 | −5.459 | 57.656 | 26.099 | 1.00 | 37.54 |
| ATOM | 1202 | C | ASP | A | 189 | −5.509 | 59.071 | 25.556 | 1.00 | 40.79 |
| ATOM | 1203 | O | ASP | A | 189 | −5.529 | 60.038 | 26.305 | 1.00 | 40.71 |
| ATOM | 1204 | CB | ASP | A | 189 | −5.572 | 57.637 | 27.621 | 1.00 | 38.75 |
| ATOM | 1205 | CG | ASP | A | 189 | −6.984 | 57.966 | 28.107 | 1.00 | 46.14 |
| ATOM | 1206 | OD1 | ASP | A | 189 | −7.948 | 57.794 | 27.320 | 1.00 | 44.96 |
| ATOM | 1207 | OD2 | ASP | A | 189 | −7.126 | 58.416 | 29.268 | 1.00 | 53.43 |
| ATOM | 1208 | N | VAL | A | 190 | −5.533 | 59.178 | 24.240 | 1.00 | 36.21 |
| ATOM | 1209 | CA | VAL | A | 190 | −5.641 | 60.453 | 23.594 | 1.00 | 35.11 |
| ATOM | 1210 | C | VAL | A | 190 | −7.122 | 60.842 | 23.543 | 1.00 | 39.05 |
| ATOM | 1211 | O | VAL | A | 190 | −7.975 | 60.055 | 23.117 | 1.00 | 38.07 |
| ATOM | 1212 | CB | VAL | A | 190 | −5.073 | 60.401 | 22.152 | 1.00 | 38.44 |
| ATOM | 1213 | CG1 | VAL | A | 190 | −5.496 | 61.631 | 21.364 | 1.00 | 37.82 |
| ATOM | 1214 | CG2 | VAL | A | 190 | −3.544 | 60.259 | 22.177 | 1.00 | 38.12 |
| ATOM | 1215 | N | LYS | A | 191 | −7.418 | 62.038 | 24.041 | 1.00 | 35.76 |
| ATOM | 1216 | CA | LYS | A | 191 | −8.763 | 62.587 | 24.038 | 1.00 | 35.10 |
| ATOM | 1217 | C | LYS | A | 191 | −8.616 | 64.061 | 24.394 | 1.00 | 38.95 |
| ATOM | 1218 | O | LYS | A | 191 | −7.520 | 64.500 | 24.706 | 1.00 | 38.58 |
| ATOM | 1219 | CB | LYS | A | 191 | −9.656 | 61.846 | 25.025 | 1.00 | 37.08 |
| ATOM | 1220 | CG | LYS | A | 191 | −9.263 | 62.004 | 26.472 | 1.00 | 39.86 |
| ATOM | 1221 | CD | LYS | A | 191 | −10.073 | 61.074 | 27.336 | 1.00 | 41.76 |
| ATOM | 1222 | CE | LYS | A | 191 | −9.474 | 60.929 | 28.721 | 1.00 | 45.17 |
| ATOM | 1223 | NZ | LYS | A | 191 | −10.442 | 60.299 | 29.654 | 1.00 | 49.49 |
| ATOM | 1224 | N | PRO | A | 192 | −9.694 | 64.835 | 24.300 | 1.00 | 35.63 |
| ATOM | 1225 | CA | PRO | A | 192 | −9.599 | 66.296 | 24.525 | 1.00 | 35.49 |
| ATOM | 1226 | C | PRO | A | 192 | −9.132 | 66.751 | 25.907 | 1.00 | 40.27 |
| ATOM | 1227 | O | PRO | A | 192 | −8.425 | 67.753 | 26.031 | 1.00 | 40.46 |
| ATOM | 1228 | CB | PRO | A | 192 | −11.018 | 66.800 | 24.211 | 1.00 | 36.75 |
| ATOM | 1229 | CG | PRO | A | 192 | −11.546 | 65.806 | 23.200 | 1.00 | 40.38 |
| ATOM | 1230 | CD | PRO | A | 192 | −10.950 | 64.458 | 23.612 | 1.00 | 35.78 |
| ATOM | 1231 | N | SER | A | 193 | −9.502 | 66.005 | 26.939 | 1.00 | 36.70 |
| ATOM | 1232 | CA | SER | A | 193 | −9.121 | 66.351 | 28.302 | 1.00 | 36.00 |
| ATOM | 1233 | C | SER | A | 193 | −7.660 | 66.039 | 28.583 | 1.00 | 40.44 |
| ATOM | 1234 | O | SER | A | 193 | −7.134 | 66.399 | 29.643 | 1.00 | 39.99 |
| ATOM | 1235 | CB | SER | A | 193 | −10.008 | 65.612 | 29.307 | 1.00 | 38.52 |
| ATOM | 1236 | OG | SER | A | 193 | −9.756 | 64.217 | 29.272 | 1.00 | 44.18 |
| ATOM | 1237 | N | ASN | A | 194 | −7.012 | 65.339 | 27.651 | 1.00 | 36.67 |
| ATOM | 1238 | CA | ASN | A | 194 | −5.606 | 64.972 | 27.818 | 1.00 | 35.83 |
| ATOM | 1239 | C | ASN | A | 194 | −4.710 | 65.803 | 26.952 | 1.00 | 38.88 |
| ATOM | 1240 | O | ASN | A | 194 | −3.531 | 65.495 | 26.784 | 1.00 | 39.15 |
| ATOM | 1241 | CB | ASN | A | 194 | −5.377 | 63.481 | 27.577 | 1.00 | 34.06 |
| ATOM | 1242 | CG | ASN | A | 194 | −5.727 | 62.651 | 28.778 | 1.00 | 49.75 |
| ATOM | 1243 | OD1 | ASN | A | 194 | −5.897 | 63.181 | 29.875 | 1.00 | 39.18 |
| ATOM | 1244 | ND2 | ASN | A | 194 | −5.893 | 61.345 | 28.576 | 1.00 | 43.31 |
| ATOM | 1245 | N | ILE | A | 195 | −5.278 | 66.859 | 26.388 | 1.00 | 34.44 |
| ATOM | 1246 | CA | ILE | A | 195 | −4.507 | 67.824 | 25.621 | 1.00 | 33.70 |
| ATOM | 1247 | C | ILE | A | 195 | −4.605 | 69.153 | 26.362 | 1.00 | 38.37 |
| ATOM | 1248 | O | ILE | A | 195 | −5.671 | 69.756 | 26.441 | 1.00 | 37.24 |
| ATOM | 1249 | CB | ILE | A | 195 | −5.003 | 67.966 | 24.173 | 1.00 | 35.80 |
| ATOM | 1250 | CG1 | ILE | A | 195 | −5.068 | 66.585 | 23.501 | 1.00 | 36.08 |
| ATOM | 1251 | CG2 | ILE | A | 195 | −4.053 | 68.880 | 23.366 | 1.00 | 34.47 |
| ATOM | 1252 | CD1 | ILE | A | 195 | −5.987 | 66.532 | 22.279 | 1.00 | 37.39 |
| ATOM | 1253 | N | LEU | A | 196 | −3.504 | 69.546 | 26.995 | 1.00 | 35.79 |
| ATOM | 1254 | CA | LEU | A | 196 | −3.471 | 70.777 | 27.779 | 1.00 | 34.99 |
| ATOM | 1255 | C | LEU | A | 196 | −2.859 | 71.915 | 27.002 | 1.00 | 36.56 |
| ATOM | 1256 | O | LEU | A | 196 | −1.996 | 71.707 | 26.162 | 1.00 | 35.75 |
| ATOM | 1257 | CB | LEU | A | 196 | −2.726 | 70.558 | 29.089 | 1.00 | 35.09 |
| ATOM | 1258 | CG | LEU | A | 196 | −3.200 | 69.335 | 29.889 | 1.00 | 39.73 |
| ATOM | 1259 | CD1 | LEU | A | 196 | −2.390 | 69.165 | 31.186 | 1.00 | 40.14 |
| ATOM | 1260 | CD2 | LEU | A | 196 | −4.690 | 69.396 | 30.172 | 1.00 | 39.68 |
| ATOM | 1261 | N | VAL | A | 197 | −3.345 | 73.123 | 27.258 | 1.00 | 32.19 |
| ATOM | 1262 | CA | VAL | A | 197 | −2.864 | 74.317 | 26.559 | 1.00 | 31.10 |
| ATOM | 1263 | C | VAL | A | 197 | −2.581 | 75.445 | 27.546 | 1.00 | 32.95 |

TABLE 3-continued

Structural Coordinate of MEK1/N35/NKFCdel (corresponding to amino acids 24-373 of SEQ ID NO: 2)-ATPγS Binary Complex.

| ATOM | 1264 | O   | VAL | A | 197 | −3.055 | 75.421 | 28.674 | 1.00 | 31.09  |
|------|------|-----|-----|---|-----|--------|--------|--------|------|--------|
| ATOM | 1265 | CB  | VAL | A | 197 | −3.885 | 74.794 | 25.464 | 1.00 | 34.46  |
| ATOM | 1266 | CG1 | VAL | A | 197 | −3.906 | 73.805 | 24.298 | 1.00 | 34.31  |
| ATOM | 1267 | CG2 | VAL | A | 197 | −5.282 | 74.942 | 26.049 | 1.00 | 33.84  |
| ATOM | 1268 | N   | ASN | A | 198 | −1.768 | 76.409 | 27.134 | 1.00 | 30.55  |
| ATOM | 1269 | CA  | ASN | A | 198 | −1.422 | 77.518 | 28.030 | 1.00 | 30.82  |
| ATOM | 1270 | C   | ASN | A | 198 | −1.370 | 78.897 | 27.356 | 1.00 | 36.36  |
| ATOM | 1271 | O   | ASN | A | 198 | −1.386 | 79.003 | 26.127 | 1.00 | 34.55  |
| ATOM | 1272 | CB  | ASN | A | 198 | −0.149 | 77.214 | 28.861 | 1.00 | 26.74  |
| ATOM | 1273 | CG  | ASN | A | 198 | 1.133  | 77.258 | 28.032 | 1.00 | 42.92  |
| ATOM | 1274 | OD1 | ASN | A | 198 | 1.182  | 77.855 | 26.945 | 1.00 | 33.94  |
| ATOM | 1275 | ND2 | ASN | A | 198 | 2.188  | 76.640 | 28.557 | 1.00 | 33.50  |
| ATOM | 1276 | N   | SER | A | 199 | −1.358 | 79.947 | 28.176 | 1.00 | 35.32  |
| ATOM | 1277 | CA  | SER | A | 199 | −1.336 | 81.318 | 27.671 | 1.00 | 36.15  |
| ATOM | 1278 | C   | SER | A | 199 | −0.093 | 81.630 | 26.825 | 1.00 | 42.22  |
| ATOM | 1279 | O   | SER | A | 199 | −0.059 | 82.626 | 26.112 | 1.00 | 42.44  |
| ATOM | 1280 | CB  | SER | A | 199 | −1.474 | 82.325 | 28.816 | 1.00 | 39.30  |
| ATOM | 1281 | OG  | SER | A | 199 | −0.458 | 82.144 | 29.770 | 1.00 | 45.77  |
| ATOM | 1282 | N   | ARG | A | 200 | 0.915  | 80.766 | 26.881 | 1.00 | 39.72  |
| ATOM | 1283 | CA  | ARG | A | 200 | 2.103  | 80.970 | 26.048 | 1.00 | 40.59  |
| ATOM | 1284 | C   | ARG | A | 200 | 1.876  | 80.426 | 24.623 | 1.00 | 45.58  |
| ATOM | 1285 | O   | ARG | A | 200 | 2.664  | 80.686 | 23.715 | 1.00 | 45.25  |
| ATOM | 1286 | CB  | ARG | A | 200 | 3.342  | 80.330 | 26.682 | 1.00 | 42.16  |
| ATOM | 1287 | CG  | ARG | A | 200 | 3.955  | 81.157 | 27.794 | 1.00 | 55.01  |
| ATOM | 1288 | CD  | ARG | A | 200 | 4.828  | 80.309 | 28.701 | 1.00 | 70.71  |
| ATOM | 1289 | NE  | ARG | A | 200 | 5.991  | 81.050 | 29.178 | 1.00 | 85.95  |
| ATOM | 1290 | CZ  | ARG | A | 200 | 7.228  | 80.566 | 29.204 | 1.00 | 102.21 |
| ATOM | 1291 | NH1 | ARG | A | 200 | 7.468  | 79.335 | 28.767 | 1.00 | 86.36  |
| ATOM | 1292 | NH2 | ARG | A | 200 | 8.229  | 81.319 | 29.651 | 1.00 | 92.86  |
| ATOM | 1293 | N   | GLY | A | 201 | 0.788  | 79.670 | 24.440 | 1.00 | 41.85  |
| ATOM | 1294 | CA  | GLY | A | 201 | 0.454  | 79.122 | 23.128 | 1.00 | 41.23  |
| ATOM | 1295 | C   | GLY | A | 201 | 0.986  | 77.706 | 22.960 | 1.00 | 43.37  |
| ATOM | 1296 | O   | GLY | A | 201 | 1.135  | 77.210 | 21.843 | 1.00 | 43.04  |
| ATOM | 1297 | N   | GLU | A | 202 | 1.296  | 77.072 | 24.075 | 1.00 | 38.20  |
| ATOM | 1298 | CA  | GLU | A | 202 | 1.815  | 75.725 | 24.044 | 1.00 | 37.06  |
| ATOM | 1299 | C   | GLU | A | 202 | 0.685  | 74.717 | 24.123 | 1.00 | 39.35  |
| ATOM | 1300 | O   | GLU | A | 202 | −0.308 | 74.935 | 24.810 | 1.00 | 37.90  |
| ATOM | 1301 | CB  | GLU | A | 202 | 2.800  | 75.498 | 25.189 | 1.00 | 38.07  |
| ATOM | 1302 | CG  | GLU | A | 202 | 4.014  | 76.414 | 25.146 | 1.00 | 45.19  |
| ATOM | 1303 | CD  | GLU | A | 202 | 4.947  | 76.205 | 26.331 | 1.00 | 60.89  |
| ATOM | 1304 | OE1 | GLU | A | 202 | 4.477  | 76.290 | 27.493 | 1.00 | 44.79  |
| ATOM | 1305 | OE2 | GLU | A | 202 | 6.146  | 75.938 | 26.102 | 1.00 | 52.24  |
| ATOM | 1306 | N   | ILE | A | 203 | 0.856  | 73.613 | 23.404 | 1.00 | 35.00  |
| ATOM | 1307 | CA  | ILE | A | 203 | −0.106 | 72.530 | 23.389 | 1.00 | 34.27  |
| ATOM | 1308 | C   | ILE | A | 203 | 0.664  | 71.276 | 23.773 | 1.00 | 37.30  |
| ATOM | 1309 | O   | ILE | A | 203 | 1.731  | 71.026 | 23.235 | 1.00 | 36.05  |
| ATOM | 1310 | CB  | ILE | A | 203 | −0.749 | 72.387 | 21.984 | 1.00 | 36.90  |
| ATOM | 1311 | CG1 | ILE | A | 203 | −1.302 | 73.755 | 21.529 | 1.00 | 36.68  |
| ATOM | 1312 | CG2 | ILE | A | 203 | −1.876 | 71.343 | 22.018 | 1.00 | 36.43  |
| ATOM | 1313 | CD1 | ILE | A | 203 | −1.175 | 74.026 | 20.055 | 1.00 | 37.04  |
| ATOM | 1314 | N   | LYS | A | 204 | 0.174  | 70.546 | 24.778 | 1.00 | 33.74  |
| ATOM | 1315 | CA  | LYS | A | 204 | 0.910  | 69.396 | 25.304 | 1.00 | 33.36  |
| ATOM | 1316 | C   | LYS | A | 204 | 0.049  | 68.226 | 25.700 | 1.00 | 38.05  |
| ATOM | 1317 | O   | LYS | A | 204 | −1.080 | 68.391 | 26.152 | 1.00 | 38.40  |
| ATOM | 1318 | CB  | LYS | A | 204 | 1.758  | 69.811 | 26.515 | 1.00 | 34.67  |
| ATOM | 1319 | CG  | LYS | A | 204 | 2.686  | 70.990 | 26.254 | 1.00 | 37.25  |
| ATOM | 1320 | CD  | LYS | A | 204 | 3.461  | 71.377 | 27.507 | 1.00 | 34.93  |
| ATOM | 1321 | CE  | LYS | A | 204 | 4.548  | 72.392 | 27.186 | 1.00 | 38.52  |
| ATOM | 1322 | NZ  | LYS | A | 204 | 5.350  | 72.781 | 28.390 | 1.00 | 41.91  |
| ATOM | 1323 | N   | LEU | A | 205 | 0.605  | 67.030 | 25.569 | 1.00 | 34.62  |
| ATOM | 1324 | CA  | LEU | A | 205 | −0.108 | 65.835 | 25.976 | 1.00 | 34.60  |
| ATOM | 1325 | C   | LEU | A | 205 | 0.190  | 65.491 | 27.437 | 1.00 | 39.53  |
| ATOM | 1326 | O   | LEU | A | 205 | 1.282  | 65.770 | 27.959 | 1.00 | 38.81  |
| ATOM | 1327 | CB  | LEU | A | 205 | 0.284  | 64.659 | 25.095 | 1.00 | 34.42  |
| ATOM | 1328 | CG  | LEU | A | 205 | 0.069  | 64.842 | 23.603 | 1.00 | 38.35  |
| ATOM | 1329 | CD1 | LEU | A | 205 | 0.864  | 63.785 | 22.835 | 1.00 | 38.40  |
| ATOM | 1330 | CD2 | LEU | A | 205 | −1.392 | 64.753 | 23.292 | 1.00 | 38.38  |
| ATOM | 1331 | N   | CYS | A | 206 | −0.770 | 64.857 | 28.084 | 1.00 | 37.38  |
| ATOM | 1332 | CA  | CYS | A | 206 | −0.579 | 64.409 | 29.451 | 1.00 | 37.86  |
| ATOM | 1333 | C   | CYS | A | 206 | −1.308 | 63.097 | 29.645 | 1.00 | 42.78  |
| ATOM | 1334 | O   | CYS | A | 206 | −2.101 | 62.684 | 28.798 | 1.00 | 41.19  |
| ATOM | 1335 | CB  | CYS | A | 206 | −1.116 | 65.446 | 30.439 | 1.00 | 38.31  |
| ATOM | 1336 | SG  | CYS | A | 206 | −2.932 | 65.599 | 30.439 | 1.00 | 42.22  |
| ATOM | 1337 | N   | ASP | A | 207 | −1.042 | 62.450 | 30.773 | 1.00 | 41.70  |
| ATOM | 1338 | CA  | ASP | A | 207 | −1.739 | 61.226 | 31.149 | 1.00 | 42.72  |
| ATOM | 1339 | C   | ASP | A | 207 | −1.559 | 60.015 | 30.247 | 1.00 | 49.53  |
| ATOM | 1340 | O   | ASP | A | 207 | −2.523 | 59.335 | 29.926 | 1.00 | 47.22  |

TABLE 3-continued

Structural Coordinate of MEK1/N35/NKFCdel (corresponding to amino acids 24-373 of SEQ ID NO: 2)-ATPγS Binary Complex.

| ATOM | 1341 | CB | ASP | A | 207 | −3.223 | 61.497 | 31.378 | 1.00 | 44.71 |
|---|---|---|---|---|---|---|---|---|---|---|
| ATOM | 1342 | CG | ASP | A | 207 | −3.491 | 62.204 | 32.698 | 1.00 | 54.89 |
| ATOM | 1343 | OD1 | ASP | A | 207 | −2.615 | 62.179 | 33.576 | 1.00 | 55.15 |
| ATOM | 1344 | OD2 | ASP | A | 207 | −4.573 | 62.810 | 32.843 | 1.00 | 63.16 |
| ATOM | 1345 | N | PHE | A | 208 | −0.315 | 59.728 | 29.869 | 1.00 | 51.05 |
| ATOM | 1346 | CA | PHE | A | 208 | −0.002 | 58.511 | 29.126 | 1.00 | 53.13 |
| ATOM | 1347 | C | PHE | A | 208 | 0.421 | 57.496 | 30.195 | 1.00 | 61.97 |
| ATOM | 1348 | O | PHE | A | 208 | 1.269 | 57.788 | 31.033 | 1.00 | 62.56 |
| ATOM | 1349 | CB | PHE | A | 208 | 1.134 | 58.742 | 28.118 | 1.00 | 54.93 |
| ATOM | 1350 | CG | PHE | A | 208 | 2.103 | 59.812 | 28.524 | 1.00 | 56.63 |
| ATOM | 1351 | CD1 | PHE | A | 208 | 3.288 | 59.489 | 29.171 | 1.00 | 59.79 |
| ATOM | 1352 | CD2 | PHE | A | 208 | 1.826 | 61.143 | 28.267 | 1.00 | 58.58 |
| ATOM | 1353 | CE1 | PHE | A | 208 | 4.176 | 60.477 | 29.552 | 1.00 | 60.55 |
| ATOM | 1354 | CE2 | PHE | A | 208 | 2.706 | 62.132 | 28.641 | 1.00 | 61.34 |
| ATOM | 1355 | CZ | PHE | A | 208 | 3.882 | 61.802 | 29.290 | 1.00 | 59.46 |
| ATOM | 1356 | N | GLY | A | 209 | −0.219 | 56.331 | 30.206 | 1.00 | 61.60 |
| ATOM | 1357 | CA | GLY | A | 209 | 0.043 | 55.314 | 31.228 | 1.00 | 62.70 |
| ATOM | 1358 | C | GLY | A | 209 | 1.453 | 54.720 | 31.212 | 1.00 | 69.58 |
| ATOM | 1359 | O | GLY | A | 209 | 1.717 | 53.752 | 30.501 | 1.00 | 70.24 |
| ATOM | 1360 | N | VAL | A | 210 | 2.340 | 55.271 | 32.040 | 1.00 | 66.94 |
| ATOM | 1361 | CA | VAL | A | 210 | 3.699 | 54.762 | 32.133 | 1.00 | 67.15 |
| ATOM | 1362 | C | VAL | A | 210 | 3.841 | 53.718 | 33.253 | 1.00 | 71.97 |
| ATOM | 1363 | O | VAL | A | 210 | 4.849 | 53.018 | 33.338 | 1.00 | 71.18 |
| ATOM | 1364 | CB | VAL | A | 210 | 4.720 | 55.899 | 32.344 | 1.00 | 71.15 |
| ATOM | 1365 | CG1 | VAL | A | 210 | 6.133 | 55.346 | 32.377 | 1.00 | 71.06 |
| ATOM | 1366 | CG2 | VAL | A | 210 | 4.583 | 56.943 | 31.257 | 1.00 | 70.92 |
| ATOM | 1367 | N | SER | A | 211 | 2.827 | 53.618 | 34.104 | 1.00 | 69.66 |
| ATOM | 1368 | CA | SER | A | 211 | 2.851 | 52.668 | 35.216 | 1.00 | 69.96 |
| ATOM | 1369 | C | SER | A | 211 | 1.743 | 51.603 | 35.112 | 1.00 | 74.88 |
| ATOM | 1370 | O | SER | A | 211 | 0.554 | 51.920 | 35.158 | 1.00 | 73.71 |
| ATOM | 1371 | CB | SER | A | 211 | 2.715 | 53.412 | 36.548 | 1.00 | 73.35 |
| ATOM | 1372 | OG | SER | A | 211 | 1.892 | 52.697 | 37.461 | 1.00 | 80.46 |
| ATOM | 1373 | N | GLY | A | 212 | 2.141 | 50.343 | 34.991 | 1.00 | 73.07 |
| ATOM | 1374 | CA | GLY | A | 212 | 1.184 | 49.239 | 34.892 | 1.00 | 73.68 |
| ATOM | 1375 | C | GLY | A | 212 | 0.421 | 49.041 | 36.205 | 1.00 | 79.25 |
| ATOM | 1376 | O | GLY | A | 212 | −0.783 | 48.778 | 36.199 | 1.00 | 78.59 |
| ATOM | 1377 | N | GLN | A | 213 | 1.107 | 49.178 | 37.322 | 1.00 | 77.27 |
| ATOM | 1378 | CA | GLN | A | 213 | 0.462 | 49.014 | 38.613 | 1.00 | 78.06 |
| ATOM | 1379 | C | GLN | A | 213 | −0.689 | 49.996 | 38.829 | 1.00 | 83.84 |
| ATOM | 1380 | O | GLN | A | 213 | −1.798 | 49.591 | 39.134 | 1.00 | 83.37 |
| ATOM | 1381 | CB | GLN | A | 213 | 1.489 | 49.155 | 39.740 | 1.00 | 79.49 |
| ATOM | 1382 | CG | GLN | A | 213 | 1.426 | 48.031 | 40.769 | 1.00 | 94.29 |
| ATOM | 1383 | CD | GLN | A | 213 | 0.075 | 47.263 | 40.817 | 1.00 | 111.26 |
| ATOM | 1384 | OE2 | GLN | A | 213 | −0.974 | 47.868 | 40.763 | 1.00 | 106.71 |
| ATOM | 1385 | NE2 | GLN | A | 213 | 0.168 | 45.964 | 41.000 | 1.00 | 102.06 |
| ATOM | 1386 | N | LEU | A | 214 | −0.402 | 51.290 | 38.696 | 1.00 | 81.71 |
| ATOM | 1387 | CA | LEU | A | 214 | −1.421 | 52.308 | 38.872 | 1.00 | 82.09 |
| ATOM | 1388 | C | LEU | A | 214 | −2.603 | 52.002 | 37.961 | 1.00 | 86.86 |
| ATOM | 1389 | O | LEU | A | 214 | −3.766 | 52.244 | 38.310 | 1.00 | 86.30 |
| ATOM | 1390 | CB | LEU | A | 214 | −0.852 | 53.695 | 38.563 | 1.00 | 82.11 |
| ATOM | 1391 | CG | LEU | A | 214 | −1.827 | 54.860 | 38.609 | 1.00 | 86.64 |
| ATOM | 1392 | CD1 | LEU | A | 214 | −2.500 | 54.936 | 39.974 | 1.00 | 86.71 |
| ATOM | 1393 | CD2 | LEU | A | 214 | −1.085 | 56.150 | 38.298 | 1.00 | 88.48 |
| ATOM | 1394 | N | ILE | A | 215 | −2.295 | 51.461 | 36.793 | 1.00 | 83.92 |
| ATOM | 1395 | CA | ILE | A | 215 | −3.321 | 51.097 | 35.838 | 1.00 | 83.90 |
| ATOM | 1396 | C | ILE | A | 215 | −4.213 | 50.005 | 36.447 | 1.00 | 85.96 |
| ATOM | 1397 | O | ILE | A | 215 | −5.433 | 50.166 | 36.550 | 1.00 | 85.39 |
| ATOM | 1398 | CB | ILE | A | 215 | −2.714 | 50.594 | 34.509 | 1.00 | 87.41 |
| ATOM | 1399 | CG1 | ILE | A | 215 | −2.456 | 51.772 | 33.559 | 1.00 | 87.96 |
| ATOM | 1400 | CG2 | ILE | A | 215 | −3.643 | 49.573 | 33.861 | 1.00 | 88.24 |
| ATOM | 1401 | CD1 | ILE | A | 215 | −1.685 | 51.402 | 32.301 | 1.00 | 94.18 |
| ATOM | 1402 | N | ASP | A | 216 | −3.585 | 48.925 | 36.898 | 1.00 | 81.24 |
| ATOM | 1403 | CA | ASP | A | 216 | −4.313 | 47.817 | 37.499 | 1.00 | 80.65 |
| ATOM | 1404 | C | ASP | A | 216 | −5.136 | 48.239 | 38.720 | 1.00 | 84.01 |
| ATOM | 1405 | O | ASP | A | 216 | −6.360 | 48.092 | 38.734 | 1.00 | 83.92 |
| ATOM | 1406 | CB | ASP | A | 216 | −3.361 | 46.678 | 37.875 | 1.00 | 82.34 |
| ATOM | 1407 | CG | ASP | A | 216 | −2.722 | 46.034 | 36.671 | 1.00 | 91.15 |
| ATOM | 1408 | OD1 | ASP | A | 216 | −3.262 | 46.187 | 35.555 | 1.00 | 91.28 |
| ATOM | 1409 | OD2 | ASP | A | 216 | −1.659 | 45.398 | 36.835 | 1.00 | 97.72 |
| ATOM | 1410 | N | SER | A | 217 | −4.457 | 48.733 | 39.751 | 1.00 | 79.51 |
| ATOM | 1411 | CA | SER | A | 217 | −5.117 | 49.155 | 40.980 | 1.00 | 78.83 |
| ATOM | 1412 | C | SER | A | 217 | −6.279 | 50.099 | 40.720 | 1.00 | 82.02 |
| ATOM | 1413 | O | SER | A | 217 | −7.233 | 50.155 | 41.503 | 1.00 | 81.70 |
| ATOM | 1414 | CB | SER | A | 217 | −4.114 | 49.805 | 41.925 | 1.00 | 82.55 |
| ATOM | 1415 | OG | SER | A | 217 | −2.790 | 49.609 | 41.466 | 1.00 | 92.39 |
| ATOM | 1416 | N | MET | A | 218 | −6.191 | 50.853 | 39.631 | 1.00 | 79.24 |
| ATOM | 1417 | CA | MET | A | 218 | −7.245 | 51.789 | 39.264 | 1.00 | 78.96 |

TABLE 3-continued

Structural Coordinate of MEK1/N35/NKFCdel (corresponding to amino acids 24-373 of SEQ ID NO: 2)-ATPγS Binary Complex.

| ATOM | 1418 | C   | MET | A | 218 | −8.324  | 51.091 | 38.445 | 1.00 | 83.42  |
|------|------|-----|-----|---|-----|---------|--------|--------|------|--------|
| ATOM | 1419 | O   | MET | A | 218 | −9.453  | 51.565 | 38.376 | 1.00 | 84.11  |
| ATOM | 1420 | CB  | MET | A | 218 | −6.669  | 52.962 | 38.474 | 1.00 | 81.30  |
| ATOM | 1421 | CG  | MET | A | 218 | −5.932  | 53.977 | 39.319 | 1.00 | 84.76  |
| ATOM | 1422 | SD  | MET | A | 218 | −5.612  | 55.521 | 38.424 | 1.00 | 89.07  |
| ATOM | 1423 | CE  | MET | A | 218 | −5.015  | 54.881 | 36.820 | 1.00 | 85.46  |
| ATOM | 1424 | N   | ALA | A | 219 | −7.958  | 49.971 | 37.822 | 1.00 | 82.00  |
| ATOM | 1425 | CA  | ALA | A | 219 | −8.890  | 49.195 | 37.013 | 1.00 | 83.34  |
| ATOM | 1426 | C   | ALA | A | 219 | −10.133 | 48.923 | 37.840 | 1.00 | 88.71  |
| ATOM | 1427 | O   | ALA | A | 219 | −11.240 | 48.796 | 37.308 | 1.00 | 89.06  |
| ATOM | 1428 | CB  | ALA | A | 219 | −8.246  | 47.881 | 36.578 | 1.00 | 84.05  |
| ATOM | 1429 | N   | ASN | A | 220 | −9.947  | 48.876 | 39.150 | 1.00 | 86.94  |
| ATOM | 1430 | CA  | ASN | A | 220 | −11.041 | 48.636 | 40.068 | 1.00 | 86.90  |
| ATOM | 1431 | C   | ASN | A | 220 | −12.134 | 49.686 | 39.892 | 1.00 | 89.45  |
| ATOM | 1432 | O   | ASN | A | 220 | −13.018 | 49.538 | 39.041 | 1.00 | 89.85  |
| ATOM | 1433 | CB  | ASN | A | 220 | −10.524 | 48.625 | 41.506 | 1.00 | 89.25  |
| ATOM | 1434 | CG  | ASN | A | 220 | −9.337  | 47.710 | 41.684 | 1.00 | 117.91 |
| ATOM | 1435 | OD1 | ASN | A | 220 | −9.322  | 46.595 | 41.175 | 1.00 | 113.07 |
| ATOM | 1436 | ND2 | ASN | A | 220 | −8.309  | 48.201 | 42.361 | 1.00 | 111.67 |
| ATOM | 1437 | N   | SER | A | 221 | −12.062 | 50.754 | 40.675 | 1.00 | 84.14  |
| ATOM | 1438 | CA  | SER | A | 221 | −13.069 | 51.810 | 40.609 | 1.00 | 83.64  |
| ATOM | 1439 | C   | SER | A | 221 | −12.594 | 53.059 | 39.862 | 1.00 | 86.58  |
| ATOM | 1440 | O   | SER | A | 221 | −13.070 | 54.172 | 40.132 | 1.00 | 86.17  |
| ATOM | 1441 | CB  | SER | A | 221 | −13.504 | 52.197 | 42.019 | 1.00 | 87.91  |
| ATOM | 1442 | OG  | SER | A | 221 | −12.527 | 53.014 | 42.643 | 1.00 | 98.28  |
| ATOM | 1443 | N   | PHE | A | 222 | −11.671 | 52.891 | 38.921 | 1.00 | 81.11  |
| ATOM | 1444 | CA  | PHE | A | 222 | −11.132 | 54.043 | 38.193 | 1.00 | 80.24  |
| ATOM | 1445 | C   | PHE | A | 222 | −11.152 | 53.900 | 36.665 | 1.00 | 80.45  |
| ATOM | 1446 | O   | PHE | A | 222 | −10.166 | 54.226 | 36.007 | 1.00 | 79.28  |
| ATOM | 1447 | CB  | PHE | A | 222 | −9.690  | 54.338 | 38.645 | 1.00 | 82.59  |
| ATOM | 1448 | CG  | PHE | A | 222 | −9.526  | 54.471 | 40.138 | 1.00 | 85.09  |
| ATOM | 1449 | CD1 | PHE | A | 222 | −9.868  | 53.424 | 40.985 | 1.00 | 87.79  |
| ATOM | 1450 | CD2 | PHE | A | 222 | −8.964  | 55.627 | 40.685 | 1.00 | 87.17  |
| ATOM | 1451 | CE1 | PHE | A | 222 | −9.704  | 53.549 | 42.356 | 1.00 | 88.39  |
| ATOM | 1452 | CE2 | PHE | A | 222 | −8.791  | 55.743 | 42.057 | 1.00 | 89.66  |
| ATOM | 1453 | CZ  | PHE | A | 222 | −9.197  | 54.721 | 42.890 | 1.00 | 87.51  |
| ATOM | 1454 | N   | VAL | A | 223 | −12.273 | 53.458 | 36.098 | 1.00 | 71.87  |
| ATOM | 1455 | CA  | VAL | A | 223 | −12.356 | 53.291 | 34.643 | 1.00 | 69.31  |
| ATOM | 1456 | C   | VAL | A | 223 | −12.752 | 54.583 | 33.896 | 1.00 | 67.93  |
| ATOM | 1457 | O   | VAL | A | 223 | −13.813 | 55.158 | 34.156 | 1.00 | 68.30  |
| ATOM | 1458 | CB  | VAL | A | 223 | −13.303 | 52.131 | 34.251 | 1.00 | 73.25  |
| ATOM | 1459 | CG1 | VAL | A | 223 | −14.626 | 52.229 | 35.013 | 1.00 | 72.69  |
| ATOM | 1460 | CG2 | VAL | A | 223 | −13.533 | 52.103 | 32.741 | 1.00 | 72.72  |
| ATOM | 1461 | N   | GLY | A | 224 | −11.883 | 55.034 | 32.986 | 1.00 | 59.03  |
| ATOM | 1462 | CA  | GLY | A | 224 | −12.129 | 56.247 | 32.191 | 1.00 | 56.95  |
| ATOM | 1463 | C   | GLY | A | 224 | −12.777 | 55.891 | 30.845 | 1.00 | 56.73  |
| ATOM | 1464 | O   | GLY | A | 224 | −12.635 | 54.769 | 30.366 | 1.00 | 56.41  |
| ATOM | 1465 | N   | THR | A | 224 | −13.482 | 56.858 | 30.245 | 1.00 | 49.18  |
| ATOM | 1466 | CA  | THR | A | 225 | −14.209 | 56.642 | 28.984 | 1.00 | 47.11  |
| ATOM | 1467 | C   | THR | A | 225 | −13.484 | 55.869 | 27.882 | 1.00 | 47.60  |
| ATOM | 1468 | O   | THR | A | 225 | −12.316 | 56.124 | 27.586 | 1.00 | 46.57  |
| ATOM | 1469 | CB  | THR | A | 225 | −14.781 | 57.964 | 28.396 | 1.00 | 55.36  |
| ATOM | 1470 | OG1 | THR | A | 225 | −15.895 | 57.661 | 27.549 | 1.00 | 58.96  |
| ATOM | 1471 | CG2 | THR | A | 225 | −13.729 | 58.681 | 27.567 | 1.00 | 52.02  |
| ATOM | 1472 | N   | ARG | A | 226 | −14.227 | 54.973 | 27.230 | 1.00 | 42.60  |
| ATOM | 1473 | CA  | ARG | A | 226 | −13.722 | 54.172 | 26.109 | 1.00 | 40.95  |
| ATOM | 1474 | C   | ARG | A | 226 | −14.221 | 54.754 | 24.779 | 1.00 | 41.00  |
| ATOM | 1475 | O   | ARG | A | 226 | −13.918 | 54.236 | 23.704 | 1.00 | 39.24  |
| ATOM | 1476 | CB  | ARG | A | 226 | −14.222 | 52.730 | 26.229 | 1.00 | 40.03  |
| ATOM | 1477 | CG  | ARG | A | 226 | −13.989 | 52.080 | 27.595 | 1.00 | 47.31  |
| ATOM | 1478 | CD  | ARG | A | 226 | −13.941 | 50.533 | 27.473 | 1.00 | 50.43  |
| ATOM | 1479 | NE  | ARG | A | 226 | −12.580 | 50.032 | 27.641 | 1.00 | 52.95  |
| ATOM | 1480 | CZ  | ARG | A | 226 | −12.023 | 49.090 | 26.892 | 1.00 | 58.66  |
| ATOM | 1481 | NH1 | ARG | A | 226 | −12.717 | 48.503 | 25.918 | 1.00 | 37.20  |
| ATOM | 1482 | NH2 | ARG | A | 226 | −10.771 | 48.723 | 27.127 | 1.00 | 43.54  |
| ATOM | 1483 | N   | SER | A | 227 | −14.990 | 55.825 | 24.871 | 1.00 | 37.40  |
| ATOM | 1484 | CA  | SER | A | 227 | −15.587 | 56.468 | 23.694 | 1.00 | 37.40  |
| ATOM | 1485 | C   | SER | A | 227 | −14.601 | 57.030 | 22.673 | 1.00 | 40.32  |
| ATOM | 1486 | O   | SER | A | 227 | −14.993 | 57.353 | 21.553 | 1.00 | 39.19  |
| ATOM | 1487 | CB  | SER | A | 227 | −16.607 | 57.532 | 24.110 | 1.00 | 41.19  |
| ATOM | 1488 | OG  | SER | A | 227 | −15.995 | 58.553 | 24.874 | 1.00 | 52.23  |
| ATOM | 1489 | N   | TYR | A | 228 | −13.317 | 57.092 | 23.031 | 1.00 | 36.99  |
| ATOM | 1490 | CA  | TYR | A | 228 | −12.287 | 57.583 | 22.091 | 1.00 | 36.61  |
| ATOM | 1491 | C   | TYR | A | 228 | −11.367 | 56.472 | 21.586 | 1.00 | 44.51  |
| ATOM | 1492 | O   | TYR | A | 228 | −10.416 | 56.726 | 20.821 | 1.00 | 44.33  |
| ATOM | 1493 | CB  | TYR | A | 228 | −11.473 | 58.706 | 22.733 | 1.00 | 36.39  |
| ATOM | 1494 | CG  | TYR | A | 228 | −12.290 | 59.966 | 22.959 | 1.00 | 35.70  |

TABLE 3-continued

Structural Coordinate of MEK1/N35/NKFCdel (corresponding to amino acids 24-373 of SEQ ID NO: 2)-ATPγS Binary Complex.

| ATOM | 1495 | CD1 | TYR | A | 228 | −12.542 | 60.846 | 21.921 | 1.00 | 37.18 |
|------|------|-----|-----|---|-----|---------|--------|--------|------|-------|
| ATOM | 1496 | CD2 | TYR | A | 228 | −12.904 | 60.199 | 24.178 | 1.00 | 35.42 |
| ATOM | 1497 | CE1 | TYR | A | 228 | −13.319 | 61.963 | 22.105 | 1.00 | 37.81 |
| ATOM | 1498 | CE2 | TYR | A | 228 | −13.667 | 61.326 | 24.376 | 1.00 | 35.97 |
| ATOM | 1499 | CZ  | TYR | A | 228 | −13.880 | 62.205 | 23.341 | 1.00 | 42.38 |
| ATOM | 1500 | OH  | TYR | A | 228 | −14.640 | 63.332 | 23.531 | 1.00 | 40.08 |
| ATOM | 1501 | N   | MET | A | 229 | −11.654 | 55.240 | 22.005 | 1.00 | 42.62 |
| ATOM | 1502 | CA  | MET | A | 229 | −10.864 | 54.081 | 21.606 | 1.00 | 42.98 |
| ATOM | 1503 | C   | MET | A | 229 | −11.124 | 53.691 | 20.158 | 1.00 | 44.97 |
| ATOM | 1504 | O   | MET | A | 229 | −12.253 | 53.751 | 19.677 | 1.00 | 44.57 |
| ATOM | 1505 | CB  | MET | A | 229 | −11.180 | 52.892 | 22.516 | 1.00 | 46.06 |
| ATOM | 1506 | CG  | MET | A | 229 | −10.763 | 53.102 | 23.960 | 1.00 | 50.65 |
| ATOM | 1507 | SD  | MET | A | 229 | −10.269 | 51.572 | 24.757 | 1.00 | 55.63 |
| ATOM | 1508 | CE  | MET | A | 229 | −9.624  | 52.201 | 26.290 | 1.00 | 52.52 |
| ATOM | 1509 | N   | SER | A | 230 | −10.085 | 53.253 | 19.476 | 1.00 | 40.58 |
| ATOM | 1510 | CA  | SER | A | 230 | −10.234 | 52.834 | 18.095 | 1.00 | 40.72 |
| ATOM | 1511 | C   | SER | A | 230 | −11.036 | 51.550 | 18.048 | 1.00 | 45.77 |
| ATOM | 1512 | O   | SER | A | 230 | −11.236 | 50.898 | 19.067 | 1.00 | 45.93 |
| ATOM | 1513 | CB  | SER | A | 230 | −8.865  | 52.619 | 17.455 | 1.00 | 43.20 |
| ATOM | 1514 | OG  | SER | A | 230 | −8.109  | 51.684 | 18.198 | 1.00 | 47.73 |
| ATOM | 1515 | N   | PRO | A | 231 | −11.483 | 51.178 | 16.859 | 1.00 | 43.15 |
| ATOM | 1516 | CA  | PRO | A | 231 | −12.258 | 49.943 | 16.682 | 1.00 | 42.57 |
| ATOM | 1517 | C   | PRO | A | 231 | −11.425 | 48.701 | 17.029 | 1.00 | 46.28 |
| ATOM | 1518 | O   | PRO | A | 231 | −11.893 | 47.811 | 17.725 | 1.00 | 44.99 |
| ATOM | 1519 | CB  | PRO | A | 231 | −12.593 | 49.949 | 15.182 | 1.00 | 43.65 |
| ATOM | 1520 | CG  | PRO | A | 231 | −12.464 | 51.367 | 14.766 | 1.00 | 48.11 |
| ATOM | 1521 | CD  | PRO | A | 231 | −11.366 | 51.939 | 15.606 | 1.00 | 43.61 |
| ATOM | 1522 | N   | GLU | A | 232 | −10.185 | 48.657 | 16.549 | 1.00 | 43.93 |
| ATOM | 1523 | CA  | GLU | A | 232 | −9.323  | 47.504 | 16.801 | 1.00 | 44.64 |
| ATOM | 1524 | C   | GLU | A | 232 | −9.033  | 47.278 | 18.290 | 1.00 | 52.24 |
| ATOM | 1525 | O   | GLU | A | 232 | −8.895  | 46.138 | 18.732 | 1.00 | 52.92 |
| ATOM | 1526 | CB  | GLU | A | 232 | −8.030  | 47.576 | 15.980 | 1.00 | 45.62 |
| ATOM | 1527 | CG  | GLU | A | 232 | −6.968  | 48.493 | 16.558 | 1.00 | 54.23 |
| ATOM | 1528 | CD  | GLU | A | 232 | −7.022  | 49.891 | 15.976 | 1.00 | 63.62 |
| ATOM | 1529 | OE1 | GLU | A | 232 | −8.006  | 50.216 | 15.274 | 1.00 | 43.57 |
| ATOM | 1530 | OE2 | GLU | A | 232 | −6.079  | 50.564 | 16.211 | 1.00 | 59.06 |
| ATOM | 1531 | N   | ARG | A | 233 | −8.977  | 48.363 | 19.061 | 1.00 | 50.02 |
| ATOM | 1532 | CA  | ARG | A | 233 | −8.750  | 48.267 | 20.503 | 1.00 | 50.18 |
| ATOM | 1533 | C   | ARG | A | 233 | −10.035 | 47.647 | 21.221 | 1.00 | 54.57 |
| ATOM | 1534 | O   | ARG | A | 233 | −9.994  | 47.195 | 22.267 | 1.00 | 53.32 |
| ATOM | 1535 | CB  | ARG | A | 233 | −8.257  | 49.600 | 21.063 | 1.00 | 49.94 |
| ATOM | 1536 | CG  | ARG | A | 233 | −6.744  | 49.730 | 21.084 | 1.00 | 59.51 |
| ATOM | 1537 | CD  | ARG | A | 233 | −6.292  | 50.851 | 22.011 | 1.00 | 65.81 |
| ATOM | 1538 | NE  | ARG | A | 233 | −6.386  | 50.471 | 23.421 | 1.00 | 70.44 |
| ATOM | 1539 | CZ  | ARG | A | 233 | −6.209  | 51.316 | 24.434 | 1.00 | 81.89 |
| ATOM | 1540 | NH1 | ARG | A | 233 | −5.925  | 52.590 | 24.191 | 1.00 | 66.53 |
| ATOM | 1541 | NH2 | ARG | A | 233 | −6.308  | 50.886 | 25.689 | 1.00 | 67.48 |
| ATOM | 1542 | N   | LEU | A | 234 | −11.171 | 48.237 | 20.657 | 1.00 | 52.34 |
| ATOM | 1543 | CA  | LEU | A | 234 | −12.465 | 47.885 | 21.230 | 1.00 | 53.00 |
| ATOM | 1544 | C   | LEU | A | 234 | −12.836 | 46.436 | 20.863 | 1.00 | 59.29 |
| ATOM | 1545 | O   | LEU | A | 234 | −13.784 | 45.866 | 21.412 | 1.00 | 58.86 |
| ATOM | 1546 | CB  | LEU | A | 234 | −13.546 | 48.842 | 20.712 | 1.00 | 52.81 |
| ATOM | 1547 | CG  | LEU | A | 234 | −13.608 | 50.241 | 21.330 | 1.00 | 57.07 |
| ATOM | 1548 | CD1 | LEU | A | 234 | −14.767 | 51.036 | 20.735 | 1.00 | 57.03 |
| ATOM | 1549 | CD2 | LEU | A | 234 | −13.727 | 50.167 | 22.857 | 1.00 | 58.36 |
| ATOM | 1550 | N   | GLN | A | 235 | −12.084 | 45.857 | 19.924 | 1.00 | 57.12 |
| ATOM | 1551 | CA  | GLN | A | 235 | −12.339 | 44.504 | 19.444 | 1.00 | 57.49 |
| ATOM | 1552 | C   | GLN | A | 235 | −11.287 | 43.515 | 19.937 | 1.00 | 64.01 |
| ATOM | 1553 | O   | GLN | A | 235 | −11.041 | 42.493 | 19.299 | 1.00 | 63.07 |
| ATOM | 1554 | CB  | GLN | A | 235 | −12.372 | 44.488 | 17.916 | 1.00 | 58.66 |
| ATOM | 1555 | CG  | GLN | A | 235 | −13.761 | 44.520 | 17.306 | 1.00 | 72.25 |
| ATOM | 1556 | CD  | GLN | A | 235 | −13.766 | 44.060 | 15.853 | 1.00 | 95.60 |
| ATOM | 1557 | OE1 | GLN | A | 235 | −12.726 | 43.679 | 15.304 | 1.00 | 90.27 |
| ATOM | 1558 | NE2 | GLN | A | 235 | −14.936 | 44.099 | 15.222 | 1.00 | 91.08 |
| ATOM | 1559 | N   | GLY | A | 236 | −10.661 | 43.835 | 21.065 | 1.00 | 63.03 |
| ATOM | 1560 | CA  | GLY | A | 236 | −9.645  | 42.976 | 21.652 | 1.00 | 64.03 |
| ATOM | 1561 | C   | GLY | A | 236 | −8.364  | 42.928 | 20.821 | 1.00 | 72.04 |
| ATOM | 1562 | O   | GLY | A | 236 | −7.274  | 42.708 | 21.356 | 1.00 | 72.29 |
| ATOM | 1563 | N   | THR | A | 237 | −8.498  | 43.116 | 19.512 | 1.00 | 71.23 |
| ATOM | 1564 | CA  | THR | A | 237 | −7.341  | 43.089 | 18.609 | 1.00 | 72.15 |
| ATOM | 1565 | C   | THR | A | 237 | −6.237  | 44.019 | 19.107 | 1.00 | 79.00 |
| ATOM | 1566 | O   | THR | A | 237 | −6.447  | 45.231 | 19.223 | 1.00 | 79.19 |
| ATOM | 1567 | CB  | THR | A | 237 | −7.737  | 43.509 | 17.191 | 1.00 | 78.52 |
| ATOM | 1568 | OG1 | THR | A | 237 | −8.179  | 42.361 | 16.459 | 1.00 | 78.52 |
| ATOM | 1569 | CG2 | THR | A | 237 | −6.558  | 44.143 | 16.478 | 1.00 | 76.79 |
| ATOM | 1570 | N   | HIS | A | 238 | −5.063  | 43.455 | 19.398 | 1.00 | 76.83 |
| ATOM | 1571 | CA  | HIS | A | 238 | −3.950  | 44.256 | 19.907 | 1.00 | 77.21 |

TABLE 3-continued

Structural Coordinate of MEK1/N35/NKFCdel (corresponding to amino acids 24-373 of SEQ ID NO: 2)-ATPγS Binary Complex.

| ATOM | 1572 | C | HIS | A | 238 | −3.682 | 45.490 | 19.064 | 1.00 | 79.37 |
|---|---|---|---|---|---|---|---|---|---|---|
| ATOM | 1573 | O | HIS | A | 238 | −3.833 | 45.474 | 17.839 | 1.00 | 79.17 |
| ATOM | 1574 | CB | HIS | A | 238 | −2.668 | 43.419 | 20.134 | 1.00 | 78.73 |
| ATOM | 1575 | CG | HIS | A | 238 | −2.000 | 43.693 | 21.451 | 1.00 | 82.79 |
| ATOM | 1576 | ND1 | HIS | A | 238 | −2.712 | 43.918 | 22.612 | 1.00 | 84.91 |
| ATOM | 1577 | CD2 | HIS | A | 238 | −0.692 | 43.815 | 21.783 | 1.00 | 85.02 |
| ATOM | 1578 | CE1 | HIS | A | 238 | −1.871 | 44.150 | 23.606 | 1.00 | 84.54 |
| ATOM | 1579 | NE2 | HIS | A | 238 | −0.639 | 44.094 | 23.129 | 1.00 | 84.88 |
| ATOM | 1580 | N | TYR | A | 239 | −3.348 | 46.580 | 19.742 | 1.00 | 74.16 |
| ATOM | 1581 | CA | TYR | A | 239 | −3.161 | 47.868 | 19.098 | 1.00 | 72.66 |
| ATOM | 1582 | C | TYR | A | 239 | −1.723 | 48.361 | 19.113 | 1.00 | 71.95 |
| ATOM | 1583 | O | TYR | A | 239 | −0.858 | 47.808 | 19.798 | 1.00 | 71.05 |
| ATOM | 1584 | CB | TYR | A | 239 | −4.046 | 48.906 | 19.787 | 1.00 | 74.18 |
| ATOM | 1585 | CG | TYR | A | 239 | −3.789 | 49.012 | 21.279 | 1.00 | 76.43 |
| ATOM | 1586 | CD1 | TYR | A | 239 | −3.962 | 47.909 | 22.118 | 1.00 | 78.45 |
| ATOM | 1587 | CD2 | TYR | A | 239 | −3.343 | 50.201 | 21.844 | 1.00 | 77.20 |
| ATOM | 1588 | CE1 | TYR | A | 239 | −3.713 | 47.997 | 23.479 | 1.00 | 79.20 |
| ATOM | 1589 | CE2 | TYR | A | 239 | −3.097 | 50.299 | 23.204 | 1.00 | 78.14 |
| ATOM | 1590 | CZ | TYR | A | 239 | −3.283 | 49.194 | 24.017 | 1.00 | 84.83 |
| ATOM | 1591 | OH | TYR | A | 239 | −3.038 | 49.294 | 25.369 | 1.00 | 84.64 |
| ATOM | 1592 | N | SER | A | 240 | −1.494 | 49.442 | 18.381 | 1.00 | 65.44 |
| ATOM | 1593 | CA | SER | A | 240 | −0.195 | 50.084 | 18.322 | 1.00 | 63.57 |
| ATOM | 1594 | C | SER | A | 240 | −0.407 | 51.583 | 18.442 | 1.00 | 62.93 |
| ATOM | 1595 | O | SER | A | 240 | −1.426 | 52.034 | 18.974 | 1.00 | 61.99 |
| ATOM | 1596 | CB | SER | A | 240 | 0.490 | 49.767 | 16.997 | 1.00 | 67.56 |
| ATOM | 1597 | OG | SER | A | 240 | −0.428 | 49.860 | 15.921 | 1.00 | 78.32 |
| ATOM | 1598 | N | VAL | A | 241 | 0.544 | 52.355 | 17.925 | 1.00 | 56.50 |
| ATOM | 1599 | CA | VAL | A | 241 | 0.438 | 53.810 | 17.945 | 1.00 | 54.43 |
| ATOM | 1600 | C | VAL | A | 241 | −0.729 | 54.202 | 17.064 | 1.00 | 53.69 |
| ATOM | 1601 | O | VAL | A | 241 | −1.331 | 55.263 | 17.235 | 1.00 | 52.19 |
| ATOM | 1602 | CB | VAL | A | 241 | 1.723 | 54.480 | 17.412 | 1.00 | 58.22 |
| ATOM | 1603 | CG1 | VAL | A | 241 | 2.153 | 53.840 | 16.100 | 1.00 | 58.15 |
| ATOM | 1604 | CG2 | VAL | A | 241 | 1.521 | 55.982 | 17.244 | 1.00 | 57.96 |
| ATOM | 1605 | N | GLN | A | 242 | −1.048 | 53.324 | 16.124 | 1.00 | 48.07 |
| ATOM | 1606 | CA | GLN | A | 242 | −2.150 | 53.543 | 15.207 | 1.00 | 47.01 |
| ATOM | 1607 | C | GLN | A | 242 | −3.430 | 53.835 | 15.969 | 1.00 | 49.12 |
| ATOM | 1608 | O | GLN | A | 242 | −4.253 | 54.628 | 15.529 | 1.00 | 48.70 |
| ATOM | 1609 | CB | GLN | A | 242 | −2.345 | 52.317 | 14.309 | 1.00 | 48.00 |
| ATOM | 1610 | CG | GLN | A | 242 | −1.253 | 52.144 | 13.254 | 1.00 | 48.14 |
| ATOM | 1611 | CD | GLN | A | 242 | −1.112 | 53.359 | 12.363 | 1.00 | 57.51 |
| ATOM | 1612 | OE1 | GLN | A | 242 | −0.223 | 54.188 | 12.557 | 1.00 | 51.74 |
| ATOM | 1613 | NE2 | GLN | A | 242 | −1.998 | 53.476 | 11.384 | 1.00 | 49.04 |
| ATOM | 1614 | N | SER | A | 243 | −3.594 | 53.182 | 17.115 | 1.00 | 44.55 |
| ATOM | 1615 | CA | SER | A | 243 | −4.789 | 53.364 | 17.931 | 1.00 | 43.48 |
| ATOM | 1616 | C | SER | A | 243 | −4.918 | 54.794 | 18.455 | 1.00 | 44.15 |
| ATOM | 1617 | O | SER | A | 243 | −6.028 | 55.311 | 18.615 | 1.00 | 43.93 |
| ATOM | 1618 | CB | SER | A | 243 | −4.800 | 52.378 | 19.082 | 1.00 | 47.31 |
| ATOM | 1619 | OG | SER | A | 243 | −5.982 | 51.610 | 19.059 | 1.00 | 58.55 |
| ATOM | 1620 | N | ASP | A | 244 | −3.778 | 55.422 | 18.706 | 1.00 | 38.29 |
| ATOM | 1621 | CA | ASP | A | 244 | −3.718 | 56.791 | 19.198 | 1.00 | 37.23 |
| ATOM | 1622 | C | ASP | A | 244 | −4.109 | 57.789 | 18.088 | 1.00 | 40.90 |
| ATOM | 1623 | O | ASP | A | 244 | −4.744 | 58.814 | 18.352 | 1.00 | 40.12 |
| ATOM | 1624 | CB | ASP | A | 244 | −2.301 | 57.103 | 19.704 | 1.00 | 38.06 |
| ATOM | 1625 | CG | ASP | A | 244 | −2.026 | 56.510 | 21.068 | 1.00 | 41.20 |
| ATOM | 1626 | OD1 | ASP | A | 244 | −2.995 | 56.234 | 21.816 | 1.00 | 39.57 |
| ATOM | 1627 | OD2 | ASP | A | 244 | −0.836 | 56.337 | 21.402 | 1.00 | 46.32 |
| ATOM | 1628 | N | ILE | A | 245 | −3.741 | 57.462 | 16.851 | 1.00 | 37.01 |
| ATOM | 1629 | CA | ILE | A | 245 | −4.066 | 58.297 | 15.694 | 1.00 | 36.60 |
| ATOM | 1630 | C | ILE | A | 245 | −5.583 | 58.371 | 15.480 | 1.00 | 39.44 |
| ATOM | 1631 | O | ILE | A | 245 | −6.122 | 59.420 | 15.102 | 1.00 | 39.33 |
| ATOM | 1632 | CB | ILE | A | 245 | −3.373 | 57.774 | 14.422 | 1.00 | 39.90 |
| ATOM | 1633 | CG1 | ILE | A | 245 | −1.844 | 58.013 | 14.511 | 1.00 | 40.18 |
| ATOM | 1634 | CG2 | ILE | A | 245 | −3.990 | 58.397 | 13.165 | 1.00 | 39.98 |
| ATOM | 1635 | CD1 | ILE | A | 245 | −1.064 | 57.462 | 13.336 | 1.00 | 45.69 |
| ATOM | 1636 | N | TRP | A | 246 | −6.276 | 57.276 | 15.770 | 1.00 | 34.70 |
| ATOM | 1637 | CA | TRP | A | 246 | −7.723 | 57.250 | 15.642 | 1.00 | 34.03 |
| ATOM | 1638 | C | TRP | A | 246 | −8.317 | 58.186 | 16.693 | 1.00 | 39.14 |
| ATOM | 1639 | O | TRP | A | 246 | −9.202 | 58.994 | 16.403 | 1.00 | 39.66 |
| ATOM | 1640 | CB | TRP | A | 246 | −8.267 | 55.823 | 15.838 | 1.00 | 32.42 |
| ATOM | 1641 | CG | TRP | A | 246 | −9.727 | 55.804 | 16.235 | 1.00 | 33.11 |
| ATOM | 1642 | CD1 | TRP | A | 246 | −10.250 | 56.054 | 17.476 | 1.00 | 35.87 |
| ATOM | 1643 | CD2 | TRP | A | 246 | −10.847 | 55.592 | 15.366 | 1.00 | 32.86 |
| ATOM | 1644 | NE1 | TRP | A | 246 | −11.628 | 56.023 | 17.426 | 1.00 | 35.26 |
| ATOM | 1645 | CE2 | TRP | A | 246 | −12.015 | 55.728 | 16.144 | 1.00 | 36.61 |
| ATOM | 1646 | CE3 | TRP | A | 246 | −10.973 | 55.255 | 14.016 | 1.00 | 33.92 |
| ATOM | 1647 | CZ2 | TRP | A | 246 | −13.285 | 55.573 | 15.610 | 1.00 | 36.05 |
| ATOM | 1648 | CZ3 | TRP | A | 246 | −12.242 | 55.128 | 13.482 | 1.00 | 35.26 |

TABLE 3-continued

Structural Coordinate of MEK1/N35/NKFCdel (corresponding to amino acids 24-373 of SEQ ID NO: 2)-ATPγS Binary Complex.

| ATOM | 1649 | CH2 | TRP | A | 246 | −13.379 | 55.284 | 14.279 | 1.00 | 35.99 |
|---|---|---|---|---|---|---|---|---|---|---|
| ATOM | 1650 | N | SER | A | 247 | −7.839 | 58.052 | 17.926 | 1.00 | 35.34 |
| ATOM | 1651 | CA | SER | A | 247 | −8.327 | 58.886 | 19.025 | 1.00 | 34.77 |
| ATOM | 1652 | C | SER | A | 247 | −8.120 | 60.372 | 18.690 | 1.00 | 39.27 |
| ATOM | 1653 | O | SER | A | 247 | −8.983 | 61.217 | 18.987 | 1.00 | 39.62 |
| ATOM | 1654 | CB | SER | A | 247 | −7.605 | 58.519 | 20.332 | 1.00 | 36.72 |
| ATOM | 1655 | OG | SER | A | 247 | −7.735 | 57.129 | 20.614 | 1.00 | 40.72 |
| ATOM | 1656 | N | MET | A | 248 | −6.986 | 60.686 | 18.054 | 1.00 | 34.47 |
| ATOM | 1657 | CA | MET | A | 248 | −6.700 | 62.056 | 17.676 | 1.00 | 33.71 |
| ATOM | 1658 | C | MET | A | 248 | −7.695 | 62.533 | 16.647 | 1.00 | 37.49 |
| ATOM | 1659 | O | MET | A | 248 | −8.298 | 63.601 | 16.800 | 1.00 | 36.81 |
| ATOM | 1660 | CB | MET | A | 248 | −5.292 | 62.192 | 17.115 | 1.00 | 35.68 |
| ATOM | 1661 | CG | MET | A | 248 | −5.021 | 63.580 | 16.556 | 1.00 | 38.44 |
| ATOM | 1662 | SD | MET | A | 248 | −3.407 | 63.746 | 15.872 | 1.00 | 41.69 |
| ATOM | 1663 | CE | MET | A | 248 | −2.642 | 62.909 | 14.284 | 1.00 | 38.33 |
| ATOM | 1664 | N | GLY | A | 249 | −7.856 | 61.742 | 15.585 | 1.00 | 33.96 |
| ATOM | 1665 | CA | GLY | A | 249 | −8.793 | 62.071 | 14.506 | 1.00 | 33.35 |
| ATOM | 1666 | C | GLY | A | 249 | −10.205 | 62.275 | 15.044 | 1.00 | 37.26 |
| ATOM | 1667 | O | GLY | A | 249 | −10.899 | 63.230 | 14.665 | 1.00 | 37.23 |
| ATOM | 1668 | N | LEU | A | 250 | −10.625 | 61.387 | 15.938 | 1.00 | 33.37 |
| ATOM | 1669 | CA | LEU | A | 250 | −11.961 | 61.474 | 16.530 | 1.00 | 33.22 |
| ATOM | 1670 | C | LEU | A | 250 | −12.112 | 62.754 | 17.379 | 1.00 | 35.88 |
| ATOM | 1671 | O | LEU | A | 250 | −13.137 | 63.432 | 17.320 | 1.00 | 34.13 |
| ATOM | 1672 | CB | LEU | A | 250 | −12.278 | 60.215 | 17.368 | 1.00 | 33.29 |
| ATOM | 1673 | CG | LEU | A | 250 | −13.663 | 60.232 | 18.033 | 1.00 | 38.11 |
| ATOM | 1674 | CD1 | LEU | A | 250 | −14.759 | 60.499 | 17.011 | 1.00 | 38.43 |
| ATOM | 1675 | CD2 | LEU | A | 250 | −13.948 | 58.975 | 18.824 | 1.00 | 39.75 |
| ATOM | 1676 | N | SER | A | 251 | −11.077 | 63.066 | 18.161 | 1.00 | 32.69 |
| ATOM | 1677 | CA | SER | A | 251 | −11.054 | 64.272 | 19.011 | 1.00 | 32.03 |
| ATOM | 1678 | C | SER | A | 251 | −11.067 | 65.549 | 18.173 | 1.00 | 36.57 |
| ATOM | 1679 | O | SER | A | 251 | −11.695 | 66.544 | 18.547 | 1.00 | 36.60 |
| ATOM | 1680 | CB | SER | A | 251 | −9.802 | 64.283 | 19.890 | 1.00 | 33.33 |
| ATOM | 1681 | OG | SER | A | 251 | −9.766 | 63.173 | 20.746 | 1.00 | 38.09 |
| ATOM | 1682 | N | LEU | A | 252 | −10.328 | 65.532 | 17.068 | 1.00 | 33.15 |
| ATOM | 1683 | CA | LEU | A | 252 | −10.246 | 66.691 | 16.188 | 1.00 | 32.96 |
| ATOM | 1684 | C | LEU | A | 252 | −11.611 | 66.997 | 15.585 | 1.00 | 36.34 |
| ATOM | 1685 | O | LEU | A | 252 | −11.984 | 68.153 | 15.425 | 1.00 | 35.46 |
| ATOM | 1686 | CB | LEU | A | 252 | −9.238 | 66.438 | 15.058 | 1.00 | 32.80 |
| ATOM | 1687 | CG | LEU | A | 252 | −7.767 | 66.612 | 15.396 | 1.00 | 36.90 |
| ATOM | 1688 | CD1 | LEU | A | 252 | −6.901 | 66.216 | 14.208 | 1.00 | 35.89 |
| ATOM | 1689 | CD2 | LEU | A | 252 | −7.482 | 68.062 | 15.839 | 1.00 | 39.05 |
| ATOM | 1690 | N | VAL | A | 253 | −12.336 | 65.952 | 15.209 | 1.00 | 33.26 |
| ATOM | 1691 | CA | VAL | A | 253 | −13.660 | 66.129 | 14.609 | 1.00 | 32.75 |
| ATOM | 1692 | C | VAL | A | 253 | −14.622 | 66.685 | 15.635 | 1.00 | 36.73 |
| ATOM | 1693 | O | VAL | A | 253 | −15.436 | 67.565 | 15.341 | 1.00 | 36.06 |
| ATOM | 1694 | CB | VAL | A | 253 | −14.223 | 64.808 | 14.088 | 1.00 | 36.39 |
| ATOM | 1695 | CG1 | VAL | A | 253 | −15.711 | 64.956 | 13.747 | 1.00 | 36.02 |
| ATOM | 1696 | CG2 | VAL | A | 253 | −13.406 | 64.301 | 12.878 | 1.00 | 35.99 |
| ATOM | 1697 | N | GLU | A | 254 | −14.543 | 66.169 | 16.851 | 1.00 | 34.39 |
| ATOM | 1698 | CA | GLU | A | 254 | −15.432 | 66.647 | 17.900 | 1.00 | 34.59 |
| ATOM | 1699 | C | GLU | A | 254 | −15.228 | 68.135 | 18.103 | 1.00 | 39.54 |
| ATOM | 1700 | O | GLU | A | 254 | −16.154 | 68.890 | 18.230 | 1.00 | 40.30 |
| ATOM | 1701 | CB | GLU | A | 254 | −15.175 | 65.923 | 19.209 | 1.00 | 35.77 |
| ATOM | 1702 | CG | GLU | A | 254 | −15.770 | 66.652 | 20.414 | 1.00 | 42.66 |
| ATOM | 1703 | CD | GLU | A | 254 | −15.763 | 65.812 | 21.672 | 1.00 | 46.98 |
| ATOM | 1704 | OE1 | GLU | A | 254 | −15.032 | 64.808 | 21.729 | 1.00 | 47.97 |
| ATOM | 1705 | OE2 | GLU | A | 254 | −16.480 | 66.162 | 22.609 | 1.00 | 38.11 |
| ATOM | 1706 | N | MET | A | 255 | −13.961 | 68.552 | 18.142 | 1.00 | 34.84 |
| ATOM | 1707 | CA | MET | A | 255 | −13.610 | 65.946 | 18.369 | 1.00 | 34.34 |
| ATOM | 1708 | C | MET | A | 255 | −13.990 | 70.867 | 17.217 | 1.00 | 38.21 |
| ATOM | 1709 | O | MET | A | 255 | −14.365 | 72.019 | 17.439 | 1.00 | 37.92 |
| ATOM | 1710 | CB | MET | A | 255 | −12.123 | 70.081 | 18.724 | 1.00 | 36.58 |
| ATOM | 1711 | CG | MET | A | 255 | −11.762 | 69.459 | 20.079 | 1.00 | 39.99 |
| ATOM | 1712 | SD | MET | A | 255 | −10.009 | 69.532 | 20.479 | 1.00 | 44.63 |
| ATOM | 1713 | CE | MET | A | 255 | −9.300 | 68.690 | 19.115 | 1.00 | 40.89 |
| ATOM | 1714 | N | ALA | A | 256 | −13.920 | 70.355 | 15.993 | 1.00 | 34.69 |
| ATOM | 1715 | CA | ALA | A | 256 | −14.271 | 71.147 | 14.809 | 1.00 | 35.09 |
| ATOM | 1716 | C | ALA | A | 256 | −15.772 | 71.409 | 14.700 | 1.00 | 39.54 |
| ATOM | 1717 | O | ALA | A | 256 | −16.193 | 72.473 | 14.264 | 1.00 | 39.51 |
| ATOM | 1718 | CB | ALA | A | 256 | −13.769 | 70.464 | 13.536 | 1.00 | 35.81 |
| ATOM | 1719 | N | VAL | A | 257 | −16.571 | 70.415 | 15.054 | 1.00 | 36.59 |
| ATOM | 1720 | CA | VAL | A | 257 | −18.012 | 70.541 | 14.953 | 1.00 | 36.86 |
| ATOM | 1721 | C | VAL | A | 257 | −18.693 | 70.955 | 16.264 | 1.00 | 41.56 |
| ATOM | 1722 | O | VAL | A | 257 | −19.832 | 71.407 | 16.260 | 1.00 | 41.07 |
| ATOM | 1723 | CB | VAL | A | 257 | −18.658 | 69.267 | 14.340 | 1.00 | 40.04 |
| ATOM | 1724 | CG1 | VAL | A | 257 | −17.971 | 68.930 | 13.022 | 1.00 | 39.35 |
| ATOM | 1725 | CG2 | VAL | A | 257 | −18.564 | 68.105 | 15.301 | 1.00 | 39.65 |

TABLE 3-continued

Structural Coordinate of MEK1/N35/NKFCdel (corresponding to amino acids 24-373 of SEQ ID NO: 2)-ATPγS Binary Complex.

| ATOM | 1726 | N   | GLY | A | 258 | −17.971 | 70.839 | 17.373 | 1.00 | 40.71  |
|------|------|-----|-----|---|-----|---------|--------|--------|------|--------|
| ATOM | 1727 | CA  | GLY | A | 258 | −18.487 | 71.277 | 18.675 | 1.00 | 41.19  |
| ATOM | 1728 | C   | GLY | A | 258 | −19.295 | 70.235 | 19.459 | 1.00 | 45.62  |
| ATOM | 1729 | O   | GLY | A | 258 | −19.987 | 70.573 | 20.419 | 1.00 | 46.28  |
| ATOM | 1730 | N   | ARG | A | 259 | −19.171 | 68.975 | 19.088 | 1.00 | 41.79  |
| ATOM | 1731 | CA  | ARG | A | 259 | −19.870 | 67.916 | 19.815 | 1.00 | 41.55  |
| ATOM | 1732 | C   | ARG | A | 259 | −19.272 | 66.526 | 19.525 | 1.00 | 42.91  |
| ATOM | 1733 | O   | ARG | A | 259 | −18.682 | 66.306 | 18.463 | 1.00 | 40.41  |
| ATOM | 1734 | CB  | ARG | A | 259 | −21.373 | 67.957 | 19.504 | 1.00 | 42.53  |
| ATOM | 1735 | CG  | ARG | A | 259 | −22.009 | 66.608 | 19.291 | 1.00 | 56.82  |
| ATOM | 1736 | CD  | ARG | A | 259 | −23.022 | 66.648 | 18.163 | 1.00 | 67.52  |
| ATOM | 1737 | NE  | ARG | A | 259 | −22.790 | 65.579 | 17.200 | 1.00 | 76.54  |
| ATOM | 1738 | CZ  | ARG | A | 259 | −23.582 | 64.524 | 17.041 | 1.00 | 88.17  |
| ATOM | 1739 | NH1 | ARG | A | 259 | −24.680 | 64.397 | 17.765 | 1.00 | 71.02  |
| ATOM | 1740 | NH2 | ARG | A | 259 | −23.273 | 63.599 | 16.151 | 1.00 | 79.09  |
| ATOM | 1741 | N   | TYR | A | 260 | −19.375 | 65.615 | 20.494 | 1.00 | 39.24  |
| ATOM | 1742 | CA  | TYR | A | 260 | −18.871 | 64.257 | 20.294 | 1.00 | 39.40  |
| ATOM | 1743 | C   | TYR | A | 260 | −19.555 | 63.725 | 19.036 | 1.00 | 45.95  |
| ATOM | 1744 | O   | TYR | A | 260 | −20.778 | 63.598 | 18.998 | 1.00 | 46.24  |
| ATOM | 1745 | CB  | TYR | A | 260 | −19.185 | 63.364 | 21.510 | 1.00 | 39.59  |
| ATOM | 1746 | CG  | TYR | A | 260 | −18.707 | 61.934 | 21.347 | 1.00 | 39.52  |
| ATOM | 1747 | CD1 | TYR | A | 260 | −17.363 | 61.607 | 21.508 | 1.00 | 41.05  |
| ATOM | 1748 | CD2 | TYR | A | 260 | −19.584 | 60.926 | 20.964 | 1.00 | 39.59  |
| ATOM | 1749 | CE1 | TYR | A | 260 | −16.916 | 60.308 | 21.324 | 1.00 | 40.63  |
| ATOM | 1750 | CE2 | TYR | A | 260 | −19.154 | 59.627 | 20.783 | 1.00 | 40.11  |
| ATOM | 1751 | CZ  | TYR | A | 260 | −17.818 | 59.321 | 20.997 | 1.00 | 45.42  |
| ATOM | 1752 | OH  | TYR | A | 260 | −17.388 | 58.027 | 20.820 | 1.00 | 43.61  |
| ATOM | 1753 | N   | PRO | A | 261 | −18.757 | 63.485 | 17.996 | 1.00 | 44.51  |
| ATOM | 1754 | CA  | PRO | A | 261 | −19.247 | 63.116 | 16.656 | 1.00 | 44.93  |
| ATOM | 1755 | C   | PRO | A | 261 | −20.110 | 61.860 | 16.426 | 1.00 | 51.80  |
| ATOM | 1756 | O   | PRO | A | 261 | −20.771 | 61.761 | 15.395 | 1.00 | 52.12  |
| ATOM | 1757 | CB  | PRO | A | 261 | −17.964 | 63.046 | 15.822 | 1.00 | 46.41  |
| ATOM | 1758 | CG  | PRO | A | 261 | −16.889 | 62.711 | 16.806 | 1.00 | 50.34  |
| ATOM | 1759 | CD  | PRO | A | 261 | −17.286 | 63.404 | 18.093 | 1.00 | 45.43  |
| ATOM | 1760 | N   | ILE | A | 262 | −20.070 | 60.890 | 17.335 | 1.00 | 49.56  |
| ATOM | 1761 | CA  | ILE | A | 262 | −20.855 | 59.659 | 17.153 | 1.00 | 50.17  |
| ATOM | 1762 | C   | ILE | A | 262 | −22.081 | 59.622 | 18.071 | 1.00 | 56.19  |
| ATOM | 1763 | O   | ILE | A | 262 | −21.970 | 59.870 | 19.263 | 1.00 | 55.52  |
| ATOM | 1764 | CB  | ILE | A | 262 | −20.007 | 58.394 | 17.418 | 1.00 | 53.16  |
| ATOM | 1765 | CG1 | ILE | A | 262 | −18.738 | 58.412 | 16.571 | 1.00 | 53.07  |
| ATOM | 1766 | CG2 | ILE | A | 262 | −20.821 | 57.142 | 17.145 | 1.00 | 53.96  |
| ATOM | 1767 | CD1 | ILE | A | 262 | −17.788 | 57.297 | 16.879 | 1.00 | 56.29  |
| ATOM | 1768 | N   | PRO | A | 263 | −23.245 | 59.304 | 17.509 | 1.00 | 54.73  |
| ATOM | 1769 | CA  | PRO | A | 263 | −23.378 | 59.001 | 16.092 | 1.00 | 54.90  |
| ATOM | 1770 | C   | PRO | A | 263 | −23.434 | 60.301 | 15.306 | 1.00 | 60.28  |
| ATOM | 1771 | O   | PRO | A | 263 | −23.647 | 61.359 | 15.874 | 1.00 | 59.26  |
| ATOM | 1772 | CB  | PRO | A | 263 | −24.739 | 58.324 | 16.031 | 1.00 | 56.24  |
| ATOM | 1773 | CG  | PRO | A | 263 | −25.557 | 59.056 | 17.110 | 1.00 | 60.45  |
| ATOM | 1774 | CD  | PRO | A | 263 | −24.543 | 59.675 | 18.095 | 1.00 | 55.55  |
| ATOM | 1775 | N   | PRO | A | 264 | −23.266 | 60.210 | 13.994 | 1.00 | 59.41  |
| ATOM | 1776 | CA  | PRO | A | 264 | −23.252 | 61.397 | 13.141 | 1.00 | 60.04  |
| ATOM | 1777 | C   | PRO | A | 264 | −24.461 | 62.316 | 13.304 | 1.00 | 67.53  |
| ATOM | 1778 | O   | PRO | A | 264 | −25.574 | 61.870 | 13.596 | 1.00 | 66.22  |
| ATOM | 1779 | CB  | PRO | A | 264 | −23.190 | 60.815 | 11.718 | 1.00 | 61.12  |
| ATOM | 1780 | CG  | PRO | A | 264 | −23.625 | 59.408 | 11.855 | 1.00 | 65.08  |
| ATOM | 1781 | CD  | PRO | A | 264 | −23.197 | 58.968 | 13.211 | 1.00 | 60.10  |
| ATOM | 1782 | N   | PRO | A | 265 | −24.222 | 63.611 | 13.120 | 1.00 | 67.91  |
| ATOM | 1783 | CA  | PRO | A | 265 | −25.277 | 64.612 | 13.218 | 1.00 | 68.88  |
| ATOM | 1784 | C   | PRO | A | 265 | −26.138 | 64.533 | 11.975 | 1.00 | 77.04  |
| ATOM | 1785 | O   | PRO | A | 265 | −25.623 | 64.415 | 10.861 | 1.00 | 76.47  |
| ATOM | 1786 | CB  | PRO | A | 265 | −24.504 | 65.937 | 13.217 | 1.00 | 70.10  |
| ATOM | 1787 | CG  | PRO | A | 265 | −23.166 | 65.594 | 13.765 | 1.00 | 74.07  |
| ATOM | 1788 | CD  | PRO | A | 265 | −22.879 | 64.188 | 13.318 | 1.00 | 68.89  |
| ATOM | 1789 | N   | ASP | A | 266 | −27.447 | 64.587 | 12.160 | 1.00 | 76.99  |
| ATOM | 1790 | CA  | ASP | A | 266 | −28.355 | 64.544 | 11.029 | 1.00 | 78.32  |
| ATOM | 1791 | C   | ASP | A | 266 | −28.347 | 65.905 | 10.324 | 1.00 | 84.64  |
| ATOM | 1792 | O   | ASP | A | 266 | −27.886 | 66.898 | 10.889 | 1.00 | 84.46  |
| ATOM | 1793 | CB  | ASP | A | 266 | −29.757 | 64.140 | 11.479 | 1.00 | 80.44  |
| ATOM | 1794 | CG  | ASP | A | 266 | −29.801 | 62.724 | 12.044 | 1.00 | 92.97  |
| ATOM | 1795 | OD1 | ASP | A | 266 | −29.069 | 61.849 | 11.525 | 1.00 | 93.71  |
| ATOM | 1796 | OD2 | ASP | A | 266 | −30.558 | 62.491 | 13.010 | 1.00 | 100.34 |
| ATOM | 1797 | N   | ALA | A | 267 | −28.790 | 65.924 | 9.069  | 1.00 | 82.74  |
| ATOM | 1798 | CA  | ALA | A | 267 | −28.777 | 67.143 | 8.249  | 1.00 | 83.30  |
| ATOM | 1799 | C   | ALA | A | 267 | −29.216 | 68.422 | 8.970  | 1.00 | 88.43  |
| ATOM | 1800 | O   | ALA | A | 267 | −28.535 | 69.448 | 8.895  | 1.00 | 88.02  |
| ATOM | 1801 | CB  | ALA | A | 267 | −29.577 | 66.941 | 6.972  | 1.00 | 84.08  |
| ATOM | 1802 | N   | LYS | A | 268 | −30.353 | 68.364 | 9.655  | 1.00 | 85.63  |

TABLE 3-continued

Structural Coordinate of MEK1/N35/NKFCdel (corresponding to amino acids 24-373 of SEQ ID NO: 2)-ATPγS Binary Complex.

| ATOM | 1803 | CA | LYS | A | 268 | −30.853 | 69.527 | 10.374 | 1.00 | 85.77 |
|---|---|---|---|---|---|---|---|---|---|---|
| ATOM | 1804 | C | LYS | A | 268 | −29.885 | 69.929 | 11.478 | 1.00 | 90.02 |
| ATOM | 1805 | O | LYS | A | 268 | −29.667 | 71.117 | 11.723 | 1.00 | 89.86 |
| ATOM | 1806 | CB | LYS | A | 268 | −32.240 | 69.250 | 10.950 | 1.00 | 88.73 |
| ATOM | 1807 | CG | LYS | A | 268 | −33.372 | 69.402 | 9.938 | 1.00 | 105.23 |
| ATOM | 1808 | CD | LYS | A | 268 | −34.450 | 70.346 | 10.451 | 1.00 | 117.00 |
| ATOM | 1809 | CE | LYS | A | 268 | −35.398 | 70.765 | 9.334 | 1.00 | 129.01 |
| ATOM | 1810 | NZ | LYS | A | 268 | −34.853 | 71.903 | 8.536 | 1.00 | 137.93 |
| ATOM | 1811 | N | GLU | A | 269 | −29.288 | 68.933 | 12.130 | 1.00 | 86.40 |
| ATOM | 1812 | CA | GLU | A | 269 | −28.318 | 69.185 | 13.194 | 1.00 | 86.11 |
| ATOM | 1813 | C | GLU | A | 269 | −27.173 | 70.059 | 12.678 | 1.00 | 89.14 |
| ATOM | 1814 | O | GLU | A | 269 | −26.721 | 70.976 | 13.364 | 1.00 | 88.53 |
| ATOM | 1815 | CB | GLU | A | 269 | −27.759 | 67.867 | 13.738 | 1.00 | 87.58 |
| ATOM | 1816 | CG | GLU | A | 269 | −28.804 | 66.784 | 13.966 | 1.00 | 99.38 |
| ATOM | 1817 | CD | GLU | A | 269 | −28.349 | 65.739 | 14.972 | 1.00 | 120.91 |
| ATOM | 1818 | OE1 | GLU | A | 269 | −27.879 | 66.129 | 16.063 | 1.00 | 112.93 |
| ATOM | 1819 | OE2 | GLU | A | 269 | −28.452 | 64.532 | 14.668 | 1.00 | 116.34 |
| ATOM | 1820 | N | LEU | A | 270 | −26.710 | 69.759 | 11.465 | 1.00 | 85.10 |
| ATOM | 1821 | CA | LEU | A | 270 | −25.623 | 70.508 | 10.839 | 1.00 | 84.75 |
| ATOM | 1822 | C | LEU | A | 270 | −26.091 | 71.880 | 10.377 | 1.00 | 88.46 |
| ATOM | 1823 | O | LEU | A | 270 | −25.323 | 72.844 | 10.374 | 1.00 | 87.87 |
| ATOM | 1824 | CB | LEU | A | 270 | −25.070 | 69.735 | 9.644 | 1.00 | 84.71 |
| ATOM | 1825 | CG | LEU | A | 270 | −24.150 | 68.563 | 9.966 | 1.00 | 89.32 |
| ATOM | 1826 | CD1 | LEU | A | 270 | −24.154 | 67.568 | 8.821 | 1.00 | 89.47 |
| ATOM | 1827 | CD2 | LEU | A | 270 | −22.739 | 69.056 | 10.255 | 1.00 | 91.41 |
| ATOM | 1828 | N | GLU | A | 271 | −27.349 | 71.954 | 9.964 | 1.00 | 85.14 |
| ATOM | 1829 | CA | GLU | A | 271 | −27.925 | 73.201 | 9.489 | 1.00 | 85.04 |
| ATOM | 1830 | C | GLU | A | 271 | −27.949 | 74.241 | 10.608 | 1.00 | 88.48 |
| ATOM | 1831 | O | GLU | A | 271 | −27.831 | 75.440 | 10.357 | 1.00 | 88.16 |
| ATOM | 1832 | CB | GLU | A | 271 | −29.332 | 72.950 | 8.940 | 1.00 | 86.48 |
| ATOM | 1833 | CG | GLU | A | 271 | −30.103 | 74.222 | 8.607 | 1.00 | 98.36 |
| ATOM | 1834 | CD | GLU | A | 271 | −31.597 | 74.060 | 8.821 | 1.00 | 121.66 |
| ATOM | 1835 | OE1 | GLU | A | 271 | −32.222 | 73.259 | 8.090 | 1.00 | 117.24 |
| ATOM | 1836 | OE2 | GLU | A | 271 | −32.141 | 74.716 | 9.735 | 1.00 | 116.18 |
| ATOM | 1837 | N | LEU | A | 272 | −28.079 | 73.774 | 11.845 | 1.00 | 84.60 |
| ATOM | 1838 | CA | LEU | A | 272 | −28.096 | 74.669 | 12.998 | 1.00 | 84.29 |
| ATOM | 1839 | C | LEU | A | 272 | −26.682 | 74.875 | 13.534 | 1.00 | 87.39 |
| ATOM | 1840 | O | LEU | A | 272 | −26.407 | 75.846 | 14.245 | 1.00 | 86.84 |
| ATOM | 1841 | CB | LEU | A | 272 | −28.995 | 74.107 | 14.106 | 1.00 | 84.43 |
| ATOM | 1842 | CG | LEU | A | 272 | −30.312 | 73.446 | 13.689 | 1.00 | 89.31 |
| ATOM | 1843 | CD1 | LEU | A | 272 | −30.620 | 72.249 | 14.592 | 1.00 | 89.51 |
| ATOM | 1844 | CD2 | LEU | A | 272 | −31.458 | 74.457 | 13.714 | 1.00 | 91.38 |
| ATOM | 1845 | N | MET | A | 273 | −25.789 | 73.946 | 13.198 | 1.00 | 83.23 |
| ATOM | 1846 | CA | MET | A | 273 | −24.407 | 74.003 | 13.661 | 1.00 | 82.55 |
| ATOM | 1847 | C | MET | A | 273 | −23.565 | 74.978 | 12.853 | 1.00 | 86.09 |
| ATOM | 1848 | O | MET | A | 273 | −22.795 | 75.755 | 13.413 | 1.00 | 85.80 |
| ATOM | 1849 | CB | MET | A | 273 | −23.771 | 72.612 | 13.626 | 1.00 | 84.70 |
| ATOM | 1850 | CG | MET | A | 273 | −24.332 | 71.651 | 14.656 | 1.00 | 88.11 |
| ATOM | 1851 | SD | MET | A | 273 | −23.820 | 69.956 | 14.359 | 1.00 | 92.11 |
| ATOM | 1852 | CE | MET | A | 273 | −22.237 | 69.934 | 15.194 | 1.00 | 88.81 |
| ATOM | 1853 | N | PHE | A | 274 | −23.703 | 74.923 | 11.535 | 1.00 | 82.38 |
| ATOM | 1854 | CA | PHE | A | 274 | −22.932 | 75.788 | 10.660 | 1.00 | 82.08 |
| ATOM | 1855 | C | PHE | A | 274 | −23.820 | 76.581 | 9.708 | 1.00 | 86.39 |
| ATOM | 1856 | O | PHE | A | 274 | −23.360 | 77.523 | 9.057 | 1.00 | 85.67 |
| ATOM | 1857 | CB | PHE | A | 274 | −21.906 | 74.969 | 9.875 | 1.00 | 83.65 |
| ATOM | 1858 | CG | PHE | A | 274 | −20.970 | 74.172 | 10.743 | 1.00 | 84.93 |
| ATOM | 1859 | CD1 | PHE | A | 274 | −21.350 | 72.939 | 11.246 | 1.00 | 87.88 |
| ATOM | 1860 | CD2 | PHE | A | 274 | −19.704 | 74.650 | 11.045 | 1.00 | 86.85 |
| ATOM | 1861 | CE1 | PHE | A | 274 | −20.487 | 72.200 | 12.033 | 1.00 | 88.61 |
| ATOM | 1862 | CE2 | PHE | A | 274 | −18.840 | 73.916 | 11.836 | 1.00 | 89.50 |
| ATOM | 1863 | CZ | PHE | A | 274 | −19.231 | 72.692 | 12.328 | 1.00 | 87.57 |
| ATOM | 1864 | N | GLY | A | 275 | −25.093 | 76.196 | 9.631 | 1.00 | 83.49 |
| ATOM | 1865 | CA | GLY | A | 275 | −26.047 | 76.873 | 8.756 | 1.00 | 83.22 |
| ATOM | 1866 | C | GLY | A | 275 | −25.831 | 76.487 | 7.293 | 1.00 | 86.68 |
| ATOM | 1867 | O | GLY | A | 275 | −26.099 | 77.275 | 6.391 | 1.00 | 86.36 |
| ATOM | 1868 | N | CYS | A | 276 | −25.226 | 75.323 | 7.078 | 1.00 | 82.69 |
| ATOM | 1869 | N | PRO | A | 305 | −31.367 | 57.249 | 21.703 | 1.00 | 79.39 |
| ATOM | 1870 | CA | PRO | A | 305 | −30.844 | 58.581 | 22.018 | 1.00 | 78.71 |
| ATOM | 1871 | C | PRO | A | 305 | −31.442 | 59.131 | 23.320 | 1.00 | 81.45 |
| ATOM | 1872 | O | PRO | A | 305 | −32.665 | 59.208 | 23.468 | 1.00 | 81.69 |
| ATOM | 1873 | CB | PRO | A | 305 | −31.302 | 59.424 | 20.823 | 1.00 | 80.36 |
| ATOM | 1874 | CG | PRO | A | 305 | −32.545 | 58.754 | 20.347 | 1.00 | 84.73 |
| ATOM | 1875 | CD | PRO | A | 305 | −32.359 | 57.280 | 20.610 | 1.00 | 80.02 |
| ATOM | 1876 | N | PRO | A | 306 | −30.574 | 59.509 | 24.259 | 1.00 | 76.27 |
| ATOM | 1877 | CA | PRO | A | 306 | −29.134 | 59.415 | 24.056 | 1.00 | 74.96 |
| ATOM | 1878 | C | PRO | A | 306 | −28.666 | 57.966 | 23.977 | 1.00 | 75.88 |
| ATOM | 1879 | O | PRO | A | 306 | −29.331 | 57.052 | 24.479 | 1.00 | 75.99 |

TABLE 3-continued

Structural Coordinate of MEK1/N35/NKFCdel (corresponding to amino acids 24-373 of SEQ ID NO: 2)-ATPγS Binary Complex.

| ATOM | 1880 | CB | PRO | A | 306 | −28.567 | 60.088 | 25.304 | 1.00 | 76.76 |
|------|------|-----|-----|---|-----|---------|--------|--------|------|-------|
| ATOM | 1881 | CG | PRO | A | 306 | −29.592 | 61.105 | 25.665 | 1.00 | 81.46 |
| ATOM | 1882 | CD | PRO | A | 306 | −30.922 | 60.483 | 25.312 | 1.00 | 76.79 |
| ATOM | 1883 | N | MET | A | 307 | −27.527 | 57.762 | 23.326 | 1.00 | 69.14 |
| ATOM | 1884 | CA | MET | A | 307 | −26.964 | 56.434 | 23.167 | 1.00 | 67.41 |
| ATOM | 1885 | C | MET | A | 307 | −26.166 | 56.028 | 24.404 | 1.00 | 67.82 |
| ATOM | 1886 | O | MET | A | 307 | −25.322 | 56.790 | 24.895 | 1.00 | 66.61 |
| ATOM | 1887 | CB | MET | A | 307 | −26.060 | 56.397 | 21.931 | 1.00 | 69.63 |
| ATOM | 1888 | CG | MET | A | 307 | −26.009 | 55.052 | 21.214 | 1.00 | 73.12 |
| ATOM | 1889 | SD | MET | A | 307 | −24.996 | 55.120 | 19.704 | 1.00 | 77.00 |
| ATOM | 1890 | CE | MET | A | 307 | −25.888 | 54.023 | 18.633 | 1.00 | 73.84 |
| ATOM | 1891 | N | ALA | A | 308 | −26.434 | 54.824 | 24.906 | 1.00 | 62.03 |
| ATOM | 1892 | CA | ALA | A | 308 | −25.693 | 54.300 | 26.042 | 1.00 | 60.52 |
| ATOM | 1893 | C | ALA | A | 308 | −24.283 | 53.964 | 25.568 | 1.00 | 61.86 |
| ATOM | 1894 | O | ALA | A | 308 | −24.058 | 53.718 | 24.379 | 1.00 | 60.70 |
| ATOM | 1895 | CB | ALA | A | 308 | −26.380 | 53.058 | 26.608 | 1.00 | 61.15 |
| ATOM | 1896 | N | ILE | A | 309 | −23.332 | 53.991 | 26.494 | 1.00 | 57.37 |
| ATOM | 1897 | CA | ILE | A | 309 | −21.936 | 53.710 | 26.176 | 1.00 | 56.39 |
| ATOM | 1898 | C | ILE | A | 309 | −21.780 | 52.427 | 25.362 | 1.00 | 56.76 |
| ATOM | 1899 | O | ILE | A | 309 | −21.111 | 52.421 | 24.322 | 1.00 | 56.28 |
| ATOM | 1900 | CB | ILE | A | 309 | −21.072 | 53.614 | 27.457 | 1.00 | 59.77 |
| ATOM | 1901 | CG1 | ILE | A | 309 | −21.602 | 54.579 | 28.523 | 1.00 | 60.91 |
| ATOM | 1902 | CG2 | ILE | A | 309 | −19.614 | 53.898 | 27.145 | 1.00 | 59.83 |
| ATOM | 1903 | CD1 | ILE | A | 309 | −20.506 | 55.261 | 29.360 | 1.00 | 71.52 |
| ATOM | 1904 | N | PHE | A | 310 | −22.401 | 51.344 | 25.830 | 1.00 | 50.33 |
| ATOM | 1905 | CA | PHE | A | 310 | −22.300 | 50.057 | 25.146 | 1.00 | 48.82 |
| ATOM | 1906 | C | PHE | A | 310 | −22.818 | 50.104 | 23.711 | 1.00 | 52.35 |
| ATOM | 1907 | O | PHE | A | 310 | −22.236 | 49.495 | 22.813 | 1.00 | 51.80 |
| ATOM | 1903 | CB | PHE | A | 310 | −22.956 | 48.922 | 25.958 | 1.00 | 49.98 |
| ATOM | 1909 | CG | PHE | A | 310 | −24.306 | 49.273 | 26.532 | 1.00 | 51.02 |
| ATOM | 1910 | CD1 | PHE | A | 310 | −25.465 | 49.069 | 25.793 | 1.00 | 54.02 |
| ATOM | 1911 | CD2 | PHE | A | 310 | −24.420 | 49.758 | 27.827 | 1.00 | 52.75 |
| ATOM | 1912 | CE1 | PHE | A | 310 | −26.713 | 49.371 | 26.327 | 1.00 | 55.15 |
| ATOM | 1913 | CE2 | PHE | A | 310 | −25.662 | 50.070 | 28.369 | 1.00 | 55.52 |
| ATOM | 1914 | CZ | PHE | A | 310 | −26.810 | 49.876 | 27.621 | 1.00 | 53.88 |
| ATOM | 1915 | N | GLU | A | 311 | −23.901 | 50.849 | 23.496 | 1.00 | 49.46 |
| ATOM | 1916 | CA | GLU | A | 311 | −24.465 | 51.020 | 22.154 | 1.00 | 49.23 |
| ATOM | 1917 | C | GLU | A | 311 | −23.479 | 51.825 | 21.325 | 1.00 | 52.61 |
| ATOM | 1918 | O | GLU | A | 311 | −23.239 | 51.536 | 20.153 | 1.00 | 53.06 |
| ATOM | 1919 | CB | GLU | A | 311 | −25.796 | 51.759 | 22.227 | 1.00 | 50.52 |
| ATOM | 1920 | CG | GLU | A | 311 | −26.791 | 51.138 | 23.177 | 1.00 | 61.40 |
| ATOM | 1921 | CD | GLU | A | 311 | −27.998 | 52.020 | 23.416 | 1.00 | 78.78 |
| ATOM | 1922 | OE1 | GLU | A | 311 | −27.811 | 53.223 | 23.679 | 1.00 | 76.19 |
| ATOM | 1923 | OE2 | GLU | A | 311 | −29.133 | 51.510 | 23.325 | 1.00 | 70.35 |
| ATOM | 1924 | N | LEU | A | 312 | −22.881 | 52.817 | 21.965 | 1.00 | 48.00 |
| ATOM | 1925 | CA | LEU | A | 312 | −21.879 | 53.651 | 21.337 | 1.00 | 47.83 |
| ATOM | 1926 | C | LEU | A | 312 | −20.686 | 52.805 | 20.893 | 1.00 | 50.63 |
| ATOM | 1927 | O | LEU | A | 312 | −20.279 | 52.845 | 19.731 | 1.00 | 49.42 |
| ATOM | 1928 | CB | LEU | A | 312 | −21.403 | 54.716 | 22.332 | 1.00 | 48.12 |
| ATOM | 1929 | CG | LEU | A | 312 | −20.867 | 56.026 | 21.772 | 1.00 | 52.84 |
| ATOM | 1930 | CD1 | LEU | A | 312 | −20.198 | 56.817 | 22.876 | 1.00 | 52.64 |
| ATOM | 1931 | CD2 | LEU | A | 312 | −19.906 | 55.767 | 20.625 | 1.00 | 55.74 |
| ATOM | 1932 | N | LEU | A | 313 | −20.114 | 52.056 | 21.831 | 1.00 | 47.36 |
| ATOM | 1933 | CA | LEU | A | 313 | −18.956 | 51.223 | 21.525 | 1.00 | 47.10 |
| ATOM | 1934 | C | LEU | A | 313 | −19.221 | 50.281 | 20.351 | 1.00 | 52.03 |
| ATOM | 1935 | O | LEU | A | 313 | −18.396 | 50.161 | 19.445 | 1.00 | 51.92 |
| ATOM | 1936 | CB | LEU | A | 313 | −18.481 | 50.465 | 22.761 | 1.00 | 46.82 |
| ATOM | 1937 | CG | LEU | A | 313 | −17.979 | 51.352 | 23.909 | 1.00 | 51.06 |
| ATOM | 1938 | CD1 | LEU | A | 313 | −17.103 | 50.560 | 24.864 | 1.00 | 50.80 |
| ATOM | 1939 | CD2 | LEU | A | 313 | −17.228 | 52.584 | 23.370 | 1.00 | 52.11 |
| ATOM | 1940 | N | ASP | A | 314 | −20.398 | 49.668 | 20.334 | 1.00 | 49.39 |
| ATOM | 1941 | CA | ASP | A | 314 | −20.767 | 48.768 | 19.240 | 1.00 | 49.73 |
| ATOM | 1942 | C | ASP | A | 314 | −20.843 | 49.536 | 17.922 | 1.00 | 53.72 |
| ATOM | 1943 | O | ASP | A | 314 | −20.319 | 49.088 | 16.898 | 1.00 | 53.43 |
| ATOM | 1944 | CB | ASP | A | 314 | −22.104 | 48.079 | 19.537 | 1.00 | 52.04 |
| ATOM | 1945 | CG | ASP | A | 314 | −22.525 | 47.137 | 18.437 | 1.00 | 65.24 |
| ATOM | 1946 | OD1 | ASP | A | 314 | −21.938 | 46.038 | 18.334 | 1.00 | 66.13 |
| ATOM | 1947 | OD2 | ASP | A | 314 | −23.435 | 47.500 | 17.664 | 1.00 | 73.57 |
| ATOM | 1948 | N | TYR | A | 315 | −21.471 | 50.710 | 17.964 | 1.00 | 49.98 |
| ATOM | 1949 | CA | TYR | A | 315 | −21.577 | 51.575 | 16.794 | 1.00 | 49.89 |
| ATOM | 1950 | C | TYR | A | 315 | −20.192 | 51.859 | 16.205 | 1.00 | 52.91 |
| ATOM | 1951 | O | TYR | A | 315 | −19.958 | 51.648 | 15.020 | 1.00 | 53.30 |
| ATOM | 1952 | CB | TYR | A | 315 | −22.267 | 52.891 | 17.173 | 1.00 | 51.89 |
| ATOM | 1953 | CG | TYR | A | 315 | −22.639 | 53.764 | 15.988 | 1.00 | 54.75 |
| ATOM | 1954 | CD1 | TYR | A | 315 | −21.660 | 54.416 | 15.239 | 1.00 | 56.67 |
| ATOM | 1955 | CD2 | TYR | A | 315 | −23.975 | 53.947 | 15.627 | 1.00 | 55.99 |
| ATOM | 1956 | CE1 | TYR | A | 315 | −21.998 | 55.213 | 14.154 | 1.00 | 57.96 |

TABLE 3-continued

Structural Coordinate of MEK1/N35/NKFCdel (corresponding to amino acids 24-373 of SEQ ID NO: 2)-ATPγS Binary Complex.

| ATOM | 1957 | CE2 | TYR | A | 315 | −24.327 | 54.748 | 14.545 | 1.00 | 57.16 |
|---|---|---|---|---|---|---|---|---|---|---|
| ATOM | 1958 | CZ | TYR | A | 315 | −23.339 | 55.377 | 13.812 | 1.00 | 66.34 |
| ATOM | 1959 | OH | TYR | A | 315 | −23.692 | 56.166 | 12.741 | 1.00 | 68.75 |
| ATOM | 1960 | N | ILE | A | 316 | −19.274 | 52.329 | 17.045 | 1.00 | 48.17 |
| ATOM | 1961 | CA | ILE | A | 316 | −17.912 | 52.625 | 16.612 | 1.00 | 47.32 |
| ATOM | 1962 | C | ILE | A | 316 | −17.304 | 51.423 | 15.897 | 1.00 | 51.41 |
| ATOM | 1963 | O | ILE | A | 316 | −16.662 | 51.562 | 14.860 | 1.00 | 51.04 |
| ATOM | 1964 | CB | ILE | A | 316 | −16.999 | 52.993 | 17.818 | 1.00 | 50.14 |
| ATOM | 1965 | CG1 | ILE | A | 316 | −17.464 | 54.303 | 18.476 | 1.00 | 50.42 |
| ATOM | 1966 | CG2 | ILE | A | 316 | −15.522 | 53.073 | 17.389 | 1.00 | 50.06 |
| ATOM | 1967 | CD1 | ILE | A | 316 | −16.778 | 54.606 | 19.804 | 1.00 | 51.78 |
| ATOM | 1968 | N | VAL | A | 317 | −17.501 | 50.240 | 16.466 | 1.00 | 48.13 |
| ATOM | 1969 | CA | VAL | A | 317 | −16.938 | 49.021 | 15.899 | 1.00 | 47.88 |
| ATOM | 1970 | C | VAL | A | 317 | −17.647 | 48.555 | 14.631 | 1.00 | 51.42 |
| ATOM | 1971 | O | VAL | A | 317 | −17.015 | 48.011 | 13.724 | 1.00 | 50.45 |
| ATOM | 1972 | CB | VAL | A | 317 | −16.967 | 47.865 | 16.915 | 1.00 | 51.65 |
| ATOM | 1973 | CG1 | VAL | A | 317 | −16.600 | 46.542 | 16.233 | 1.00 | 51.16 |
| ATOM | 1974 | CG2 | VAL | A | 317 | −16.040 | 48.158 | 18.080 | 1.00 | 51.40 |
| ATOM | 1975 | N | ASN | A | 318 | −18.958 | 48.748 | 14.575 | 1.00 | 48.32 |
| ATOM | 1976 | CA | ASN | A | 318 | −19.733 | 48.260 | 13.441 | 1.00 | 48.50 |
| ATOM | 1977 | C | ASN | A | 318 | −20.117 | 49.259 | 12.358 | 1.00 | 52.96 |
| ATOM | 1978 | O | ASN | A | 318 | −20.445 | 48.864 | 11.247 | 1.00 | 53.20 |
| ATOM | 1979 | CB | ASN | A | 318 | −20.952 | 47.486 | 13.921 | 1.00 | 48.15 |
| ATOM | 1980 | CG | ASN | A | 318 | −20.574 | 46.262 | 14.717 | 1.00 | 63.75 |
| ATOM | 1981 | OD1 | ASN | A | 318 | −19.811 | 45.410 | 14.245 | 1.00 | 58.36 |
| ATOM | 1982 | ND2 | ASN | A | 318 | −21.042 | 46.197 | 15.955 | 1.00 | 52.36 |
| ATOM | 1983 | N | GLU | A | 319 | −20.091 | 50.547 | 12.678 | 1.00 | 49.15 |
| ATOM | 1984 | CA | GLU | A | 319 | −20.451 | 51.569 | 11.701 | 1.00 | 48.57 |
| ATOM | 1985 | C | GLU | A | 319 | −19.235 | 52.134 | 10.983 | 1.00 | 51.92 |
| ATOM | 1986 | O | GLU | A | 319 | −18.096 | 51.794 | 11.295 | 1.00 | 52.07 |
| ATOM | 1987 | CB | GLU | A | 319 | −21.220 | 52.707 | 12.377 | 1.00 | 49.86 |
| ATOM | 1988 | CG | GLU | A | 319 | −22.688 | 52.405 | 12.632 | 1.00 | 58.62 |
| ATOM | 1989 | CD | GLU | A | 319 | −23.281 | 51.486 | 11.583 | 1.00 | 79.38 |
| ATOM | 1990 | OE1 | GLU | A | 319 | −23.588 | 51.967 | 10.472 | 1.00 | 74.71 |
| ATOM | 1991 | OE2 | GLU | A | 319 | −23.432 | 50.283 | 11.866 | 1.00 | 74.57 |
| ATOM | 1992 | N | PRO | A | 320 | −19.486 | 53.011 | 10.019 | 1.00 | 47.91 |
| ATOM | 1993 | CA | PRO | A | 320 | −18.408 | 53.684 | 9.299 | 1.00 | 46.72 |
| ATOM | 1994 | C | PRO | A | 320 | −17.963 | 54.876 | 10.139 | 1.00 | 47.84 |
| ATOM | 1995 | O | PRO | A | 320 | −18.782 | 55.508 | 10.823 | 1.00 | 46.64 |
| ATOM | 1996 | CB | PRO | A | 320 | −19.092 | 54.153 | 8.014 | 1.00 | 48.52 |
| ATOM | 1997 | CG | PRO | A | 320 | −20.151 | 53.118 | 7.775 | 1.00 | 53.08 |
| ATOM | 1998 | CD | PRO | A | 320 | −20.654 | 52.748 | 9.153 | 1.00 | 48.47 |
| ATOM | 1999 | N | PRO | A | 321 | −16.663 | 55.142 | 10.144 | 1.00 | 43.00 |
| ATOM | 2000 | CA | PRO | A | 321 | −16.121 | 56.215 | 10.966 | 1.00 | 42.19 |
| ATOM | 2001 | C | PRO | A | 321 | −16.752 | 57.561 | 10.624 | 1.00 | 46.31 |
| ATOM | 2002 | O | PRO | A | 321 | −17.115 | 57.819 | 9.472 | 1.00 | 45.59 |
| ATOM | 2003 | CB | PRO | A | 321 | −14.633 | 56.209 | 10.614 | 1.00 | 43.62 |
| ATOM | 2004 | CG | PRO | A | 321 | −14.575 | 55.673 | 9.213 | 1.00 | 47.50 |
| ATOM | 2005 | CD | PRO | A | 321 | −15.742 | 54.742 | 9.058 | 1.00 | 42.74 |
| ATOM | 2006 | N | PRO | A | 322 | −16.895 | 58.410 | 11.635 | 1.00 | 42.82 |
| ATOM | 2007 | CA | PRO | A | 322 | −17.452 | 59.743 | 11.434 | 1.00 | 42.57 |
| ATOM | 2008 | C | PRO | A | 322 | −16.575 | 60.548 | 10.472 | 1.00 | 45.65 |
| ATOM | 2009 | O | PRO | A | 322 | −15.494 | 60.101 | 10.054 | 1.00 | 44.99 |
| ATOM | 2010 | CB | PRO | A | 322 | −17.386 | 60.374 | 12.840 | 1.00 | 44.21 |
| ATOM | 2011 | CG | PRO | A | 322 | −16.698 | 59.319 | 13.745 | 1.00 | 48.02 |
| ATOM | 2012 | CD | PRO | A | 322 | −16.049 | 58.345 | 12.834 | 1.00 | 43.10 |
| ATOM | 2013 | N | LYS | A | 323 | −17.023 | 61.743 | 10.148 | 1.00 | 41.27 |
| ATOM | 2014 | CA | LYS | A | 323 | −16.272 | 62.596 | 9.268 | 1.00 | 40.96 |
| ATOM | 2015 | C | LYS | A | 323 | −16.749 | 64.025 | 9.381 | 1.00 | 44.57 |
| ATOM | 2016 | O | LYS | A | 323 | −17.859 | 64.292 | 9.842 | 1.00 | 44.58 |
| ATOM | 2017 | CB | LYS | A | 323 | −16.393 | 62.108 | 7.819 | 1.00 | 43.88 |
| ATOM | 2018 | CG | LYS | A | 323 | −17.724 | 62.442 | 7.161 | 1.00 | 55.19 |
| ATOM | 2019 | CD | LYS | A | 323 | −17.944 | 61.597 | 5.921 | 1.00 | 63.53 |
| ATOM | 2020 | CE | LYS | A | 323 | −19.424 | 61.348 | 5.686 | 1.00 | 70.60 |
| ATOM | 2021 | NZ | LYS | A | 323 | −20.012 | 62.356 | 4.766 | 1.00 | 79.07 |
| ATOM | 2022 | N | LEU | A | 324 | −15.918 | 64.950 | 8.937 | 1.00 | 40.44 |
| ATOM | 2023 | CA | LEU | A | 324 | −16.279 | 66.349 | 8.981 | 1.00 | 39.81 |
| ATOM | 2024 | C | LEU | A | 324 | −17.348 | 66.625 | 7.956 | 1.00 | 45.49 |
| ATOM | 2025 | O | LEU | A | 324 | −17.355 | 66.030 | 6.878 | 1.00 | 45.04 |
| ATOM | 2026 | CB | LEU | A | 324 | −15.069 | 67.215 | 8.675 | 1.00 | 39.28 |
| ATOM | 2027 | CG | LEU | A | 324 | −13.998 | 67.263 | 9.750 | 1.00 | 42.51 |
| ATOM | 2028 | CD1 | LEU | A | 324 | −12.708 | 67.818 | 9.161 | 1.00 | 41.94 |
| ATOM | 2029 | CD2 | LEU | A | 324 | −14.485 | 68.111 | 10.927 | 1.00 | 43.16 |
| ATOM | 2030 | N | PRO | A | 325 | −18.231 | 67.561 | 8.270 | 1.00 | 43.11 |
| ATOM | 2031 | CA | PRO | A | 325 | −19.257 | 67.968 | 7.320 | 1.00 | 43.00 |
| ATOM | 2032 | C | PRO | A | 325 | −18.534 | 68.667 | 6.181 | 1.00 | 47.42 |
| ATOM | 2033 | O | PRO | A | 325 | −17.523 | 69.343 | 6.400 | 1.00 | 46.56 |

TABLE 3-continued

Structural Coordinate of MEK1/N35/NKFCdel (corresponding to amino acids 24-373 of SEQ ID NO: 2)-ATPγS Binary Complex.

| ATOM | 2034 CB | PRO | A | 325 | −20.086 | 68.988 | 8.115 | 1.00 | 44.66 |
|---|---|---|---|---|---|---|---|---|---|
| ATOM | 2035 CG | PRO | A | 325 | −19.156 | 69.482 | 9.174 | 1.00 | 48.51 |
| ATOM | 2036 CD | PRO | A | 325 | −18.339 | 68.290 | 9.543 | 1.00 | 43.48 |
| ATOM | 2037 N | SER | A | 326 | −19.031 | 68.487 | 4.967 | 1.00 | 45.11 |
| ATOM | 2038 CA | SER | A | 326 | −18.399 | 69.082 | 3.801 | 1.00 | 45.46 |
| ATOM | 2039 C | SER | A | 326 | −18.854 | 70.509 | 3.551 | 1.00 | 49.85 |
| ATOM | 2040 O | SER | A | 326 | −19.930 | 70.914 | 3.982 | 1.00 | 49.34 |
| ATOM | 2041 CB | SER | A | 326 | −18.629 | 68.216 | 2.561 | 1.00 | 49.79 |
| ATOM | 2042 OG | SER | A | 326 | −19.998 | 68.199 | 2.212 | 1.00 | 60.68 |
| ATOM | 2043 N | GLY | A | 327 | −18.020 | 71.269 | 2.862 | 1.00 | 47.39 |
| ATOM | 2044 CA | GLY | A | 327 | −18.337 | 72.657 | 2.545 | 1.00 | 47.28 |
| ATOM | 2045 C | GLY | A | 327 | −17.757 | 73.631 | 3.572 | 1.00 | 51.46 |
| ATOM | 2046 O | GLY | A | 327 | −17.237 | 74.691 | 3.212 | 1.00 | 51.98 |
| ATOM | 2047 N | VAL | A | 328 | −17.842 | 73.271 | 4.848 | 1.00 | 46.47 |
| ATOM | 2048 CA | VAL | A | 328 | −17.356 | 74.150 | 5.913 | 1.00 | 45.15 |
| ATOM | 2049 C | VAL | A | 328 | −15.871 | 74.022 | 6.253 | 1.00 | 45.14 |
| ATOM | 2050 O | VAL | A | 328 | −15.306 | 74.897 | 6.887 | 1.00 | 45.13 |
| ATOM | 2051 CB | VAL | A | 328 | −18.211 | 74.039 | 7.186 | 1.00 | 49.31 |
| ATOM | 2052 CG1 | VAL | A | 328 | −19.491 | 74.817 | 7.012 | 1.00 | 49.29 |
| ATOM | 2053 CG2 | VAL | A | 328 | −18.508 | 72.582 | 7.510 | 1.00 | 49.12 |
| ATOM | 2054 N | PHE | A | 329 | −15.248 | 72.928 | 5.842 | 1.00 | 38.62 |
| ATOM | 2055 CA | PHE | A | 329 | −13.830 | 72.723 | 6.121 | 1.00 | 36.85 |
| ATOM | 2056 C | PHE | A | 329 | −13.070 | 72.468 | 4.845 | 1.00 | 38.65 |
| ATOM | 2057 O | PHE | A | 329 | −13.640 | 72.015 | 3.861 | 1.00 | 38.79 |
| ATOM | 2058 CB | PHE | A | 329 | −13.634 | 71.553 | 7.088 | 1.00 | 38.07 |
| ATOM | 2059 CG | PHE | A | 329 | −14.283 | 71.762 | 8.420 | 1.00 | 38.83 |
| ATOM | 2060 CD1 | PHE | A | 329 | −13.674 | 72.555 | 9.387 | 1.00 | 40.53 |
| ATOM | 2061 CD2 | PHE | A | 329 | −15.511 | 71.192 | 8.702 | 1.00 | 40.39 |
| ATOM | 2062 CE1 | PHE | A | 329 | −14.269 | 72.761 | 10.604 | 1.00 | 40.80 |
| ATOM | 2063 CE2 | PHE | A | 329 | −16.105 | 71.382 | 9.935 | 1.00 | 42.80 |
| ATOM | 2064 CZ | PHE | A | 329 | −15.484 | 72.182 | 10.882 | 1.00 | 40.52 |
| ATOM | 2065 N | SER | A | 330 | −11.776 | 72.761 | 4.857 | 1.00 | 33.45 |
| ATOM | 2066 CA | SER | A | 330 | −10.960 | 72.542 | 3.675 | 1.00 | 33.02 |
| ATOM | 2067 C | SEF | A | 330 | −10.895 | 71.047 | 3.357 | 1.00 | 37.70 |
| ATOM | 2068 O | SER | A | 330 | −11.059 | 70.210 | 4.231 | 1.00 | 37.53 |
| ATOM | 2069 CB | SER | A | 330 | −9.548 | 73.114 | 3.862 | 1.00 | 34.22 |
| ATOM | 2070 OG | SER | A | 330 | −8.805 | 72.324 | 4.773 | 1.00 | 38.23 |
| ATOM | +2071 N | LEU | A | 331 | −10.657 | 70.727 | 2.099 | 1.00 | 34.97 |
| ATOM | 2072 CA | LEU | A | 331 | −10.560 | 69.344 | 1.674 | 1.00 | 34.84 |
| ATOM | 2073 C | LEU | A | 331 | −9.353 | 68.724 | 2.320 | 1.00 | 38.81 |
| ATOM | 2074 O | LEU | A | 331 | −9.375 | 67.552 | 2.703 | 1.00 | 40.25 |
| ATOM | 2075 CB | LEU | A | 331 | −10.454 | 69.270 | 0.152 | 1.00 | 35.16 |
| ATOM | 2076 CG | LEU | A | 331 | −11.787 | 69.396 | −0.597 | 1.00 | 40.25 |
| ATOM | 2077 CD1 | LEU | A | 331 | −11.562 | 69.401 | −2.093 | 1.00 | 40.72 |
| ATOM | 2078 CD2 | LEU | A | 331 | −12.706 | 68.250 | −0.198 | 1.00 | 43.38 |
| ATOM | 2079 N | GLU | A | 332 | −8.305 | 69.521 | 2.494 | 1.00 | 33.28 |
| ATOM | 2080 CA | GLU | A | 332 | −7.092 | 69.034 | 3.142 | 1.00 | 32.14 |
| ATOM | 2081 C | GLU | A | 332 | −7.344 | 68.602 | 4.581 | 1.00 | 35.58 |
| ATOM | 2082 O | GLU | A | 332 | −6.825 | 67.567 | 5.020 | 1.00 | 36.88 |
| ATOM | 2083 CB | GLU | A | 332 | −5.979 | 70.062 | 3.054 | 1.00 | 33.18 |
| ATOM | 2084 CG | GLU | A | 332 | −5.519 | 70.299 | 1.622 | 1.00 | 42.68 |
| ATOM | 2085 CD | GLU | A | 332 | −4.486 | 71.382 | 1.516 | 1.00 | 57.24 |
| ATOM | 2086 OE1 | GLU | A | 332 | −4.536 | 72.331 | 2.318 | 1.00 | 48.84 |
| ATOM | 2087 OE2 | GLU | A | 332 | −3.609 | 71.277 | 0.638 | 1.00 | 53.58 |
| ATOM | 2088 N | PHE | A | 333 | −8.169 | 69.368 | 5.302 | 1.00 | 29.27 |
| ATOM | 2089 CA | PHE | A | 333 | −8.524 | 69.026 | 6.684 | 1.00 | 28.28 |
| ATOM | 2090 C | PHE | A | 333 | −9.396 | 67.760 | 6.708 | 1.00 | 33.22 |
| ATOM | 2091 O | PHE | A | 333 | −9.085 | 66.800 | 7.422 | 1.00 | 32.97 |
| ATOM | 2092 CB | PHE | A | 333 | −9.239 | 70.198 | 7.383 | 1.00 | 29.50 |
| ATOM | 2093 CG | PHE | A | 333 | −9.413 | 70.006 | 8.864 | 1.00 | 30.19 |
| ATOM | 2094 CD1 | PHE | A | 333 | −8.549 | 69.171 | 9.583 | 1.00 | 31.83 |
| ATOM | 2095 CD2 | PHE | A | 333 | −10.462 | 70.628 | 9.546 | 1.00 | 30.96 |
| ATOM | 2096 CE1 | PHE | A | 333 | −8.696 | 69.010 | 10.960 | 1.00 | 31.39 |
| ATOM | 2097 CE2 | PHE | A | 333 | −10.615 | 70.455 | 10.904 | 1.00 | 32.99 |
| ATOM | 2098 CZ | PHE | A | 333 | −9.722 | 69.646 | 11.612 | 1.00 | 30.97 |
| ATOM | 2099 N | GLN | A | 334 | −10.464 | 67.747 | 5.908 | 1.00 | 30.24 |
| ATOM | 2100 CA | GLN | A | 334 | −11.324 | 66.558 | 5.796 | 1.00 | 30.66 |
| ATOM | 2101 C | GLN | A | 334 | −10.501 | 65.291 | 5.432 | 1.00 | 36.69 |
| ATOM | 2102 O | GLN | A | 334 | −10.717 | 64.214 | 5.994 | 1.00 | 37.96 |
| ATOM | 2103 CB | GLN | A | 334 | −12.416 | 65.766 | 4.730 | 1.00 | 31.63 |
| ATOM | 2104 CG | GLN | A | 334 | −13.291 | 67.977 | 4.945 | 1.00 | 33.35 |
| ATOM | 2105 CD | GLN | A | 334 | −14.273 | 68.185 | 3.808 | 1.00 | 41.34 |
| ATOM | 2106 OE1 | GLN | A | 334 | −14.979 | 67.270 | 3.412 | 1.00 | 35.55 |
| ATOM | 2107 NE2 | GLN | A | 334 | −14.292 | 69.383 | 3.259 | 1.00 | 30.24 |
| ATOM | 2108 N | ASP | A | 335 | −9.582 | 65.418 | 4.482 | 1.00 | 32.37 |
| ATOM | 2109 CA | ASP | A | 335 | −8.772 | 64.269 | 4.089 | 1.00 | 32.22 |
| ATOM | 2110 C | ASP | A | 335 | −7.893 | 63.821 | 5.259 | 1.00 | 37.26 |

TABLE 3-continued

Structural Coordinate of MEK1/N35/NKFCdel (corresponding to amino acids 24-373 of SEQ ID NO: 2)-ATPγS Binary Complex.

| ATOM | 2111 | O | ASP | A | 335 | −7.756 | 62.621 | 5.524 | 1.00 | 38.52 |
| --- | --- | --- | --- | --- | --- | --- | --- | --- | --- | --- |
| ATOM | 2112 | CB | ASP | A | 335 | −7.924 | 64.573 | 2.839 | 1.00 | 33.42 |
| ATOM | 2113 | CG | ASP | A | 335 | −7.064 | 63.365 | 2.392 | 1.00 | 37.13 |
| ATOM | 2114 | OD1 | ASP | A | 335 | −7.633 | 62.400 | 1.829 | 1.00 | 36.78 |
| ATOM | 2115 | OD2 | ASP | A | 335 | −5.818 | 63.417 | 2.558 | 1.00 | 37.00 |
| ATOM | 2116 | N | PHE | A | 336 | −7.321 | 64.788 | 5.971 | 1.00 | 32.39 |
| ATOM | 2117 | CA | PHE | A | 336 | −6.466 | 64.489 | 7.124 | 1.00 | 31.25 |
| ATOM | 2118 | C | PHE | A | 336 | −7.212 | 63.660 | 8.179 | 1.00 | 36.05 |
| ATOM | 2119 | O | PHE | A | 336 | −6.716 | 62.626 | 8.628 | 1.00 | 36.42 |
| ATOM | 2120 | CB | PHE | A | 336 | −5.916 | 65.782 | 7.744 | 1.00 | 32.10 |
| ATOM | 2121 | CG | PHE | A | 336 | −5.075 | 65.559 | 8.972 | 1.00 | 32.43 |
| ATOM | 2122 | CD1 | PHE | A | 336 | −3.710 | 65.321 | 8.863 | 1.00 | 34.34 |
| ATOM | 2123 | CD2 | PHE | A | 336 | −5.651 | 65.573 | 10.237 | 1.00 | 33.54 |
| ATOM | 2124 | CE1 | PHE | A | 336 | −2.930 | 65.107 | 10.004 | 1.00 | 34.94 |
| ATOM | 2125 | CE2 | PHE | A | 336 | −4.884 | 65.355 | 11.372 | 1.00 | 36.13 |
| ATOM | 2126 | CZ | PHE | A | 336 | −3.519 | 65.139 | 11.258 | 1.00 | 34.28 |
| ATOM | 2127 | N | VAL | A | 337 | −8.402 | 64.114 | 8.572 | 1.00 | 32.46 |
| ATOM | 2128 | CA | VAL | A | 337 | −9.206 | 63.383 | 9.559 | 1.00 | 32.33 |
| ATOM | 2129 | C | VAL | A | 337 | −9.614 | 62.024 | 8.999 | 1.00 | 37.81 |
| ATOM | 2130 | O | VAL | A | 337 | −9.502 | 61.014 | 9.679 | 1.00 | 37.74 |
| ATOM | 2131 | CB | VAL | A | 337 | −10.485 | 64.166 | 9.990 | 1.00 | 35.40 |
| ATOM | 2132 | CG1 | VAL | A | 337 | −10.114 | 65.442 | 10.762 | 1.00 | 34.97 |
| ATOM | 2133 | CG2 | VAL | A | 337 | −11.329 | 64.488 | 8.798 | 1.00 | 35.00 |
| ATOM | 2134 | N | ASN | A | 338 | −10.075 | 62.008 | 7.746 | 1.00 | 34.89 |
| ATOM | 2135 | CA | ASN | A | 338 | −10.455 | 60.762 | 7.087 | 1.00 | 34.59 |
| ATOM | 2136 | C | ASN | A | 338 | −9.311 | 59.740 | 7.170 | 1.00 | 39.26 |
| ATOM | 2137 | O | ASN | A | 338 | −9.530 | 58.556 | 7.459 | 1.00 | 39.04 |
| ATOM | 2138 | CB | ASN | A | 338 | −10.774 | 61.073 | 5.614 | 1.00 | 32.62 |
| ATOM | 2139 | CG | ASN | A | 338 | −12.187 | 61.534 | 5.394 | 1.00 | 42.83 |
| ATOM | 2140 | OD1 | ASN | A | 338 | −12.912 | 61.813 | 6.331 | 1.00 | 38.77 |
| ATOM | 2141 | ND2 | ASN | A | 338 | −12.560 | 61.685 | 4.142 | 1.00 | 32.76 |
| ATOM | 2142 | N | LYS | A | 339 | −8.092 | 60.189 | 6.898 | 1.00 | 35.70 |
| ATOM | 2143 | CA | LYS | A | 339 | −6.940 | 59.282 | 6.919 | 1.00 | 35.70 |
| ATOM | 2144 | C | LYS | A | 339 | −6.605 | 58.794 | 8.334 | 1.00 | 41.19 |
| ATOM | 2145 | O | LYS | A | 339 | −5.907 | 57.781 | 8.508 | 1.00 | 41.35 |
| ATOM | 2146 | CB | LYS | A | 339 | −5.729 | 59.927 | 6.241 | 1.00 | 37.26 |
| ATOM | 2147 | CG | LYS | A | 339 | −5.736 | 59.822 | 4.694 | 1.00 | 36.84 |
| ATOM | 2148 | CD | LYS | A | 339 | −4.334 | 60.076 | 4.110 | 1.00 | 41.70 |
| ATOM | 2149 | CE | LYS | A | 339 | −4.387 | 60.323 | 2.598 | 1.00 | 40.95 |
| ATOM | 2150 | NZ | LYS | A | 339 | −5.688 | 59.883 | 2.046 | 1.00 | 46.62 |
| ATOM | 2151 | N | CYS | A | 340 | −7.091 | 59.529 | 9.336 | 1.00 | 37.53 |
| ATOM | 2152 | CA | CYS | A | 340 | −6.875 | 59.194 | 10.746 | 1.00 | 37.14 |
| ATOM | 2153 | C | CYS | A | 340 | −7.966 | 58.231 | 11.240 | 1.00 | 40.99 |
| ATOM | 2154 | O | CYS | A | 340 | −7.751 | 57.463 | 12.177 | 1.00 | 39.72 |
| ATOM | 2155 | CB | CYS | A | 340 | −6.954 | 60.477 | 11.603 | 1.00 | 37.33 |
| ATOM | 2156 | SG | CYS | A | 340 | −5.449 | 61.483 | 11.706 | 1.00 | 41.16 |
| ATOM | 2157 | N | LEU | A | 341 | −9.160 | 58.340 | 10.654 | 1.00 | 38.00 |
| ATOM | 2158 | CA | LEU | A | 341 | −10.307 | 57.565 | 11.114 | 1.00 | 38.15 |
| ATOM | 2159 | C | LEU | A | 341 | −10.628 | 56.306 | 10.300 | 1.00 | 44.15 |
| ATOM | 2160 | O | LEU | A | 341 | −11.738 | 55.760 | 10.383 | 1.00 | 43.60 |
| ATOM | 2161 | CB | LEU | A | 341 | −11.529 | 58.465 | 11.256 | 1.00 | 37.90 |
| ATOM | 2162 | CG | LEU | A | 341 | −11.329 | 59.537 | 12.335 | 1.00 | 42.02 |
| ATOM | 2163 | CD1 | LEU | A | 341 | −12.565 | 60.391 | 12.532 | 1.00 | 41.53 |
| ATOM | 2164 | CD2 | LEU | A | 341 | −10.899 | 58.892 | 13.639 | 1.00 | 44.03 |
| ATOM | 2165 | N | ILE | A | 342 | −9.645 | 55.841 | 9.535 | 1.00 | 41.76 |
| ATOM | 2166 | CA | ILE | A | 342 | −9.782 | 54.623 | 8.761 | 1.00 | 41.83 |
| ATOM | 2167 | C | ILE | A | 342 | −9.766 | 53.444 | 9.749 | 1.00 | 47.02 |
| ATOM | 2168 | O | ILE | A | 342 | −8.823 | 53.300 | 10.541 | 1.00 | 46.00 |
| ATOM | 2169 | CB | ILE | A | 342 | −8.622 | 54.470 | 7.768 | 1.00 | 44.80 |
| ATOM | 2170 | CG1 | ILE | A | 342 | −8.855 | 55.348 | 6.528 | 1.00 | 44.35 |
| ATOM | 2171 | CG2 | ILE | A | 342 | −8.429 | 52.995 | 7.390 | 1.00 | 46.30 |
| ATOM | 2172 | CD1 | ILE | A | 342 | −7.597 | 55.665 | 5.750 | 1.00 | 39.39 |
| ATOM | 2173 | N | LYS | A | 343 | −10.835 | 52.646 | 9.735 | 1.00 | 44.65 |
| ATOM | 2174 | CA | LYS | A | 343 | −10.974 | 51.507 | 10.656 | 1.00 | 45.01 |
| ATOM | 2175 | C | LYS | A | 343 | −9.836 | 50.459 | 10.605 | 1.00 | 49.70 |
| ATOM | 2176 | O | LYS | A | 343 | −9.447 | 49.915 | 11.626 | 1.00 | 49.07 |
| ATOM | 2177 | CB | LYS | A | 343 | −12.343 | 50.852 | 10.504 | 1.00 | 47.44 |
| ATOM | 2178 | CG | LYS | A | 343 | −13.434 | 51.821 | 10.054 | 1.00 | 60.81 |
| ATOM | 2179 | CD | LYS | A | 343 | −14.594 | 51.847 | 11.028 | 1.00 | 67.81 |
| ATOM | 2180 | CE | LYS | A | 343 | −15.575 | 50.727 | 10.743 | 1.00 | 69.65 |
| ATOM | 2181 | NZ | LYS | A | 343 | −16.390 | 50.391 | 11.935 | 1.00 | 68.48 |
| ATOM | 2182 | N | ASN | A | 344 | −9.296 | 50.202 | 9.425 | 1.00 | 47.38 |
| ATOM | 2183 | CA | ASN | A | 344 | −8.194 | 49.256 | 9.309 | 1.00 | 47.80 |
| ATOM | 2184 | C | ASN | A | 344 | −6.899 | 49.948 | 9.712 | 1.00 | 51.62 |
| ATOM | 2185 | O | ASN | A | 344 | −6.337 | 50.735 | 8.946 | 1.00 | 51.01 |
| ATOM | 2186 | CB | ASN | A | 344 | −8.093 | 48.710 | 7.874 | 1.00 | 50.39 |
| ATOM | 2187 | CG | ASN | A | 344 | −6.964 | 47.687 | 7.700 | 1.00 | 70.04 |

TABLE 3-continued

Structural Coordinate of MEK1/N35/NKFCdel (corresponding to amino acids 24-373 of SEQ ID NO: 2)-ATPγS Binary Complex.

| ATOM | 2188 | OD1 | ASN | A | 344 | −6.069 | 47.570 | 8.540 | 1.00 | 59.25 |
|---|---|---|---|---|---|---|---|---|---|---|
| ATOM | 2189 | ND2 | ASN | A | 344 | −6.988 | 46.975 | 6.582 | 1.00 | 64.14 |
| ATOM | 2190 | N | PRO | A | 345 | −6.431 | 49.651 | 10.918 | 1.00 | 48.57 |
| ATOM | 2191 | CA | PRO | A | 345 | −5.209 | 50.262 | 11.436 | 1.00 | 48.01 |
| ATOM | 2192 | C | PRO | A | 345 | −4.064 | 50.122 | 10.447 | 1.00 | 52.08 |
| ATOM | 2193 | O | PRO | A | 345 | −3.113 | 50.913 | 10.458 | 1.00 | 51.83 |
| ATOM | 2194 | CB | PRO | A | 345 | −4.920 | 49.458 | 12.720 | 1.00 | 49.24 |
| ATOM | 2195 | CG | PRO | A | 345 | −5.713 | 48.225 | 12.604 | 1.00 | 53.44 |
| ATOM | 2196 | CD | PRO | A | 345 | −6.917 | 48.568 | 11.784 | 1.00 | 49.02 |
| ATOM | 2197 | N | ALA | A | 346 | −4.167 | 49.121 | 9.577 | 1.00 | 48.25 |
| ATOM | 2198 | CA | ALA | A | 346 | −3.136 | 48.877 | 8.570 | 1.00 | 47.92 |
| ATOM | 2199 | C | ALA | A | 346 | −3.191 | 49.949 | 7.484 | 1.00 | 50.25 |
| ATOM | 2200 | O | ALA | A | 346 | −2.164 | 50.477 | 7.058 | 1.00 | 49.06 |
| ATOM | 2201 | CB | ALA | A | 346 | −3.309 | 47.482 | 7.962 | 1.00 | 48.79 |
| ATOM | 2202 | N | GLU | A | 347 | −4.404 | 50.261 | 7.044 | 1.00 | 46.91 |
| ATOM | 2203 | CA | GLU | A | 347 | −4.613 | 51.277 | 6.029 | 1.00 | 46.99 |
| ATOM | 2204 | C | GLU | A | 347 | −4.417 | 52.664 | 6.643 | 1.00 | 49.74 |
| ATOM | 2205 | O | GLU | A | 347 | −3.809 | 53.545 | 6.029 | 1.00 | 48.84 |
| ATOM | 2206 | CB | GLU | A | 347 | −6.028 | 51.169 | 5.463 | 1.00 | 46.77 |
| ATOM | 2207 | CG | GLU | A | 347 | −6.295 | 49.905 | 4.678 | 1.00 | 63.75 |
| ATOM | 2208 | CD | GLU | A | 347 | −7.701 | 49.870 | 4.113 | 1.00 | 96.20 |
| ATOM | 2209 | OE1 | GLU | A | 347 | −8.615 | 49.393 | 4.821 | 1.00 | 97.37 |
| ATOM | 2210 | OE2 | GLU | A | 347 | −7.900 | 50.360 | 2.977 | 1.00 | 96.17 |
| ATOM | 2211 | N | ARG | A | 348 | −4.963 | 52.839 | 7.854 | 1.00 | 44.97 |
| ATOM | 2212 | CA | ARG | A | 348 | −4.897 | 54.089 | 8.597 | 1.00 | 43.31 |
| ATOM | 2213 | C | ARG | A | 348 | −3.515 | 54.707 | 8.526 | 1.00 | 46.50 |
| ATOM | 2214 | O | ARG | A | 348 | −2.514 | 54.002 | 8.555 | 1.00 | 46.48 |
| ATOM | 2215 | CB | ARG | A | 348 | −5.301 | 53.857 | 10.054 | 1.00 | 41.29 |
| ATOM | 2216 | CG | ARG | A | 348 | −5.542 | 55.139 | 10.850 | 1.00 | 44.45 |
| ATOM | 2217 | CD | ARG | A | 348 | −6.040 | 54.843 | 12.264 | 1.00 | 43.28 |
| ATOM | 2218 | NE | ARG | A | 348 | −7.104 | 53.837 | 12.282 | 1.00 | 43.15 |
| ATOM | 2219 | CZ | ARG | A | 348 | −7.283 | 52.959 | 13.268 | 1.00 | 50.47 |
| ATOM | 2220 | NH1 | ARG | A | 348 | −6.466 | 52.953 | 14.315 | 1.00 | 39.02 |
| ATOM | 2221 | NH2 | ARG | A | 348 | −8.270 | 52.086 | 13.208 | 1.00 | 35.19 |
| ATOM | 2222 | N | ALA | A | 349 | −3.467 | 56.025 | 8.381 | 1.00 | 42.62 |
| ATOM | 2223 | CA | ALA | A | 349 | −2.199 | 56.732 | 8.268 | 1.00 | 42.22 |
| ATOM | 2224 | C | ALA | A | 349 | −1.372 | 56.599 | 9.526 | 1.00 | 46.23 |
| ATOM | 2225 | O | ALA | A | 349 | −1.907 | 56.402 | 10.611 | 1.00 | 46.28 |
| ATOM | 2226 | CB | ALA | A | 349 | −2.438 | 58.188 | 7.947 | 1.00 | 43.07 |
| ATOM | 2227 | N | ASP | A | 350 | −0.057 | 56.721 | 9.383 | 1.00 | 42.78 |
| ATOM | 2228 | CA | ASP | A | 350 | 0.838 | 56.618 | 10.526 | 1.00 | 42.33 |
| ATOM | 2229 | C | ASP | A | 350 | 1.542 | 57.935 | 10.843 | 1.00 | 44.38 |
| ATOM | 2230 | O | ASP | A | 350 | 1.488 | 58.883 | 10.058 | 1.00 | 43.34 |
| ATOM | 2231 | CB | ASP | A | 350 | 1.832 | 55.443 | 10.367 | 1.00 | 44.34 |
| ATOM | 2232 | CG | ASP | A | 350 | 2.874 | 55.683 | 9.275 | 1.00 | 57.12 |
| ATOM | 2233 | OD1 | ASP | A | 350 | 2.956 | 56.808 | 8.737 | 1.00 | 57.71 |
| ATOM | 2234 | OD2 | ASP | A | 350 | 3.631 | 54.737 | 8.969 | 1.00 | 64.19 |
| ATOM | 2235 | N | LEU | A | 351 | 2.181 | 57.992 | 12.002 | 1.00 | 40.61 |
| ATOM | 2236 | CA | LEU | A | 351 | 2.840 | 59.209 | 12.454 | 1.00 | 40.60 |
| ATOM | 2237 | C | LEU | A | 351 | 3.716 | 59.863 | 11.404 | 1.00 | 45.29 |
| ATOM | 2238 | O | LEU | A | 351 | 3.714 | 61.085 | 11.255 | 1.00 | 45.97 |
| ATOM | 2239 | CB | LEU | A | 351 | 3.638 | 58.957 | 13.736 | 1.00 | 40.33 |
| ATOM | 2240 | CG | LEU | A | 351 | 2.829 | 58.740 | 15.017 | 1.00 | 44.15 |
| ATOM | 2241 | CD1 | LEU | A | 351 | 3.748 | 58.528 | 16.189 | 1.00 | 44.21 |
| ATOM | 2242 | CD2 | LEU | A | 351 | 1.870 | 59.887 | 15.272 | 1.00 | 45.14 |
| ATOM | 2243 | N | LYS | A | 352 | 4.469 | 59.052 | 10.679 | 1.00 | 41.88 |
| ATOM | 2244 | CA | LYS | A | 352 | 5.390 | 59.561 | 9.666 | 1.00 | 41.48 |
| ATOM | 2245 | C | LYS | A | 352 | 4.651 | 60.185 | 8.500 | 1.00 | 43.92 |
| ATOM | 2246 | O | LYS | A | 352 | 5.034 | 61.229 | 8.001 | 1.00 | 43.42 |
| ATOM | 2247 | CB | LYS | A | 352 | 6.316 | 58.438 | 9.175 | 1.00 | 44.12 |
| ATOM | 2248 | CG | LYS | A | 352 | 7.121 | 58.787 | 7.933 | 1.00 | 62.12 |
| ATOM | 2249 | CD | LYS | A | 352 | 8.523 | 58.191 | 7.999 | 1.00 | 73.09 |
| ATOM | 2250 | CE | LYS | A | 352 | 9.210 | 58.216 | 6.643 | 1.00 | 80.18 |
| ATOM | 2251 | NZ | LYS | A | 352 | 10.604 | 58.735 | 6.742 | 1.00 | 87.82 |
| ATOM | 2252 | N | GLN | A | 353 | 3.580 | 59.539 | 8.077 | 1.00 | 40.36 |
| ATOM | 2253 | CA | GLN | A | 353 | 2.792 | 60.021 | 6.956 | 1.00 | 39.75 |
| ATOM | 2254 | C | GLN | A | 353 | 2.054 | 61.287 | 7.328 | 1.00 | 45.00 |
| ATOM | 2255 | O | GLN | A | 353 | 2.006 | 62.235 | 6.558 | 1.00 | 45.89 |
| ATOM | 2256 | CB | GLN | A | 353 | 1.799 | 58.952 | 6.509 | 1.00 | 40.51 |
| ATOM | 2257 | CG | GLN | A | 353 | 2.445 | 57.657 | 6.045 | 1.00 | 48.12 |
| ATOM | 2258 | CD | GLN | A | 353 | 1.422 | 56.559 | 5.774 | 1.00 | 65.18 |
| ATOM | 2259 | OE1 | GLN | A | 353 | 0.256 | 56.670 | 6.155 | 1.00 | 60.77 |
| ATOM | 2260 | NE2 | GLN | A | 353 | 1.852 | 55.509 | 5.100 | 1.00 | 55.21 |
| ATOM | 2261 | N | LEU | A | 354 | 1.467 | 61.296 | 8.520 | 1.00 | 40.66 |
| ATOM | 2262 | CA | LEU | A | 354 | 0.736 | 62.459 | 8.984 | 1.00 | 39.79 |
| ATOM | 2263 | C | LEU | A | 354 | 1.610 | 63.699 | 9.041 | 1.00 | 43.41 |
| ATOM | 2264 | O | LEU | A | 354 | 1.194 | 64.766 | 8.610 | 1.00 | 42.46 |

TABLE 3-continued

Structural Coordinate of MEK1/N35/NKFCdel (corresponding to amino acids 24-373 of SEQ ID NO: 2)-ATPγS Binary Complex.

| ATOM | 2265 | CB | LEU | A | 354 | 0.074 | 62.181 | 10.326 | 1.00 | 39.82 |
|---|---|---|---|---|---|---|---|---|---|---|
| ATOM | 2266 | CG | LEU | A | 354 | −1.012 | 61.106 | 10.237 | 1.00 | 44.45 |
| ATOM | 2267 | CD1 | LEU | A | 354 | −1.499 | 60.686 | 11.608 | 1.00 | 44.83 |
| ATOM | 2268 | CD2 | LEU | A | 354 | −2.163 | 61.563 | 9.359 | 1.00 | 45.68 |
| ATOM | 2269 | N | MET | A | 355 | 2.840 | 63.550 | 9.521 | 1.00 | 40.74 |
| ATOM | 2270 | CA | MET | A | 355 | 3.760 | 64.684 | 9.610 | 1.00 | 41.52 |
| ATOM | 2271 | C | MET | A | 355 | 3.945 | 65.406 | 8.275 | 1.00 | 44.68 |
| ATOM | 2272 | O | MET | A | 355 | 4.226 | 66.616 | 8.243 | 1.00 | 43.59 |
| ATOM | 2273 | CB | MET | A | 355 | 5.114 | 64.245 | 10.167 | 1.00 | 44.89 |
| ATOM | 2274 | CG | MET | A | 355 | 5.265 | 64.450 | 11.682 | 1.00 | 50.02 |
| ATOM | 2275 | SD | MET | A | 355 | 5.168 | 66.209 | 12.171 | 1.00 | 55.56 |
| ATOM | 2276 | CE | MET | A | 355 | 3.433 | 66.361 | 12.511 | 1.00 | 52.58 |
| ATOM | 2277 | N | VAL | A | 356 | 3.801 | 64.664 | 7.172 | 1.00 | 40.68 |
| ATOM | 2278 | CA | VAL | A | 356 | 3.948 | 65.239 | 5.847 | 1.00 | 39.65 |
| ATOM | 2279 | C | VAL | A | 356 | 2.629 | 65.356 | 5.070 | 1.00 | 41.64 |
| ATOM | 2280 | O | VAL | A | 356 | 2.621 | 65.708 | 3.883 | 1.00 | 41.57 |
| ATOM | 2281 | CB | VAL | A | 356 | 5.030 | 64.524 | 5.024 | 1.00 | 43.95 |
| ATOM | 2282 | CG1 | VAL | A | 356 | 6.380 | 64.626 | 5.746 | 1.00 | 44.15 |
| ATOM | 2283 | CG2 | VAL | A | 356 | 4.653 | 63.055 | 4.780 | 1.00 | 43.54 |
| ATOM | 2284 | N | HIS | A | 357 | 1.513 | 65.108 | 5.752 | 1.00 | 35.73 |
| ATOM | 2285 | CA | HIS | A | 357 | 0.204 | 65.258 | 5.124 | 1.00 | 34.05 |
| ATOM | 2286 | C | HIS | A | 357 | 0.009 | 66.733 | 4.761 | 1.00 | 37.68 |
| ATOM | 2287 | O | HIS | A | 357 | 0.482 | 67.626 | 5.480 | 1.00 | 37.19 |
| ATOM | 2288 | CB | HIS | A | 357 | −0.906 | 64.792 | 6.073 | 1.00 | 34.03 |
| ATOM | 2289 | CG | HIS | A | 357 | −2.267 | 64.771 | 5.444 | 1.00 | 36.92 |
| ATOM | 2290 | ND1 | HIS | A | 357 | −3.003 | 65.918 | 5.219 | 1.00 | 38.26 |
| ATOM | 2291 | CD2 | HIS | A | 357 | −3.019 | 63.744 | 4.980 | 1.00 | 37.92 |
| ATOM | 2292 | CE1 | HIS | A | 357 | −4.157 | 65.593 | 4.664 | 1.00 | 37.28 |
| ATOM | 2293 | NE2 | HIS | A | 357 | −4.189 | 64.282 | 4.502 | 1.00 | 37.55 |
| ATOM | 2294 | N | ALA | A | 358 | −0.640 | 66.978 | 3.620 | 1.00 | 33.50 |
| ATOM | 2295 | CA | ALA | A | 358 | −0.868 | 68.335 | 3.107 | 1.00 | 32.56 |
| ATOM | 2296 | C | ALA | A | 358 | −1.489 | 69.290 | 4.122 | 1.00 | 36.64 |
| ATOM | 2297 | O | ALA | A | 358 | −1.272 | 70.512 | 4.057 | 1.00 | 37.11 |
| ATOM | 2298 | CB | ALA | A | 358 | −1.710 | 68.288 | 1.876 | 1.00 | 33.16 |
| ATOM | 2299 | N | PHE | A | 359 | −2.299 | 68.757 | 5.035 | 1.00 | 31.31 |
| ATOM | 2300 | CA | PHE | A | 359 | −2.938 | 69.604 | 6.026 | 1.00 | 30.79 |
| ATOM | 2301 | C | PHE | A | 359 | −1.945 | 70.049 | 7.075 | 1.00 | 36.81 |
| ATOM | 2302 | O | PHE | A | 359 | −1.988 | 71.188 | 7.546 | 1.00 | 35.68 |
| ATOM | 2303 | CB | PHE | A | 359 | −4.118 | 68.888 | 6.664 | 1.00 | 32.00 |
| ATOM | 2304 | CG | PHE | A | 359 | −4.677 | 69.587 | 7.874 | 1.00 | 33.12 |
| ATOM | 2305 | CD1 | PHE | A | 359 | −5.380 | 70.765 | 7.743 | 1.00 | 35.48 |
| ATOM | 2306 | CD2 | PHE | A | 359 | −4.526 | 69.065 | 9.123 | 1.00 | 34.43 |
| ATOM | 2307 | CE1 | PHE | A | 359 | −5.875 | 71.443 | 8.849 | 1.00 | 35.90 |
| ATOM | 2308 | CE2 | PHE | A | 359 | −5.113 | 69.679 | 10.234 | 1.00 | 36.83 |
| ATOM | 2309 | CZ | PHE | A | 359 | −5.802 | 70.861 | 10.078 | 1.00 | 34.97 |
| ATOM | 2310 | N | ILE | A | 360 | −1.055 | 69.139 | 7.452 | 1.00 | 34.44 |
| ATOM | 2311 | CA | ILE | A | 360 | −0.044 | 69.431 | 8.444 | 1.00 | 34.33 |
| ATOM | 2312 | C | ILE | A | 360 | 1.000 | 70.405 | 7.891 | 1.00 | 39.99 |
| ATOM | 2313 | O | ILE | A | 360 | 1.329 | 71.404 | 8.528 | 1.00 | 40.13 |
| ATOM | 2314 | CB | ILE | A | 360 | 0.629 | 68.130 | 8.946 | 1.00 | 36.87 |
| ATOM | 2315 | CG1 | ILE | A | 360 | −0.348 | 67.339 | 9.835 | 1.00 | 36.07 |
| ATOM | 2316 | CG2 | ILE | A | 360 | 1.918 | 68.446 | 9.704 | 1.00 | 37.09 |
| ATOM | 2317 | CD1 | ILE | A | 360 | −1.053 | 68.203 | 10.909 | 1.00 | 31.13 |
| ATOM | 2318 | N | LYS | A | 361 | 1.478 | 70.134 | 6.686 | 1.00 | 37.87 |
| ATOM | 2319 | CA | LYS | A | 361 | 2.462 | 70.994 | 6.034 | 1.00 | 38.04 |
| ATOM | 2320 | C | LYS | A | 361 | 1.919 | 72.406 | 5.860 | 1.00 | 42.35 |
| ATOM | 2321 | O | LYS | A | 361 | 2.621 | 73.381 | 6.102 | 1.00 | 42.56 |
| ATOM | 2322 | CB | LYS | A | 361 | 2.865 | 70.412 | 4.679 | 1.00 | 40.74 |
| ATOM | 2323 | CG | LYS | A | 361 | 4.069 | 69.509 | 4.738 | 1.00 | 54.10 |
| ATOM | 2324 | CD | LYS | A | 361 | 3.829 | 68.225 | 3.976 | 1.00 | 65.94 |
| ATOM | 2325 | CB | LYS | A | 361 | 3.832 | 68.452 | 2.473 | 1.00 | 73.16 |
| ATOM | 2326 | NZ | LYS | A | 361 | 3.044 | 67.406 | 1.761 | 1.00 | 80.60 |
| ATOM | 2327 | N | ARG | A | 362 | 0.664 | 72.508 | 5.442 | 1.00 | 38.96 |
| ATOM | 2328 | CA | ARG | A | 362 | 0.016 | 73.809 | 5.280 | 1.00 | 38.95 |
| ATOM | 2329 | C | ARG | A | 362 | −0.096 | 74.515 | 6.641 | 1.00 | 45.56 |
| ATOM | 2330 | O | ARG | A | 362 | 0.200 | 75.702 | 6.765 | 1.00 | 46.13 |
| ATOM | 2331 | CB | ARG | A | 362 | −1.376 | 73.643 | 4.670 | 1.00 | 36.35 |
| ATOM | 2332 | CG | ARG | A | 362 | −2.032 | 74.951 | 4.229 | 1.00 | 39.05 |
| ATOM | 2333 | CD | ARG | A | 362 | −3.544 | 74.799 | 4.049 | 1.00 | 37.27 |
| ATOM | 2334 | NE | ARG | A | 362 | −4.261 | 74.789 | 5.334 | 1.00 | 35.14 |
| ATOM | 2335 | CZ | ARG | A | 362 | −5.460 | 74.244 | 5.518 | 1.00 | 41.42 |
| ATOM | 2336 | NH1 | ARG | A | 362 | −6.078 | 73.638 | 4.508 | 1.00 | 24.66 |
| ATOM | 2337 | NH2 | ARG | A | 362 | −6.046 | 74.303 | 6.708 | 1.00 | 25.38 |
| ATOM | 2338 | N | SER | A | 363 | −0.496 | 73.761 | 7.659 | 1.00 | 42.40 |
| ATOM | 2339 | CA | SER | A | 363 | −0.666 | 74.301 | 8.999 | 1.00 | 42.43 |
| ATOM | 2340 | C | SER | A | 363 | 0.646 | 74.818 | 9.575 | 1.00 | 48.61 |
| ATOM | 2341 | O | SER | A | 363 | 0.588 | 75.881 | 10.193 | 1.00 | 48.04 |

TABLE 3-continued

Structural Coordinate of MEK1/N35/NKFCdel (corresponding to amino acids 24-373 of SEQ ID NO: 2)-ATPγS Binary Complex.

| ATOM | 2342 | CB | SER | A | 363 | −1.270 | 73.246 | 9.930 | 1.00 | 44.67 |
| --- | --- | --- | --- | --- | --- | --- | --- | --- | --- | --- |
| ATOM | 2343 | OG | SER | A | 363 | −2.610 | 72.953 | 9.577 | 1.00 | 49.02 |
| ATOM | 2344 | N | ASP | A | 364 | 1.712 | 74.050 | 9.385 | 1.00 | 47.04 |
| ATOM | 2345 | CA | ASP | A | 364 | 3.027 | 74.422 | 9.898 | 1.00 | 47.11 |
| ATOM | 2346 | C | ASP | A | 364 | 3.492 | 75.765 | 9.350 | 1.00 | 50.65 |
| ATOM | 2347 | O | ASP | A | 364 | 4.144 | 76.539 | 10.053 | 1.00 | 50.84 |
| ATOM | 2348 | CB | ASP | A | 364 | 4.054 | 73.336 | 9.565 | 1.00 | 49.13 |
| ATOM | 2349 | CG | ASP | A | 364 | 4.897 | 72.930 | 10.774 | 1.00 | 61.15 |
| ATOM | 2350 | OD1 | ASP | A | 364 | 5.157 | 73.793 | 11.639 | 1.00 | 62.63 |
| ATOM | 2351 | OD2 | ASP | A | 364 | 5.326 | 71.753 | 10.840 | 1.00 | 66.63 |
| ATOM | 2352 | N | ALA | A | 365 | 3.161 | 76.036 | 8.092 | 1.00 | 46.50 |
| ATOM | 2353 | CA | ALA | A | 365 | 3.575 | 77.277 | 7.438 | 1.00 | 46.30 |
| ATOM | 2354 | C | ALA | A | 365 | 2.594 | 78.417 | 7.694 | 1.00 | 51.12 |
| ATOM | 2355 | O | ALA | A | 365 | 2.728 | 79.511 | 7.128 | 1.00 | 51.56 |
| ATOM | 2356 | CB | ALA | A | 365 | 3.753 | 77.054 | 5.934 | 1.00 | 46.87 |
| ATOM | 2357 | N | GLU | A | 366 | 1.590 | 78.151 | 8.516 | 1.00 | 46.89 |
| ATOM | 2358 | CA | GLU | A | 366 | 0.600 | 79.159 | 8.840 | 1.00 | 46.38 |
| ATOM | 2359 | C | GLU | A | 366 | 1.023 | 79.932 | 10.077 | 1.00 | 51.46 |
| ATOM | 2360 | O | GLU | A | 366 | 1.396 | 79.348 | 11.089 | 1.00 | 51.01 |
| ATOM | 2361 | CB | GLU | A | 366 | −0.762 | 78.517 | 9.069 | 1.00 | 47.31 |
| ATOM | 2362 | CG | GLU | A | 366 | −1.678 | 78.544 | 7.858 | 1.00 | 50.12 |
| ATOM | 2363 | CD | GLU | A | 366 | −2.811 | 77.552 | 7.976 | 1.00 | 55.67 |
| ATOM | 2364 | OE1 | GLU | A | 366 | −3.017 | 77.013 | 9.090 | 1.00 | 37.31 |
| ATOM | 2365 | OE2 | GLU | A | 366 | −3.481 | 77.291 | 6.954 | 1.00 | 45.47 |
| ATOM | 2366 | N | GLU | A | 367 | 0.977 | 81.253 | 9.983 | 1.00 | 49.32 |
| ATOM | 2367 | CA | GLU | A | 367 | 1.329 | 82.114 | 11.111 | 1.00 | 49.62 |
| ATOM | 2368 | C | GLU | A | 367 | 0.076 | 82.330 | 11.906 | 1.00 | 52.60 |
| ATOM | 2369 | O | GLU | A | 367 | −0.635 | 83.311 | 11.704 | 1.00 | 51.88 |
| ATOM | 2370 | CB | GLU | A | 367 | 1.878 | 83.470 | 10.623 | 1.00 | 51.35 |
| ATOM | 2371 | CG | GLU | A | 367 | 2.906 | 83.374 | 9.481 | 1.00 | 63.53 |
| ATOM | 2372 | CD | GLU | A | 367 | 4.099 | 82.509 | 9.839 | 1.00 | 88.72 |
| ATOM | 2373 | OE1 | GLU | A | 367 | 4.104 | 81.916 | 10.939 | 1.00 | 83.80 |
| ATOM | 2374 | OE2 | GLU | A | 367 | 5.043 | 82.414 | 9.016 | 1.00 | 87.05 |
| ATOM | 2375 | N | VAL | A | 368 | −0.239 | 81.370 | 12.762 | 1.00 | 48.90 |
| ATOM | 2376 | CA | VAL | A | 368 | −1.463 | 81.418 | 13.544 | 1.00 | 48.10 |
| ATOM | 2377 | C | VAL | A | 368 | −1.156 | 81.731 | 14.999 | 1.00 | 49.60 |
| ATOM | 2378 | O | VAL | A | 368 | −0.335 | 81.068 | 15.627 | 1.00 | 49.00 |
| ATOM | 2379 | CB | VAL | A | 368 | −2.238 | 80.071 | 13.436 | 1.00 | 52.01 |
| ATOM | 2380 | CG1 | VAL | A | 368 | −3.298 | 79.964 | 14.509 | 1.00 | 51.80 |
| ATOM | 2381 | CG2 | VAL | A | 368 | −2.848 | 79.927 | 12.064 | 1.00 | 51.85 |
| ATOM | 2382 | N | ASP | A | 369 | −1.795 | 82.766 | 15.527 | 1.00 | 44.47 |
| ATOM | 2383 | CA | ASP | A | 369 | −1.574 | 83.150 | 16.913 | 1.00 | 43.03 |
| ATOM | 2384 | C | ASP | A | 369 | −2.507 | 82.364 | 17.828 | 1.00 | 43.31 |
| ATOM | 2385 | O | ASP | A | 369 | −3.615 | 82.798 | 18.131 | 1.00 | 44.11 |
| ATOM | 2386 | CB | ASP | A | 369 | −1.772 | 84.648 | 17.105 | 1.00 | 44.59 |
| ATOM | 2387 | CG | ASP | A | 369 | −1.469 | 85.088 | 18.508 | 1.00 | 54.79 |
| ATOM | 2388 | OD1 | ASP | A | 369 | −0.436 | 84.653 | 19.051 | 1.00 | 55.39 |
| ATOM | 2389 | OD2 | ASP | A | 369 | −2.291 | 85.820 | 19.091 | 1.00 | 63.47 |
| ATOM | 2390 | N | PHE | A | 370 | −2.060 | 81.190 | 18.235 | 1.00 | 36.16 |
| ATOM | 2391 | CA | PHE | A | 370 | −2.854 | 80.324 | 19.086 | 1.00 | 34.38 |
| ATOM | 2392 | C | PHE | A | 370 | −3.081 | 80.938 | 20.473 | 1.00 | 37.05 |
| ATOM | 2393 | O | PHE | A | 370 | −4.202 | 80.941 | 20.983 | 1.00 | 36.56 |
| ATOM | 2394 | CB | PHE | A | 370 | −2.204 | 78.943 | 19.206 | 1.00 | 35.28 |
| ATOM | 2395 | CG | PHE | A | 370 | −2.849 | 78.065 | 20.241 | 1.00 | 36.42 |
| ATOM | 2396 | CD1 | PHE | A | 370 | −4.107 | 77.542 | 20.031 | 1.00 | 39.84 |
| ATOM | 2397 | CD2 | PHE | A | 370 | −2.226 | 77.821 | 21.445 | 1.00 | 37.64 |
| ATOM | 2398 | CE1 | PHE | A | 370 | −4.716 | 76.757 | 20.995 | 1.00 | 40.63 |
| ATOM | 2399 | CE2 | PHE | A | 370 | −2.825 | 77.037 | 22.399 | 1.00 | 40.55 |
| ATOM | 2400 | CZ | PHE | A | 370 | −4.066 | 76.504 | 22.175 | 1.00 | 38.96 |
| ATOM | 2401 | N | ALA | A | 371 | −2.011 | 81.451 | 21.077 | 1.00 | 33.13 |
| ATOM | 2402 | CA | ALA | A | 371 | −2.108 | 82.073 | 22.397 | 1.00 | 32.86 |
| ATOM | 2403 | C | ALA | A | 371 | −3.178 | 83.145 | 22.401 | 1.00 | 36.60 |
| ATOM | 2404 | O | ALA | A | 371 | −4.119 | 83.094 | 23.189 | 1.00 | 37.76 |
| ATOM | 2405 | CB | ALA | A | 371 | −0.763 | 82.654 | 22.822 | 1.00 | 33.45 |
| ATOM | 2406 | N | GLY | A | 372 | −3.037 | 84.112 | 21.507 | 1.00 | 32.47 |
| ATOM | 2407 | CA | GLY | A | 372 | −4.006 | 85.194 | 21.392 | 1.00 | 32.13 |
| ATOM | 2408 | C | GLY | A | 372 | −5.409 | 84.632 | 21.246 | 1.00 | 36.18 |
| ATOM | 2409 | O | GLY | A | 372 | −6.297 | 84.978 | 22.014 | 1.00 | 36.34 |
| ATOM | 2410 | N | TRP | A | 373 | −5.601 | 83.742 | 20.269 | 1.00 | 31.93 |
| ATOM | 2411 | CA | TRP | A | 373 | −6.916 | 83.130 | 20.056 | 1.00 | 31.44 |
| ATOM | 2412 | C | TRP | A | 373 | −7.391 | 82.472 | 21.323 | 1.00 | 36.35 |
| ATOM | 2413 | O | TRP | A | 373 | −8.549 | 82.627 | 21.718 | 1.00 | 36.63 |
| ATOM | 2414 | CB | TRP | A | 373 | −6.879 | 82.077 | 18.932 | 1.00 | 29.43 |
| ATOM | 2415 | CG | TRP | A | 373 | −8.168 | 81.261 | 18.862 | 1.00 | 29.63 |
| ATOM | 2416 | CD1 | TRP | A | 373 | −9.273 | 81.533 | 18.101 | 1.00 | 32.47 |
| ATOM | 2417 | CD2 | TRP | A | 373 | −8.499 | 80.100 | 19.644 | 1.00 | 28.88 |
| ATOM | 2418 | NE1 | TRP | A | 373 | −10.258 | 80.604 | 18.347 | 1.00 | 31.57 |

TABLE 3-continued

Structural Coordinate of MEK1/N35/NKFCdel (corresponding to amino acids 24-373 of SEQ ID NO: 2)-ATPγS Binary Complex.

| ATOM | 2419 | CE2 | TRP | A | 373 | −9.807 | 79.717 | 19.291 | 1.00 | 32.79 |
|---|---|---|---|---|---|---|---|---|---|---|
| ATOM | 2420 | CE3 | TRP | A | 373 | −7.810 | 79.339 | 20.590 | 1.00 | 29.57 |
| ATOM | 2421 | CZ2 | TRP | A | 373 | −10.436 | 78.605 | 19.851 | 1.00 | 32.00 |
| ATOM | 2422 | CZ3 | TRP | A | 373 | −8.437 | 78.242 | 21.145 | 1.00 | 30.75 |
| ATOM | 2423 | CH2 | TRP | A | 373 | −9.735 | 77.889 | 20.779 | 1.00 | 31.50 |
| ATOM | 2424 | N | LEU | A | 374 | −6.500 | 81.717 | 21.960 | 1.00 | 33.16 |
| ATOM | 2425 | CA | LEU | A | 374 | −6.856 | 81.017 | 23.192 | 1.00 | 33.50 |
| ATOM | 2426 | C | LEU | A | 374 | −7.272 | 81.979 | 24.307 | 1.00 | 38.34 |
| ATOM | 2427 | O | LEU | A | 374 | −8.301 | 81.788 | 24.945 | 1.00 | 37.68 |
| ATOM | 2428 | CB | LEU | A | 374 | −5.717 | 80.111 | 23.662 | 1.00 | 33.58 |
| ATOM | 2429 | CG | LEU | A | 374 | −5.899 | 79.531 | 25.076 | 1.00 | 38.67 |
| ATOM | 2430 | CD1 | LEU | A | 374 | −7.081 | 78.605 | 25.116 | 1.00 | 39.03 |
| ATOM | 2431 | CD2 | LEU | A | 374 | −4.646 | 78.819 | 25.547 | 1.00 | 40.78 |
| ATOM | 2432 | N | CYS | A | 375 | −6.479 | 83.018 | 24.532 | 1.00 | 36.70 |
| ATOM | 2433 | CA | CYS | A | 375 | −6.783 | 83.969 | 25.605 | 1.00 | 37.68 |
| ATOM | 2434 | C | CYS | A | 375 | −8.110 | 84.704 | 25.449 | 1.00 | 39.93 |
| ATOM | 2435 | O | CYS | A | 375 | −8.850 | 84.853 | 26.414 | 1.00 | 38.93 |
| ATOM | 2436 | CB | CYS | A | 375 | −5.617 | 84.923 | 25.861 | 1.00 | 38.67 |
| ATOM | 2437 | SG | CYS | A | 375 | −4.129 | 84.047 | 26.457 | 1.00 | 43.09 |
| ATOM | 2438 | N | SER | A | 376 | −8.443 | 85.094 | 24.228 | 1.00 | 36.31 |
| ATOM | 2439 | CA | SER | A | 376 | −9.722 | 85.776 | 23.981 | 1.00 | 36.59 |
| ATOM | 2440 | C | SER | A | 376 | −10.911 | 84.828 | 24.086 | 1.00 | 39.80 |
| ATOM | 2441 | O | SER | A | 376 | −11.995 | 85.223 | 24.495 | 1.00 | 39.05 |
| ATOM | 2442 | CB | SER | A | 376 | −9.726 | 86.463 | 22.617 | 1.00 | 39.67 |
| ATOM | 2443 | OG | SER | A | 376 | −8.459 | 86.384 | 22.023 | 1.00 | 51.54 |
| ATOM | 2444 | N | THR | A | 377 | −10.695 | 83.575 | 23.722 | 1.00 | 36.28 |
| ATOM | 2445 | CA | THR | A | 377 | −11.755 | 82.587 | 23.747 | 1.00 | 35.99 |
| ATOM | 2446 | C | THR | A | 377 | −12.171 | 82.164 | 25.151 | 1.00 | 40.71 |
| ATOM | 2447 | O | THR | A | 377 | −13.353 | 81.896 | 25.403 | 1.00 | 40.63 |
| ATOM | 2448 | CB | THR | A | 377 | −11.384 | 81.355 | 22.927 | 1.00 | 40.94 |
| ATOM | 2449 | OG1 | THR | A | 377 | −11.143 | 81.751 | 21.575 | 1.00 | 36.69 |
| ATOM | 2450 | CG2 | THR | A | 377 | −12.503 | 80.339 | 22.965 | 1.00 | 38.93 |
| ATOM | 2451 | N | ILE | A | 378 | −11.210 | 82.061 | 26.061 | 1.00 | 37.53 |
| ATOM | 2452 | CA | ILE | A | 378 | −11.547 | 81.657 | 27.420 | 1.00 | 37.78 |
| ATOM | 2453 | C | ILE | A | 378 | −11.534 | 82.800 | 28.409 | 1.00 | 43.45 |
| ATOM | 2454 | O | ILE | A | 378 | −11.781 | 82.604 | 29.583 | 1.00 | 43.32 |
| ATOM | 2455 | CB | ILE | A | 378 | −10.699 | 80.459 | 27.936 | 1.00 | 40.42 |
| ATOM | 2456 | CG1 | ILE | A | 378 | −9.272 | 80.883 | 28.245 | 1.00 | 40.30 |
| ATOM | 2457 | CG2 | ILE | A | 378 | −10.734 | 79.306 | 26.949 | 1.00 | 41.11 |
| ATOM | 2458 | CD1 | ILE | A | 378 | −8.379 | 79.720 | 28.602 | 1.00 | 45.64 |
| ATOM | 2459 | N | GLY | A | 379 | −11.290 | 84.004 | 27.919 | 1.00 | 42.13 |
| ATOM | 2460 | CA | GLY | A | 379 | −11.292 | 85.177 | 28.776 | 1.00 | 43.39 |
| ATOM | 2461 | C | GLY | A | 379 | −10.072 | 85.173 | 29.674 | 1.00 | 51.72 |
| ATOM | 2462 | O | GLY | A | 379 | −10.061 | 85.798 | 30.726 | 1.00 | 51.01 |
| ATOM | 2463 | N | LEU | A | 380 | −9.035 | 84.476 | 29.238 | 1.00 | 52.39 |
| ATOM | 2464 | CA | LEU | A | 380 | −7.813 | 84.392 | 30.000 | 1.00 | 54.24 |
| ATOM | 2465 | C | LEU | A | 380 | −7.175 | 85.752 | 30.130 | 1.00 | 65.03 |
| ATOM | 2466 | O | LEU | A | 380 | −6.759 | 86.354 | 29.139 | 1.00 | 64.33 |
| ATOM | 2467 | CB | LEU | A | 380 | −6.838 | 83.434 | 29.337 | 1.00 | 54.22 |
| ATOM | 2468 | CG | LEU | A | 380 | −6.458 | 82.212 | 30.161 | 1.00 | 58.89 |
| ATOM | 2469 | CD1 | LEU | A | 380 | −5.407 | 81.381 | 29.439 | 1.00 | 58.67 |
| ATOM | 2470 | CD2 | LEU | A | 380 | −5.956 | 82.652 | 31.520 | 1.00 | 61.91 |
| ATOM | 2471 | N | ASN | A | 381 | −7.117 | 86.244 | 31.356 | 1.00 | 65.42 |
| ATOM | 2472 | CA | ASN | A | 381 | −6.466 | 87.501 | 31.622 | 1.00 | 66.91 |
| ATOM | 2473 | C | ASN | A | 381 | −5.059 | 87.160 | 32.081 | 1.00 | 75.34 |
| ATOM | 2474 | O | ASN | A | 381 | −4.799 | 86.982 | 33.280 | 1.00 | 73.40 |
| ATOM | 2475 | CB | ASN | A | 381 | −7.217 | 88.280 | 32.701 | 1.00 | 69.11 |
| ATOM | 2476 | CG | ASN | A | 381 | −8.246 | 89.240 | 32.118 | 1.00 | 92.46 |
| ATOM | 2477 | OD1 | ASN | A | 381 | −7.901 | 90.173 | 31.391 | 1.00 | 84.96 |
| ATOM | 2478 | ND2 | ASN | A | 381 | −9.516 | 88.979 | 32.389 | 1.00 | 84.25 |
| ATOM | 2479 | N | GLN | A | 382 | −4.173 | 86.987 | 31.094 | 1.00 | 71.96 |
| ATOM | 2480 | CA | GLN | A | 382 | −2.777 | 86.654 | 31.338 | 1.00 | 76.37 |
| ATOM | 2481 | C | GLN | A | 382 | −1.939 | 86.803 | 30.067 | 1.00 | 97.16 |
| ATOM | 2482 | O | GLN | A | 382 | −0.734 | 86.482 | 30.101 | 1.00 | 97.72 |
| ATOM | 2483 | CB | GLN | A | 382 | −2.645 | 85.233 | 31.900 | 1.00 | 77.20 |
| ATOM | 2484 | CG | GLN | A | 382 | −2.538 | 85.170 | 33.423 | 1.00 | 96.81 |
| ATOM | 2485 | CD | GLN | A | 382 | −2.784 | 83.764 | 33.984 | 1.00 | 117.77 |
| ATOM | 2486 | OE1 | GLN | A | 382 | −3.602 | 83.572 | 34.877 | 1.00 | 116.29 |
| ATOM | 2487 | NE2 | GLN | A | 382 | −2.070 | 82.788 | 33.421 | 1.00 | 111.31 |
| ATOM | 2488 | OH | OXY | A | 383 | −2.483 | 87.265 | 29.028 | 1.00 | 102.92 |
| ATOM | 2489 | OW | WAT | W | 1 | −4.677 | 75.012 | 8.897 | 1.00 | 29.92 |
| ATOM | 2490 | OW | WAT | W | 2 | −2.646 | 76.265 | 11.688 | 1.00 | 43.10 |
| ATOM | 2491 | OW | WAT | W | 3 | −3.542 | 69.196 | −0.989 | 1.00 | 25.79 |
| ATOM | 2492 | OW | WAT | W | 4 | −14.637 | 74.665 | 13.584 | 1.00 | 37.39 |
| ATOM | 2493 | OW | WAT | W | 5 | −12.047 | 57.559 | 7.325 | 1.00 | 38.13 |
| ATOM | 2494 | OW | WAT | W | 7 | −13.861 | 59.413 | 8.131 | 1.00 | 37.79 |
| ATOM | 2495 | OW | WAT | W | 9 | 3.886 | 72.894 | 22.594 | 1.00 | 44.90 |

TABLE 3-continued

Structural Coordinate of MEK1/N35/NKFCdel (corresponding to amino acids 24-373 of SEQ ID NO: 2)-ATPγS Binary Complex.

| ATOM | 2496 | OW | WAT | W | 10 | −7.972 | 61.813 | −0.942 | 1.00 | 35.63 |
|------|------|----|-----|---|----|--------|--------|--------|------|-------|
| ATOM | 2497 | OW | WAT | W | 11 | −11.435 | 56.720 | 25.315 | 1.00 | 46.19 |
| ATOM | 2498 | OW | WAT | W | 12 | −5.122 | 56.927 | 22.437 | 1.00 | 44.04 |
| ATOM | 2499 | OW | WAT | W | 13 | −11.727 | 63.993 | 26.923 | 1.00 | 36.75 |
| ATOM | 2500 | OW | WAT | W | 14 | 0.335 | 77.923 | 32.134 | 1.00 | 43.16 |
| ATOM | 2501 | OW | WAT | W | 15 | −15.596 | 65.065 | 5.230 | 1.00 | 45.81 |
| ATOM | 2502 | OW | WAT | W | 17 | −13.836 | 55.971 | 19.338 | 1.00 | 44.33 |
| ATOM | 2503 | OW | WAT | W | 19 | 6.296 | 61.088 | 12.869 | 1.00 | 47.22 |
| ATOM | 2504 | OW | WAT | W | 21 | −16.352 | 53.847 | 28.747 | 1.00 | 43.38 |
| ATOM | 2505 | OW | WAT | W | 22 | −13.557 | 86.315 | 26.448 | 1.00 | 43.30 |
| ATOM | 2506 | OW | WAT | W | 23 | −9.962 | 61.079 | 2.335 | 1.00 | 33.74 |
| ATOM | 2507 | OW | WAT | W | 24 | 0.800 | 81.118 | 19.767 | 1.00 | 45.67 |
| ATOM | 2508 | OW | WAT | W | 25 | −14.545 | 67.283 | 24.731 | 1.00 | 34.47 |
| ATOM | 2509 | OW | WAT | W | 26 | −16.130 | 69.784 | 25.742 | 1.00 | 36.46 |
| ATOM | 2510 | OW | WAT | W | 27 | 9.844 | 66.723 | 21.240 | 1.00 | 53.69 |
| ATOM | 2511 | OW | WAT | W | 28 | −2.946 | 70.139 | 47.704 | 1.00 | 39.92 |
| ATOM | 2512 | OW | WAT | W | 29 | 4.611 | 56.076 | 12.722 | 1.00 | 54.38 |
| ATOM | 2513 | OW | WAT | W | 30 | −7.608 | 54.046 | 20.786 | 1.00 | 39.58 |
| ATOM | 2514 | OW | WAT | W | 31 | −14.003 | 64.412 | 7.297 | 1.00 | 37.71 |
| ATOM | 2515 | OW | WAT | W | 33 | −12.903 | 75.723 | 7.970 | 1.00 | 44.47 |
| ATOM | 2516 | OW | WAT | W | 35 | −19.004 | 72.509 | 22.021 | 1.00 | 45.20 |
| ATOM | 2517 | OW | WAT | W | 36 | −13.336 | 82.004 | 20.014 | 1.00 | 37.66 |
| ATOM | 2518 | OW | WAT | W | 38 | −0.061 | 71.463 | 1.999 | 1.00 | 37.04 |
| ATOM | 2519 | OW | WAT | W | 39 | −8.643 | 57.869 | 24.959 | 1.00 | 43.69 |
| ATOM | 2520 | OW | WAT | W | 41 | 7.283 | 70.928 | 27.903 | 1.00 | 43.53 |
| ATOM | 2521 | OW | WAT | W | 43 | −16.400 | 53.830 | 13.182 | 1.00 | 41.38 |
| ATOM | 2522 | OW | WAT | W | 44 | 5.463 | 73.319 | 6.228 | 1.00 | 54.69 |
| ATOM | 2523 | OW | WAT | W | 45 | 7.692 | 75.328 | 24.020 | 1.00 | 43.18 |
| ATOM | 2524 | OW | WAT | W | 47 | −18.307 | 68.157 | 22.750 | 1.00 | 42.43 |
| ATOM | 2525 | OW | WAT | W | 48 | −2.078 | 57.184 | 4.813 | 1.00 | 45.19 |
| ATOM | 2526 | OW | WAT | W | 49 | 6.108 | 55.206 | 7.090 | 1.00 | 66.19 |
| ATOM | 2527 | OW | WAT | W | 51 | 9.568 | 73.890 | 24.843 | 1.00 | 49.20 |
| ATOM | 2528 | OW | WAT | W | 52 | −3.328 | 49.531 | 16.566 | 1.00 | 62.04 |
| ATOM | 2529 | OW | WAT | W | 54 | −16.516 | 66.659 | 1.082 | 1.00 | 48.24 |
| ATOM | 2530 | OW | WAT | W | 55 | −7.652 | 55.380 | 23.236 | 1.00 | 50.26 |
| ATOM | 2531 | OW | WAT | W | 56 | −20.024 | 65.688 | 11.384 | 1.00 | 72.50 |
| ATOM | 2532 | OW | WAT | W | 57 | −9.925 | 76.205 | 30.057 | 1.00 | 54.47 |
| ATOM | 2533 | OW | WAT | W | 58 | −1.233 | 64.940 | 1.639 | 1.00 | 42.66 |
| ATOM | 2534 | OW | WAT | W | 61 | −10.892 | 50.466 | 6.274 | 1.00 | 48.29 |
| ATOM | 2535 | OW | WAT | W | 65 | 9.299 | 61.484 | 41.958 | 1.00 | 46.44 |
| ATOM | 2536 | OW | WAT | W | 67 | −20.065 | 61.496 | 10.613 | 1.00 | 55.80 |
| ATOM | 2537 | OW | WAT | W | 69 | −23.666 | 49.910 | 8.247 | 1.00 | 86.15 |
| ATOM | 2538 | OW | WAT | W | 70 | 7.604 | 62.554 | 8.540 | 1.00 | 47.98 |
| ATOM | 2539 | OW | WAT | W | 71 | −16.205 | 68.309 | 45.189 | 1.00 | 81.66 |
| ATOM | 2540 | OW | WAT | W | 501 | −6.848 | 61.106 | 32.328 | 1.00 | 34.79 |
| ATOM | 2541 | OW | WAT | W | 502 | −6.056 | 65.611 | 32.053 | 1.00 | 44.95 |
| ATOM | 2542 | OW | WAT | W | 504 | −12.609 | 65.934 | 33.134 | 1.00 | 54.08 |
| ATOM | 2543 | OW | WAT | W | 505 | −0.492 | 58.965 | 33.916 | 1.00 | 60.61 |
| ATOM | 2544 | OW | WAT | W | 506 | 1.663 | 60.618 | 31.895 | 1.00 | 41.18 |
| ATOM | 2545 | OW | WAT | W | 901 | −18.586 | 78.319 | 18.429 | 1.00 | 60.92 |
| ATOM | 2546 | OW | WAT | W | 902 | −20.581 | 76.915 | 18.100 | 1.00 | 33.96 |
| ATOM | 2547 | OW | WAT | W | 903 | −7.654 | 66.937 | −0.440 | 1.00 | 30.48 |
| ATOM | 2548 | OW | WAT | W | 904 | −4.986 | 66.790 | 0.007 | 1.00 | 41.90 |
| ATOM | 2549 | PG | AGS | Z | 2 | −10.329 | 60.690 | 33.363 | 1.00 | 79.15 |
| ATOM | 2550 | S1G | AGS | Z | 2 | −11.702 | 59.734 | 33.241 | 1.00 | 83.90 |
| ATOM | 2551 | O2G | AGS | Z | 2 | −9.285 | 60.260 | 32.335 | 1.00 | 78.86 |
| ATOM | 2552 | O3G | AGS | Z | 2 | −9.721 | 60.649 | 34.846 | 1.00 | 79.35 |
| ATOM | 2553 | PB | AGS | Z | 2 | −9.901 | 63.477 | 32.944 | 1.00 | 62.99 |
| ATOM | 2554 | O1B | AGS | Z | 2 | −8.660 | 63.229 | 32.106 | 1.00 | 60.14 |
| ATOM | 2555 | O2B | AGS | Z | 2 | −10.664 | 64.619 | 32.336 | 1.00 | 62.79 |
| ATOM | 2556 | O3B | AGS | Z | 2 | −10.803 | 62.183 | 33.069 | 1.00 | 71.46 |
| ATOM | 2557 | PA | AGS | Z | 2 | −8.122 | 64.094 | 35.161 | 1.00 | 55.72 |
| ATOM | 2558 | O1A | AGS | Z | 2 | −8.066 | 63.574 | 36.566 | 1.00 | 55.06 |
| ATOM | 2559 | O2A | AGS | Z | 2 | −6.946 | 63.541 | 34.424 | 1.00 | 54.80 |
| ATOM | 2560 | O3A | AGS | Z | 2 | −9.521 | 63.850 | 34.465 | 1.00 | 60.13 |
| ATOM | 2561 | O5* | AGS | Z | 2 | −7.974 | 65.663 | 35.192 | 1.00 | 52.60 |
| ATOM | 2562 | C5* | AGS | Z | 2 | −9.160 | 66.468 | 35.413 | 1.00 | 50.53 |
| ATOM | 2563 | C4* | AGS | Z | 2 | −8.904 | 67.803 | 34.746 | 1.00 | 48.57 |
| ATOM | 2564 | O4* | AGS | Z | 2 | −7.772 | 68.484 | 35.344 | 1.00 | 47.09 |
| ATOM | 2565 | C3* | AGS | Z | 2 | −8.500 | 67.740 | 33.287 | 1.00 | 47.90 |
| ATOM | 2566 | O3* | AGS | Z | 2 | −9.654 | 67.478 | 32.491 | 1.00 | 49.04 |
| ATOM | 2567 | C2* | AGS | Z | 2 | −7.815 | 69.108 | 33.114 | 1.00 | 46.21 |
| ATOM | 2568 | O2* | AGS | Z | 2 | −8.785 | 70.121 | 32.912 | 1.00 | 46.76 |
| ATOM | 2569 | C1* | AGS | Z | 2 | −7.169 | 69.382 | 34.481 | 1.00 | 46.52 |
| ATOM | 2570 | N9 | AGS | Z | 2 | −5.705 | 69.200 | 34.508 | 1.00 | 45.57 |
| ATOM | 2571 | C8 | AGS | Z | 2 | −5.001 | 68.031 | 34.652 | 1.00 | 45.35 |
| ATOM | 2572 | N7 | AGS | Z | 2 | −3.650 | 68.191 | 34.558 | 1.00 | 45.65 |

TABLE 3-continued

Structural Coordinate of MEK1/N35/NKFCdel (corresponding to amino acids 24-373 of SEQ ID NO: 2)-ATPγS Binary Complex.

| ATOM | 2573 | C5 | AGS | Z | 2 | −3.458 | 69.562 | 34.374 | 1.00 | 44.27 |
|---|---|---|---|---|---|---|---|---|---|---|
| ATOM | 2374 | C6 | AGS | Z | 2 | −2.272 | 70.329 | 34.280 | 1.00 | 42.72 |
| ATOM | 2575 | N6 | AGS | Z | 2 | −1.054 | 69.951 | 34.355 | 1.00 | 42.71 |
| ATOM | 2576 | N1 | AGS | Z | 2 | −2.576 | 71.655 | 34.070 | 1.00 | 41.48 |
| ATOM | 2577 | C2 | AGS | Z | 2 | −3.839 | 72.241 | 34.081 | 1.00 | 42.68 |
| ATOM | 2578 | N3 | AGS | Z | 2 | −4.954 | 71.541 | 34.188 | 1.00 | 43.81 |
| ATOM | 2579 | C4 | AGS | Z | 2 | −4.730 | 70.201 | 34.367 | 1.00 | 44.20 |
| ATOM | 2580 | MG + 2 | MG | Z | 3 | −6.425 | 63.318 | 32.114 | 1.00 | 33.19 |
| END | | | | | | | | | | |

TABLE 4

Structural Coordinate of MEK1/N35/NKFCdel (corresponding to amino acids 24 373 of SEQ ID NO: 2)-Compound 2 Binary Complex.

| ATOM | 1 | N | GLU | A | 38 | 11.364 | 65.007 | 12.944 | 1.00 | 94.23 |
|---|---|---|---|---|---|---|---|---|---|---|
| ATOM | 2 | CA | GLU | A | 38 | 10.260 | 65.768 | 13.530 | 1.00 | 93.90 |
| ATOM | 3 | C | GLU | A | 38 | 10.492 | 66.016 | 15.019 | 1.00 | 96.86 |
| ATOM | 4 | O | GLU | A | 38 | 9.847 | 66.874 | 15.624 | 1.00 | 96.19 |
| ATOM | 5 | CB | GLU | A | 38 | 8.921 | 65.046 | 13.311 | 1.00 | 95.25 |
| ATOM | 6 | CG | GLU | A | 38 | 8.976 | 63.536 | 13.525 | 1.00 | 105.67 |
| ATOM | 7 | CD | GLU | A | 38 | 9.039 | 62.756 | 12.218 | 1.00 | 125.88 |
| ATOM | 8 | OE1 | GLU | A | 38 | 8.093 | 61.990 | 11.933 | 1.00 | 119.76 |
| ATOM | 9 | OE2 | GLU | A | 38 | 10.040 | 62.901 | 11.484 | 1.00 | 119.54 |
| ATOM | 10 | N | LEU | A | 39 | 11.423 | 65.266 | 15.599 | 1.00 | 92.97 |
| ATOM | 11 | CA | LEU | A | 39 | 11.742 | 65.411 | 17.012 | 1.00 | 92.61 |
| ATOM | 12 | C | LEU | A | 39 | 12.810 | 66.488 | 17.242 | 1.00 | 95.48 |
| ATOM | 13 | O | LEU | A | 39 | 13.358 | 66.613 | 18.340 | 1.00 | 94.86 |
| ATOM | 14 | CB | LEU | A | 39 | 12.169 | 64.067 | 17.619 | 1.00 | 92.68 |
| ATOM | 15 | CG | LEU | A | 39 | 11.052 | 63.020 | 17.794 | 1.00 | 97.37 |
| ATOM | 16 | CD1 | LEU | A | 39 | 11.434 | 61.961 | 18.824 | 1.00 | 97.35 |
| ATOM | 17 | CD2 | LEU | A | 39 | 9.724 | 63.685 | 18.169 | 1.00 | 99.83 |
| ATOM | 18 | N | GLU | A | 40 | 13.081 | 67.275 | 16.202 | 1.00 | 91.39 |
| ATOM | 19 | CA | GLU | A | 40 | 14.048 | 68.367 | 16.294 | 1.00 | 90.84 |
| ATOM | 20 | C | GLU | A | 40 | 13.477 | 69.466 | 17.185 | 1.00 | 92.87 |
| ATOM | 21 | O | GLU | A | 40 | 12.259 | 69.677 | 17.221 | 1.00 | 92.72 |
| ATOM | 22 | CB | GLU | A | 40 | 14.351 | 68.931 | 14.906 | 1.00 | 92.36 |
| ATOM | 23 | CG | GLU | A | 40 | 15.624 | 68.391 | 14.270 | 1.00 | 104.94 |
| ATOM | 24 | CD | GLU | A | 40 | 15.661 | 68.613 | 12.765 | 1.00 | 128.91 |
| ATOM | 25 | OE1 | GLU | A | 40 | 14.680 | 69.164 | 12.217 | 1.00 | 124.65 |
| ATOM | 26 | OE2 | GLU | A | 40 | 16.668 | 68.230 | 12.128 | 1.00 | 123.86 |
| ATOM | 27 | N | LEU | A | 41 | 14.350 | 70.163 | 17.906 | 1.00 | 87.25 |
| ATOM | 28 | CA | LEU | A | 41 | 13.908 | 71.211 | 18.814 | 1.00 | 85.95 |
| ATOM | 29 | C | LEU | A | 41 | 14.212 | 72.622 | 18.327 | 1.00 | 87.43 |
| ATOM | 30 | O | LEU | A | 41 | 15.314 | 72.914 | 17.863 | 1.00 | 86.77 |
| ATOM | 31 | CB | LEU | A | 41 | 14.494 | 70.998 | 20.212 | 1.00 | 85.96 |
| ATOM | 32 | CG | LEU | A | 41 | 13.630 | 70.231 | 21.216 | 1.00 | 90.53 |
| ATOM | 33 | CD1 | LEU | A | 41 | 13.522 | 70.994 | 22.525 | 1.00 | 90.64 |
| ATOM | 34 | CD2 | LEU | A | 41 | 12.251 | 69.953 | 20.639 | 1.00 | 93.18 |
| ATOM | 35 | N | ASP | A | 42 | 13.225 | 73.499 | 18.461 | 1.00 | 82.52 |
| ATOM | 36 | CA | ASP | A | 42 | 13.371 | 74.899 | 18.100 | 1.00 | 81.55 |
| ATOM | 37 | C | ASP | A | 42 | 14.330 | 75.532 | 19.098 | 1.00 | 83.06 |
| ATOM | 38 | O | ASP | A | 42 | 14.729 | 74.894 | 20.073 | 1.00 | 82.66 |
| ATOM | 39 | CB | ASP | A | 42 | 12.011 | 75.594 | 18.202 | 1.00 | 83.57 |
| ATOM | 40 | CG | ASP | A | 42 | 11.943 | 76.863 | 17.391 | 1.00 | 96.67 |
| ATOM | 41 | OD1 | ASP | A | 42 | 11.321 | 76.837 | 16.305 | 1.00 | 97.42 |
| ATOM | 42 | OD2 | ASP | A | 42 | 12.491 | 77.894 | 17.847 | 1.00 | 103.75 |
| ATOM | 43 | N | GLU | A | 43 | 14.677 | 76.792 | 18.878 | 1.00 | 77.61 |
| ATOM | 44 | CA | GLU | A | 43 | 15.561 | 77.492 | 19.800 | 1.00 | 76.42 |
| ATOM | 45 | C | GLU | A | 43 | 14.814 | 77.822 | 21.088 | 1.00 | 76.72 |
| ATOM | 46 | O | GLU | A | 43 | 15.297 | 77.553 | 22.186 | 1.00 | 75.55 |
| ATOM | 47 | CB | GLU | A | 43 | 16.105 | 78.767 | 19.160 | 1.00 | 78.01 |
| ATOM | 48 | CG | GLU | A | 43 | 17.587 | 78.702 | 18.825 | 1.00 | 90.32 |
| ATOM | 49 | CD | GLU | A | 43 | 18.242 | 80.071 | 18.804 | 1.00 | 117.01 |
| ATOM | 50 | OE1 | GLU | A | 43 | 17.519 | 81.081 | 18.959 | 1.00 | 117.21 |
| ATOM | 51 | OE2 | GLU | A | 43 | 19.477 | 80.137 | 18.629 | 1.00 | 111.89 |
| ATOM | 52 | N | GLN | A | 44 | 13.617 | 78.383 | 20.939 | 1.00 | 71.40 |
| ATOM | 53 | CA | GLN | A | 44 | 12.785 | 78.739 | 22.078 | 1.00 | 70.25 |
| ATOM | 54 | C | GLN | A | 44 | 12.270 | 77.487 | 22.788 | 1.00 | 71.92 |
| ATOM | 55 | O | GLN | A | 44 | 11.991 | 77.513 | 23.988 | 1.00 | 71.46 |
| ATOM | 56 | CB | GLN | A | 44 | 11.623 | 79.627 | 21.528 | 1.00 | 71.50 |
| ATOM | 57 | CG | GLN | A | 44 | 10.350 | 79.461 | 22.426 | 1.00 | 85.85 |
| ATOM | 58 | CD | GLN | A | 44 | 9.188 | 80.235 | 21.824 | 1.00 | 104.91 |
| ATOM | 59 | OE1 | GLN | A | 44 | 8.380 | 79.683 | 21.071 | 1.00 | 99.35 |

TABLE 4-continued

Structural Coordinate of MEK1/N35/NKFCdel (corresponding to amino acids 24 373 of SEQ ID NO: 2)-Compound 2 Binary Complex.

| | | | | | | | | | | |
|---|---|---|---|---|---|---|---|---|---|---|
| ATOM | 60 | NE2 | GLN | A | 44 | 9.113 | 81.524 | 22.134 | 1.00 | 97.89 |
| ATOM | 61 | N | GLN | A | 45 | 12.184 | 76.386 | 22.046 | 1.00 | 66.67 |
| ATOM | 62 | CA | GLN | A | 45 | 11.733 | 75.115 | 22.604 | 1.00 | 65.65 |
| ATOM | 63 | C | GLN | A | 45 | 12.826 | 74.487 | 23.456 | 1.00 | 68.35 |
| ATOM | 64 | O | GLN | A | 45 | 12.547 | 73.829 | 24.454 | 1.00 | 67.99 |
| ATOM | 65 | CB | GLN | A | 45 | 11.334 | 74.148 | 21.486 | 1.00 | 66.67 |
| ATOM | 66 | CG | GLN | A | 45 | 9.931 | 74.365 | 20.930 | 1.00 | 68.96 |
| ATOM | 67 | CD | GLN | A | 45 | 9.552 | 73.324 | 19.897 | 1.00 | 74.35 |
| ATOM | 68 | OE1 | GLN | A | 45 | 10.356 | 72.962 | 19.043 | 1.00 | 65.88 |
| ATOM | 69 | NE2 | GLN | A | 45 | 8.328 | 72.820 | 19.986 | 1.00 | 64.85 |
| ATOM | 70 | N | ARG | A | 46 | 14.073 | 74.684 | 23.043 | 1.00 | 64.31 |
| ATOM | 71 | CA | ARG | A | 46 | 15.219 | 74.147 | 23.765 | 1.00 | 63.64 |
| ATOM | 72 | C | ARG | A | 46 | 15.477 | 74.966 | 25.031 | 1.00 | 65.48 |
| ATOM | 73 | O | ARG | A | 46 | 15.742 | 74.418 | 26.101 | 1.00 | 64.40 |
| ATOM | 74 | CB | ARG | A | 46 | 16.456 | 74.154 | 22.869 | 1.00 | 65.30 |
| ATOM | 75 | CG | ARG | A | 46 | 17.423 | 73.019 | 23.145 | 1.00 | 80.39 |
| ATOM | 76 | CD | ARG | A | 46 | 18.851 | 73.535 | 23.296 | 1.00 | 94.98 |
| ATOM | 77 | NE | ARG | A | 46 | 19.195 | 73.798 | 24.692 | 1.00 | 106.87 |
| ATOM | 78 | CZ | ARG | A | 46 | 18.970 | 72.949 | 25.691 | 1.00 | 122.78 |
| ATOM | 79 | NH1 | ARG | A | 46 | 18.391 | 71.776 | 25.455 | 1.00 | 111.07 |
| ATOM | 80 | NH2 | ARG | A | 46 | 19.321 | 73.271 | 26.927 | 1.00 | 109.55 |
| ATOM | 81 | N | LYS | A | 47 | 15.377 | 76.282 | 24.904 | 1.00 | 61.12 |
| ATOM | 82 | CA | LYS | A | 47 | 15.567 | 77.159 | 26.038 | 1.00 | 60.64 |
| ATOM | 83 | C | LYS | A | 47 | 14.477 | 76.888 | 27.079 | 1.00 | 64.19 |
| ATOM | 84 | O | LYS | A | 47 | 14.744 | 76.878 | 28.285 | 1.00 | 64.40 |
| ATOM | 85 | CB | LYS | A | 47 | 15.542 | 78.624 | 25.591 | 1.00 | 63.03 |
| ATOM | 86 | CG | LYS | A | 47 | 14.479 | 79.469 | 26.272 | 1.00 | 81.39 |
| ATOM | 87 | CD | LYS | A | 47 | 13.709 | 80.313 | 25.260 | 1.00 | 92.21 |
| ATOM | 88 | CE | LYS | A | 47 | 14.650 | 80.981 | 24.261 | 1.00 | 103.34 |
| ATOM | 89 | NZ | LYS | A | 47 | 13.919 | 81.851 | 23.289 | 1.00 | 111.26 |
| ATOM | 90 | N | ARG | A | 48 | 13.260 | 76.630 | 26.603 | 1.00 | 59.35 |
| ATOM | 91 | CA | ARG | A | 48 | 12.129 | 76.345 | 27.485 | 1.00 | 58.49 |
| ATOM | 92 | C | ARG | A | 48 | 12.304 | 75.016 | 28.224 | 1.00 | 61.47 |
| ATOM | 93 | O | ARG | A | 48 | 12.088 | 74.935 | 29.437 | 1.00 | 60.66 |
| ATOM | 94 | CB | ARG | A | 48 | 10.818 | 76.349 | 26.696 | 1.00 | 57.92 |
| ATOM | 95 | CG | ARG | A | 48 | 10.372 | 77.733 | 26.259 | 1.00 | 66.13 |
| ATOM | 96 | CD | ARG | A | 48 | 8.863 | 77.834 | 26.167 | 1.00 | 72.22 |
| ATOM | 97 | NE | ARG | A | 48 | 8.426 | 79.164 | 25.732 | 1.00 | 77.69 |
| ATOM | 98 | CZ | ARG | A | 48 | 7.879 | 79.424 | 24.555 | 1.00 | 87.14 |
| ATOM | 99 | NH1 | ARG | A | 48 | 7.671 | 78.444 | 23.684 | 1.00 | 73.31 |
| ATOM | 100 | NH2 | ARG | A | 48 | 7.532 | 80.663 | 24.244 | 1.00 | 71.30 |
| ATOM | 101 | N | LEU | A | 49 | 12.705 | 73.980 | 27.492 | 1.00 | 57.75 |
| ATOM | 102 | CA | LEU | A | 49 | 12.920 | 72.665 | 28.084 | 1.00 | 57.68 |
| ATOM | 103 | C | LEU | A | 49 | 14.015 | 72.746 | 29.140 | 1.00 | 62.31 |
| ATOM | 104 | O | LEU | A | 49 | 13.910 | 72.152 | 30.212 | 1.00 | 62.45 |
| ATOM | 105 | CB | LEU | A | 49 | 13.311 | 71.655 | 27.003 | 1.00 | 57.75 |
| ATOM | 106 | CG | LEU | A | 49 | 12.446 | 70.395 | 26.959 | 1.00 | 62.42 |
| ATOM | 107 | CD1 | LEU | A | 49 | 11.124 | 70.547 | 27.585 | 1.00 | 62.42 |
| ATOM | 108 | CD2 | LEU | A | 49 | 12.220 | 70.060 | 25.397 | 1.00 | 64.85 |
| ATOM | 109 | N | GLU | A | 50 | 15.062 | 73.499 | 28.823 | 1.00 | 58.91 |
| ATOM | 110 | CA | GLU | A | 50 | 16.200 | 73.692 | 29.713 | 1.00 | 58.46 |
| ATOM | 111 | C | GLU | A | 50 | 15.763 | 74.334 | 31.029 | 1.00 | 61.08 |
| ATOM | 112 | O | GLU | A | 50 | 16.076 | 73.831 | 32.111 | 1.00 | 60.77 |
| ATOM | 113 | CB | GLU | A | 50 | 17.234 | 74.572 | 29.022 | 1.00 | 59.93 |
| ATOM | 114 | CG | GLU | A | 50 | 18.642 | 74.447 | 29.561 | 1.00 | 72.13 |
| ATOM | 115 | CD | GLU | A | 50 | 19.633 | 75.327 | 28.795 | 1.00 | 93.82 |
| ATOM | 116 | OE1 | GLU | A | 50 | 19.347 | 75.674 | 27.622 | 1.00 | 77.95 |
| ATOM | 117 | OE2 | GLU | A | 50 | 20.698 | 75.662 | 29.361 | 1.00 | 91.32 |
| ATOM | 118 | N | ALA | A | 51 | 15.066 | 75.463 | 30.925 | 1.00 | 56.30 |
| ATOM | 119 | CA | ALA | A | 51 | 14.596 | 76.195 | 32.102 | 1.00 | 55.36 |
| ATOM | 120 | C | ALA | A | 51 | 13.795 | 75.312 | 33.055 | 1.00 | 58.33 |
| ATOM | 121 | O | ALA | A | 51 | 14.013 | 75.337 | 34.267 | 1.00 | 58.00 |
| ATOM | 122 | CB | ALA | A | 51 | 13.781 | 77.400 | 31.684 | 1.00 | 55.91 |
| ATOM | 123 | N | PHE | A | 52 | 12.873 | 74.529 | 32.500 | 1.00 | 53.72 |
| ATOM | 124 | CA | PHE | A | 52 | 12.032 | 73.645 | 33.298 | 1.00 | 52.48 |
| ATOM | 125 | C | PHE | A | 52 | 12.851 | 72.676 | 34.142 | 1.00 | 56.68 |
| ATOM | 126 | O | PHE | A | 52 | 12.520 | 72.415 | 35.304 | 1.00 | 56.03 |
| ATOM | 127 | CB | PHE | A | 52 | 11.076 | 72.867 | 32.403 | 1.00 | 53.39 |
| ATOM | 128 | CG | PHE | A | 52 | 10.231 | 71.870 | 33.146 | 1.00 | 54.05 |
| ATOM | 129 | CD1 | PHE | A | 52 | 9.052 | 72.266 | 33.771 | 1.00 | 56.50 |
| ATOM | 130 | CD2 | PHE | A | 52 | 10.618 | 70.541 | 33.232 | 1.00 | 55.13 |
| ATOM | 131 | CE1 | PHE | A | 52 | 8.276 | 71.356 | 34.459 | 1.00 | 57.04 |
| ATOM | 132 | CE2 | PHE | A | 52 | 9.841 | 69.622 | 33.919 | 1.00 | 57.84 |
| ATOM | 133 | CZ | PHE | A | 52 | 8.673 | 70.030 | 34.536 | 1.00 | 56.08 |
| ATOM | 134 | N | LEU | A | 53 | 13.907 | 72.125 | 33.552 | 1.00 | 53.39 |
| ATOM | 135 | CA | LEU | A | 53 | 14.757 | 71.175 | 34.261 | 1.00 | 53.28 |
| ATOM | 136 | C | LEU | A | 53 | 15.527 | 71.867 | 35.366 | 1.00 | 57.13 |

TABLE 4-continued

Structural Coordinate of MEK1/N35/NKFCdel (corresponding to amino acids 24 373 of SEQ ID NO: 2)-Compound 2 Binary Complex.

| ATOM | 137 | O | LEU | A | 53 | 15.704 | 71.319 | 36.451 | 1.00 | 56.47 |
|---|---|---|---|---|---|---|---|---|---|---|
| ATOM | 138 | CB | LEU | A | 53 | 15.717 | 70.489 | 33.299 | 1.00 | 53.31 |
| ATOM | 139 | CG | LEU | A | 53 | 15.097 | 69.346 | 32.499 | 1.00 | 58.13 |
| ATOM | 140 | CD1 | LEU | A | 53 | 15.410 | 69.498 | 31.015 | 1.00 | 58.26 |
| ATOM | 141 | CD2 | LEU | A | 53 | 15.569 | 67.999 | 33.028 | 1.00 | 60.20 |
| ATOM | 142 | N | THR | A | 54 | 15.975 | 73.086 | 35.089 | 1.00 | 53.82 |
| ATOM | 143 | CA | THR | A | 54 | 16.700 | 73.858 | 36.076 | 1.00 | 53.74 |
| ATOM | 144 | C | THR | A | 54 | 15.802 | 74.099 | 37.292 | 1.00 | 58.71 |
| ATOM | 145 | O | THR | A | 54 | 16.240 | 73.951 | 38.436 | 1.00 | 58.77 |
| ATOM | 146 | CB | THR | A | 54 | 17.181 | 75.209 | 35.501 | 1.00 | 59.18 |
| ATOM | 147 | OG1 | THR | A | 54 | 18.087 | 74.976 | 34.412 | 1.00 | 56.89 |
| ATOM | 148 | CG2 | THR | A | 54 | 17.884 | 76.021 | 36.573 | 1.00 | 56.46 |
| ATOM | 149 | N | GLN | A | 55 | 14.537 | 74.438 | 37.041 | 1.00 | 55.26 |
| ATOM | 150 | CA | GLN | A | 55 | 13.581 | 74.676 | 38.123 | 1.00 | 55.19 |
| ATOM | 151 | C | GLN | A | 55 | 13.315 | 73.389 | 38.900 | 1.00 | 58.61 |
| ATOM | 152 | O | GLN | A | 55 | 13.377 | 73.373 | 40.128 | 1.00 | 58.51 |
| ATOM | 153 | CB | GLN | A | 55 | 12.260 | 75.245 | 37.578 | 1.00 | 56.73 |
| ATOM | 154 | CG | GLN | A | 55 | 12.343 | 76.696 | 37.111 | 1.00 | 77.43 |
| ATOM | 155 | CD | GLN | A | 55 | 11.038 | 77.193 | 36.483 | 1.00 | 101.45 |
| ATOM | 156 | OE1 | GLN | A | 55 | 10.461 | 76.538 | 35.606 | 1.00 | 96.70 |
| ATOM | 157 | NE2 | GLN | A | 55 | 10.580 | 78.365 | 36.921 | 1.00 | 94.32 |
| ATOM | 158 | N | LYS | A | 56 | 13.032 | 72.315 | 38.169 | 1.00 | 54.63 |
| ATOM | 159 | CA | LYS | A | 56 | 12.754 | 71.006 | 38.762 | 1.00 | 54.04 |
| ATOM | 160 | C | LYS | A | 56 | 13.960 | 70.483 | 39.539 | 1.00 | 57.91 |
| ATOM | 161 | O | LYS | A | 56 | 13.820 | 69.698 | 40.476 | 1.00 | 57.28 |
| ATOM | 162 | CB | LYS | A | 56 | 12.356 | 70.012 | 37.663 | 1.00 | 55.84 |
| ATOM | 163 | CG | LYS | A | 56 | 12.561 | 68.561 | 38.020 | 1.00 | 61.89 |
| ATOM | 164 | CD | LYS | A | 56 | 12.204 | 67.660 | 36.846 | 1.00 | 68.68 |
| ATOM | 165 | CE | LYS | A | 56 | 11.855 | 66.242 | 37.300 | 1.00 | 78.41 |
| ATOM | 166 | NZ | LYS | A | 56 | 11.455 | 55.385 | 36.164 | 1.00 | 87.30 |
| ATOM | 167 | N | GLN | A | 57 | 15.144 | 70.935 | 39.146 | 1.00 | 54.72 |
| ATOM | 168 | CA | GLN | A | 57 | 16.381 | 70.534 | 39.802 | 1.00 | 54.47 |
| ATOM | 169 | C | GLN | A | 57 | 16.442 | 71.113 | 41.215 | 1.00 | 57.54 |
| ATOM | 170 | O | GLN | A | 57 | 16.959 | 70.482 | 42.133 | 1.00 | 57.00 |
| ATOM | 171 | CB | GLN | A | 57 | 17.588 | 71.007 | 38.984 | 1.00 | 55.93 |
| ATOM | 172 | CG | GLN | A | 57 | 18.605 | 69.917 | 38.680 | 1.00 | 73.68 |
| ATOM | 173 | CD | GLN | A | 57 | 18.089 | 68.892 | 37.683 | 1.00 | 98.07 |
| ATOM | 174 | OE1 | GLN | A | 57 | 18.821 | 67.993 | 37.268 | 1.00 | 95.99 |
| ATOM | 175 | NE2 | GLN | A | 57 | 16.826 | 69.032 | 37.289 | 1.00 | 89.35 |
| ATOM | 176 | N | LYS | A | 58 | 15.901 | 72.318 | 41.375 | 1.00 | 53.77 |
| ATOM | 177 | CA | LYS | A | 58 | 15.874 | 72.997 | 42.667 | 1.00 | 53.47 |
| ATOM | 178 | C | LYS | A | 58 | 14.855 | 72.372 | 43.629 | 1.00 | 58.59 |
| ATOM | 179 | O | LYS | A | 58 | 14.914 | 72.590 | 44.847 | 1.00 | 58.52 |
| ATOM | 180 | CB | LYS | A | 58 | 15.587 | 74.482 | 42.483 | 1.00 | 55.07 |
| ATOM | 181 | CG | LYS | A | 58 | 16.668 | 75.227 | 41.729 | 1.00 | 66.07 |
| ATOM | 182 | CD | LYS | A | 58 | 16.223 | 76.628 | 41.358 | 1.00 | 75.91 |
| ATOM | 183 | CE | LYS | A | 58 | 17.338 | 77.391 | 40.656 | 1.00 | 89.42 |
| ATOM | 184 | NZ | LYS | A | 58 | 17.139 | 78.869 | 40.727 | 1.00 | 98.43 |
| ATOM | 185 | N | VAL | A | 59 | 13.926 | 71.592 | 43.079 | 1.00 | 55.14 |
| ATOM | 186 | CA | VAL | A | 59 | 12.922 | 70.917 | 43.889 | 1.00 | 54.75 |
| ATOM | 187 | C | VAL | A | 59 | 13.515 | 69.605 | 44.372 | 1.00 | 58.86 |
| ATOM | 188 | O | VAL | A | 59 | 14.225 | 68.918 | 43.628 | 1.00 | 59.10 |
| ATOM | 189 | CB | VAL | A | 59 | 11.645 | 70.613 | 43.071 | 1.00 | 58.69 |
| ATOM | 190 | CG1 | VAL | A | 59 | 10.804 | 69.547 | 43.765 | 1.00 | 58.57 |
| ATOM | 191 | CG2 | VAL | A | 59 | 10.835 | 71.876 | 42.855 | 1.00 | 58.38 |
| ATOM | 192 | N | GLY | A | 60 | 13.254 | 69.257 | 45.617 | 1.00 | 54.99 |
| ATOM | 193 | CA | GLY | A | 60 | 13.793 | 68.023 | 46.154 | 1.00 | 54.88 |
| ATOM | 194 | C | GLY | A | 60 | 12.712 | 66.970 | 46.227 | 1.00 | 59.47 |
| ATOM | 195 | O | GLY | A | 60 | 11.819 | 66.916 | 45.371 | 1.00 | 59.50 |
| ATOM | 196 | N | GLU | A | 61 | 12.784 | 66.142 | 47.258 | 1.00 | 55.75 |
| ATOM | 197 | CA | GLU | A | 61 | 11.791 | 65.109 | 47.475 | 1.00 | 55.67 |
| ATOM | 198 | C | GLU | A | 61 | 10.453 | 65.786 | 47.764 | 1.00 | 58.66 |
| ATOM | 199 | O | GLU | A | 61 | 10.399 | 66.776 | 48.498 | 1.00 | 58.71 |
| ATOM | 200 | CB | GLU | A | 61 | 12.208 | 64.237 | 48.661 | 1.00 | 57.33 |
| ATOM | 201 | CG | GLU | A | 61 | 11.936 | 62.757 | 48.482 | 1.00 | 71.09 |
| ATOM | 202 | CD | GLU | A | 61 | 11.809 | 62.033 | 49.810 | 1.00 | 96.62 |
| ATOM | 203 | OE1 | GLU | A | 61 | 12.100 | 62.656 | 50.854 | 1.00 | 87.13 |
| ATOM | 204 | OE2 | GLU | A | 61 | 11.407 | 60.846 | 49.811 | 1.00 | 94.32 |
| ATOM | 205 | N | LEU | A | 62 | 9.382 | 65.274 | 47.167 | 1.00 | 54.05 |
| ATOM | 206 | CA | LEU | A | 62 | 8.049 | 65.850 | 47.363 | 1.00 | 53.14 |
| ATOM | 207 | C | LEU | A | 62 | 7.371 | 65.228 | 48.567 | 1.00 | 55.67 |
| ATOM | 208 | O | LEU | A | 62 | 7.486 | 64.031 | 48.798 | 1.00 | 55.98 |
| ATOM | 209 | CB | LEU | A | 62 | 7.194 | 65.666 | 46.115 | 1.00 | 52.97 |
| ATOM | 210 | CG | LEU | A | 62 | 7.793 | 66.239 | 44.834 | 1.00 | 57.41 |
| ATOM | 211 | CD1 | LEU | A | 62 | 6.965 | 65.835 | 43.620 | 1.00 | 57.63 |
| ATOM | 212 | CD2 | LEU | A | 62 | 7.924 | 67.759 | 44.932 | 1.00 | 59.03 |
| ATOM | 213 | N | LYS | A | 63 | 6.686 | 66.050 | 49.349 | 1.00 | 50.53 |

TABLE 4-continued

Structural Coordinate of MEK1/N35/NKFCdel (corresponding to amino acids 24 373 of SEQ ID NO: 2)-Compound 2 Binary Complex.

| ATOM | 214 | CA | LYS | A | 63 | 6.026 | 65.580 | 50.552 | 1.00 | 49.18 |
| ATOM | 215 | C | LYS | A | 63 | 4.688 | 66.258 | 50.741 | 1.00 | 50.71 |
| ATOM | 216 | O | LYS | A | 63 | 4.559 | 67.451 | 50.488 | 1.00 | 50.18 |
| ATOM | 217 | CB | LYS | A | 63 | 6.909 | 65.840 | 51.785 | 1.00 | 51.62 |
| ATOM | 218 | CG | LYS | A | 63 | 8.162 | 64.986 | 51.836 | 1.00 | 66.14 |
| ATOM | 219 | CD | LYS | A | 63 | 9.210 | 65.603 | 52.753 | 1.00 | 76.67 |
| ATOM | 220 | CE | LYS | A | 63 | 10.327 | 64.611 | 53.070 | 1.00 | 88.55 |
| ATOM | 221 | NZ | LYS | A | 63 | 10.011 | 63.761 | 54.260 | 1.00 | 96.98 |
| ATOM | 222 | N | ASP | A | 64 | 3.697 | 65.480 | 51.173 | 1.00 | 46.02 |
| ATOM | 223 | CA | ASP | A | 64 | 2.326 | 65.958 | 51.362 | 1.00 | 45.18 |
| ATOM | 224 | C | ASP | A | 64 | 2.242 | 67.335 | 52.005 | 1.00 | 48.34 |
| ATOM | 225 | O | ASP | A | 64 | 1.743 | 68.287 | 51.397 | 1.00 | 47.71 |
| ATOM | 226 | CB | ASP | A | 64 | 1.487 | 64.919 | 52.154 | 1.00 | 46.97 |
| ATOM | 227 | CG | ASP | A | 64 | 0.236 | 65.529 | 52.809 | 1.00 | 59.80 |
| ATOM | 228 | OD1 | ASP | A | 64 | −0.680 | 65.967 | 52.067 | 1.00 | 61.18 |
| ATOM | 229 | OD2 | ASP | A | 64 | 0.143 | 65.500 | 54.074 | 1.00 | 66.09 |
| ATOM | 230 | N | ASP | A | 65 | 2.765 | 67.444 | 53.218 | 1.00 | 44.49 |
| ATOM | 231 | CA | ASP | A | 65 | 2.693 | 68.682 | 53.978 | 1.00 | 44.06 |
| ATOM | 232 | C | ASP | A | 65 | 3.424 | 69.865 | 53.334 | 1.00 | 46.93 |
| ATOM | 233 | O | ASP | A | 65 | 3.393 | 70.970 | 53.858 | 1.00 | 46.21 |
| ATOM | 234 | CB | ASP | A | 65 | 3.156 | 68.454 | 55.423 | 1.00 | 46.11 |
| ATOM | 235 | CG | ASP | A | 65 | 2.314 | 67.398 | 56.159 | 1.00 | 59.44 |
| ATOM | 236 | OD1 | ASP | A | 65 | 1.291 | 66.929 | 55.590 | 1.00 | 60.07 |
| ATOM | 237 | OD2 | ASP | A | 65 | 2.672 | 67.044 | 57.317 | 1.00 | 68.08 |
| ATOM | 238 | N | ASP | A | 66 | 4.050 | 69.632 | 52.179 | 1.00 | 43.26 |
| ATOM | 239 | CA | ASP | A | 66 | 4.777 | 70.683 | 51.462 | 1.00 | 42.94 |
| ATOM | 240 | C | ASP | A | 66 | 3.885 | 71.397 | 50.454 | 1.00 | 47.21 |
| ATOM | 241 | O | ASP | A | 66 | 4.299 | 72.367 | 49.817 | 1.00 | 46.53 |
| ATOM | 242 | CB | ASP | A | 66 | 5.969 | 70.086 | 50.718 | 1.00 | 44.94 |
| ATOM | 243 | CG | ASP | A | 66 | 7.184 | 69.900 | 51.610 | 1.00 | 57.85 |
| ATOM | 244 | OD1 | ASP | A | 66 | 7.164 | 70.392 | 52.761 | 1.00 | 58.28 |
| ATOM | 245 | OD2 | ASP | A | 66 | 8.165 | 69.267 | 51.152 | 1.00 | 63.75 |
| ATOM | 246 | N | PHE | A | 67 | 2.673 | 70.890 | 50.284 | 1.00 | 44.43 |
| ATOM | 247 | CA | PHE | A | 67 | 1.762 | 71.445 | 49.299 | 1.00 | 44.14 |
| ATOM | 248 | C | PHE | A | 67 | 0.628 | 72.278 | 49.867 | 1.00 | 49.31 |
| ATOM | 249 | O | PHE | A | 67 | 0.156 | 72.052 | 50.980 | 1.00 | 48.04 |
| ATOM | 250 | CB | PHE | A | 67 | 1.226 | 70.344 | 48.374 | 1.00 | 45.53 |
| ATOM | 251 | CG | PHE | A | 67 | 2.268 | 69.772 | 47.454 | 1.00 | 46.37 |
| ATOM | 252 | CD1 | PHE | A | 67 | 2.655 | 70.457 | 46.314 | 1.00 | 48.99 |
| ATOM | 253 | CD2 | PHE | A | 67 | 2.897 | 68.578 | 47.755 | 1.00 | 48.22 |
| ATOM | 254 | CE1 | PHE | A | 67 | 3.628 | 69.943 | 45.472 | 1.00 | 49.55 |
| ATOM | 255 | CE2 | PHE | A | 67 | 3.877 | 68.064 | 46.923 | 1.00 | 50.82 |
| ATOM | 256 | CZ | PHE | A | 67 | 4.240 | 68.750 | 45.777 | 1.00 | 48.68 |
| ATOM | 257 | N | GLU | A | 68 | 0.192 | 73.244 | 49.072 | 1.00 | 47.71 |
| ATOM | 258 | CA | GLU | A | 68 | −0.898 | 74.117 | 49.441 | 1.00 | 48.09 |
| ATOM | 259 | C | GLU | A | 68 | −1.886 | 74.209 | 48.264 | 1.00 | 52.99 |
| ATOM | 260 | O | GLU | A | 68 | −1.545 | 74.716 | 47.192 | 1.00 | 52.26 |
| ATOM | 261 | CB | GLU | A | 68 | −0.350 | 75.504 | 49.802 | 1.00 | 49.48 |
| ATOM | 262 | CG | GLU | A | 68 | −1.405 | 76.540 | 50.149 | 1.00 | 61.32 |
| ATOM | 263 | CD | GLU | A | 68 | −0.861 | 77.962 | 50.092 | 1.00 | 85.36 |
| ATOM | 264 | OE1 | GLU | A | 68 | 0.232 | 78.207 | 50.665 | 1.00 | 70.92 |
| ATOM | 265 | OE2 | GLU | A | 68 | −1.510 | 78.828 | 49.463 | 1.00 | 86.45 |
| ATOM | 266 | N | LYS | A | 69 | −3.094 | 73.685 | 48.461 | 1.00 | 50.54 |
| ATOM | 267 | CA | LYS | A | 69 | −4.115 | 73.721 | 47.417 | 1.00 | 50.65 |
| ATOM | 268 | C | LYS | A | 69 | −4.511 | 75.156 | 47.044 | 1.00 | 55.17 |
| ATOM | 269 | O | LYS | A | 69 | −4.681 | 76.014 | 47.916 | 1.00 | 54.88 |
| ATOM | 270 | CB | LYS | A | 69 | −5.347 | 72.927 | 47.835 | 1.00 | 53.15 |
| ATOM | 271 | CG | LYS | A | 69 | −6.540 | 73.119 | 46.906 | 1.00 | 68.90 |
| ATOM | 272 | CD | LYS | A | 69 | −7.514 | 71.951 | 47.002 | 1.00 | 78.49 |
| ATOM | 273 | CE | LYS | A | 69 | −8.902 | 72.344 | 46.523 | 1.00 | 88.16 |
| ATOM | 274 | NZ | LYS | A | 69 | −9.975 | 71.617 | 47.262 | 1.00 | 96.17 |
| ATOM | 275 | N | ILE | A | 70 | −4.643 | 75.402 | 45.742 | 1.00 | 52.11 |
| ATOM | 276 | CA | ILE | A | 70 | −5.017 | 76.716 | 45.221 | 1.00 | 51.80 |
| ATOM | 277 | C | ILE | A | 70 | −6.419 | 76.553 | 44.625 | 1.00 | 56.97 |
| ATOM | 278 | O | ILE | A | 70 | −7.226 | 77.548 | 44.826 | 1.00 | 57.33 |
| ATOM | 279 | CB | ILE | A | 70 | −4.058 | 77.178 | 44.114 | 1.00 | 54.44 |
| ATOM | 280 | CG1 | ILE | A | 70 | −2.659 | 77.407 | 44.671 | 1.00 | 54.38 |
| ATOM | 281 | CG2 | ILE | A | 70 | −4.576 | 78.436 | 43.467 | 1.00 | 55.45 |
| ATOM | 282 | CD1 | ILE | A | 70 | −1.682 | 77.937 | 43.655 | 1.00 | 57.36 |
| ATOM | 283 | N | SER | A | 71 | −6.693 | 75.589 | 43.882 | 1.00 | 53.92 |
| ATOM | 284 | CA | SER | A | 71 | −7.998 | 75.400 | 43.268 | 1.00 | 53.90 |
| ATOM | 285 | C | SER | A | 71 | −8.115 | 73.998 | 42.685 | 1.00 | 58.70 |
| ATOM | 286 | O | SER | A | 71 | −7.170 | 73.210 | 42.750 | 1.00 | 58.33 |
| ATOM | 287 | CB | SER | A | 71 | −8.238 | 76.447 | 42.172 | 1.00 | 57.07 |
| ATOM | 286 | OG | SER | A | 71 | −7.055 | 76.709 | 41.431 | 1.00 | 64.78 |
| ATOM | 289 | N | GLU | A | 72 | −9.281 | 73.697 | 42.115 | 1.00 | 55.85 |
| ATOM | 290 | CA | GLU | A | 72 | −9.538 | 72.402 | 41.485 | 1.00 | 55.65 |

TABLE 4-continued

Structural Coordinate of MEK1/N35/NKFCdel (corresponding to amino acids 24 373 of SEQ ID NO: 2)-Compound 2 Binary Complex.

| ATOM | 291 | C | GLU | A | 72 | −9.407 | 72.564 | 39.971 | 1.00 | 58.89 |
|------|-----|-----|-----|---|----|--------|--------|--------|------|-------|
| ATOM | 292 | O | GLU | A | 72 | −10.017 | 73.457 | 39.385 | 1.00 | 58.46 |
| ATOM | 293 | CB | GLU | A | 72 | −10.954 | 71.930 | 41.819 | 1.00 | 57.18 |
| ATOM | 294 | CG | GLU | A | 72 | −11.028 | 70.631 | 42.599 | 1.00 | 69.46 |
| ATOM | 295 | CD | GLU | A | 72 | −11.937 | 70.743 | 43.816 | 1.00 | 92.54 |
| ATOM | 296 | OE1 | GLU | A | 72 | −12.248 | 71.885 | 44.218 | 1.00 | 88.61 |
| ATOM | 297 | OE2 | GLU | A | 72 | −12.337 | 69.695 | 44.368 | 1.00 | 85.56 |
| ATOM | 298 | N | LEU | A | 73 | −8.601 | 71.713 | 39.344 | 1.00 | 55.26 |
| ATOM | 299 | CA | LEU | A | 73 | −8.398 | 71.784 | 37.896 | 1.00 | 54.72 |
| ATOM | 300 | C | LEU | A | 73 | −9.350 | 70.846 | 37.176 | 1.00 | 59.25 |
| ATOM | 301 | O | LEU | A | 73 | −9.514 | 70.919 | 25.962 | 1.00 | 58.66 |
| ATOM | 302 | CB | LEU | A | 73 | −6.957 | 71.433 | 37.536 | 1.00 | 54.41 |
| ATOM | 303 | CG | LEU | A | 73 | −5.902 | 72.392 | 38.061 | 1.00 | 58.56 |
| ATOM | 304 | CD1 | LEU | A | 73 | −4.527 | 72.025 | 37.525 | 1.00 | 58.43 |
| ATOM | 305 | CD2 | LEU | A | 73 | −6.271 | 73.816 | 37.699 | 1.00 | 60.21 |
| ATOM | 306 | N | GLY | A | 74 | −9.969 | 69.949 | 37.933 | 1.00 | 56.58 |
| ATOM | 307 | CA | GLY | A | 74 | −10.907 | 69.006 | 37.363 | 1.00 | 56.76 |
| ATOM | 308 | C | GLY | A | 74 | −10.561 | 67.566 | 37.695 | 1.00 | 61.83 |
| ATOM | 309 | O | GLY | A | 74 | −9.403 | 67.225 | 37.906 | 1.00 | 61.23 |
| ATOM | 310 | N | ALA | A | 75 | −11.584 | 66.724 | 37.736 | 1.00 | 60.03 |
| ATOM | 311 | CA | ALA | A | 75 | −11.411 | 65.313 | 38.008 | 1.00 | 60.82 |
| ATOM | 312 | C | ALA | A | 75 | −11.135 | 64.581 | 36.710 | 1.00 | 67.05 |
| ATOM | 313 | O | ALA | A | 75 | −11.610 | 64.989 | 35.648 | 1.00 | 66.64 |
| ATOM | 314 | CB | ALA | A | 75 | −12.657 | 64.752 | 38.683 | 1.00 | 61.56 |
| ATOM | 315 | N | GLY | A | 76 | −10.365 | 63.502 | 36.795 | 1.00 | 65.54 |
| ATOM | 316 | CA | GLY | A | 76 | −10.027 | 62.711 | 35.615 | 1.00 | 65.92 |
| ATOM | 317 | C | GLY | A | 76 | −9.202 | 61.480 | 35.984 | 1.00 | 71.56 |
| ATOM | 318 | O | GLY | A | 76 | −8.242 | 61.567 | 36.751 | 1.00 | 71.14 |
| ATOM | 319 | N | ASN | A | 77 | −9.593 | 60.333 | 35.437 | 1.00 | 69.41 |
| ATOM | 320 | CA | ASN | A | 77 | −8.898 | 59.079 | 35.678 | 1.00 | 69.80 |
| ATOM | 321 | C | ASN | A | 77 | −8.721 | 58.692 | 37.139 | 1.00 | 74.63 |
| ATOM | 322 | O | ASN | A | 77 | −7.602 | 58.625 | 37.639 | 1.00 | 74.74 |
| ATOM | 323 | CB | ASN | A | 77 | −7.549 | 59.045 | 34.970 | 1.00 | 72.17 |
| ATOM | 324 | CG | ASN | A | 77 | −7.076 | 57.635 | 34.683 | 1.00 | 101.57 |
| ATOM | 325 | OD1 | ASN | A | 77 | −7.861 | 56.688 | 34.722 | 1.00 | 99.40 |
| ATOM | 326 | ND2 | ASN | A | 77 | −5.781 | 57.478 | 34.419 | 1.00 | 93.06 |
| ATOM | 327 | N | GLY | A | 78 | −9.825 | 58.337 | 37.779 | 1.00 | 71.28 |
| ATOM | 328 | CA | GLY | A | 78 | −9.793 | 57.854 | 39.154 | 1.00 | 70.79 |
| ATOM | 329 | C | GLY | A | 78 | −9.237 | 58.843 | 40.168 | 1.00 | 73.23 |
| ATOM | 330 | O | GLY | A | 78 | −9.000 | 58.479 | 41.323 | 1.00 | 73.64 |
| ATOM | 331 | N | GLY | A | 79 | −9.048 | 60.088 | 39.755 | 1.00 | 67.77 |
| ATOM | 332 | CA | GLY | A | 79 | −8.522 | 61.092 | 40.675 | 1.00 | 66.64 |
| ATOM | 333 | C | GLY | A | 79 | −8.804 | 62.523 | 40.264 | 1.00 | 67.63 |
| ATOM | 334 | O | GLY | A | 79 | −2.986 | 62.823 | 39.082 | 1.00 | 67.61 |
| ATOM | 335 | N | VAL | A | 80 | −8.827 | 63.411 | 41.248 | 1.00 | 61.25 |
| ATOM | 336 | CA | VAL | A | 80 | −9.053 | 64.820 | 41.001 | 1.00 | 59.70 |
| ATOM | 337 | C | VAL | A | 80 | −7.699 | 65.488 | 40.799 | 1.00 | 60.81 |
| ATOM | 338 | O | VAL | A | 80 | −6.674 | 64.959 | 41.230 | 1.00 | 60.49 |
| ATOM | 339 | CB | VAL | A | 80 | −9.767 | 65.473 | 42.189 | 1.00 | 63.48 |
| ATOM | 340 | CG1 | VAL | A | 80 | −10.424 | 66.781 | 41.773 | 1.00 | 63.34 |
| ATOM | 341 | CG2 | VAL | A | 80 | −10.793 | 64.509 | 42.775 | 1.00 | 63.31 |
| ATOM | 342 | N | VAL | A | 81 | −7.693 | 66.623 | 40.127 | 1.00 | 54.51 |
| ATOM | 343 | CA | VAL | A | 81 | −6.455 | 67.362 | 39.893 | 1.00 | 52.88 |
| ATOM | 344 | C | VAL | A | 81 | −6.562 | 68.752 | 40.492 | 1.00 | 55.16 |
| ATOM | 345 | O | VAL | A | 81 | −7.511 | 69.488 | 40.223 | 1.00 | 54.74 |
| ATOM | 346 | CB | VAL | A | 81 | −6.111 | 67.457 | 38.383 | 1.00 | 55.97 |
| ATOM | 347 | CG1 | VAL | A | 81 | −4.830 | 68.245 | 35.169 | 1.00 | 55.24 |
| ATOM | 348 | CG2 | VAL | A | 81 | −5.991 | 66.070 | 37.783 | 1.00 | 55.66 |
| ATOM | 349 | N | PHE | A | 82 | −5.553 | 69.096 | 41.330 | 1.00 | 50.44 |
| ATOM | 350 | CA | PHE | A | 82 | −5.583 | 70.382 | 41.997 | 1.00 | 49.07 |
| ATOM | 351 | C | PHE | A | 82 | −4.430 | 71.236 | 41.522 | 1.00 | 50.45 |
| ATOM | 352 | O | PHE | A | 82 | −3.331 | 70.737 | 41.279 | 1.00 | 49.51 |
| ATOM | 353 | CB | PHE | A | 82 | −5.465 | 70.183 | 43.515 | 1.00 | 50.81 |
| ATOM | 354 | CG | PHE | A | 82 | −6.663 | 69.536 | 44.135 | 1.00 | 52.89 |
| ATOM | 355 | CD1 | PHE | A | 82 | −6.702 | 68.169 | 44.339 | 1.00 | 56.58 |
| ATOM | 356 | CD2 | PHE | A | 82 | −7.762 | 70.296 | 44.517 | 1.00 | 55.66 |
| ATOM | 357 | CE1 | PHE | A | 82 | −7.814 | 67.566 | 44.907 | 1.00 | 57.77 |
| ATOM | 358 | CE2 | PHE | A | 82 | −8.870 | 69.704 | 45.093 | 1.00 | 58.55 |
| ATOM | 359 | CZ | PHE | A | 82 | −8.899 | 68.337 | 45.287 | 1.00 | 56.83 |
| ATOM | 360 | N | LYS | A | 83 | −4.677 | 72.533 | 41.409 | 1.00 | 45.86 |
| ATOM | 361 | CA | LYS | A | 83 | −3.614 | 73.458 | 41.097 | 1.00 | 44.97 |
| ATOM | 362 | C | LYS | A | 83 | −3.084 | 73.806 | 42.471 | 1.00 | 48.98 |
| ATOM | 363 | O | LYS | A | 83 | −3.841 | 74.228 | 43.350 | 1.00 | 48.79 |
| ATOM | 364 | CB | LYS | A | 83 | −4.140 | 74.709 | 40.399 | 1.00 | 46.62 |
| ATOM | 365 | CG | LYS | A | 83 | −3.043 | 75.628 | 39.908 | 1.00 | 50.39 |
| ATOM | 366 | CD | LYS | A | 83 | −3.545 | 77.044 | 39.741 | 1.00 | 58.01 |
| ATOM | 367 | CE | LYS | A | 83 | −2.390 | 78.018 | 39.665 | 1.00 | 70.87 |

TABLE 4-continued

Structural Coordinate of MEK1/N35/NKFCdel (corresponding to amino acids 24 373 of SEQ ID NO: 2)-Compound 2 Binary Complex.

| ATOM | 368 | NZ | LYS | A | 83 | −2.712 | 79.203 | 38.825 | 1.00 | 83.70 |
|---|---|---|---|---|---|---|---|---|---|---|
| ATOM | 369 | N | VAL | A | 84 | −1.812 | 73.519 | 42.695 | 1.00 | 44.65 |
| ATOM | 370 | CA | VAL | A | 84 | −1.236 | 73.704 | 43.996 | 1.00 | 44.12 |
| ATOM | 371 | C | VAL | A | 84 | 0.022 | 74.530 | 43.951 | 1.00 | 48.26 |
| ATOM | 372 | O | VAL | A | 84 | 0.561 | 74.834 | 42.880 | 1.00 | 47.86 |
| ATOM | 373 | CB | VAL | A | 84 | −0.881 | 72.339 | 44.641 | 1.00 | 47.52 |
| ATOM | 374 | CG1 | VAL | A | 84 | −2.070 | 71.383 | 44.579 | 1.00 | 46.97 |
| ATOM | 375 | CG2 | VAL | A | 84 | 0.338 | 71.729 | 43.951 | 1.00 | 47.09 |
| ATOM | 376 | N | SER | A | 85 | 0.512 | 74.851 | 45.136 | 1.00 | 44.45 |
| ATOM | 377 | CA | SER | A | 85 | 1.742 | 75.588 | 45.285 | 1.00 | 43.97 |
| ATOM | 378 | C | SER | A | 85 | 2.689 | 74.747 | 46.138 | 1.00 | 47.30 |
| ATOM | 379 | O | SER | A | 85 | 2.323 | 74.310 | 47.237 | 1.00 | 46.66 |
| ATOM | 380 | CB | SER | A | 85 | 1.470 | 76.928 | 45.975 | 1.00 | 46.47 |
| ATOM | 381 | OG | SER | A | 85 | 2.671 | 77.547 | 46.378 | 1.00 | 52.52 |
| ATOM | 382 | N | HIS | A | 86 | 3.874 | 74.471 | 45.609 | 1.00 | 42.95 |
| ATOM | 383 | CA | HIS | A | 86 | 4.881 | 73.750 | 46.389 | 1.00 | 44.46 |
| ATOM | 384 | C | HIS | A | 86 | 5.611 | 74.808 | 47.200 | 1.00 | 49.29 |
| ATOM | 385 | O | HIS | A | 86 | 6.519 | 75.488 | 46.700 | 1.00 | 48.58 |
| ATOM | 386 | CB | HIS | A | 86 | 5.876 | 73.028 | 45.445 | 1.00 | 45.24 |
| ATOM | 387 | CG | HIS | A | 86 | 6.859 | 72.171 | 46.181 | 1.00 | 48.80 |
| ATOM | 388 | ND1 | HIS | A | 86 | 8.186 | 72.517 | 46.329 | 1.00 | 50.67 |
| ATOM | 389 | CD2 | HIS | A | 86 | 6.692 | 71.016 | 46.868 | 1.00 | 50.44 |
| ATOM | 390 | CE1 | HIS | A | 86 | 8.799 | 71.598 | 47.053 | 1.00 | 49.98 |
| ATOM | 391 | NE2 | HIS | A | 86 | 7.914 | 70.677 | 47.394 | 1.00 | 50.24 |
| ATOM | 392 | N | LYS | A | 87 | 5.141 | 74.996 | 48.434 | 1.00 | 45.79 |
| ATOM | 393 | CA | LYS | A | 87 | 5.653 | 76.021 | 49.348 | 1.00 | 45.59 |
| ATOM | 394 | C | LYS | A | 87 | 7.164 | 75.262 | 49.306 | 1.00 | 49.96 |
| ATOM | 395 | O | LYS | A | 87 | 7.624 | 77.383 | 49.024 | 1.00 | 50.19 |
| ATOM | 396 | CB | LYS | A | 87 | 5.199 | 75.733 | 50.782 | 1.00 | 47.74 |
| ATOM | 397 | CG | LYS | A | 87 | 3.696 | 75.929 | 51.013 | 1.00 | 60.83 |
| ATOM | 398 | CD | LYS | A | 87 | 3.050 | 74.664 | 51.564 | 1.00 | 72.58 |
| ATOM | 399 | CE | LYS | A | 87 | 2.483 | 74.690 | 52.962 | 1.00 | 83.13 |
| ATOM | 400 | NZ | LYS | A | 87 | 3.251 | 74.147 | 54.008 | 1.00 | 91.12 |
| ATOM | 401 | N | PRO | A | 88 | 7.932 | 75.225 | 49.606 | 1.00 | 45.73 |
| ATOM | 402 | CA | PRO | A | 88 | 5.391 | 75.345 | 49.649 | 1.00 | 44.96 |
| ATOM | 403 | C | PRO | A | 88 | 9.985 | 76.018 | 48.411 | 1.00 | 48.48 |
| ATOM | 404 | O | PRO | A | 88 | 10.703 | 77.014 | 48.522 | 1.00 | 48.44 |
| ATOM | 405 | CB | PRO | A | 88 | 9.859 | 73.894 | 49.761 | 1.00 | 46.42 |
| ATOM | 406 | CG | PRO | A | 88 | 6.669 | 73.146 | 50.294 | 1.00 | 50.61 |
| ATOM | 407 | CD | PRO | A | 88 | 7.487 | 73.826 | 49.707 | 1.00 | 45.98 |
| ATOM | 408 | N | SER | A | 89 | 9.574 | 75.482 | 47.236 | 1.00 | 44.82 |
| ATOM | 409 | CA | SER | A | 89 | 10.209 | 76.014 | 45.981 | 1.00 | 44.38 |
| ATOM | 410 | C | SER | A | 89 | 9.479 | 77.268 | 45.494 | 1.00 | 48.20 |
| ATOM | 411 | O | SER | A | 89 | 10.041 | 78.072 | 44.761 | 1.00 | 47.64 |
| ATOM | 412 | CB | SER | A | 89 | 10.175 | 74.940 | 44.892 | 1.00 | 47.22 |
| ATOM | 413 | OG | SER | A | 89 | 8.853 | 74.484 | 44.680 | 1.00 | 54.86 |
| ATOM | 414 | N | GLY | A | 90 | 8.224 | 77.418 | 45.890 | 1.00 | 45.16 |
| ATOM | 415 | CA | GLY | A | 90 | 7.424 | 78.546 | 45.447 | 1.00 | 45.24 |
| ATOM | 416 | C | GLY | A | 90 | 6.821 | 78.234 | 44.075 | 1.00 | 49.99 |
| ATOM | 417 | O | GLY | A | 90 | 6.099 | 79.054 | 43.495 | 1.00 | 49.57 |
| ATOM | 418 | N | LEU | A | 91 | 7.119 | 77.038 | 43.567 | 1.00 | 46.88 |
| ATOM | 419 | CA | LEU | A | 91 | 6.607 | 76.597 | 42.268 | 1.00 | 46.97 |
| ATOM | 420 | C | LEU | A | 91 | 5.137 | 76.209 | 42.330 | 1.00 | 50.37 |
| ATOM | 421 | O | LEU | A | 91 | 4.679 | 75.626 | 43.309 | 1.00 | 50.04 |
| ATOM | 422 | CB | LEU | A | 91 | 7.409 | 75.394 | 41.748 | 1.00 | 47.07 |
| ATOM | 423 | CG | LEU | A | 91 | 8.880 | 75.597 | 41.397 | 1.00 | 52.23 |
| ATOM | 424 | CD1 | LEU | A | 91 | 9.636 | 74.271 | 41.512 | 1.00 | 52.62 |
| ATOM | 425 | CD2 | LEU | A | 91 | 9.026 | 76.174 | 40.003 | 1.00 | 53.80 |
| ATOM | 426 | N | VAL | A | 92 | 4.416 | 76.486 | 41.250 | 1.00 | 46.43 |
| ATOM | 427 | CA | VAL | A | 92 | 3.021 | 76.087 | 41.133 | 1.00 | 45.92 |
| ATOM | 428 | C | VAL | A | 92 | 3.007 | 74.817 | 40.285 | 1.00 | 48.32 |
| ATOM | 429 | O | VAL | A | 92 | 3.808 | 74.681 | 39.364 | 1.00 | 48.27 |
| ATOM | 430 | CB | VAL | A | 92 | 2.174 | 77.172 | 40.428 | 1.00 | 49.56 |
| ATOM | 431 | CG1 | VAL | A | 92 | 0.734 | 76.722 | 40.293 | 1.00 | 49.23 |
| ATOM | 432 | CG2 | VAL | A | 92 | 2.252 | 78.479 | 41.190 | 1.00 | 49.37 |
| ATOM | 433 | N | MET | A | 93 | 2.146 | 73.866 | 40.639 | 1.00 | 42.86 |
| ATOM | 434 | CA | MET | A | 93 | 2.058 | 72.618 | 39.892 | 1.00 | 41.36 |
| ATOM | 435 | C | MET | A | 93 | 0.646 | 72.078 | 39.852 | 1.00 | 44.48 |
| ATOM | 436 | O | MET | A | 93 | −0.265 | 72.613 | 40.483 | 1.00 | 43.57 |
| ATOM | 437 | CB | MET | A | 93 | 2.985 | 71.541 | 40.478 | 1.00 | 43.09 |
| ATOM | 438 | CG | MET | A | 93 | 4.014 | 72.036 | 41.461 | 1.00 | 46.22 |
| ATOM | 439 | SD | MET | A | 93 | 5.038 | 70.667 | 42.131 | 1.00 | 49.73 |
| ATOM | 440 | CE | MET | A | 93 | 6.690 | 71.373 | 41.941 | 1.00 | 46.12 |
| ATOM | 441 | N | ALA | A | 94 | 0.482 | 70.994 | 39.104 | 1.00 | 40.99 |
| ATOM | 442 | CA | ALA | A | 94 | −0.781 | 70.290 | 39.025 | 1.00 | 40.45 |
| ATOM | 443 | C | ALA | A | 94 | −0.582 | 69.017 | 39.821 | 1.00 | 43.64 |
| ATOM | 444 | O | ALA | A | 94 | 0.337 | 68.245 | 39.553 | 1.00 | 42.58 |

TABLE 4-continued

Structural Coordinate of MEK1/N35/NKFCdel (corresponding to amino acids 24 373 of SEQ ID NO: 2)-Compound 2 Binary Complex.

| ATOM | 445 | CB | ALA | A | 94 | −1.123 | 69.960 | 37.569 | 1.00 | 40.89 |
|---|---|---|---|---|---|---|---|---|---|---|
| ATOM | 446 | N | ARG | A | 95 | −1.385 | 68.843 | 40.855 | 1.00 | 41.19 |
| ATOM | 447 | CA | ARG | A | 95 | −1.280 | 67.665 | 41.695 | 1.00 | 41.36 |
| ATOM | 448 | C | ARG | A | 95 | −2.446 | 66.721 | 41.421 | 1.00 | 47.13 |
| ATOM | 449 | O | ARG | A | 95 | −3.593 | 67.037 | 41.728 | 1.00 | 45.98 |
| ATOM | 450 | CB | ARG | A | 95 | −1.254 | 68.059 | 43.176 | 1.00 | 39.82 |
| ATOM | 451 | CG | ARG | A | 95 | −0.851 | 66.921 | 44.121 | 1.00 | 43.88 |
| ATOM | 452 | CD | ARG | A | 95 | −0.819 | 67.394 | 45.572 | 1.00 | 47.54 |
| ATOM | 453 | NE | ARG | A | 95 | −0.572 | 66.294 | 46.508 | 1.00 | 56.35 |
| ATOM | 454 | CZ | ARG | A | 95 | −0.716 | 66.388 | 47.830 | 1.00 | 69.89 |
| ATOM | 455 | NH1 | ARG | A | 95 | −1.106 | 67.533 | 48.381 | 1.00 | 55.00 |
| ATOM | 456 | NH2 | ARG | A | 95 | −0.469 | 65.339 | 48.604 | 1.00 | 59.52 |
| ATOM | 457 | N | LYS | A | 96 | −2.150 | 65.572 | 40.827 | 1.00 | 45.69 |
| ATOM | 458 | CA | LYS | A | 96 | −3.173 | 64.571 | 40.567 | 1.00 | 46.52 |
| ATOM | 459 | C | LYS | A | 96 | −3.224 | 63.631 | 41.766 | 1.00 | 53.30 |
| ATOM | 460 | O | LYS | A | 96 | −2.199 | 63.094 | 42.190 | 1.00 | 52.73 |
| ATOM | 461 | CB | LYS | A | 96 | −2.863 | 63.787 | 39.292 | 1.00 | 49.08 |
| ATOM | 462 | CG | LYS | A | 96 | −3.684 | 62.501 | 39.135 | 1.00 | 62.35 |
| ATOM | 463 | CD | LYS | A | 96 | −3.990 | 62.208 | 37.669 | 1.00 | 69.15 |
| ATOM | 464 | CE | LYS | A | 96 | −5.216 | 61.199 | 37.521 | 1.00 | 75.56 |
| ATOM | 465 | NZ | LYS | A | 96 | −4.842 | 60.221 | 36.430 | 1.00 | 82.67 |
| ATOM | 466 | N | LEU | A | 97 | −4.407 | 63.478 | 42.343 | 1.00 | 52.14 |
| ATOM | 467 | CA | LEU | A | 97 | −4.570 | 62.636 | 43.505 | 1.00 | 53.33 |
| ATOM | 468 | C | LEU | A | 97 | −5.390 | 61.409 | 43.187 | 1.00 | 60.18 |
| ATOM | 469 | O | LEU | A | 97 | −6.534 | 61.509 | 42.734 | 1.00 | 59.94 |
| ATOM | 470 | CB | LEU | A | 97 | −5.214 | 63.417 | 44.647 | 1.00 | 53.55 |
| ATOM | 471 | CG | LEU | A | 97 | −4.417 | 64.616 | 45.151 | 1.00 | 58.71 |
| ATOM | 472 | CD1 | LEU | A | 97 | −5.349 | 65.764 | 45.496 | 1.00 | 58.91 |
| ATOM | 473 | CD2 | LEU | A | 97 | −3.543 | 64.229 | 46.349 | 1.00 | 60.65 |
| ATOM | 474 | N | ILE | A | 98 | −4.804 | 60.249 | 43.439 | 1.00 | 58.65 |
| ATOM | 475 | CA | ILE | A | 98 | −5.478 | 58.952 | 43.200 | 1.00 | 59.11 |
| ATOM | 476 | C | ILE | A | 98 | −5.635 | 58.249 | 44.515 | 1.00 | 65.98 |
| ATOM | 477 | O | ILE | A | 98 | −4.652 | 57.794 | 45.101 | 1.00 | 65.00 |
| ATOM | 478 | CB | ILE | A | 98 | −4.691 | 58.117 | 42.217 | 1.00 | 61.75 |
| ATOM | 479 | CG1 | ILE | A | 98 | −4.490 | 58.856 | 40.895 | 1.00 | 61.70 |
| ATOM | 480 | CG2 | ILE | A | 98 | −5.400 | 56.792 | 42.002 | 1.00 | 62.25 |
| ATOM | 481 | CD1 | ILE | A | 98 | −3.511 | 58.189 | 39.963 | 1.00 | 64.71 |
| ATOM | 482 | N | HIS | A | 99 | −6.871 | 58.146 | 44.992 | 1.00 | 65.70 |
| ATOM | 483 | CA | HIS | A | 99 | −7.130 | 57.454 | 46.241 | 1.00 | 67.05 |
| ATOM | 484 | C | HIS | A | 99 | −7.105 | 55.945 | 46.060 | 1.00 | 72.54 |
| ATOM | 485 | O | HIS | A | 99 | −7.886 | 55.386 | 45.291 | 1.00 | 71.73 |
| ATOM | 486 | CB | HIS | A | 99 | −8.449 | 57.892 | 46.870 | 1.00 | 68.33 |
| ATOM | 487 | CG | HIS | A | 99 | −8.652 | 57.363 | 48.254 | 1.00 | 72.32 |
| ATOM | 488 | ND1 | HIS | A | 99 | −8.549 | 58.157 | 49.378 | 1.00 | 74.43 |
| ATOM | 489 | CD2 | HIS | A | 99 | −8.894 | 56.106 | 48.702 | 1.00 | 74.36 |
| ATOM | 490 | CE1 | HIS | A | 99 | −8.748 | 57.417 | 50.456 | 1.00 | 74.02 |
| ATOM | 491 | NE2 | HIS | A | 99 | −8.954 | 56.169 | 50.073 | 1.00 | 74.36 |
| ATOM | 492 | N | LEU | A | 100 | −6.194 | 55.294 | 46.770 | 1.00 | 70.70 |
| ATOM | 493 | CA | LEU | A | 100 | −6.041 | 53.855 | 46.682 | 1.00 | 71.48 |
| ATOM | 494 | C | LEU | A | 100 | −5.648 | 53.249 | 48.027 | 1.00 | 77.47 |
| ATOM | 495 | O | LEU | A | 100 | −4.872 | 53.834 | 48.791 | 1.00 | 77.07 |
| ATOM | 496 | CB | LEU | A | 100 | −5.002 | 53.499 | 45.620 | 1.00 | 71.49 |
| ATOM | 497 | CG | LEU | A | 100 | −5.525 | 53.477 | 44.186 | 1.00 | 76.29 |
| ATOM | 498 | CD1 | LEU | A | 100 | −4.622 | 52.644 | 43.287 | 1.00 | 76.50 |
| ATOM | 499 | CD2 | LEU | A | 100 | −6.946 | 52.944 | 44.162 | 1.00 | 79.04 |
| ATOM | 500 | N | GLU | A | 101 | −6.197 | 52.077 | 48.316 | 1.00 | 75.65 |
| ATOM | 501 | CA | GLU | A | 101 | −5.891 | 51.377 | 49.552 | 1.00 | 76.09 |
| ATOM | 502 | C | GLU | A | 101 | −5.114 | 50.116 | 49.216 | 1.00 | 81.17 |
| ATOM | 503 | O | GLU | A | 101 | −5.698 | 49.071 | 48.918 | 1.00 | 80.95 |
| ATOM | 504 | CB | GLU | A | 101 | −7.176 | 51.035 | 50.307 | 1.00 | 77.49 |
| ATOM | 505 | CG | GLU | A | 101 | −8.196 | 52.166 | 50.332 | 1.00 | 88.88 |
| ATOM | 506 | CD | GLU | A | 101 | −7.912 | 53.188 | 51.420 | 1.00 | 111.88 |
| ATOM | 507 | OE1 | GLU | A | 101 | −8.263 | 52.924 | 52.589 | 1.00 | 109.11 |
| ATOM | 508 | OE2 | GLU | A | 101 | −7.349 | 54.258 | 51.103 | 1.00 | 105.84 |
| ATOM | 509 | N | ILE | A | 102 | −3.791 | 50.231 | 49.210 | 1.00 | 78.09 |
| ATOM | 510 | CA | ILE | A | 102 | −2.939 | 49.105 | 48.870 | 1.00 | 78.07 |
| ATOM | 511 | C | ILE | A | 102 | −1.746 | 48.972 | 49.805 | 1.00 | 81.90 |
| ATOM | 512 | O | ILE | A | 102 | −1.316 | 49.941 | 50.429 | 1.00 | 81.14 |
| ATOM | 513 | CB | ILE | A | 102 | −2.444 | 49.188 | 47.416 | 1.00 | 81.21 |
| ATOM | 514 | CG1 | ILE | A | 102 | −3.062 | 50.396 | 46.715 | 1.00 | 81.67 |
| ATOM | 515 | CG2 | ILE | A | 102 | −2.791 | 47.909 | 46.665 | 1.00 | 82.05 |
| ATOM | 516 | CD1 | ILE | A | 102 | −4.496 | 50.122 | 46.283 | 1.00 | 89.77 |
| ATOM | 517 | N | LYS | A | 103 | −1.225 | 47.756 | 49.902 | 1.00 | 78.68 |
| ATOM | 518 | CA | LYS | A | 103 | −0.085 | 47.467 | 50.757 | 1.00 | 78.58 |
| ATOM | 519 | C | LYS | A | 103 | 1.101 | 48.342 | 50.381 | 1.00 | 82.23 |
| ATOM | 520 | O | LYS | A | 103 | 1.320 | 48.633 | 49.202 | 1.00 | 81.81 |
| ATOM | 521 | CB | LYS | A | 103 | 0.298 | 45.991 | 50.630 | 1.00 | 81.15 |

TABLE 4-continued

Structural Coordinate of MEK1/N35/NKFCdel (corresponding to amino acids 24 373 of SEQ ID NO: 2)-Compound 2 Binary Complex.

| ATOM | 522 | CG | LYS | A | 103 | −0.209 | 45.339 | 49.348 | 1.00 | 93.74 |
|---|---|---|---|---|---|---|---|---|---|---|
| ATOM | 523 | CD | LYS | A | 103 | −0.539 | 43.868 | 49.562 | 1.00 | 102.90 |
| ATOM | 524 | CE | LYS | A | 103 | −2.001 | 43.676 | 49.937 | 1.00 | 111.03 |
| ATOM | 525 | NZ | LYS | A | 103 | −2.414 | 42.255 | 49.838 | 1.00 | 117.15 |
| ATOM | 526 | N | PRO | A | 104 | 1.863 | 48.764 | 51.385 | 1.00 | 78.58 |
| ATOM | 527 | CA | PRO | A | 104 | 3.033 | 49.604 | 51.160 | 1.00 | 78.14 |
| ATOM | 528 | C | PRO | A | 104 | 3.945 | 49.014 | 50.082 | 1.00 | 82.01 |
| ATOM | 529 | O | PRO | A | 104 | 4.618 | 49.747 | 49.355 | 1.00 | 81.68 |
| ATOM | 530 | CB | PRO | A | 104 | 3.737 | 49.596 | 52.520 | 1.00 | 79.62 |
| ATOM | 531 | CG | PRO | A | 104 | 3.316 | 48.323 | 53.145 | 1.00 | 83.91 |
| ATOM | 532 | CD | PRO | A | 104 | 1.911 | 48.083 | 52.592 | 1.00 | 79.11 |
| ATOM | 533 | N | ALA | A | 105 | 3.950 | 47.689 | 49.974 | 1.00 | 78.30 |
| ATOM | 534 | CA | ALA | A | 105 | 4.761 | 47.012 | 48.965 | 1.00 | 77.92 |
| ATOM | 535 | C | ALA | A | 105 | 4.248 | 47.372 | 47.577 | 1.00 | 81.15 |
| ATOM | 536 | O | ALA | A | 105 | 5.017 | 47.789 | 46.704 | 1.00 | 80.55 |
| ATOM | 537 | CB | ALA | A | 105 | 4.719 | 45.502 | 49.172 | 1.00 | 78.72 |
| ATOM | 538 | N | ILE | A | 106 | 2.939 | 47.228 | 47.392 | 1.00 | 77.18 |
| ATOM | 539 | CA | ILE | A | 106 | 2.288 | 47.541 | 46.123 | 1.00 | 76.81 |
| ATOM | 540 | C | ILE | A | 106 | 2.524 | 48.998 | 45.706 | 1.00 | 80.36 |
| ATOM | 541 | O | ILE | A | 105 | 3.059 | 49.270 | 44.626 | 1.00 | 79.75 |
| ATOM | 542 | CB | ILE | A | 106 | 0.768 | 47.283 | 46.203 | 1.00 | 79.86 |
| ATOM | 543 | CG1 | ILE | A | 106 | 0.434 | 45.883 | 45.689 | 1.00 | 80.25 |
| ATOM | 544 | CG2 | ILE | A | 106 | 0.005 | 48.339 | 45.427 | 1.00 | 80.42 |
| ATOM | 545 | CD1 | ILE | A | 106 | −1.023 | 45.505 | 45.845 | 1.00 | 87.47 |
| ATOM | 546 | N | ARG | A | 107 | 2.116 | 49.930 | 46.565 | 1.00 | 76.49 |
| ATOM | 547 | CA | ARG | A | 107 | 2.263 | 51.357 | 46.287 | 1.00 | 75.91 |
| ATOM | 548 | C | ARG | A | 107 | 3.712 | 51.746 | 45.971 | 1.00 | 78.71 |
| ATOM | 549 | O | ARG | A | 107 | 3.973 | 52.523 | 45.044 | 1.00 | 77.55 |
| ATOM | 550 | CB | ARG | A | 107 | 1.737 | 52.188 | 47.461 | 1.00 | 75.59 |
| ATOM | 551 | CG | ARG | A | 107 | 2.721 | 52.302 | 48.611 | 1.00 | 86.25 |
| ATOM | 552 | CD | ARG | A | 107 | 2.186 | 53.238 | 49.683 | 1.00 | 99.21 |
| ATOM | 553 | NE | ARG | A | 107 | 3.249 | 53.678 | 50.585 | 1.00 | 110.98 |
| ATOM | 554 | CZ | ARG | A | 107 | 3.365 | 53.282 | 51.849 | 1.00 | 127.14 |
| ATOM | 555 | NH1 | ARG | A | 107 | 2.482 | 52.437 | 52.365 | 1.00 | 114.16 |
| ATOM | 556 | NH2 | ARG | A | 107 | 4.360 | 53.738 | 52.594 | 1.00 | 115.38 |
| ATOM | 557 | N | ASN | A | 108 | 4.646 | 51.206 | 46.749 | 1.00 | 75.04 |
| ATOM | 558 | CA | ASN | A | 108 | 6.068 | 51.506 | 46.572 | 1.00 | 74.59 |
| ATOM | 559 | C | ASN | A | 108 | 6.590 | 51.118 | 45.186 | 1.00 | 77.13 |
| ATOM | 560 | O | ASN | A | 108 | 7.565 | 51.696 | 44.697 | 1.00 | 76.45 |
| ATOM | 561 | CB | ASN | A | 108 | 6.896 | 50.843 | 47.669 | 1.00 | 76.15 |
| ATOM | 562 | CG | ASN | A | 108 | 6.879 | 51.631 | 48.963 | 1.00 | 102.33 |
| ATOM | 563 | OD1 | ASN | A | 108 | 7.258 | 52.802 | 48.993 | 1.00 | 98.66 |
| ATOM | 564 | ND2 | ASN | A | 108 | 6.410 | 51.004 | 50.035 | 1.00 | 93.82 |
| ATOM | 565 | N | GLN | A | 109 | 5.934 | 50.147 | 44.556 | 1.00 | 72.87 |
| ATOM | 566 | CA | GLN | A | 109 | 6.317 | 49.714 | 43.217 | 1.00 | 72.24 |
| ATOM | 567 | C | GLN | A | 109 | 5.777 | 50.714 | 42.202 | 1.00 | 74.92 |
| ATOM | 568 | O | GLN | A | 109 | 6.453 | 51.067 | 41.234 | 1.00 | 74.56 |
| ATOM | 569 | CB | GLN | A | 109 | 5.759 | 48.318 | 42.920 | 1.00 | 73.60 |
| ATOM | 570 | CG | GLN | A | 109 | 6.324 | 47.681 | 41.656 | 1.00 | 89.98 |
| ATOM | 571 | CD | GLN | A | 109 | 5.388 | 46.656 | 41.052 | 1.00 | 113.47 |
| ATOM | 572 | OE1 | GLN | A | 109 | 5.358 | 45.502 | 41.475 | 1.00 | 111.91 |
| ATOM | 573 | NE2 | GLN | A | 109 | 4.621 | 47.070 | 40.049 | 1.00 | 105.49 |
| ATOM | 574 | N | ILE | A | 110 | 4.552 | 51.171 | 42.438 | 1.00 | 70.19 |
| ATOM | 575 | CA | ILE | A | 110 | 3.922 | 52.146 | 41.569 | 1.00 | 69.44 |
| ATOM | 576 | C | ILE | A | 110 | 4.825 | 53.363 | 41.441 | 1.00 | 71.94 |
| ATOM | 577 | O | ILE | A | 110 | 5.197 | 53.757 | 40.338 | 1.00 | 71.41 |
| ATOM | 578 | CB | ILE | A | 110 | 2.553 | 52.586 | 42.123 | 1.00 | 72.43 |
| ATOM | 579 | CG1 | ILE | A | 110 | 1.492 | 51.524 | 41.827 | 1.00 | 72.62 |
| ATOM | 580 | CG2 | ILE | A | 110 | 2.150 | 53.941 | 41.547 | 1.00 | 73.13 |
| ATOM | 581 | CD1 | ILE | A | 110 | 0.492 | 51.336 | 42.940 | 1.00 | 78.25 |
| ATOM | 582 | N | ILE | A | 111 | 5.193 | 53.941 | 42.582 | 1.00 | 67.94 |
| ATOM | 583 | CA | ILE | A | 111 | 6.079 | 55.102 | 42.605 | 1.00 | 67.36 |
| ATOM | 584 | C | ILE | A | 111 | 7.337 | 54.803 | 41.802 | 1.00 | 71.00 |
| ATOM | 585 | O | ILE | A | 111 | 7.893 | 55.683 | 41.139 | 1.00 | 70.62 |
| ATOM | 586 | CB | ILE | A | 111 | 6.462 | 55.468 | 44.040 | 1.00 | 70.11 |
| ATOM | 587 | CG1 | ILE | A | 111 | 5.232 | 55.991 | 44.796 | 1.00 | 70.48 |
| ATOM | 588 | CG2 | ILE | A | 111 | 7.545 | 56.544 | 44.036 | 1.00 | 70.45 |
| ATOM | 589 | CD1 | ILE | A | 111 | 3.979 | 56.057 | 43.947 | 1.00 | 75.91 |
| ATOM | 590 | N | ARG | A | 112 | 7.753 | 53.542 | 41.833 | 1.00 | 67.17 |
| ATOM | 591 | CA | ARG | A | 112 | 8.917 | 53.087 | 41.085 | 1.00 | 66.85 |
| ATOM | 592 | C | ARG | A | 112 | 8.676 | 53.243 | 39.585 | 1.00 | 69.04 |
| ATOM | 593 | O | ARG | A | 112 | 9.456 | 53.890 | 38.885 | 1.00 | 68.61 |
| ATOM | 594 | CB | ARG | A | 112 | 9.206 | 51.616 | 41.405 | 1.00 | 68.88 |
| ATOM | 595 | CG | ARG | A | 112 | 10.144 | 51.399 | 42.583 | 1.00 | 83.98 |
| ATOM | 596 | CD | ARG | A | 112 | 10.559 | 49.942 | 42.694 | 1.00 | 98.85 |
| ATOM | 597 | NE | ARG | A | 112 | 10.210 | 49.373 | 43.993 | 1.00 | 114.29 |
| ATOM | 598 | CZ | ARG | A | 112 | 10.988 | 48.534 | 44.671 | 1.00 | 135.30 |

TABLE 4-continued

Structural Coordinate of MEK1/N35/NKFCdel (corresponding to amino acids 24 373 of SEQ ID NO: 2)-Compound 2 Binary Complex.

| ATOM | 599 | NH1 | ARG | A | 112 | 12.161 | 48.164 | 44.174 | 1.00 | 125.73 |
|------|-----|-----|-----|---|-----|--------|--------|--------|------|--------|
| ATOM | 600 | NH2 | ARG | A | 112 | 10.595 | 48.071 | 45.852 | 1.00 | 124.83 |
| ATOM | 601 | N | GLU | A | 113 | 7.591 | 52.636 | 39.105 | 1.00 | 63.88 |
| ATOM | 602 | CA | GLU | A | 113 | 7.225 | 52.687 | 37.687 | 1.00 | 62.77 |
| ATOM | 603 | C | GLU | A | 113 | 7.029 | 54.120 | 37.170 | 1.00 | 64.58 |
| ATOM | 604 | O | GLU | A | 113 | 7.385 | 54.432 | 36.034 | 1.00 | 64.10 |
| ATOM | 605 | CB | GLU | A | 113 | 5.963 | 51.841 | 37.425 | 1.00 | 64.01 |
| ATOM | 606 | CG | GLU | A | 113 | 5.788 | 50.661 | 38.378 | 1.00 | 73.60 |
| ATOM | 607 | CD | GLU | A | 113 | 4.785 | 49.627 | 37.871 | 1.00 | 91.54 |
| ATOM | 608 | OE1 | GLU | A | 113 | 3.618 | 49.996 | 37.619 | 1.00 | 81.88 |
| ATOM | 609 | OE2 | GLU | A | 113 | 5.160 | 48.443 | 37.751 | 1.00 | 84.27 |
| ATOM | 610 | N | LEU | A | 114 | 6.470 | 54.986 | 38.011 | 1.00 | 59.56 |
| ATOM | 611 | CA | LEU | A | 114 | 6.233 | 56.381 | 37.627 | 1.00 | 58.44 |
| ATOM | 612 | C | LEU | A | 114 | 7.533 | 57.160 | 37.470 | 1.00 | 61.50 |
| ATOM | 613 | O | LEU | A | 114 | 7.555 | 58.231 | 36.861 | 1.00 | 60.77 |
| ATOM | 614 | CB | LEU | A | 114 | 5.331 | 57.072 | 38.646 | 1.00 | 58.02 |
| ATOM | 615 | CG | LEU | A | 114 | 3.929 | 56.500 | 38.748 | 1.00 | 61.89 |
| ATOM | 616 | CD1 | LEU | A | 114 | 3.261 | 56.967 | 40.024 | 1.00 | 61.88 |
| ATOM | 617 | CD2 | LEU | A | 114 | 3.125 | 56.902 | 37.535 | 1.00 | 63.69 |
| ATOM | 618 | N | GLN | A | 115 | 8.612 | 56.620 | 38.032 | 1.00 | 57.79 |
| ATOM | 619 | CA | GLN | A | 115 | 9.923 | 57.255 | 37.954 | 1.00 | 57.28 |
| ATOM | 620 | C | GLN | A | 115 | 10.343 | 57.484 | 36.510 | 1.00 | 60.97 |
| ATOM | 621 | O | GLN | A | 115 | 11.105 | 58.399 | 36.218 | 1.00 | 60.67 |
| ATOM | 622 | CB | GLN | A | 115 | 10.971 | 56.410 | 38.678 | 1.00 | 58.35 |
| ATOM | 623 | CG | GLN | A | 115 | 10.774 | 56.344 | 40.185 | 1.00 | 61.59 |
| ATOM | 624 | CD | GLN | A | 115 | 10.404 | 57.590 | 40.782 | 1.00 | 65.34 |
| ATOM | 625 | OE1 | GLN | A | 115 | 11.217 | 58.618 | 40.808 | 1.00 | 60.79 |
| ATOM | 626 | NE2 | GLN | A | 115 | 9.171 | 57.806 | 41.253 | 1.00 | 46.06 |
| ATOM | 627 | N | VAL | A | 116 | 9.830 | 56.648 | 35.612 | 1.00 | 57.59 |
| ATOM | 628 | CA | VAL | A | 116 | 10.133 | 56.744 | 34.184 | 1.00 | 57.53 |
| ATOM | 629 | C | VAL | A | 116 | 9.812 | 58.124 | 33.595 | 1.00 | 60.52 |
| ATOM | 630 | O | VAL | A | 116 | 10.459 | 58.568 | 32.646 | 1.00 | 59.73 |
| ATOM | 631 | CB | VAL | A | 116 | 9.361 | 55.671 | 33.380 | 1.00 | 61.88 |
| ATOM | 632 | CG1 | VAL | A | 116 | 9.608 | 55.839 | 31.895 | 1.00 | 61.94 |
| ATOM | 633 | CG2 | VAL | A | 116 | 9.762 | 54.277 | 33.833 | 1.00 | 61.81 |
| ATOM | 634 | N | LEU | A | 117 | 8.600 | 58.782 | 34.158 | 1.00 | 56.96 |
| ATOM | 635 | CA | LEU | A | 117 | 8.358 | 60.099 | 33.693 | 1.00 | 56.26 |
| ATOM | 636 | C | LEU | A | 117 | 9.425 | 61.179 | 33.815 | 1.00 | 59.27 |
| ATOM | 637 | O | LEU | A | 117 | 9.266 | 62.276 | 33.283 | 1.00 | 58.67 |
| ATOM | 638 | CB | LEU | A | 117 | 7.105 | 60.535 | 34.449 | 1.00 | 56.17 |
| ATOM | 639 | CG | LEU | A | 117 | 5.840 | 59.702 | 34.255 | 1.00 | 60.62 |
| ATOM | 640 | CD1 | LEU | A | 117 | 4.801 | 60.072 | 35.312 | 1.00 | 60.81 |
| ATOM | 641 | CD2 | LEU | A | 117 | 5.281 | 59.907 | 32.859 | 1.00 | 62.48 |
| ATOM | 642 | N | HIS | A | 118 | 10.496 | 60.883 | 34.539 | 1.00 | 56.09 |
| ATOM | 643 | CA | HIS | A | 118 | 11.576 | 61.848 | 34.725 | 1.00 | 56.22 |
| ATOM | 644 | C | HIS | A | 118 | 12.448 | 61.923 | 33.478 | 1.00 | 62.04 |
| ATOM | 645 | O | HIS | A | 118 | 13.231 | 62.861 | 33.313 | 1.00 | 61.83 |
| ATOM | 646 | CB | HIS | A | 118 | 12.441 | 61.474 | 35.942 | 1.00 | 56.62 |
| ATOM | 647 | CG | HIS | A | 118 | 11.865 | 61.911 | 37.255 | 1.00 | 59.55 |
| ATOM | 648 | ND1 | HIS | A | 118 | 11.368 | 61.017 | 38.192 | 1.00 | 61.03 |
| ATOM | 649 | CD2 | HIS | A | 118 | 11.725 | 63.141 | 37.804 | 1.00 | 60.96 |
| ATOM | 650 | CE1 | HIS | A | 118 | 10.959 | 61.681 | 39.252 | 1.00 | 60.36 |
| ATOM | 651 | NE2 | HIS | A | 118 | 11.158 | 62.971 | 39.045 | 1.00 | 60.62 |
| ATOM | 652 | N | GLU | A | 119 | 12.302 | 60.935 | 32.597 | 1.00 | 59.57 |
| ATOM | 653 | CA | GLU | A | 119 | 13.081 | 60.891 | 31.366 | 1.00 | 59.61 |
| ATOM | 654 | C | GLU | A | 119 | 12.303 | 61.419 | 30.164 | 1.00 | 63.22 |
| ATOM | 655 | O | GLU | A | 119 | 12.868 | 61.604 | 29.080 | 1.00 | 62.78 |
| ATOM | 656 | CB | GLU | A | 119 | 13.556 | 59.471 | 31.086 | 1.00 | 61.14 |
| ATOM | 657 | CG | GLU | A | 119 | 13.647 | 58.583 | 32.313 | 1.00 | 73.91 |
| ATOM | 658 | CD | GLU | A | 119 | 14.048 | 57.162 | 31.965 | 1.00 | 97.57 |
| ATOM | 659 | OE1 | GLU | A | 119 | 15.091 | 56.988 | 31.296 | 1.00 | 87.98 |
| ATOM | 660 | OE2 | GLU | A | 119 | 13.306 | 56.222 | 32.329 | 1.00 | 95.04 |
| ATOM | 661 | N | CYS | A | 120 | 11.004 | 61.639 | 30.350 | 1.00 | 59.32 |
| ATOM | 662 | CA | CYS | A | 120 | 10.152 | 62.134 | 29.271 | 1.00 | 58.90 |
| ATOM | 663 | C | CYS | A | 120 | 10.294 | 63.643 | 29.123 | 1.00 | 61.52 |
| ATOM | 664 | O | CYS | A | 120 | 9.629 | 64.409 | 29.818 | 1.00 | 61.49 |
| ATOM | 665 | CB | CYS | A | 120 | 8.694 | 61.747 | 29.512 | 1.00 | 59.20 |
| ATOM | 666 | SG | CYS | A | 120 | 8.361 | 59.961 | 29.327 | 1.00 | 63.29 |
| ATOM | 667 | N | ASN | A | 121 | 11.181 | 64.061 | 28.227 | 1.00 | 56.43 |
| ATOM | 668 | CA | ASN | A | 121 | 11.436 | 65.474 | 28.013 | 1.00 | 55.45 |
| ATOM | 669 | C | ASN | A | 121 | 11.159 | 65.918 | 26.581 | 1.00 | 56.61 |
| ATOM | 670 | O | ASN | A | 121 | 11.985 | 65.753 | 25.685 | 1.00 | 55.66 |
| ATOM | 671 | CB | ASN | A | 121 | 12.850 | 65.833 | 28.454 | 1.00 | 57.58 |
| ATOM | 672 | CG | ASN | A | 121 | 13.159 | 65.324 | 29.862 | 1.00 | 80.43 |
| ATOM | 673 | OD1 | ASN | A | 121 | 12.368 | 65.522 | 30.792 | 1.00 | 68.34 |
| ATOM | 674 | ND2 | ASN | A | 121 | 14.264 | 64.589 | 30.000 | 1.00 | 73.80 |
| ATOM | 675 | N | SER | A | 122 | 9.973 | 66.476 | 26.381 | 1.00 | 51.46 |

TABLE 4-continued

Structural Coordinate of MEK1/N35/NKFCdel (corresponding to amino acids 24 373 of SEQ ID NO: 2)-Compound 2 Binary Complex.

| ATOM | 676 | CA | SER | A | 122 | 9.535 | 66.919 | 25.069 | 1.00 | 49.97 |
|---|---|---|---|---|---|---|---|---|---|---|
| ATOM | 677 | C | SER | A | 122 | 8.631 | 68.135 | 25.228 | 1.00 | 51.71 |
| ATOM | 678 | O | SER | A | 122 | 7.915 | 68.261 | 26.213 | 1.00 | 51.38 |
| ATOM | 679 | CB | SER | A | 122 | 8.767 | 65.785 | 24.373 | 1.00 | 52.53 |
| ATOM | 680 | OG | SER | A | 122 | 8.024 | 66.262 | 23.270 | 1.00 | 60.26 |
| ATOM | 681 | N | PRO | A | 123 | 8.678 | 69.033 | 24.257 | 1.00 | 46.73 |
| ATOM | 682 | CA | PRO | A | 123 | 7.844 | 70.228 | 24.283 | 1.00 | 45.59 |
| ATOM | 683 | C | PRO | A | 123 | 6.368 | 69.851 | 24.141 | 1.00 | 47.56 |
| ATOM | 684 | O | PRO | A | 123 | 5.486 | 70.693 | 24.277 | 1.00 | 46.81 |
| ATOM | 685 | CB | PRO | A | 123 | 8.289 | 70.985 | 23.025 | 1.00 | 47.30 |
| ATOM | 686 | CG | PRO | A | 123 | 9.656 | 70.490 | 22.741 | 1.00 | 51.79 |
| ATOM | 687 | CD | PRO | A | 123 | 9.677 | 69.069 | 23.177 | 1.00 | 47.18 |
| ATOM | 688 | N | TYR | A | 124 | 6.120 | 68.580 | 23.839 | 1.00 | 43.10 |
| ATOM | 689 | CA | TYR | A | 124 | 4.778 | 68.087 | 23.575 | 1.00 | 42.60 |
| ATOM | 690 | C | TYR | A | 124 | 4.270 | 67.125 | 24.641 | 1.00 | 47.27 |
| ATOM | 691 | O | TYR | A | 124 | 3.251 | 66.433 | 24.455 | 1.00 | 46.75 |
| ATOM | 692 | CB | TYR | A | 124 | 4.743 | 67.440 | 22.191 | 1.00 | 43.35 |
| ATOM | 693 | CG | TYR | A | 124 | 5.336 | 68.330 | 21.114 | 1.00 | 44.58 |
| ATOM | 694 | CD1 | TYR | A | 124 | 4.694 | 69.497 | 20.731 | 1.00 | 46.09 |
| ATOM | 695 | CD2 | TYR | A | 124 | 6.576 | 68.045 | 20.546 | 1.00 | 45.28 |
| ATOM | 696 | CE1 | TYR | A | 124 | 5.235 | 70.336 | 19.784 | 1.00 | 46.86 |
| ATOM | 697 | CE2 | TYR | A | 124 | 7.127 | 68.873 | 19.585 | 1.00 | 46.29 |
| ATOM | 698 | CZ | TYR | A | 124 | 6.451 | 70.030 | 19.214 | 1.00 | 55.18 |
| ATOM | 699 | OH | TYR | A | 124 | 6.979 | 70.878 | 18.255 | 1.00 | 56.84 |
| ATOM | 700 | N | ILE | A | 125 | 4.973 | 67.099 | 25.768 | 1.00 | 43.66 |
| ATOM | 701 | CA | ILE | A | 125 | 4.615 | 66.257 | 26.892 | 1.00 | 43.27 |
| ATOM | 702 | C | ILE | A | 125 | 4.682 | 67.135 | 28.118 | 1.00 | 48.08 |
| ATOM | 703 | O | ILE | A | 125 | 5.611 | 67.924 | 28.262 | 1.00 | 47.58 |
| ATOM | 704 | CB | ILE | A | 125 | 5.614 | 65.100 | 27.052 | 1.00 | 46.34 |
| ATOM | 705 | CG1 | ILE | A | 125 | 5.741 | 64.310 | 25.717 | 1.00 | 46.42 |
| ATOM | 706 | CG2 | ILE | A | 125 | 5.213 | 64.195 | 28.213 | 1.00 | 47.09 |
| ATOM | 707 | CD1 | ILE | A | 125 | 4.474 | 63.597 | 25.325 | 1.00 | 49.13 |
| ATOM | 708 | N | VAL | A | 126 | 3.671 | 67.053 | 28.974 | 1.00 | 45.58 |
| ATOM | 709 | CA | VAL | A | 126 | 3.628 | 67.895 | 30.172 | 1.00 | 45.60 |
| ATOM | 710 | C | VAL | A | 126 | 4.800 | 67.597 | 31.106 | 1.00 | 48.93 |
| ATOM | 711 | O | VAL | A | 126 | 5.113 | 66.437 | 31.370 | 1.00 | 48.59 |
| ATOM | 712 | CB | VAL | A | 126 | 2.298 | 67.723 | 30.951 | 1.00 | 49.70 |
| ATOM | 713 | CG1 | VAL | A | 126 | 2.020 | 68.953 | 31.812 | 1.00 | 49.35 |
| ATOM | 714 | CG2 | VAL | A | 126 | 1.150 | 67.469 | 29.990 | 1.00 | 49.69 |
| ATOM | 715 | N | GLY | A | 127 | 5.442 | 68.650 | 31.607 | 1.00 | 45.04 |
| ATOM | 716 | CA | GLY | A | 127 | 6.563 | 68.494 | 32.534 | 1.00 | 44.59 |
| ATOM | 717 | C | GLY | A | 127 | 6.126 | 67.698 | 33.761 | 1.00 | 48.14 |
| ATOM | 718 | O | GLY | A | 127 | 5.045 | 67.916 | 34.296 | 1.00 | 47.02 |
| ATOM | 719 | N | PHE | A | 128 | 6.969 | 66.761 | 34.183 | 1.00 | 44.92 |
| ATOM | 720 | CA | PHE | A | 128 | 6.683 | 65.914 | 35.347 | 1.00 | 44.18 |
| ATOM | 721 | C | PHE | A | 128 | 7.670 | 66.236 | 36.458 | 1.00 | 47.96 |
| ATOM | 722 | O | PHE | A | 128 | 8.883 | 66.213 | 36.248 | 1.00 | 47.02 |
| ATOM | 723 | CB | PHE | A | 128 | 6.799 | 64.435 | 34.956 | 1.00 | 45.56 |
| ATOM | 724 | CG | PHE | A | 128 | 6.819 | 53.484 | 36.127 | 1.00 | 46.80 |
| ATOM | 725 | CD1 | PHE | A | 128 | 5.637 | 63.082 | 36.736 | 1.00 | 49.68 |
| ATOM | 726 | CD2 | PHE | A | 128 | 8.013 | 62.923 | 36.563 | 1.00 | 48.71 |
| ATOM | 727 | CE1 | PHE | A | 128 | 5.648 | 62.175 | 37.788 | 1.00 | 50.48 |
| ATOM | 728 | CE2 | PHE | A | 128 | 8.031 | 62.011 | 27.608 | 1.00 | 51.55 |
| ATOM | 729 | CZ | PHE | A | 128 | 6.845 | 61.642 | 38.226 | 1.00 | 49.63 |
| ATOM | 730 | N | TYR | A | 129 | 7.150 | 66.528 | 37.644 | 1.00 | 45.21 |
| ATOM | 731 | CA | TYR | A | 129 | 8.004 | 66.848 | 38.790 | 1.00 | 44.90 |
| ATOM | 732 | C | TYR | A | 129 | 8.361 | 65.616 | 39.617 | 1.00 | 50.37 |
| ATOM | 733 | O | TYR | A | 129 | 9.529 | 65.366 | 39.899 | 1.00 | 50.95 |
| ATOM | 734 | CB | TYR | A | 129 | 7.349 | 67.902 | 39.673 | 1.00 | 45.26 |
| ATOM | 735 | CG | TYR | A | 129 | 7.335 | 69.272 | 39.061 | 1.00 | 45.91 |
| ATOM | 736 | CD1 | TYR | A | 129 | 8.505 | 69.993 | 38.905 | 1.00 | 47.70 |
| ATOM | 737 | CD2 | TYR | A | 129 | 6.148 | 69.844 | 38.623 | 1.00 | 46.34 |
| ATOM | 738 | CE1 | TYR | A | 129 | 8.495 | 71.251 | 38.342 | 1.00 | 48.02 |
| ATOM | 739 | CE2 | TYR | A | 129 | 6.127 | 71.099 | 38.067 | 1.00 | 46.97 |
| ATOM | 740 | CZ | TYR | A | 129 | 7.305 | 71.799 | 37.925 | 1.00 | 52.51 |
| ATOM | 741 | OH | TYR | A | 129 | 7.292 | 73.049 | 37.354 | 1.00 | 51.22 |
| ATOM | 742 | N | GLY | A | 130 | 7.351 | 64.854 | 40.011 | 1.00 | 47.11 |
| ATOM | 743 | CA | GLY | A | 130 | 7.584 | 63.667 | 40.813 | 1.00 | 46.94 |
| ATOM | 744 | C | GLY | A | 130 | 6.281 | 62.996 | 41.225 | 1.00 | 51.61 |
| ATOM | 745 | O | GLY | A | 130 | 5.192 | 63.484 | 40.916 | 1.00 | 50.95 |
| ATOM | 746 | N | ALA | A | 131 | 6.412 | 61.868 | 41.924 | 1.00 | 49.13 |
| ATOM | 747 | CA | ALA | A | 131 | 5.278 | 61.092 | 42.400 | 1.00 | 49.25 |
| ATOM | 748 | C | ALA | A | 131 | 5.577 | 60.513 | 43.784 | 1.00 | 53.88 |
| ATOM | 749 | O | ALA | A | 131 | 6.658 | 59.962 | 44.021 | 1.00 | 53.41 |
| ATOM | 750 | CB | ALA | A | 131 | 4.973 | 59.977 | 41.432 | 1.00 | 50.13 |
| ATOM | 751 | N | PHE | A | 132 | 4.612 | 60.628 | 44.688 | 1.00 | 50.29 |
| ATOM | 752 | CA | PHE | A | 132 | 4.768 | 60.109 | 46.037 | 1.00 | 50.06 |

TABLE 4-continued

Structural Coordinate of MEK1/N35/NKFCdel (corresponding to amino acids 24 373 of SEQ ID NO: 2)-Compound 2 Binary Complex.

| ATOM | 753 | C   | PHE | A | 132 | 3.431  | 59.604 | 46.580 | 1.00 | 56.60 |
|------|-----|-----|-----|---|-----|--------|--------|--------|------|-------|
| ATOM | 754 | O   | PHE | A | 132 | 2.373  | 59.895 | 46.022 | 1.00 | 55.64 |
| ATOM | 755 | CB  | PHE | A | 132 | 5.342  | 61.190 | 46.962 | 1.00 | 51.11 |
| ATOM | 756 | CG  | PHE | A | 132 | 4.449  | 62.392 | 47.123 | 1.00 | 51.71 |
| ATOM | 757 | CD1 | PHE | A | 132 | 4.490  | 63.434 | 46.205 | 1.00 | 54.27 |
| ATOM | 758 | CD2 | PHE | A | 132 | 3.580  | 62.489 | 48.198 | 1.00 | 52.92 |
| ATOM | 759 | CE1 | PHE | A | 132 | 3.678  | 64.540 | 46.353 | 1.00 | 54.56 |
| ATOM | 760 | CE2 | PHE | A | 132 | 2.762  | 63.596 | 48.351 | 1.00 | 55.26 |
| ATOM | 761 | CZ  | PHE | A | 132 | 2.813  | 64.620 | 47.432 | 1.00 | 53.28 |
| ATOM | 762 | N   | TYR | A | 133 | 3.487  | 58.850 | 47.671 | 1.00 | 55.63 |
| ATOM | 763 | CA  | TYR | A | 133 | 2.269  | 58.337 | 48.279 | 1.00 | 56.75 |
| ATOM | 764 | C   | TYR | A | 133 | 2.087  | 58.911 | 49.675 | 1.00 | 62.10 |
| ATOM | 765 | O   | TYR | A | 133 | 3.066  | 59.198 | 50.372 | 1.00 | 61.82 |
| ATOM | 766 | CB  | TYR | A | 133 | 2.287  | 56.819 | 48.343 | 1.00 | 58.47 |
| ATOM | 767 | CG  | TYR | A | 133 | 1.165  | 56.227 | 49.154 | 1.00 | 60.84 |
| ATOM | 768 | CD1 | TYR | A | 133 | 1.273  | 56.095 | 50.528 | 1.00 | 62.94 |
| ATOM | 769 | CD2 | TYR | A | 133 | −0.014 | 55.830 | 48.547 | 1.00 | 61.83 |
| ATOM | 770 | CE1 | TYR | A | 133 | 0.232  | 55.574 | 51.278 | 1.00 | 64.17 |
| ATOM | 771 | CE2 | TYR | A | 133 | −1.047 | 55.274 | 49.282 | 1.00 | 62.87 |
| ATOM | 772 | CZ  | TYR | A | 133 | −0.908 | 55.153 | 50.653 | 1.00 | 71.74 |
| ATOM | 773 | OH  | TYR | A | 133 | −1.938 | 54.631 | 51.392 | 1.00 | 74.81 |
| ATOM | 774 | N   | SER | A | 134 | 0.835  | 59.089 | 50.079 | 1.00 | 59.34 |
| ATOM | 775 | CA  | SER | A | 134 | 0.548  | 59.549 | 51.383 | 1.00 | 59.42 |
| ATOM | 776 | C   | SER | A | 134 | −0.900 | 59.460 | 51.807 | 1.00 | 64.54 |
| ATOM | 777 | O   | SER | A | 134 | −1.831 | 59.852 | 51.102 | 1.00 | 63.94 |
| ATOM | 778 | CB  | SER | A | 134 | 0.923  | 61.127 | 51.422 | 1.00 | 63.01 |
| ATOM | 779 | OG  | SER | A | 134 | 0.414  | 61.749 | 52.591 | 1.00 | 73.80 |
| ATOM | 780 | N   | ASP | A | 135 | −1.072 | 58.874 | 52.984 | 1.00 | 62.30 |
| ATOM | 781 | CA  | ASP | A | 135 | −2.382 | 58.648 | 53.572 | 1.00 | 62.36 |
| ATOM | 782 | C   | ASP | A | 135 | −3.446 | 58.132 | 52.602 | 1.00 | 66.30 |
| ATOM | 783 | O   | ASP | A | 135 | −4.475 | 58.775 | 52.395 | 1.00 | 65.98 |
| ATOM | 784 | CB  | ASP | A | 135 | −2.862 | 59.891 | 54.320 | 1.00 | 64.33 |
| ATOM | 785 | CG  | ASP | A | 135 | −1.980 | 60.227 | 55.528 | 1.00 | 75.83 |
| ATOM | 786 | OD1 | ASP | A | 135 | −2.039 | 61.378 | 56.016 | 1.00 | 76.54 |
| ATOM | 787 | OD2 | ASP | A | 135 | −1.222 | 59.337 | 55.984 | 1.00 | 81.57 |
| ATOM | 788 | N   | GLY | A | 136 | −3.197 | 56.961 | 52.030 | 1.00 | 62.65 |
| ATOM | 789 | CA  | GLY | A | 136 | −4.156 | 56.311 | 51.150 | 1.00 | 62.39 |
| ATOM | 790 | C   | GLY | A | 136 | −4.377 | 56.997 | 49.802 | 1.00 | 65.44 |
| ATOM | 791 | O   | GLY | A | 136 | −5.445 | 56.868 | 49.207 | 1.00 | 65.38 |
| ATOM | 792 | N   | GLU | A | 137 | −3.373 | 57.714 | 49.312 | 1.00 | 60.78 |
| ATOM | 793 | CA  | GLU | A | 137 | −3.513 | 58.396 | 48.025 | 1.00 | 59.73 |
| ATOM | 794 | C   | GLU | A | 137 | −2.191 | 58.697 | 47.335 | 1.00 | 60.58 |
| ATOM | 795 | O   | GLU | A | 137 | −1.269 | 59.244 | 47.943 | 1.00 | 59.90 |
| ATOM | 796 | CB  | GLU | A | 137 | −4.354 | 59.676 | 48.171 | 1.00 | 61.23 |
| ATOM | 797 | CG  | GLU | A | 137 | −3.960 | 60.559 | 49.332 | 1.00 | 73.26 |
| ATOM | 798 | CD  | GLU | A | 137 | −4.666 | 61.901 | 49.297 | 1.00 | 97.17 |
| ATOM | 799 | OE1 | GLU | A | 137 | −5.670 | 62.026 | 48.561 | 1.00 | 94.06 |
| ATOM | 800 | OE2 | GLU | A | 137 | −4.211 | 62.833 | 49.996 | 1.00 | 90.32 |
| ATOM | 801 | N   | ILE | A | 138 | −2.109 | 58.330 | 46.057 | 1.00 | 54.82 |
| ATOM | 802 | CA  | ILE | A | 138 | −0.915 | 58.581 | 45.264 | 1.00 | 53.51 |
| ATOM | 803 | C   | ILE | A | 138 | −0.999 | 59.962 | 44.647 | 1.00 | 55.50 |
| ATOM | 804 | O   | ILE | A | 138 | −2.062 | 60.386 | 44.192 | 1.00 | 55.56 |
| ATOM | 805 | CB  | ILE | A | 138 | −0.743 | 57.549 | 44.132 | 1.00 | 56.38 |
| ATOM | 806 | CG1 | ILE | A | 138 | −0.552 | 56.141 | 44.707 | 1.00 | 56.83 |
| ATOM | 807 | CG2 | ILE | A | 138 | 0.438  | 57.918 | 43.260 | 1.00 | 56.56 |
| ATOM | 808 | CD1 | ILE | A | 138 | 0.881  | 55.805 | 45.038 | 1.00 | 63.27 |
| ATOM | 809 | N   | SER | A | 139 | 0.121  | 60.665 | 44.642 | 1.00 | 50.00 |
| ATOM | 810 | CA  | SER | A | 139 | 0.171  | 61.997 | 44.080 | 1.00 | 48.88 |
| ATOM | 811 | C   | SER | A | 139 | 1.138  | 62.079 | 42.910 | 1.00 | 51.15 |
| ATOM | 812 | O   | SER | A | 139 | 2.311  | 61.713 | 43.026 | 1.00 | 50.67 |
| ATOM | 813 | CB  | SER | A | 139 | 0.563  | 63.018 | 45.153 | 1.00 | 52.13 |
| ATOM | 814 | OG  | SER | A | 139 | −0.580 | 63.583 | 45.773 | 1.00 | 60.44 |
| ATOM | 815 | N   | ILE | A | 140 | 0.645  | 62.583 | 41.788 | 1.00 | 46.60 |
| ATOM | 816 | CA  | ILE | A | 140 | 1.474  | 62.795 | 40.619 | 1.00 | 45.73 |
| ATOM | 817 | C   | ILE | A | 140 | 1.519  | 64.300 | 40.381 | 1.00 | 48.69 |
| ATOM | 818 | O   | ILE | A | 140 | 0.491  | 64.938 | 40.163 | 1.00 | 47.62 |
| ATOM | 819 | CB  | ILE | A | 140 | 0.920  | 62.057 | 39.376 | 1.00 | 48.69 |
| ATOM | 820 | CG1 | ILE | A | 140 | 1.231  | 60.555 | 39.471 | 1.00 | 49.26 |
| ATOM | 821 | CG2 | ILE | A | 140 | 1.528  | 62.627 | 38.103 | 1.00 | 48.37 |
| ATOM | 822 | CD1 | ILE | A | 140 | 0.008  | 59.665 | 39.458 | 1.00 | 52.57 |
| ATOM | 823 | N   | CYS | A | 141 | 2.702  | 64.874 | 40.528 | 1.00 | 45.88 |
| ATOM | 824 | CA  | CYS | A | 141 | 2.873  | 66.312 | 40.389 | 1.00 | 45.84 |
| ATOM | 825 | C   | CYS | A | 141 | 3.548  | 66.643 | 39.094 | 1.00 | 49.16 |
| ATOM | 826 | O   | CYS | A | 141 | 4.581  | 66.069 | 38.760 | 1.00 | 48.76 |
| ATOM | 827 | CB  | CYS | A | 141 | 3.687  | 66.869 | 41.554 | 1.00 | 46.19 |
| ATOM | 828 | SG  | CYS | A | 141 | 2.983  | 66.484 | 43.180 | 1.00 | 50.12 |
| ATOM | 829 | N   | MET | A | 142 | 2.976  | 67.587 | 38.364 | 1.00 | 45.92 |

TABLE 4-continued

Structural Coordinate of MEK1/N35/NKFCdel (corresponding to amino acids 24 373 of SEQ ID NO: 2)-Compound 2 Binary Complex.

| ATOM | 830 | CA | MET | A | 142 | 3.548 | 67.976 | 37.095 | 1.00 | 45.84 |
|---|---|---|---|---|---|---|---|---|---|---|
| ATOM | 831 | C | MET | A | 142 | 3.392 | 69.433 | 36.799 | 1.00 | 48.14 |
| ATOM | 832 | O | MET | A | 142 | 2.825 | 70.193 | 37.588 | 1.00 | 47.40 |
| ATOM | 833 | CB | MET | A | 142 | 2.947 | 67.162 | 35.957 | 1.00 | 48.55 |
| ATOM | 834 | CG | MET | A | 142 | 1.502 | 66.867 | 36.109 | 1.00 | 52.93 |
| ATOM | 835 | SD | MET | A | 142 | 1.164 | 65.166 | 35.670 | 1.00 | 57.75 |
| ATOM | 836 | CE | MET | A | 142 | −0.142 | 64.775 | 36.869 | 1.00 | 54.45 |
| ATOM | 837 | N | GLU | A | 143 | 3.893 | 69.813 | 35.629 | 1.00 | 43.87 |
| ATOM | 838 | CA | GLU | A | 143 | 3.815 | 71.170 | 35.168 | 1.00 | 43.45 |
| ATOM | 839 | C | GLU | A | 143 | 2.352 | 71.600 | 35.008 | 1.00 | 47.32 |
| ATOM | 840 | O | GLU | A | 143 | 1.520 | 74.847 | 34.495 | 1.00 | 46.84 |
| ATOM | 841 | CB | GLU | A | 143 | 4.565 | 71.286 | 33.841 | 1.00 | 44.56 |
| ATOM | 842 | CG | GLU | A | 143 | 4.251 | 72.511 | 33.040 | 1.00 | 51.71 |
| ATOM | 843 | CD | GLU | A | 143 | 4.739 | 72.383 | 31.625 | 1.00 | 64.61 |
| ATOM | 844 | OE1 | GLU | A | 143 | 5.218 | 73.294 | 31.266 | 1.00 | 53.96 |
| ATOM | 845 | OE2 | GLU | A | 143 | 4.659 | 73.368 | 30.873 | 1.00 | 59.20 |
| ATOM | 846 | N | HIS | A | 144 | 2.049 | 72.805 | 35.480 | 1.00 | 44.14 |
| ATOM | 847 | CA | HIS | A | 144 | 0.705 | 73.354 | 35.406 | 1.00 | 43.44 |
| ATOM | 848 | C | HIS | A | 144 | 0.501 | 74.042 | 34.058 | 1.00 | 46.34 |
| ATOM | 849 | O | HIS | A | 144 | 1.348 | 74.811 | 33.616 | 1.00 | 45.77 |
| ATOM | 850 | CB | HIS | A | 144 | 0.471 | 74.358 | 36.568 | 1.00 | 43.97 |
| ATOM | 851 | CG | HIS | A | 144 | −0.697 | 75.271 | 36.354 | 1.00 | 47.20 |
| ATOM | 852 | ND1 | HIS | A | 144 | −2.001 | 74.871 | 36.547 | 1.00 | 48.77 |
| ATOM | 853 | CD2 | HIS | A | 144 | −0.758 | 76.561 | 35.941 | 1.00 | 48.69 |
| ATOM | 854 | CE1 | HIS | A | 144 | −2.814 | 75.873 | 36.267 | 1.00 | 48.05 |
| ATOM | 855 | NE2 | HIS | A | 144 | −2.085 | 76.908 | 35.892 | 1.00 | 48.34 |
| ATOM | 856 | N | MET | A | 145 | −0.606 | 73.721 | 33.389 | 1.00 | 42.32 |
| ATOM | 857 | CA | MET | A | 145 | −0.941 | 74.313 | 32.092 | 1.00 | 41.53 |
| ATOM | 858 | C | MET | A | 145 | −2.172 | 75.208 | 32.272 | 1.00 | 45.49 |
| ATOM | 859 | O | MET | A | 145 | −3.290 | 74.724 | 32.519 | 1.00 | 44.66 |
| ATOM | 860 | CB | MET | A | 145 | −1.204 | 73.224 | 31.060 | 1.00 | 43.57 |
| ATOM | 861 | CG | MET | A | 145 | −0.030 | 72.294 | 30.834 | 1.00 | 46.88 |
| ATOM | 862 | SD | MET | A | 145 | 1.285 | 73.021 | 29.806 | 1.00 | 51.07 |
| ATOM | 863 | CE | MET | A | 145 | 0.477 | 73.079 | 28.185 | 1.00 | 47.27 |
| ATOM | 864 | N | ASP | A | 146 | −1.947 | 76.515 | 32.198 | 1.00 | 42.08 |
| ATOM | 865 | CA | ASP | A | 146 | −2.982 | 77.507 | 32.476 | 1.00 | 41.21 |
| ATOM | 866 | C | ASP | A | 146 | −4.178 | 77.547 | 31.542 | 1.00 | 44.17 |
| ATOM | 867 | O | ASP | A | 146 | −5.231 | 78.075 | 31.903 | 1.00 | 43.79 |
| ATOM | 868 | CB | ASP | A | 146 | −2.371 | 78.892 | 32.644 | 1.00 | 42.46 |
| ATOM | 869 | CG | ASP | A | 146 | −1.763 | 79.402 | 31.380 | 1.00 | 51.14 |
| ATOM | 870 | OD1 | ASP | A | 146 | −1.897 | 78.718 | 30.337 | 1.00 | 51.56 |
| ATOM | 871 | OD2 | ASP | A | 146 | −1.175 | 80.501 | 31.416 | 1.00 | 55.54 |
| ATOM | 872 | N | GLY | A | 147 | −4.027 | 76.993 | 30.344 | 1.00 | 39.86 |
| ATOM | 873 | CA | GLY | A | 147 | −5.126 | 76.968 | 29.376 | 1.00 | 38.73 |
| ATOM | 874 | C | GLY | A | 147 | −6.091 | 75.810 | 29.660 | 1.00 | 40.83 |
| ATOM | 875 | O | GLY | A | 147 | −7.227 | 75.803 | 29.172 | 1.00 | 40.05 |
| ATOM | 876 | N | GLY | A | 148 | −5.630 | 74.837 | 30.451 | 1.00 | 37.02 |
| ATOM | 877 | CA | GLY | A | 148 | −6.433 | 73.656 | 30.793 | 1.00 | 36.77 |
| ATOM | 878 | C | GLY | A | 148 | −6.402 | 72.628 | 29.653 | 1.00 | 40.99 |
| ATOM | 879 | O | GLY | A | 148 | −5.504 | 72.660 | 28.796 | 1.00 | 40.29 |
| ATOM | 880 | N | SER | A | 149 | −7.391 | 71.734 | 29.634 | 1.00 | 37.58 |
| ATOM | 881 | CA | SER | A | 149 | −7.489 | 70.722 | 28.583 | 1.00 | 37.07 |
| ATOM | 882 | C | SER | A | 149 | −8.481 | 71.139 | 27.477 | 1.00 | 40.02 |
| ATOM | 883 | O | SER | A | 149 | −9.330 | 72.015 | 27.689 | 1.00 | 38.94 |
| ATOM | 884 | CB | SER | A | 149 | −7.844 | 69.359 | 29.168 | 1.00 | 40.53 |
| ATOM | 885 | OG | SER | A | 149 | −8.816 | 69.485 | 30.185 | 1.00 | 52.30 |
| ATOM | 886 | N | LEU | A | 150 | −8.345 | 70.527 | 26.297 | 1.00 | 36.51 |
| ATOM | 887 | CA | LEU | A | 150 | −9.170 | 70.878 | 25.132 | 1.00 | 36.41 |
| ATOM | 888 | C | LEU | A | 150 | −10.649 | 70.551 | 25.269 | 1.00 | 40.18 |
| ATOM | 889 | O | LEU | A | 150 | −11.498 | 71.164 | 24.610 | 1.00 | 39.36 |
| ATOM | 890 | CB | LEU | A | 150 | −8.577 | 70.326 | 23.837 | 1.00 | 36.44 |
| ATOM | 891 | CG | LEU | A | 150 | −7.318 | 71.080 | 23.398 | 1.00 | 40.93 |
| ATOM | 892 | CD1 | LEU | A | 150 | −6.800 | 70.564 | 22.069 | 1.00 | 41.05 |
| ATOM | 893 | CD2 | LEU | A | 150 | −7.615 | 72.563 | 23.325 | 1.00 | 43.05 |
| ATOM | 894 | N | ASP | A | 151 | −10.969 | 69.624 | 26.157 | 1.00 | 36.82 |
| ATOM | 895 | CA | ASP | A | 151 | −12.360 | 69.320 | 26.426 | 1.00 | 36.82 |
| ATOM | 896 | C | ASP | A | 151 | −12.979 | 70.566 | 27.051 | 1.00 | 41.39 |
| ATOM | 897 | O | ASP | A | 151 | −14.077 | 70.965 | 26.703 | 1.00 | 41.56 |
| ATOM | 898 | CB | ASP | A | 151 | −12.470 | 68.142 | 27.387 | 1.00 | 38.67 |
| ATOM | 899 | CG | ASP | A | 151 | −11.880 | 68.439 | 28.733 | 1.00 | 50.99 |
| ATOM | 900 | OD1 | ASP | A | 151 | −12.448 | 67.970 | 29.745 | 1.00 | 53.01 |
| ATOM | 901 | OD2 | ASP | A | 151 | −10.866 | 69.170 | 28.789 | 1.00 | 56.15 |
| ATOM | 902 | N | GLN | A | 152 | −12.225 | 71.199 | 27.945 | 1.00 | 38.90 |
| ATOM | 903 | CA | GLN | A | 152 | −12.657 | 72.420 | 28.622 | 1.00 | 38.49 |
| ATOM | 904 | C | GLN | A | 152 | −12.680 | 73.594 | 27.651 | 1.00 | 43.22 |
| ATOM | 905 | O | GLN | A | 152 | −13.594 | 74.422 | 27.685 | 1.00 | 43.37 |
| ATOM | 906 | CB | GLN | A | 152 | −11.720 | 72.734 | 29.805 | 1.00 | 39.44 |

TABLE 4-continued

Structural Coordinate of MEK1/N35/NKFCdel (corresponding to amino acids 24 373 of SEQ ID NO: 2)-Compound 2 Binary Complex.

| ATOM | 907 | CG | GLN | A | 152 | −11.855 | 71.760 | 31.000 | 1.00 | 50.55 |
|------|-----|-----|-----|---|-----|---------|--------|--------|------|-------|
| ATOM | 908 | CD | GLN | A | 152 | −10.575 | 71.659 | 31.884 | 1.00 | 67.08 |
| ATOM | 909 | OE1 | GLN | A | 152 | −9.526 | 72.250 | 31.587 | 1.00 | 57.19 |
| ATOM | 910 | NE2 | GLN | A | 152 | −10.679 | 70.902 | 32.973 | 1.00 | 62.28 |
| ATOM | 911 | N | VAL | A | 153 | −11.663 | 73.674 | 26.796 | 1.00 | 39.66 |
| ATOM | 912 | CA | VAL | A | 153 | −11.571 | 74.760 | 25.821 | 1.00 | 39.45 |
| ATOM | 913 | C | VAL | A | 153 | −12.742 | 74.688 | 24.838 | 1.00 | 43.97 |
| ATOM | 914 | O | VAL | A | 153 | −13.355 | 75.719 | 24.488 | 1.00 | 43.21 |
| ATOM | 915 | CB | VAL | A | 153 | −10.237 | 74.710 | 25.038 | 1.00 | 43.07 |
| ATOM | 916 | CG1 | VAL | A | 153 | −10.247 | 75.733 | 23.898 | 1.00 | 42.80 |
| ATOM | 917 | CG2 | VAL | A | 153 | −9.056 | 74.952 | 25.972 | 1.00 | 42.56 |
| ATOM | 918 | N | LEU | A | 154 | −13.058 | 73.466 | 24.407 | 1.00 | 40.58 |
| ATOM | 919 | CA | LEU | A | 154 | −14.168 | 73.222 | 23.491 | 1.00 | 40.15 |
| ATOM | 920 | C | LEU | A | 154 | −15.482 | 73.735 | 24.072 | 1.00 | 44.35 |
| ATOM | 921 | O | LEU | A | 154 | −16.181 | 74.527 | 23.444 | 1.00 | 42.94 |
| ATOM | 922 | CB | LEU | A | 154 | −14.285 | 71.729 | 23.191 | 1.00 | 39.93 |
| ATOM | 923 | CG | LEU | A | 154 | −15.316 | 71.333 | 22.134 | 1.00 | 43.73 |
| ATOM | 924 | CD1 | LEU | A | 154 | −15.186 | 72.218 | 20.924 | 1.00 | 43.84 |
| ATOM | 925 | CD2 | LEU | A | 154 | −15.158 | 69.874 | 21.755 | 1.00 | 44.96 |
| ATOM | 926 | N | LYS | A | 155 | −15.809 | 73.278 | 25.277 | 1.00 | 42.74 |
| ATOM | 927 | CA | LYS | A | 155 | −17.039 | 73.687 | 25.962 | 1.00 | 43.76 |
| ATOM | 928 | C | LYS | A | 155 | −17.203 | 75.197 | 25.953 | 1.00 | 49.78 |
| ATOM | 929 | O | LYS | A | 155 | −18.309 | 75.711 | 25.822 | 1.00 | 49.56 |
| ATOM | 930 | CB | LYS | A | 155 | −17.036 | 73.190 | 27.410 | 1.00 | 46.59 |
| ATOM | 931 | CG | LYS | A | 155 | −17.823 | 71.923 | 27.638 | 1.00 | 60.18 |
| ATOM | 932 | CD | LYS | A | 155 | −17.330 | 71.192 | 28.872 | 1.00 | 72.19 |
| ATOM | 933 | CE | LYS | A | 155 | −17.002 | 72.160 | 29.998 | 1.00 | 87.61 |
| ATOM | 934 | NZ | LYS | A | 155 | −15.823 | 71.708 | 30.799 | 1.00 | 99.56 |
| ATOM | 935 | N | LYS | A | 156 | −16.086 | 75.504 | 26.102 | 1.00 | 47.45 |
| ATOM | 936 | CA | LYS | A | 156 | −16.088 | 77.367 | 26.124 | 1.00 | 46.99 |
| ATOM | 937 | C | LYS | A | 156 | −16.226 | 77.971 | 24.727 | 1.00 | 50.79 |
| ATOM | 938 | O | LYS | A | 156 | −17.044 | 78.854 | 24.508 | 1.00 | 51.46 |
| ATOM | 939 | CB | LYS | A | 156 | −14.817 | 77.888 | 26.801 | 1.00 | 49.12 |
| ATOM | 940 | CG | LYS | A | 156 | −14.937 | 79.291 | 27.352 | 1.00 | 66.39 |
| ATOM | 941 | CD | LYS | A | 156 | −14.372 | 79.390 | 28.767 | 1.00 | 76.30 |
| ATOM | 942 | CE | LYS | A | 156 | −14.184 | 80.846 | 29.181 | 1.00 | 90.65 |
| ATOM | 943 | NZ | LYS | A | 156 | −13.810 | 80.991 | 30.620 | 1.00 | 101.26 |
| ATOM | 944 | N | ALA | A | 157 | −15.414 | 77.490 | 23.786 | 1.00 | 45.87 |
| ATOM | 945 | CA | ALA | A | 157 | −15.418 | 78.002 | 22.114 | 1.00 | 44.28 |
| ATOM | 946 | C | ALA | A | 157 | −16.611 | 77.538 | 21.568 | 1.00 | 45.76 |
| ATOM | 947 | O | ALA | A | 157 | −16.978 | 78.189 | 20.587 | 1.00 | 45.19 |
| ATOM | 948 | CB | ALA | A | 157 | −14.116 | 77.643 | 21.721 | 1.00 | 44.94 |
| ATOM | 949 | N | GLY | A | 158 | −17.193 | 75.402 | 21.926 | 1.00 | 40.97 |
| ATOM | 950 | CA | GLY | A | 158 | −18.308 | 75.854 | 21.154 | 1.00 | 40.41 |
| ATOM | 951 | C | GLY | A | 158 | −17.749 | 74.947 | 20.062 | 1.00 | 43.51 |
| ATOM | 952 | O | GLY | A | 158 | −18.198 | 73.828 | 19.882 | 1.00 | 43.47 |
| ATOM | 953 | N | ARG | A | 159 | −16.747 | 75.436 | 19.358 | 1.00 | 39.94 |
| ATOM | 954 | CA | ARG | A | 159 | −16.074 | 74.649 | 18.344 | 1.00 | 39.66 |
| ATOM | 955 | C | ARG | A | 159 | −14.790 | 75.331 | 17.890 | 1.00 | 42.70 |
| ATOM | 956 | O | ARG | A | 159 | −14.756 | 76.550 | 17.703 | 1.00 | 43.42 |
| ATOM | 957 | CB | ARG | A | 159 | −17.012 | 74.282 | 17.182 | 1.00 | 39.62 |
| ATOM | 958 | CG | ARG | A | 159 | −17.228 | 75.344 | 16.137 | 1.00 | 43.06 |
| ATOM | 959 | CD | ARG | A | 159 | −18.307 | 74.887 | 15.137 | 1.00 | 47.42 |
| ATOM | 960 | NE | ARG | A | 159 | −18.372 | 75.760 | 13.964 | 1.00 | 54.84 |
| ATOM | 961 | CZ | ARG | A | 159 | −19.423 | 76.508 | 13.646 | 1.00 | 64.12 |
| ATOM | 962 | NH1 | ARG | A | 159 | −20.507 | 76.475 | 14.397 | 1.00 | 47.16 |
| ATOM | 963 | NH2 | ARG | A | 159 | −19.388 | 77.292 | 12.576 | 1.00 | 51.12 |
| ATOM | 964 | N | ILE | A | 160 | −13.716 | 74.548 | 17.800 | 1.00 | 36.74 |
| ATOM | 965 | CA | ILE | A | 160 | −12.390 | 75.062 | 17.466 | 1.00 | 35.31 |
| ATOM | 966 | C | ILE | A | 160 | −12.105 | 75.172 | 15.951 | 1.00 | 38.20 |
| ATOM | 967 | O | ILE | A | 160 | −12.357 | 74.236 | 15.184 | 1.00 | 37.97 |
| ATOM | 968 | CB | ILE | A | 160 | −11.297 | 74.249 | 18.217 | 1.00 | 37.93 |
| ATOM | 969 | CG1 | ILE | A | 160 | −11.609 | 74.249 | 19.731 | 1.00 | 37.66 |
| ATOM | 970 | CG2 | ILE | A | 160 | −9.907 | 74.820 | 17.955 | 1.00 | 38.25 |
| ATOM | 971 | CD1 | ILE | A | 160 | −10.858 | 73.212 | 20.536 | 1.00 | 37.51 |
| ATOM | 972 | N | PRO | A | 161 | −11.622 | 76.339 | 15.518 | 1.00 | 33.76 |
| ATOM | 973 | CA | PRO | A | 161 | −11.355 | 76.566 | 14.085 | 1.00 | 32.53 |
| ATOM | 974 | C | PRO | A | 161 | −10.291 | 73.616 | 13.517 | 1.00 | 36.91 |
| ATOM | 975 | O | PRO | A | 161 | −9.361 | 75.193 | 14.228 | 1.00 | 36.05 |
| ATOM | 976 | CB | PRO | A | 161 | −10.885 | 78.027 | 14.024 | 1.00 | 33.73 |
| ATOM | 977 | CG | PRO | A | 161 | −10.898 | 78.539 | 15.462 | 1.00 | 38.37 |
| ATOM | 978 | CD | PRO | A | 161 | −10.979 | 77.354 | 16.365 | 1.00 | 33.83 |
| ATOM | 979 | N | GLU | A | 162 | −10.464 | 75.258 | 12.244 | 1.00 | 33.45 |
| ATOM | 980 | CA | GLU | A | 162 | −9.569 | 74.345 | 11.549 | 1.00 | 33.38 |
| ATOM | 981 | C | GLU | A | 162 | −8.087 | 74.688 | 11.705 | 1.00 | 39.00 |
| ATOM | 982 | O | GLU | A | 162 | −7.248 | 73.790 | 11.924 | 1.00 | 38.85 |
| ATOM | 983 | CB | GLU | A | 162 | −9.929 | 74.285 | 10.073 | 1.00 | 34.50 |

TABLE 4-continued

Structural Coordinate of MEK1/N35/NKFCdel (corresponding to amino acids 24 373 of SEQ ID NO: 2)-Compound 2 Binary Complex.

| ATOM | 984 | CG | GLU | A | 162 | −9.101 | 73.311 | 9.279 | 1.00 | 43.03 |
|---|---|---|---|---|---|---|---|---|---|---|
| ATOM | 985 | CD | GLU | A | 162 | −9.493 | 73.273 | 7.811 | 1.00 | 54.64 |
| ATOM | 986 | OE1 | GLU | A | 162 | −10.689 | 73.492 | 7.506 | 1.00 | 39.72 |
| ATOM | 987 | OE2 | GLU | A | 162 | −8.606 | 73.010 | 6.966 | 1.00 | 42.42 |
| ATOM | 988 | N | GLN | A | 163 | −7.754 | 75.974 | 11.565 | 1.00 | 35.24 |
| ATOM | 989 | CA | GLN | A | 163 | −6.363 | 76.403 | 11.662 | 1.00 | 34.76 |
| ATOM | 990 | C | GLN | A | 163 | −5.793 | 76.145 | 13.027 | 1.00 | 38.34 |
| ATOM | 991 | O | GLN | A | 163 | −4.610 | 75.842 | 13.163 | 1.00 | 38.69 |
| ATOM | 992 | CB | GLN | A | 163 | −6.199 | 77.869 | 11.269 | 1.00 | 36.22 |
| ATOM | 993 | CG | GLN | A | 163 | −5.979 | 78.074 | 9.771 | 1.00 | 46.84 |
| ATOM | 994 | CD | GLN | A | 163 | −5.502 | 79.477 | 9.424 | 1.00 | 60.12 |
| ATOM | 995 | OE1 | GLN | A | 163 | −5.645 | 80.414 | 10.212 | 1.00 | 52.93 |
| ATOM | 996 | NE2 | GLN | A | 163 | −4.943 | 79.627 | 1.228 | 1.00 | 51.04 |
| ATOM | 997 | N | ILE | A | 164 | −6.642 | 76.249 | 14.047 | 1.00 | 34.20 |
| ATOM | 998 | CA | ILE | A | 164 | −6.213 | 75.976 | 15.417 | 1.00 | 33.21 |
| ATOM | 999 | C | ILE | A | 164 | −6.030 | 74.478 | 15.579 | 1.00 | 36.38 |
| ATOM | 1000 | O | ILE | A | 164 | −5.093 | 74.017 | 16.241 | 1.00 | 35.52 |
| ATOM | 1001 | CB | ILE | A | 164 | −7.253 | 76.485 | 16.462 | 1.00 | 35.85 |
| ATOM | 1002 | CG1 | ILE | A | 164 | −7.194 | 78.023 | 16.568 | 1.00 | 36.27 |
| ATOM | 1003 | CG2 | ILE | A | 164 | −7.014 | 75.840 | 17.818 | 1.00 | 34.36 |
| ATOM | 1004 | CD1 | ILE | A | 164 | −5.772 | 78.584 | 16.754 | 1.00 | 34.07 |
| ATOM | 1005 | N | LEU | A | 165 | −6.908 | 73.717 | 14.937 | 1.00 | 32.18 |
| ATOM | 1006 | CA | LEU | A | 165 | −6.840 | 72.266 | 15.007 | 1.00 | 31.78 |
| ATOM | 1007 | C | LEU | A | 165 | −5.633 | 71.746 | 14.261 | 1.00 | 34.01 |
| ATOM | 1008 | O | LEU | A | 165 | −5.105 | 70.699 | 14.591 | 1.00 | 32.99 |
| ATOM | 1009 | CB | LEU | A | 165 | −8.140 | 71.628 | 14.503 | 1.00 | 31.78 |
| ATOM | 1010 | CG | LEU | A | 165 | −9.322 | 72.862 | 15.447 | 1.00 | 35.65 |
| ATOM | 1011 | CD1 | LEU | A | 265 | −10.596 | 71.213 | 14.929 | 1.00 | 35.50 |
| ATOM | 1012 | CD2 | LEU | A | 165 | −8.979 | 71.367 | 16.852 | 1.00 | 36.71 |
| ATOM | 1013 | N | GLY | A | 166 | −5.167 | 72.520 | 13.290 | 1.00 | 31.50 |
| ATOM | 1014 | CA | GLY | A | 166 | −3.965 | 72.169 | 12.534 | 1.00 | 31.39 |
| ATOM | 1015 | C | GLY | A | 166 | −2.769 | 72.131 | 13.482 | 1.00 | 36.13 |
| ATOM | 1016 | O | GLY | A | 166 | −1.977 | 71.191 | 13.450 | 1.00 | 36.27 |
| ATOM | 1017 | N | LYS | A | 167 | −2.664 | 73.152 | 14.343 | 1.00 | 32.54 |
| ATOM | 1018 | CA | LYS | A | 167 | −1.573 | 73.245 | 15.330 | 1.00 | 32.27 |
| ATOM | 1019 | C | LYS | A | 167 | −1.664 | 72.099 | 16.351 | 1.00 | 36.82 |
| ATOM | 1020 | O | LYS | A | 167 | −0.662 | 71.463 | 16.682 | 1.00 | 37.08 |
| ATOM | 1021 | CB | LYS | A | 167 | −1.628 | 74.593 | 16.062 | 1.00 | 34.17 |
| ATOM | 1022 | CG | LYS | A | 167 | −0.608 | 75.626 | 15.583 | 1.00 | 43.40 |
| ATOM | 1023 | CD | LYS | A | 167 | −0.023 | 75.258 | 14.224 | 1.00 | 52.27 |
| ATOM | 1024 | CE | LYS | A | 167 | 0.063 | 76.471 | 13.307 | 1.00 | 62.02 |
| ATOM | 1025 | NZ | LYS | A | 167 | 1.333 | 76.494 | 12.523 | 1.00 | 69.77 |
| ATOM | 1026 | N | VAL | A | 168 | −2.871 | 71.841 | 16.838 | 1.00 | 32.92 |
| ATOM | 1027 | CA | VAL | A | 168 | −3.093 | 70.745 | 17.769 | 1.00 | 32.69 |
| ATOM | 1028 | C | VAL | A | 168 | −2.638 | 69.426 | 17.137 | 1.00 | 37.24 |
| ATOM | 1029 | O | VAL | A | 168 | −1.912 | 68.647 | 17.759 | 1.00 | 37.65 |
| ATOM | 1030 | CB | VAL | A | 168 | −4.580 | 70.625 | 18.149 | 1.00 | 36.24 |
| ATOM | 1031 | CG1 | VAL | A | 168 | −4.805 | 69.423 | 19.054 | 1.00 | 35.54 |
| ATOM | 1032 | CG2 | VAL | A | 168 | −5.070 | 71.918 | 18.807 | 1.00 | 35.94 |
| ATOM | 1033 | N | SER | A | 169 | −3.059 | 69.188 | 15.896 | 1.00 | 33.33 |
| ATOM | 1034 | CA | SER | A | 169 | −2.688 | 67.964 | 15.179 | 1.00 | 32.91 |
| ATOM | 1035 | C | SER | A | 169 | −1.165 | 67.753 | 15.200 | 1.00 | 36.68 |
| ATOM | 1036 | O | SER | A | 169 | −0.676 | 66.679 | 15.564 | 1.00 | 35.19 |
| ATOM | 1037 | CB | SER | A | 169 | −3.190 | 68.019 | 13.728 | 1.00 | 35.58 |
| ATOM | 1038 | OG | SER | A | 169 | −4.600 | 68.122 | 13.677 | 1.00 | 39.39 |
| ATOM | 1039 | N | ILE | A | 170 | −0.426 | 68.787 | 14.805 | 1.00 | 33.78 |
| ATOM | 1040 | CA | ILE | A | 170 | 1.028 | 68.723 | 14.793 | 1.00 | 33.70 |
| ATOM | 1041 | C | ILE | A | 170 | 1.573 | 68.347 | 16.176 | 1.00 | 38.47 |
| ATOM | 1042 | O | ILE | A | 170 | 2.486 | 67.532 | 16.288 | 1.00 | 38.71 |
| ATOM | 1043 | CB | ILE | A | 170 | 1.646 | 70.074 | 14.365 | 1.00 | 36.78 |
| ATOM | 1044 | CG1 | ILE | A | 170 | 1.208 | 70.442 | 12.941 | 1.00 | 36.95 |
| ATOM | 1045 | CG2 | ILE | A | 170 | 3.172 | 70.028 | 14.475 | 1.00 | 37.27 |
| ATOM | 1046 | CD1 | ILE | A | 170 | 1.516 | 71.877 | 12.565 | 1.00 | 40.82 |
| ATOM | 1047 | N | ALA | A | 171 | 1.018 | 68.953 | 17.224 | 1.00 | 34.95 |
| ATOM | 1048 | CA | ALA | A | 171 | 1.481 | 68.693 | 18.583 | 1.00 | 34.51 |
| ATOM | 1049 | C | ALA | A | 171 | 1.174 | 67.267 | 19.022 | 1.00 | 38.62 |
| ATOM | 1050 | O | ALA | A | 171 | 2.024 | 66.583 | 19.594 | 1.00 | 37.69 |
| ATOM | 1051 | CB | ALA | A | 171 | 0.894 | 69.702 | 19.555 | 1.00 | 35.11 |
| ATOM | 1052 | N | VAL | A | 172 | −0.035 | 66.808 | 18.743 | 1.00 | 36.14 |
| ATOM | 1053 | CA | VAL | A | 172 | −0.385 | 65.446 | 19.103 | 1.00 | 36.48 |
| ATOM | 1054 | C | VAL | A | 172 | 0.463 | 64.422 | 18.334 | 1.00 | 42.34 |
| ATOM | 1055 | O | VAL | A | 172 | 0.902 | 63.426 | 18.901 | 1.00 | 42.60 |
| ATOM | 1056 | CB | VAL | A | 172 | −1.878 | 65.156 | 18.908 | 1.00 | 39.89 |
| ATOM | 1057 | CG1 | VAL | A | 172 | −2.162 | 63.676 | 19.205 | 1.00 | 39.47 |
| ATOM | 1058 | CG2 | VAL | A | 172 | −2.727 | 66.078 | 19.821 | 1.00 | 39.38 |
| ATOM | 1059 | N | ILE | A | 173 | 0.703 | 64.676 | 17.047 | 1.00 | 39.43 |
| ATOM | 1060 | CA | ILE | A | 173 | 1.505 | 63.753 | 16.248 | 1.00 | 39.85 |

TABLE 4-continued

Structural Coordinate of MEK1/N35/NKFCdel (corresponding to amino acids 24 373 of SEQ ID NO: 2)-Compound 2 Binary Complex.

| ATOM | 1061 | C   | ILE | A | 173 | 2.940  | 63.674 | 16.772 | 1.00 | 43.75  |
|------|------|-----|-----|---|-----|--------|--------|--------|------|--------|
| ATOM | 1062 | O   | ILE | A | 173 | 3.481  | 62.583 | 16.945 | 1.00 | 43.05  |
| ATOM | 1063 | CB  | ILE | A | 173 | 1.544  | 64.131 | 14.745 | 1.00 | 42.95  |
| ATOM | 1064 | CG1 | ILE | A | 173 | 0.223  | 63.788 | 14.065 | 1.00 | 43.44  |
| ATOM | 1065 | CG2 | ILE | A | 173 | 2.670  | 63.387 | 14.047 | 1.00 | 43.53  |
| ATOM | 1066 | CD1 | ILE | A | 173 | 0.061  | 64.447 | 12.704 | 1.00 | 50.79  |
| ATOM | 1067 | N   | LYS | A | 174 | 3.553  | 64.838 | 16.996 | 1.00 | 39.83  |
| ATOM | 1068 | CA  | LYS | A | 174 | 4.927  | 64.909 | 17.497 | 1.00 | 39.25  |
| ATOM | 1069 | C   | LYS | A | 174 | 5.041  | 64.370 | 18.919 | 1.00 | 44.13  |
| ATOM | 1070 | O   | LYS | A | 174 | 6.088  | 63.862 | 19.314 | 1.00 | 44.16  |
| ATOM | 1071 | CB  | LYS | A | 174 | 5.453  | 66.337 | 17.433 | 1.00 | 40.42  |
| ATOM | 1072 | CG  | LYS | A | 174 | 5.652  | 66.853 | 16.034 | 1.00 | 39.99  |
| ATOM | 1073 | CD  | LYS | A | 174 | 6.397  | 68.167 | 16.055 | 1.00 | 46.57  |
| ATOM | 1074 | CE  | LYS | A | 174 | 6.692  | 68.652 | 14.652 | 1.00 | 52.59  |
| ATOM | 1075 | NZ  | LYS | A | 174 | 7.494  | 69.898 | 14.671 | 1.00 | 62.62  |
| ATOM | 1076 | N   | GLY | A | 175 | 3.959  | 64.466 | 19.683 | 1.00 | 41.41  |
| ATOM | 1077 | CA  | GLY | A | 175 | 3.924  | 63.967 | 21.044 | 1.00 | 41.15  |
| ATOM | 1078 | C   | GLY | A | 175 | 3.963  | 62.436 | 20.996 | 1.00 | 45.46  |
| ATOM | 1079 | O   | GLY | A | 175 | 4.770  | 61.802 | 21.672 | 1.00 | 44.62  |
| ATOM | 1080 | N   | LEU | A | 176 | 3.104  | 61.851 | 20.168 | 1.00 | 42.77  |
| ATOM | 1081 | CA  | LEU | A | 176 | 3.054  | 60.401 | 20.024 | 1.00 | 43.20  |
| ATOM | 1082 | C   | LEU | A | 176 | 4.346  | 59.857 | 19.403 | 1.00 | 49.80  |
| ATOM | 1083 | O   | LEU | A | 176 | 4.766  | 58.730 | 19.695 | 1.00 | 49.37  |
| ATOM | 1084 | CB  | LEU | A | 176 | 1.860  | 59.990 | 19.171 | 1.00 | 42.97  |
| ATOM | 1085 | CG  | LEU | A | 176 | 0.466  | 60.242 | 19.742 | 1.00 | 46.91  |
| ATOM | 1086 | CD1 | LEU | A | 176 | −0.598 | 59.981 | 18.673 | 1.00 | 46.81  |
| ATOM | 1087 | CD2 | LEU | A | 176 | 0.225  | 59.385 | 20.956 | 1.00 | 47.57  |
| ATOM | 1088 | N   | THR | A | 177 | 4.960  | 60.651 | 18.529 | 1.00 | 47.66  |
| ATOM | 1089 | CA  | THR | A | 177 | 6.194  | 60.244 | 17.876 | 1.00 | 47.88  |
| ATOM | 1090 | C   | THR | A | 177 | 7.316  | 60.197 | 18.898 | 1.00 | 53.24  |
| ATOM | 1091 | O   | THR | A | 177 | 8.146  | 59.293 | 18.882 | 1.00 | 52.88  |
| ATOM | 1092 | CB  | THR | A | 177 | 6.577  | 61.198 | 16.732 | 1.00 | 54.28  |
| ATOM | 1093 | OG1 | THR | A | 177 | 5.578  | 61.138 | 15.707 | 1.00 | 55.23  |
| ATOM | 1094 | CG2 | THR | A | 177 | 7.919  | 60.805 | 16.135 | 1.00 | 50.82  |
| ATOM | 1095 | N   | TYR | A | 178 | 7.316  | 61.162 | 19.810 | 1.00 | 50.35  |
| ATOM | 1096 | CA  | TYR | A | 178 | 8.326  | 61.211 | 20.846 | 1.00 | 50.37  |
| ATOM | 1097 | C   | TYR | A | 178 | 8.192  | 60.027 | 21.793 | 1.00 | 55.61  |
| ATOM | 1098 | O   | TYR | A | 178 | 9.176  | 59.365 | 22.117 | 1.00 | 55.49  |
| ATOM | 1099 | CB  | TYR | A | 178 | 8.234  | 62.514 | 21.640 | 1.00 | 51.28  |
| ATOM | 1100 | CG  | TYR | A | 178 | 9.125  | 62.511 | 22.860 | 1.00 | 52.68  |
| ATOM | 1101 | CD1 | TYR | A | 178 | 8.708  | 61.926 | 24.048 | 1.00 | 54.76  |
| ATOM | 1102 | CD2 | TYR | A | 178 | 10.414 | 63.024 | 22.803 | 1.00 | 53.10  |
| ATOM | 1103 | CE1 | TYR | A | 178 | 9.539  | 61.884 | 25.155 | 1.00 | 55.55  |
| ATOM | 1104 | CE2 | TYR | A | 178 | 11.247 | 62.987 | 23.903 | 1.00 | 53.82  |
| ATOM | 1105 | CZ  | TYR | A | 178 | 10.803 | 62.417 | 25.074 | 1.00 | 61.05  |
| ATOM | 1106 | OH  | TYR | A | 178 | 11.625 | 62.386 | 26.168 | 1.00 | 63.32  |
| ATOM | 1107 | N   | LEU | A | 179 | 6.974  | 59.786 | 22.262 | 1.00 | 52.84  |
| ATOM | 1108 | CA  | LEU | A | 179 | 6.710  | 58.695 | 23.183 | 1.00 | 53.03  |
| ATOM | 1109 | C   | LEU | A | 179 | 7.171  | 57.367 | 22.609 | 1.00 | 60.24  |
| ATOM | 1110 | O   | LEU | A | 179 | 7.776  | 56.549 | 23.307 | 1.00 | 60.50  |
| ATOM | 1111 | CB  | LEU | A | 179 | 5.230  | 58.638 | 23.524 | 1.00 | 52.72  |
| ATOM | 1112 | CG  | LEU | A | 179 | 4.790  | 59.744 | 24.478 | 1.00 | 56.94  |
| ATOM | 1113 | CD1 | LEU | A | 179 | 3.365  | 59.520 | 24.966 | 1.00 | 57.08  |
| ATOM | 1114 | CD2 | LEU | A | 179 | 5.754  | 59.828 | 25.640 | 1.00 | 58.57  |
| ATOM | 1115 | N   | ARG | A | 180 | 6.895  | 57.165 | 21.328 | 1.00 | 58.35  |
| ATOM | 1116 | CA  | ARG | A | 180 | 7.276  | 55.943 | 20.644 | 1.00 | 59.02  |
| ATOM | 1117 | C   | ARG | A | 180 | 8.797  | 55.848 | 20.452 | 1.00 | 65.22  |
| ATOM | 1118 | O   | AEG | A | 180 | 9.435  | 54.898 | 20.911 | 1.00 | 65.19  |
| ATOM | 1119 | CB  | ARG | A | 180 | 6.577  | 55.872 | 19.288 | 1.00 | 59.33  |
| ATOM | 1120 | CG  | ARG | A | 180 | 6.215  | 54.480 | 18.846 | 1.00 | 69.79  |
| ATOM | 1121 | CD  | ARG | A | 180 | 6.442  | 54.306 | 17.359 | 1.00 | 60.95  |
| ATOM | 1122 | NE  | ARG | A | 180 | 6.685  | 55.581 | 16.684 | 1.00 | 89.63  |
| ATOM | 1123 | CZ  | ARG | A | 180 | 6.693  | 55.734 | 15.363 | 1.00 | 104.71 |
| ATOM | 1124 | NH1 | ARG | A | 160 | 6.465  | 54.692 | 14.575 | 1.00 | 93.72  |
| ATOM | 1125 | NH2 | ARG | A | 180 | 6.928  | 56.928 | 14.830 | 1.00 | 90.85  |
| ATOM | 1126 | N   | GLU | A | 181 | 9.362  | 56.833 | 19.759 | 1.00 | 62.74  |
| ATOM | 1127 | CA  | GLU | A | 181 | 10.791 | 56.855 | 19.454 | 1.00 | 63.13  |
| ATOM | 1128 | C   | GLU | A | 181 | 11.689 | 56.777 | 20.678 | 1.00 | 68.24  |
| ATOM | 1129 | O   | GLU | A | 181 | 12.388 | 55.787 | 20.884 | 1.00 | 68.02  |
| ATOM | 1130 | CB  | GLU | A | 181 | 11.149 | 58.098 | 18.632 | 1.00 | 64.54  |
| ATOM | 1131 | CG  | GLU | A | 181 | 10.713 | 58.035 | 17.176 | 1.00 | 78.49  |
| ATOM | 1132 | CD  | GLU | A | 181 | 10.665 | 56.613 | 16.640 | 1.00 | 104.09 |
| ATOM | 1133 | OE1 | GLU | A | 181 | 9.594  | 56.198 | 16.148 | 1.00 | 102.85 |
| ATOM | 1134 | OE2 | GLU | A | 181 | 11.701 | 55.914 | 16.708 | 1.00 | 100.60 |
| ATOM | 1135 | N   | LYS | A | 182 | 11.699 | 57.848 | 21.464 | 1.00 | 65.68  |
| ATOM | 1136 | CA  | LYS | A | 182 | 12.565 | 57.942 | 22.633 | 1.00 | 65.59  |
| ATOM | 1137 | C   | LYS | A | 182 | 12.303 | 56.940 | 23.760 | 1.00 | 69.72  |

TABLE 4-continued

Structural Coordinate of MEK1/N35/NKFCdel (corresponding to amino acids 24 373 of SEQ ID NO: 2)-Compound 2 Binary Complex.

| ATOM | 1138 | O   | LYS | A | 182 | 13.231  | 56.528 | 24.446 | 1.00 | 69.62  |
|------|------|-----|-----|---|-----|---------|--------|--------|------|--------|
| ATOM | 1139 | CB  | LYS | A | 182 | 12.578  | 59.373 | 23.185 | 1.00 | 68.09  |
| ATOM | 1140 | CG  | LYS | A | 182 | 12.892  | 60.446 | 22.141 | 1.00 | 81.36  |
| ATOM | 1141 | CD  | LYS | A | 182 | 14.270  | 60.237 | 21.528 | 1.00 | 91.59  |
| ATOM | 1142 | CE  | LYS | A | 182 | 15.205  | 61.398 | 21.847 | 1.00 | 102.75 |
| ATOM | 1143 | NZ  | LYS | A | 182 | 16.596  | 61.144 | 21.369 | 1.00 | 110.60 |
| ATOM | 1144 | N   | HIS | A | 183 | 11.049  | 56.560 | 23.969 | 1.00 | 66.47  |
| ATOM | 1145 | CA  | HIS | A | 183 | 10.730  | 55.663 | 25.078 | 1.00 | 66.63  |
| ATOM | 1146 | C   | HIS | A | 183 | 10.041  | 54.360 | 24.706 | 1.00 | 70.30  |
| ATOM | 1147 | O   | HIS | A | 183 | 9.655   | 53.589 | 25.586 | 1.00 | 69.38  |
| ATOM | 1148 | CB  | HIS | A | 183 | 9.926   | 56.406 | 26.165 | 1.00 | 67.67  |
| ATOM | 1149 | CG  | HIS | A | 183 | 10.494  | 57.744 | 26.524 | 1.00 | 71.22  |
| ATOM | 1150 | ND1 | HIS | A | 183 | 11.335  | 57.933 | 27.599 | 1.00 | 73.07  |
| ATOM | 1151 | CD2 | HIS | A | 183 | 10.353  | 58.958 | 25.939 | 1.00 | 73.09  |
| ATOM | 1152 | CE1 | HIS | A | 183 | 11.680  | 59.207 | 27.669 | 1.00 | 72.55  |
| ATOM | 1153 | NE2 | HIS | A | 183 | 11.098  | 59.851 | 26.673 | 1.00 | 72.92  |
| ATOM | 1154 | N   | LYS | A | 184 | 9.907   | 54.107 | 23.407 | 1.00 | 67.53  |
| ATOM | 1155 | CA  | LYS | A | 184 | 9.272   | 52.884 | 22.916 | 1.00 | 67.33  |
| ATOM | 1156 | C   | LYS | A | 184 | 7.948   | 52.610 | 23.622 | 1.00 | 71.45  |
| ATOM | 1157 | O   | LYS | A | 184 | 7.712   | 51.508 | 24.119 | 1.00 | 71.01  |
| ATOM | 1158 | CB  | LYS | A | 184 | 10.213  | 51.686 | 23.066 | 1.00 | 69.82  |
| ATOM | 1159 | CG  | LYS | A | 184 | 11.250  | 51.564 | 21.951 | 1.00 | 83.92  |
| ATOM | 1160 | CD  | LYS | A | 184 | 12.000  | 50.237 | 22.031 | 1.00 | 94.31  |
| ATOM | 1161 | CE  | LYS | A | 184 | 12.630  | 49.870 | 20.689 | 1.00 | 105.69 |
| ATOM | 1162 | NZ  | LYS | A | 184 | 12.849  | 48.401 | 20.549 | 1.00 | 112.90 |
| ATOM | 1163 | N   | ILE | A | 185 | 7.099   | 53.630 | 23.685 | 1.00 | 68.17  |
| ATOM | 1164 | CA  | ILE | A | 185 | 5.792   | 53.497 | 24.317 | 1.00 | 67.69  |
| ATOM | 1165 | C   | ILE | A | 185 | 4.742   | 54.343 | 23.612 | 1.00 | 70.55  |
| ATOM | 1166 | O   | ILE | A | 185 | 5.070   | 55.275 | 22.880 | 1.00 | 69.96  |
| ATOM | 1167 | CB  | ILE | A | 185 | 5.834   | 53.838 | 25.814 | 1.00 | 70.63  |
| ATOM | 1168 | CG1 | ILE | A | 185 | 6.168   | 55.318 | 26.020 | 1.00 | 70.85  |
| ATOM | 1169 | CG2 | ILE | A | 185 | 6.833   | 52.939 | 26.533 | 1.00 | 71.29  |
| ATOM | 1170 | CD1 | ILE | A | 185 | 6.191   | 55.740 | 27.477 | 1.00 | 75.31  |
| ATOM | 1171 | N   | MET | A | 186 | 3.480   | 53.976 | 23.804 | 1.00 | 66.38  |
| ATOM | 1172 | CA  | MET | A | 186 | 2.372   | 54.677 | 23.180 | 1.00 | 65.69  |
| ATOM | 1173 | C   | MET | A | 186 | 1.501   | 55.294 | 24.254 | 1.00 | 66.55  |
| ATOM | 1174 | O   | MET | A | 186 | 1.494   | 54.834 | 25.397 | 1.00 | 66.44  |
| ATOM | 1175 | CB  | MET | A | 186 | 1.547   | 53.710 | 22.336 | 1.00 | 68.43  |
| ATOM | 1176 | CG  | MET | A | 186 | 0.526   | 52.920 | 23.130 | 1.00 | 72.60  |
| ATOM | 1177 | SD  | MET | A | 186 | −0.376  | 51.753 | 22.104 | 1.00 | 77.44  |
| ATOM | 1178 | CE  | MET | A | 186 | −2.052  | 52.517 | 22.103 | 1.00 | 74.17  |
| ATOM | 1179 | N   | HIS | A | 187 | 0.768   | 56.339 | 23.891 | 1.00 | 60.23  |
| ATOM | 1180 | CA  | HIS | A | 187 | −0.098  | 57.014 | 24.846 | 1.00 | 58.75  |
| ATOM | 1181 | C   | HIS | A | 187 | −1.161  | 56.084 | 25.416 | 1.00 | 60.40  |
| ATOM | 1182 | O   | HIS | A | 187 | −1.222  | 55.875 | 26.623 | 1.00 | 59.98  |
| ATOM | 1183 | CB  | HIS | A | 187 | −0.757  | 58.247 | 24.215 | 1.00 | 59.04  |
| ATOM | 1184 | CG  | HIS | A | 187 | −1.385  | 59.164 | 23.214 | 1.00 | 61.90  |
| ATOM | 1185 | ND1 | HIS | A | 187 | −2.642  | 58.948 | 25.732 | 1.00 | 63.48  |
| ATOM | 1186 | CD2 | HIS | A | 187 | −0.914  | 60.279 | 25.817 | 1.00 | 63.38  |
| ATOM | 1187 | CE1 | HIS | A | 187 | −2.930  | 59.907 | 26.594 | 1.00 | 62.84  |
| ATOM | 1188 | NE2 | HIS | A | 187 | −1.896  | 60.727 | 26.666 | 1.00 | 63.08  |
| ATOM | 1189 | N   | ARG | A | 188 | −2.010  | 55.561 | 24.531 | 1.00 | 55.48  |
| ATOM | 1190 | CA  | ARG | A | 188 | −3.090  | 54.633 | 24.895 | 1.00 | 54.18  |
| ATOM | 1191 | C   | ARG | A | 188 | −4.357  | 55.316 | 25.386 | 1.00 | 54.87  |
| ATOM | 1192 | O   | ARG | A | 188 | −5.352  | 54.649 | 25.572 | 1.00 | 54.92  |
| ATOM | 1193 | CB  | ARG | A | 188 | −2.617  | 53.583 | 25.910 | 1.00 | 54.64  |
| ATOM | 1194 | CG  | ARG | A | 188 | −2.287  | 52.233 | 25.302 | 1.00 | 65.91  |
| ATOM | 1195 | CD  | ARG | A | 188 | −1.768  | 51.269 | 26.354 | 1.00 | 76.71  |
| ATOM | 1196 | NE  | ARG | A | 188 | −0.308  | 51.279 | 26.434 | 1.00 | 84.42  |
| ATOM | 1197 | CZ  | ARG | A | 188 | 0.476   | 50.333 | 25.924 | 1.00 | 94.98  |
| ATOM | 1198 | NH1 | ARG | A | 188 | −0.058  | 49.296 | 25.291 | 1.00 | 77.49  |
| ATOM | 1199 | NH2 | ARG | A | 188 | 1.793   | 50.431 | 26.040 | 1.00 | 81.92  |
| ATOM | 1200 | N   | ASP | A | 189 | −4.325  | 56.639 | 25.501 | 1.00 | 48.56  |
| ATOM | 1201 | CA  | ASP | A | 189 | −5.495  | 57.376 | 25.966 | 1.00 | 47.20  |
| ATOM | 1202 | C   | ASP | A | 189 | −5.584  | 58.801 | 25.428 | 1.00 | 48.88  |
| ATOM | 1203 | O   | ASP | A | 189 | −5.696  | 59.760 | 26.191 | 1.00 | 47.81  |
| ATOM | 1204 | CB  | ASP | A | 189 | −5.585  | 57.368 | 27.490 | 1.00 | 48.73  |
| ATOM | 1205 | CG  | ASP | A | 189 | −6.980  | 57.743 | 27.998 | 1.00 | 58.39  |
| ATOM | 1206 | OD1 | ASP | A | 189 | −7.965  | 57.571 | 27.242 | 1.00 | 57.97  |
| ATOM | 1207 | OD2 | ASP | A | 189 | −7.085  | 58.202 | 29.159 | 1.00 | 66.51  |
| ATOM | 1208 | N   | VAL | A | 190 | −5.561  | 58.927 | 24.106 | 1.00 | 44.12  |
| ATOM | 1209 | CA  | VAL | A | 190 | −5.701  | 60.220 | 23.466 | 1.00 | 42.91  |
| ATOM | 1210 | C   | VAL | A | 190 | −7.176  | 60.633 | 23.477 | 1.00 | 45.01  |
| ATOM | 1211 | O   | VAL | A | 190 | −8.048  | 59.857 | 23.112 | 1.00 | 44.16  |
| ATOM | 1212 | CB  | VAL | A | 190 | −5.199  | 60.186 | 22.002 | 1.00 | 46.39  |
| ATOM | 1213 | CG1 | VAL | A | 190 | −5.526  | 61.502 | 21.283 | 1.00 | 45.99  |
| ATOM | 1214 | CG2 | VAL | A | 190 | −3.712  | 59.883 | 21.950 | 1.00 | 45.93  |

TABLE 4-continued

Structural Coordinate of MEK1/N35/NKFCdel (corresponding to amino acids 24 373 of SEQ ID NO: 2)-Compound 2 Binary Complex.

| ATOM | 1215 | N   | LYS | A | 191 | −7.432  | 61.852 | 23.936 | 1.00 | 41.14  |
|------|------|-----|-----|---|-----|---------|--------|--------|------|--------|
| ATOM | 1216 | CA  | LYS | A | 191 | −8.777  | 62.433 | 23.979 | 1.00 | 40.25  |
| ATOM | 1217 | C   | LYS | A | 191 | −8.633  | 63.898 | 24.385 | 1.00 | 42.77  |
| ATOM | 1218 | O   | LYS | A | 191 | −7.577  | 64.308 | 24.862 | 1.00 | 41.69  |
| ATOM | 1219 | CB  | LYS | A | 191 | −9.676  | 61.679 | 24.960 | 1.00 | 42.19  |
| ATOM | 1220 | CG  | LYS | A | 191 | −9.079  | 61.487 | 26.343 | 1.00 | 43.31  |
| ATOM | 1221 | CD  | LYS | A | 191 | −9.941  | 60.586 | 27.182 | 1.00 | 43.52  |
| ATOM | 1222 | CE  | LYS | A | 191 | −9.637  | 60.744 | 28.658 | 1.00 | 47.27  |
| ATOM | 1223 | NZ  | LYS | A | 191 | −10.648 | 60.064 | 29.511 | 1.00 | 49.19  |
| ATOM | 1224 | N   | PRO | A | 192 | −9.680  | 64.690 | 24.167 | 1.00 | 39.33  |
| ATOM | 1225 | CA  | PRO | A | 192 | −9.623  | 66.135 | 24.448 | 1.00 | 38.46  |
| ATOM | 1226 | C   | PRO | A | 192 | −9.175  | 66.496 | 25.864 | 1.00 | 42.26  |
| ATOM | 1227 | O   | PRO | A | 192 | −8.405  | 67.442 | 26.066 | 1.00 | 41.65  |
| ATOM | 1228 | CB  | PRO | A | 192 | −11.062 | 66.594 | 24.197 | 1.00 | 39.56  |
| ATOM | 1229 | CG  | PRO | A | 192 | −11.564 | 65.662 | 23.164 | 1.00 | 43.80  |
| ATOM | 1230 | CD  | PRO | A | 192 | −10.932 | 64.315 | 23.485 | 1.00 | 39.42  |
| ATOM | 1231 | N   | SER | A | 193 | −9.660  | 65.748 | 26.841 | 1.00 | 38.97  |
| ATOM | 1232 | CA  | SER | A | 193 | −9.322  | 66.005 | 28.234 | 1.00 | 38.85  |
| ATOM | 1233 | C   | SER | A | 193 | −7.874  | 65.634 | 28.566 | 1.00 | 42.38  |
| ATOM | 1234 | O   | SER | A | 193 | −7.393  | 65.912 | 29.664 | 1.00 | 41.39  |
| ATOM | 1235 | CB  | SER | A | 193 | −10.287 | 65.265 | 29.158 | 1.00 | 42.60  |
| ATOM | 1236 | OG  | SER | A | 193 | −9.923  | 63.904 | 29.274 | 1.00 | 53.68  |
| ATOM | 1237 | N   | ASN | A | 194 | −7.185  | 65.002 | 27.615 | 1.00 | 38.83  |
| ATOM | 1238 | CA  | ASN | A | 194 | −5.786  | 64.613 | 27.814 | 1.00 | 37.82  |
| ATOM | 1239 | C   | ASN | A | 194 | −4.831  | 65.459 | 26.975 | 1.00 | 40.11  |
| ATOM | 1240 | O   | ASN | A | 194 | −3.630  | 65.180 | 26.899 | 1.00 | 39.34  |
| ATOM | 1241 | CB  | ASN | A | 194 | −5.577  | 63.115 | 27.590 | 1.00 | 35.71  |
| ATOM | 1242 | CG  | ASN | A | 194 | −5.982  | 62.293 | 28.797 | 1.00 | 51.10  |
| ATOM | 1243 | OD1 | ASN | A | 194 | −6.377  | 62.846 | 29.824 | 1.00 | 45.44  |
| ATOM | 1244 | ND2 | ASN | A | 194 | −5.934  | 60.968 | 28.666 | 1.00 | 38.51  |
| ATOM | 1245 | N   | ILE | A | 195 | −5.368  | 66.526 | 26.394 | 1.00 | 35.88  |
| ATOM | 1246 | CA  | ILE | A | 195 | −4.558  | 67.479 | 25.648 | 1.00 | 35.59  |
| ATOM | 1247 | C   | ILE | A | 195 | −4.582  | 68.818 | 26.369 | 1.00 | 39.99  |
| ATOM | 1248 | O   | ILE | A | 195 | −5.621  | 69.456 | 26.482 | 1.00 | 39.22  |
| ATOM | 1249 | CB  | ILE | A | 195 | −5.033  | 67.657 | 24.203 | 1.00 | 38.13  |
| ATOM | 1250 | CG1 | ILE | A | 195 | −5.163  | 66.288 | 23.523 | 1.00 | 38.60  |
| ATOM | 1251 | CG2 | ILE | A | 195 | −4.054  | 68.548 | 23.438 | 1.00 | 37.41  |
| ATOM | 1252 | CD1 | ILE | A | 195 | −5.872  | 66.326 | 22.186 | 1.00 | 43.43  |
| ATOM | 1253 | N   | LEU | A | 196 | −3.435  | 69.210 | 26.907 | 1.00 | 37.22  |
| ATOM | 1254 | CA  | LEU | A | 196 | −3.340  | 70.447 | 27.656 | 1.00 | 36.78  |
| ATOM | 1255 | C   | LEU | A | 196 | −2.729  | 71.565 | 26.840 | 1.00 | 40.05  |
| ATOM | 1256 | O   | LEU | A | 196 | −1.895  | 71.331 | 25.979 | 1.00 | 39.54  |
| ATOM | 1257 | CB  | LEU | A | 196 | −2.564  | 70.231 | 28.951 | 1.00 | 36.78  |
| ATOM | 1258 | CG  | LEU | A | 196 | −3.165  | 69.189 | 29.885 | 1.00 | 41.49  |
| ATOM | 1259 | CD1 | LEU | A | 196 | −2.084  | 68.535 | 30.723 | 1.00 | 41.99  |
| ATOM | 1260 | CD2 | LEU | A | 196 | −4.196  | 69.817 | 30.759 | 1.00 | 44.69  |
| ATOM | 1261 | N   | VAL | A | 197 | −3.182  | 72.779 | 27.101 | 1.00 | 36.97  |
| ATOM | 1262 | CA  | VAL | A | 197 | −2.701  | 73.953 | 26.388 | 1.00 | 36.70  |
| ATOM | 1263 | C   | VAL | A | 197 | −2.389  | 75.061 | 27.395 | 1.00 | 39.84  |
| ATOM | 1264 | O   | VAL | A | 197 | −2.861  | 75.023 | 28.535 | 1.00 | 38.46  |
| ATOM | 1265 | CB  | VAL | A | 197 | −3.756  | 74.460 | 25.352 | 1.00 | 40.27  |
| ATOM | 1266 | CG1 | VAL | A | 197 | −3.905  | 73.462 | 24.222 | 1.00 | 40.16  |
| ATOM | 1267 | CG2 | VAL | A | 197 | −5.103  | 74.704 | 26.026 | 1.00 | 39.69  |
| ATOM | 1268 | N   | ASN | A | 198 | −1.568  | 76.023 | 26.986 | 1.00 | 36.84  |
| ATOM | 1269 | CA  | ASN | A | 198 | −1.219  | 77.131 | 27.869 | 1.00 | 37.15  |
| ATOM | 1270 | C   | ASN | A | 198 | −1.145  | 78.484 | 27.152 | 1.00 | 43.66  |
| ATOM | 1271 | O   | ASN | A | 198 | −1.168  | 78.552 | 25.916 | 1.00 | 42.29  |
| ATOM | 1272 | CB  | ASN | A | 198 | 0.050   | 76.831 | 28.718 | 1.00 | 33.66  |
| ATOM | 1273 | CG  | ASN | A | 198 | 1.345   | 76.834 | 27.892 | 1.00 | 45.53  |
| ATOM | 1274 | OD1 | ASN | A | 198 | 1.505   | 77.616 | 26.947 | 1.00 | 37.29  |
| ATOM | 1275 | ND2 | ASN | A | 198 | 2.299   | 76.006 | 28.302 | 1.00 | 33.83  |
| ATOM | 1276 | N   | SER | A | 199 | −1.116  | 79.559 | 27.940 | 1.00 | 42.82  |
| ATOM | 1277 | CA  | SER | A | 199 | −1.077  | 80.910 | 27.398 | 1.00 | 43.39  |
| ATOM | 1278 | C   | SER | A | 199 | 0.160   | 81.189 | 26.549 | 1.00 | 49.10  |
| ATOM | 1279 | O   | SER | A | 199 | 0.200   | 82.174 | 25.810 | 1.00 | 49.86  |
| ATOM | 1280 | CB  | SER | A | 199 | −1.211  | 81.944 | 28.511 | 1.00 | 47.18  |
| ATOM | 1281 | OG  | SER | A | 199 | −0.374  | 81.634 | 29.606 | 1.00 | 56.20  |
| ATOM | 1282 | N   | ARG | A | 200 | 1.163   | 80.322 | 26.637 | 1.00 | 45.81  |
| ATOM | 1283 | CA  | ARG | A | 200 | 2.365   | 80.493 | 25.823 | 1.00 | 45.84  |
| ATOM | 1284 | C   | ARG | A | 200 | 2.163   | 79.920 | 24.413 | 1.00 | 49.34  |
| ATOM | 1285 | O   | ARG | A | 200 | 3.045   | 80.022 | 23.561 | 1.00 | 49.34  |
| ATOM | 1286 | CB  | ARG | A | 200 | 3.575   | 79.840 | 26.491 | 1.00 | 47.59  |
| ATOM | 1287 | CG  | ARG | A | 200 | 4.018   | 80.519 | 27.765 | 1.00 | 61.46  |
| ATOM | 1288 | CD  | ARG | A | 200 | 4.953   | 79.629 | 28.552 | 1.00 | 81.13  |
| ATOM | 1289 | NE  | ARG | A | 200 | 6.111   | 80.360 | 29.056 | 1.00 | 98.43  |
| ATOM | 1290 | CZ  | ARG | A | 200 | 7.347   | 79.874 | 29.077 | 1.00 | 115.62 |
| ATOM | 1291 | NH1 | ARG | A | 200 | 7.586   | 78.651 | 28.617 | 1.00 | 101.79 |

TABLE 4-continued

Structural Coordinate of MEK1/N35/NKFCdel (corresponding to amino acids 24 373 of SEQ ID NO: 2)-Compound 2 Binary Complex.

| ATOM | 1292 | NH2 | ARG | A | 200 | 8.342 | 80.606 | 29.557 | 1.00 | 104.72 |
|---|---|---|---|---|---|---|---|---|---|---|
| ATOM | 1293 | N | GLY | A | 201 | 1.000 | 79.314 | 24.178 | 1.00 | 44.83 |
| ATOM | 1294 | CA | GLY | A | 201 | 0.676 | 78.744 | 22.871 | 1.00 | 44.06 |
| ATOM | 1295 | C | GLY | A | 201 | 1.184 | 77.309 | 22.722 | 1.00 | 46.16 |
| ATOM | 1296 | O | GLY | A | 201 | 1.341 | 76.802 | 21.600 | 1.00 | 46.06 |
| ATOM | 1297 | N | GLU | A | 202 | 1.433 | 76.662 | 23.855 | 1.00 | 40.38 |
| ATOM | 1298 | CA | GLU | A | 202 | 1.943 | 75.300 | 23.874 | 1.00 | 39.05 |
| ATOM | 1299 | C | GLU | A | 202 | 0.832 | 74.252 | 23.960 | 1.00 | 41.82 |
| ATOM | 1300 | O | GLU | A | 202 | −0.172 | 74.439 | 24.661 | 1.00 | 40.92 |
| ATOM | 1301 | CB | GLU | A | 202 | 2.904 | 75.112 | 25.048 | 1.00 | 40.09 |
| ATOM | 1302 | CG | GLU | A | 202 | 4.220 | 75.852 | 24.902 | 1.00 | 47.45 |
| ATOM | 1303 | CD | GLU | A | 202 | 5.103 | 75.706 | 26.129 | 1.00 | 65.03 |
| ATOM | 1304 | OE1 | GLU | A | 202 | 4.598 | 75.895 | 27.261 | 1.00 | 56.38 |
| ATOM | 1305 | OE2 | GLU | A | 202 | 6.298 | 75.389 | 25.962 | 1.00 | 58.84 |
| ATOM | 1306 | N | ILE | A | 203 | 1.053 | 73.129 | 23.284 | 1.00 | 37.73 |
| ATOM | 1307 | CA | ILE | A | 203 | 0.115 | 72.015 | 23.285 | 1.00 | 37.36 |
| ATOM | 1308 | C | ILE | A | 203 | 0.852 | 70.755 | 23.740 | 1.00 | 41.58 |
| ATOM | 1309 | O | ILE | A | 203 | 1.926 | 70.430 | 23.213 | 1.00 | 41.07 |
| ATOM | 1310 | CB | ILE | A | 243 | −0.530 | 71.814 | 21.881 | 1.00 | 39.94 |
| ATOM | 1311 | CG1 | ILE | A | 203 | −1.212 | 73.114 | 21.436 | 1.00 | 39.84 |
| ATOM | 1312 | CG2 | ILE | A | 203 | −1.558 | 70.684 | 21.923 | 1.00 | 40.58 |
| ATOM | 1313 | CD1 | ILE | A | 203 | −1.171 | 73.356 | 19.949 | 1.00 | 43.22 |
| ATOM | 1314 | N | LYS | A | 204 | 0.319 | 70.091 | 24.765 | 1.00 | 38.53 |
| ATOM | 1315 | CA | LYS | A | 204 | 0.986 | 68.912 | 25.341 | 1.00 | 38.67 |
| ATOM | 1316 | C | LYS | A | 204 | 0.059 | 67.760 | 25.681 | 1.00 | 45.07 |
| ATOM | 1317 | O | LYS | A | 204 | −1.112 | 67.959 | 26.005 | 1.00 | 44.36 |
| ATOM | 1318 | CB | LYS | A | 204 | 1.786 | 69.302 | 26.592 | 1.00 | 39.37 |
| ATOM | 1319 | CG | LYS | A | 204 | 3.067 | 70.051 | 26.293 | 1.00 | 38.47 |
| ATOM | 1320 | CD | LYS | A | 204 | 3.440 | 71.003 | 27.410 | 1.00 | 35.91 |
| ATOM | 1321 | CE | LYS | A | 204 | 4.833 | 71.586 | 27.191 | 1.00 | 39.17 |
| ATOM | 1322 | NZ | LYS | A | 204 | 5.307 | 72.396 | 28.350 | 1.00 | 42.66 |
| ATOM | 1323 | N | LEU | A | 205 | 0.607 | 66.549 | 25.645 | 1.00 | 43.98 |
| ATOM | 1324 | CA | LEU | A | 205 | −0.149 | 65.355 | 26.006 | 1.00 | 44.78 |
| ATOM | 1325 | C | LEU | A | 205 | 0.104 | 65.009 | 27.463 | 1.00 | 52.20 |
| ATOM | 1326 | O | LEU | A | 205 | 1.176 | 65.286 | 28.000 | 1.00 | 51.40 |
| ATOM | 1327 | CB | LEU | A | 205 | 0.279 | 64.167 | 25.144 | 1.00 | 44.64 |
| ATOM | 1328 | CG | LEU | A | 205 | 0.111 | 64.238 | 23.635 | 1.00 | 48.60 |
| ATOM | 1329 | CD1 | LEU | A | 205 | 0.581 | 62.926 | 23.012 | 1.00 | 48.35 |
| ATOM | 1330 | CD2 | LEU | A | 205 | −1.335 | 64.527 | 23.280 | 1.00 | 50.23 |
| ATOM | 1331 | N | CYS | A | 206 | −0.866 | 64.351 | 28.082 | 1.00 | 52.50 |
| ATOM | 1332 | CA | CYS | A | 206 | −0.727 | 63.906 | 29.465 | 1.00 | 53.92 |
| ATOM | 1333 | C | CYS | A | 206 | −1.528 | 62.633 | 29.716 | 1.00 | 60.41 |
| ATOM | 1334 | O | CYS | A | 206 | −2.328 | 62.216 | 28.879 | 1.00 | 59.71 |
| ATOM | 1335 | CB | CYS | A | 206 | −1.153 | 65.010 | 30.441 | 1.00 | 54.37 |
| ATOM | 1336 | SG | CYS | A | 206 | −2.951 | 65.314 | 30.519 | 1.00 | 58.54 |
| ATOM | 1337 | N | ASP | A | 207 | −1.296 | 62.020 | 30.871 | 1.00 | 59.87 |
| ATOM | 1338 | CA | ASP | A | 207 | −2.008 | 60.805 | 31.279 | 1.00 | 61.16 |
| ATOM | 1339 | C | ASP | A | 207 | −1.808 | 59.576 | 30.381 | 1.00 | 67.08 |
| ATOM | 1340 | O | ASP | A | 207 | −2.762 | 58.857 | 30.078 | 1.00 | 66.46 |
| ATOM | 1341 | CB | ASP | A | 207 | −3.500 | 61.085 | 31.514 | 1.00 | 63.53 |
| ATOM | 1342 | CG | ASP | A | 207 | −3.779 | 61.669 | 32.908 | 1.00 | 78.02 |
| ATOM | 1343 | OD1 | ASP | A | 207 | −2.818 | 62.112 | 33.580 | 1.00 | 78.87 |
| ATOM | 1344 | OD2 | ASP | A | 207 | −4.961 | 61.693 | 33.322 | 1.00 | 85.61 |
| ATOM | 1345 | N | PHE | A | 208 | −0.559 | 59.316 | 30.001 | 1.00 | 65.57 |
| ATOM | 1346 | CA | PHE | A | 208 | −0.233 | 58.138 | 29.203 | 1.00 | 66.48 |
| ATOM | 1347 | C | PHE | A | 208 | 0.328 | 57.053 | 30.126 | 1.00 | 73.29 |
| ATOM | 1348 | O | PHE | A | 208 | 1.321 | 57.272 | 30.816 | 1.00 | 73.06 |
| ATOM | 1349 | CB | PHE | A | 208 | 0.775 | 58.476 | 28.101 | 1.00 | 68.15 |
| ATOM | 1350 | CG | PHE | A | 208 | 1.840 | 59.446 | 28.525 | 1.00 | 69.60 |
| ATOM | 1351 | CD1 | PHE | A | 208 | 3.015 | 58.996 | 29.103 | 1.00 | 72.28 |
| ATOM | 1352 | CD2 | PHE | A | 208 | 1.676 | 60.811 | 28.321 | 1.00 | 71.65 |
| ATOM | 1353 | CE1 | PHE | A | 208 | 3.997 | 59.883 | 29.488 | 1.00 | 73.10 |
| ATOM | 1354 | CE2 | PHE | A | 208 | 2.653 | 61.703 | 28.701 | 1.00 | 74.33 |
| ATOM | 1355 | CZ | PHE | A | 208 | 3.817 | 61.239 | 29.288 | 1.00 | 72.39 |
| ATOM | 1356 | N | GLY | A | 209 | −0.342 | 55.902 | 30.157 | 1.00 | 71.60 |
| ATOM | 1357 | CA | GLY | A | 209 | 0.043 | 54.786 | 31.025 | 1.00 | 72.29 |
| ATOM | 1358 | C | GLY | A | 209 | 1.548 | 54.505 | 31.060 | 1.00 | 77.96 |
| ATOM | 1359 | O | GLY | A | 209 | 2.190 | 54.354 | 30.017 | 1.00 | 77.94 |
| ATOM | 1360 | N | VAL | A | 210 | 2.099 | 54.428 | 32.269 | 1.00 | 75.35 |
| ATOM | 1361 | CA | VAL | A | 210 | 3.519 | 54.150 | 32.453 | 1.00 | 75.57 |
| ATOM | 1362 | C | VAL | A | 210 | 3.722 | 53.146 | 33.586 | 1.00 | 80.95 |
| ATOM | 1363 | O | VAL | A | 210 | 4.735 | 52.449 | 33.640 | 1.00 | 80.43 |
| ATOM | 1364 | CB | VAL | A | 210 | 4.314 | 55.436 | 32.757 | 1.00 | 79.27 |
| ATOM | 1365 | CG1 | VAL | A | 210 | 5.746 | 55.098 | 33.126 | 1.00 | 79.07 |
| ATOM | 1366 | CG2 | VAL | A | 210 | 4.275 | 56.378 | 31.566 | 1.00 | 78.97 |
| ATOM | 1367 | N | SER | A | 211 | 2.742 | 53.072 | 34.482 | 1.00 | 78.75 |
| ATOM | 1368 | CA | SER | A | 211 | 2.800 | 52.153 | 35.611 | 1.00 | 79.09 |

TABLE 4-continued

Structural Coordinate of MEK1/N35/NKFCdel (corresponding to amino acids 24 373 of SEQ ID NO: 2)-Compound 2 Binary Complex.

| ATOM | 1369 | C | SER | A | 211 | 1.713 | 51.081 | 35.500 | 1.00 | 84.05 |
|------|------|-----|-----|---|-----|---------|--------|--------|------|-------|
| ATOM | 1370 | O | SER | A | 211 | 3.530 | 51.355 | 35.716 | 1.00 | 83.43 |
| ATOM | 1371 | CB | SER | A | 211 | 2.667 | 52.915 | 36.937 | 1.00 | 82.77 |
| ATOM | 1372 | OG | SER | A | 211 | 2.122 | 52.092 | 37.960 | 1.00 | 91.55 |
| ATOM | 1373 | N | GLY | A | 212 | 2.119 | 49.864 | 35.152 | 1.00 | 81.64 |
| ATOM | 1374 | CA | GLY | A | 212 | 1.182 | 48.755 | 35.030 | 1.00 | 81.86 |
| ATOM | 1375 | C | GLY | A | 212 | 0.446 | 48.551 | 36.355 | 1.00 | 86.67 |
| ATOM | 1376 | O | GLY | A | 212 | −0.787 | 48.503 | 36.394 | 1.00 | 86.31 |
| ATOM | 1377 | N | GLN | A | 213 | 1.210 | 48.460 | 37.441 | 1.00 | 83.80 |
| ATOM | 1378 | CA | GLN | A | 213 | 0.637 | 48.274 | 38.769 | 1.00 | 83.91 |
| ATOM | 1379 | C | GLN | A | 213 | −0.465 | 49.297 | 39.060 | 1.00 | 88.50 |
| ATOM | 1380 | O | GLN | A | 213 | −1.563 | 48.933 | 39.492 | 1.00 | 88.07 |
| ATOM | 1381 | CB | GLN | A | 213 | 1.722 | 48.334 | 39.844 | 1.00 | 85.22 |
| ATOM | 1382 | CG | GLN | A | 213 | 1.453 | 47.438 | 41.060 | 1.00 | 98.46 |
| ATOM | 1383 | CD | GLN | A | 213 | 0.085 | 46.770 | 41.005 | 1.00 | 114.62 |
| ATOM | 1384 | OE1 | GLN | A | 213 | −0.948 | 47.431 | 41.121 | 1.00 | 109.32 |
| ATOM | 1385 | NE2 | GLN | A | 213 | 0.070 | 45.453 | 40.888 | 1.00 | 106.23 |
| ATOM | 1386 | N | LEU | A | 214 | −0.176 | 50.571 | 38.813 | 1.00 | 85.28 |
| ATOM | 1387 | CA | LEU | A | 214 | −1.165 | 51.619 | 39.030 | 1.00 | 85.25 |
| ATOM | 1388 | C | LEU | A | 214 | −2.444 | 51.285 | 38.260 | 1.00 | 90.51 |
| ATOM | 1389 | O | LEU | A | 214 | −3.542 | 51.300 | 38.823 | 1.00 | 90.20 |
| ATOM | 1390 | CB | LEU | A | 214 | −0.619 | 52.974 | 38.577 | 1.00 | 84.97 |
| ATOM | 1391 | CG | LEU | A | 214 | −1.592 | 54.152 | 38.677 | 1.00 | 88.93 |
| ATOM | 1392 | CD1 | LEU | A | 214 | −2.240 | 54.197 | 40.046 | 1.00 | 88.74 |
| ATOM | 1393 | CD2 | LEU | A | 214 | −0.884 | 55.463 | 38.364 | 1.00 | 90.67 |
| ATOM | 1394 | N | ILE | A | 215 | −2.286 | 50.967 | 36.974 | 1.00 | 87.75 |
| ATOM | 1395 | CA | ILE | A | 215 | −3.418 | 50.619 | 36.121 | 1.00 | 87.74 |
| ATOM | 1396 | C | ILE | A | 215 | −4.260 | 49.518 | 36.762 | 1.00 | 91.91 |
| ATOM | 1397 | O | ILE | A | 215 | −5.484 | 49.632 | 36.860 | 1.00 | 91.40 |
| ATOM | 1398 | CB | ILE | A | 215 | −2.948 | 50.149 | 34.725 | 1.00 | 90.82 |
| ATOM | 1399 | CG1 | ILE | A | 215 | −3.080 | 51.285 | 33.707 | 1.00 | 91.33 |
| ATOM | 1400 | CG2 | ILE | A | 215 | −3.747 | 48.934 | 34.276 | 1.00 | 91.15 |
| ATOM | 1401 | CD1 | ILE | A | 215 | −1.925 | 51.272 | 32.726 | 1.00 | 98.32 |
| ATOM | 1402 | N | ASP | A | 216 | −3.590 | 48.460 | 37.211 | 1.00 | 88.51 |
| ATOM | 1403 | CA | ASP | A | 216 | −4.261 | 47.333 | 37.850 | 1.00 | 88.33 |
| ATOM | 1404 | C | ASP | A | 216 | −5.127 | 47.783 | 39.026 | 1.00 | 92.07 |
| ATOM | 1405 | O | ASP | A | 216 | −6.356 | 47.693 | 38.977 | 1.00 | 91.70 |
| ATOM | 1406 | CB | ASP | A | 216 | −3.235 | 46.303 | 38.329 | 1.00 | 90.23 |
| ATOM | 1407 | CG | ASP | A | 216 | −2.398 | 45.744 | 37.196 | 1.00 | 100.15 |
| ATOM | 1408 | OD1 | ASP | A | 216 | −2.773 | 45.941 | 36.022 | 1.00 | 101.05 |
| ATOM | 1409 | OD2 | ASP | A | 216 | −1.365 | 45.096 | 37.482 | 1.00 | 105.09 |
| ATOM | 1410 | N | SER | A | 217 | −4.474 | 48.259 | 40.084 | 1.00 | 88.31 |
| ATOM | 1411 | CA | SER | A | 217 | −5.169 | 48.715 | 41.283 | 1.00 | 87.91 |
| ATOM | 1412 | C | SER | A | 217 | −6.168 | 49.829 | 40.984 | 1.00 | 91.38 |
| ATOM | 1413 | O | SER | A | 217 | −7.138 | 50.021 | 41.723 | 1.00 | 90.84 |
| ATOM | 1414 | CB | SER | A | 217 | −4.165 | 49.178 | 42.340 | 1.00 | 91.22 |
| ATOM | 1415 | OG | SER | A | 217 | −2.860 | 48.700 | 42.049 | 1.00 | 99.33 |
| ATOM | 1416 | N | MET | A | 218 | −5.899 | 50.593 | 39.930 | 1.00 | 87.95 |
| ATOM | 1417 | CA | GLY | A | 224 | −12.073 | 55.924 | 32.174 | 1.00 | 51.00 |
| ATOM | 1418 | C | GLY | A | 224 | −12.850 | 55.606 | 30.892 | 1.00 | 54.54 |
| ATOM | 1419 | O | GLY | A | 224 | −12.908 | 54.455 | 30.460 | 1.00 | 54.03 |
| ATOM | 1420 | N | THR | A | 225 | −13.436 | 56.636 | 30.285 | 1.00 | 50.41 |
| ATOM | 1421 | CA | THR | A | 225 | −14.215 | 56.469 | 29.063 | 1.00 | 49.73 |
| ATOM | 1422 | C | THR | A | 225 | −13.470 | 55.704 | 27.964 | 1.00 | 51.92 |
| ATOM | 1423 | O | THR | A | 225 | −12.281 | 55.928 | 27.731 | 1.00 | 51.83 |
| ATOM | 1424 | CB | THR | A | 225 | −14.676 | 57.820 | 28.497 | 1.00 | 58.66 |
| ATOM | 1425 | OG1 | THR | A | 225 | −15.947 | 57.661 | 27.862 | 1.00 | 60.63 |
| ATOM | 1426 | CG2 | THR | A | 225 | −13.673 | 58.342 | 27.476 | 1.00 | 56.21 |
| ATOM | 1427 | N | ARG | A | 226 | −14.201 | 54.840 | 27.261 | 1.00 | 46.46 |
| ATOM | 1428 | CA | ARG | A | 226 | −13.647 | 54.067 | 26.156 | 1.00 | 44.99 |
| ATOM | 1429 | C | ARG | A | 226 | −14.180 | 54.585 | 24.825 | 1.00 | 46.52 |
| ATOM | 1430 | O | ARG | A | 226 | −13.881 | 54.029 | 23.768 | 1.00 | 45.96 |
| ATOM | 1431 | CB | ARG | A | 226 | −14.004 | 52.586 | 26.301 | 1.00 | 43.54 |
| ATOM | 1432 | CG | ARG | A | 226 | −13.812 | 52.030 | 27.700 | 1.00 | 47.86 |
| ATOM | 1433 | CD | ARG | A | 226 | −13.910 | 50.514 | 27.691 | 1.00 | 50.10 |
| ATOM | 1434 | NE | ARG | A | 225 | −12.590 | 49.892 | 27.696 | 1.00 | 53.24 |
| ATOM | 1435 | CZ | ARG | A | 226 | −12.229 | 48.890 | 26.904 | 1.00 | 61.97 |
| ATOM | 1436 | NH1 | ARG | A | 226 | −13.094 | 48.383 | 26.033 | 1.00 | 48.65 |
| ATOM | 1437 | NH2 | ARG | A | 226 | −11.007 | 48.388 | 26.989 | 1.00 | 45.92 |
| ATOM | 1438 | N | SER | A | 227 | −14.981 | 55.642 | 24.886 | 1.00 | 41.79 |
| ATOM | 1439 | CA | SER | A | 227 | −15.591 | 56.219 | 23.686 | 1.00 | 41.30 |
| ATOM | 1440 | C | SER | A | 227 | −14.605 | 56.770 | 22.642 | 1.00 | 43.63 |
| ATOM | 1441 | O | SER | A | 227 | −15.004 | 57.135 | 21.545 | 1.00 | 42.91 |
| ATOM | 1442 | CB | SER | A | 227 | −16.634 | 57.277 | 24.060 | 1.00 | 44.89 |
| ATOM | 1443 | OG | SER | A | 227 | −16.049 | 58.331 | 24.802 | 1.00 | 55.35 |
| ATOM | 1444 | N | TYR | A | 228 | −13.320 | 56.808 | 22.975 | 1.00 | 40.05 |
| ATOM | 1445 | CA | TYR | A | 228 | −12.310 | 57.302 | 22.027 | 1.00 | 39.45 |

TABLE 4-continued

Structural Coordinate of MEK1/N35/NKFCdel (corresponding to amino acids 24 373 of SEQ ID NO: 2)-Compound 2 Binary Complex.

| ATOM | 1446 | C   | TYR | A | 228 | −11.386 | 56.181 | 21.559 | 1.00 | 45.05 |
|------|------|-----|-----|---|-----|---------|--------|--------|------|-------|
| ATOM | 1447 | O   | TYR | A | 228 | −10.394 | 56.425 | 20.862 | 1.00 | 45.05 |
| ATOM | 1448 | CB  | TYR | A | 228 | −11.502 | 58.452 | 22.640 | 1.00 | 39.38 |
| ATOM | 1449 | CG  | TYR | A | 228 | −12.324 | 59.703 | 22.877 | 1.00 | 39.22 |
| ATOM | 1450 | CD1 | TYR | A | 228 | −12.550 | 60.613 | 21.856 | 1.00 | 40.69 |
| ATOM | 1451 | CD2 | TYR | A | 228 | −12.911 | 59.948 | 24.111 | 1.00 | 39.22 |
| ATOM | 1452 | CE1 | TYR | A | 228 | −13.318 | 61.742 | 22.065 | 1.00 | 40.69 |
| ATOM | 1453 | CE2 | TYR | A | 228 | −13.677 | 61.075 | 24.329 | 1.00 | 39.41 |
| ATOM | 1454 | CZ  | TYR | A | 228 | −13.860 | 61.978 | 23.310 | 1.00 | 45.47 |
| ATOM | 1455 | OH  | TYR | A | 228 | −14.643 | 63.093 | 23.528 | 1.00 | 44.39 |
| ATOM | 1456 | N   | MET | A | 229 | −11.733 | 54.948 | 21.921 | 1.00 | 42.39 |
| ATOM | 1457 | CA  | MET | A | 229 | −10.937 | 53.783 | 21.554 | 1.00 | 42.47 |
| ATOM | 1458 | C   | MET | A | 229 | −11.210 | 53.319 | 20.139 | 1.00 | 45.87 |
| ATOM | 1459 | O   | MET | A | 229 | −12.352 | 53.332 | 19.678 | 1.00 | 45.68 |
| ATOM | 1460 | CB  | MET | A | 229 | −11.196 | 52.642 | 22.524 | 1.00 | 45.28 |
| ATOM | 1461 | CG  | MET | A | 229 | −10.745 | 52.927 | 23.935 | 1.00 | 49.39 |
| ATOM | 1462 | SD  | MET | A | 229 | −10.418 | 51.427 | 24.842 | 1.00 | 54.15 |
| ATOM | 1463 | CE  | MET | A | 229 | −10.636 | 52.009 | 26.504 | 1.00 | 50.79 |
| ATOM | 1464 | N   | SER | A | 230 | −10.159 | 52.877 | 19.461 | 1.00 | 42.43 |
| ATOM | 1465 | CA  | SER | A | 230 | −10.281 | 52.390 | 18.097 | 1.00 | 42.55 |
| ATOM | 1466 | C   | SER | A | 230 | −11.089 | 51.105 | 18.050 | 1.00 | 48.03 |
| ATOM | 1467 | O   | SER | A | 230 | −11.181 | 50.376 | 19.039 | 1.00 | 48.19 |
| ATOM | 1468 | CB  | SER | A | 230 | −8.903  | 52.153 | 17.492 | 1.00 | 45.98 |
| ATOM | 1469 | OG  | SER | A | 230 | −8.176  | 51.198 | 18.250 | 1.00 | 55.14 |
| ATOM | 1470 | N   | PRO | A | 231 | −11.664 | 50.825 | 16.887 | 1.00 | 45.06 |
| ATOM | 1471 | CA  | PRO | A | 231 | −12.446 | 49.616 | 16.690 | 1.00 | 44.36 |
| ATOM | 1472 | C   | PRO | A | 231 | −11.633 | 48.368 | 17.032 | 1.00 | 47.79 |
| ATOM | 1473 | O   | PRO | A | 231 | −12.150 | 47.434 | 17.633 | 1.00 | 47.41 |
| ATOM | 1474 | CB  | PRO | A | 231 | −12.745 | 49.644 | 15.187 | 1.00 | 45.76 |
| ATOM | 1475 | CG  | PRO | A | 231 | −12.708 | 51.056 | 14.825 | 1.00 | 50.03 |
| ATOM | 1476 | CD  | PRO | A | 231 | −11.663 | 51.681 | 15.688 | 1.00 | 45.46 |
| ATOM | 1477 | N   | GLU | A | 232 | −10.361 | 48.357 | 16.637 | 1.00 | 44.32 |
| ATOM | 1478 | CA  | GLU | A | 232 | −9.486  | 47.205 | 16.880 | 1.00 | 44.36 |
| ATOM | 1479 | C   | GLU | A | 232 | −9.165  | 46.966 | 18.358 | 1.00 | 50.32 |
| ATOM | 1480 | O   | GLU | A | 232 | −8.903  | 45.832 | 18.764 | 1.00 | 50.79 |
| ATOM | 1481 | CB  | GLU | A | 232 | −8.203  | 47.282 | 16.038 | 1.00 | 45.35 |
| ATOM | 1482 | CG  | GLU | A | 232 | −7.183  | 48.291 | 16.531 | 1.00 | 52.47 |
| ATOM | 1483 | CD  | GLU | A | 232 | −7.301  | 49.628 | 15.828 | 1.00 | 62.98 |
| ATOM | 1484 | OE1 | GLU | A | 232 | −8.362  | 49.896 | 15.222 | 1.00 | 43.15 |
| ATOM | 1485 | OE2 | GLU | A | 232 | −6.333  | 50.414 | 15.858 | 1.00 | 57.26 |
| ATOM | 1486 | N   | ARG | A | 233 | −9.214  | 43.021 | 19.160 | 1.00 | 47.31 |
| ATOM | 1487 | CA  | ARG | A | 233 | −8.967  | 47.893 | 20.590 | 1.00 | 47.31 |
| ATOM | 1488 | C   | ARG | A | 233 | −10.238 | 47.453 | 21.303 | 1.00 | 51.94 |
| ATOM | 1489 | O   | ARG | A | 233 | −10.193 | 46.764 | 22.208 | 1.00 | 51.42 |
| ATOM | 1490 | CB  | ARG | A | 233 | −8.448  | 49.204 | 21.178 | 1.00 | 46.85 |
| ATOM | 1491 | CG  | ARG | A | 233 | −6.929  | 49.283 | 21.220 | 1.00 | 53.10 |
| ATOM | 1492 | CD  | ARG | A | 233 | −6.454  | 50.438 | 22.070 | 1.00 | 55.67 |
| ATOM | 1493 | NE  | ARG | A | 233 | −6.358  | 50.083 | 23.483 | 1.00 | 58.30 |
| ATOM | 1494 | CZ  | ARG | A | 233 | −6.100  | 50.953 | 24.454 | 1.00 | 71.14 |
| ATOM | 1495 | NH1 | ARG | A | 233 | −5.898  | 52.239 | 24.160 | 1.00 | 54.30 |
| ATOM | 1496 | NH2 | ARG | A | 233 | −6.040  | 50.542 | 25.720 | 1.00 | 58.79 |
| ATOM | 1497 | N   | LEU | A | 234 | −11.382 | 47.848 | 20.764 | 1.00 | 49.90 |
| ATOM | 1498 | CA  | LEU | A | 234 | −12.667 | 47.474 | 21.343 | 1.00 | 50.33 |
| ATOM | 1499 | C   | LEU | A | 234 | −13.011 | 46.032 | 20.954 | 1.00 | 56.31 |
| ATOM | 1500 | O   | LEU | A | 234 | −13.972 | 45.449 | 21.462 | 1.00 | 54.93 |
| ATOM | 1501 | CB  | LEU | A | 234 | −13.768 | 48.409 | 20.830 | 1.00 | 50.27 |
| ATOM | 1502 | CG  | LEU | A | 234 | −13.753 | 49.866 | 21.285 | 1.00 | 54.72 |
| ATOM | 1503 | CD1 | LEU | A | 234 | −14.979 | 50.589 | 20.740 | 1.00 | 54.34 |
| ATOM | 1504 | CD2 | LEU | A | 234 | −13.702 | 49.953 | 22.808 | 1.00 | 57.30 |
| ATOM | 1505 | N   | GLN | A | 235 | −12.237 | 45.478 | 20.024 | 1.00 | 55.21 |
| ATOM | 1506 | CA  | GLN | A | 235 | −12.485 | 44.134 | 19.523 | 1.00 | 56.04 |
| ATOM | 1507 | C   | GLN | A | 235 | −11.496 | 43.123 | 20.070 | 1.00 | 63.39 |
| ATOM | 1508 | O   | GLN | A | 235 | −11.496 | 41.967 | 19.659 | 1.00 | 63.02 |
| ATOM | 1509 | CB  | GLN | A | 235 | −12.451 | 44.122 | 17.999 | 1.00 | 57.16 |
| ATOM | 1510 | CG  | GLN | A | 235 | −13.819 | 44.250 | 17.345 | 1.00 | 73.73 |
| ATOM | 1511 | CD  | GLN | A | 235 | −13.786 | 43.929 | 15.857 | 1.00 | 98.56 |
| ATOM | 1512 | OE1 | GLN | A | 235 | −12.715 | 43.827 | 15.254 | 1.00 | 94.22 |
| ATOM | 1513 | NE2 | GLN | A | 235 | −14.964 | 43.779 | 15.257 | 1.00 | 93.06 |
| ATOM | 1514 | N   | GLY | A | 236 | −10.651 | 43.564 | 20.995 | 1.00 | 62.67 |
| ATOM | 1515 | CA  | GLY | A | 236 | −9.666  | 42.690 | 21.605 | 1.00 | 63.77 |
| ATOM | 1516 | C   | GLY | A | 236 | −8.428  | 42.550 | 20.732 | 1.00 | 71.88 |
| ATOM | 1517 | O   | GLY | A | 236 | −7.346  | 42.219 | 21.226 | 1.00 | 72.01 |
| ATOM | 1518 | N   | THR | A | 237 | −8.582  | 42.793 | 19.434 | 1.00 | 71.24 |
| ATOM | 1519 | CA  | THR | A | 237 | −7.447  | 42.704 | 18.514 | 1.00 | 72.48 |
| ATOM | 1520 | C   | THR | A | 237 | −6.327  | 43.624 | 18.992 | 1.00 | 79.34 |
| ATOM | 1521 | O   | THR | A | 237 | −6.529  | 44.831 | 19.150 | 1.00 | 79.03 |
| ATOM | 1522 | CB  | THR | A | 237 | −7.837  | 43.100 | 17.092 | 1.00 | 80.43 |

TABLE 4-continued

Structural Coordinate of MEK1/N35/NKFCdel (corresponding to amino acids 24 373 of SEQ ID NO: 2)-Compound 2 Binary Complex.

| ATOM | 1523 | OG1 | THR | A | 237 | −8.461 | 41.985 | 16.442 | 1.00 | 80.39 |
|---|---|---|---|---|---|---|---|---|---|---|
| ATOM | 1524 | CG2 | THR | A | 237 | −6.604 | 43.517 | 16.308 | 1.00 | 78.79 |
| ATOM | 1525 | N | HIS | A | 238 | −5.153 | 43.052 | 19.247 | 1.00 | 77.92 |
| ATOM | 1526 | CA | HIS | A | 238 | −4.038 | 43.846 | 19.753 | 1.00 | 78.42 |
| ATOM | 1527 | C | HIS | A | 238 | −3.758 | 45.120 | 18.960 | 1.00 | 80.72 |
| ATOM | 1528 | O | HIS | A | 238 | −3.823 | 45.139 | 17.722 | 1.00 | 80.32 |
| ATOM | 1529 | CB | HIS | A | 238 | −2.773 | 43.011 | 19.984 | 1.00 | 79.87 |
| ATOM | 1530 | CG | HIS | A | 238 | −2.095 | 43.313 | 21.284 | 1.00 | 83.80 |
| ATOM | 1531 | ND1 | HIS | A | 238 | −2.778 | 43.364 | 22.482 | 1.00 | 85.91 |
| ATOM | 1532 | CD2 | HIS | A | 238 | −0.812 | 43.644 | 21.568 | 1.00 | 85.89 |
| ATOM | 1533 | CE1 | HIS | A | 238 | −1.938 | 43.683 | 23.452 | 1.00 | 85.44 |
| ATOM | 1534 | NE2 | HIS | A | 238 | −0.740 | 43.859 | 22.924 | 1.00 | 85.81 |
| ATOM | 1535 | N | TYR | A | 239 | −3.482 | 46.192 | 19.697 | 1.00 | 75.51 |
| ATOM | 1536 | CA | TYR | A | 239 | −2.295 | 47.510 | 19.122 | 1.00 | 74.27 |
| ATOM | 1537 | C | TYR | A | 239 | −1.843 | 47.995 | 19.127 | 1.00 | 75.07 |
| ATOM | 1538 | O | TYR | A | 239 | −0.963 | 47.405 | 19.763 | 1.00 | 74.49 |
| ATOM | 1539 | CB | TYR | A | 239 | −4.128 | 48.513 | 19.892 | 1.00 | 75.47 |
| ATOM | 1540 | CG | TYR | A | 239 | −3.829 | 48.518 | 21.378 | 1.00 | 77.30 |
| ATOM | 1541 | CD1 | TYR | A | 239 | −4.067 | 47.391 | 22.159 | 1.00 | 79.17 |
| ATOM | 1542 | CD2 | TYR | A | 239 | −3.287 | 49.639 | 21.996 | 1.00 | 77.98 |
| ATOM | 1543 | CE1 | TYR | A | 239 | −3.797 | 47.390 | 23.515 | 1.00 | 79.94 |
| ATOM | 1544 | CE2 | TYR | A | 239 | −3.017 | 49.650 | 23.354 | 1.00 | 78.79 |
| ATOM | 1545 | CZ | TYR | A | 239 | −3.269 | 48.523 | 24.109 | 1.00 | 85.40 |
| ATOM | 1546 | OH | TYR | A | 239 | −2.997 | 48.530 | 25.460 | 1.00 | 84.74 |
| ATOM | 1547 | N | SER | A | 240 | −1.640 | 49.124 | 18.455 | 1.00 | 69.15 |
| ATOM | 1548 | CA | SER | A | 240 | −0.354 | 49.788 | 18.387 | 1.00 | 67.52 |
| ATOM | 1549 | C | SER | A | 240 | −0.623 | 51.287 | 18.403 | 1.00 | 67.85 |
| ATOM | 1550 | O | SER | A | 240 | −1.729 | 51.717 | 18.724 | 1.00 | 67.55 |
| ATOM | 1551 | CB | SER | A | 240 | 0.372 | 49.406 | 17.101 | 1.00 | 71.07 |
| ATOM | 1552 | OG | SER | A | 240 | −0.191 | 50.074 | 15.987 | 1.00 | 80.28 |
| ATOM | 1553 | N | VAL | A | 241 | 0.379 | 52.079 | 18.342 | 1.00 | 61.75 |
| ATOM | 1554 | CA | VAL | A | 241 | 0.223 | 53.531 | 18.001 | 1.00 | 59.90 |
| ATOM | 1555 | C | VAL | A | 241 | −0.923 | 53.898 | 17.066 | 1.00 | 60.01 |
| ATOM | 1556 | O | VAL | A | 241 | −1.472 | 54.997 | 17.134 | 1.00 | 59.20 |
| ATOM | 1557 | CB | VAL | A | 241 | 1.512 | 54.223 | 17.519 | 1.00 | 63.67 |
| ATOM | 1558 | CG1 | VAL | A | 241 | 1.734 | 53.959 | 16.044 | 1.00 | 63.49 |
| ATOM | 1559 | CG2 | VAL | A | 241 | 1.451 | 55.710 | 17.791 | 1.00 | 63.44 |
| ATOM | 1560 | N | GLN | A | 242 | −1.287 | 52.958 | 16.202 | 1.00 | 54.26 |
| ATOM | 1561 | CA | GLN | A | 242 | −2.367 | 53.165 | 15.250 | 1.00 | 53.01 |
| ATOM | 1562 | C | GLN | A | 242 | −3.701 | 53.410 | 15.948 | 1.00 | 55.09 |
| ATOM | 1563 | O | GLN | A | 242 | −4.621 | 53.977 | 15.361 | 1.00 | 54.90 |
| ATOM | 1564 | CB | GLN | A | 242 | −2.478 | 51.976 | 14.303 | 1.00 | 54.09 |
| ATOM | 1565 | CG | GLN | A | 242 | −1.290 | 51.824 | 13.371 | 1.00 | 62.48 |
| ATOM | 1566 | CD | GLN | A | 242 | −1.221 | 52.924 | 12.331 | 1.00 | 78.14 |
| ATOM | 1567 | OE1 | GLN | A | 242 | −0.399 | 53.838 | 12.431 | 1.00 | 71.54 |
| ATOM | 1568 | NE2 | GLN | A | 242 | −2.078 | 52.835 | 11.315 | 1.00 | 71.78 |
| ATOM | 1569 | N | SER | A | 243 | −3.803 | 52.985 | 17.203 | 1.00 | 49.60 |
| ATOM | 1570 | CA | SER | A | 243 | −5.021 | 53.196 | 17.972 | 1.00 | 48.12 |
| ATOM | 1571 | C | SER | A | 243 | −5.068 | 54.641 | 18.467 | 1.00 | 48.31 |
| ATOM | 1572 | O | SER | A | 243 | −6.134 | 55.250 | 18.566 | 1.00 | 47.13 |
| ATOM | 1573 | CB | SER | A | 243 | −5.082 | 52.230 | 19.146 | 1.00 | 51.93 |
| ATOM | 1574 | CG | SER | A | 243 | −5.147 | 50.898 | 18.688 | 1.00 | 62.25 |
| ATOM | 1575 | N | ASP | A | 244 | −3.896 | 55.187 | 18.747 | 1.00 | 42.87 |
| ATOM | 1576 | CA | ASP | A | 244 | −3.781 | 56.558 | 19.213 | 1.00 | 41.70 |
| ATOM | 1577 | C | ASP | A | 244 | −4.098 | 57.535 | 18.085 | 1.00 | 44.16 |
| ATOM | 1578 | O | ASP | A | 244 | −4.654 | 58.603 | 18.320 | 1.00 | 44.23 |
| ATOM | 1579 | CB | ASP | A | 244 | −2.385 | 56.811 | 19.783 | 1.00 | 42.93 |
| ATOM | 1580 | CG | ASP | A | 244 | −2.160 | 56.093 | 21.098 | 1.00 | 48.67 |
| ATOM | 1581 | CD1 | ASP | A | 244 | −3.154 | 55.885 | 21.844 | 1.00 | 48.79 |
| ATOM | 1582 | CD2 | ASP | A | 244 | −1.004 | 55.711 | 21.374 | 1.00 | 51.75 |
| ATOM | 1583 | N | ILE | A | 245 | −3.789 | 57.134 | 16.854 | 1.00 | 39.08 |
| ATOM | 1584 | CA | ILE | A | 245 | −4.080 | 57.958 | 15.683 | 1.00 | 38.11 |
| ATOM | 1585 | C | ILE | A | 245 | −5.594 | 58.024 | 15.462 | 1.00 | 41.38 |
| ATOM | 1586 | O | ILE | A | 245 | −6.144 | 59.080 | 15.143 | 1.00 | 40.96 |
| ATOM | 1587 | CB | ILE | A | 245 | −3.371 | 57.420 | 14.418 | 1.00 | 40.49 |
| ATOM | 1588 | CG1 | ILE | A | 245 | −1.869 | 57.768 | 14.458 | 1.00 | 40.07 |
| ATOM | 1589 | CG2 | ILE | A | 245 | −4.037 | 57.957 | 13.151 | 1.00 | 40.33 |
| ATOM | 1590 | CD1 | ILE | A | 245 | −1.088 | 57.237 | 13.284 | 1.00 | 41.82 |
| ATOM | 1591 | N | TRP | A | 246 | −6.270 | 56.907 | 15.686 | 1.00 | 37.64 |
| ATOM | 1592 | CA | TRP | A | 246 | −7.715 | 56.876 | 15.545 | 1.00 | 37.39 |
| ATOM | 1593 | C | TRP | A | 246 | −8.324 | 57.854 | 16.536 | 1.00 | 41.57 |
| ATOM | 1594 | O | TRP | A | 246 | −9.210 | 58.636 | 16.192 | 1.00 | 42.32 |
| ATOM | 1595 | CB | TRP | A | 246 | −8.258 | 55.464 | 15.826 | 1.00 | 35.87 |
| ATOM | 1596 | CG | TRP | A | 246 | −9.720 | 55.464 | 16.217 | 1.00 | 36.79 |
| ATOM | 1597 | CD1 | TRP | A | 246 | −10.252 | 55.767 | 17.454 | 1.00 | 39.55 |
| ATOM | 1598 | CD2 | TRP | A | 246 | −10.834 | 55.206 | 15.359 | 1.00 | 36.57 |
| ATOM | 1599 | NE1 | TRP | A | 246 | −11.625 | 55.691 | 17.410 | 1.00 | 38.75 |

TABLE 4-continued

Structural Coordinate of MEK1/N35/NKFCdel (corresponding to amino acids 24 373 of SEQ ID NO: 2)-Compound 2 Binary Complex.

| ATOM | 1600 | CE2 | TRP | A | 246 | −12.010 | 55.355 | 16.139 | 1.00 | 40.25 |
|---|---|---|---|---|---|---|---|---|---|---|
| ATOM | 1601 | CE3 | TRP | A | 246 | −10.957 | 54.822 | 14.021 | 1.00 | 37.90 |
| ATOM | 1602 | CZ2 | TRP | A | 246 | −13.285 | 55.144 | 15.616 | 1.00 | 39.78 |
| ATOM | 1603 | CZ3 | TRP | A | 246 | −12.234 | 54.622 | 13.497 | 1.00 | 39.41 |
| ATOM | 1604 | CH2 | TRP | A | 246 | −13.376 | 54.786 | 14.295 | 1.00 | 40.12 |
| ATOM | 1605 | N | SER | A | 247 | −7.868 | 57.765 | 17.785 | 1.00 | 36.94 |
| ATOM | 1606 | CA | SER | A | 247 | −8.368 | 58.602 | 18.871 | 1.00 | 35.64 |
| ATOM | 1607 | C | SER | A | 247 | −8.131 | 60.071 | 18.567 | 1.00 | 39.21 |
| ATOM | 1608 | O | SER | A | 247 | −8.981 | 60.920 | 18.855 | 1.00 | 38.67 |
| ATOM | 1609 | CB | SER | A | 247 | −7.687 | 58.220 | 20.193 | 1.00 | 37.39 |
| ATOM | 1610 | OG | SER | A | 247 | −7.855 | 56.841 | 20.466 | 1.00 | 41.56 |
| ATOM | 1611 | N | MET | A | 248 | −6.972 | 60.375 | 17.983 | 1.00 | 34.98 |
| ATOM | 1612 | CA | MET | A | 248 | −6.673 | 61.739 | 17.624 | 1.00 | 34.50 |
| ATOM | 1613 | C | MET | A | 248 | −7.682 | 62.203 | 16.594 | 1.00 | 37.58 |
| ATOM | 1614 | O | MET | A | 248 | −8.251 | 63.293 | 16.714 | 1.00 | 37.19 |
| ATOM | 1615 | CB | MET | A | 248 | −5.261 | 61.870 | 17.071 | 1.00 | 36.91 |
| ATOM | 1616 | CG | MET | A | 248 | −4.938 | 63.289 | 16.616 | 1.00 | 40.41 |
| ATOM | 1617 | SD | MET | A | 248 | −3.378 | 63.426 | 15.807 | 1.00 | 44.67 |
| ATOM | 1618 | CE | MET | A | 248 | −3.649 | 62.370 | 14.361 | 1.00 | 41.23 |
| ATOM | 1619 | N | GLY | A | 249 | −7.929 | 61.353 | 15.595 | 1.00 | 33.38 |
| ATOM | 1620 | CA | GLY | A | 249 | −8.895 | 61.651 | 14.534 | 1.00 | 33.05 |
| ATOM | 1621 | C | GLY | A | 249 | −10.301 | 61.893 | 15.095 | 1.00 | 37.52 |
| ATOM | 1622 | O | GLY | A | 249 | −10.998 | 62.833 | 14.685 | 1.00 | 37.85 |
| ATOM | 1623 | N | LEU | A | 250 | −10.725 | 61.045 | 16.022 | 1.00 | 33.69 |
| ATOM | 1624 | CA | LEU | A | 250 | −12.049 | 61.197 | 16.625 | 1.00 | 34.09 |
| ATOM | 1625 | C | LEU | A | 250 | −12.158 | 62.506 | 17.446 | 1.00 | 37.41 |
| ATOM | 1626 | O | LEU | A | 250 | −13.153 | 63.230 | 17.361 | 1.00 | 36.25 |
| ATOM | 1627 | CB | LEU | A | 250 | −12.400 | 59.978 | 17.499 | 1.00 | 34.10 |
| ATOM | 1628 | CG | LEU | A | 250 | −13.851 | 59.956 | 17.991 | 1.00 | 38.67 |
| ATOM | 1629 | CD1 | LEU | A | 250 | −14.806 | 59.844 | 16.819 | 1.00 | 38.90 |
| ATOM | 1630 | CD2 | LEU | A | 250 | −14.085 | 58.651 | 18.999 | 1.00 | 40.43 |
| ATOM | 1631 | N | SER | A | 251 | −11.125 | 62.787 | 18.236 | 1.00 | 33.92 |
| ATOM | 1632 | CA | SER | A | 251 | −11.075 | 64.001 | 19.047 | 1.00 | 33.46 |
| ATOM | 1633 | C | SER | A | 251 | −11.093 | 65.257 | 18.159 | 1.00 | 37.66 |
| ATOM | 1634 | O | SER | A | 251 | −11.734 | 66.257 | 18.490 | 1.00 | 37.13 |
| ATOM | 1635 | CB | SER | A | 251 | −9.820 | 63.996 | 19.930 | 1.00 | 35.87 |
| ATOM | 1636 | OG | SER | A | 251 | −9.746 | 62.813 | 20.707 | 1.00 | 41.13 |
| ATOM | 1637 | N | LEU | A | 252 | −10.407 | 65.185 | 17.021 | 1.00 | 34.60 |
| ATOM | 1638 | CA | LEU | A | 252 | −10.348 | 65.307 | 16.088 | 1.00 | 34.61 |
| ATOM | 1639 | C | LEU | A | 252 | −11.713 | 66.646 | 15.497 | 1.00 | 38.65 |
| ATOM | 1640 | O | LEU | A | 252 | −12.079 | 67.816 | 15.390 | 1.00 | 38.56 |
| ATOM | 1641 | CB | LEU | A | 252 | −9.324 | 66.038 | 14.977 | 1.00 | 34.62 |
| ATOM | 1642 | CG | LEU | A | 252 | −7.860 | 65.248 | 15.401 | 1.00 | 39.14 |
| ATOM | 1643 | CD1 | LEU | A | 252 | −6.877 | 65.790 | 14.324 | 1.00 | 38.67 |
| ATOM | 1644 | CD2 | LEU | A | 252 | −7.608 | 67.712 | 15.791 | 1.00 | 40.91 |
| ATOM | 1645 | N | VAL | A | 253 | −12.461 | 65.622 | 15.106 | 1.00 | 35.10 |
| ATOM | 1646 | CA | VAL | A | 253 | −13.790 | 65.824 | 14.536 | 1.00 | 34.41 |
| ATOM | 1647 | C | VAL | A | 253 | −14.726 | 66.415 | 15.585 | 1.00 | 37.88 |
| ATOM | 1648 | O | VAL | A | 253 | −15.511 | 67.330 | 15.303 | 1.00 | 36.86 |
| ATOM | 1649 | CB | VAL | A | 253 | −14.391 | 64.503 | 14.007 | 1.00 | 38.11 |
| ATOM | 1650 | CG1 | VAL | A | 253 | −15.828 | 64.717 | 13.555 | 1.00 | 37.78 |
| ATOM | 1651 | CG2 | VAL | A | 253 | −13.537 | 63.941 | 12.869 | 1.00 | 37.79 |
| ATOM | 1652 | N | GLU | A | 254 | −14.634 | 65.908 | 16.806 | 1.00 | 34.84 |
| ATOM | 1653 | CA | GLU | A | 254 | −15.480 | 66.413 | 17.869 | 1.00 | 34.60 |
| ATOM | 1654 | C | GLU | A | 254 | −15.242 | 67.893 | 18.083 | 1.00 | 39.49 |
| ATOM | 1655 | O | GLU | A | 254 | −16.193 | 68.576 | 18.186 | 1.00 | 40.17 |
| ATOM | 1656 | CB | GLU | A | 254 | −15.239 | 65.672 | 19.166 | 1.00 | 35.03 |
| ATOM | 1657 | CG | GLU | A | 254 | −15.695 | 66.475 | 20.386 | 1.00 | 43.24 |
| ATOM | 1658 | CD | GLU | A | 254 | −15.806 | 65.638 | 21.639 | 1.00 | 48.03 |
| ATOM | 1659 | OE1 | GLU | A | 254 | −15.134 | 21.736 | 1.00 | 38.84 |
| ATOM | 1660 | OE2 | GLU | A | 254 | −16.554 | 66.038 | 22.540 | 1.00 | 39.22 |
| ATOM | 1661 | N | MET | A | 255 | −13.969 | 58.279 | 18.154 | 1.00 | 35.02 |
| ATOM | 1662 | CA | MET | A | 255 | −13.596 | 59.673 | 18.394 | 1.00 | 34.71 |
| ATOM | 1663 | C | MET | A | 255 | −13.960 | 70.518 | 17.258 | 1.00 | 39.19 |
| ATOM | 1664 | O | MET | A | 255 | −14.327 | 71.765 | 17.497 | 1.00 | 39.09 |
| ATOM | 1665 | CB | MET | A | 255 | −12.105 | 69.787 | 18.741 | 1.00 | 36.92 |
| ATOM | 1666 | CG | MET | A | 255 | −11.715 | 69.056 | 20.013 | 1.00 | 40.35 |
| ATOM | 1667 | SD | MET | A | 255 | −9.994 | 69.277 | 20.476 | 1.00 | 44.80 |
| ATOM | 1668 | CE | MET | A | 255 | −9.180 | 68.154 | 19.349 | 1.00 | 41.04 |
| ATOM | 1669 | N | ALA | A | 255 | −13.870 | 70.131 | 16.020 | 1.00 | 36.01 |
| ATOM | 1670 | CA | ALA | A | 256 | −14.201 | 70.944 | 14.846 | 1.00 | 35.73 |
| ATOM | 1671 | C | ALA | A | 256 | −15.708 | 71.136 | 14.689 | 1.00 | 40.24 |
| ATOM | 1672 | O | ALA | A | 256 | −16.166 | 72.173 | 14.210 | 1.00 | 39.14 |
| ATOM | 1673 | CB | ALA | A | 256 | −13.625 | 70.320 | 13.595 | 1.00 | 36.49 |
| ATOM | 1674 | N | VAL | A | 257 | −16.477 | 70.116 | 15.053 | 1.00 | 37.86 |
| ATOM | 1675 | CA | VAL | A | 257 | −17.917 | 70.200 | 14.924 | 1.00 | 37.90 |
| ATOM | 1676 | C | VAL | A | 257 | −18.554 | 70.638 | 16.216 | 1.00 | 42.96 |

TABLE 4-continued

Structural Coordinate of MEK1/N35/NKFCdel (corresponding to amino acids 24 373 of SEQ ID NO: 2)-Compound 2 Binary Complex.

| ATOM | 1677 | O   | VAL | A | 257 | −19.721 | 71.086 | 16.207 | 1.00 | 42.29 |
|------|------|-----|-----|---|-----|---------|--------|--------|------|-------|
| ATOM | 1678 | CB  | VAL | A | 257 | −18.534 | 68.899 | 14.354 | 1.00 | 41.41 |
| ATOM | 1679 | CG1 | VAL | A | 257 | −17.803 | 68.494 | 13.078 | 1.00 | 40.88 |
| ATOM | 1680 | CG2 | VAL | A | 257 | −18.492 | 67.771 | 15.386 | 1.00 | 41.29 |
| ATOM | 1681 | N   | GLY | A | 258 | −17.840 | 70.558 | 17.320 | 1.00 | 40.92 |
| ATOM | 1682 | CA  | GLY | A | 258 | −18.336 | 70.995 | 18.622 | 1.00 | 41.01 |
| ATOM | 1683 | C   | GLY | A | 258 | −19.228 | 69.963 | 19.316 | 1.00 | 45.42 |
| ATOM | 1684 | O   | GLY | A | 258 | −20.041 | 70.309 | 20.164 | 1.00 | 45.12 |
| ATOM | 1685 | N   | ARG | A | 259 | −19.045 | 68.696 | 18.989 | 1.00 | 42.55 |
| ATOM | 1686 | CA  | ARG | A | 259 | −19.850 | 67.647 | 19.607 | 1.00 | 43.04 |
| ATOM | 1687 | C   | ARG | A | 259 | −19.243 | 66.262 | 19.367 | 1.00 | 47.11 |
| ATOM | 1688 | O   | ARG | A | 259 | −18.663 | 66.008 | 18.308 | 1.00 | 47.22 |
| ATOM | 1689 | CB  | ARG | A | 259 | −21.277 | 67.698 | 19.047 | 1.00 | 44.79 |
| ATOM | 1690 | CG  | ARG | A | 259 | −22.087 | 66.445 | 19.270 | 1.00 | 55.86 |
| ATOM | 1691 | CD  | ARG | A | 259 | −23.063 | 66.210 | 18.128 | 1.00 | 67.50 |
| ATOM | 1692 | NE  | ARG | A | 259 | −22.583 | 65.175 | 17.219 | 1.00 | 76.61 |
| ATOM | 1693 | CZ  | ARG | A | 259 | −23.209 | 64.028 | 16.989 | 1.00 | 85.04 |
| ATOM | 1694 | NH1 | ARG | A | 259 | −24.361 | 63.766 | 17.586 | 1.00 | 68.22 |
| ATOM | 1695 | NH2 | ARG | A | 259 | −22.682 | 63.145 | 16.156 | 1.00 | 72.71 |
| ATOM | 1696 | N   | TYR | A | 260 | −19.347 | 65.384 | 20.363 | 1.00 | 42.99 |
| ATOM | 1697 | CA  | TYR | A | 260 | −18.855 | 64.029 | 20.205 | 1.00 | 42.99 |
| ATOM | 1698 | C   | TYR | A | 260 | −19.564 | 63.476 | 18.967 | 1.00 | 49.21 |
| ATOM | 1699 | O   | TYR | A | 260 | −20.785 | 63.347 | 18.956 | 1.00 | 49.14 |
| ATOM | 1700 | CB  | TYR | A | 260 | −19.169 | 63.182 | 21.442 | 1.00 | 43.12 |
| ATOM | 1701 | CG  | TYR | A | 260 | −18.707 | 61.745 | 21.309 | 1.00 | 42.91 |
| ATOM | 1702 | CD1 | TYR | A | 260 | −17.372 | 61.396 | 21.526 | 1.00 | 44.14 |
| ATOM | 1703 | CD2 | TYR | A | 260 | −19.586 | 60.751 | 20.896 | 1.00 | 42.76 |
| ATOM | 1704 | CE1 | TYR | A | 260 | −16.947 | 60.091 | 21.373 | 1.00 | 43.39 |
| ATOM | 1705 | CE2 | TYR | A | 260 | −19.167 | 59.452 | 20.737 | 1.00 | 42.93 |
| ATOM | 1706 | CZ  | TYR | A | 260 | −17.855 | 59.122 | 20.975 | 1.00 | 47.95 |
| ATOM | 1707 | OH  | TYR | A | 260 | −17.452 | 57.815 | 20.821 | 1.00 | 46.61 |
| ATOM | 1708 | N   | PRO | A | 261 | −18.787 | 63.248 | 17.906 | 1.00 | 47.53 |
| ATOM | 1709 | CA  | PRO | A | 261 | −19.294 | 62.875 | 16.576 | 1.00 | 47.54 |
| ATOM | 1710 | C   | PRO | A | 261 | −20.097 | 61.581 | 16.353 | 1.00 | 53.60 |
| ATOM | 1711 | O   | PRO | A | 261 | −20.493 | 61.295 | 15.217 | 1.00 | 53.58 |
| ATOM | 1712 | CB  | PRO | A | 261 | −18.024 | 62.856 | 15.720 | 1.00 | 48.86 |
| ATOM | 1713 | CG  | PRO | A | 261 | −16.943 | 62.493 | 16.667 | 1.00 | 52.82 |
| ATOM | 1714 | CD  | PRO | A | 261 | −17.317 | 63.129 | 17.988 | 1.00 | 48.16 |
| ATOM | 1715 | N   | ILE | A | 262 | −20.330 | 60.802 | 17.399 | 1.00 | 51.36 |
| ATOM | 1716 | CA  | ILE | A | 262 | −21.074 | 59.549 | 17.243 | 1.00 | 51.94 |
| ATOM | 1717 | C   | ILE | A | 262 | −22.296 | 59.487 | 18.151 | 1.00 | 58.19 |
| ATOM | 1718 | O   | ILE | A | 262 | −22.207 | 59.785 | 19.334 | 1.00 | 57.62 |
| ATOM | 1719 | CB  | ILE | A | 262 | −20.180 | 58.324 | 17.507 | 1.00 | 54.85 |
| ATOM | 1720 | CG1 | ILE | A | 262 | −18.923 | 58.389 | 16.643 | 1.00 | 54.86 |
| ATOM | 1721 | CG2 | ILE | A | 262 | −20.945 | 57.033 | 17.242 | 1.00 | 55.67 |
| ATOM | 1722 | CD1 | ILE | A | 262 | −17.780 | 57.577 | 17.181 | 1.00 | 59.51 |
| ATOM | 1723 | N   | PRO | A | 263 | −23.440 | 59.097 | 17.590 | 1.00 | 57.19 |
| ATOM | 1724 | CA  | PRO | A | 263 | −23.542 | 58.760 | 16.181 | 1.00 | 57.55 |
| ATOM | 1725 | C   | PRO | A | 263 | −23.563 | 60.033 | 15.365 | 1.00 | 63.72 |
| ATOM | 1726 | O   | PRO | A | 263 | −23.714 | 61.113 | 15.911 | 1.00 | 63.00 |
| ATOM | 1727 | CB  | PRO | A | 263 | −24.903 | 56.081 | 16.100 | 1.00 | 58.93 |
| ATOM | 1728 | CG  | PRO | A | 263 | −25.731 | 58.789 | 17.151 | 1.00 | 63.03 |
| ATOM | 1729 | CD  | PRO | A | 263 | −24.761 | 59.385 | 18.171 | 1.00 | 58.11 |
| ATOM | 1730 | N   | PRO | A | 264 | −23.428 | 59.898 | 14.052 | 1.00 | 63.33 |
| ATOM | 1731 | CA  | PRO | A | 264 | −23.399 | 61.049 | 13.156 | 1.00 | 64.04 |
| ATOM | 1732 | C   | PRO | A | 264 | −24.549 | 62.034 | 13.365 | 1.00 | 71.72 |
| ATOM | 1733 | O   | PRO | A | 264 | −25.639 | 61.659 | 13.805 | 1.00 | 70.66 |
| ATOM | 1734 | CB  | PRO | A | 264 | −23.484 | 60.412 | 11.760 | 1.00 | 65.21 |
| ATOM | 1735 | CG  | PRO | A | 264 | −23.232 | 58.928 | 11.958 | 1.00 | 69.05 |
| ATOM | 1736 | CD  | PRO | A | 264 | −22.907 | 58.692 | 13.399 | 1.00 | 64.22 |
| ATOM | 1737 | N   | PRO | A | 265 | −24.287 | 63.299 | 13.045 | 1.00 | 72.26 |
| ATOM | 1738 | CA  | PRO | A | 265 | −25.284 | 64.361 | 13.178 | 1.00 | 73.10 |
| ATOM | 1739 | C   | PRO | A | 265 | −26.159 | 64.429 | 11.937 | 1.00 | 80.87 |
| ATOM | 1740 | O   | PRO | A | 265 | −25.658 | 64.578 | 10.823 | 1.00 | 80.64 |
| ATOM | 1741 | CB  | PRO | A | 265 | −24.430 | 65.629 | 13.265 | 1.00 | 74.48 |
| ATOM | 1742 | CG  | PRO | A | 255 | −23.112 | 65.164 | 13.796 | 1.00 | 78.40 |
| ATOM | 1743 | CD  | PRO | A | 265 | −22.911 | 63.795 | 13.230 | 1.00 | 73.18 |
| ATOM | 1744 | N   | ASP | A | 266 | −27.468 | 64.325 | 12.132 | 1.00 | 80.23 |
| ATOM | 1745 | CA  | ASP | A | 266 | −28.409 | 64.386 | 11.019 | 1.00 | 81.38 |
| ATOM | 1746 | C   | ASP | A | 266 | −28.318 | 65.738 | 10.313 | 1.00 | 87.63 |
| ATOM | 1747 | O   | ASP | A | 266 | −27.832 | 66.715 | 10.886 | 1.00 | 87.25 |
| ATOM | 1748 | CB  | ASP | A | 266 | −29.834 | 64.140 | 11.514 | 1.00 | 83.52 |
| ATOM | 1749 | CG  | ASP | A | 266 | −29.967 | 62.833 | 12.276 | 1.00 | 96.05 |
| ATOM | 1750 | OD1 | ASP | A | 266 | −29.039 | 61.997 | 12.195 | 1.00 | 96.73 |
| ATOM | 1751 | OD2 | ASP | A | 266 | −31.004 | 62.640 | 12.950 | 1.00 | 102.85 |
| ATOM | 1752 | N   | ALA | A | 267 | −28.774 | 65.783 | 9.062  | 1.00 | 85.94 |
| ATOM | 1753 | CA  | ALA | A | 267 | −28.726 | 67.011 | 8.265  | 1.00 | 86.57 |

TABLE 4-continued

Structural Coordinate of MEK1/N35/NKFCdel (corresponding to amino acids 24 373 of SEQ ID NO: 2)-Compound 2 Binary Complex.

| ATOM | 1754 | C   | ALA | A | 267 | −29.275 | 68.222 | 9.021  | 1.00 | 92.25  |
|------|------|-----|-----|---|-----|---------|--------|--------|------|--------|
| ATOM | 1755 | O   | ALA | A | 267 | −28.734 | 69.326 | 8.926  | 1.00 | 91.87  |
| ATOM | 1756 | CB  | ALA | A | 267 | −29.473 | 66.821 | 6.949  | 1.00 | 87.30  |
| ATOM | 1757 | N   | LYS | A | 268 | −30.353 | 68.009 | 9.767  | 1.00 | 89.96  |
| ATOM | 1758 | CA  | LYS | A | 268 | −30.978 | 69.082 | 10.526 | 1.00 | 90.28  |
| ATOM | 1759 | C   | LYS | A | 268 | −30.075 | 69.591 | 11.648 | 1.00 | 94.50  |
| ATOM | 1760 | O   | LYS | A | 268 | −30.044 | 70.789 | 11.936 | 1.00 | 94.28  |
| ATOM | 1761 | CB  | LYS | A | 268 | −32.329 | 68.628 | 11.083 | 1.00 | 93.13  |
| ATOM | 1762 | CG  | LYS | A | 268 | −33.459 | 68.636 | 10.054 | 1.00 | 108.19 |
| ATOM | 1763 | CD  | LYS | A | 268 | −34.040 | 70.034 | 9.881  | 1.00 | 118.55 |
| ATOM | 1764 | CE  | LYS | A | 268 | −34.103 | 70.433 | 8.414  | 1.00 | 128.99 |
| ATOM | 1765 | NZ  | LYS | A | 268 | −34.114 | 71.912 | 8.242  | 1.00 | 137.24 |
| ATOM | 1766 | N   | GLU | A | 269 | −29.334 | 68.681 | 12.273 | 1.00 | 90.99  |
| ATOM | 1767 | CA  | GLU | A | 269 | −28.420 | 69.052 | 13.352 | 1.00 | 90.68  |
| ATOM | 1768 | C   | GLU | A | 269 | −27.247 | 69.866 | 12.810 | 1.00 | 94.18  |
| ATOM | 1769 | O   | GLU | A | 269 | −26.716 | 70.739 | 13.500 | 1.00 | 93.68  |
| ATOM | 1770 | CB  | GLU | A | 269 | −27.903 | 67.806 | 14.071 | 1.00 | 92.05  |
| ATOM | 1771 | CG  | GLU | A | 269 | −28.783 | 66.580 | 13.899 | 1.00 | 102.91 |
| ATOM | 1772 | CD  | GLU | A | 269 | −28.376 | 65.443 | 14.815 | 1.00 | 123.46 |
| ATOM | 1773 | OE1 | GLU | A | 269 | −27.782 | 65.722 | 15.881 | 1.00 | 120.18 |
| ATOM | 1774 | OE2 | GLU | A | 269 | −28.639 | 64.272 | 14.468 | 1.00 | 115.08 |
| ATOM | 1775 | N   | LEU | A | 270 | −26.852 | 69.575 | 11.574 | 1.00 | 90.55  |
| ATOM | 1776 | CA  | LEU | A | 270 | −25.752 | 70.280 | 10.927 | 1.00 | 90.12  |
| ATOM | 1777 | C   | LEU | A | 270 | −26.206 | 71.665 | 10.501 | 1.00 | 93.85  |
| ATOM | 1778 | O   | LEU | A | 270 | −25.458 | 72.638 | 10.607 | 1.00 | 93.05  |
| ATOM | 1779 | CB  | LEU | A | 270 | −25.270 | 69.501 | 9.703  | 1.00 | 90.19  |
| ATOM | 1780 | CG  | LEU | A | 270 | −24.472 | 68.228 | 9.980  | 1.00 | 94.77  |
| ATOM | 1781 | CD1 | LEU | A | 270 | −24.606 | 67.253 | 8.822  | 1.00 | 94.94  |
| ATOM | 1782 | CD2 | LEU | A | 270 | −23.010 | 68.561 | 10.247 | 1.00 | 97.28  |
| ATOM | 1783 | N   | GLU | A | 271 | −27.440 | 71.742 | 10.013 | 1.00 | 90.66  |
| ATOM | 1784 | CA  | GLU | A | 271 | −28.014 | 72.999 | 9.555  | 1.00 | 90.52  |
| ATOM | 1785 | C   | GLU | A | 271 | −28.004 | 74.062 | 10.658 | 1.00 | 94.01  |
| ATOM | 1786 | O   | GLU | A | 271 | −27.795 | 75.250 | 10.391 | 1.00 | 93.62  |
| ATOM | 1787 | CB  | GLU | A | 271 | −29.435 | 72.777 | 9.029  | 1.00 | 91.90  |
| ATOM | 1788 | CG  | GLU | A | 271 | −30.158 | 74.043 | 8.611  | 1.00 | 102.63 |
| ATOM | 1789 | CD  | GLU | A | 271 | −31.615 | 74.052 | 9.033  | 1.00 | 122.03 |
| ATOM | 1790 | OE1 | GLU | A | 271 | −32.450 | 73.499 | 8.287  | 1.00 | 119.39 |
| ATOM | 1791 | OE2 | GLU | A | 271 | −31.923 | 74.595 | 10.117 | 1.00 | 112.81 |
| ATOM | 1792 | N   | LEU | A | 272 | −28.211 | 73.629 | 11.898 | 1.00 | 90.31  |
| ATOM | 1793 | CA  | LEU | A | 272 | −28.214 | 74.547 | 13.033 | 1.00 | 90.00  |
| ATOM | 1794 | C   | LEU | A | 272 | −26.808 | 74.722 | 13.602 | 1.00 | 93.37  |
| ATOM | 1795 | O   | LEU | A | 272 | −26.551 | 75.649 | 14.375 | 1.00 | 93.08  |
| ATOM | 1796 | CB  | LEU | A | 272 | −29.168 | 74.056 | 14.127 | 1.00 | 90.01  |
| ATOM | 1797 | CG  | LEU | A | 272 | −30.192 | 72.987 | 13.733 | 1.00 | 94.82  |
| ATOM | 1798 | CD1 | LEU | A | 272 | −30.476 | 72.052 | 14.908 | 1.00 | 94.90  |
| ATOM | 1799 | CD2 | LEU | A | 272 | −31.477 | 73.633 | 13.228 | 1.00 | 97.17  |
| ATOM | 1800 | N   | MET | A | 273 | −25.900 | 73.829 | 13.216 | 1.00 | 89.26  |
| ATOM | 1801 | CA  | MET | A | 273 | −24.524 | 73.882 | 13.698 | 1.00 | 88.59  |
| ATOM | 1802 | C   | MET | A | 273 | −23.697 | 74.903 | 12.927 | 1.00 | 91.98  |
| ATOM | 1803 | O   | MET | A | 273 | −23.058 | 75.773 | 13.522 | 1.00 | 91.58  |
| ATOM | 1804 | CB  | MET | A | 273 | −23.871 | 72.501 | 13.616 | 1.00 | 90.74  |
| ATOM | 1805 | CG  | MET | A | 273 | −24.284 | 71.559 | 14.733 | 1.00 | 94.14  |
| ATOM | 1806 | SD  | MET | A | 273 | −23.671 | 69.883 | 14.506 | 1.00 | 98.13  |
| ATOM | 1807 | CE  | MET | A | 273 | −22.608 | 69.725 | 15.922 | 1.00 | 94.70  |
| ATOM | 1808 | N   | PHE | A | 274 | −23.718 | 74.794 | 11.601 | 1.00 | 88.08  |
| ATOM | 1809 | CA  | PHE | A | 274 | −22.955 | 75.702 | 10.747 | 1.00 | 87.45  |
| ATOM | 1810 | C   | PHE | A | 274 | −23.858 | 76.526 | 9.842  | 1.00 | 90.64  |
| ATOM | 1811 | O   | PHE | A | 274 | −23.381 | 77.356 | 9.070  | 1.00 | 89.83  |
| ATOM | 1812 | CB  | PHE | A | 274 | −21.939 | 74.919 | 9.910  | 1.00 | 89.08  |
| ATOM | 1813 | CG  | PHE | A | 274 | −21.049 | 74.018 | 10.721 | 1.00 | 90.42  |
| ATOM | 1814 | CD1 | PHE | A | 274 | −21.522 | 72.813 | 11.214 | 1.00 | 93.31  |
| ATOM | 1815 | CD2 | PHE | A | 274 | −19.739 | 74.378 | 10.991 | 1.00 | 92.44  |
| ATOM | 1816 | CE1 | PHE | A | 274 | −20.707 | 71.987 | 11.964 | 1.00 | 94.10  |
| ATOM | 1817 | CE2 | PHE | A | 274 | −18.919 | 73.552 | 11.741 | 1.00 | 95.17  |
| ATOM | 1818 | CZ  | PHE | A | 274 | −19.402 | 72.354 | 12.221 | 1.00 | 93.20  |
| ATOM | 1819 | N   | PRO | A | 306 | −30.639 | 59.550 | 24.276 | 1.00 | 73.43  |
| ATOM | 1820 | CA  | PRO | A | 306 | −29.207 | 59.493 | 23.984 | 1.00 | 72.52  |
| ATOM | 1821 | C   | PRO | A | 306 | −28.682 | 58.060 | 24.069 | 1.00 | 74.80  |
| ATOM | 1822 | O   | PRO | A | 306 | −29.168 | 57.255 | 24.872 | 1.00 | 75.01  |
| ATOM | 1823 | CB  | PRO | A | 306 | −28.588 | 60.353 | 25.091 | 1.00 | 74.12  |
| ATOM | 1824 | CG  | PRO | A | 306 | −29.676 | 61.279 | 25.502 | 1.00 | 78.78  |
| ATOM | 1825 | CD  | PRO | A | 306 | −30.948 | 60.499 | 25.361 | 1.00 | 74.04  |
| ATOM | 1826 | N   | MET | A | 307 | −27.693 | 57.751 | 23.232 | 1.00 | 69.00  |
| ATOM | 1827 | CA  | MET | A | 307 | −27.097 | 56.419 | 23.179 | 1.00 | 67.46  |
| ATOM | 1828 | C   | MET | A | 307 | −26.323 | 56.068 | 24.448 | 1.00 | 68.89  |
| ATOM | 1829 | O   | MET | A | 307 | −25.616 | 56.906 | 25.010 | 1.00 | 67.67  |
| ATOM | 1830 | CB  | MET | A | 307 | −26.165 | 56.312 | 21.970 | 1.00 | 69.59  |

TABLE 4-continued

Structural Coordinate of MEK1/N35/NKFCdel (corresponding to amino acids 24 373 of SEQ ID NO: 2)-Compound 2 Binary Complex.

| ATOM | 1831 | CG  | MET | A | 307 | −26.362 | 55.064 | 21.136 | 1.00 | 73.03 |
| ---- | ---- | --- | --- | - | --- | ------- | ------ | ------ | ---- | ----- |
| ATOM | 1832 | SD  | MET | A | 307 | −25.117 | 54.897 | 19.841 | 1.00 | 77.00 |
| ATOM | 1833 | CE  | MET | A | 307 | −26.128 | 54.973 | 18.385 | 1.00 | 73.64 |
| ATOM | 1834 | N   | ALA | A | 308 | −26.440 | 54.810 | 24.876 | 1.00 | 64.10 |
| ATOM | 1835 | CA  | ALA | A | 308 | −25.708 | 54.320 | 26.039 | 1.00 | 63.30 |
| ATOM | 1836 | C   | ALA | A | 308 | −24.341 | 53.810 | 25.586 | 1.00 | 65.47 |
| ATOM | 1837 | O   | ALA | A | 308 | −24.167 | 53.433 | 24.424 | 1.00 | 64.78 |
| ATOM | 1838 | CB  | ALA | A | 308 | −26.489 | 53.218 | 26.736 | 1.00 | 63.97 |
| ATOM | 1839 | N   | ILE | A | 309 | −23.374 | 53.815 | 26.505 | 1.00 | 60.87 |
| ATOM | 1840 | CA  | ILE | A | 309 | −21.996 | 53.398 | 26.212 | 1.00 | 60.11 |
| ATOM | 1841 | C   | ILE | A | 309 | −21.867 | 52.158 | 25.338 | 1.00 | 62.20 |
| ATOM | 1842 | O   | ILE | A | 309 | −21.270 | 52.211 | 24.269 | 1.00 | 62.41 |
| ATOM | 1843 | CB  | ILE | A | 309 | −21.168 | 53.186 | 27.496 | 1.00 | 63.23 |
| ATOM | 1844 | CG1 | ILE | A | 309 | −21.894 | 53.765 | 28.708 | 1.00 | 63.88 |
| ATOM | 1845 | CG2 | ILE | A | 309 | −19.787 | 53.799 | 27.338 | 1.00 | 63.47 |
| ATOM | 1846 | CD1 | ILE | A | 309 | −22.060 | 55.282 | 22.668 | 1.00 | 72.01 |
| ATOM | 1847 | N   | PHE | A | 310 | −22.394 | 51.034 | 25.812 | 1.00 | 56.64 |
| ATOM | 1848 | CA  | PHE | A | 310 | −22.308 | 49.784 | 25.065 | 1.00 | 55.43 |
| ATOM | 1849 | C   | PHE | A | 310 | −22.834 | 49.935 | 23.641 | 1.00 | 58.27 |
| ATOM | 1850 | O   | PHE | A | 310 | −22.231 | 49.431 | 22.692 | 1.00 | 57.81 |
| ATOM | 1851 | CB  | PHE | A | 310 | −23.025 | 48.651 | 25.801 | 1.00 | 57.02 |
| ATOM | 1852 | CG  | PHE | A | 310 | −24.352 | 49.057 | 26.399 | 1.00 | 58.15 |
| ATOM | 1853 | CD1 | PHE | A | 310 | −25.535 | 48.864 | 25.699 | 1.00 | 61.02 |
| ATOM | 1854 | CD2 | PHE | A | 310 | −24.410 | 49.606 | 27.670 | 1.00 | 60.26 |
| ATOM | 1855 | CE1 | PHE | A | 310 | −26.755 | 49.229 | 26.252 | 1.00 | 62.04 |
| ATOM | 1856 | CE2 | PHE | A | 310 | −25.629 | 49.973 | 28.229 | 1.00 | 63.06 |
| ATOM | 1857 | CZ  | PHE | A | 310 | −26.803 | 49.722 | 27.517 | 1.00 | 61.16 |
| ATOM | 1858 | N   | GLU | A | 311 | −23.960 | 50.636 | 23.497 | 1.00 | 54.06 |
| ATOM | 1859 | CA  | GLU | A | 311 | −24.559 | 50.873 | 22.187 | 1.00 | 53.37 |
| ATOM | 1860 | C   | GLU | A | 311 | −23.599 | 51.699 | 21.361 | 1.00 | 56.37 |
| ATOM | 1861 | O   | GLU | A | 311 | −23.377 | 51.437 | 20.174 | 1.00 | 56.14 |
| ATOM | 1862 | CB  | GLU | A | 311 | −25.883 | 51.624 | 22.332 | 1.00 | 54.74 |
| ATOM | 1863 | CG  | GLU | A | 311 | −26.784 | 51.098 | 23.432 | 1.00 | 65.19 |
| ATOM | 1864 | CD  | GLU | A | 311 | −28.130 | 51.795 | 23.465 | 1.00 | 84.58 |
| ATOM | 1865 | OE1 | GLU | A | 311 | −28.153 | 53.039 | 23.559 | 1.00 | 82.82 |
| ATOM | 1866 | OE2 | GLU | A | 311 | −29.165 | 51.097 | 23.405 | 1.00 | 77.20 |
| ATOM | 1867 | N   | LEU | A | 312 | −23.008 | 52.693 | 22.006 | 1.00 | 51.70 |
| ATOM | 1868 | CA  | LEU | A | 312 | −22.048 | 53.557 | 21.355 | 1.00 | 51.07 |
| ATOM | 1869 | C   | LEU | A | 312 | −20.847 | 52.751 | 20.870 | 1.00 | 54.28 |
| ATOM | 1870 | O   | LEU | A | 312 | −20.449 | 52.845 | 19.709 | 1.00 | 54.05 |
| ATOM | 1871 | CB  | LEU | A | 312 | −21.595 | 54.646 | 22.325 | 1.00 | 50.96 |
| ATOM | 1872 | CG  | LEU | A | 312 | −20.963 | 55.895 | 21.722 | 1.00 | 55.13 |
| ATOM | 1873 | CD1 | LEU | A | 312 | −20.724 | 56.916 | 22.804 | 1.00 | 54.87 |
| ATOM | 1874 | CD2 | LEU | A | 312 | −19.668 | 55.533 | 21.025 | 1.00 | 57.92 |
| ATOM | 1875 | N   | LEU | A | 313 | −20.274 | 51.956 | 21.767 | 1.00 | 50.39 |
| ATOM | 1876 | CA  | LEU | A | 313 | −19.105 | 51.147 | 21.434 | 1.00 | 49.85 |
| ATOM | 1877 | C   | LEU | A | 313 | −19.368 | 50.198 | 20.277 | 1.00 | 53.39 |
| ATOM | 1878 | O   | LEU | A | 313 | −18.551 | 50.082 | 19.367 | 1.00 | 52.79 |
| ATOM | 1879 | CB  | LEU | A | 313 | −18.602 | 50.392 | 22.659 | 1.00 | 49.65 |
| ATOM | 1880 | CG  | LEU | A | 313 | −18.115 | 51.306 | 23.790 | 1.00 | 53.75 |
| ATOM | 1881 | CD1 | LEU | A | 313 | −17.506 | 50.501 | 24.928 | 1.00 | 53.25 |
| ATOM | 1882 | CD2 | LEU | A | 313 | −17.123 | 52.341 | 23.252 | 1.00 | 55.51 |
| ATOM | 1883 | N   | ASP | A | 314 | −20.522 | 49.546 | 20.295 | 1.00 | 50.39 |
| ATOM | 1884 | CA  | ASP | A | 314 | −20.887 | 48.641 | 19.216 | 1.00 | 50.69 |
| ATOM | 1885 | C   | ASP | A | 314 | −20.941 | 49.426 | 17.900 | 1.00 | 54.34 |
| ATOM | 1886 | O   | ASP | A | 314 | −20.404 | 48.986 | 16.873 | 1.00 | 53.55 |
| ATOM | 1887 | CB  | ASP | A | 314 | −22.238 | 47.971 | 19.512 | 1.00 | 53.25 |
| ATOM | 1888 | CG  | ASP | A | 314 | −22.645 | 46.969 | 18.440 | 1.00 | 66.96 |
| ATOM | 1889 | OD1 | ASP | A | 314 | −22.020 | 45.891 | 18.355 | 1.00 | 68.20 |
| ATOM | 1890 | OD2 | ASP | A | 314 | −23.513 | 47.250 | 17.701 | 1.00 | 74.96 |
| ATOM | 1891 | N   | TYR | A | 315 | −21.539 | 50.617 | 17.952 | 1.00 | 51.03 |
| ATOM | 1892 | CA  | TYR | A | 315 | −21.620 | 51.487 | 16.785 | 1.00 | 50.95 |
| ATOM | 1893 | C   | TYR | A | 315 | −20.221 | 51.724 | 16.198 | 1.00 | 54.02 |
| ATOM | 1894 | O   | TYR | A | 315 | −20.022 | 51.576 | 14.990 | 1.00 | 53.77 |
| ATOM | 1895 | CB  | TYR | A | 315 | −22.267 | 52.830 | 17.149 | 1.00 | 52.64 |
| ATOM | 1896 | CG  | TYR | A | 315 | −22.634 | 53.668 | 15.944 | 1.00 | 55.01 |
| ATOM | 1897 | CD1 | TYR | A | 315 | −21.652 | 54.303 | 15.186 | 1.00 | 56.88 |
| ATOM | 1898 | CD2 | TYR | A | 315 | −23.961 | 53.793 | 15.538 | 1.00 | 56.33 |
| ATOM | 1899 | CE1 | TYR | A | 315 | −21.984 | 55.057 | 14.059 | 1.00 | 57.98 |
| ATOM | 1900 | CE2 | TYR | A | 315 | −24.308 | 54.545 | 14.416 | 1.00 | 57.50 |
| ATOM | 1901 | CZ  | TYR | A | 315 | −23.315 | 55.177 | 13.682 | 1.00 | 65.59 |
| ATOM | 1902 | OH  | TYR | A | 315 | −23.658 | 55.916 | 12.568 | 1.00 | 65.66 |
| ATOM | 1903 | N   | ILE | A | 316 | −19.287 | 52.091 | 17.062 | 1.00 | 49.49 |
| ATOM | 1904 | CA  | ILE | A | 316 | −17.912 | 52.340 | 16.642 | 1.00 | 48.94 |
| ATOM | 1905 | C   | ILE | A | 316 | −17.325 | 51.135 | 15.908 | 1.00 | 52.51 |
| ATOM | 1906 | O   | ILE | A | 316 | −16.712 | 51.277 | 14.850 | 1.00 | 52.27 |
| ATOM | 1907 | CB  | ILE | A | 316 | −16.997 | 52.666 | 17.852 | 1.00 | 52.20 |

TABLE 4-continued

Structural Coordinate of MEK1/N35/NKFCdel (corresponding to amino acids 24 373 of SEQ ID NO: 2)-Compound 2 Binary Complex.

| ATOM | 1908 | CG1 | ILE | A | 316 | −17.380 | 54.013 | 18.484 | 1.00 | 52.39 |
|---|---|---|---|---|---|---|---|---|---|---|
| ATOM | 1909 | CG2 | ILE | A | 316 | −15.520 | 52.640 | 17.437 | 1.00 | 52.81 |
| ATOM | 1910 | CD1 | ILE | A | 316 | −16.896 | 54.178 | 19.916 | 1.00 | 55.78 |
| ATOM | 1911 | N | VAL | A | 317 | −17.493 | 49.953 | 16.485 | 1.00 | 48.68 |
| ATOM | 1912 | CA | VAL | A | 317 | −16.943 | 48.737 | 15.894 | 1.00 | 48.05 |
| ATOM | 1913 | C | VAL | A | 317 | −17.713 | 48.271 | 14.665 | 1.00 | 51.58 |
| ATOM | 1914 | O | VAL | A | 317 | −17.143 | 47.641 | 13.771 | 1.00 | 51.25 |
| ATOM | 1915 | CB | VAL | A | 317 | −16.915 | 47.580 | 16.906 | 1.00 | 51.62 |
| ATOM | 1916 | CG1 | VAL | A | 317 | −16.165 | 46.393 | 16.339 | 1.00 | 51.23 |
| ATOM | 1917 | CG2 | VAL | A | 317 | −16.314 | 48.029 | 18.215 | 1.00 | 51.43 |
| ATOM | 1918 | N | ASN | A | 318 | −19.008 | 48.572 | 14.627 | 1.00 | 47.64 |
| ATOM | 1919 | CA | ASN | A | 318 | −19.865 | 48.097 | 13.545 | 1.00 | 47.09 |
| ATOM | 1920 | C | ASN | A | 318 | −20.209 | 49.060 | 12.414 | 1.00 | 50.25 |
| ATOM | 1921 | O | ASN | A | 318 | −20.425 | 48.631 | 11.285 | 1.00 | 49.16 |
| ATOM | 1922 | CB | ASN | A | 318 | −21.123 | 47.460 | 14.113 | 1.00 | 46.66 |
| ATOM | 1923 | CG | ASN | A | 318 | −20.828 | 46.191 | 14.855 | 1.00 | 60.86 |
| ATOM | 1924 | OD1 | ASN | A | 318 | −20.081 | 45.340 | 14.369 | 1.00 | 49.77 |
| ATOM | 1925 | ND2 | ASN | A | 318 | −21.315 | 46.098 | 16.084 | 1.00 | 53.58 |
| ATOM | 1926 | N | GLU | A | 319 | −20.298 | 50.350 | 12.719 | 1.00 | 46.79 |
| ATOM | 1927 | CA | GLU | A | 319 | −20.645 | 51.341 | 11.707 | 1.00 | 46.19 |
| ATOM | 1928 | C | GLU | A | 319 | −19.404 | 51.940 | 11.056 | 1.00 | 48.94 |
| ATOM | 1929 | O | GLU | A | 319 | −18.280 | 51.635 | 11.446 | 1.00 | 48.03 |
| ATOM | 1930 | CB | GLU | A | 319 | −21.511 | 52.447 | 12.312 | 1.00 | 47.56 |
| ATOM | 1931 | CG | GLU | A | 319 | −22.970 | 52.073 | 12.466 | 1.00 | 56.32 |
| ATOM | 1932 | CD | GLU | A | 319 | −23.449 | 51.143 | 11.372 | 1.00 | 76.49 |
| ATOM | 1933 | OE1 | GLU | A | 319 | −23.326 | 51.502 | 10.185 | 1.00 | 75.45 |
| ATOM | 1934 | OE2 | GLU | A | 319 | −23.947 | 50.048 | 11.698 | 1.00 | 70.91 |
| ATOM | 1935 | N | PRO | A | 320 | −19.614 | 52.786 | 10.050 | 1.00 | 45.18 |
| ATOM | 1936 | CA | PRO | A | 320 | −18.498 | 53.437 | 9.363 | 1.00 | 44.08 |
| ATOM | 1937 | C | PRO | A | 320 | −18.044 | 54.655 | 10.158 | 1.00 | 45.40 |
| ATOM | 1938 | O | PRO | A | 320 | −18.842 | 55.312 | 10.821 | 1.00 | 44.03 |
| ATOM | 1939 | CB | PRO | A | 320 | −19.104 | 53.849 | 8.017 | 1.00 | 45.63 |
| ATOM | 1940 | CG | PRO | A | 320 | −20.195 | 52.853 | 7.791 | 1.00 | 50.24 |
| ATOM | 1941 | CD | PRO | A | 320 | −20.776 | 52.600 | 9.158 | 1.00 | 45.54 |
| ATOM | 1942 | N | PRO | A | 321 | −16.747 | 54.919 | 10.120 | 1.00 | 41.90 |
| ATOM | 1943 | CA | PRO | A | 321 | −16.163 | 56.011 | 10.881 | 1.00 | 41.63 |
| ATOM | 1944 | C | PRO | A | 321 | −16.825 | 57.351 | 10.609 | 1.00 | 46.31 |
| ATOM | 1945 | O | PRO | A | 321 | −17.334 | 57.597 | 9.512 | 1.00 | 46.07 |
| ATOM | 1946 | CB | PRO | A | 321 | −14.713 | 56.026 | 10.402 | 1.00 | 43.06 |
| ATOM | 1947 | CG | PRO | A | 321 | −14.776 | 55.489 | 9.028 | 1.00 | 46.91 |
| ATOM | 1948 | CD | PRO | A | 321 | −15.870 | 54.477 | 9.021 | 1.00 | 42.19 |
| ATOM | 1949 | N | PRO | A | 322 | −16.813 | 58.217 | 11.619 | 1.00 | 42.65 |
| ATOM | 1950 | CA | PRO | A | 322 | −17.377 | 59.559 | 11.492 | 1.00 | 41.89 |
| ATOM | 1951 | C | PRO | A | 322 | −16.570 | 60.341 | 10.470 | 1.00 | 44.24 |
| ATOM | 1952 | O | PRO | A | 322 | −15.510 | 59.897 | 10.036 | 1.00 | 43.91 |
| ATOM | 1953 | CB | PRO | A | 322 | −17.165 | 60.172 | 12.892 | 1.00 | 43.60 |
| ATOM | 1954 | CG | PRO | A | 322 | −16.799 | 59.016 | 13.791 | 1.00 | 47.85 |
| ATOM | 1955 | CD | PRO | A | 322 | −16.143 | 58.012 | 12.914 | 1.00 | 43.09 |
| ATOM | 1956 | N | LYS | A | 323 | −17.060 | 61.516 | 10.105 | 1.00 | 39.92 |
| ATOM | 1957 | CA | LYS | A | 323 | −16.363 | 62.363 | 9.151 | 1.00 | 39.46 |
| ATOM | 1958 | C | LYS | A | 323 | −16.828 | 63.807 | 9.272 | 1.00 | 43.88 |
| ATOM | 1959 | O | LYS | A | 323 | −17.967 | 64.076 | 9.668 | 1.00 | 43.64 |
| ATOM | 1960 | CB | LYS | A | 323 | −16.574 | 61.853 | 7.717 | 1.00 | 41.71 |
| ATOM | 1961 | CG | LYS | A | 323 | −17.879 | 62.286 | 7.086 | 1.00 | 54.72 |
| ATOM | 1962 | CD | LYS | A | 323 | −18.430 | 61.196 | 6.184 | 1.00 | 65.68 |
| ATOM | 1963 | CE | LYS | A | 323 | −19.730 | 61.624 | 5.526 | 1.00 | 72.89 |
| ATOM | 1964 | NZ | LYS | A | 323 | −19.490 | 62.340 | 4.242 | 1.00 | 81.65 |
| ATOM | 1965 | N | LEU | A | 324 | −15.948 | 64.741 | 8.933 | 1.00 | 40.16 |
| ATOM | 1966 | CA | LEU | A | 324 | −16.307 | 66.145 | 8.995 | 1.00 | 39.86 |
| ATOM | 1967 | C | LEU | A | 324 | −17.369 | 66.433 | 7.948 | 1.00 | 44.51 |
| ATOM | 1968 | O | LEU | A | 324 | −17.430 | 65.767 | 6.923 | 1.00 | 44.20 |
| ATOM | 1969 | CB | LEU | A | 324 | −15.082 | 67.026 | 8.734 | 1.00 | 39.56 |
| ATOM | 1970 | CG | LEU | A | 324 | −13.986 | 67.028 | 9.796 | 1.00 | 43.31 |
| ATOM | 1971 | CD1 | LEU | A | 324 | −12.711 | 67.608 | 9.212 | 1.00 | 43.13 |
| ATOM | 1972 | CD2 | LEU | A | 324 | −14.429 | 67.812 | 11.031 | 1.00 | 44.36 |
| ATOM | 1973 | N | PRO | A | 325 | −18.197 | 67.438 | 8.200 | 1.00 | 41.82 |
| ATOM | 1974 | CA | PRO | A | 325 | −19.200 | 67.838 | 7.221 | 1.00 | 41.62 |
| ATOM | 1975 | C | PRO | A | 325 | −18.491 | 68.507 | 6.043 | 1.00 | 45.88 |
| ATOM | 1976 | O | PRO | A | 325 | −17.480 | 69.191 | 6.220 | 1.00 | 45.15 |
| ATOM | 1977 | CB | PRO | A | 325 | −20.051 | 68.879 | 7.985 | 1.00 | 43.07 |
| ATOM | 1978 | CG | PRO | A | 325 | −19.279 | 69.190 | 9.241 | 1.00 | 47.16 |
| ATOM | 1979 | CD | PRO | A | 325 | −18.510 | 67.950 | 9.542 | 1.00 | 42.29 |
| ATOM | 1980 | N | SER | A | 326 | −19.024 | 68.312 | 4.846 | 1.00 | 43.38 |
| ATOM | 1981 | CA | SER | A | 326 | −18.440 | 68.911 | 3.654 | 1.00 | 43.87 |
| ATOM | 1982 | C | SER | A | 326 | −18.881 | 70.349 | 3.503 | 1.00 | 48.67 |
| ATOM | 1983 | O | SER | A | 326 | −19.936 | 70.743 | 4.002 | 1.00 | 48.35 |
| ATOM | 1984 | CB | SER | A | 326 | −18.829 | 68.121 | 2.405 | 1.00 | 47.70 |

TABLE 4-continued

Structural Coordinate of MEK1/N35/NKFCdel (corresponding to amino acids 24 373 of SEQ ID NO: 2)-Compound 2 Binary Complex.

| ATOM | 1985 | OG  | SER | A | 326 | −19.585 | 66.980 | 2.746  | 1.00 | 57.87 |
| ---- | ---- | --- | --- | - | --- | ------- | ------ | ------ | ---- | ----- |
| ATOM | 1986 | N   | GLY | A | 327 | −18.079 | 71.127 | 2.788  | 1.00 | 46.32 |
| ATOM | 1987 | CA  | GLY | A | 327 | −18.391 | 72.528 | 2.550  | 1.00 | 46.24 |
| ATOM | 1988 | C   | GLY | A | 327 | −17.727 | 73.429 | 3.582  | 1.00 | 50.33 |
| ATOM | 1989 | O   | GLY | A | 327 | −17.021 | 74.386 | 3.226  | 1.00 | 50.48 |
| ATOM | 1990 | N   | VAL | A | 328 | −17.939 | 73.112 | 4.859  | 1.00 | 45.26 |
| ATOM | 1991 | CA  | VAL | A | 328 | −17.400 | 73.918 | 5.952  | 1.00 | 44.41 |
| ATOM | 1992 | C   | VAL | A | 328 | −15.900 | 73.761 | 6.247  | 1.00 | 46.05 |
| ATOM | 1993 | O   | VAL | A | 328 | −15.285 | 74.654 | 6.830  | 1.00 | 46.82 |
| ATOM | 1994 | CB  | VAL | A | 328 | −18.225 | 73.746 | 7.256  | 1.00 | 48.57 |
| ATOM | 1995 | CG1 | VAL | A | 328 | −19.463 | 74.607 | 7.201  | 1.00 | 48.45 |
| ATOM | 1996 | CG2 | VAL | A | 328 | −18.609 | 72.290 | 7.468  | 1.00 | 48.49 |
| ATOM | 1997 | N   | PHE | A | 329 | −15.313 | 72.634 | 5.861  | 1.00 | 39.33 |
| ATOM | 1998 | CA  | PHE | A | 329 | −13.893 | 72.404 | 6.130  | 1.00 | 37.23 |
| ATOM | 1999 | C   | PHE | A | 329 | −13.095 | 72.160 | 4.860  | 1.00 | 39.17 |
| ATOM | 2000 | O   | PHE | A | 329 | −13.647 | 71.733 | 3.842  | 1.00 | 39.14 |
| ATOM | 2001 | CB  | PHE | A | 329 | −13.712 | 71.241 | 7.099  | 1.00 | 38.27 |
| ATOM | 2002 | CG  | PHE | A | 329 | −14.266 | 71.504 | 8.464  | 1.00 | 39.19 |
| ATOM | 2003 | CD1 | PHE | A | 329 | −13.563 | 72.284 | 9.377  | 1.00 | 40.73 |
| ATOM | 2004 | CD2 | PHE | A | 329 | −15.503 | 70.996 | 8.836  | 1.00 | 41.09 |
| ATOM | 2005 | CE1 | PHE | A | 329 | −14.074 | 72.533 | 10.630 | 1.00 | 40.64 |
| ATOM | 2006 | CE2 | PHE | A | 329 | −16.017 | 71.246 | 10.102 | 1.00 | 43.05 |
| ATOM | 2007 | CZ  | PHE | A | 329 | −15.300 | 72.025 | 10.991 | 1.00 | 40.33 |
| ATOM | 2008 | N   | SER | A | 330 | −11.794 | 72.441 | 4.913  | 1.00 | 32.90 |
| ATOM | 2009 | CA  | SER | A | 330 | −10.949 | 72.228 | 3.750  | 1.00 | 31.42 |
| ATOM | 2010 | C   | SER | A | 330 | −10.891 | 70.742 | 3.428  | 1.00 | 35.79 |
| ATOM | 2011 | O   | SER | A | 330 | −11.042 | 69.888 | 4.314  | 1.00 | 34.36 |
| ATOM | 2012 | CB  | SER | A | 330 | −9.538  | 72.803 | 3.963  | 1.00 | 32.00 |
| ATOM | 2013 | OG  | SER | A | 330 | −8.750  | 71.960 | 4.778  | 1.00 | 37.87 |
| ATOM | 2014 | N   | LEU | A | 331 | −10.723 | 70.435 | 2.147  | 1.00 | 33.56 |
| ATOM | 2015 | CA  | LEU | A | 331 | −10.647 | 69.062 | 1.703  | 1.00 | 32.81 |
| ATOM | 2016 | C   | LEU | A | 331 | −9.439  | 68.411 | 2.339  | 1.00 | 35.96 |
| ATOM | 2017 | O   | LEU | A | 331 | −9.495  | 67.259 | 2.755  | 1.00 | 36.84 |
| ATOM | 2018 | CB  | LEU | A | 331 | −10.564 | 68.997 | 0.176  | 1.00 | 32.83 |
| ATOM | 2019 | CG  | LEU | A | 331 | −11.908 | 69.078 | −0.562 | 1.00 | 38.09 |
| ATOM | 2020 | CD1 | LEU | A | 331 | −11.728 | 68.907 | −2.068 | 1.00 | 38.59 |
| ATOM | 2021 | CD2 | LEU | A | 331 | −12.870 | 68.027 | −0.023 | 1.00 | 41.23 |
| ATOM | 2022 | N   | GLU | A | 332 | −8.356  | 69.169 | 2.457  | 1.00 | 30.96 |
| ATOM | 2023 | CA  | GLU | A | 332 | −7.124  | 68.653 | 3.065  | 1.00 | 30.65 |
| ATOM | 2024 | C   | GLU | A | 332 | −7.368  | 68.196 | 4.490  | 1.00 | 35.13 |
| ATOM | 2025 | O   | GLU | A | 332 | −6.867  | 67.157 | 4.906  | 1.00 | 35.47 |
| ATOM | 2026 | CB  | GLU | A | 332 | −6.022  | 69.711 | 3.043  | 1.00 | 31.87 |
| ATOM | 2027 | CG  | GLU | A | 332 | −5.218  | 69.746 | 1.758  | 1.00 | 38.65 |
| ATOM | 2028 | CD  | GLU | A | 332 | −4.454  | 71.034 | 1.589  | 1.00 | 57.75 |
| ATOM | 2029 | OE1 | GLU | A | 332 | −4.615  | 71.934 | 2.433  | 1.00 | 57.70 |
| ATOM | 2030 | OE2 | GLU | A | 332 | −3.685  | 71.148 | 0.616  | 1.00 | 53.72 |
| ATOM | 2031 | N   | PHE | A | 333 | −8.130  | 68.990 | 5.238  | 1.00 | 31.46 |
| ATOM | 2032 | CA  | PHE | A | 333 | −8.469  | 68.665 | 6.622  | 1.00 | 30.98 |
| ATOM | 2033 | C   | PHE | A | 333 | −9.341  | 67.398 | 6.672  | 1.00 | 36.08 |
| ATOM | 2034 | O   | PHE | A | 333 | −9.076  | 66.476 | 7.459  | 1.00 | 36.58 |
| ATOM | 2035 | CE  | PHE | A | 333 | −9.190  | 69.851 | 7.284  | 1.00 | 32.36 |
| ATOM | 2036 | CG  | PHE | A | 333 | −9.440  | 69.673 | 8.761  | 1.00 | 33.55 |
| ATOM | 2037 | CD1 | PHE | A | 333 | −8.559  | 68.933 | 9.552  | 1.00 | 35.94 |
| ATOM | 2038 | CD2 | PHE | A | 333 | −10.559 | 70.245 | 9.365  | 1.00 | 35.10 |
| ATOM | 2039 | OE1 | PHE | A | 333 | −8.787  | 68.777 | 10.917 | 1.00 | 35.47 |
| ATOM | 2040 | CE2 | PHE | A | 333 | −10.794 | 70.089 | 10.737 | 1.00 | 37.67 |
| ATOM | 2041 | CS  | PHE | A | 333 | −9.914  | 69.360 | 11.510 | 1.00 | 35.69 |
| ATOM | 2042 | N   | GLN | A | 334 | −10.360 | 67.346 | 5.814  | 1.00 | 32.72 |
| ATOM | 2043 | CA  | GLN | A | 334 | −11.245 | 66.178 | 5.747  | 1.00 | 32.61 |
| ATOM | 2044 | C   | GLN | A | 334 | −10.437 | 64.927 | 5.385  | 1.00 | 38.01 |
| ATOM | 2045 | O   | GLN | A | 334 | −10.593 | 63.862 | 6.001  | 1.00 | 38.40 |
| ATOM | 2046 | CB  | GLN | A | 334 | −12.342 | 66.391 | 4.705  | 1.00 | 33.53 |
| ATOM | 2047 | CG  | GLN | A | 334 | −13.110 | 67.672 | 4.852  | 1.00 | 38.40 |
| ATOM | 2048 | CD  | GLN | A | 334 | −14.180 | 67.815 | 3.799  | 1.00 | 48.70 |
| ATOM | 2049 | OE1 | GLN | A | 334 | −14.779 | 66.839 | 3.387  | 1.00 | 44.73 |
| ATOM | 2050 | NE2 | GLN | A | 334 | −14.401 | 69.032 | 3.339  | 1.00 | 39.07 |
| ATOM | 2051 | N   | ASP | A | 335 | −9.573  | 65.051 | 4.392  | 1.00 | 33.66 |
| ATOM | 2052 | CA  | ASP | A | 335 | −8.765  | 63.925 | 4.011  | 1.00 | 33.57 |
| ATOM | 2053 | C   | ASP | A | 335 | −7.936  | 63.459 | 5.197  | 1.00 | 36.47 |
| ATOM | 2054 | O   | ASP | A | 335 | −7.860  | 62.257 | 5.478  | 1.00 | 36.86 |
| ATOM | 2055 | CB  | ASP | A | 335 | −7.860  | 64.256 | 2.821  | 1.00 | 35.18 |
| ATOM | 2056 | CO  | ASP | A | 335 | −7.080  | 63.034 | 2.323  | 1.00 | 39.38 |
| ATOM | 2057 | OD1 | ASP | A | 335 | −7.712  | 62.109 | 1.777  | 1.00 | 39.01 |
| ATOM | 2058 | OD2 | ASP | A | 335 | −5.850  | 62.985 | 2.525  | 1.00 | 43.27 |
| ATOM | 2059 | N   | PHE | A | 336 | −7.325  | 64.415 | 5.899  | 1.00 | 31.38 |
| ATOM | 2060 | CA  | PHE | A | 336 | −6.481  | 64.104 | 7.062  | 1.00 | 30.62 |
| ATOM | 2061 | C   | PHE | A | 336 | −7.231  | 63.299 | 8.136  | 1.00 | 35.05 |

TABLE 4-continued

Structural Coordinate of MEK1/N35/NKFCdel (corresponding to amino acids 24 373 of SEQ ID NO: 2)-Compound 2 Binary Complex.

| ATOM | 2062 | O   | PHE | A | 336 | −6.783  | 62.232 | 8.534  | 1.00 | 34.72 |
|------|------|-----|-----|---|-----|---------|--------|--------|------|-------|
| ATOM | 2063 | CB  | PHE | A | 336 | −5.872  | 65.382 | 7.659  | 1.00 | 31.75 |
| ATOM | 2064 | CG  | PHE | A | 336 | −4.978  | 65.135 | 8.856  | 1.00 | 32.14 |
| ATOM | 2065 | CD1 | PHE | A | 336 | −3.634  | 64.825 | 8.686  | 1.00 | 34.30 |
| ATOM | 2066 | CD2 | PHE | A | 336 | −5.478  | 65.227 | 10.142 | 1.00 | 33.29 |
| ATOM | 2067 | CE1 | PHE | A | 336 | −2.803  | 64.602 | 9.790  | 1.00 | 34.74 |
| ATOM | 2068 | CE2 | PHE | A | 336 | −4.657  | 64.997 | 11.247 | 1.00 | 35.71 |
| ATOM | 2069 | CZ  | PHE | A | 336 | −3.314  | 64.682 | 11.062 | 1.00 | 33.62 |
| ATOM | 2070 | N   | VAL | A | 337 | −8.378  | 63.802 | 8.595  | 1.00 | 32.05 |
| ATOM | 2071 | CA  | VAL | A | 337 | −9.151  | 63.063 | 9.599  | 1.00 | 32.40 |
| ATOM | 2072 | C   | VAL | A | 337 | −9.518  | 61.719 | 9.035  | 1.00 | 37.60 |
| ATOM | 2073 | O   | VAL | A | 337 | −9.641  | 60.719 | 9.748  | 1.00 | 37.18 |
| ATOM | 2074 | CB  | VAL | A | 337 | −10.383 | 63.866 | 10.141 | 1.00 | 36.05 |
| ATOM | 2075 | CG1 | VAL | A | 337 | −9.932  | 65.158 | 10.840 | 1.00 | 35.81 |
| ATOM | 2076 | CG2 | VAL | A | 337 | −11.353 | 64.156 | 9.046  | 1.00 | 35.72 |
| ATOM | 2077 | N   | ASN | A | 338 | −9.978  | 61.701 | 7.747  | 1.00 | 34.40 |
| ATOM | 2078 | CA  | ASN | A | 338 | −10.427 | 60.469 | 7.084  | 1.00 | 33.83 |
| ATOM | 2079 | C   | ASN | A | 338 | −9.351  | 59.373 | 7.167  | 1.00 | 39.23 |
| ATOM | 2080 | O   | ASN | A | 338 | −9.656  | 58.211 | 7.440  | 1.00 | 39.14 |
| ATOM | 2081 | CB  | ASN | A | 338 | −10.772 | 60.737 | 5.616  | 1.00 | 27.49 |
| ATOM | 2082 | CG  | ASN | A | 336 | −12.217 | 61.208 | 5.414  | 1.00 | 37.50 |
| ATOM | 2083 | OD1 | ASN | A | 338 | −12.979 | 61.354 | 6.364  | 1.00 | 37.07 |
| ATOM | 2084 | ND2 | ASN | A | 338 | −12.572 | 61.479 | 4.179  | 1.00 | 27.35 |
| ATOM | 2085 | N   | LYS | A | 339 | −8.096  | 89.751 | 6.920  | 1.00 | 35.69 |
| ATOM | 2086 | CA  | LYS | A | 339 | −6.986  | 58.801 | 6.955  | 1.00 | 35.12 |
| ATOM | 2087 | C   | LYS | A | 339 | −6.657  | 58.350 | 8.386  | 1.00 | 40.03 |
| ATOM | 2088 | O   | LYS | A | 339 | −5.976  | 57.335 | 8.588  | 1.00 | 39.57 |
| ATOM | 2089 | CB  | LYS | A | 339 | −5.747  | 59.404 | 6.290  | 1.00 | 36.70 |
| ATOM | 2090 | CG  | LYS | A | 339 | −5.774  | 59.406 | 4.757  | 1.00 | 31.89 |
| ATOM | 2091 | CD  | LYS | A | 339 | −4.549  | 60.118 | 4.214  | 1.00 | 36.91 |
| ATOM | 2092 | CE  | LYS | A | 339 | −4.292  | 59.782 | 2.753  | 1.00 | 39.46 |
| ATOM | 2093 | NZ  | LYS | A | 339 | −5.532  | 59.863 | 1.929  | 1.00 | 39.18 |
| ATOM | 2094 | N   | CYS | A | 340 | −7.138  | 59.106 | 9.372  | 1.00 | 37.24 |
| ATOM | 2095 | CA  | CYS | A | 340 | −5.918  | 58.776 | 10.787 | 1.00 | 37.06 |
| ATOM | 2096 | C   | CYS | A | 340 | −8.011  | 57.815 | 11.258 | 1.00 | 41.14 |
| ATOM | 2097 | O   | CYS | A | 340 | −7.777  | 56.961 | 12.114 | 1.00 | 39.95 |
| ATOM | 2098 | CB  | CYS | A | 340 | −6.996  | 60.045 | 11.654 | 1.00 | 37.27 |
| ATOM | 2099 | SG  | CYS | A | 340 | −5.507  | 61.086 | 11.700 | 1.00 | 41.23 |
| ATOM | 2100 | N   | LEU | A | 341 | −9.215  | 58.000 | 10.713 | 1.00 | 38.31 |
| ATOM | 2101 | CA  | LEU | A | 341 | −10.389 | 57.241 | 11.123 | 1.00 | 38.32 |
| ATOM | 2102 | C   | LEU | A | 341 | −10.701 | 55.998 | 10.277 | 1.00 | 44.58 |
| ATOM | 2103 | O   | LEU | A | 341 | −11.820 | 55.472 | 10.319 | 1.00 | 44.15 |
| ATOM | 2104 | CB  | LEU | A | 341 | −11.605 | 58.169 | 11.202 | 1.00 | 37.79 |
| ATOM | 2105 | CG  | LEU | A | 341 | −11.457 | 59.276 | 12.254 | 1.00 | 41.32 |
| ATOM | 2106 | CD1 | LEU | A | 341 | −12.616 | 50.263 | 12.197 | 1.00 | 40.99 |
| ATOM | 2107 | CD2 | LEU | A | 341 | −11.329 | 58.675 | 13.640 | 1.00 | 41.77 |
| ATOM | 2108 | N   | ILE | A | 342 | −9.705  | 55.518 | 9.540  | 1.00 | 42.72 |
| ATOM | 2109 | CA  | ILE | A | 342 | −9.858  | 54.311 | 8.742  | 1.00 | 43.06 |
| ATOM | 2110 | C   | ILE | A | 342 | −9.872  | 53.105 | 9.695  | 1.00 | 48.09 |
| ATOM | 2111 | O   | ILE | A | 342 | −8.873  | 52.823 | 10.371 | 1.00 | 47.79 |
| ATOM | 2112 | CB  | ILE | A | 342 | −8.699  | 54.151 | 7.747  | 1.00 | 46.44 |
| ATOM | 2113 | CG1 | ILE | A | 342 | −8.926  | 55.054 | 6.524  | 1.00 | 46.60 |
| ATOM | 2114 | CG2 | ILE | A | 342 | −8.528  | 52.701 | 7.342  | 1.00 | 47.84 |
| ATOM | 2115 | CD1 | ILE | A | 342 | −7.686  | 55.294 | 5.700  | 1.00 | 48.39 |
| ATOM | 2116 | N   | LYS | A | 343 | −11.020 | 52.428 | 9.775  | 1.00 | 44.92 |
| ATOM | 2117 | CA  | LYS | A | 343 | −11.205 | 51.282 | 10.682 | 1.00 | 44.71 |
| ATOM | 2118 | C   | LYS | A | 343 | −10.092 | 50.221 | 10.670 | 1.00 | 48.96 |
| ATOM | 2119 | O   | LYS | A | 343 | −9.673  | 49.747 | 11.725 | 1.00 | 48.62 |
| ATOM | 2120 | CB  | LYS | A | 343 | −12.572 | 50.642 | 10.476 | 1.00 | 46.72 |
| ATOM | 2121 | CG  | LYS | A | 343 | −13.704 | 51.652 | 10.333 | 1.00 | 53.84 |
| ATOM | 2122 | CD  | LYS | A | 343 | −14.804 | 51.396 | 11.349 | 1.00 | 58.54 |
| ATOM | 2123 | CE  | LYS | A | 343 | −15.841 | 50.433 | 10.805 | 1.00 | 61.04 |
| ATOM | 2124 | NZ  | LYS | A | 343 | −16.530 | 49.698 | 11.887 | 1.00 | 64.56 |
| ATOM | 2125 | N   | ASN | A | 344 | −9.626  | 49.842 | 9.486  | 1.00 | 45.55 |
| ATOM | 2126 | CA  | ASN | A | 344 | −8.555  | 48.862 | 9.394  | 1.00 | 45.53 |
| ATOM | 2127 | C   | ASN | A | 344 | −7.229  | 49.527 | 9.762  | 1.00 | 50.33 |
| ATOM | 2128 | O   | ASN | A | 344 | −6.690  | 50.331 | 8.996  | 1.00 | 50.26 |
| ATOM | 2129 | CB  | ASN | A | 344 | −8.497  | 48.238 | 7.990  | 1.00 | 44.97 |
| ATOM | 2130 | CG  | ASN | A | 344 | −7.298  | 47.294 | 7.807  | 1.00 | 66.54 |
| ATOM | 2131 | OD1 | ASN | A | 344 | −6.548  | 47.022 | 8.753  | 1.00 | 58.45 |
| ATOM | 2132 | ND2 | ASN | A | 344 | −7.107  | 46.818 | 6.581  | 1.00 | 57.44 |
| ATOM | 2133 | N   | PRO | A | 345 | −6.719  | 49.199 | 10.944 | 1.00 | 47.24 |
| ATOM | 2134 | CA  | PRO | A | 345 | −5.475  | 49.789 | 11.436 | 1.00 | 46.96 |
| ATOM | 2135 | C   | PRO | A | 345 | −4.350  | 49.626 | 10.432 | 1.00 | 52.66 |
| ATOM | 2136 | O   | PRO | A | 345 | −3.362  | 50.374 | 10.457 | 1.00 | 52.02 |
| ATOM | 2137 | CB  | PRO | A | 345 | −5.174  | 48.981 | 12.719 | 1.00 | 48.28 |
| ATOM | 2138 | CG  | PRO | A | 345 | −5.998  | 47.746 | 12.612 | 1.00 | 52.10 |

TABLE 4-continued

Structural Coordinate of MEK1/N35/NKFCdel (corresponding to amino acids 24 373 of SEQ ID NO: 2)-Compound 2 Binary Complex.

| | | | | | | | | | |
|---|---|---|---|---|---|---|---|---|---|
| ATOM | 2139 | CD | PRO | A | 345 | −7.214 | 48.128 | 11.830 | 1.00 | 47.63 |
| ATOM | 2140 | N | ALA | A | 346 | −4.495 | 48.642 | 9.553 | 1.00 | 50.57 |
| ATOM | 2141 | CA | ALA | A | 346 | −3.479 | 48.377 | 8.543 | 1.00 | 50.78 |
| ATOM | 2142 | C | ALA | A | 346 | −3.504 | 49.471 | 7.479 | 1.00 | 54.61 |
| ATOM | 2143 | O | ALA | A | 346 | −2.459 | 50.005 | 7.095 | 1.00 | 54.04 |
| ATOM | 2144 | CB | ALA | A | 346 | −3.700 | 47.003 | 7.913 | 1.00 | 51.65 |
| ATOM | 2145 | N | GLU | A | 347 | −4.708 | 49.811 | 7.026 | 1.00 | 51.28 |
| ATOM | 2146 | CA | GLU | A | 347 | −4.890 | 50.853 | 6.020 | 1.00 | 51.00 |
| ATOM | 2147 | C | GLU | A | 347 | −4.729 | 52.246 | 6.632 | 1.00 | 53.52 |
| ATOM | 2148 | O | GLU | A | 347 | −4.268 | 53.171 | 5.969 | 1.00 | 57.83 |
| ATOM | 2149 | CB | GLU | A | 347 | −6.271 | 50.734 | 5.381 | 1.00 | 52.60 |
| ATOM | 2150 | CG | GLU | A | 347 | −6.477 | 49.463 | 4.590 | 1.00 | 66.92 |
| ATOM | 2151 | CD | GLU | A | 347 | −7.936 | 49.216 | 4.271 | 1.00 | 97.76 |
| ATOM | 2152 | OE1 | GLU | A | 347 | −8.595 | 48.474 | 5.031 | 1.00 | 97.92 |
| ATOM | 2153 | OE2 | GLU | A | 347 | −8.435 | 49.724 | 3.273 | 1.00 | 97.70 |
| ATOM | 2154 | N | ARG | A | 348 | −5.133 | 52.379 | 7.897 | 1.00 | 48.83 |
| ATOM | 2155 | CA | ARG | A | 348 | −5.054 | 53.645 | 8.612 | 1.00 | 47.31 |
| ATOM | 2156 | C | ARG | A | 348 | −3.667 | 54.243 | 8.481 | 1.00 | 49.67 |
| ATOM | 2157 | O | ARG | A | 348 | −2.678 | 53.519 | 8.445 | 1.00 | 49.45 |
| ATOM | 2158 | CB | ARG | A | 348 | −5.412 | 53.445 | 10.086 | 1.00 | 45.18 |
| ATOM | 2159 | CG | ARG | A | 348 | −5.266 | 54.697 | 10.944 | 1.00 | 47.88 |
| ATOM | 2160 | CD | ARG | A | 348 | −6.042 | 54.571 | 12.241 | 1.00 | 45.61 |
| ATOM | 2161 | NE | ARG | A | 348 | −7.086 | 53.549 | 12.157 | 1.00 | 46.91 |
| ATOM | 2162 | CZ | ARG | A | 348 | −7.330 | 52.645 | 13.102 | 1.00 | 55.15 |
| ATOM | 2163 | NH1 | ARG | A | 348 | −6.614 | 52.630 | 14.211 | 1.00 | 40.79 |
| ATOM | 2164 | NH2 | ARG | A | 348 | −8.295 | 51.758 | 12.941 | 1.00 | 41.64 |
| ATOM | 2165 | N | ALA | A | 349 | −3.599 | 55.570 | 8.400 | 1.00 | 44.69 |
| ATOM | 2166 | CA | ALA | A | 349 | −2.324 | 56.263 | 8.257 | 1.00 | 43.85 |
| ATOM | 2167 | C | ALA | A | 349 | −1.479 | 56.129 | 9.503 | 1.00 | 45.93 |
| ATOM | 2168 | O | ALA | A | 349 | −2.001 | 55.999 | 10.604 | 1.00 | 46.35 |
| ATOM | 2169 | CB | ALA | A | 349 | −2.550 | 57.741 | 7.929 | 1.00 | 44.44 |
| ATOM | 2170 | N | ASP | A | 350 | −0.166 | 56.198 | 9.331 | 1.00 | 43.62 |
| ATOM | 2171 | CA | ASP | A | 350 | 0.743 | 56.113 | 10.456 | 1.00 | 43.17 |
| ATOM | 2172 | C | ASP | A | 350 | 1.403 | 57.462 | 10.739 | 1.00 | 46.08 |
| ATOM | 2173 | O | ASP | A | 350 | 1.293 | 58.398 | 9.942 | 1.00 | 45.76 |
| ATOM | 2174 | CB | ASP | A | 350 | 1.781 | 54.992 | 10.260 | 1.00 | 45.05 |
| ATOM | 2175 | CG | ASP | A | 350 | 2.700 | 55.231 | 9.065 | 1.00 | 56.68 |
| ATOM | 2176 | OD1 | ASP | A | 350 | 3.080 | 56.394 | 8.805 | 1.00 | 57.50 |
| ATOM | 2177 | OD2 | ASP | A | 350 | 3.109 | 54.234 | 8.434 | 1.00 | 63.60 |
| ATOM | 2178 | N | LEU | A | 351 | 2.075 | 57.557 | 11.878 | 1.00 | 41.50 |
| ATOM | 2179 | CA | LEU | A | 351 | 2.705 | 58.794 | 12.284 | 1.00 | 41.44 |
| ATOM | 2180 | C | LEU | A | 351 | 3.590 | 59.414 | 11.205 | 1.00 | 45.71 |
| ATOM | 2181 | O | LEU | A | 351 | 3.546 | 60.618 | 10.976 | 1.00 | 46.12 |
| ATOM | 2182 | CB | LEU | A | 351 | 3.494 | 58.599 | 13.593 | 1.00 | 41.46 |
| ATOM | 2183 | CG | LEU | A | 351 | 2.683 | 58.295 | 14.860 | 1.00 | 45.72 |
| ATOM | 2184 | CD1 | LEU | A | 351 | 3.589 | 57.846 | 15.988 | 1.00 | 45.86 |
| ATOM | 2185 | CD2 | LEU | A | 351 | 1.837 | 59.488 | 15.289 | 1.00 | 47.17 |
| ATOM | 2186 | N | LYS | A | 352 | 4.409 | 58.598 | 10.562 | 1.00 | 42.41 |
| ATOM | 2187 | CA | LYS | A | 352 | 5.326 | 59.102 | 9.540 | 1.00 | 42.43 |
| ATOM | 2188 | C | LYS | A | 352 | 4.584 | 59.662 | 8.333 | 1.00 | 46.73 |
| ATOM | 2189 | O | LYS | A | 352 | 4.999 | 60.653 | 7.749 | 1.00 | 46.71 |
| ATOM | 2190 | CB | LYS | A | 352 | 6.313 | 58.013 | 9.112 | 1.00 | 44.97 |
| ATOM | 2191 | CG | LYS | A | 352 | 6.858 | 58.193 | 7.703 | 1.00 | 62.12 |
| ATOM | 2192 | CD | LYS | A | 352 | 8.226 | 57.530 | 7.534 | 1.00 | 70.56 |
| ATOM | 2193 | CE | LYS | A | 352 | 9.252 | 58.512 | 6.981 | 1.00 | 78.34 |
| ATOM | 2194 | NZ | LYS | A | 352 | 10.473 | 57.822 | 6.473 | 1.00 | 86.81 |
| ATOM | 2195 | N | GLN | A | 353 | 3.477 | 59.023 | 7.972 | 1.00 | 43.24 |
| ATOM | 2196 | CA | GLN | A | 353 | 2.668 | 59.462 | 6.833 | 1.00 | 42.58 |
| ATOM | 2197 | C | GLN | A | 353 | 1.884 | 60.709 | 7.197 | 1.00 | 45.79 |
| ATOM | 2198 | O | GLN | A | 353 | 1.656 | 61.586 | 6.355 | 1.00 | 45.48 |
| ATOM | 2199 | CB | GLN | A | 353 | 1.702 | 58.352 | 6.407 | 1.00 | 43.97 |
| ATOM | 2200 | CG | GLN | A | 353 | 2.365 | 56.994 | 6.173 | 1.00 | 58.19 |
| ATOM | 2201 | CD | GLN | A | 353 | 1.360 | 55.884 | 5.878 | 1.00 | 77.84 |
| ATOM | 2202 | OE1 | GLN | A | 353 | 0.498 | 55.569 | 6.702 | 1.00 | 74.20 |
| ATOM | 2203 | NE2 | GLN | A | 353 | 1.497 | 55.260 | 4.717 | 1.00 | 68.99 |
| ATOM | 2204 | N | LEU | A | 354 | 1.472 | 60.791 | 8.460 | 1.00 | 41.38 |
| ATOM | 2205 | CA | LEU | A | 354 | 0.715 | 61.937 | 8.938 | 1.00 | 40.41 |
| ATOM | 2206 | C | LEU | A | 354 | 1.603 | 63.171 | 9.023 | 1.00 | 44.07 |
| ATOM | 2207 | O | LEU | A | 354 | 1.195 | 64.261 | 8.532 | 1.00 | 43.23 |
| ATOM | 2208 | CB | LEU | A | 354 | 0.062 | 61.629 | 10.285 | 1.00 | 40.10 |
| ATOM | 2239 | CG | LEU | A | 354 | −1.134 | 60.672 | 10.178 | 1.00 | 43.76 |
| ATOM | 2210 | CD1 | LEU | A | 354 | −1.681 | 50.316 | 11.538 | 1.00 | 43.39 |
| ATOM | 2211 | CD2 | LEU | A | 354 | −2.217 | 61.251 | 9.287 | 1.00 | 44.97 |
| ATOM | 2212 | N | MET | A | 355 | 2.838 | 62.963 | 9.474 | 1.00 | 40.96 |
| ATOM | 2213 | CA | MET | A | 355 | 3.785 | 64.087 | 9.585 | 1.00 | 41.29 |
| ATOM | 2214 | C | MET | A | 355 | 3.965 | 64.853 | 8.270 | 1.00 | 45.21 |
| ATOM | 2215 | O | MET | A | 355 | 4.222 | 45.067 | 8.278 | 1.00 | 44.54 |

TABLE 4-continued

Structural Coordinate of MEK1/N35/NKFCdel (corresponding to amino acids 24 373 of SEQ ID NO: 2)-Compound 2 Binary Complex.

| ATOM | 2216 | CB | MET | A | 355 | 5.136 | 63.598 | 10.112 | 1.00 | 44.03 |
|---|---|---|---|---|---|---|---|---|---|---|
| ATOM | 2217 | CG | MET | A | 355 | 5.315 | 63.771 | 11.643 | 1.00 | 48.31 |
| ATOM | 2218 | SD | MET | A | 355 | 5.172 | 65.521 | 12.196 | 1.00 | 52.98 |
| ATOM | 2219 | CE | MET | A | 355 | 3.417 | 65.692 | 12.313 | 1.00 | 49.82 |
| ATOM | 2220 | N | VAL | A | 355 | 3.816 | 64.148 | 7.143 | 1.00 | 41.28 |
| ATOM | 2221 | CA | VAL | A | 356 | 3.962 | 64.772 | 5.830 | 1.00 | 40.34 |
| ATOM | 2222 | C | VAL | A | 356 | 2.672 | 64.871 | 5.046 | 1.00 | 43.06 |
| ATOM | 2223 | O | VAL | A | 356 | 2.690 | 65.009 | 3.821 | 1.00 | 43.16 |
| ATOM | 2224 | CB | VAL | A | 356 | 5.028 | 64.083 | 4.972 | 1.00 | 44.24 |
| ATOM | 2225 | CG1 | VAL | A | 356 | 6.416 | 64.301 | 5.577 | 1.00 | 44.10 |
| ATOM | 2226 | CG2 | VAL | A | 356 | 4.713 | 62.595 | 4.807 | 1.00 | 43.85 |
| ATOM | 2227 | N | HIS | A | 357 | 1.546 | 64.814 | 5.742 | 1.00 | 38.27 |
| ATOM | 2228 | CA | HIS | A | 357 | 0.254 | 64.959 | 5.086 | 1.00 | 36.78 |
| ATOM | 2229 | C | HIS | A | 357 | 0.062 | 66.440 | 4.730 | 1.00 | 40.05 |
| ATOM | 2230 | O | HIS | A | 357 | 0.464 | 67.325 | 5.488 | 1.00 | 40.00 |
| ATOM | 2231 | CB | HIS | A | 357 | −0.875 | 64.482 | 6.016 | 1.00 | 37.03 |
| ATOM | 2232 | CG | HIS | A | 357 | −2.225 | 64.447 | 5.368 | 1.00 | 40.43 |
| ATOM | 2233 | ND1 | HIS | A | 357 | −2.985 | 65.581 | 5.161 | 1.00 | 42.30 |
| ATOM | 2234 | CD2 | HIS | A | 357 | −2.962 | 63.410 | 4.902 | 1.00 | 41.86 |
| ATOM | 2235 | CE1 | HIS | A | 357 | −4.129 | 65.243 | 4.594 | 1.00 | 41.52 |
| ATOM | 2236 | NE2 | HIS | A | 357 | −4.141 | 63.932 | 4.424 | 1.00 | 41.76 |
| ATOM | 2237 | N | ALA | A | 358 | −0.529 | 66.694 | 3.564 | 1.00 | 35.48 |
| ATOM | 2238 | CA | ALA | A | 358 | −0.790 | 68.045 | 3.075 | 1.00 | 34.01 |
| ATOM | 2239 | C | ALA | A | 358 | −1.357 | 68.963 | 4.151 | 1.00 | 39.22 |
| ATOM | 2240 | O | ALA | A | 358 | −1.011 | 70.147 | 4.207 | 1.00 | 40.32 |
| ATOM | 2241 | CB | ALA | A | 358 | −1.730 | 67.997 | 1.908 | 1.00 | 34.16 |
| ATOM | 2242 | N | PHE | A | 359 | −2.283 | 68.443 | 4.960 | 1.00 | 34.57 |
| ATOM | 2243 | CA | PHE | A | 359 | −2.912 | 69.255 | 5.999 | 1.00 | 33.38 |
| ATOM | 2244 | C | PHE | A | 359 | −1.881 | 69.720 | 7.023 | 1.00 | 38.30 |
| ATOM | 2245 | O | PHE | A | 359 | −1.927 | 70.848 | 7.500 | 1.00 | 36.99 |
| ATOM | 2246 | CB | PHE | A | 359 | −4.061 | 68.501 | 6.677 | 1.00 | 33.99 |
| ATOM | 2247 | CG | PHE | A | 359 | −4.621 | 69.193 | 7.897 | 1.00 | 34.00 |
| ATOM | 2248 | CD1 | PHE | A | 359 | −5.301 | 70.394 | 7.771 | 1.00 | 35.67 |
| ATOM | 2249 | CD2 | PHE | A | 359 | −4.478 | 68.622 | 9.154 | 1.00 | 34.37 |
| ATOM | 2250 | CE1 | PHE | A | 359 | −5.814 | 71.041 | 8.904 | 1.00 | 35.60 |
| ATOM | 2251 | CE2 | PHE | A | 359 | −4.983 | 69.265 | 10.273 | 1.00 | 36.33 |
| ATOM | 2252 | CZ | PHE | A | 359 | −5.655 | 70.474 | 10.150 | 1.00 | 34.19 |
| ATOM | 2253 | N | ILE | A | 360 | −0.964 | 68.824 | 7.365 | 1.00 | 36.54 |
| ATOM | 2254 | CA | ILE | A | 360 | 0.063 | 69.105 | 8.352 | 1.00 | 36.94 |
| ATOM | 2255 | C | ILE | A | 360 | 1.107 | 70.041 | 7.778 | 1.00 | 42.20 |
| ATOM | 2256 | O | ILE | A | 360 | 1.497 | 71.024 | 8.409 | 1.00 | 41.97 |
| ATOM | 2257 | CB | ILE | A | 360 | 0.729 | 67.797 | 8.839 | 1.00 | 39.83 |
| ATOM | 2258 | CG1 | ILE | A | 350 | −0.275 | 66.959 | 9.637 | 1.00 | 39.95 |
| ATOM | 2259 | CG2 | ILE | A | 360 | 1.966 | 68.097 | 9.684 | 1.00 | 40.38 |
| ATOM | 2260 | CD1 | ILE | A | 360 | −0.859 | 67.676 | 10.845 | 1.00 | 41.38 |
| ATOM | 2261 | N | LYS | A | 361 | 1.536 | 69.745 | 5.563 | 1.00 | 39.80 |
| ATOM | 2262 | CA | LYS | A | 361 | 2.501 | 70.569 | 5.876 | 1.00 | 39.61 |
| ATOM | 2263 | C | LYS | A | 361 | 1.952 | 71.983 | 5.743 | 1.00 | 43.38 |
| ATOM | 2264 | O | LYS | A | 351 | 2.642 | 72.954 | 6.042 | 1.00 | 43.36 |
| ATOM | 2265 | CB | LYS | A | 361 | 2.814 | 69.978 | 4.502 | 1.00 | 41.98 |
| ATOM | 2266 | CG | LYS | A | 361 | 4.018 | 69.054 | 4.494 | 1.00 | 55.37 |
| ATOM | 2267 | CD | LYS | A | 361 | 3.770 | 67.824 | 3.624 | 1.00 | 69.40 |
| ATOM | 2268 | CE | LYS | A | 361 | 3.866 | 68.149 | 2.137 | 1.00 | 76.80 |
| ATOM | 2269 | NZ | LYS | A | 361 | 3.056 | 67.202 | 1.310 | 1.00 | 85.51 |
| ATOM | 2270 | N | ARG | A | 362 | 0.697 | 72.090 | 5.323 | 1.00 | 39.61 |
| ATOM | 2271 | CA | ARG | A | 362 | 0.053 | 73.390 | 5.169 | 1.00 | 39.29 |
| ATOM | 2272 | C | ARG | A | 362 | −0.102 | 74.105 | 6.521 | 1.00 | 44.74 |
| ATOM | 2273 | O | ARG | A | 362 | 0.039 | 75.325 | 6.605 | 1.00 | 45.17 |
| ATOM | 2274 | CB | ARG | A | 362 | −1.307 | 73.239 | 4.488 | 1.00 | 37.40 |
| ATOM | 2275 | CG | ARG | A | 362 | −2.085 | 74.564 | 4.344 | 1.00 | 43.09 |
| ATOM | 2276 | CD | ARG | A | 362 | −3.596 | 74.327 | 4.146 | 1.00 | 43.39 |
| ATOM | 2277 | NE | ARG | A | 362 | −4.344 | 74.396 | 5.413 | 1.00 | 39.98 |
| ATOM | 2278 | CZ | ARG | A | 362 | −5.568 | 73.500 | 5.592 | 1.00 | 45.67 |
| ATOM | 2279 | NH1 | ARG | A | 362 | −6.192 | 73.293 | 4.590 | 1.00 | 33.42 |
| ATOM | 2280 | NH2 | ARG | A | 362 | −6.175 | 74.019 | 6.772 | 1.00 | 25.08 |
| ATOM | 2281 | N | SER | A | 363 | −0.373 | 73.336 | 7.572 | 1.00 | 41.12 |
| ATOM | 2282 | CA | SER | A | 363 | −0.549 | 73.888 | 8.909 | 1.00 | 41.02 |
| ATOM | 2283 | C | SER | A | 363 | 0.774 | 74.338 | 9.508 | 1.00 | 48.46 |
| ATOM | 2284 | O | SER | A | 363 | 0.830 | 75.339 | 10.223 | 1.00 | 48.09 |
| ATOM | 2285 | CB | SER | A | 363 | −1.226 | 72.869 | 9.833 | 1.00 | 42.89 |
| ATOM | 2286 | OG | SER | A | 363 | −2.557 | 72.595 | 9.420 | 1.00 | 45.88 |
| ATOM | 2287 | N | ASP | A | 364 | 1.844 | 73.597 | 9.220 | 1.00 | 47.51 |
| ATOM | 2288 | CA | ASP | A | 364 | 3.165 | 73.949 | 9.737 | 1.00 | 48.11 |
| ATOM | 2289 | C | ASP | A | 364 | 3.625 | 75.276 | 9.160 | 1.00 | 53.33 |
| ATOM | 2290 | O | ASP | A | 364 | 4.274 | 76.069 | 9.842 | 1.00 | 53.94 |
| ATOM | 2291 | CB | ASP | A | 364 | 4.191 | 72.851 | 9.433 | 1.00 | 50.15 |
| ATOM | 2292 | CG | ASP | A | 364 | 5.086 | 72.533 | 10.632 | 1.00 | 64.03 |

TABLE 4-continued

Structural Coordinate of MEK1/N35/NKFCdel (corresponding to amino acids 24 373 of SEQ ID NO: 2)-Compound 2 Binary Complex.

| ATOM | 2293 | OD1 | ASP | A | 364 | 5.172 | 73.370 | 11.557 | 1.00 | 65.41 |
|------|------|-----|-----|---|-----|-------|--------|--------|------|-------|
| ATOM | 2294 | OD2 | ASP | A | 364 | 5.713 | 71.449 | 10.647 | 1.00 | 71.20 |
| ATOM | 2295 | N | ALA | A | 365 | 3.262 | 75.529 | 7.908 | 1.00 | 49.96 |
| ATOM | 2296 | CA | ALA | A | 365 | 3.643 | 76.763 | 7.230 | 1.00 | 50.13 |
| ATOM | 2297 | C | ALA | A | 365 | 2.702 | 77.910 | 7.567 | 1.00 | 56.07 |
| ATOM | 2298 | O | ALA | A | 365 | 2.852 | 79.027 | 7.057 | 1.00 | 56.87 |
| ATOM | 2299 | CB | ALA | A | 365 | 3.688 | 76.546 | 5.729 | 1.00 | 50.69 |
| ATOM | 2300 | N | GLU | A | 366 | 1.709 | 77.629 | 8.393 | 1.00 | 52.72 |
| ATOM | 2301 | CA | GLU | A | 366 | 0.742 | 78.641 | 8.767 | 1.00 | 52.63 |
| ATOM | 2302 | C | GLU | A | 366 | 1.186 | 79.400 | 10.010 | 1.00 | 58.54 |
| ATOM | 2303 | O | GLU | A | 366 | 1.569 | 78.800 | 11.020 | 1.00 | 58.58 |
| ATOM | 2304 | CB | GLU | A | 366 | −0.631 | 78.015 | 8.955 | 1.00 | 53.61 |
| ATOM | 2305 | CG | GLU | A | 366 | −1.611 | 78.229 | 7.855 | 1.00 | 57.41 |
| ATOM | 2306 | CD | GLU | A | 366 | −2.715 | 77.189 | 7.836 | 1.00 | 64.87 |
| ATOM | 2307 | OE1 | GLU | A | 366 | −2.886 | 76.475 | 8.858 | 1.00 | 51.93 |
| ATOM | 2308 | OE2 | GLU | A | 366 | −3.400 | 77.067 | 6.797 | 1.00 | 49.68 |
| ATOM | 2309 | N | GLU | A | 367 | 1.138 | 80.720 | 9.931 | 1.00 | 55.76 |
| ATOM | 2310 | CA | GLU | A | 367 | 1.495 | 81.554 | 11.067 | 1.00 | 55.95 |
| ATOM | 2311 | C | GLU | A | 367 | 0.224 | 81.767 | 11.870 | 1.00 | 58.50 |
| ATOM | 2312 | O | GLU | A | 367 | −0.524 | 82.724 | 11.624 | 1.00 | 58.24 |
| ATOM | 2313 | CB | GLU | A | 367 | 2.068 | 82.903 | 10.594 | 1.00 | 57.68 |
| ATOM | 2314 | CG | GLU | A | 367 | 3.064 | 82.792 | 9.423 | 1.00 | 69.80 |
| ATOM | 2315 | CD | GLU | A | 367 | 4.311 | 81.986 | 9.778 | 1.00 | 93.95 |
| ATOM | 2316 | OE1 | GLU | A | 367 | 4.361 | 81.402 | 10.888 | 1.00 | 88.27 |
| ATOM | 2317 | OE2 | GLU | A | 367 | 5.249 | 81.945 | 8.947 | 1.00 | 89.22 |
| ATOM | 2318 | N | VAL | A | 368 | −0.052 | 80.836 | 12.783 | 1.00 | 53.03 |
| ATOM | 2319 | CA | VAL | A | 368 | −1.275 | 80.886 | 13.574 | 1.00 | 51.80 |
| ATOM | 2320 | C | VAL | A | 368 | −1.037 | 81.279 | 15.029 | 1.00 | 52.54 |
| ATOM | 2321 | O | VAL | A | 368 | −0.329 | 80.587 | 15.765 | 1.00 | 51.39 |
| ATOM | 2322 | CB | VAL | A | 368 | −2.048 | 79.541 | 13.503 | 1.00 | 55.79 |
| ATOM | 2323 | CG1 | VAL | A | 368 | −2.892 | 79.339 | 14.742 | 1.00 | 55.47 |
| ATOM | 2324 | CG2 | VAL | A | 368 | −2.914 | 79.498 | 12.262 | 1.00 | 55.59 |
| ATOM | 2325 | N | ASP | A | 369 | −1.641 | 82.389 | 15.442 | 1.00 | 47.32 |
| ATOM | 2326 | CA | ASP | A | 369 | −1.514 | 82.847 | 16.816 | 1.00 | 46.47 |
| ATOM | 2327 | C | ASP | A | 369 | −2.426 | 82.035 | 17.727 | 1.00 | 49.09 |
| ATOM | 2328 | O | ASP | A | 369 | −3.521 | 82.468 | 18.071 | 1.00 | 47.86 |
| ATOM | 2329 | CB | ASP | A | 369 | −1.847 | 84.330 | 16.932 | 1.00 | 48.19 |
| ATOM | 2330 | CG | ASP | A | 369 | −1.569 | 84.878 | 18.318 | 1.00 | 57.79 |
| ATOM | 2331 | OD1 | ASP | A | 369 | −0.475 | 84.606 | 18.850 | 1.00 | 57.84 |
| ATOM | 2332 | OD2 | ASP | A | 369 | −2.461 | 85.541 | 18.891 | 1.00 | 64.56 |
| ATOM | 2333 | N | PHE | A | 370 | −1.970 | 80.848 | 18.100 | 1.00 | 42.73 |
| ATOM | 2334 | CA | PHE | A | 370 | −2.745 | 79.965 | 18.950 | 1.00 | 41.31 |
| ATOM | 2335 | C | PHE | A | 370 | −3.006 | 80.575 | 20.328 | 1.00 | 43.47 |
| ATOM | 2336 | O | PHE | A | 370 | −4.131 | 80.550 | 20.816 | 1.00 | 42.61 |
| ATOM | 2337 | CB | PHE | A | 370 | −2.061 | 78.603 | 19.074 | 1.00 | 42.70 |
| ATOM | 2338 | CG | PHE | A | 370 | −2.639 | 77.738 | 20.148 | 1.00 | 44.38 |
| ATOM | 2339 | CD1 | PHE | A | 370 | −3.909 | 77.217 | 20.023 | 1.00 | 47.77 |
| ATOM | 2340 | CD2 | PHE | A | 370 | −1.928 | 77.477 | 21.298 | 1.00 | 46.49 |
| ATOM | 2341 | CE1 | PHE | A | 370 | −4.447 | 76.443 | 21.017 | 1.00 | 48.82 |
| ATOM | 2342 | CE2 | PHE | A | 370 | −2.462 | 76.699 | 22.289 | 1.00 | 49.54 |
| ATOM | 2343 | CZ | PHE | A | 370 | −3.720 | 76.180 | 22.149 | 1.00 | 47.81 |
| ATOM | 2344 | N | ALA | A | 371 | −1.968 | 81.133 | 20.945 | 1.00 | 40.03 |
| ATOM | 2345 | CA | ALA | A | 371 | −2.100 | 81.749 | 22.272 | 1.00 | 39.82 |
| ATOM | 2346 | C | ALA | A | 371 | −3.124 | 82.870 | 22.264 | 1.00 | 43.08 |
| ATOM | 2347 | O | ALA | A | 371 | −4.018 | 82.908 | 23.100 | 1.00 | 43.77 |
| ATOM | 2348 | CB | ALA | A | 371 | −0.759 | 82.256 | 22.768 | 1.00 | 40.54 |
| ATOM | 2349 | N | GLY | A | 372 | −2.988 | 83.785 | 21.315 | 1.00 | 38.67 |
| ATOM | 2350 | CA | GLY | A | 372 | −3.930 | 84.891 | 21.176 | 1.00 | 37.87 |
| ATOM | 2351 | C | GLY | A | 372 | −5.352 | 84.337 | 21.117 | 1.00 | 40.50 |
| ATOM | 2352 | O | GLY | A | 372 | −6.203 | 84.695 | 21.940 | 1.00 | 40.40 |
| ATOM | 2353 | N | TRP | A | 373 | −5.586 | 83.418 | 20.176 | 1.00 | 34.91 |
| ATOM | 2354 | CA | TRP | A | 373 | −6.897 | 82.799 | 20.018 | 1.00 | 33.52 |
| ATOM | 2355 | C | TRP | A | 373 | −7.354 | 82.164 | 21.312 | 1.00 | 37.68 |
| ATOM | 2356 | O | TRP | A | 373 | −8.466 | 82.384 | 21.757 | 1.00 | 37.35 |
| ATOM | 2357 | CB | TRP | A | 373 | −6.874 | 81.734 | 18.917 | 1.00 | 31.24 |
| ATOM | 2358 | CG | TRP | A | 373 | −8.171 | 80.954 | 18.842 | 1.00 | 31.42 |
| ATOM | 2359 | CD1 | TRP | A | 373 | −9.264 | 81.248 | 18.068 | 1.00 | 34.14 |
| ATOM | 2360 | CD2 | TRP | A | 373 | −8.527 | 79.795 | 19.614 | 1.00 | 30.85 |
| ATOM | 2361 | NE1 | TRP | A | 373 | −10.263 | 80.329 | 18.294 | 1.00 | 33.31 |
| ATOM | 2362 | CE2 | TRP | A | 373 | −9.836 | 79.429 | 19.238 | 1.00 | 34.57 |
| ATOM | 2363 | CE3 | TRP | A | 373 | −7.857 | 79.019 | 20.566 | 1.00 | 31.74 |
| ATOM | 2364 | CZ2 | TRP | A | 373 | −10.489 | 78.325 | 19.786 | 1.00 | 33.71 |
| ATOM | 2365 | CZ3 | TRP | A | 373 | −8.508 | 77.929 | 21.112 | 1.00 | 33.01 |
| ATOM | 2366 | CH2 | TRP | A | 373 | −9.812 | 77.594 | 20.721 | 1.00 | 33.65 |
| ATOM | 2367 | N | LEU | A | 374 | −6.481 | 81.361 | 21.904 | 1.00 | 35.27 |
| ATOM | 2368 | CA | LEU | A | 374 | −6.787 | 80.666 | 23.146 | 1.00 | 35.60 |
| ATOM | 2369 | C | LEU | A | 374 | −7.196 | 81.632 | 24.252 | 1.00 | 40.90 |

TABLE 4-continued

Structural Coordinate of MEK1/N35/NKFCdel (corresponding to amino acids 24 373 of SEQ ID NO: 2)-Compound 2 Binary Complex.

| ATOM | 2370 | O | LEU | A | 374 | −8.235 | 81.460 | 24.888 | 1.00 | 40.32 |
|---|---|---|---|---|---|---|---|---|---|---|
| ATOM | 2371 | CB | LEU | A | 374 | −5.584 | 79.835 | 23.600 | 1.00 | 35.35 |
| ATOM | 2372 | CG | LEU | A | 374 | −5.711 | 79.184 | 24.973 | 1.00 | 39.66 |
| ATOM | 2373 | CD1 | LEU | A | 374 | −6.726 | 78.054 | 24.916 | 1.00 | 39.62 |
| ATOM | 2374 | CD2 | LEU | A | 374 | −4.357 | 78.669 | 25.445 | 1.00 | 41.73 |
| ATOM | 2375 | N | CYS | A | 375 | −6.373 | 82.646 | 24.480 | 1.00 | 39.04 |
| ATOM | 2376 | CA | CYS | A | 375 | −6.638 | 83.623 | 25.537 | 1.00 | 39.98 |
| ATOM | 2377 | C | CYS | A | 375 | −7.958 | 84.363 | 25.398 | 1.00 | 43.82 |
| ATOM | 2378 | O | CYS | A | 375 | −8.652 | 84.581 | 26.385 | 1.00 | 42.59 |
| ATOM | 2379 | CB | CYS | A | 375 | −5.468 | 84.584 | 25.695 | 1.00 | 40.64 |
| ATOM | 2380 | SG | CYS | A | 375 | −3.964 | 83.736 | 26.271 | 1.00 | 44.74 |
| ATOM | 2381 | N | SER | A | 376 | −8.322 | 84.722 | 24.166 | 1.00 | 41.18 |
| ATOM | 2382 | CA | SER | A | 376 | −9.580 | 85.432 | 23.912 | 1.00 | 41.32 |
| ATOM | 2383 | C | SER | A | 376 | −10.792 | 84.530 | 24.112 | 1.00 | 46.53 |
| ATOM | 2384 | O | SER | A | 376 | −11.872 | 84.998 | 24.470 | 1.00 | 46.16 |
| ATOM | 2385 | CB | SER | A | 376 | −9.607 | 86.003 | 22.493 | 1.00 | 44.12 |
| ATOM | 2386 | OG | SER | A | 376 | −8.321 | 86.391 | 22.072 | 1.00 | 53.59 |
| ATOM | 2387 | N | THR | A | 377 | −10.608 | 83.238 | 23.849 | 1.00 | 43.48 |
| ATOM | 2388 | CA | THR | A | 377 | −11.688 | 82.265 | 23.943 | 1.00 | 43.03 |
| ATOM | 2389 | C | THR | A | 377 | −12.080 | 81.912 | 25.367 | 1.00 | 46.82 |
| ATOM | 2390 | O | THR | A | 377 | −13.265 | 81.841 | 25.687 | 1.00 | 46.03 |
| ATOM | 2391 | CB | THR | A | 377 | −11.348 | 80.970 | 23.179 | 1.00 | 47.99 |
| ATOM | 2392 | OG1 | THR | A | 377 | −10.627 | 81.299 | 21.997 | 1.00 | 47.27 |
| ATOM | 2393 | CG2 | THR | A | 377 | −12.607 | 80.234 | 22.791 | 1.00 | 45.64 |
| ATOM | 2394 | N | ILE | A | 378 | −11.091 | 81.640 | 26.209 | 1.00 | 44.34 |
| ATOM | 2395 | CA | ILE | A | 378 | −11.375 | 81.249 | 27.586 | 1.00 | 44.87 |
| ATOM | 2396 | C | ILE | A | 378 | −11.280 | 82.403 | 28.571 | 1.00 | 51.76 |
| ATOM | 2397 | O | ILE | A | 378 | −11.265 | 82.191 | 29.779 | 1.00 | 51.95 |
| ATOM | 2398 | CB | ILE | A | 378 | −10.487 | 80.062 | 28.059 | 1.00 | 47.23 |
| ATOM | 2399 | CG1 | ILE | A | 378 | −9.028 | 80.481 | 28.150 | 1.00 | 47.15 |
| ATOM | 2400 | CG2 | ILE | A | 378 | −10.651 | 78.861 | 27.138 | 1.00 | 46.98 |
| ATOM | 2401 | CD1 | ILE | A | 378 | −8.144 | 79.409 | 28.713 | 1.00 | 50.00 |
| ATOM | 2402 | N | GLY | A | 379 | −11.232 | 83.623 | 28.046 | 1.00 | 50.47 |
| ATOM | 2403 | CA | GLY | A | 379 | −11.158 | 84.822 | 28.875 | 1.00 | 51.42 |
| ATOM | 2404 | C | GLY | A | 379 | −9.900 | 84.845 | 29.732 | 1.00 | 58.97 |
| ATOM | 2405 | O | GLY | A | 379 | −9.874 | 85.464 | 30.795 | 1.00 | 58.13 |
| ATOM | 2406 | N | LEU | A | 380 | −8.855 | 84.178 | 29.261 | 1.00 | 59.15 |
| ATOM | 2407 | CA | LEU | A | 380 | −7.598 | 84.119 | 29.995 | 1.00 | 60.62 |
| ATOM | 2408 | C | LEU | A | 380 | −6.996 | 85.500 | 30.213 | 1.00 | 68.23 |
| ATOM | 2409 | O | LEU | A | 380 | −6.925 | 86.325 | 29.288 | 1.00 | 68.01 |
| ATOM | 2410 | CB | LEU | A | 380 | −6.593 | 83.200 | 29.296 | 1.00 | 60.74 |
| ATOM | 2411 | CG | LEU | A | 380 | −6.046 | 82.052 | 30.151 | 1.00 | 65.43 |
| ATOM | 2412 | CD1 | LEU | A | 380 | −5.579 | 80.905 | 29.281 | 1.00 | 65.42 |
| ATOM | 2413 | CD2 | LEU | A | 380 | −4.918 | 82.538 | 31.045 | 1.00 | 68.28 |
| ATOM | 2414 | N | ASN | A | 381 | −6.566 | 85.748 | 31.447 | 1.00 | 67.05 |
| ATOM | 2415 | CA | ASN | A | 381 | −5.948 | 87.017 | 31.817 | 1.00 | 67.66 |
| ATOM | 2416 | C | ASN | A | 381 | −4.629 | 86.755 | 32.543 | 1.00 | 72.60 |
| ATOM | 2417 | O | ASN | A | 381 | −4.614 | 86.141 | 33.616 | 1.00 | 72.36 |
| ATOM | 2418 | CB | ASN | A | 381 | −6.884 | 87.822 | 32.723 | 1.00 | 69.06 |
| ATOM | 2419 | CG | ASN | A | 381 | −8.084 | 88.366 | 31.980 | 1.00 | 89.62 |
| ATOM | 2420 | OD1 | ASN | A | 381 | −7.942 | 89.116 | 31.015 | 1.00 | 83.72 |
| ATOM | 2421 | ND2 | ASN | A | 381 | −9.276 | 87.984 | 32.423 | 1.00 | 80.65 |
| TER | 2422 | | GLN | A | 382 | | | | | |
| ATOM | 2423 | C01 | SCH | Z | 1 | −2.366 | 69.257 | 34.186 | 1.00 | 52.86 |
| ATOM | 2424 | C02 | SCH | Z | 1 | −3.717 | 69.508 | 34.220 | 1.00 | 50.11 |
| ATOM | 2425 | N03 | SCH | Z | 1 | −3.848 | 70.879 | 34.039 | 1.00 | 48.90 |
| ATOM | 2426 | N04 | SCH | Z | 1 | −2.628 | 71.508 | 34.001 | 1.00 | 49.93 |
| ATOM | 2427 | C05 | SCH | Z | 1 | −1.740 | 70.496 | 34.107 | 1.00 | 51.38 |
| ATOM | 2428 | N06 | SCH | Z | 1 | −4.780 | 68.701 | 34.406 | 1.00 | 50.15 |
| ATOM | 2429 | C07 | SCH | Z | 1 | −5.926 | 69.153 | 34.049 | 1.00 | 49.91 |
| ATOM | 2430 | C08 | SCH | Z | 1 | −6.210 | 70.618 | 33.803 | 1.00 | 49.21 |
| ATOM | 2431 | C09 | SCH | Z | 1 | −5.130 | 71.460 | 33.871 | 1.00 | 48.28 |
| ATOM | 2432 | N10 | SCH | Z | 1 | −5.206 | 72.835 | 33.822 | 1.00 | 47.03 |
| ATOM | 2433 | C11 | SCH | Z | 1 | −7.028 | 68.099 | 33.875 | 1.00 | 49.84 |
| ATOM | 2434 | C12 | SCH | Z | 1 | −7.413 | 67.825 | 32.437 | 1.00 | 51.03 |
| ATOM | 2435 | N13 | SCH | Z | 1 | −8.223 | 66.605 | 32.351 | 1.00 | 51.54 |
| ATOM | 2436 | C14 | SCH | Z | 1 | −9.427 | 66.681 | 33.191 | 1.00 | 50.53 |
| ATOM | 2437 | C15 | SCH | Z | 1 | −9.096 | 67.007 | 34.660 | 1.00 | 49.54 |
| ATOM | 2438 | C16 | SCH | Z | 1 | −8.241 | 68.265 | 34.773 | 1.00 | 49.61 |
| ATOM | 2439 | BR17 | SCH | Z | 1 | −1.514 | 67.591 | 34.330 | 1.00 | 56.51 |
| END | | | | | | | | | | |

\*\*\*\*\*\*\*\*\*\*\*\*\*\*\*\*\*\*\*\*\*\*\*\*\*\*\*\*

The present invention is not to be limited in scope by the specific embodiments described herein. indeed, various modifications of the invention in addition to those described herein will become apparent to those skilled in the art from the foregoing description. Such modifications are intended to fall within the scope of the appended claims.

Patents, patent applications, publications, product descriptions, and protocols are cited throughout this application, the disclosures of which are incorporated herein by reference in their entireties for all purposes.

We claim:

1. An isolated polypeptide comprising the amino acid sequence of SEQ ID NO:1, the amino acid sequence of SEQ ID NO:2, the amino acid sequence of amino acids 25-383 of SEQ ID NO: 1, or the amino acid sequence of amino acids 25-373 of SEQ ID NO:2.

2. The polypeptide of claim 1 comprising the amino acid sequence of SEQ ID NO: 1 or the amino acid sequence of SEQ ID NO: 2.

3. A composition comprising the polypeptide of claim 1.

4. An isolated fusion protein comprising the polypeptide of claim 1 fused to a heterologous protein.

* * * * *